(12) United States Patent
Hicklin et al.

(10) Patent No.: US 10,232,053 B2
(45) Date of Patent: Mar. 19, 2019

(54) IMMUNOMODULATORY ONCOLYTIC ADENOVIRAL VECTORS, AND METHODS OF PRODUCTION AND USE THEREOF FOR TREATMENT OF CANCER

(71) Applicant: Trieza Therapeutics, Inc., Cambridge, MA (US)

(72) Inventors: Daniel Hicklin, Montclair, NJ (US); Kenneth Nelson Wills, Carlsbad, CA (US); Cynthia Seidel-Dugan, Belmont, MA (US); William Winston, Newton, MA (US); Philipp Steiner, Washington, DC (US)

(73) Assignee: Trieza Therapeutics, Inc., Cambridge, MA (US)

( * ) Notice: Subject to any disclaimer, the term of this patent is extended or adjusted under 35 U.S.C. 154(b) by 0 days.

(21) Appl. No.: 15/834,690

(22) Filed: Dec. 7, 2017

(65) Prior Publication Data

US 2018/0185515 A1   Jul. 5, 2018

Related U.S. Application Data

(60) Provisional application No. 62/572,206, filed on Oct. 13, 2017, provisional application No. 62/440,670, filed on Dec. 30, 2016, provisional application No. 62/440,646, filed on Dec. 30, 2016.

(51) Int. Cl.
| | |
|---|---|
| *A61K 35/761* | (2015.01) |
| *A61P 35/00* | (2006.01) |
| *C12N 15/861* | (2006.01) |
| *A61K 48/00* | (2006.01) |
| *C07K 14/705* | (2006.01) |
| *C07K 14/54* | (2006.01) |
| *C12N 15/86* | (2006.01) |
| *A61K 39/00* | (2006.01) |

(52) U.S. Cl.
CPC ........ *A61K 48/0008* (2013.01); *A61K 35/761* (2013.01); *A61K 48/0058* (2013.01); *A61P 35/00* (2018.01); *C07K 14/5418* (2013.01); *C07K 14/5428* (2013.01); *C07K 14/5434* (2013.01); *C07K 14/70575* (2013.01); *C07K 14/70578* (2013.01); *C12N 15/86* (2013.01); *A61K 2039/5256* (2013.01); *A61K 2039/585* (2013.01); *C12N 2710/10041* (2013.01); *C12N 2710/10332* (2013.01); *C12N 2710/10343* (2013.01); *C12N 2710/10371* (2013.01); *C12N 2800/24* (2013.01); *C12N 2830/008* (2013.01); *C12N 2830/30* (2013.01); *C12N 2830/60* (2013.01); *C12N 2840/203* (2013.01)

(58) Field of Classification Search
CPC ............... A61K 35/761; A61K 48/005; A61K 48/0075; A61K 2039/585; A61K 2039/5256; A61P 35/00; C07K 14/5418; C07K 14/5428; C07K 14/5434; C07K 14/70575; C07K 14/70578; C12N 15/861; C12N 2710/10032; C12N 2710/10043; C12N 2710/10371; C12N 2800/24; C12N 2830/60; C12N 2840/203

See application file for complete search history.

(56) References Cited

U.S. PATENT DOCUMENTS

| | | | |
|---|---|---|---|
| 7,364,727 B2 * | 4/2008 | Li | A61K 48/0058 424/93.2 |
| 2007/0054360 A1 | 3/2007 | Gao et al. | |
| 2009/0258013 A1 | 10/2009 | Clark et al. | |
| 2011/0318311 A1 * | 12/2011 | Reid | C07K 14/005 424/93.6 |
| 2015/0017121 A1 * | 1/2015 | Becher | A61K 38/20 424/85.2 |
| 2016/0176963 A1 | 6/2016 | Maurer et al. | |

FOREIGN PATENT DOCUMENTS

| | | |
|---|---|---|
| KR | 2012 0010697 A | 2/2012 |
| WO | WO 14/170389 * | 10/2014 |
| WO | WO 2014/170389 A1 | 10/2014 |
| WO | WO 2015/009856 A2 | 1/2015 |
| WO | WO 15/153417 * | 10/2015 |
| WO | WO 2016/028656 A1 | 2/2016 |

OTHER PUBLICATIONS

Wang et al, Nature Biotechnol. 21(11): 1328-1335, 2003.*
Hu et al, Cancer Gene Therapy 15:173-182, 2008.*
Putzer et al, PNAS 94:10889-10894, 1997.*
Choi et al, Gene Therapy 18:898-909, 2011.*
Lieschke et al, Nature Biotechnol. 15: 35-40, 1997.*
Rohmer et al, Virology 395: 243-254, 2009.*
Zou et al, Virology 326:240-249, 2004.*
PCT International Search Report and Written Opinion, PCT Application No. PCT/US2018/012113, May 14, 2018, 17 pages.
Choi, I-K. et al., "Oncolytic Adenovirus Co-Expressing IL-12 and IL-18 Improves Tumor-Specific Immunity Via Differentiation of T Cells Expressing IL-12Rβ2 and IL-18Rα," Gene Therapy, Sep. 2011, pp. 898-909, vol. 18, No. 9.
Choi, I-K. et al., "Recent Developments in Oncolytic Adenovirus-Based Immunotherapeutic Agents for Use Against Metastatic Cancers," Cancer Gene Therapy, Jan. 11, 2013, pp. 70-76, vol. 20, No. 2.
Hedjran, F. et al., "Deletion Analysis of Ad5 E1 a Transcriptional Control Region: Impact on Tumor-Selective Expression of E1a and E1b," Cancer Gene Therapy, Oct. 2011, pp. 717-723, vol. 18, No. 10.

(Continued)

*Primary Examiner* — Kevin K Hill
(74) *Attorney, Agent, or Firm* — Fenwick & West LLP

(57) ABSTRACT

Disclosed herein are compositions and methods for treating cancer in a subject. This involves administering an oncolytic virus containing a heterologous DNA sequence encoding one or more immunomodulatory and/or immunostimulatory polypeptide(s) of interest to the subject under conditions effective to enhance an anti-tumor immune response in the subject, and to treat cancer. It also relates to a method of enhancing the delivery to and distribution within a tumor mass of therapeutic viruses.

5 Claims, 53 Drawing Sheets

Specification includes a Sequence Listing.

(56) References Cited

OTHER PUBLICATIONS

Bin Dhuban K, D'Hennezel E, Nashi E, Bar-Or A, Rieder S, Shevach EM, et al. Coexpression of TIGIT and FCRL3 Identifies Helios+ Human Memory Regulatory T Cells. J Immunol [Internet]. 2015; Available from: http://www.jimmunol.org/cgi/doi/10.4049/jimmunol.1401803.

Blake SJ, Dougall WC, Miles JJ, Teng MW, Smyth MJ. Molecular Pathways: Targeting CD96 and TIGIT for Cancer Immunotherapy. Clin Cancer Res [Internet]. 2016;vol. 22(17):21. Available from: http://clincancerres.aacrjournals.org/cgi/doi/10.1158/1078-0432.CCR-16-0933.

Boerman GH, van Ostaijen-ten Dam MM, Kraal KCJM, Santos SJ, Ball LM, Lankester AC, et al. Role of NKG2D, DNAM-1 and natural cytotoxicity receptors in cytotoxicity toward rhabdomyosarcoma cell lines mediated by resting and IL-15-activated human natural killer cells. Cancer Immunol Immunother [Internet]. May 2015 [cited Aug. 10, 2015];64(5):573-83. Available from: http://www.pubmedcentral.nih.gov/articlerender.fcgi?artid=4412555&tool=pmcentrez&rendertype=abstract.

Bottino C, Castriconi R, Pende D, Rivera P, Nanni M, Carnemolla B, et al. Identification of PVR (CD155) and Nectin-2 (CD112) as cell surface ligands for the human DNAM-1 (CD226) activating molecule. J Exp Med [Internet]. Aug. 18, 2003 [cited Sep. 15, 2014];198(4):557-67. Available from: http://www.pubmedcentral.nih.gov/articlerender.fcgi?artid=2194180&tool=pmcentrez&rendertype=abstract.

Braun FK, Fecker LF, Schwarz C, Walden P, Assaf C, Dürkop H, et al. Blockade of death receptor-mediated pathways early in the signaling cascade coincides with distinct apoptosis resistance in cutaneous T-cell lymphoma cells. J Invest Dermatol. 2007;127(10):2425-37.

Burton BR, Britton GJ, Fang H, Verhagen J, Smithers B, Sabatos-Peyton CA, et al. Sequential transcriptional changes dictate safe and effective antigen-specific immunotherapy. Nat Commun [Internet]. Sep. 3, 2014 [cited Sep. 3, 2014];5:4741. Available from: http://www.ncbi.nlm.nih.gov/pubmed/25182274.

Butcher MJ, Filipowicz AR, Waseem TC, McGary C, Crow KJ, Magilnick N, et al. Atherosclerosis-Driven Treg Plasticity Results in Formation of a Dysfunctional Subset of Plastic IFN$\gamma^+$ Th1/Tregs. Circ Res [Internet]. 2016;CIRCRESAHA.116.309764. Available from: http://circres.ahajournals.org/lookup/doi/10.1161/CIRCRESAHA.116.309764.

Chan CJ, Martinet L, Gilfillan S, Souza-Fonseca-Guimaraes F, Chow MT, Town L, et al. The receptors CD96 and CD226 oppose each other in the regulation of natural killer cell functions. Nat Immunol [Internet]. May 2014 [cited Jul. 9, 2014];15(5):431-8. Available from: http://www.ncbi.nlm.nih.gov/pubmed/24658051.

Chew GM, Fujita T, Webb GM, Burwitz BJ, Wu HL, Reed JS, et al. TIGIT Marks Exhausted T Cells, Correlates with Disease Progression, and Serves as a Target for Immune Restoration in HIV and SIV Infection. Silvestri G, editor. PLOS Pathog [Internet]. Jan. 7, 2016 [cited Jan. 8, 2016];12(1):e1005349. Available from: http://www.ncbi.nlm.nih.gov/pubmed/26741490.

Chruscinski A, Sadozai H, Rojas-Luengas V, Bartczak A, Khattar R, Selzner N, et al. Role of Regulatory T Cells (Treg) and the Treg Effector Molecule Fibrinogen-like Protein 2 in Alloimmunity and Autoimmunity. Rambam Maimonides Med J [Internet]. 2015;6(3):e0024. Available from: http://www.rmmj.org.il/(S(lqc1xxzwjebf4uhwr4wlawx0))/Pages/Article.aspx?manuId=507.

El-Sherbiny YM, Meade JL, Holmes TD, McGonagle D, Mackie SL, Morgan AW, et al. The requirement for DNAM-1, NKG2D, and NKp46 in the natural killer cell-mediated killing of myeloma cells. Cancer Res. 2007;67(18):8444-9.

Fionda C, Abruzzese MP, Zingoni A, Soriani A, Ricci B, Molfetta R, et al. Nitric oxide donors increase PVR/CD155 DNAM-1 ligand expression in multiple myeloma cells: role of DNA damage response activation. BMC Cancer [Internet]. Jan. 2015 [cited Jan. 11, 2016];15:17. Available from: http://www.pubmedcentral.nih.gov/articlerender.fcgi?artid=4311457&tool=pmcentrez&rendertype=abstract.

Foks AC, Ran I a, Frodermann V, Bot I, van Santbrink PJ, Kuiper J, et al. Agonistic anti-TIGIT treatment inhibits T cell responses in LDLr deficient mice without affecting atherosclerotic lesion development. PLoS One [Internet]. Jan. 2013 [cited Aug. 13, 2014];8(12):e83134. Available from: http://www.pubmedcentral.nih.gov/articlerender.fcgi?artid=3869776&tool=pmcentrez&rendertype=abstract.

Fromentin R, Bakeman W, Lawani MB, Khoury G, Hartogensis W, DaFonseca S, et al. CD4+ T Cells Expressing PD-1, TIGIT and LAG-3 Contribute to HIV Persistence during ART. PLOS Pathog [Internet]. 2016;12(7):e1005761. Available from: http://dx.plos.org/10.1371/journal.ppat.1005761.

Fuhrman C a., Yeh W-I, Seay HR, Saikumar Lakshmi P, Chopra G, Zhang L, et al. Divergent Phenotypes of Human Regulatory T Cells Expressing the Receptors TIGIT and CD226. J Immunol [Internet]. 2015; Available from: http://www.jimmunol.org/cgi/doi/10.4049/jimmunol.1402381.

Gao Y, Cui J, He W, Yue J, Yu D, Cai L, et al. Generation and characterization of polyclonal antibodies against mouse T-cell immunoglobulin and immunoreceptor tyrosine-based inhibitory domain by DNA-based immunization. Transplant Proc [Internet]. 2014 [cited Sep. 4, 2014];46(1):260-5. Available from: http://www.ncbi.nlm.nih.gov/pubmed/24507063.

Georgiev H, Danisch S, Chambers BJ, Shibuya A, Förster R, Bernhardt G. To the Editor TIGIT versus CD226: Hegemony or coexistence? Eur J Immunol. 2014;44(1):307-8.

Godefroy E, Zhong H, Pham P, Friedman D, Yazdanbakhsh K. TIGIT+ Circulating Follicular Helper T cells Display Robust B cell Help Functions: Potential Role in Sickle Cell Alloimmunization. Haematologica [Internet]. 2015; Available from: http://www.haematologica.org/cgi/doi/10.3324/haematol.2015.132738.

Goding S, Wilson K, Xie Y. Restoring immune function of tumor-specific CD4+ T cells during recurrence of melanoma. J . . . [Internet]. 2013 [cited Aug. 13, 2014];190(9):4899-909. Available from: http://www.jimmunol.org/content/190/9/4899.short.

Shon HK. Survivin reduces activation-induced T cell death in G1 phase. Mol Cells. 2003;15(2):159-63.

Guillerey C, Andrade LF De, Vuckovic S, Miles K, Ngiow SF, Yong MCR, et al. Immunosurveillance and therapy of multiple myeloma are CD226 dependent. J Clin Invest. 2015;125(5):2077-89.

Gur C, Ibrahim Y, Isaacson B, Yamin R, Abed J, Gamliel M, et al. Binding of the Fap2 Protein of Fusobacterium nucleatum to Human Inhibitory Receptor TIGIT Protects Tumors from Immune Cell Attack. Immunity [Internet]. Feb. 6, 2015 [cited Feb. 17, 2015];344-55. Available from: http://www.ncbi.nlm.nih.gov/pubmed/25680274.

Hosken BN a, Hosken BN a, Shibuya K, Shibuya K, Heath AW, Heath AW, et al. Brief Definitive Report. Development. 1995;182 (Nov.):20-2.

Huntington ND, Martinet L, Smyth MJ. DNAM-1: would the real natural killer cell please stand up! Oncotarget [Internet]. 2015;6(30):28537-8. Available from: http://www.oncotarget.com/abstract/595.

Iguchi-Manaka A, Okumura G, Kojima H, Cho Y, Hirochika R, Bando H, et al. Increased Soluble CD155 in the Serum of Cancer Patients. PLoS One [Internet]. 2016;11(4):e0152982. Available from: http://dx.plos.org/10.1371/journal.pone.0152982.

Inozume T, Yaguchi T, Furuta J, Harada K, Kawakami Y, Shimada S. Melanoma Cells Control Anti-Melanoma CTL Responses via Interaction between TIGIT and CD155 in the Effector Phase. J Invest Dermatol [Internet]. Nature Publishing Group; Oct. 12, 2015 [cited Oct. 13, 2015];(Aug.). Available from: http://www.nature.com/doifinder/10.1038/jid.2015.404.

Jariwala N, Benoit B, Kossenkov A V., Oetjen LK, Whelan TM, Cornejo CM, et al. TIGIT and Helios are highly expressed on CD4+ T cells in Sezary syndrome patients. J Invest Dermatol [Internet]. 2016;2-5. Available from: http://linkinghub.elsevier.com/retrieve/pii/S0022202X16323508.

Jian JL, Zhu CS, Xu ZW, Ouyang WM, Ma DC, Zhang Y, et al. Identification and characterization of the CD226 gene promoter. J Biol Chem. 2006;281(39):28731-6.

(56) References Cited

OTHER PUBLICATIONS

Jinhua X, Ji W, Shouliang C, Liangfeng Z, Feiyue J. Expression of immune checkpoints in T cells of esophageal cancer patients. Oncotarget. 2016;1-10.
Johnston RJ, Comps-Agrar L, Hackney J, Yu X, Huseni M, Yang Y, et al. The Immunoreceptor Tigit Regulates Antitumor and Antiviral CD8+ T Cell Effector Function. Cancer Cell [Internet]. Elsevier Inc.; Nov. 2014 [cited Nov. 30, 2014];1-15. Available from: http://dx.doi.org/10.1016/j.ccell.2014.10.018.
Joller, N; Peters, A; Anderson AC KV. Immune Checkpoints in CNS Autoimmunity. 2013;248(1):122-39.
Joller N, Lozano E, Burkett PR, Patel B, Xiao S, Zhu C, et al. Treg cells expressing the coinhibitory molecule TIGIT selectively inhibit proinflammatory Th1 and Th17 cell responses. Immunity [Internet]. Elsevier Inc.; Apr. 17, 2014 [cited Aug. 1, 2014];40(4):569-81. Available from: http://www.ncbi.nlm.nih.gov/pubmed/24745333.
Kamran N, Takai Y, Miyoshi J, Biswas SK, Wong JSB, Gasser S. Toll-like receptor ligands induce expression of the costimulatory molecule CD155 on antigen-presenting cells. PLoS One [Internet]. Jan. 2013 [cited Jul. 28, 2014];8(1):e54406. Available from: http://www.pubmedcentral.nih.gov/articlerender.fcgi?artid=3547938&tool=pmcentrez&rendertype=abstract.
Klemke CD, Brenner D, Weiβ EM, Schmidt M, Leverkus M, Gülow K, et al. Lack of T-cell receptor-induced signaling is crucial for CD95 ligand up-regulation and protects cutaneous T-cell lymphoma cells from activation-induced cell death. Cancer Res. 2009;69(10):4175-83.
Kong Y, Zhu L, Schell TD, Zhang J, Claxton DF, Ehmann WC, et al. T-cell Immunoglobulin and ITIM Domain (TIGIT) Associates with CD8+ T cell Exhaustion and Poor Clinical Outcome in AML Patients. Clin Cancer Res [Internet]. Jan. 13, 2016 [cited Jan. 15, 2016]; Available from: http://www.ncbi.nlm.nih.gov/pubmed/26763253.
Kourepini E, Paschalidis N, Simoes DCM, Aggelakopoulou M, Grogan JL, Panoutsakopoulou V. TIGIT Enhances Antigen-Specific Th2 Recall Responses and Allergic Disease. J Immunol [Internet]. 2016; Available from: http://www.jimmunol.org/cgi/doi/10.4049/jimmunol.1501591.
Le Mercier I, Lines JL, Noelle RJ. Beyond CTLA-4 and PD-1, the Generation Z of Negative Checkpoint Regulators. Front Immunol [Internet]. 2015;Aug. 6:1-15. Available from: http://journal.frontiersin.org/article/10.3389/fimmu.2015.00418.
Levin SD, Taft DW, Brandt CS, Bucher C, Howard ED, Chadwick EM, et al. Vstm3 is a member of the CD28 family and an important modulator of T-cell function. Eur J Immunol [Internet]. Apr. 2011 [cited Aug. 13, 2014];41(4):902-15. Available from: http://www.pubmedcentral.nih.gov/articlerender.fcgi?artid=3733993&tool=pmcentrez&rendertype=abstract.
Liu J, Qian X, Chen Z, Xu X, Gao F, Zhang S, et al. Crystal structure of cell adhesion molecule nectin-2/CD112 and its binding to immune receptor DNAM-1/CD226. J Immunol [Internet]. Jun. 1, 2012 [cited Sep. 16, 2014];188(11):5511-20. Available from: http://www.ncbi.nlm.nih.gov/pubmed/22547693.
Liu S, Zhang H, Li M, Hu D, Li C, Ge B, et al. Recruitment of Grb2 and SHIP1 by the ITT-like motif of TIGIT suppresses granule polarization and cytotoxicity of NK cells. Cell Death Differ [Internet]. Mar. 2013 [cited Aug. 13, 2014];20(3):456-64. Available from: http://www.pubmedcentral.nih.gov/articlerender.fcgi?artid=3569986&tool=pmcentrez&rendertype=abstract.
Lozano E, Dominguez-Villar M, Kuchroo V, Hafler D a. The TIGIT/CD226 axis regulates human T cell function. J Immunol [Internet]. Apr. 15, 2012 [cited Aug. 13, 2014];188(8):3869-75. Available from: http://www.pubmedcentral.nih.gov/articlerender.fcgi?artid=3324669&tool=pmcentrez&rendertype=abstract.
Manieri NA, Chiang EY, Grogan JL. TIGIT: A Key Inhibitor of the Cancer Immunity Cycle. Trends Immunol [Internet]. Elsevier Ltd; 2016;xx:1-9. Available from: http://linkinghub.elsevier.com/retrieve/pii/S1471490616301508.
Moorman JP, Wang JM, Zhang Y, Ji XJ, Ma CJ, Wu XY, et al. Tim-3 pathway controls regulatory and effector T cell balance during hepatitis C virus infection. J Immunol [Internet]. Jul. 15, 2012 [cited Aug. 13, 2014];189(2):755-66. Available from: http://www.ncbi.nlm.nih.gov/pubmed/22706088.
Nagumo Y, Iguchi-Manaka A, Yamashita-Kanemaru Y, Abe F, Bernhardt G, Shibuya A, et al. Increased CD112 Expression in Methylcholanthrene-Induced Tumors in CD155-Deficient Mice. PLoS One [Internet]. Jan. 2014 [cited Nov. 11, 2014];9(11):e112415. Available from: http://www.ncbi.nlm.nih.gov/pubmed/25384044.
Ni X, Zhang C, Talpur R, Duvic M. Resistance to activation-induced cell death and bystander cytotoxicity via the Fas/Fas ligand pathway are implicated in the pathogenesis of cutaneous T cell lymphomas. J Invest Dermatol. 2005;124(4):741-50.
Oshima T, Sato S, Kato J, Ito Y, Watanabe T, Tsuji I, et al. Nectin-2 is a potential target for antibody therapy of breast and ovarian cancers. Mol Cancer [Internet]. Molecular Cancer; 2013;12(1):60. Available from: http://www.pubmedcentral.nih.gov/articlerender.fcgi?artid=3698035&tool=pmcentrez&rendertype=abstract.
Peng Y, Xi C, Zhu Y, Yin L, Wei J. Altered expression of CD226 and CD96 on natural killer cells in patients with pancreatic cancer. Oncotarget. 2016.
Pirenne F. TIGIT-positive circulating follicular helper T cells and sickle cell alloimmunization. Haematologica [Internet]. 2015;100(11):1371-3. Available from: http://www.haematologica.org/cgi/doi/10.3324/haematol.2015.136135.
Sheiko MA, Golden-Mason L, Giugliano S, Hurtado CW, Mack CL, Narkewicz MR, et al. CD4+ and CD8+ T Cell Activation in Children with Hepatitis C. J Pediatr [Internet]. Elsevier Inc; 2016;170:142-148.e1. Available from: http://linkinghub.elsevier.com/retrieve/pii/S0022347615014675.
Shibuya K., Campbell D, Hannum C, Yssel H, Franz-Bacon K, McClanashan T, et al. DNAM-1, a novel adhesion molecule involved in the cytolytic function of T lymphocytes. Immunity. 1996;4(6):573-81.
Shibuya K, Shirakawa J, Kameyama T, Honda S-I, Tahara-Hanaoka S, Miyamoto A, et al. CD226 (DNAM-1) is involved in lymphocyte function-associated antigen 1 costimulatory signal for naive T cell differentiation and proliferation. J Exp Med [Internet]. Dec. 15, 2003 [cited Sep. 15, 2014];198(12):1829-39. Available from: http://www.pubmedcentral.nih.gov/articlerender.fcgi?artid=2194159&tool=pmcentrez&rendertype=abstract.
Son Y, Lee B, Choi Y-J, Jeon SA, Kim J-H, Lee H-K, et al. Nectin-2 (CD112) Is Expressed on Outgrowth Endothelial Cells and Regulates Cell Proliferation and Angiogenic Function. PLoS One [Internet]. 2016;11(9):e0163301. Available from: http://dx.plos.org/10.1371/journal.pone.0163301.
Stanietsky N, Mandelboim O. Paired NK cell receptors controlling NK cytotoxicity. FEBS Lett [Internet]. Dec. 15, 2010 [cited Sep. 4, 2014];584(24):4895-900. Available from: http://www.ncbi.nlm.nih.gov/pubmed/20828570.
Stanietsky N, Rovis TL, Glasner A, Seidel E, Tsukerman P, Yamin R, et al. Mouse TIGIT inhibits NK-cell cytotoxicity upon interaction with PVR. Eur J Immunol [Internet]. Aug. 2013 [cited Aug. 13, 2014];43(8):2138-50. Available from: http://www.pubmedcentral.nih.gov/articlerender.fcgi?artid=3863769&tool=pmcentrez&rendertype=abstract.
Stanietsky N, The interaction of TIGIT with PVR and PVRL2 inhibits human NK Cell cytotoxicity, PNAS 2009.
Stengel KF, Harden-Bowles K, Yu X, Rouge L, Yin J, Comps-Agrar L, et al. Structure of TIGIT immunoreceptor bound to poliovirus receptor reveals a cell-cell adhesion and signaling mechanism that requires cis-trans receptor clustering. Proc Natl Acad Sci [Internet]. Apr. 3, 2012 [cited Aug. 13, 2014];109(14):5399-404. Available from: http://www.pubmedcentral.nih.gov/articlerender.fcgi?artid=3325733&tool=pmcentrez&rendertype=abstract.
Tahara-Hanaoka S. Functional characterization of DNAM-1 (CD226) interaction with its ligands PVR (CD155) and nectin-2 (PRR-2/CD112). Int Immunol [Internet]. Apr. 1, 2004 [cited Sep. 16, 2014];16(4):533-8. Available from: http://www.intimm.oupjournals.org/cgi/doi/10.1093/intimm/dxh059.

(56) References Cited

OTHER PUBLICATIONS

Tassi E, Grazia G, Vegetti C, Bersani I, Bertolini G, Molla A, et al. Early effector T lymphocytes coexpress multiple inhibitory receptors in primary non-small cell lung cancer. Cancer Res [Internet]. Dec. 15, 2016 [cited Dec. 19, 2016]; Available from: http://www.ncbi.nlm.nih.gov/pubmed/27979840.

Tauriainen J, Scharf L, Frederiksen J, Naji A, Ljunggren H-G, Sönnerborg A, et al. Perturbed CD8+ T cell TIGIT/CD226/PVR axis despite early initiation of antiretroviral treatment in HIV infected individuals. Sci Rep [Internet]. Jan. 13, 2017 [cited Jan. 16, 2017];7:40354. Available from: http://www.ncbi.nlm.nih.gov/pubmed/28084312.

White AM, Wraith DC. Tr1-Like T Cells—An Enigmatic Regulatory T Cell Lineage. Front Immunol [Internet]. 2016;Sep. 7:1-7. Available from: http://journal.frontiersin.org/article/10.3389/fimmu.2016.00355.

Yamamoto M, Tsuji-Takayama K, Suzuki M, Harashima A, Sugimoto A, Motoda R, et al. Comprehensive analysis of FOXP3 mRNA expression in leukemia and transformed cell lines. Leuk Res. 2008;32(4):651-8.

Yano H, Ishida T, Inagaki A, Ishii T, Ding J, Kusumoto S, et al. Defucosylated anti-CC chemokine receptor 4 monoclonal antibody combined with immunomodulatory cytokines: A novel immunotherapy for aggressive/refractory mycosis fungoides and Sézary syndrome. Clin Cancer Res. 2007;13(21):6494-500.

Yasuma K, Yasunaga J-I, Takemoto K, Sugata K, Mitobe Y, Takenouchi N, et al. HTLV-1 bZIP Factor Impairs Anti-viral Immunity by Inducing Co-inhibitory Molecule, T Cell Immunoglobulin and ITIM Domain (TIGIT). PLoS Pathog [Internet]. Jan. 8, 2016 [cited Jan. 7, 2016];12(1):e1005372. Available from: http://www.ncbi.nlm.nih.gov/pubmed/26735971.

Yu X, Harden K, Gonzalez LC, Francesco M, Chiang E, Irving B, et al. The surface protein TIGIT suppresses T cell activation by promoting the generation of mature immunoregulatory dendritic cells. Nat Immunol [Internet]. Jan. 2009 [cited Sep. 4, 2014];10(1):48-57. Available from: http://www.ncbi.nlm.nih.gov/pubmed/19011627.

Zhang B, Zhao W, Li H, Chen Y, Tian H, Li L, et al. Immunoreceptor TIGIT inhibits the cytotoxicity of human cytokine-induced killer cells by interacting with CD155. Cancer Immunol Immunother [Internet]. Mar. 2016 [cited Jun. 21, 2016];65(3):305-14. Available from: http://www.ncbi.nlm.nih.gov/pubmed/26842126.

Zhang R, Zeng H, Zhang Y, Chen K, Zhang C. CD226 ligation protects against EAE by promoting IL-10 expression via regulation of CD4 + T cell differentiation. Oncotarget. 2016;1.

Zhang Y, Maksimovic J, Naselli G. Genome-wide DNA methylation analysis identifies hypomethylated genes regulated by FOXP3 in human regulatory T cells. Blood [Internet]. 2013 [cited Sep. 9, 2014];122(16):2823-36. Available from: http://bloodjournal.hematologylibrary.org/content/early/2013/08/23/blood-2013-02-481788.short.

Zhu Y, Paniccia A, Schulick AC, Chen W, Koenig MR, Byers JT, et al. Identification of CD112R as a novel checkpoint for human T cells. J Exp Med [Internet]. 2016;jem.20150785. Available from: http://www.jem.org/lookup/doi/10.1084/jem.20150785.

Chauvin J-M, Pagliano O, Fourcade J, Sun Z, Wang H, Sander C, et al. TIGIT and PD-1 impair tumor antigen—specific CD8 + T cells in melanoma patients. J Clin Invest [Internet]. Apr. 13, 2015 [cited Apr. 14, 2015];1-13. Available from: http://www.ncbi.nlm.nih.gov/pubmed/25866972.

Joller N, Hafler JP, Brynedal B, Kassam N, Spoerl S, Levin SD, et al. Cutting edge: TIGIT has T cell-intrinsic inhibitory functions. J Immunol [Internet]. Feb. 1, 2011 [cited Aug. 13, 2014];186(3):1338-42. Available from: http://www.pubmedcentral.nih.gov/articlerender.fcgi?artid=3128994&tool=pmcentrez&rendertype=abstract.

Kurtulus S, Sakuishi K, Ngiow S, Joller N, Tan DJ, Teng MWL, et al. TIGIT predominantly regulates the immune response via regulatory T cells. J Clin Invest. 2015;1(6):1-10.

Wang F, Hou H, Wu S, Tang Q, Liu W, Huang M, et al. TIGIT expression levels on human NK cells correlate with functional heterogeneity among healthy individuals. Eur J Immunol [Internet]. Jul. 14, 2015 [cited Jul. 15, 2015]; Available from: http://www.ncbi.nlm.nih.gov/pubmed/26171588.

Zhang L, Wang J, Wei F, Wang K, Sun Q. Profiling the dynamic expression of checkpoint molecules on cytokine-induced killer cells from non-small-cell lung cancer patients. 2016; Oncotarget.

\* cited by examiner

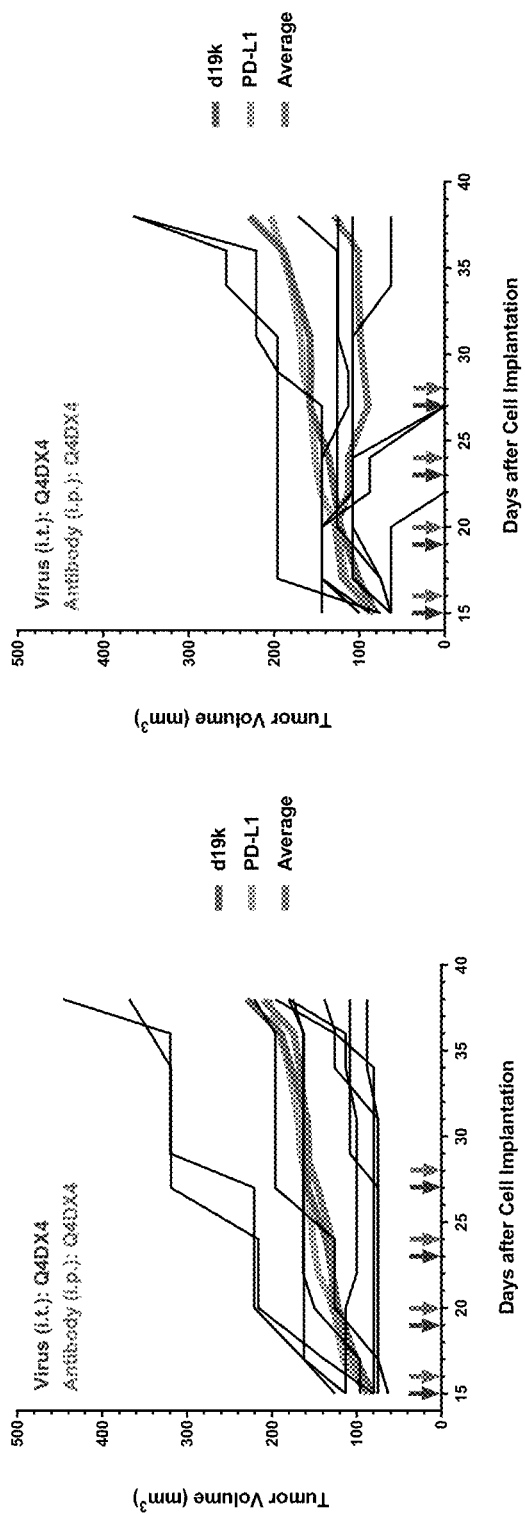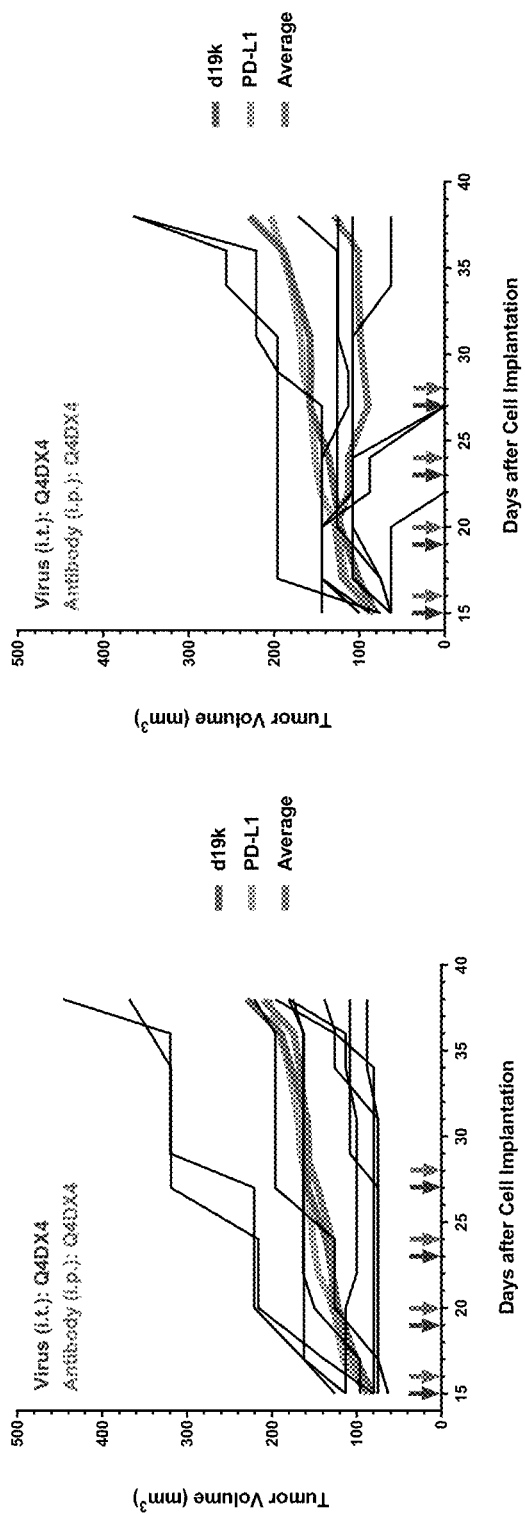
Figure 6F

SEQUENCE LISTING

<160> NUMBER OF SEQ ID NOS: 107

<210> SEQ ID NO 1
<211> LENGTH: 199
<212> TYPE: PRT
<213> ORGANISM: Homo sapiens

<400> SEQUENCE: 1

Met Thr Leu His Pro Ser Pro Ile Thr Cys Glu Phe Leu Phe Ser Thr
1               5                   10                  15

Ala Leu Ile Ser Pro Lys Met Cys Leu Ser His Leu Glu Asn Met Pro
            20                  25                  30

Leu Ser His Ser Arg Thr Gln Gly Ala Gln Arg Ser Ser Trp Lys Leu
        35                  40                  45

Trp Leu Phe Cys Ser Ile Val Met Leu Leu Phe Leu Cys Ser Phe Ser
    50                  55                  60

Trp Leu Ile Phe Ile Phe Leu Gln Leu Glu Thr Ala Lys Glu Pro Cys
65                  70                  75                  80

```
Met Ala Lys Phe Gly Pro Leu Pro Ser Lys Trp Gln Met Ala Ser Ser
                    85                  90                  95

Glu Pro Pro Cys Val Asn Lys Val Ser Asp Trp Lys Leu Glu Ile Leu
            100                 105                 110

Gln Asn Gly Leu Tyr Leu Ile Tyr Gly Gln Val Ala Pro Asn Ala Asn
        115                 120                 125

Tyr Asn Asp Val Ala Pro Phe Glu Val Arg Leu Tyr Lys Asn Lys Asp
    130                 135                 140

Met Ile Gln Thr Leu Thr Asn Lys Ser Lys Ile Gln Asn Val Gly Gly
145                 150                 155                 160

Thr Tyr Glu Leu His Val Gly Asp Thr Ile Asp Leu Ile Phe Asn Ser
                165                 170                 175

Glu His Gln Val Leu Lys Asn Asn Thr Tyr Trp Gly Ile Ile Leu Leu
            180                 185                 190

Ala Asn Pro Gln Phe Ile Ser
        195

<210> SEQ ID NO 2
<211> LENGTH: 173
<212> TYPE: PRT
<213> ORGANISM: Mus musculus

<400> SEQUENCE: 2

Met Glu Glu Met Pro Leu Arg Glu Ser Ser Pro Gln Arg Ala Glu Arg
1               5                   10                  15

Cys Lys Lys Ser Trp Leu Leu Cys Ile Val Ala Leu Leu Leu Met Leu
                20                  25                  30

Leu Cys Ser Leu Gly Thr Leu Ile Tyr Thr Ser Leu Lys Pro Thr Ala
            35                  40                  45

Ile Glu Ser Cys Met Val Lys Phe Glu Leu Ser Ser Ser Lys Trp His
    50                  55                  60

Met Thr Ser Pro Lys Pro His Cys Val Asn Thr Thr Ser Asp Gly Lys
65                  70                  75                  80

Leu Lys Ile Leu Gln Ser Gly Thr Tyr Leu Ile Tyr Gly Gln Val Ile
                85                  90                  95

Pro Val Asp Lys Lys Tyr Ile Lys Asp Asn Ala Pro Phe Val Val Gln
            100                 105                 110

Ile Tyr Lys Lys Asn Asp Val Leu Gln Thr Leu Met Asn Asp Phe Gln
        115                 120                 125

Ile Leu Pro Ile Gly Gly Val Tyr Glu Leu His Ala Gly Asp Asn Ile
    130                 135                 140

Tyr Leu Lys Phe Asn Ser Lys Asp His Ile Gln Lys Thr Asn Thr Tyr
145                 150                 155                 160

Trp Gly Ile Ile Leu Met Pro Asp Leu Pro Phe Ile Ser
                165                 170

<210> SEQ ID NO 3
<211> LENGTH: 288
<212> TYPE: PRT
<213> ORGANISM: Homo sapiens

<400> SEQUENCE: 3

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
                20                  25                  30
```

```
Ser Gly Val Ile His Val Thr Lys Glu Val Lys Glu Val Ala Thr Leu
         35                  40                  45

Ser Cys Gly His Asn Val Ser Val Glu Glu Leu Ala Gln Thr Arg Ile
 50                  55                  60

Tyr Trp Gln Lys Glu Lys Lys Met Val Leu Thr Met Met Ser Gly Asp
 65                  70                  75                  80

Met Asn Ile Trp Pro Glu Tyr Lys Asn Arg Thr Ile Phe Asp Ile Thr
                 85                  90                  95

Asn Asn Leu Ser Ile Val Ile Leu Ala Leu Arg Pro Ser Asp Glu Gly
                100                 105                 110

Thr Tyr Glu Cys Val Val Leu Lys Tyr Glu Lys Asp Ala Phe Lys Arg
            115                 120                 125

Glu His Leu Ala Glu Val Thr Leu Ser Val Lys Ala Asp Phe Pro Thr
        130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
                260                 265                 270

Glu Arg Arg Arg Asn Glu Arg Leu Arg Arg Glu Ser Val Arg Pro Val
            275                 280                 285

<210> SEQ ID NO 4
<211> LENGTH: 233
<212> TYPE: PRT
<213> ORGANISM: Homo sapiens

<400> SEQUENCE: 4

Met Ser Thr Glu Ser Met Ile Arg Asp Val Glu Leu Ala Glu Glu Ala
 1               5                  10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
        50                  55                  60

Arg Asp Leu Ser Leu Ile Ser Pro Leu Ala Gln Ala Val Arg Ser Ser
 65                  70                  75                  80

Ser Arg Thr Pro Ser Asp Lys Pro Val Ala His Val Val Ala Asn Pro
                 85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125
```

Glu Gly Leu Tyr Leu Ile Tyr Ser Gln Val Leu Phe Lys Gly Gln Gly
            130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
                195                 200                 205

Ser Ala Glu Ile Asn Arg Pro Asp Tyr Leu Asp Phe Ala Glu Ser Gly
            210                 215                 220

Gln Val Tyr Phe Gly Ile Ile Ala Leu
225                 230

<210> SEQ ID NO 5
<211> LENGTH: 255
<212> TYPE: PRT
<213> ORGANISM: Mus musculus

<400> SEQUENCE: 5

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
                20                  25                  30

Ile Thr Gln Met Ile Gly Ser Val Leu Phe Ala Val Tyr Leu His Arg
            35                  40                  45

Arg Leu Asp Lys Val Glu Glu Glu Val Asn Leu His Glu Asp Phe Val
        50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asp Glu Asp Pro Val
            100                 105                 110

Ala His Val Val Ala Asn His Gln Val Glu Glu Gln Leu Glu Trp Leu
        115                 120                 125

Ser Gln Arg Ala Asn Ala Leu Leu Ala Asn Gly Met Asp Leu Lys Asp
            130                 135                 140

Asn Gln Leu Val Val Pro Ala Asp Gly Leu Tyr Leu Val Tyr Ser Gln
145                 150                 155                 160

Val Leu Phe Lys Gly Gln Gly Cys Pro Asp Tyr Val Leu Leu Thr His
                165                 170                 175

Thr Val Ser Arg Phe Ala Ile Ser Tyr Gln Glu Lys Val Asn Leu Leu
            180                 185                 190

Ser Ala Val Lys Ser Pro Cys Pro Lys Asp Thr Pro Glu Gly Ala Glu
        195                 200                 205

Leu Lys Pro Trp Tyr Glu Pro Ile Tyr Leu Gly Gly Val Phe Gln Leu
    210                 215                 220

Glu Lys Gly Asp Gln Leu Ser Ala Glu Val Asn Leu Pro Lys Tyr Leu
225                 230                 235                 240

Asp Phe Ala Glu Ser Gly Gln Val Tyr Phe Gly Ile Ile Ala Leu
                245                 250                 255

```
<210> SEQ ID NO 6
<211> LENGTH: 141
<212> TYPE: PRT
<213> ORGANISM: Mus musculus

<400> SEQUENCE: 6

Met Trp Leu Gln Asn Leu Leu Phe Leu Gly Ile Val Val Tyr Ser Leu
1               5                   10                  15

Ser Ala Pro Thr Arg Ser Pro Ile Thr Val Thr Arg Pro Trp Lys His
            20                  25                  30

Val Glu Ala Ile Lys Glu Ala Leu Asn Leu Leu Asp Asp Met Pro Val
        35                  40                  45

Thr Leu Asn Glu Glu Val Glu Val Val Ser Asn Glu Phe Ser Phe Lys
    50                  55                  60

Lys Leu Thr Cys Val Gln Thr Arg Leu Lys Ile Phe Glu Gln Gly Leu
65                  70                  75                  80

Arg Gly Asn Phe Thr Lys Leu Lys Gly Ala Leu Asn Met Thr Ala Ser
                85                  90                  95

Tyr Tyr Gln Thr Tyr Cys Pro Pro Thr Pro Glu Thr Asp Cys Glu Thr
            100                 105                 110

Gln Val Thr Thr Tyr Ala Asp Phe Ile Asp Ser Leu Lys Thr Phe Leu
        115                 120                 125

Thr Asp Ile Pro Phe Glu Cys Lys Lys Pro Gly Gln Lys
    130                 135                 140

<210> SEQ ID NO 7
<211> LENGTH: 302
<212> TYPE: PRT
<213> ORGANISM: Homo sapiens

<400> SEQUENCE: 7

Met Arg Leu Gly Ser Pro Gly Leu Leu Phe Leu Leu Phe Ser Ser Leu
1               5                   10                  15

Arg Ala Asp Thr Gln Glu Lys Glu Val Arg Ala Met Val Gly Ser Asp
            20                  25                  30

Val Glu Leu Ser Cys Ala Cys Pro Glu Gly Ser Arg Phe Asp Leu Asn
        35                  40                  45

Asp Val Tyr Val Tyr Trp Gln Thr Ser Glu Ser Lys Thr Val Val Thr
    50                  55                  60

Tyr His Ile Pro Gln Asn Ser Ser Leu Glu Asn Val Asp Ser Arg Tyr
65                  70                  75                  80

Arg Asn Arg Ala Leu Met Ser Pro Ala Gly Met Leu Arg Gly Asp Phe
                85                  90                  95

Ser Leu Arg Leu Phe Asn Val Thr Pro Gln Asp Glu Gln Lys Phe His
            100                 105                 110

Cys Leu Val Leu Ser Gln Ser Leu Gly Phe Gln Glu Val Leu Ser Val
        115                 120                 125

Glu Val Thr Leu His Val Ala Ala Asn Phe Ser Val Pro Val Val Ser
    130                 135                 140

Ala Pro His Ser Pro Ser Gln Asp Glu Leu Thr Phe Thr Cys Thr Ser
145                 150                 155                 160

Ile Asn Gly Tyr Pro Arg Pro Asn Val Tyr Trp Ile Asn Lys Thr Asp
                165                 170                 175

Asn Ser Leu Leu Asp Gln Ala Leu Gln Asn Asp Thr Val Phe Leu Asn
            180                 185                 190

Met Arg Gly Leu Tyr Asp Val Val Ser Val Leu Arg Ile Ala Arg Thr
```

```
              195                 200                 205
Pro Ser Val Asn Ile Gly Cys Cys Ile Glu Asn Val Leu Leu Gln Gln
210                 215                 220

Asn Leu Thr Val Gly Ser Gln Thr Gly Asn Asp Ile Gly Glu Arg Asp
225                 230                 235                 240

Lys Ile Thr Glu Asn Pro Val Ser Thr Gly Glu Lys Asn Ala Ala Thr
                245                 250                 255

Trp Ser Ile Leu Ala Val Leu Cys Leu Leu Val Val Ala Val Ala
                260                 265                 270

Ile Gly Trp Val Cys Arg Asp Arg Cys Leu Gln His Ser Tyr Ala Gly
                275                 280                 285

Ala Trp Ala Val Ser Pro Glu Thr Glu Leu Thr Gly His Val
290                 295                 300

<210> SEQ ID NO 8
<211> LENGTH: 254
<212> TYPE: PRT
<213> ORGANISM: Homo sapiens

<400> SEQUENCE: 8

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
                20                  25                  30

Ala Gly Leu Leu Leu Leu Leu Leu Ala Ala Ala Cys Ala Val Phe
            35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
                100                 105                 110

Pro Gly Leu Ala Gly Val Ser Leu Thr Gly Gly Leu Ser Tyr Lys Glu
            115                 120                 125

Asp Thr Lys Glu Leu Val Val Ala Lys Ala Gly Val Tyr Tyr Val Phe
130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
                180                 185                 190

Arg Asn Ser Ala Phe Gly Phe Gln Gly Arg Leu Leu His Leu Ser Ala
                195                 200                 205

Gly Gln Arg Leu Gly Val His Leu His Thr Glu Ala Arg Ala Arg His
            210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 9
<211> LENGTH: 277
```

```
<212> TYPE: PRT
<213> ORGANISM: Homo sapiens

<400> SEQUENCE: 9

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 10
<211> LENGTH: 198
<212> TYPE: PRT
<213> ORGANISM: Mus musculus

<400> SEQUENCE: 10

Met Glu Gly Glu Gly Val Gln Pro Leu Asp Glu Asn Leu Glu Asn Gly
1               5                   10                  15

Ser Arg Pro Arg Phe Lys Trp Lys Lys Thr Leu Arg Leu Val Val Ser
            20                  25                  30

Gly Ile Lys Gly Ala Gly Met Leu Leu Cys Phe Ile Tyr Val Cys Leu
        35                  40                  45

Gln Leu Ser Ser Ser Pro Ala Lys Asp Pro Pro Ile Gln Arg Leu Arg
    50                  55                  60
```

```
Gly Ala Val Thr Arg Cys Glu Asp Gly Gln Leu Phe Ile Ser Ser Tyr
 65                  70                  75                  80

Lys Asn Glu Tyr Gln Thr Met Glu Val Gln Asn Asn Ser Val Val Ile
                 85                  90                  95

Lys Cys Asp Gly Leu Tyr Ile Ile Tyr Leu Lys Gly Ser Phe Phe Gln
            100                 105                 110

Glu Val Lys Ile Asp Leu His Phe Arg Glu Asp His Asn Pro Ile Ser
            115                 120                 125

Ile Pro Met Leu Asn Asp Gly Arg Arg Ile Val Phe Thr Val Val Ala
        130                 135                 140

Ser Leu Ala Phe Lys Asp Lys Val Tyr Leu Thr Val Asn Ala Pro Asp
145                 150                 155                 160

Thr Leu Cys Glu His Leu Gln Ile Asn Asp Gly Glu Leu Ile Val Val
                165                 170                 175

Gln Leu Thr Pro Gly Tyr Cys Ala Pro Glu Gly Ser Tyr His Ser Thr
            180                 185                 190

Val Asn Gln Val Pro Leu
            195

<210> SEQ ID NO 11
<211> LENGTH: 261
<212> TYPE: PRT
<213> ORGANISM: Homo sapiens

<400> SEQUENCE: 11

Met Ile Glu Thr Tyr Asn Gln Thr Ser Pro Arg Ser Ala Ala Thr Gly
  1               5                  10                  15

Leu Pro Ile Ser Met Lys Ile Phe Met Tyr Leu Leu Thr Val Phe Leu
                 20                  25                  30

Ile Thr Gln Met Ile Gly Ser Ala Leu Phe Ala Val Tyr Leu His Arg
             35                  40                  45

Arg Leu Asp Lys Ile Glu Asp Glu Arg Asn Leu His Glu Asp Phe Val
         50                  55                  60

Phe Met Lys Thr Ile Gln Arg Cys Asn Thr Gly Glu Arg Ser Leu Ser
 65                  70                  75                  80

Leu Leu Asn Cys Glu Glu Ile Lys Ser Gln Phe Glu Gly Phe Val Lys
                 85                  90                  95

Asp Ile Met Leu Asn Lys Glu Thr Lys Lys Glu Asn Ser Phe Glu
            100                 105                 110

Met Gln Lys Gly Asp Gln Asn Pro Gln Ile Ala Ala His Val Ile Ser
            115                 120                 125

Glu Ala Ser Ser Lys Thr Thr Ser Val Leu Gln Trp Ala Glu Lys Gly
130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
            195                 200                 205

Ala Asn Thr His Ser Ser Ala Lys Pro Cys Gly Gln Gln Ser Ile His
        210                 215                 220

Leu Gly Gly Val Phe Glu Leu Gln Pro Gly Ala Ser Val Phe Val Asn
225                 230                 235                 240
```

Val Thr Asp Pro Ser Gln Val Ser His Gly Thr Gly Phe Thr Ser Phe
            245                 250                 255

Gly Leu Leu Lys Leu
            260

<210> SEQ ID NO 12
<211> LENGTH: 260
<212> TYPE: PRT
<213> ORGANISM: Mus musculus

<400> SEQUENCE: 12

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Met Leu Glu Asn Gly Lys Gln Leu
145                 150                 155                 160

Thr Val Lys Arg Glu Gly Leu Tyr Tyr Val Tyr Thr Gln Val Thr Phe
                165                 170                 175

Cys Ser Asn Arg Glu Pro Ser Ser Gln Arg Pro Phe Ile Val Gly Leu
            180                 185                 190

Trp Leu Lys Pro Ser Ser Gly Ser Glu Arg Ile Leu Leu Lys Ala Ala
        195                 200                 205

Asn Thr His Ser Ser Ser Gln Leu Cys Glu Gln Gln Ser Val His Leu
    210                 215                 220

Gly Gly Val Phe Glu Leu Gln Ala Gly Ala Ser Val Phe Val Asn Val
225                 230                 235                 240

Thr Glu Ala Ser Gln Val Ile His Arg Val Gly Phe Ser Ser Phe Gly
                245                 250                 255

Leu Leu Lys Leu
            260

<210> SEQ ID NO 13
<211> LENGTH: 193
<212> TYPE: PRT
<213> ORGANISM: Homo sapiens

<400> SEQUENCE: 13

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30

```
Cys Leu Val Val Cys Ile Gln Arg Phe Ala Gln Ala Gln Gln Gln Leu
                35                  40                  45

Pro Leu Glu Ser Leu Gly Trp Asp Val Ala Glu Leu Gln Leu Asn His
 50                  55                  60

Thr Gly Pro Gln Gln Asp Pro Arg Leu Tyr Trp Gln Gly Gly Pro Ala
 65                  70                  75                  80

Leu Gly Arg Ser Phe Leu His Gly Pro Glu Leu Asp Lys Gly Gln Leu
                 85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Val Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro
```

<210> SEQ ID NO 14
<211> LENGTH: 195
<212> TYPE: PRT
<213> ORGANISM: Mus musculus

<400> SEQUENCE: 14

```
Met Pro Glu Glu Gly Arg Pro Cys Pro Trp Val Arg Trp Ser Gly Thr
 1               5                  10                  15

Ala Phe Gln Arg Gln Trp Pro Trp Leu Leu Leu Val Val Phe Ile Thr
                20                  25                  30

Val Phe Cys Cys Trp Phe His Cys Ser Gly Leu Leu Ser Lys Gln Gln
                35                  40                  45

Gln Arg Leu Leu Glu His Pro Glu Pro His Thr Ala Glu Leu Gln Leu
 50                  55                  60

Asn Leu Thr Val Pro Arg Lys Asp Pro Thr Leu Arg Trp Gly Ala Gly
 65                  70                  75                  80

Pro Ala Leu Gly Arg Ser Phe Thr His Gly Pro Glu Leu Glu Glu Gly
                 85                  90                  95

His Leu Arg Ile His Gln Asp Gly Leu Tyr Arg Leu His Ile Gln Val
            100                 105                 110

Thr Leu Ala Asn Cys Ser Ser Pro Gly Ser Thr Leu Gln His Arg Ala
        115                 120                 125

Thr Leu Ala Val Gly Ile Cys Ser Pro Ala Ala His Gly Ile Ser Leu
    130                 135                 140

Leu Arg Gly Arg Phe Gly Gln Asp Cys Thr Val Ala Leu Gln Arg Leu
145                 150                 155                 160

Thr Tyr Leu Val His Gly Asp Val Leu Cys Thr Asn Leu Thr Leu Pro
                165                 170                 175

Leu Leu Pro Ser Arg Asn Ala Asp Glu Thr Phe Phe Gly Val Gln Trp
            180                 185                 190

Ile Cys Pro
195
```

<210> SEQ ID NO 15
<211> LENGTH: 153
<212> TYPE: PRT
<213> ORGANISM: Homo sapiens

<400> SEQUENCE: 15

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr
145                 150

<210> SEQ ID NO 16
<211> LENGTH: 177
<212> TYPE: PRT
<213> ORGANISM: Homo sapiens

<400> SEQUENCE: 16

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His

<210> SEQ ID NO 17
<211> LENGTH: 154
<212> TYPE: PRT
<213> ORGANISM: Mus musculus

<400> SEQUENCE: 17

Met Phe His Val Ser Phe Arg Tyr Ile Phe Gly Ile Pro Pro Leu Ile
1               5                   10                  15

Leu Val Leu Leu Pro Val Thr Ser Ser Glu Cys His Ile Lys Asp Lys
            20                  25                  30

Glu Gly Lys Ala Tyr Glu Ser Val Leu Met Ile Ser Ile Asp Glu Leu
        35                  40                  45

Asp Lys Met Thr Gly Thr Asp Ser Asn Cys Pro Asn Asn Glu Pro Asn
    50                  55                  60

Phe Phe Arg Lys His Val Cys Asp Asp Thr Lys Glu Ala Ala Phe Leu
65                  70                  75                  80

Asn Arg Ala Ala Arg Lys Leu Lys Gln Phe Leu Lys Met Asn Ile Ser
                85                  90                  95

Glu Glu Phe Asn Val His Leu Leu Thr Val Ser Gln Gly Thr Gln Thr
            100                 105                 110

Leu Val Asn Cys Thr Ser Lys Glu Glu Lys Asn Val Lys Glu Gln Lys
        115                 120                 125

Lys Asn Asp Ala Cys Phe Leu Lys Arg Leu Leu Arg Glu Ile Lys Thr
    130                 135                 140

Cys Trp Asn Lys Ile Leu Lys Gly Ser Ile
145                 150

<210> SEQ ID NO 18
<211> LENGTH: 253
<212> TYPE: PRT
<213> ORGANISM: Homo sapiens

<400> SEQUENCE: 18

Met Trp Pro Pro Gly Ser Ala Ser Gln Pro Pro Pro Ser Pro Ala Ala
1               5                   10                  15

Ala Thr Gly Leu His Pro Ala Ala Arg Pro Val Ser Leu Gln Cys Arg
            20                  25                  30

Leu Ser Met Cys Pro Ala Arg Ser Leu Leu Leu Val Ala Thr Leu Val
        35                  40                  45

Leu Leu Asp His Leu Ser Leu Ala Arg Asn Leu Pro Val Ala Thr Pro
    50                  55                  60

Asp Pro Gly Met Phe Pro Cys Leu His His Ser Gln Asn Leu Leu Arg
65                  70                  75                  80

Ala Val Ser Asn Met Leu Gln Lys Ala Arg Gln Thr Leu Glu Phe Tyr
                85                  90                  95

Pro Cys Thr Ser Glu Glu Ile Asp His Glu Asp Ile Thr Lys Asp Lys
            100                 105                 110

Thr Ser Thr Val Glu Ala Cys Leu Pro Leu Glu Leu Thr Lys Asn Glu
        115                 120                 125

Ser Cys Leu Asn Ser Arg Glu Thr Ser Phe Ile Thr Asn Gly Ser Cys
    130                 135                 140

Leu Ala Ser Arg Lys Thr Ser Phe Met Met Ala Leu Cys Leu Ser Ser
145                 150                 155                 160

```
Ile Tyr Glu Asp Leu Lys Met Tyr Gln Val Glu Phe Lys Thr Met Asn
            165                 170                 175

Ala Lys Leu Leu Met Asp Pro Lys Arg Gln Ile Phe Leu Asp Gln Asn
            180                 185                 190

Met Leu Ala Val Ile Asp Glu Leu Met Gln Ala Leu Asn Phe Asn Ser
            195                 200                 205

Glu Thr Val Pro Gln Lys Ser Ser Leu Glu Glu Pro Asp Phe Tyr Lys
            210                 215                 220

Thr Lys Ile Lys Leu Cys Ile Leu Leu His Ala Phe Arg Ile Arg Ala
225                 230                 235                 240

Val Thr Ile Asp Arg Val Met Ser Tyr Leu Asn Ala Ser
                245                 250

<210> SEQ ID NO 19
<211> LENGTH: 662
<212> TYPE: PRT
<213> ORGANISM: Homo sapiens

<400> SEQUENCE: 19

Met Glu Pro Leu Val Thr Trp Val Val Pro Leu Leu Phe Leu Phe Leu
1               5                   10                  15

Leu Ser Arg Gln Gly Ala Ala Cys Arg Thr Ser Glu Cys Cys Phe Gln
            20                  25                  30

Asp Pro Pro Tyr Pro Asp Ala Asp Ser Gly Ser Ala Ser Gly Pro Arg
        35                  40                  45

Asp Leu Arg Cys Tyr Arg Ile Ser Ser Asp Arg Tyr Glu Cys Ser Trp
    50                  55                  60

Gln Tyr Glu Gly Pro Thr Ala Gly Val Ser His Phe Leu Arg Cys Cys
65              70                  75                  80

Leu Ser Ser Gly Arg Cys Cys Tyr Phe Ala Ala Gly Ser Ala Thr Arg
            85                  90                  95

Leu Gln Phe Ser Asp Gln Ala Gly Val Ser Val Leu Tyr Thr Val Thr
            100                 105                 110

Leu Trp Val Glu Ser Trp Ala Arg Asn Gln Thr Glu Lys Ser Pro Glu
            115                 120                 125

Val Thr Leu Gln Leu Tyr Asn Ser Val Lys Tyr Glu Pro Pro Leu Gly
            130                 135                 140

Asp Ile Lys Val Ser Lys Leu Ala Gly Gln Leu Arg Met Glu Trp Glu
145                 150                 155                 160

Thr Pro Asp Asn Gln Val Gly Ala Glu Val Gln Phe Arg His Arg Thr
                165                 170                 175

Pro Ser Ser Pro Trp Lys Leu Gly Asp Cys Gly Pro Gln Asp Asp Asp
            180                 185                 190

Thr Glu Ser Cys Leu Cys Pro Leu Glu Met Asn Val Ala Gln Glu Phe
            195                 200                 205

Gln Leu Arg Arg Arg Gln Leu Gly Ser Gln Gly Ser Ser Trp Ser Lys
            210                 215                 220

Trp Ser Ser Pro Val Cys Val Pro Pro Glu Asn Pro Gln Pro Gln
225                 230                 235                 240

Val Arg Phe Ser Val Glu Gln Leu Gly Gln Asp Gly Arg Arg Leu
                245                 250                 255

Thr Leu Lys Glu Gln Pro Thr Gln Leu Glu Leu Pro Glu Gly Cys Gln
            260                 265                 270

Gly Leu Ala Pro Gly Thr Glu Val Thr Tyr Arg Leu Gln Leu His Met
            275                 280                 285
```

```
Leu Ser Cys Pro Cys Lys Ala Lys Ala Thr Arg Thr Leu His Leu Gly
    290                 295                 300

Lys Met Pro Tyr Leu Ser Gly Ala Ala Tyr Asn Val Ala Val Ile Ser
305                 310                 315                 320

Ser Asn Gln Phe Gly Pro Gly Leu Asn Gln Thr Trp His Ile Pro Ala
            325                 330                 335

Asp Thr His Thr Glu Pro Val Ala Leu Asn Ile Ser Val Gly Thr Asn
                340                 345                 350

Gly Thr Thr Met Tyr Trp Pro Ala Arg Ala Gln Ser Met Thr Tyr Cys
            355                 360                 365

Ile Glu Trp Gln Pro Val Gly Gln Asp Gly Gly Leu Ala Thr Cys Ser
    370                 375                 380

Leu Thr Ala Pro Gln Asp Pro Asp Pro Ala Gly Met Ala Thr Tyr Ser
385                 390                 395                 400

Trp Ser Arg Glu Ser Gly Ala Met Gly Gln Glu Lys Cys Tyr Tyr Ile
                405                 410                 415

Thr Ile Phe Ala Ser Ala His Pro Glu Lys Leu Thr Leu Trp Ser Thr
                420                 425                 430

Val Leu Ser Thr Tyr His Phe Gly Gly Asn Ala Ser Ala Ala Gly Thr
            435                 440                 445

Pro His His Val Ser Val Lys Asn His Ser Leu Asp Ser Val Ser Val
    450                 455                 460

Asp Trp Ala Pro Ser Leu Leu Ser Thr Cys Pro Gly Val Leu Lys Glu
465                 470                 475                 480

Tyr Val Val Arg Cys Arg Asp Glu Asp Ser Lys Gln Val Ser Glu His
                485                 490                 495

Pro Val Gln Pro Thr Glu Thr Gln Val Thr Leu Ser Gly Leu Arg Ala
            500                 505                 510

Gly Val Ala Tyr Thr Val Gln Val Arg Ala Asp Thr Ala Trp Leu Arg
            515                 520                 525

Gly Val Trp Ser Gln Pro Gln Arg Phe Ser Ile Glu Val Gln Val Ser
    530                 535                 540

Asp Trp Leu Ile Phe Phe Ala Ser Leu Gly Ser Phe Leu Ser Ile Leu
545                 550                 555                 560

Leu Val Gly Val Leu Gly Tyr Leu Gly Leu Asn Arg Ala Ala Arg His
                565                 570                 575

Leu Cys Pro Pro Leu Pro Thr Pro Cys Ala Ser Ser Ala Ile Glu Phe
            580                 585                 590

Pro Gly Gly Lys Glu Thr Trp Gln Trp Ile Asn Pro Val Asp Phe Gln
            595                 600                 605

Glu Glu Ala Ser Leu Gln Glu Ala Leu Val Val Glu Met Ser Trp Asp
    610                 615                 620

Lys Gly Glu Arg Thr Glu Pro Leu Glu Lys Thr Glu Leu Pro Glu Gly
625                 630                 635                 640

Ala Pro Glu Leu Ala Leu Asp Thr Glu Leu Ser Leu Glu Asp Gly Asp
                645                 650                 655

Arg Cys Lys Ala Lys Met
            660

<210> SEQ ID NO 20
<211> LENGTH: 543
<212> TYPE: PRT
<213> ORGANISM: Mus musculus
```

```
<400> SEQUENCE: 20

Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
            20                  25                  30

Val Glu Val Asp Trp Thr Pro Asp Ala Pro Gly Glu Thr Val Asn Leu
        35                  40                  45

Thr Cys Asp Thr Pro Glu Glu Asp Asp Ile Thr Trp Thr Ser Asp Gln
    50                  55                  60

Arg His Gly Val Ile Gly Ser Gly Lys Thr Leu Thr Ile Thr Val Lys
65                  70                  75                  80

Glu Phe Leu Asp Ala Gly Gln Tyr Thr Cys His Lys Gly Gly Glu Thr
                85                  90                  95

Leu Ser His Ser His Leu Leu Leu His Lys Lys Glu Asn Gly Ile Trp
            100                 105                 110

Ser Thr Glu Ile Leu Lys Asn Phe Lys Asn Lys Thr Phe Leu Lys Cys
        115                 120                 125

Glu Ala Pro Asn Tyr Ser Gly Arg Phe Thr Cys Ser Trp Leu Val Gln
    130                 135                 140

Arg Asn Met Asp Leu Lys Phe Asn Ile Lys Ser Ser Ser Ser Ser Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
            180                 185                 190

Glu Asp Val Thr Cys Pro Thr Ala Glu Glu Thr Leu Pro Ile Glu Leu
        195                 200                 205

Ala Leu Glu Ala Arg Gln Gln Asn Lys Tyr Glu Asn Tyr Ser Thr Ser
    210                 215                 220

Phe Phe Ile Arg Asp Ile Ile Lys Pro Asp Pro Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
            260                 265                 270

Arg Ile Gln Arg Lys Lys Glu Lys Met Lys Glu Thr Glu Glu Gly Cys
        275                 280                 285

Asn Gln Lys Gly Ala Phe Leu Val Glu Lys Thr Ser Thr Glu Val Gln
    290                 295                 300

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser Gly
                325                 330                 335

Gly Gly Gly Ser Gly Gly Gly Ser Gly Gly Gly Gly Ser Arg Val
            340                 345                 350

Ile Pro Val Ser Gly Pro Ala Arg Cys Leu Ser Gln Ser Arg Asn Leu
        355                 360                 365

Leu Lys Thr Thr Asp Asp Met Val Lys Thr Ala Arg Glu Lys Leu Lys
    370                 375                 380

His Tyr Ser Cys Thr Ala Glu Asp Ile Asp His Glu Asp Ile Thr Arg
385                 390                 395                 400

Asp Gln Thr Ser Thr Leu Lys Thr Cys Leu Pro Leu Glu Leu His Lys
                405                 410                 415
```

```
Asn Glu Ser Cys Leu Ala Thr Arg Glu Thr Ser Ser Thr Thr Arg Gly
            420                 425                 430

Ser Cys Leu Pro Pro Gln Lys Thr Ser Leu Met Met Thr Leu Cys Leu
            435                 440                 445

Gly Ser Ile Tyr Glu Asp Leu Lys Met Tyr Gln Thr Glu Phe Gln Ala
            450                 455                 460

Ile Asn Ala Ala Leu Gln Asn His Asn His Gln Gln Ile Ile Leu Asp
465                 470                 475                 480

Lys Gly Met Leu Val Ala Ile Asp Glu Leu Met Gln Ser Leu Asn His
                485                 490                 495

Asn Gly Glu Thr Leu Arg Gln Lys Pro Pro Val Gly Glu Ala Asp Pro
            500                 505                 510

Tyr Arg Val Lys Met Lys Leu Cys Ile Leu Leu His Ala Phe Ser Thr
            515                 520                 525

Arg Val Val Thr Ile Asn Arg Val Met Gly Tyr Leu Ser Ser Ala
            530                 535                 540

<210> SEQ ID NO 21
<211> LENGTH: 162
<212> TYPE: PRT
<213> ORGANISM: Homo sapiens

<400> SEQUENCE: 21

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
            115                 120                 125

Thr Glu Ser Gly Cys Lys Glu Cys Glu Glu Leu Glu Glu Lys Asn Ile
            130                 135                 140

Lys Glu Phe Leu Gln Ser Phe Val His Ile Val Gln Met Phe Ile Asn
145                 150                 155                 160

Thr Ser

<210> SEQ ID NO 22
<211> LENGTH: 357
<212> TYPE: PRT
<213> ORGANISM: Mus musculus

<400> SEQUENCE: 22

Met Lys Ile Leu Lys Pro Tyr Met Arg Asn Thr Ser Ile Ser Cys Tyr
1               5                   10                  15

Leu Cys Phe Leu Leu Asn Ser His Phe Leu Thr Glu Ala Gly Ile His
            20                  25                  30
```

Val Phe Ile Leu Gly Cys Val Ser Val Gly Leu Pro Lys Thr Glu Ala
            35                  40                  45

Asn Trp Ile Asp Val Arg Tyr Asp Leu Glu Lys Ile Glu Ser Leu Ile
 50                  55                  60

Gln Ser Ile His Ile Asp Thr Thr Leu Tyr Thr Asp Ser Asp Phe His
 65                  70                  75                  80

Pro Ser Cys Lys Val Thr Ala Met Asn Cys Phe Leu Leu Glu Leu Gln
                85                  90                  95

Val Ile Leu His Glu Tyr Ser Asn Met Thr Leu Asn Glu Thr Val Arg
            100                 105                 110

Asn Val Leu Tyr Leu Ala Asn Ser Thr Leu Ser Ser Asn Lys Asn Val
            115                 120                 125

Ala Glu Ser Gly Cys Lys Glu Cys Glu Glu Leu Glu Glu Lys Thr Phe
130                 135                 140

Thr Glu Phe Leu Gln Ser Phe Ile Arg Ile Val Gln Met Phe Ile Asn
145                 150                 155                 160

Thr Ser Gly Ser Gly Ala Thr Asn Phe Ser Leu Leu Lys Gln Ala Gly
                165                 170                 175

Asp Val Glu Glu Asn Pro Gly Pro Gly Thr Thr Cys Pro Pro Pro Val
            180                 185                 190

Ser Ile Glu His Ala Asp Ile Arg Val Lys Asn Tyr Ser Val Asn Ser
            195                 200                 205

Arg Glu Arg Tyr Val Cys Asn Ser Gly Phe Lys Arg Lys Ala Gly Thr
            210                 215                 220

Ser Thr Leu Ile Glu Cys Val Ile Asn Lys Asn Thr Asn Val Ala His
225                 230                 235                 240

Trp Thr Thr Pro Ser Leu Lys Cys Ile Arg Asp Pro Ser Leu Ala His
                245                 250                 255

Tyr Ser Pro Val Pro Thr Val Val Thr Pro Lys Val Thr Ser Gln Pro
            260                 265                 270

Glu Ser Pro Ser Pro Ser Ala Lys Glu Pro Glu Ala Phe Ser Pro Lys
            275                 280                 285

Ser Asp Thr Ala Met Thr Thr Glu Thr Ala Ile Met Pro Gly Ser Arg
290                 295                 300

Leu Thr Pro Ser Gln Thr Thr Ser Ala Gly Thr Thr Gly Thr Gly Ser
305                 310                 315                 320

His Lys Ser Ser Arg Ala Pro Ser Leu Ala Ala Thr Met Thr Leu Glu
                325                 330                 335

Pro Thr Ala Ser Thr Ser Leu Arg Ile Thr Glu Ile Ser Pro His Ser
            340                 345                 350

Ser Lys Met Thr Lys
        355

<210> SEQ ID NO 23
<211> LENGTH: 578
<212> TYPE: PRT
<213> ORGANISM: Homo sapiens

<400> SEQUENCE: 23

Met Leu Pro Cys Leu Val Val Leu Leu Ala Ala Leu Leu Ser Leu Arg
 1               5                  10                  15

Leu Gly Ser Asp Ala His Gly Thr Glu Leu Pro Ser Pro Pro Ser Val
            20                  25                  30

Trp Phe Glu Ala Glu Phe Phe His His Ile Leu His Trp Thr Pro Ile
            35                  40                  45

```
Pro Asn Gln Ser Glu Ser Thr Cys Tyr Glu Val Ala Leu Leu Arg Tyr
    50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
                100                 105                 110

Val Thr Asn Thr Arg Phe Ser Val Asp Glu Val Thr Leu Thr Val Gly
            115                 120                 125

Ser Val Asn Leu Glu Ile His Asn Gly Phe Ile Leu Gly Lys Ile Gln
        130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
                180                 185                 190

Leu Thr Ser Gly Glu Val Gly Glu Phe Cys Val Gln Val Lys Pro Ser
        195                 200                 205

Val Ala Ser Arg Ser Asn Lys Gly Met Trp Ser Lys Glu Glu Cys Ile
    210                 215                 220

Ser Leu Thr Arg Gln Tyr Phe Thr Val Thr Asn Val Ile Ile Phe Phe
225                 230                 235                 240

Ala Phe Val Leu Leu Leu Ser Gly Ala Leu Ala Tyr Cys Leu Ala Leu
                245                 250                 255

Gln Leu Tyr Val Arg Arg Arg Lys Lys Leu Pro Ser Val Leu Leu Phe
            260                 265                 270

Lys Lys Pro Ser Pro Phe Ile Phe Ile Ser Gln Arg Pro Ser Pro Glu
        275                 280                 285

Thr Gln Asp Thr Ile His Pro Leu Asp Glu Glu Ala Phe Leu Lys Val
    290                 295                 300

Ser Pro Glu Leu Lys Asn Leu Asp Leu His Gly Ser Thr Asp Ser Gly
305                 310                 315                 320

Phe Gly Ser Thr Lys Pro Ser Leu Gln Thr Glu Glu Pro Gln Phe Leu
                325                 330                 335

Leu Pro Asp Pro His Pro Gln Ala Asp Arg Thr Leu Gly Asn Arg Glu
                340                 345                 350

Pro Pro Val Leu Gly Asp Ser Cys Ser Ser Gly Ser Ser Asn Ser Thr
            355                 360                 365

Asp Ser Gly Ile Cys Leu Gln Glu Pro Ser Leu Ser Pro Ser Thr Gly
        370                 375                 380

Pro Thr Trp Glu Gln Gln Val Gly Ser Asn Ser Arg Gly Gln Asp Asp
385                 390                 395                 400

Ser Gly Ile Asp Leu Val Gln Asn Ser Glu Gly Arg Ala Gly Asp Thr
                405                 410                 415

Gln Gly Gly Ser Ala Leu Gly His His Ser Pro Pro Glu Pro Glu Val
            420                 425                 430

Pro Gly Glu Glu Asp Pro Ala Ala Val Ala Phe Gln Gly Tyr Leu Arg
        435                 440                 445

Gln Thr Arg Cys Ala Glu Glu Lys Ala Thr Lys Thr Gly Cys Leu Glu
    450                 455                 460
```

```
Glu Glu Ser Pro Leu Thr Asp Gly Leu Gly Pro Lys Phe Gly Arg Cys
465                 470                 475                 480

Leu Val Asp Glu Ala Gly Leu His Pro Pro Ala Leu Ala Lys Gly Tyr
                485                 490                 495

Leu Lys Gln Asp Pro Leu Glu Met Thr Leu Ala Ser Ser Gly Ala Pro
            500                 505                 510

Thr Gly Gln Trp Asn Gln Pro Thr Glu Glu Trp Ser Leu Leu Ala Leu
        515                 520                 525

Ser Ser Cys Ser Asp Leu Gly Ile Ser Asp Trp Ser Phe Ala His Asp
530                 535                 540

Leu Ala Pro Leu Gly Cys Val Ala Ala Pro Gly Gly Leu Leu Gly Ser
545                 550                 555                 560

Phe Asn Ser Asp Leu Val Thr Leu Pro Leu Ile Ser Ser Leu Gln Ser
                565                 570                 575

Ser Glu

<210> SEQ ID NO 24
<211> LENGTH: 479
<212> TYPE: PRT
<213> ORGANISM: Mus musculus

<400> SEQUENCE: 24

Met Leu Ser Arg Leu Leu Pro Phe Leu Val Thr Ile Ser Ser Leu Ser
1               5                   10                  15

Leu Glu Phe Ile Ala Tyr Gly Thr Glu Leu Pro Ser Pro Ser Tyr Val
                20                  25                  30

Trp Phe Glu Ala Arg Phe Phe Gln His Ile Leu His Trp Lys Pro Ile
            35                  40                  45

Pro Asn Gln Ser Glu Ser Thr Tyr Tyr Glu Val Ala Leu Lys Gln Tyr
50                  55                  60

Gly Asn Ser Thr Trp Asn Asp Ile His Ile Cys Arg Lys Ala Gln Ala
65                  70                  75                  80

Leu Ser Cys Asp Leu Thr Thr Phe Thr Leu Asp Leu Tyr His Arg Ser
                85                  90                  95

Tyr Gly Tyr Arg Ala Arg Val Arg Ala Val Asp Asn Ser Gln Tyr Ser
            100                 105                 110

Asn Trp Thr Thr Thr Glu Thr Arg Phe Thr Val Asp Glu Val Ile Leu
        115                 120                 125

Thr Val Asp Ser Val Thr Leu Lys Ala Met Asp Gly Ile Ile Tyr Gly
130                 135                 140

Thr Ile His Pro Pro Arg Pro Thr Ile Thr Pro Ala Gly Asp Glu Tyr
145                 150                 155                 160

Glu Gln Val Phe Lys Asp Leu Arg Val Tyr Lys Ile Ser Ile Arg Lys
                165                 170                 175

Phe Ser Glu Leu Lys Asn Ala Thr Lys Arg Val Lys Gln Glu Thr Phe
            180                 185                 190

Thr Leu Thr Val Pro Ile Gly Val Arg Lys Phe Cys Val Lys Val Leu
        195                 200                 205

Pro Arg Leu Glu Ser Arg Ile Asn Lys Ala Glu Trp Ser Glu Glu Gln
210                 215                 220

Cys Leu Leu Ile Thr Thr Glu Gln Tyr Phe Thr Val Thr Asn Leu Ser
225                 230                 235                 240

His Pro Ala Ser Ser Thr Lys Val Asp Lys Lys Ile Val Pro Arg Asp
                245                 250                 255
```

-continued

```
Cys Gly Cys Lys Pro Cys Ile Cys Thr Val Pro Glu Val Ser Ser Val
            260                 265                 270

Phe Ile Phe Pro Pro Lys Pro Lys Asp Val Leu Thr Ile Thr Leu Thr
            275                 280                 285

Pro Lys Val Thr Cys Val Val Val Asp Ile Ser Lys Asp Asp Pro Glu
        290                 295                 300

Val Gln Phe Ser Trp Phe Val Asp Asp Val Glu Val His Thr Ala Gln
305                 310                 315                 320

Thr Gln Pro Arg Glu Glu Gln Phe Asn Ser Thr Phe Arg Ser Val Ser
                325                 330                 335

Glu Leu Pro Ile Met His Gln Asp Trp Leu Asn Gly Lys Glu Phe Lys
            340                 345                 350

Cys Arg Val Asn Ser Ala Ala Phe Pro Ala Pro Ile Glu Lys Thr Ile
        355                 360                 365

Ser Lys Thr Lys Gly Arg Pro Lys Ala Pro Gln Val Tyr Thr Ile Pro
    370                 375                 380

Pro Pro Lys Glu Gln Met Ala Lys Asp Lys Val Ser Leu Thr Cys Met
385                 390                 395                 400

Ile Thr Asp Phe Phe Pro Glu Asp Ile Thr Val Glu Trp Gln Trp Asn
                405                 410                 415

Gly Gln Pro Ala Glu Asn Tyr Lys Asn Thr Gln Pro Ile Met Asp Thr
            420                 425                 430

Asp Gly Ser Tyr Phe Val Tyr Ser Lys Leu Asn Val Gln Lys Ser Asn
        435                 440                 445

Trp Glu Ala Gly Asn Thr Phe Thr Cys Ser Val Leu His Glu Gly Leu
    450                 455                 460

His Asn His His Thr Glu Lys Ser Leu Ser His Ser Pro Gly Lys
465                 470                 475

<210> SEQ ID NO 25
<211> LENGTH: 636
<212> TYPE: PRT
<213> ORGANISM: Homo sapiens

<400> SEQUENCE: 25

Met Arg Gly Gly Arg Gly Ala Pro Phe Trp Leu Trp Pro Leu Pro Lys
1               5                   10                  15

Leu Ala Leu Leu Pro Leu Leu Trp Val Leu Phe Gln Arg Thr Arg Pro
            20                  25                  30

Gln Gly Ser Ala Gly Pro Leu Gln Cys Tyr Gly Val Gly Pro Leu Gly
        35                  40                  45

Asp Leu Asn Cys Ser Trp Glu Pro Leu Gly Asp Leu Gly Ala Pro Ser
    50                  55                  60

Glu Leu His Leu Gln Ser Gln Lys Tyr Arg Ser Asn Lys Thr Gln Thr
65                  70                  75                  80

Val Ala Val Ala Ala Gly Arg Ser Trp Val Ala Ile Pro Arg Glu Gln
                85                  90                  95

Leu Thr Met Ser Asp Lys Leu Leu Val Trp Gly Thr Lys Ala Gly Gln
            100                 105                 110

Pro Leu Trp Pro Pro Val Phe Val Asn Leu Glu Thr Gln Met Lys Pro
        115                 120                 125

Asn Ala Pro Arg Leu Gly Pro Asp Val Asp Phe Ser Glu Asp Asp Pro
    130                 135                 140

Leu Glu Ala Thr Val His Trp Ala Pro Pro Thr Trp Pro Ser His Lys
145                 150                 155                 160
```

-continued

Val Leu Ile Cys Gln Phe His Tyr Arg Arg Cys Gln Glu Ala Ala Trp
                165                 170                 175

Thr Leu Leu Glu Pro Glu Leu Lys Thr Ile Pro Leu Thr Pro Val Glu
            180                 185                 190

Ile Gln Asp Leu Glu Leu Ala Thr Gly Tyr Lys Val Tyr Gly Arg Cys
        195                 200                 205

Arg Met Glu Lys Glu Glu Asp Leu Trp Gly Glu Trp Ser Pro Ile Leu
    210                 215                 220

Ser Phe Gln Thr Pro Pro Ser Ala Pro Lys Asp Val Trp Val Ser Gly
225                 230                 235                 240

Asn Leu Cys Gly Thr Pro Gly Gly Glu Glu Pro Leu Leu Leu Trp Lys
                245                 250                 255

Ala Pro Gly Pro Cys Val Gln Val Ser Tyr Lys Val Trp Phe Trp Val
            260                 265                 270

Gly Gly Arg Glu Leu Ser Pro Glu Gly Ile Thr Cys Cys Ser Leu
        275                 280                 285

Ile Pro Ser Gly Ala Glu Trp Ala Arg Val Ser Ala Val Asn Ala Thr
    290                 295                 300

Ser Trp Glu Pro Leu Thr Asn Leu Ser Leu Val Cys Leu Asp Ser Ala
305                 310                 315                 320

Ser Ala Pro Arg Ser Val Ala Val Ser Ser Ile Ala Gly Ser Thr Glu
                325                 330                 335

Leu Leu Val Thr Trp Gln Pro Gly Pro Gly Glu Pro Leu Glu His Val
            340                 345                 350

Val Asp Trp Ala Arg Asp Gly Asp Pro Leu Glu Lys Leu Asn Trp Val
        355                 360                 365

Arg Leu Pro Pro Gly Asn Leu Ser Ala Leu Leu Pro Gly Asn Phe Thr
    370                 375                 380

Val Gly Val Pro Tyr Arg Ile Thr Val Thr Ala Val Ser Ala Ser Gly
385                 390                 395                 400

Leu Ala Ser Ala Ser Ser Val Trp Gly Phe Arg Glu Glu Leu Ala Pro
                405                 410                 415

Leu Val Gly Pro Thr Leu Trp Arg Leu Gln Asp Ala Pro Pro Gly Thr
            420                 425                 430

Pro Ala Ile Ala Trp Gly Glu Val Pro Arg His Gln Leu Arg Gly His
        435                 440                 445

Leu Thr His Tyr Thr Leu Cys Ala Gln Ser Gly Thr Ser Pro Ser Val
    450                 455                 460

Cys Met Asn Val Ser Gly Asn Thr Gln Ser Val Thr Leu Pro Asp Leu
465                 470                 475                 480

Pro Trp Gly Pro Cys Glu Leu Trp Val Thr Ala Ser Thr Ile Ala Gly
                485                 490                 495

Gln Gly Pro Pro Gly Pro Ile Leu Arg Leu His Leu Pro Asp Asn Thr
            500                 505                 510

Leu Arg Trp Lys Val Leu Pro Gly Ile Leu Phe Leu Trp Gly Leu Phe
        515                 520                 525

Leu Leu Gly Cys Gly Leu Ser Leu Ala Thr Ser Gly Arg Cys Tyr His
    530                 535                 540

Leu Arg His Lys Val Leu Pro Arg Trp Val Trp Glu Lys Val Pro Asp
545                 550                 555                 560

Pro Ala Asn Ser Ser Ser Gly Gln Pro His Met Glu Gln Val Pro Glu
                565                 570                 575

```
Ala Gln Pro Leu Gly Asp Leu Pro Ile Leu Glu Val Glu Glu Met Glu
            580                 585                 590

Pro Pro Pro Val Met Glu Ser Ser Gln Pro Ala Gln Ala Thr Ala Pro
            595                 600                 605

Leu Asp Ser Gly Tyr Glu Lys His Phe Leu Pro Thr Pro Glu Glu Leu
            610                 615                 620

Gly Leu Leu Gly Pro Pro Arg Pro Gln Val Leu Ala
625                 630                 635
```

<210> SEQ ID NO 26
<211> LENGTH: 81
<212> TYPE: PRT
<213> ORGANISM: Homo sapiens

<400> SEQUENCE: 26

```
Met Val Trp Ser Ile Asn Leu Thr Ala Gly Met Tyr Cys Ala Ala Leu
1               5                   10                  15

Glu Ser Leu Ile Asn Val Ser Gly Cys Ser Ala Ile Glu Lys Thr Gln
            20                  25                  30

Arg Met Leu Ser Gly Phe Cys Pro His Lys Val Ser Ala Gly Gln Phe
        35                  40                  45

Ser Ser Leu His Val Arg Asp Thr Lys Ile Glu Val Ala Gln Phe Val
    50                  55                  60

Lys Asp Leu Leu Leu His Leu Lys Lys Leu Phe Arg Glu Gly Arg Phe
65                  70                  75                  80

Asn
```

<210> SEQ ID NO 27
<211> LENGTH: 155
<212> TYPE: PRT
<213> ORGANISM: Homo sapiens

<400> SEQUENCE: 27

```
Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
            20                  25                  30

Cys Pro Asn Ser Glu Asp Lys Asn Phe Pro Arg Thr Val Met Val Asn
        35                  40                  45

Leu Asn Ile His Asn Arg Asn Thr Asn Thr Asn Pro Lys Arg Ser Ser
    50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
            85                  90                  95

Leu Gly Cys Ile Asn Ala Asp Gly Asn Val Asp Tyr His Met Asn Ser
        100                 105                 110

Val Pro Ile Gln Gln Glu Ile Leu Val Leu Arg Arg Glu Pro Pro His
    115                 120                 125

Cys Pro Asn Ser Phe Arg Leu Glu Lys Ile Leu Val Ser Val Gly Cys
130                 135                 140

Thr Cys Val Thr Pro Ile Val His His Val Ala
145                 150                 155
```

<210> SEQ ID NO 28
<211> LENGTH: 270
<212> TYPE: PRT

<213> ORGANISM: Homo sapiens

<400> SEQUENCE: 28

```
Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
                20                  25                  30

Gln Gln Lys Ala Lys Glu Val Cys Pro Met Tyr Phe Met Lys Leu Arg
            35                  40                  45

Ser Gly Leu Met Ile Lys Lys Glu Ala Cys Tyr Phe Arg Arg Glu Thr
        50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
            100                 105                 110

Ile Thr Gly Ile Ser Pro Ile Thr Glu Tyr Leu Ala Ser Leu Ser Thr
        115                 120                 125

Tyr Asn Asp Gln Ser Ile Thr Phe Ala Leu Glu Asp Glu Ser Tyr Glu
130                 135                 140

Ile Tyr Val Glu Asp Leu Lys Lys Asp Glu Lys Lys Asp Lys Val Leu
145                 150                 155                 160

Leu Ser Tyr Tyr Glu Ser Gln His Pro Ser Asn Glu Ser Gly Asp Gly
                165                 170                 175

Val Asp Gly Lys Met Leu Met Val Thr Leu Ser Pro Thr Lys Asp Phe
            180                 185                 190

Trp Leu His Ala Asn Asn Lys Glu His Ser Val Glu Leu His Lys Cys
        195                 200                 205

Glu Lys Pro Leu Pro Asp Gln Ala Phe Phe Val Leu His Asn Met His
    210                 215                 220

Ser Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Ser Ser Glu
                245                 250                 255

Asn Leu Cys Thr Glu Asn Ile Leu Phe Lys Leu Ser Glu Thr
            260                 265                 270
```

<210> SEQ ID NO 29
<211> LENGTH: 270
<212> TYPE: PRT
<213> ORGANISM: Homo sapiens

<400> SEQUENCE: 29

```
Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
                20                  25                  30

Gln Gln Lys Ala Lys Glu Val Cys Pro Met Tyr Phe Met Lys Leu Arg
            35                  40                  45

Ser Gly Leu Met Ile Lys Lys Glu Ala Cys Tyr Phe Arg Arg Glu Thr
        50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
```

```
                    85                  90                  95
Gly Ile Ser Gly Val Gln Lys Tyr Thr Arg Ala Leu His Asp Ser Ser
            100                 105                 110
Ile Thr Gly Ile Ser Pro Ile Thr Glu Tyr Leu Ala Ser Leu Ser Thr
            115                 120                 125
Tyr Asn Asp Gln Ser Ile Thr Phe Ala Leu Glu Asp Glu Ser Tyr Glu
            130                 135                 140
Ile Tyr Val Glu Asp Leu Lys Lys Asp Glu Lys Lys Asp Lys Val Leu
145                 150                 155                 160
Leu Ser Tyr Tyr Glu Ser Gln His Pro Ser Asn Glu Ser Gly Asp Gly
            165                 170                 175
Val Asp Gly Lys Met Leu Met Val Thr Leu Ser Pro Thr Lys Asp Phe
            180                 185                 190
Trp Leu His Ala Asn Asn Lys Glu His Ser Val Glu Leu His Lys Cys
            195                 200                 205
Glu Lys Pro Leu Pro Asp Gln Ala Phe Phe Val Leu His Asn Met His
            210                 215                 220
Ser Asn Cys Val Ser Phe Glu Cys Lys Thr Asp Pro Gly Val Phe Ile
225                 230                 235                 240
Gly Val Lys Asp Asn His Leu Ala Leu Ile Lys Val Asp Ser Ser Glu
            245                 250                 255
Asn Leu Cys Thr Glu Asn Ile Leu Phe Lys Leu Ser Glu Thr
            260                 265                 270

<210> SEQ ID NO 30
<211> LENGTH: 228
<212> TYPE: PRT
<213> ORGANISM: Homo sapiens

<400> SEQUENCE: 30

Met Lys Pro Lys Met Lys Tyr Ser Thr Asn Lys Ile Ser Thr Ala Lys
1               5                   10                  15
Trp Lys Asn Thr Ala Ser Lys Ala Leu Cys Phe Lys Leu Gly Lys Ser
            20                  25                  30
Gln Gln Lys Ala Lys Glu Val Cys Pro Met Tyr Phe Met Lys Leu Arg
            35                  40                  45
Ser Gly Leu Met Ile Lys Lys Glu Ala Cys Tyr Phe Arg Arg Glu Thr
50                  55                  60
Thr Lys Arg Pro Ser Leu Lys Thr Gly Arg Lys His Lys Arg His Leu
65                  70                  75                  80
Val Leu Ala Ala Cys Gln Gln Ser Thr Val Glu Cys Phe Ala Phe
            85                  90                  95
Gly Ile Ser Gly Val Gln Lys Tyr Thr Arg Ala Leu His Asp Ser Ser
            100                 105                 110
Ile Thr Asp Lys Val Leu Leu Ser Tyr Tyr Glu Ser Gln His Pro Ser
            115                 120                 125
Asn Glu Ser Gly Asp Gly Val Asp Gly Lys Met Leu Met Val Thr Leu
130                 135                 140
Ser Pro Thr Lys Asp Phe Trp Leu His Ala Asn Asn Lys Glu His Ser
145                 150                 155                 160
Val Glu Leu His Lys Cys Glu Lys Pro Leu Pro Asp Gln Ala Phe Phe
            165                 170                 175
Val Leu His Asn Met His Ser Asn Cys Val Ser Phe Glu Cys Lys Thr
            180                 185                 190
```

```
Asp Pro Gly Val Phe Ile Gly Val Lys Asp Asn His Leu Ala Leu Ile
        195                 200                 205

Lys Val Asp Ser Ser Glu Asn Leu Cys Thr Glu Asn Ile Leu Phe Lys
    210                 215                 220

Leu Ser Glu Thr
225

<210> SEQ ID NO 31
<211> LENGTH: 144
<212> TYPE: PRT
<213> ORGANISM: Homo sapiens

<400> SEQUENCE: 31

Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Asn Lys
            20                  25                  30

Val Leu Leu Ser Tyr Tyr Glu Ser Gln His Pro Ser Asn Glu Ser Gly
        35                  40                  45

Asp Gly Val Asp Gly Lys Met Leu Met Val Thr Leu Ser Pro Thr Lys
    50                  55                  60

Asp Phe Trp Leu His Ala Asn Asn Lys Glu His Ser Val Glu Leu His
65                  70                  75                  80

Lys Cys Glu Lys Pro Leu Pro Asp Gln Ala Phe Phe Val Leu His Asn
                85                  90                  95

Met His Ser Asn Cys Val Ser Phe Glu Cys Lys Thr Asp Pro Gly Val
            100                 105                 110

Phe Ile Gly Val Lys Asp Asn His Leu Ala Leu Ile Lys Val Asp Ser
        115                 120                 125

Ser Glu Asn Leu Cys Thr Glu Asn Ile Leu Phe Lys Leu Ser Glu Thr
    130                 135                 140

<210> SEQ ID NO 32
<211> LENGTH: 264
<212> TYPE: PRT
<213> ORGANISM: Homo sapiens

<400> SEQUENCE: 32

Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
            20                  25                  30

Gln Gln Lys Ala Lys Glu Val Cys Pro Met Tyr Phe Met Lys Leu Arg
        35                  40                  45

Ser Gly Leu Met Ile Lys Lys Glu Ala Cys Tyr Phe Arg Arg Glu Thr
    50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
            100                 105                 110

Ile Thr Glu Tyr Leu Ala Ser Leu Ser Thr Tyr Asn Asp Gln Ser Ile
        115                 120                 125

Thr Phe Ala Leu Glu Asp Glu Ser Tyr Glu Ile Tyr Val Glu Asp Leu
    130                 135                 140
```

```
Lys Lys Asp Glu Lys Lys Asp Lys Val Leu Leu Ser Tyr Tyr Glu Ser
145                 150                 155                 160

Gln His Pro Ser Asn Glu Ser Gly Asp Gly Val Asp Gly Lys Met Leu
            165                 170                 175

Met Val Thr Leu Ser Pro Thr Lys Asp Phe Trp Leu His Ala Asn Asn
            180                 185                 190

Lys Glu His Ser Val Glu Leu His Lys Cys Glu Lys Pro Leu Pro Asp
            195                 200                 205

Gln Ala Phe Phe Val Leu His Asn Met His Ser Asn Cys Val Ser Phe
            210                 215                 220

Glu Cys Lys Thr Asp Pro Gly Val Phe Ile Gly Val Lys Asp Asn His
225                 230                 235                 240

Leu Ala Leu Ile Lys Val Asp Ser Ser Glu Asn Leu Cys Thr Glu Asn
                245                 250                 255

Ile Leu Phe Lys Leu Ser Glu Thr
            260

<210> SEQ ID NO 33
<211> LENGTH: 228
<212> TYPE: PRT
<213> ORGANISM: Homo sapiens

<400> SEQUENCE: 33

Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
            20                  25                  30

Gln Gln Lys Ala Lys Glu Val Cys Pro Met Tyr Phe Met Lys Leu Arg
        35                  40                  45

Ser Gly Leu Met Ile Lys Lys Glu Ala Cys Tyr Phe Arg Arg Glu Thr
    50                  55                  60

Thr Lys Arg Pro Ser Leu Lys Thr Gly Ile Ser Pro Ile Thr Glu Tyr
65                  70                  75                  80

Leu Ala Ser Leu Ser Thr Tyr Asn Asp Gln Ser Ile Thr Phe Ala Leu
                85                  90                  95

Glu Asp Glu Ser Tyr Glu Ile Tyr Val Asp Leu Lys Lys Asp Glu
            100                 105                 110

Lys Lys Asp Lys Val Leu Leu Ser Tyr Tyr Glu Ser Gln His Pro Ser
            115                 120                 125

Asn Glu Ser Gly Asp Gly Val Asp Gly Lys Met Leu Met Val Thr Leu
130                 135                 140

Ser Pro Thr Lys Asp Phe Trp Leu His Ala Asn Asn Lys Glu His Ser
145                 150                 155                 160

Val Glu Leu His Lys Cys Glu Lys Pro Leu Pro Asp Gln Ala Phe Phe
            165                 170                 175

Val Leu His Asn Met His Ser Asn Cys Val Ser Phe Glu Cys Lys Thr
            180                 185                 190

Asp Pro Gly Val Phe Ile Gly Val Lys Asp Asn His Leu Ala Leu Ile
            195                 200                 205

Lys Val Asp Ser Ser Glu Asn Leu Cys Thr Glu Asn Ile Leu Phe Lys
            210                 215                 220

Leu Ser Glu Thr
225

<210> SEQ ID NO 34
```

-continued

```
<211> LENGTH: 166
<212> TYPE: PRT
<213> ORGANISM: Homo sapiens

<400> SEQUENCE: 34

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 35
<211> LENGTH: 495
<212> TYPE: PRT
<213> ORGANISM: Salmonella enterica

<400> SEQUENCE: 35

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Thr Leu Asn Val Gln
                165                 170                 175
```

```
Gln Lys Tyr Lys Val Ser Asp Thr Ala Ala Thr Val Thr Gly Tyr Ala
            180                 185                 190

Asp Thr Thr Ile Ala Leu Asp Asn Ser Thr Phe Lys Ala Ser Ala Thr
            195                 200                 205

Gly Leu Gly Gly Thr Asp Gln Lys Ile Asp Gly Asp Leu Lys Phe Asp
            210                 215                 220

Asp Thr Thr Gly Lys Tyr Tyr Ala Lys Val Thr Val Thr Gly Thr
225                 230                 235                 240

Gly Lys Asp Gly Tyr Tyr Glu Val Ser Val Asp Lys Thr Asn Gly Glu
            245                 250                 255

Val Thr Leu Ala Gly Gly Ala Thr Ser Pro Leu Thr Gly Gly Leu Pro
            260                 265                 270

Ala Thr Ala Thr Glu Asp Val Lys Asn Val Gln Val Ala Asn Ala Asp
            275                 280                 285

Leu Thr Glu Ala Lys Ala Ala Leu Thr Ala Ala Gly Val Thr Gly Thr
            290                 295                 300

Ala Ser Val Val Lys Met Ser Tyr Thr Asp Asn Asn Gly Lys Thr Ile
305                 310                 315                 320

Asp Gly Gly Leu Ala Val Lys Val Gly Asp Asp Tyr Tyr Ser Ala Thr
            325                 330                 335

Gln Asn Lys Asp Gly Ser Ile Ser Ile Asn Thr Thr Lys Tyr Thr Ala
            340                 345                 350

Asp Asp Gly Thr Ser Lys Thr Ala Leu Asn Lys Leu Gly Gly Ala Asp
            355                 360                 365

Gly Lys Thr Glu Val Val Ser Ile Gly Gly Lys Thr Tyr Ala Ala Ser
            370                 375                 380

Lys Ala Glu Gly His Asn Phe Lys Ala Gln Pro Asp Leu Ala Glu Ala
385                 390                 395                 400

Ala Ala Thr Thr Thr Glu Asn Pro Leu Gln Lys Ile Asp Ala Ala Leu
            405                 410                 415

Ala Gln Val Asp Thr Leu Arg Ser Asp Leu Gly Ala Val Gln Asn Arg
            420                 425                 430

Phe Asn Ser Ala Ile Thr Asn Leu Gly Asn Thr Val Asn Asn Leu Thr
            435                 440                 445

Ser Ala Arg Ser Arg Ile Glu Asp Ser Asp Tyr Ala Thr Glu Val Ser
            450                 455                 460

Asn Met Ser Arg Ala Gln Ile Leu Gln Gln Ala Gly Thr Ser Val Leu
465                 470                 475                 480

Ala Gln Ala Asn Gln Val Pro Gln Asn Val Leu Ser Leu Leu Arg
            485                 490                 495

<210> SEQ ID NO 36
<211> LENGTH: 507
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Asp Met Arg Val Pro Ala Gln Leu Leu Gly Leu Leu Leu Leu Trp
1               5                   10                  15

Leu Arg Gly Ala Arg Cys Asp Ile Val Met Thr Gln Thr Thr Leu Ser
            20                  25                  30

Leu Pro Val Ser Leu Gly Asp Gln Ala Ser Ile Ser Cys Arg Ser Ser
```

```
            35                  40                  45
Gln Ser Ile Val His Ser Asn Gly Asn Thr Tyr Leu Glu Trp Tyr Leu
 50                  55                  60

Gln Lys Pro Gly Gln Ser Pro Lys Leu Leu Ile Tyr Lys Val Ser Asn
 65                  70                  75                  80

Arg Phe Ser Gly Val Pro Asp Arg Phe Ser Gly Ser Gly Ser Gly Thr
                 85                  90                  95

Asp Phe Thr Leu Lys Ile Ser Arg Val Glu Ala Glu Asp Leu Gly Val
            100                 105                 110

Tyr Tyr Cys Phe Gln Gly Ser His Val Pro Tyr Thr Phe Gly Gly Gly
            115                 120                 125

Thr Lys Leu Glu Ile Lys Arg Ala Asp Ala Ala Pro Thr Val Ser Gly
            130                 135                 140

Ser Gly Gly Ser Gly Gly Gly Ser Gly Gly Gly Ser Glu Ala Lys
145                 150                 155                 160

Leu Gln Glu Ser Gly Pro Val Leu Val Lys Pro Gly Ala Ser Val Lys
                165                 170                 175

Met Ser Cys Lys Ala Ser Gly Tyr Thr Phe Thr Asp Tyr Tyr Met Asn
            180                 185                 190

Trp Val Lys Gln Ser His Gly Lys Ser Leu Glu Trp Ile Gly Val Ile
            195                 200                 205

Asn Pro Tyr Asn Gly Asp Thr Ser Tyr Asn Gln Lys Phe Lys Gly Lys
210                 215                 220

Ala Thr Leu Thr Val Asp Lys Ser Ser Ser Thr Ala Tyr Met Glu Leu
225                 230                 235                 240

Asn Ser Leu Thr Ser Glu Asp Ser Ala Val Tyr Tyr Cys Ala Arg Tyr
                245                 250                 255

Tyr Gly Ser Trp Phe Ala Tyr Trp Gly Gln Gly Thr Leu Ile Thr Val
            260                 265                 270

Ser Thr Glu Pro Arg Gly Pro Thr Ile Lys Pro Cys Pro Pro Cys Lys
            275                 280                 285

Cys Pro Ala Pro Asn Leu Leu Gly Gly Pro Ser Val Phe Ile Phe Pro
290                 295                 300

Pro Lys Ile Lys Asp Val Leu Met Ile Ser Leu Ser Pro Ile Val Thr
305                 310                 315                 320

Cys Val Val Val Asp Val Ser Glu Asp Asp Pro Asp Val Gln Ile Ser
                325                 330                 335

Trp Phe Val Asn Asn Val Glu Val His Thr Ala Gln Thr Gln Thr His
            340                 345                 350

Arg Glu Asp Tyr Asn Ser Thr Leu Arg Val Val Ser Ala Leu Pro Ile
            355                 360                 365

Gln His Gln Asp Trp Met Ser Gly Lys Glu Phe Lys Cys Lys Val Asn
            370                 375                 380

Asn Lys Asp Leu Pro Ala Pro Ile Glu Arg Thr Ile Ser Lys Pro Lys
385                 390                 395                 400

Gly Ser Val Arg Ala Pro Gln Val Tyr Val Leu Pro Pro Pro Glu Glu
                405                 410                 415

Glu Met Thr Lys Lys Gln Val Thr Leu Thr Cys Met Val Thr Asp Phe
            420                 425                 430

Met Pro Glu Asp Ile Tyr Val Glu Trp Thr Asn Asn Gly Lys Thr Glu
            435                 440                 445

Leu Asn Tyr Lys Asn Thr Glu Pro Val Leu Asp Ser Asp Gly Ser Tyr
450                 455                 460
```

Phe Met Tyr Ser Lys Leu Arg Val Glu Lys Lys Asn Trp Val Glu Arg
465                 470                 475                 480

Asn Ser Tyr Ser Cys Ser Val Val His Glu Gly Leu His Asn His His
                485                 490                 495

Thr Thr Lys Ser Phe Ser Arg Thr Pro Gly Lys
            500                 505

<210> SEQ ID NO 37
<211> LENGTH: 955
<212> TYPE: DNA
<213> ORGANISM: Mus musculus

<400> SEQUENCE: 37
tatcacccct gctaatcact cctcacagtg acctcaagtc ctgcaggcat gtacagcatg      60
cagctcgcat cctgtgtcac attgacactt gtgctccttg tcaacagcgc acccacttca     120
agctccactt caagtctcta cagcggaagca cagcagcagc agcagcagca gcagcagcag     180
cagcagcacc tggagcagct gttgatggac ctacaggagc tcctgagcag gatggagaat     240
tacaggaacc tgaaactccc caggatgctc accttcaaat tttacttgcc caagcaggcc     300
acagaattga agatcttca gtgcctagaa atgaacttg acctctgcg gcatgttctg        360
gatttgactc aaagcaaaag ctttcaattg gaagatgctg agaatttcat cagcaatatc     420
agagtaactg ttgtaaaact aaagggctct gacaacacat tgagtgcca attcgatgat      480
gagtcagcaa ctgtggtgga ctttctgagg agatggatag ccttctgtca agcatcatc      540
tcaacaagcc ctcaataact atgtacctcc tgcttacaac acataaggct ctctatttat     600
ttaaatattt aactttaatt tattttttgga tgtattgttt actatctttt gtaactacta     660
gtcttcagat gataaatatg gatctttaaa gattctttt gtaagcccca agggctcaaa      720
aatgttttaa actatttatc tgaaattatt tattatattg aattgttaaa tatcatgtgt     780
aggtagactc attaataaaa gtatttagat gattcaaata taaataagct cagatgtctg     840
tcatttttag gacagcacaa agtaagcgct aaaataactt ctcagttatt cctgtgaact     900
ctatgttaat cagtgttttc aagaaataaa gctctcctct aaaaaaaaaa aaaaa          955

<210> SEQ ID NO 38
<211> LENGTH: 169
<212> TYPE: PRT
<213> ORGANISM: Mus musculus

<400> SEQUENCE: 38

Met Tyr Ser Met Gln Leu Ala Ser Cys Val Thr Leu Thr Leu Val Leu
1               5                   10                  15

Leu Val Asn Ser Ala Pro Thr Ser Ser Thr Ser Ser Ser Thr Ala
            20                  25                  30

Glu Ala Gln Gln Gln Gln Gln Gln Gln Gln Gln Gln Gln His Leu
        35                  40                  45

Glu Gln Leu Leu Met Asp Leu Gln Glu Leu Leu Ser Arg Met Glu Asn
    50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
          115                 120                 125

Val Lys Leu Lys Gly Ser Asp Asn Thr Phe Glu Cys Gln Phe Asp Asp
    130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln
                165

<210> SEQ ID NO 39
<211> LENGTH: 525
<212> TYPE: DNA
<213> ORGANISM: Mus musculus

<400> SEQUENCE: 39
agcccagcaa gacctcagcc atgagacttc tcctcctgac tttcctggga gtctgctgcc      60 tcacccatg ggttgtggaa ggtgtgggga ctgaagtcct agaagagagt agctgtgtga      120
acttacaaac ccagcggctg ccagttcaaa aaatcaagac ctatatcatc tgggaggggg     180
ccatgagagc tgtaattttt gtcaccaaac gaggactaaa aatttgtgct gatccagaag     240
ccaaatgggt gaaagcagcg atcaagactg tggatggcag ggccagtacc agaaagaaca     300
tggctgaaac tgttcccaca ggagcccaga ggtccaccag cacagcgata accctgactg     360
ggtaacagcc tccaggacaa tgtttcctca ctcgttaagc agctcatctc agttcccaaa     420
cccattgcac aaatacttat ttttattttt aacgacattc acattcattt caaatgttat     480
aagtaataaa tatttattat tgatgaaaaa aaaaaaaaaa aaaaa                      525

<210> SEQ ID NO 40
<211> LENGTH: 114
<212> TYPE: PRT
<213> ORGANISM: Mus musculus

<400> SEQUENCE: 40

Met Arg Leu Leu Leu Leu Thr Phe Leu Gly Val Cys Cys Leu Thr Pro
1               5                   10                  15

Trp Val Val Glu Gly Val Gly Thr Glu Val Leu Glu Glu Ser Ser Cys
            20                  25                  30

Val Asn Leu Gln Thr Gln Arg Leu Pro Val Gln Lys Ile Lys Thr Tyr
        35                  40                  45

Ile Ile Trp Glu Gly Ala Met Arg Ala Val Ile Phe Val Thr Lys Arg
    50                  55                  60

Gly Leu Lys Ile Cys Ala Asp Pro Glu Ala Lys Trp Val Lys Ala Ala
65                  70                  75                  80

Ile Lys Thr Val Asp Gly Arg Ala Ser Thr Arg Lys Asn Met Ala Glu
                85                  90                  95

Thr Val Pro Thr Gly Ala Gln Arg Ser Thr Ser Thr Ala Ile Thr Leu
            100                 105                 110

Thr Gly

<210> SEQ ID NO 41
<211> LENGTH: 1028
<212> TYPE: DNA
<213> ORGANISM: Mus musculus

<400> SEQUENCE: 41
gagacgtgca ctgaccgacc gtggtaatgg accagcacac acttgatgtg gaggataccg      60

```
cggatgccag acatccagca ggtacttcgt gccccctcgga tgcggcgctc ctcagagata    120
ccgggctcct cgcggacgct gcgctcctct cagatactgt gcgccccaca aatgccgcgc    180
tccccacgga tgctgcctac cctgcggtta atgttcggga tcgcgaggcc gcgtggccgc    240
ctgcactgaa cttctgttcc cgccacccaa agctctatgg cctagtcgct ttggttttgc    300
tgcttctgat cgccgcctgt gttcctatct tcacccgcac cgagcctcgg ccagcgctca    360
caatcaccac ctcgcccaac ctgggtaccc gagagaataa tgcagaccag gtcacccctg    420
tttcccacat tggctgcccc aacactacac aacagggctc tcctgtgttc gccaagctac    480
tggctaaaaa ccaagcatcg ttgtgcaata caactctgaa ctggcacagc caagatggag    540
ctgggagctc ataccctatct caaggtctga ggtacgaaga agacaaaaag gagttggtgg    600
tagacagtcc cgggctctac tacgtatttt tggaactgaa gctcagtcca acattcacaa    660
acacaggcca caaggtgcag ggctgggtct ctcttgtttt gcaagcaaag cctcaggtag    720
atgactttga caacttggcc ctgacagtgg aactgttccc ttgctccatg gagaacaagt    780
tagtggaccg ttcctggagt caactgttgc tcctgaaggc tggccaccgc ctcagtgtgg    840
gtctgagggc ttatctgcat ggagcccagg atgcatacag agactgggag ctgtcttatc    900
ccaacaccac cagctttgga ctctttcttg tgaaacccga caacccatgg gaatgagaac    960
tatccttctt gtgactccta gttgctaagt cctcaagctg ctatgtttta tggggtctga   1020
gcaggggt                                                            1028
```

<210> SEQ ID NO 42
<211> LENGTH: 309
<212> TYPE: PRT
<213> ORGANISM: Mus musculus

<400> SEQUENCE: 42

```
Met Asp Gln His Thr Leu Asp Val Glu Asp Thr Ala Asp Ala Arg His
1               5                   10                  15

Pro Ala Gly Thr Ser Cys Pro Ser Asp Ala Ala Leu Leu Arg Asp Thr
            20                  25                  30

Gly Leu Leu Ala Asp Ala Ala Leu Ser Asp Thr Val Arg Pro Thr
        35                  40                  45

Asn Ala Ala Leu Pro Thr Asp Ala Ala Tyr Pro Ala Val Asn Val Arg
    50                  55                  60

Asp Arg Glu Ala Ala Trp Pro Pro Leu Asn Phe Cys Ser Arg His
65                  70                  75                  80

Pro Lys Leu Tyr Gly Leu Val Ala Leu Val Leu Leu Leu Ile Ala
                85                  90                  95

Ala Cys Val Pro Ile Phe Thr Arg Thr Glu Pro Arg Pro Ala Leu Thr
            100                 105                 110

Ile Thr Thr Ser Pro Asn Leu Gly Thr Arg Glu Asn Asn Ala Asp Gln
        115                 120                 125

Val Thr Pro Val Ser His Ile Gly Cys Pro Asn Thr Thr Gln Gln Gly
    130                 135                 140

Ser Pro Val Phe Ala Lys Leu Leu Ala Lys Asn Gln Ala Ser Leu Cys
145                 150                 155                 160

Asn Thr Thr Leu Asn Trp His Ser Gln Asp Gly Ala Gly Ser Ser Tyr
                165                 170                 175

Leu Ser Gln Gly Leu Arg Tyr Glu Glu Asp Lys Lys Glu Leu Val Val
            180                 185                 190

Asp Ser Pro Gly Leu Tyr Tyr Val Phe Leu Glu Leu Lys Leu Ser Pro
```

```
                195                 200                 205
Thr Phe Thr Asn Thr Gly His Lys Val Gln Gly Trp Val Ser Leu Val
210                 215                 220

Leu Gln Ala Lys Pro Gln Val Asp Asp Phe Asp Asn Leu Ala Leu Thr
225                 230                 235                 240

Val Glu Leu Phe Pro Cys Ser Met Glu Asn Lys Leu Val Asp Arg Ser
                245                 250                 255

Trp Ser Gln Leu Leu Leu Lys Ala Gly His Arg Leu Ser Val Gly
            260                 265                 270

Leu Arg Ala Tyr Leu His Gly Ala Gln Asp Ala Tyr Arg Asp Trp Glu
            275                 280                 285

Leu Ser Tyr Pro Asn Thr Thr Ser Phe Gly Leu Phe Leu Val Lys Pro
290                 295                 300

Asp Asn Pro Trp Glu
305

<210> SEQ ID NO 43
<211> LENGTH: 273
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Asp Met Arg Val Pro Ala Gln Leu Leu Gly Leu Leu Leu Leu Trp
1               5                   10                  15

Leu Arg Gly Ala Arg Cys Arg Met Lys Gln Ile Glu Asp Lys Ile Glu
            20                  25                  30

Glu Ile Leu Ser Lys Ile Tyr His Ile Glu Asn Glu Ile Ala Arg Ile
        35                  40                  45

Lys Lys Leu Ile Gly Glu Arg Gly Gly Ser Gly Gly Gly Ser Gly
    50                  55                  60

Gly Gly Ser Arg Thr Glu Pro Arg Pro Ala Leu Thr Ile Thr Thr Ser
65                  70                  75                  80

Pro Asn Leu Gly Thr Arg Glu Asn Asn Ala Asp Gln Val Thr Pro Val
                85                  90                  95

Ser His Ile Gly Cys Pro Asn Thr Thr Gln Gln Gly Ser Pro Val Phe
                100                 105                 110

Ala Lys Leu Leu Ala Lys Asn Gln Ala Ser Leu Cys Asn Thr Thr Leu
            115                 120                 125

Asn Trp His Ser Gln Asp Gly Ala Gly Ser Ser Tyr Leu Ser Gln Gly
        130                 135                 140

Leu Arg Tyr Glu Glu Asp Lys Lys Glu Leu Val Val Asp Ser Pro Gly
145                 150                 155                 160

Leu Tyr Tyr Val Phe Leu Glu Leu Lys Leu Ser Pro Thr Phe Thr Asn
                165                 170                 175

Thr Gly His Lys Val Gln Gly Trp Val Ser Leu Val Leu Gln Ala Lys
                180                 185                 190

Pro Gln Val Asp Asp Phe Asp Asn Leu Ala Leu Thr Val Glu Leu Phe
            195                 200                 205

Pro Cys Ser Met Glu Asn Lys Leu Val Asp Arg Ser Trp Ser Gln Leu
        210                 215                 220

Leu Leu Leu Lys Ala Gly His Arg Leu Ser Val Gly Leu Arg Ala Tyr
225                 230                 235                 240
```

```
Leu His Gly Ala Gln Asp Ala Tyr Arg Asp Trp Glu Leu Ser Tyr Pro
                245                 250                 255

Asn Thr Thr Ser Phe Gly Leu Phe Leu Val Lys Pro Asn Pro Trp
            260                 265                 270

Glu

<210> SEQ ID NO 44
<211> LENGTH: 206
<212> TYPE: PRT
<213> ORGANISM: Mus musculus

<400> SEQUENCE: 44

Arg Thr Glu Pro Arg Pro Ala Leu Thr Ile Thr Thr Ser Pro Asn Leu
1               5                   10                  15

Gly Thr Arg Glu Asn Asn Ala Asp Gln Val Thr Pro Val Ser His Ile
            20                  25                  30

Gly Cys Pro Asn Thr Thr Gln Gln Gly Ser Pro Val Phe Ala Lys Leu
        35                  40                  45

Leu Ala Lys Asn Gln Ala Ser Leu Cys Asn Thr Thr Leu Asn Trp His
    50                  55                  60

Ser Gln Asp Gly Ala Gly Ser Ser Tyr Leu Ser Gln Gly Leu Arg Tyr
65                  70                  75                  80

Glu Glu Asp Lys Lys Glu Leu Val Val Asp Ser Pro Gly Leu Tyr Tyr
                85                  90                  95

Val Phe Leu Glu Leu Lys Leu Ser Pro Thr Phe Thr Asn Thr Gly His
            100                 105                 110

Lys Val Gln Gly Trp Val Ser Leu Val Leu Gln Ala Lys Pro Gln Val
        115                 120                 125

Asp Asp Phe Asp Asn Leu Ala Leu Thr Val Glu Leu Phe Pro Cys Ser
    130                 135                 140

Met Glu Asn Lys Leu Val Asp Arg Ser Trp Ser Gln Leu Leu Leu Leu
145                 150                 155                 160

Lys Ala Gly His Arg Leu Ser Val Gly Leu Arg Ala Tyr Leu His Gly
                165                 170                 175

Ala Gln Asp Ala Tyr Arg Asp Trp Glu Leu Ser Tyr Pro Asn Thr Thr
            180                 185                 190

Ser Phe Gly Leu Phe Leu Val Lys Pro Asp Asn Pro Trp Glu
        195                 200                 205

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Gly Gly Gly Ser Gly Gly Gly Gly Ser Gly Gly Gly Gly Ser
1               5                   10                  15

<210> SEQ ID NO 46
<211> LENGTH: 540
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46
```

```
Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Gly Gly Gly Ser Gly Gly Gly Gly
                325                 330                 335

Gly Ser Gly Gly Gly Gly Ser Arg Asn Leu Pro Val Ala Thr Pro Asp
            340                 345                 350

Pro Gly Met Phe Pro Cys Leu His His Ser Gln Asn Leu Leu Arg Ala
        355                 360                 365

Val Ser Asn Met Leu Gln Lys Ala Arg Gln Thr Leu Glu Phe Tyr Pro
370                 375                 380

Cys Thr Ser Glu Glu Ile Asp His Glu Asp Ile Thr Lys Asp Lys Thr
385                 390                 395                 400

Ser Thr Val Glu Ala Cys Leu Pro Leu Glu Leu Thr Lys Asn Glu Ser
                405                 410                 415
```

```
Cys Leu Asn Ser Arg Glu Thr Ser Phe Ile Thr Asn Gly Ser Cys Leu
            420                 425                 430

Ala Ser Arg Lys Thr Ser Phe Met Met Ala Leu Cys Leu Ser Ser Ile
        435                 440                 445

Tyr Glu Asp Leu Lys Met Tyr Gln Val Glu Phe Lys Thr Met Asn Ala
    450                 455                 460

Lys Leu Leu Met Asp Pro Lys Arg Gln Ile Phe Leu Asp Gln Asn Met
465                 470                 475                 480

Leu Ala Val Ile Asp Glu Leu Met Gln Ala Leu Asn Phe Asn Ser Glu
                485                 490                 495

Thr Val Pro Gln Lys Ser Ser Leu Glu Glu Pro Asp Phe Tyr Lys Thr
            500                 505                 510

Lys Ile Lys Leu Cys Ile Leu Leu His Ala Phe Arg Ile Arg Ala Val
        515                 520                 525

Thr Ile Asp Arg Val Met Ser Tyr Leu Asn Ala Ser
            530                 535                 540

<210> SEQ ID NO 47
<211> LENGTH: 328
<212> TYPE: PRT
<213> ORGANISM: Homo sapiens

<400> SEQUENCE: 47

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255
```

```
Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 48
<211> LENGTH: 197
<212> TYPE: PRT
<213> ORGANISM: Homo sapiens

<400> SEQUENCE: 48

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195

<210> SEQ ID NO 49
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gtcgacgcca cc                                                      12

<210> SEQ ID NO 50
<211> LENGTH: 22
```

```
<212> TYPE: PRT
<213> ORGANISM: Homo sapiens

<400> SEQUENCE: 50

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 51
<211> LENGTH: 33
<212> TYPE: PRT
<213> ORGANISM: Saccharomyces cerevisiae

<400> SEQUENCE: 51

Arg Met Lys Gln Ile Glu Asp Lys Ile Glu Glu Ile Leu Ser Lys Ile
1               5                   10                  15

Tyr His Ile Glu Asn Glu Ile Ala Arg Ile Lys Lys Leu Ile Gly Glu
            20                  25                  30

Arg

<210> SEQ ID NO 52
<211> LENGTH: 126
<212> TYPE: PRT
<213> ORGANISM: Homo sapiens

<400> SEQUENCE: 52

Glu Thr Ala Lys Glu Pro Cys Met Ala Lys Phe Gly Pro Leu Pro Ser
1               5                   10                  15

Lys Trp Gln Met Ala Ser Ser Glu Pro Pro Cys Val Asn Lys Val Ser
            20                  25                  30

Asp Trp Lys Leu Glu Ile Leu Gln Asn Gly Leu Tyr Leu Ile Tyr Gly
        35                  40                  45

Gln Val Ala Pro Asn Ala Asn Tyr Asn Asp Val Ala Pro Phe Glu Val
    50                  55                  60

Arg Leu Tyr Lys Asn Lys Asp Met Ile Gln Thr Leu Thr Asn Lys Ser
65                  70                  75                  80

Lys Ile Gln Asn Val Gly Gly Thr Tyr Glu Leu His Val Gly Asp Thr
                85                  90                  95

Ile Asp Leu Ile Phe Asn Ser Glu His Gln Val Leu Lys Asn Asn Thr
            100                 105                 110

Tyr Trp Gly Ile Ile Leu Leu Ala Asn Pro Gln Phe Ile Ser
        115                 120                 125

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Gly Gly Ser Gly Gly Gly Ser Gly Gly Gly Ser
1               5                   10

<210> SEQ ID NO 54
<211> LENGTH: 245
<212> TYPE: PRT
<213> ORGANISM: Artificial Sequence
<220> FEATURE:
```

<223> OTHER INFORMATION: Description of Artificial Sequence: Synthetic polypeptide

<400> SEQUENCE: 54

```
Met Ala Pro Arg Arg Ala Arg Gly Cys Arg Thr Leu Gly Leu Pro Ala
1               5                   10                  15
Leu Leu Leu Leu Leu Leu Leu Arg Pro Pro Ala Thr Arg Gly Ile Thr
            20                  25                  30
Cys Pro Pro Pro Met Ser Val Glu His Ala Asp Ile Trp Val Lys Ser
            35                  40                  45
Tyr Ser Leu Tyr Ser Arg Glu Arg Tyr Ile Cys Asn Ser Gly Phe Lys
        50                  55                  60
Arg Lys Ala Gly Thr Ser Ser Leu Thr Glu Cys Val Leu Asn Lys Ala
65                  70                  75                  80
Thr Asn Val Ala His Trp Thr Thr Pro Ser Leu Lys Cys Ile Arg Asp
                85                  90                  95
Pro Ala Leu Val His Gln Arg Pro Ala Pro Pro Ser Thr Val Thr Thr
            100                 105                 110
Ala Ser Gly Gly Ser Gly Gly Gly Ser Gly Gly Gly Ser Gly Gly
            115                 120                 125
Gly Gly Ser Asn Trp Val Asn Val Ile Ser Asp Leu Lys Lys Ile Glu
        130                 135                 140
Asp Leu Ile Gln Ser Met His Ile Asp Ala Thr Leu Tyr Thr Glu Ser
145                 150                 155                 160
Asp Val His Pro Ser Cys Lys Val Thr Ala Met Lys Cys Phe Leu Leu
                165                 170                 175
Glu Leu Gln Val Ile Ser Leu Glu Ser Gly Asp Ala Ser Ile His Asp
            180                 185                 190
Thr Val Glu Asn Leu Ile Ile Leu Ala Asn Asn Ser Leu Ser Ser Asn
            195                 200                 205
Gly Asn Val Thr Glu Ser Gly Cys Lys Glu Cys Glu Glu Leu Glu Glu
        210                 215                 220
Lys Asn Ile Lys Glu Phe Leu Gln Ser Phe Val His Ile Val Gln Met
225                 230                 235                 240
Phe Ile Asn Thr Ser
                245
```

<210> SEQ ID NO 55
<211> LENGTH: 30
<212> TYPE: PRT
<213> ORGANISM: Homo sapiens

<400> SEQUENCE: 55

```
Met Ala Pro Arg Arg Ala Arg Gly Cys Arg Thr Leu Gly Leu Pro Ala
1               5                   10                  15
Leu Leu Leu Leu Leu Leu Leu Arg Pro Pro Ala Thr Arg Gly
            20                  25                  30
```

<210> SEQ ID NO 56
<211> LENGTH: 77
<212> TYPE: PRT
<213> ORGANISM: Homo sapiens

<400> SEQUENCE: 56

```
Met Ser Val Glu His Ala Asp Ile Trp Val Lys Ser Tyr Ser Leu Tyr
1               5                   10                  15
Ser Arg Glu Arg Tyr Ile Cys Asn Ser Gly Phe Lys Arg Lys Ala Gly
```

```
                    20                  25                  30
Thr Ser Ser Leu Thr Glu Cys Val Leu Asn Lys Ala Thr Asn Val Ala
                35                  40                  45

His Trp Thr Thr Pro Ser Leu Lys Cys Ile Arg Asp Pro Ala Leu Val
 50                  55                  60

His Gln Arg Pro Ala Pro Ser Thr Val Thr Ala
 65                  70                  75
```

<210> SEQ ID NO 57
<211> LENGTH: 114
<212> TYPE: PRT
<213> ORGANISM: Homo sapiens

<400> SEQUENCE: 57

```
Asn Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
                35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser
```

<210> SEQ ID NO 58
<211> LENGTH: 485
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Met Asp Met Arg Val Pro Ala Gln Leu Leu Gly Leu Leu Leu Leu Trp
 1               5                  10                  15

Leu Arg Gly Ala Arg Cys Glu Ile Val Leu Thr Gln Ser Pro Ala Thr
                20                  25                  30

Leu Ser Leu Ser Pro Gly Glu Arg Ala Thr Leu Ser Cys Ser Ala Ser
                35                  40                  45

Ser Ser Ile Ser Tyr Met His Trp Phe Gln Gln Arg Pro Gly Gln Ser
 50                  55                  60

Pro Arg Arg Trp Ile Tyr Asp Thr Ser Lys Leu Ala Ser Gly Val Pro
 65                  70                  75                  80

Ala Arg Phe Ser Gly Ser Gly Ser Gly Thr Asp Tyr Thr Leu Thr Ile
                85                  90                  95

Ser Ser Leu Glu Pro Glu Asp Phe Ala Thr Tyr Tyr Cys His Gln Arg
                100                 105                 110

Thr Ser Tyr Pro Leu Thr Phe Gly Gln Gly Thr Lys Leu Glu Ile Lys
                115                 120                 125

Gly Gly Gly Gly Ser Gly Gly Gly Gly Ser Gly Gly Gly Gly Ser Gln
                130                 135                 140
```

```
Val Gln Leu Val Gln Ser Gly Ala Glu Leu Lys Lys Pro Gly Ala Ser
145                 150                 155                 160

Val Lys Val Ser Cys Lys Ala Ser Gly Tyr Thr Phe Thr Ser Tyr Trp
                165                 170                 175

Ile Asn Trp Ile Arg Gln Ala Pro Gly Gln Gly Leu Glu Trp Ile Gly
            180                 185                 190

Arg Ile Ala Pro Gly Ser Gly Thr Thr Tyr Tyr Asn Glu Val Phe Lys
        195                 200                 205

Gly Arg Val Thr Ile Thr Val Asp Lys Ser Thr Ser Thr Ala Tyr Met
    210                 215                 220

Glu Leu Ser Ser Leu Arg Ser Glu Asp Thr Ala Val Tyr Phe Cys Ala
225                 230                 235                 240

Arg Gly Asp Tyr Gly Ser Tyr Trp Gly Gln Gly Thr Leu Val Thr Val
                245                 250                 255

Ser Ser Asp Lys Thr His Thr Cys Pro Pro Cys Pro Ala Pro Glu Leu
                260                 265                 270

Leu Gly Gly Pro Ser Val Phe Leu Phe Pro Pro Lys Pro Lys Asp Thr
            275                 280                 285

Leu Met Ile Ser Arg Thr Pro Glu Val Thr Cys Val Val Val Asp Val
        290                 295                 300

Ser His Glu Asp Pro Glu Val Lys Phe Asn Trp Tyr Val Asp Gly Val
305                 310                 315                 320

Glu Val His Asn Ala Lys Thr Lys Pro Arg Glu Glu Gln Tyr Asn Ser
                325                 330                 335

Thr Tyr Arg Val Val Ser Val Leu Thr Val Leu His Gln Asp Trp Leu
            340                 345                 350

Asn Gly Lys Glu Tyr Lys Cys Lys Val Ser Asn Lys Ala Leu Pro Ala
        355                 360                 365

Pro Ile Glu Lys Thr Ile Ser Lys Ala Lys Gly Gln Pro Arg Glu Pro
    370                 375                 380

Gln Val Tyr Thr Leu Pro Pro Ser Arg Glu Glu Met Thr Lys Asn Gln
385                 390                 395                 400

Val Ser Leu Thr Cys Leu Val Lys Gly Phe Tyr Pro Ser Asp Ile Ala
                405                 410                 415

Val Glu Trp Glu Ser Asn Gly Gln Pro Glu Asn Asn Tyr Lys Thr Thr
            420                 425                 430

Pro Pro Val Leu Asp Ser Asp Gly Ser Phe Phe Leu Tyr Ser Lys Leu
        435                 440                 445

Thr Val Asp Lys Ser Arg Trp Gln Gln Gly Asn Val Phe Ser Cys Ser
    450                 455                 460

Val Met His Glu Ala Leu His Asn His Tyr Thr Gln Lys Ser Leu Ser
465                 470                 475                 480

Leu Ser Pro Gly Lys
                485

<210> SEQ ID NO 59
<211> LENGTH: 106
<212> TYPE: PRT
<213> ORGANISM: Homo sapiens

<400> SEQUENCE: 59

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Ile Ser Tyr Met
```

```
                20                  25                  30

His Trp Phe Gln Gln Arg Pro Gly Gln Ser Pro Arg Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Asp Tyr Thr Leu Thr Ile Ser Ser Leu Glu Pro Glu
65                  70                  75                  80

Asp Phe Ala Thr Tyr Tyr Cys His Gln Arg Thr Ser Tyr Pro Leu Thr
                85                  90                  95

Phe Gly Gln Gly Thr Lys Leu Glu Ile Lys
            100                 105

<210> SEQ ID NO 60
<211> LENGTH: 115
<212> TYPE: PRT
<213> ORGANISM: Homo sapiens

<400> SEQUENCE: 60

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Asn Trp Ile Arg Gln Ala Pro Gly Gln Gly Leu Glu Trp Ile
        35                  40                  45

Gly Arg Ile Ala Pro Gly Ser Gly Thr Thr Tyr Tyr Asn Glu Val Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Asp Tyr Gly Ser Tyr Trp Gly Gln Gly Thr Leu Val Thr
            100                 105                 110

Val Ser Ser
        115

<210> SEQ ID NO 61
<211> LENGTH: 227
<212> TYPE: PRT
<213> ORGANISM: Homo sapiens

<400> SEQUENCE: 61

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
```

```
            115                 120                 125
Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Lys
225

<210> SEQ ID NO 62
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Ala Pro Arg Arg Ala Arg Gly Cys Arg Thr Leu Gly Leu Pro Ala
1               5                   10                  15

Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
            35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Ser Gly Gly Ser Gly Gly Gly Ser Gly Gly Gly Ser Gly Gly
            115                 120                 125

Gly Gly Ser Asn Trp Val Asn Val Ile Ser Asp Leu Lys Lys Ile Glu
            130                 135                 140

Asp Leu Ile Gln Ser Met His Ile Asp Ala Thr Leu Tyr Thr Glu Ser
145                 150                 155                 160

Asp Val His Pro Ser Cys Lys Val Thr Ala Met Lys Cys Phe Leu Leu
                165                 170                 175

Glu Leu Gln Val Ile Ser Leu Glu Ser Gly Asp Ala Ser Ile His Asp
            180                 185                 190

Thr Val Glu Asn Leu Ile Ile Leu Ala Asn Asn Ser Leu Ser Ser Asn
            195                 200                 205

Gly Asn Val Thr Glu Ser Gly Cys Lys Glu Cys Glu Glu Leu Glu Glu
            210                 215                 220

Lys Asn Ile Lys Glu Phe Leu Gln Ser Phe Val His Ile Val Gln Met
225                 230                 235                 240
```

```
Phe Ile Asn Thr Ser
            245

<210> SEQ ID NO 63
<211> LENGTH: 30
<212> TYPE: PRT
<213> ORGANISM: Homo sapiens

<400> SEQUENCE: 63

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly
            20                  25                  30

<210> SEQ ID NO 64
<211> LENGTH: 114
<212> TYPE: PRT
<213> ORGANISM: Homo sapiens

<400> SEQUENCE: 64

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 65
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110
```

Met Gln Lys Gly Asp Gln Asn Pro Gln Ile Ala Ala His Val Ile Ser
            115                 120                 125

Glu Ala Ser Ser Lys Thr Thr Ser Val Leu Gln Trp Ala Glu Lys Gly
        130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
        210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 66
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

```
<210> SEQ ID NO 67
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Leu Pro Cys Leu Val Val Leu Leu Ala Ala Leu Leu Ser Leu Arg
1               5                   10                  15

Leu Gly Ser Asp Ala His Gly Thr Glu Leu Pro Ser Pro Pro Ser Val
            20                  25                  30

Trp Phe Glu Ala Glu Phe Phe His His Ile Leu His Trp Thr Pro Ile
        35                  40                  45

Pro Asn Gln Ser Glu Ser Thr Cys Tyr Glu Val Ala Leu Leu Arg Tyr
    50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
            100                 105                 110

Val Thr Asn Thr Arg Phe Ser Val Asp Glu Val Thr Leu Thr Val Gly
        115                 120                 125

Ser Val Asn Leu Glu Ile His Asn Gly Phe Ile Leu Gly Lys Ile Gln
130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
            180                 185                 190

Leu Thr Ser Gly Glu Val Gly Glu Phe Cys Val Gln Val Lys Pro Ser
        195                 200                 205

Val Ala Ser Arg Ser Asn Lys Gly Met Trp Ser Lys Glu Glu Cys Ile
    210                 215                 220

Ser Leu Thr Arg Gln Tyr Phe Thr Val Thr Asn Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365
```

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
                435                 440                 445

Asn His Tyr Thr Gln Lys Ser Leu Ser Leu Ser Pro Gly Lys
450                 455                 460

<210> SEQ ID NO 68
<211> LENGTH: 214
<212> TYPE: PRT
<213> ORGANISM: Homo sapiens

<400> SEQUENCE: 68

His Gly Thr Glu Leu Pro Ser Pro Pro Ser Val Trp Phe Glu Ala Glu
1               5                   10                  15

Phe Phe His His Ile Leu His Trp Thr Pro Ile Pro Asn Gln Ser Glu
                20                  25                  30

Ser Thr Cys Tyr Glu Val Ala Leu Leu Arg Tyr Gly Ile Glu Ser Trp
            35                  40                  45

Asn Ser Ile Ser Asn Cys Ser Gln Thr Leu Ser Tyr Asp Leu Thr Ala
50                  55                  60

Val Thr Leu Asp Leu Tyr His Ser Asn Gly Tyr Arg Ala Arg Val Arg
65                  70                  75                  80

Ala Val Asp Gly Ser Arg His Ser Asn Trp Thr Val Thr Asn Thr Arg
                85                  90                  95

Phe Ser Val Asp Glu Val Thr Leu Thr Val Gly Ser Val Asn Leu Glu
            100                 105                 110

Ile His Asn Gly Phe Ile Leu Gly Lys Ile Gln Leu Pro Arg Pro Lys
        115                 120                 125

Met Ala Pro Ala Asn Asp Thr Tyr Glu Ser Ile Phe Ser His Phe Arg
130                 135                 140

Glu Tyr Glu Ile Ala Ile Arg Lys Val Pro Gly Asn Phe Thr Phe Thr
145                 150                 155                 160

His Lys Lys Val Lys His Glu Asn Phe Ser Leu Leu Thr Ser Gly Glu
                165                 170                 175

Val Gly Glu Phe Cys Val Gln Val Lys Pro Ser Val Ala Ser Arg Ser
            180                 185                 190

Asn Lys Gly Met Trp Ser Lys Glu Glu Cys Ile Ser Leu Thr Arg Gln
        195                 200                 205

Tyr Phe Thr Val Thr Asn
    210

<210> SEQ ID NO 69
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

```
Met Leu Pro Cys Leu Val Val Leu Leu Ala Leu Leu Ser Leu Arg
1               5                   10                  15

Leu Gly Ser Asp Ala
            20

<210> SEQ ID NO 70
<211> LENGTH: 227
<212> TYPE: PRT
<213> ORGANISM: Homo sapiens

<400> SEQUENCE: 70

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 71
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Met Asp Met Arg Val Pro Ala Gln Leu Leu Gly Leu Leu Leu Leu Trp
1               5                   10                  15

Leu Arg Gly Ala Arg Cys Arg Met Lys Gln Ile Glu Asp Lys Ile Glu
                20                  25                  30

Glu Ile Leu Ser Lys Ile Tyr His Ile Glu Asn Glu Ile Ala Arg Ile
            35                  40                  45
```

```
Lys Lys Leu Ile Gly Glu Arg Gly Gly Ser Gly Gly Ser Gly
     50                  55                  60

Gly Gly Ser Glu Thr Ala Lys Glu Pro Cys Met Ala Lys Phe Gly Pro
 65              70                  75                  80

Leu Pro Ser Lys Trp Gln Met Ala Ser Ser Glu Pro Pro Cys Val Asn
             85                  90                  95

Lys Val Ser Asp Trp Lys Leu Glu Ile Leu Gln Asn Gly Leu Tyr Leu
            100                 105                 110

Ile Tyr Gly Gln Val Ala Pro Asn Ala Asn Tyr Asn Asp Val Ala Pro
            115                 120                 125

Phe Glu Val Arg Leu Tyr Lys Asn Lys Asp Met Ile Gln Thr Leu Thr
130                 135                 140

Asn Lys Ser Lys Ile Gln Asn Val Gly Gly Thr Tyr Glu Leu His Val
145                 150                 155                 160

Gly Asp Thr Ile Asp Leu Ile Phe Asn Ser Glu His Gln Val Leu Lys
                165                 170                 175

Asn Asn Thr Tyr Trp Gly Ile Ile Leu Leu Ala Asn Pro Gln Phe Ile
                180                 185                 190

Ser

<210> SEQ ID NO 72
<211> LENGTH: 133
<212> TYPE: PRT
<213> ORGANISM: Homo sapiens

<400> SEQUENCE: 72

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
 50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu
    130

<210> SEQ ID NO 73
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Met Asp Met Arg Val Pro Ala Gln Leu Leu Gly Leu Leu Leu Leu Trp
1               5                   10                  15

Leu Arg Gly Ala Arg Cys Arg Met Lys Gln Ile Glu Asp Lys Ile Glu
```

```
                 20                  25                  30
Glu Ile Leu Ser Lys Ile Tyr His Ile Glu Asn Glu Ile Ala Arg Ile
             35                  40                  45
Lys Lys Leu Ile Gly Glu Arg Gly Gly Gly Ser Gly Gly Gly Ser Gly
         50                  55                  60
Gly Gly Ser Met Gln Lys Gly Asp Gln Asn Pro Gln Ile Ala Ala His
 65                  70                  75                  80
Val Ile Ser Glu Ala Ser Ser Lys Thr Thr Ser Val Leu Gln Trp Ala
                 85                  90                  95
Glu Lys Gly Tyr Tyr Thr Met Ser Asn Asn Leu Val Thr Leu Glu Asn
            100                 105                 110
Gly Lys Gln Leu Thr Val Lys Arg Gln Gly Leu Tyr Tyr Ile Tyr Ala
        115                 120                 125
Gln Val Thr Phe Cys Ser Asn Arg Glu Ala Ser Ser Gln Ala Pro Phe
    130                 135                 140
Ile Ala Ser Leu Cys Leu Lys Ser Pro Gly Arg Phe Glu Arg Ile Leu
145                 150                 155                 160
Leu Arg Ala Ala Asn Thr His Ser Ser Ala Lys Pro Cys Gly Gln Gln
                165                 170                 175
Ser Ile His Leu Gly Gly Val Phe Glu Leu Gln Pro Gly Ala Ser Val
            180                 185                 190
Phe Val Asn Val Thr Asp Pro Ser Gln Val Ser His Gly Thr Gly Phe
        195                 200                 205
Thr Ser Phe Gly Leu Leu Lys Leu
    210                 215
```

<210> SEQ ID NO 74

<400> SEQUENCE: 74

000

<210> SEQ ID NO 75

<400> SEQUENCE: 75

000

<210> SEQ ID NO 76
<211> LENGTH: 149
<212> TYPE: PRT
<213> ORGANISM: Homo sapiens

<400> SEQUENCE: 76

```
Met Gln Lys Gly Asp Gln Asn Pro Gln Ile Ala Ala His Val Ile Ser
  1               5                  10                  15
Glu Ala Ser Ser Lys Thr Thr Ser Val Leu Gln Trp Ala Glu Lys Gly
             20                  25                  30
Tyr Tyr Thr Met Ser Asn Asn Leu Val Thr Leu Glu Asn Gly Lys Gln
         35                  40                  45
Leu Thr Val Lys Arg Gln Gly Leu Tyr Tyr Ile Tyr Ala Gln Val Thr
     50                  55                  60
Phe Cys Ser Asn Arg Glu Ala Ser Ser Gln Ala Pro Phe Ile Ala Ser
 65                  70                  75                  80
Leu Cys Leu Lys Ser Pro Gly Arg Phe Glu Arg Ile Leu Leu Arg Ala
                 85                  90                  95
Ala Asn Thr His Ser Ser Ala Lys Pro Cys Gly Gln Gln Ser Ile His
```

```
                100               105               110
Leu Gly Gly Val Phe Glu Leu Gln Pro Gly Ala Ser Val Phe Val Asn
            115                 120                 125

Val Thr Asp Pro Ser Gln Val Ser His Gly Thr Gly Phe Thr Ser Phe
            130                 135                 140

Gly Leu Leu Lys Leu
145

<210> SEQ ID NO 77
<211> LENGTH: 177
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His

<210> SEQ ID NO 78
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
50                  55                  60
```

```
Asp Leu Gln Glu Pro Thr Cys Leu Gln Thr Arg Leu Glu Leu Tyr Lys
 65                  70                  75                  80

Gln Gly Leu Arg Gly Ser Leu Thr Lys Leu Lys Gly Pro Leu Thr Met
                 85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 79
<211> LENGTH: 144
<212> TYPE: PRT
<213> ORGANISM: Homo sapiens

<400> SEQUENCE: 79

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
                20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
        50                  55                  60

Asp Leu Gln Glu Pro Thr Cys Leu Gln Thr Arg Leu Glu Leu Tyr Lys
 65                  70                  75                  80

Gln Gly Leu Arg Gly Ser Leu Thr Lys Leu Lys Gly Pro Leu Thr Met
                 85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 80
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
                20                  25                  30

Cys Leu Val Val Cys Ile Gln Arg Phe Ala Gln Ala Gln Gln Gln Leu
            35                  40                  45

Pro Leu Glu Ser Leu Gly Trp Asp Val Ala Glu Leu Gln Leu Asn His
        50                  55                  60

Thr Gly Pro Gln Gln Asp Pro Arg Leu Tyr Trp Gln Gly Gly Pro Ala
 65                  70                  75                  80

Leu Gly Arg Ser Phe Leu His Gly Pro Glu Leu Asp Lys Gly Gln Leu
                 85                  90                  95
```

```
Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro

<210> SEQ ID NO 81
<211> LENGTH: 193
<212> TYPE: PRT
<213> ORGANISM: Homo sapiens

<400> SEQUENCE: 81

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu
        35                  40                  45

Pro Leu Glu Ser Leu Gly Trp Asp Val Ala Glu Leu Gln Leu Asn His
    50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro

<210> SEQ ID NO 82
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
atgactgaca ccctagatct agaaatggac ggaattatta cagagcagcg cctgctagaa      60
```

```
agacgcaggg cagcggccga gcaacagcgc atgaatcaag agctccaaga catggttaac    120
ttgcaccagt gcaaaagggg tatcttttgt ctggtaaagc aggccaaagt cacctacgac    180
agtaatacca ccggacaccg ccttagctac aagttgccaa ccaagcgtca gaaattggtg    240
gtcatggtgg gagaaaagcc cattaccata actcagcact cggtagaaac cgaaggctgc    300
attcactcac cttgtcaagg acctgaggat ctctgcaccc ttattaagac cctgtgcggt    360
ctcaaagatc ttattccctt taactaa                                        387
```

<210> SEQ ID NO 83
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83

```
atgaaattta ctgtgacttt tctgctgatt atttgcaccc tatctgcgtt ttgttccccg    60
acctccaagc tcaaagaca tatatcatgc agattcactc gtatatggaa tattccaagt    120
tgctacaatg aaaaaagcga tctttccgaa gcctggttat atgcaatcat ctctgttatg    180
gtgttctgca gtaccatctt agccctagct atatatccct accttgacat ggctggaac    240 gcaatagatg ccatgaacca cccaactttc ccgcgcccg ctatgcttcc actgcaacaa    300
gttgttgccg gcggctttgt cccagccaat cagcctcgcc caccttctcc cacccccact    360
gaaatcagct actttaatct aacaggagga gatgactga                           399
```

<210> SEQ ID NO 84
<211> LENGTH: 192
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84

```
atgattcctc gagtttttat attactgacc cttgttgcgc ttttttttgtg cgtgctccac    60 attggctgcg gtttctcaca tcgaagtaga ctgcattcca gccttcacag tctatttgct    120
ttacggattt gtcaccctca cgctcatctg cagcctcatc actgtggtca tcgcctttat    180
ccagtgcatt ga                                                        192
```

<210> SEQ ID NO 85
<211> LENGTH: 282
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85

```
atgaccaaca caaccaacgc ggccgccgct accggactta catctaccac aaatacaccc    60
caagtttctg cctttgtcaa taactgggat aacttgggca tgtggtggtt ctccatagcg    120
cttatgtttg tatgccttat tattatgtgg ctcatctgct gcctaaagcg caaacgcgcc    180
cgaccaccca tctatagtcc catcattgtg ctacacccaa acaatgatgg aatccataga    240
ttggacggac tgaaacacat gttcttttct cttacagtat ga                       282
```

<210> SEQ ID NO 86
<211> LENGTH: 483
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 86

```
atgattaggt acataatcct aggtttactc acccttgcgt cagcccacgg taccacccaa    60
aaggtggatt ttaaggagcc agcctgtaat gttacattcg cagctgaagc taatgagtgc   120
accactctta taaatgcac cacagaacat gaaaagctgc ttattcgcca caaaacaaa    180
attggcaagt atgctgttta tgctatttgg cagccaggtg acactacaga gtataatgtt   240
acagttttcc agggtaaaag tcataaaact tttatgtata cttttccatt ttatgaaatg   300
tgcgacatta ccatgtacat gagcaaacag tataagttgt ggccccccaca aaattgtgtg   360
gaaaacactg gcactttctg ctgcactgct atgctaatta cagtgctcgc tttggtctgt   420
accctactct atattaaata caaaagcaga cgcagcttta ttgaggaaaa gaaaatgcct   480
taa                                                                  483
```

<210> SEQ ID NO 87
<211> LENGTH: 192
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 87

```
atgaacaatt caagcaactc tacgggctat tctaattcag gtttctctag aatcggggtt    60
ggggttattc tctgtcttgt gattctcttt attcttatac taacgcttct ctgcctaagg   120
ctcgccgcct gctgtgtgca catttgcatt tattgtcagc ttttttaaacg ctggggtcgc   180
cacccaagat ga                                                        192
```

<210> SEQ ID NO 88
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 88

```
atgttaagtg gagaggcaga gcaactgcgc ctgaaacacc tggtccactg tcgccgccac    60
aagtgctttg cccgcgactc cggtgagttt tgctactttg aattgcccga ggatcatatc   120
gagggcccgg cgcacggcgt ccggcttacc gcccagggag agcttgcccg tagcctgatt   180
cgggagttta cccagcgccc cctgctagtt gagcgggaca ggggaccctg tgttctcact   240
gtgatttgca actgtcctaa ccctggatta catcaagatc tttgttgcca tctctgtgct   300
gagtataata aatacagaaa ttaa                                           324
```

<210> SEQ ID NO 89
<211> LENGTH: 379
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89

```
caccctagat ctagaaatgg acggaattat tacagagcag cgcctgctag aaagacgcag      60
ggcagcggcc gagcaacagc gcatgaatca agagctccaa gacatggtta acttgcacca     120
gtgcaaaagg ggtatctttt gtctggtaaa gcaggccaaa gtcacctacg acagtaatac     180
caccggacac cgccttagct acaagttgcc aaccaagcgt cagaaattgg tggtcatggt     240
gggagaaaag cccattacca taactcagca ctcggtagaa accgaaggct gcattcactc     300
accttgtcaa ggacctgagg atctctgcac ccttattaag accctgtgcg gtctcaaaga     360
tcttattccc tttaactaa                                                  379
```

<210> SEQ ID NO 90
<211> LENGTH: 755
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 90

```
agacgcccag gccgaagttc agatgactaa ctcaggggcg cagcttgcgg gcggctttcg      60
tcacagggtg cggtcgcccg ggcagggtat aactcacctg acaatcagag ggcgaggtat     120
tcagctcaac gacgagtcgg tgagctcctc gcttggtctc cgtccggacg ggacatttca     180
gatcggcggc gccggccgct cttcattcac gcctcgtcag gcaatcctaa ctctgcagac     240
ctcgtcctct gagccgcgct ctggaggcat tggaactctg caatttattg aggagtttgt     300
gccatcggtc tactttaacc ccttctcggg acctcccggc cactatccgg atcaatttat     360
tcctaacttt gacgcggtaa aggactcggc ggacggctac gactgaatgt taagtggaga     420
ggcagagcaa ctgcgcctga aacacctggt ccactgtcgc cgccacaagt gctttgcccg     480
cgactccggt gagttttgct actttgaatt gcccgaggat catatcgagg cccggcgca     540
cggcgtccgg cttaccgccc agggagagct tgcccgtagc ctgattcggg agtttaccca     600
gcgcccctg ctagttgagc gggacagggg accctgtgtt ctcactgtga tttgcaactg     660
tcctaaccct ggattacatc aagatcctct agttaatgtc aggtcgccta agtcgattaa     720
ctagagtacc cggggatctt attcccttta actaa                                755
```

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 91

```
gatcttattc cctttaacta a                                                21
```

<210> SEQ ID NO 92
<211> LENGTH: 279
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 92

```
atgttaagtg gagaggcaga gcaactgcgc ctgaaacacc tggtccactg tcgccgccac      60
```

```
aagtgctttg cccgcgactc cggtgagttt tgctactttg aattgcccga ggatcatatc    120
gagggcccgg cgcacggcgt ccggcttacc gcccagggag agcttgcccg tagcctgatt    180
cgggagttta cccagcgccc cctgctagtt gagcgggaca ggggaccctg tgttctcact    240
gtgatttgca actgtcctaa ccctggatta catcaagat                           279
```

<210> SEQ ID NO 93
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93

```
agacgcccag gccgaagttc agatgacta                                       29
```

<210> SEQ ID NO 94
<211> LENGTH: 33225
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94

```
ttttggattg aagccaatat gataatgagg gggtggagtt tgtgacgtgg cgcggggcgt     60
gggaacgggg cgggtgacgt agtagtgtgg cggaagtgtg atgttgcaag tgtggcggaa    120
cacatgtaag cgacggatgt ggcaaaagtg acgttttggg tgtgcgccgg tgttttgggc    180
gtaaccgagt aagatttggc cattttcgcg ggaaaactga ataagaggaa gtgaaatctg    240
aataattttg tgttactcat agcgcgtaat atttgtctag ggccgcgggg actttgaccg    300
tttacgtgga gactcgccca ggtgttttttc tcaggtgttt tccgcgttcc gggtcaaagt    360
tggcgtttta ttattatagt cagctgacgt gtagtgtatt tatacccggt gagttcctca    420
agaggccact cttgagtgcc agcgagtaga gttttctcct ccgagccgct ccgacaccgg    480
gactgaaaat gagacatatt atctgccacg gaggtgttat taccgaagaa atggccgcca    540 gtctttttgga ccagctgatc gaagaggtac tggctgataa tcttccacct cctagccatt    600
ttgaaccacc tacccttcac gaactgtatg atttagacgt gacggccccc gaagatccca    660
acgaggaggc ggtttcgcag attttttсссg actctgtaat gttggcggtg caggaaggga    720
ttgacttact cactttttccg ccggcgcccg gttctccgga gccgcctcac ctttcccggc    780
agcccgagca gccggagcag agagccttgg gtccggtttc tatgccaaac cttgtaccgg    840
aggtgatcga tcttacctgc cacgaggctg gctttccacc cagtgacgac gaggatgaag    900
agggtgagga gtttgtgtta gattatgtgg agcaccccgg gcacggttgc aggtcttgtc    960
attatcaccg gaggaatacg ggggacccag atattatgtg ttcgctttgc tatatgagga   1020
cctgtggcat gtttgtctac agtaagtgaa aattatgggc agtgggtgat agagtggtgg   1080
gtttggtgtg gtaattttttt ttttaatttt tacagttttg tggtttaaag aattttgtat   1140
tgtgattttt ttaaaaggtc ctgtgtctga acctgagcct gagcccgagc cagaaccgga   1200
gcctgcaaga cctacccgcc gtcctaaaat ggcgcctgct atcctgagac gcccgacatc   1260
acctgtgtct agagaatgca atagtagtac ggatagctgt gactccggtc cttctaacac   1320
acctcctgag atacacccgg tggtcccgct gtgccccatt aaaccagttg ccgtgagagt   1380
tggtgggcgt cgccaggctg tggaatgtat cgaggacttg cttaacgagc ctgggcaacc   1440
```

-continued

```
tttggacttg agctgtaaac gccccaggcc ataaggtgta aacctgtgat tgcgtgtgtg   1500
gttaacgcct ttgtttgctg aatgagttga tgtaagttta ataaagggtg agataatgtt   1560
taacttgcat ggcgtgttaa atggggcggg gcttaaaggg tatataatgc gccgtgggct   1620
aatcttggtt acatctgacc tcgtcgacgc ttgggagtgt ttggaagatt tttctgctgt   1680
gcgtaacttg ctggaacaga gctctaacag tacctcttgg ttttggaggt ttctgtgggg   1740
ctcatcccag gcaaagttag tctgcagaat taaggaggat tacaagtggg aatttgaaga   1800
gcttttgaaa tcctgtggtg agctgtttga ttctttgaac tcgagtcacc aggcgctttt   1860
ccaagagaag gtcatcaaga ctttggattt ttccacaccg gggcgcgctg cggctgctgt   1920
tgcttttttg agttttataa aggataaatg gagcgaagaa acccatctga gcgggggggta   1980 cctgctggat tttctggcca tgcatctgtg gagagcggtt gtgagacaca gaatcgcct   2040 gctactgttg tcttccgtcc gcccggcgat aataccgacg gaggagcagc agcagcagca   2100
ggaggaagcc aggcggcggc ggcaggagca gagcccatgg aacccgagag ccggcctgga   2160
ccctcgggaa tgaatgttgt acaggtggct gaactgtatc cagaactgag acgcattttg   2220
acaattacag aggatgggca ggggctaaag gggtaaaga gggagcgggg ggcttgtgag   2280
gctacagagg aggctaggaa tctagctttt agcttaatga ccagacaccg tcctgagtgt   2340
attacttttc aacagatcaa ggataattgc gctaatgagc ttgatctgct ggcgcagaag   2400
tattccatag agcagctgac cacttactgg ctgcagccag gggatgattt tgaggaggct   2460
attagggtat atgcaaaggt ggcacttagg ccagattgca agtacaagat cagcaaactt   2520
gtaaatatca ggaattgttg ctacatttct gggaacgggg ccgaggtgga gatagatacg   2580
gaggataggg tggcctttag atgtagcatg ataaatatgt ggccgggggt gcttggcatg   2640
gacggggtgg ttattatgaa tgtaaggttt actggcccca attttagcgg tacggttttc   2700
ctggccaata ccaaccttat cctacacggt gtaagcttct atgggtttaa caatacctgt   2760
gtggaagcct ggaccgatgt aagggttcgg ggctgtgcct tttactgctg ctggaagggg   2820
gtggtgtgtc gccccaaaag cagggcttca attaagaaat gcctctttga aaggtgtacc   2880
ttgggtatcc tgtctgaggg taactccagg gtgcgccaca atgtggcctc cgactgtggt   2940
tgcttcatgc tagtgaaaag cgtggctgtg attaagcata acatggtatg tggcaactgc   3000
gaggacaggg cctctcagat gctgacctgc tcggacggca actgtcacct gctgaagacc   3060
attcacgtag ccagccactc tcgcaaggcc tggccagtgt ttgagcataa catactgacc   3120
cgctgttcct tgcatttggg taacaggagg ggggtgttcc taccttacca atgcaatttg   3180
agtcacacta agatattgct tgagcccgag agcatgtcca aggtgaacct gaacggggtg   3240
tttgacatga ccatgaagat ctggaaggtg ctgaggtacg atgagacccg caccaggtgc   3300
agaccctgcg agtgtggcgg taaacatatt aggaaccagc ctgtgatgct ggatgtgacc   3360
gaggagctga ggcccgatca cttggtgctg gcctgcaccc gcgctgagtt tggctctagc   3420
gatgaagata cagattgagg tactgaaatg tgtgggcgtg gcttaagggt gggaaagaat   3480
atataaggtg ggggtcttat gtagttttgt atctgttttg cagcagccgc cgccgccatg   3540
agcaccaact cgtttgatgg aagcattgtg agctcatatt tgacaacgcg catgccccca   3600
tgggccgggg tgcgtcagaa tgtgatgggc tccagcattg atggtcgccc cgtcctgccc   3660
gcaaactcta ctaccttgac ctacgagacc gtgtctggaa cgccgttgga gactgcagcc   3720
tccgccgccg cttcagccgc tgcagccacc gcccgcggga ttgtgactga cttttgcttt   3780
```

```
ctgagcccgc ttgcaagcag tgcagcttcc cgttcatccg cccgcgatga caagttgacg    3840
gctcttttgg cacaattgga ttctttgacc cgggaactta atgtcgtttc tcagcagctg    3900
ttggatctgc gccagcaggt ttctgccctg aaggcttcct cccctcccaa tgcggtttaa    3960
aacataaata aaaaccagac tctgttttgg atttggatca agcaagtgtc ttgctgtctt    4020
tatttagggg ttttgcgcgc gcggtaggcc cgggaccagc ggtctcggtc gttgagggtc    4080
ctgtgtattt tttccaggac gtggtaaagg tgactctgga tgttcagata catgggcata    4140
agcccgtctc tggggtggag gtagcaccac tgcagagctt catgctgcgg ggtggtgttg    4200
tagatgatcc agtcgtagca ggagcgctgg gcgtggtgcc taaaaatgtc tttcagtagc    4260
aagctgattg ccaggggcag gcccttggtg taagtgttta caaagcggtt aagctgggat    4320
gggtgcatac gtggggatat gagatgcatc ttggactgta ttttaggtt ggctatgttc    4380 ccagccatat ccctccgggg attcatgttg tgcagaacca ccagcacagt gtatccggtg    4440
cacttgggaa atttgtcatg tagcttagaa ggaaatgcgt ggaagaactt ggagacgccc    4500
ttgtgacctc caagatttc catgcattcg tccataatga tggcaatggg cccacgggcg    4560
gcggcctggg cgaagatatt tctgggatca ctaacgtcat agttgtgttc caggatgaga    4620
tcgtcatagg ccattttac aaagcgcggg cggagggtgc cagactgcgg tataatggtt    4680
ccatccggcc caggggcgta gttaccctca cagatttgca tttcccacgc tttgagttca    4740
gatgggggga tcatgtctac ctgcggggcg atgaagaaaa cggtttccgg ggtaggggag    4800
atcagctggg aagaaagcag gttcctgagc agctgcgact taccgcagcc ggtgggcccg    4860
taaatcacac ctattaccgg ctgcaactgg tagttaagag agctgcagct gccgtcatcc    4920
ctgagcaggg gggccacttc gttaagcatg tccctgactc gcatgttttc cctgaccaaa    4980
tccgccagaa ggcgctcgcc gcccagcgat agcagttctt gcaaggaagc aaagtttttc    5040
aacggtttga gaccgtccgc cgtaggcatg cttttgagcg tttgaccaag cagttccagg    5100
cggtcccaca gctcggtcac ctgctctacg gcatctcgat ccagcatatc tcctcgtttc    5160
gcgggttggg gcggctttcg ctgtacggca gtagtcggtg ctcgtccaga cgggccaggg    5220
tcatgtcttt ccacgggcgc agggtcctcg tcagcgtagt ctgggtcacg gtgaaggggt    5280
gcgctccggg ctgcgcgctg ccagggtgc gcttgaggct ggtcctgctg gtgctgaagc    5340
gctgccggtc ttcgccctgc gcgtcggcca ggtagcattt gaccatggtg tcatagtcca    5400
gcccctccgc ggcgtggccc ttggcgcgca gcttgcccct ggaggaggcg ccgcacgagg    5460
ggcagtgcag acttttgagg gcgtagagct tgggcgcgag aaataccgat tccggggagt    5520
aggcatccgc gccgcaggcc ccgcagacgg tctcgcattc cacgagccag gtgagctctg    5580
gccgttcggt gtcaaaaacc aggtttcccc catgcttttt gatgcgtttc ttacctctgg    5640
tttccatgag ccggtgtcca cgctcggtga cgaaaaggct gtccgtgtcc ccgtatacag    5700
acttgagagg cctgtcctcg agcggtgttc cgcggtcctc ctcgtataga aactcggacc    5760
actctgagac aaaggctcgc gtccaggcca gcacgaagga ggctaagtgg gaggggtagc    5820
ggtcgttgtc cactaggggg tccactcgct ccagggtgtg aagacacatg tcgccctctt    5880
cggcatcaag gaaggtgatt ggtttgtagg tgtaggccac gtgaccgggt gttcctgaag    5940
gggggctata aaggggggtg gggcgcgtt cgtcctcact ctcttccgca tcgctgtctg    6000
cgagggccag ctgttggggt gagtactccc tctgaaaagc gggcatgact tctgcgctaa    6060
gattgtcagt ttccaaaaac gaggaggatt tgatattcac ctggcccgcg gtgatgcctt    6120
tgagggtggc cgcatccatc tggtcagaaa agacaatctt tttgttgtca agcttggtgg    6180
```

```
caaacgaccc gtagagggcg ttggacagca acttggcgat ggagcgcagg gtttggtttt    6240
tgtcgcgatc ggcgcgctcc ttggccgcga tgtttagctg cacgtattcg cgcgcaacgc    6300
accgccattc gggaaagacg gtggtgcgct cgtcgggcac caggtgcacg cgccaaccgc    6360
ggttgtgcag ggtgacaagg tcaacgctgg tggctacctc tccgcgtagg cgctcgttgg    6420
tccagcagag gcggccgccc ttgcgcgagc agaatggcgg tagggggtct agctgcgtct    6480
cgtccggggg gtctgcgtcc acggtaaaga ccccgggcag caggcgcgcg tcgaagtagt    6540
ctatcttgca tccttgcaag tctagcgcct gctgccatgc gcgggcggca agcgcgcgct    6600
cgtatgggtt gagtggggga ccccatggca tggggtgggt gagcgcggag cgtacatgc    6660 cgcaaatgtc gtaaacgtag aggggctctc tgagtattcc aagatatgta gggtagcatc    6720
ttccaccgcg gatgctggcg cgcacgtaat cgtatagttc gtgcgaggga gcgaggaggt    6780
cgggaccgag gttgctacgg gcgggctgct ctgctcggaa gactatctgc ctgaagatgg    6840
catgtgagtt ggatgatatg gttggacgct ggaagacgtt gaagctggcg tctgtgagac    6900
ctaccgcgtc acgcacgaag gaggcgtagg agtcgcgcag cttgttgacc agctcggcgg    6960
tgacctgcac gtctagggcg cagtagtcca gggtttcctt gatgatgtca tacttatcct    7020
gtcccttttt tttccacagc tcgcggttga ggacaaactc ttcgcggtct ttccagtact    7080
cttggatcgg aaaccgtcg gcctccgaac ggtaagagcc tagcatgtag aactggttga    7140
cggcctggta ggcgcagcat cccttttcta cgggtagcgc gtatgcctgc gcggccttcc    7200
ggagcgaggt gtgggtgagc gcaaaggtgt ccctgaccat gactttgagg tactggtatt    7260
tgaagtcagt gtcgtcgcat ccgccctgct cccagagcaa aaagtccgtg cgcttttgg    7320 aacgcggatt tggcagggcg aaggtgacat cgttgaagag tatctttccc gcgcgaggca    7380
taaagttgcg tgtgatgcgg aagggtcccg gcacctcgga acggttgtta attacctggg    7440
cggcgagcac gatctcgtca aagccgttga tgttgtggcc cacaatgtaa agttccaaga    7500
agcgcgggat gcccttgatg gaaggcaatt ttttaagttc ctcgtaggtg agctcttcag    7560
gggagctgag cccgtgctct gaaagggccc agtctgcaag atgagggttg gaagcgacga    7620
atgagctcca caggtcacgg gccattagca tttgcaggtg gtcgcgaaag gtcctaaact    7680
ggcgacctat ggccatttt tctggggtga tgcagtagaa ggtaagcggg tcttgttccc    7740
agcggtccca tccaaggttc gcggctaggt ctcgcgcggc agtcactaga ggctcatctc    7800
cgccgaactt catgaccagc atgaagggca cgagctgctt cccaaaggcc cccatccaag    7860
tataggtctc tacatcgtag gtgacaaaga gacgctcggt gcgaggatgc gagccgatcg    7920
ggaagaactg gatctcccgc caccaattgg aggagtggct attgatgtgg tgaaagtaga    7980
agtccctgcg acgggccgaa cactcgtgct ggcttttgta aaaacgtgcg cagtactggc    8040
agcggtgcac gggctgtaca tcctgcacga ggttgacctg acgaccgcgc acaaggaagc    8100
agagtgggaa tttgagcccc tcgcctggcg ggtttggctg gtggtcttct acttcggctg    8160
cttgtccttg accgtctggc tgctcgaggg gagttacggt ggatcggacc accacgccgc    8220
gcgagcccaa agtccagatg tccgcgcgcg gcggtcggag cttgatgaca acatcgcgca    8280
gatgggagct gtccatggtc tggagctccc gcggcgtcag gtcaggcggg agctcctgca    8340
ggtttacctc gcatagacgg gtcagggcgc gggctagatc caggtgatac ctaatttcca    8400
ggggctggtt ggtggcggcg tcgatggctt gcaagaggcc gcatccccgc ggcgcgacta    8460
cggtaccgcg cggcgggcgg tgggccgcgg gggtgtcctt ggatgatgca tctaaaagcg    8520
```

```
gtgacgcggg cgagccccg gaggtagggg gggctccgga cccgccggga gagggggcag      8580
gggcacgtcg gcgccgcgcg cgggcaggag ctggtgctgc gcgcgtaggt tgctggcgaa      8640
cgcgacgacg cggcggttga tctcctgaat ctggcgcctc tgcgtgaaga cgacgggccc      8700
ggtgagcttg aacctgaaag agagttcgac agaatcaatt tcggtgtcgt tgacggcggc      8760
ctggcgcaaa atctcctgca cgtctcctga gttgtcttga taggcgatct cggccatgaa      8820
ctgctcgatc tcttcctcct ggagatctcc gcgtccggct cgctccacgg tggcggcgag      8880
gtcgttggaa atgcgggcca tgagctgcga gaaggcgttg aggcctccct cgttccagac      8940
gcggctgtag accacgcccc cttcggcatc gcgggcgcgc atgaccacct gcgcgagatt      9000
gagctccacg tgccgggcga agacggcgta gtttcgcagg cgctgaaaga ggtagttgag      9060
ggtggtggcg gtgtgttctg ccacgaagaa gtacataacc cagcgtcgca acgtggattc      9120
gttgatatcc cccaaggcct caaggcgctc catggcctcg tagaagtcca cggcgaagtt      9180
gaaaaactgg gagttgcgcg ccgacacggt taactcctcc tccagaagac ggatgagctc      9240
ggcgacagtg tcgcgcacct cgcgctcaaa ggctacaggg gcctcttctt cttcttcaat      9300
ctcctcttcc ataagggcct ccccttcttc ttcttctggc ggcggtgggg gagggggac      9360 acggcggcga cgacggcgca ccgggaggcg gtcgacaaag cgctcgatca tctccccgcg      9420
gcgacggcgc atggtctcgg tgacggcgcg gccgttctcg cggggcgca gttggaagac      9480 gccgcccgtc atgtcccggt tatgggttgg cgggggctg ccatgcggca gggatacggc      9540
gctaacgatg catctcaaca attgttgtgt aggtactccg ccgccgaggg acctgagcga      9600
gtccgcatcg accggatcgg aaaacctctc gagaaaggcg tctaaccagt cacagtcgca      9660
aggtaggctg agcaccgtgg cgggcggcag cgggcggcgg tcggggttgt ttctggcgga      9720
ggtgctgctg atgatgtaat taaagtaggc ggtcttgaga cggcggatgg tcgacagaag      9780
caccatgtcc ttgggtccgg cctgctgaat gcgcaggcgg tcggccatgc cccaggcttc      9840
gttttgacat cggcgcaggt ctttgtagta gtccttgcatg agcctttcta ccggcacttc      9900
ttcttctcct tcctcttgtc ctgcatctct tgcatctatc gctgcggcgg cggcggagtt      9960
tggccgtagg tggcgccctc ttcctcccat gcgtgtgacc ccgaagcccc tcatcggctg     10020
aagcagggct aggtcggcga caacgcgctc ggctaatatg gcctgctgca cctgcgtgag     10080
ggtagactgg aagtcatcca tgtccacaaa gcggtggtat gcgcccgtgt tgatggtgta     10140
agtgcagttg gccataacgg accagttaac ggtctggtga cccggctgcg agagctcggt     10200
gtacctgaga cgcgagtaag ccctcgagtc aaatacgtag tcgttgcaag tccgcaccag     10260
gtactggtat cccaccaaaa agtgcggcgg cggctggcgg tagaggggcc agcgtagggt     10320
ggccggggct ccggggcga gatcttccaa cataaggcga tgatatccgt agatgtacct     10380
ggacatccag gtgatgccgg cggcggtggt ggaggcgcgc ggaaagtcgc ggacgcggtt     10440
ccagatgttg cgcagcggca aaagtgctc catggtcggg acgctctggc cggtcaggcg     10500
cgcgcaatcg ttgacgctct agcgtgcaaa aggagagcct gtaagcgggc actcttccgt     10560
ggtctggtgg ataaattcgc aagggtatca tggcggacga ccggggttcg agccccgtat     10620
ccggccgtcc gccgtgatcc atgcggttac cgcccgcgtg tcgaacccag gtgtgcgacg     10680
tcagacaacg ggggagtgct ccttttggct tccttccagg cgcggcggct gctgcgctag     10740 ctttttttggc cactgccgc gcgcagcgta agcggttagg ctggaaagcg aaagcattaa     10800
gtggctcgct ccctgtagcc ggagggttat tttccaaggg ttgagtcgcg ggaccccgg     10860 ttcgagtctc ggaccggccg gactgcggcg aacggggtt tgcctccccg tcatgcaaga     10920
```

```
ccccgcttgc aaattcctcc ggaaacaggg acgagcccct tttttgcttt tcccagatgc   10980
atccggtgct gcggcagatg cgccccctc ctcagcagcg gcaagagcaa gagcagcggc   11040
agacatgcag ggcaccctcc cctcctccta ccgcgtcagg aggggcgaca tccgcggttg   11100
acgcggcagc agatggtgat tacgaacccc cgcggcgccg ggcccggcac tacctggact   11160
tggaggaggg cgagggcctg gcgcggctag gagcgccctc tcctgagcgg cacccaaggg   11220
tgcagctgaa gcgtgatacg cgtgaggcgt acgtgccgcg gcagaacctg tttcgcgacc   11280
gcgagggaga ggagcccgag gagatgcggg atcgaaagtt ccacgcaggg cgcgagctgc   11340
ggcatggcct gaatcgcgag cggttgctgc gcgaggagga ctttgagccc gacgcgcgaa   11400
ccgggattag tcccgcgcgc gcacacgtgg cggccgccga cctggtaacc gcatacgagc   11460
agacggtgaa ccaggagatt aactttcaaa aaagctttaa caaccacgtg cgtacgcttg   11520
tggcgcgcga ggaggtggct ataggactga tgcatctgtg ggactttgta agcgcgctgg   11580
agcaaaaccc aaatagcaag ccgctcatgg cgcagctgtt ccttatagtg cagcacagca   11640
gggacaacga ggcattcagg gatgcgctgc taaacatagt agagcccgag ggccgctggc   11700
tgctcgattt gataaacatc ctgcagagca tagtggtgca ggagcgcagc ttgagcctgg   11760
ctgacaaggt ggccgccatc aactattcca tgcttagcct gggcaagttt tacgcccgca   11820
agatatacca tacccttac gttcccatag acaaggaggt aaagatcgag gggttctaca   11880
tgcgcatggc gctgaaggtg cttaccttga gcgacgacct gggcgtttat cgcaacgagc   11940
gcatccacaa ggccgtgagc gtgagccggc ggcgcgagct cagcgaccgc gagctgatgc   12000
acagcctgca aagggccctg gctggcacgg gcagcggcga tagagaggcc gagtcctact   12060
ttgacgcggg cgctgacctg cgctgggccc aagccgacg cgccctggag gcagctgggg   12120
ccggacctgg gctggcggtg gcaccccgcgc gcgctggcaa cgtcggcggc gtggaggaat   12180
atgacgagga cgatgagtac gagccagagg acggcgagta ctaagcggtg atgtttctga   12240
tcagatgatg caagacgcaa cggacccggc ggtgcgggcg gcgctgcaga gccagccgtc   12300
cggccttaac tccacggacg actgcgcca ggtcatggac cgcatcatgt cgctgactgc   12360
gcgcaatcct gacgcgttcc ggcagcagcc gcaggccaac cggctctccg caattctgga   12420
agcggtggtc ccggcgcgcg caaaccccac gcacgagaag gtgctggcga tcgtaaacgc   12480
gctggccgaa aacagggcca tccggcccga cgaggccggc ctggtctacg acgcgctgct   12540
tcagcgcgtg gctcgttaca acagcggcaa cgtgcagacc aacctggacc ggctggtggg   12600
ggatgtgcgc gaggccgtgg cgcagcgtga gcgcgcgcag cagcagggca acctgggctc   12660
catggttgca ctaaacgcct tcctgagtac acagcccgcc aacgtgccgc ggggacagga   12720
ggactacacc aactttgtga gcgcactgcg gctaatggtg actgagacac cgcaaagtga   12780
ggtgtaccag tctgggccag actatttttt ccagaccagt agacaaggcc tgcagaccgt   12840
aaacctgagc caggctttca aaaacttgca ggggctgtgg ggggtgcggg ctcccacagg   12900
cgaccgcgcg accgtgtcta gcttgctgac gcccaactcg cgcctgttgc tgctgctaat   12960 agcgccttc acggacagtg gcagcgtgtc ccgggacaca tacctaggtc acttgctgac   13020
actgtaccgc gaggccatag gtcaggcgca tgtggacgag catactttcc aggagattac   13080
aagtgtcagc cgcgcgctgg ggcaggagga cacgggcagc ctggaggcaa ccctaaacta   13140
cctgctgacc aaccgcggc agaagatccc ctcgttgcac agtttaaaca gcaggaggaa   13200
gcgcattttg cgctacgtgc agcagagcgt gagccttaac ctgatgcgcg acgggtaac   13260
```

```
gcccagcgtg gcgctggaca tgaccgcgcg caacatggaa ccgggcatgt atgcctcaaa    13320
ccggccgttt atcaaccgcc taatggacta cttgcatcgc gcggccgccg tgaaccccga    13380
gtatttcacc aatgccatct tgaacccgca ctggctaccg cccctggtt tctacaccgg     13440 gggattcgag gtgcccgagg gtaacgatgg attcctctgg gacgacatag acgacagcgt    13500
gttttccccg caaccgcaga ccctgctaga gttgcaacag cgcgagcagg cagaggcggc    13560
gctgcgaaag gaaagcttcc gcaggccaag cagcttgtcc gatctaggcg ctgcggcccc    13620
gcggtcagat gctagtagcc catttccaag cttgataggg tctcttacca gcactcgcac    13680
cacccgcccg cgcctgctgg gcgaggagga gtacctaaac aactcgctgc tgcagccgca    13740
gcgcgaaaaa aacctgcctc cggcatttcc caacaacggg atagagagcc tagtggacaa    13800
gatgagtaga tggaagacgt acgcgcagga gcacagggac gtgccaggcc cgcgcccgcc    13860
cacccgtcgt caaaggcacg accgtcagcg gggtctggtg tgggaggacg atgactcggc    13920
agacgacagc agcgtcctgg atttggggagg gagtggcaac ccgtttgcgc accttcgccc    13980
caggctgggg agaatgtttt aaaaaaaaaa aagcatgatg caaaataaaa aactcaccaa    14040
ggccatggca ccgagcgttg gttttcttgt attccccttta gtatgcggcg cgcggcgatg    14100
tatgaggaag gtcctcctcc ctcctacgag agtgtggtga gcgcggcgcc agtggcggcg    14160
gcgctgggtt ctcccttcga tgctcccctg gacccgccgt tgtgcctcc gcggtacctg     14220 cggcctaccg gggggagaaa cagcatccgt tactctgagt tggcacccct attcgacacc    14280
acccgtgtgt acctggtgga caacaagtca acggatgtgg catccctgaa ctaccagaac    14340
gaccacagca actttctgac cacggtcatt caaaacaatg actacagccc gggggaggca    14400
agcacacaga ccatcaatct tgacgaccgg tcgcactggg gcggcgacct gaaaaccatc    14460
ctgcatacca acatgccaaa tgtgaacgag ttcatgttta ccaataagtt taaggcgcgg    14520
gtgatggtgt cgcgcttgcc tactaaggac aatcaggtgg agctgaaata cgagtgggtg    14580
gagttcacgc tgcccgaggg caactactcc gagaccatga ccatagacct tatgaacaac    14640
gcgatcgtgg agcactactt gaaagtgggc agacagaacg gggttctgga agcgacatc     14700 ggggtaaagt ttgacacccg caacttcaga ctggggtttg accccgtcac tggtcttgtc    14760
atgcctgggg tatatacaaa cgaagccttc catccagaca tcattttgct gccaggatgc    14820
ggggtggact tcacccacag ccgcctgagc aacttgttgg gcatccgcaa gcggcaaccc    14880
ttccaggagg gctttaggat cacctacgat gatctggagg gtggtaacat tcccgcactg    14940
ttggatgtgg acgcctacca ggcgagcttg aaagatgaca ccgaacaggg cggggtggc    15000 gcaggcggca gcaacagcag tggcagcggc gcggaagaga actccaacgc ggcagccgcg    15060
gcaatgcagc cggtggagga catgaacgat catgccattc gcggcgacac ctttgccaca    15120
cgggctgagg agaagcgcgc tgaggccgaa gcagcggccg aagctgccgc ccccgctgcg    15180
caacccgagg tcgagaagcc tcagaagaaa ccggtgatca aacccctgac agaggacagc    15240
aagaaacgca gttacaacct aataagcaat gacagcacct tcacccagta ccgcagctgg    15300
taccttgcat acaactacgg cgaccctcag accggaatcc gctcatggac cctgcttttgc    15360 actcctgacg taacctgcgg ctcggagcag gtctactggt cgttgccaga catgatgcaa    15420
gaccccgtga ccttccgctc cacgcgccag atcagcaact ttccggtggt gggcgccgag    15480
ctgttgccgg tgcactccaa gagcttctac aacgaccagg ccgtctactc ccaactcatc    15540
cgccagttta cctctctgac ccacgtgttc aatcgctttc ccgagaacca gattttggcg    15600
cgcccgccag cccccaccat caccaccgtc agtgaaaacg ttcctgctct cacagatcac    15660
```

```
gggacgctac cgctgcgcaa cagcatcgga ggagtccagc gagtgaccat tactgacgcc   15720
agacgccgca cctgccccta cgtttacaag gccctgggca tagtctcgcc gcgcgtccta   15780
tcgagccgca cttttttgagc aagcatgtcc atccttatat cgcccagcaa taacacaggc   15840
tggggcctgc gcttcccaag caagatgttt ggcggggcca agaagcgctc cgaccaacac   15900
ccagtgcgcg tgcgcgggca ctaccgcgcg ccctggggcg cgcacaaacg cggccgcact   15960
gggcgcacca ccgtcgatga cgccatcgac gcggtggtgg aggaggcgcg caactacacg   16020
cccacgccgc caccagtgtc cacagtggac gcggccattc agaccgtggt gcgcggagcc   16080
cggcgctatg ctaaaatgaa gagacggcgg aggcgcgtag cacgtcgcca ccgccgccga   16140
cccggcactg ccgcccaacg cgcggcggcg gccctgctta accgcgcacg tcgcaccggc   16200
cgacgggcgg ccatgcgggc cgctcgaagg ctggccgcgg gtattgtcac tgtgcccccc   16260
aggtccaggc gacgagcggc cgccgcagca gccgcggcca ttagtgctat gactcagggt   16320
cgcaggggca acgtgtattg ggtgcgcgac tcggttagcg gcctgcgcgt gcccgtgcgc   16380
acccgccccc cgcgcaacta gattgcaaga aaaaactact tagactcgta ctgttgtatg   16440
tatccagcgg cggcggcgcg caacgaagct atgtccaagc gcaaaatcaa agaagagatg   16500
ctccaggtca tcgcgccgga gatctatggc cccccgaaga aggaagagca ggattacaag   16560
ccccgaaagc taaagcgggt caaaaagaaa aagaaagatg atgatgatga acttgacgac   16620
gaggtggaac tgctgcacgc taccgcgccc aggcgacggg tacagtggaa aggtcgacgc   16680
gtaaaacgtg ttttgcgacc cggcaccacc gtagtcttta cgcccggtga gcgctccacc   16740
cgcacctaca agcgcgtgta tgatgaggtg tacgcgacg aggacctgct tgagcaggcc   16800
aacgagcgcc tcggggagtt tgcctacgga aagcggcata aggacatgct ggcgttgccg   16860
ctggacgagg gcaacccaac acctagccta aagcccgtaa cactgcagca ggtgctgccc   16920
gcgcttgcac cgtccgaaga aaagcgcggc ctaaagcgcg agtctggtga cttggcaccc   16980
accgtgcagc tgatggtacc caagcgccag cgactggaag atgtcttgga aaaaatgacc   17040
gtggaacctg gctggagcc cgaggtccgc gtgcggccaa tcaagcaggt ggcgccggga   17100
ctgggcgtgc agaccgtgga cgttcagata cccactacca gtagcaccag tattgccacc   17160
gccacagagg gcatggagac acaaacgtcc ccggttgcct cagcggtggc ggatgccgcg   17220
gtgcaggcgg tcgctgcggc cgcgtccaag acctctacgg aggtgcaaac ggacccgtgg   17280
atgtttcgcg tttcagcccc ccggcgcccg cgccgttcga ggaagtacgg cgccgccagc   17340
gcgctactgc ccgaatatgc cctacatcct tccattgcgc ctaccccgg ctatcgtggc   17400 tacacctacc gccccagaag acgagcaact acccgacgcc gaaccaccac tggaacccgc   17460
cgccgccgtc gccgtcgcca gccgtgctg gccccgattt ccgtgcgcag ggtggctcgc   17520
gaaggaggca ggaccctggt gctgccaaca gcgcgctacc accccagcat cgtttaaaag   17580
ccggtctttg tggttcttgc agatatggcc ctcacctgcc gcctccgttt cccggtgccg   17640
ggattccgag gaagaatgca ccgtaggagg ggcatggccg gccacggcct gacgggcggc   17700
atgcgtcgtg cgcaccaccg gcggcggcgc gcgtcgcacc gtcgcatgcg cggcggtatc   17760
ctgcccctcc ttattccact gatcgccgcg gcgattggcg ccgtgcccgg aattgcatcc   17820
gtggccttgc aggcgcagag acactgatta aaaacaagtt gcatgtggaa aaatcaaaat   17880
aaaaagtctg gactctcacg ctcgcttggt cctgtaacta ttttgtagaa tggaagacat   17940
caactttgcg tctctggccc cgcgacacgg ctcgcgcccg ttcatgggaa actggcaaga   18000
```

```
tatcggcacc agcaatatga gcggtggcgc cttcagctgg ggctcgctgt ggagcggcat   18060
taaaaatttc ggttccaccg ttaagaacta tggcagcaag gcctggaaca gcagcacagg   18120
ccagatgctg agggataagt tgaaagagca aaatttccaa caaaaggtgg tagatggcct   18180
ggcctctggc attagcgggg tggtggacct ggccaaccag gcagtgcaaa ataagattaa   18240
cagtaagctt gatccccgcc ctcccgtaga ggagcctcca ccggccgtgg agacagtgtc   18300
tccagagggg cgtggcgaaa agcgtccgcg ccccgacagg gaagaaactc tggtgacgca   18360
aatagacgag cctccctcgt acgaggaggc actaaagcaa ggcctgccca ccacccgtcc   18420
catcgcgccc atggctaccg gagtgctggg ccagcacaca cccgtaacgc tggacctgcc   18480
tccccccgcc gacacccagc agaaacctgt gctgccaggc ccgaccgccg ttgttgtaac   18540
ccgtcctagc cgcgcgtccc tgcgccgcgc cgccagcggt ccgcgatcgt tgcggcccgt   18600
agccagtggc aactggcaaa gcacactgaa cagcatcgtg ggtctggggg tgcaatccct   18660
gaagcgccga cgatgcttct gatagctaac gtgtcgtatg tgtgtcatgt atgcgtccat   18720
gtcgccgcca gaggagctgc tgagccgccg cgcgcccgct ttccaagatg ctacccctt    18780 cgatgatgcc gcagtggtct tacatgcaca tctcgggcca ggacgcctcg gagtacctga   18840
gccccgggct ggtgcagttt gcccgcgcca ccgagacgta cttcagcctg aataacaagt   18900
ttagaaaccc cacggtggcg cctacgcacg acgtgaccac agaccggtcc cagcgtttga   18960
cgctgcggtt catccctgtg gaccgtgagg atactgcgta ctcgtacaag gcgcggttca   19020
ccctagctgt gggtgataac cgtgtgctgg acatggcttc cacgtacttt gacatccgcg   19080
gcgtgctgga cagggggccct actttttaagc cctactctgg cactgcctac aacgccctgg   19140
ctcccaaggg tgccccaaat ccttgcgaat gggatgaagc tgctactgct cttgaaataa   19200
acctagaaga agaggacgat gacaacgaag acgaagtaga cgagcaagct gagcagcaaa   19260
aaactcacgt atttgggcag gcgccttatt ctggtataaa tattacaaag gagggtattc   19320
aaataggtgt cgaaggtcaa acacctaaat atgccgataa acatttcaa cctgaacctc    19380 aaataggaga atctcagtgg tacgaaacag aaattaatca tgcagctggg agagtcctaa   19440
aaaagactac cccaatgaaa ccatgttacg gttcatatgc aaaacccaca atgaaaatg    19500 gagggcaagg cattcttgta aagcaacaaa atggaaagct agaaagtcaa gtggaaatgc   19560 aattttctc aactactgag gcagccgcag gcaatggtga taacttgact cctaaagtgg    19620
tattgtacag tgaagatgta gatatagaaa ccccagacac tcatatttct tacatgccca   19680
ctattaagga aggtaactca cgagaactaa tgggccaaca atctatgccc aacaggccta   19740
attacattgc ttttagggac aattttattg gtctaatgta ttacaacagc acgggtaata   19800
tgggtgttct ggcggggccaa gcatcgcagt tgaatgctgt tgtagatttg caagacagaa   19860
acacagagct ttcataccag cttttgcttg attccattgg tgatagaacc aggtactttt   19920
ctatgtggaa tcaggctgtt gacagctatg atccagatgt tagaattatt gaaaatcatg   19980
gaactgaaga tgaacttcca aattactgct ttccactggg aggtgtgatt aatacagaga   20040
ctcttaccaa ggtaaaacct aaaacaggtc aggaaaatgg atgggaaaaa gatgctacag   20100 aatttttcaga taaaaatgaa ataagagttg gaaataattt tgccatggaa atcaatctaa   20160
atgccaacct gtggagaaat ttcctgtact ccaacatagc gctgtatttg cccgacaagc   20220
taaagtacag tccttccaac gtaaaaattt ctgataaccc aaacacctac gactacatga   20280
acaagcgagt ggtggctccc gggctagtgg actgctacat taaccttgga gcacgctggt   20340
cccttgacta tatggacaac gtcaacccat ttaaccacca ccgcaatgct ggcctgcgct   20400
```

```
accgctcaat gttgctgggc aatggtcgct atgtgccctt ccacatccag gtgcctcaga    20460
agttctttgc cattaaaaac ctccttctcc tgccgggctc atacacctac gagtggaact    20520
tcaggaagga tgttaacatg gttctgcaga gctccctagg aaatgaccta agggttgacg    20580
gagccagcat taagtttgat agcatttgcc tttacgccac cttcttcccc atggcccaca    20640
acaccgcctc cacgcttgag gccatgctta gaaacgacac caacgaccag tcctttaacg    20700
actatctctc cgccgccaac atgctctacc ctatacccgc caacgctacc aacgtgccca    20760
tatccatccc ctcccgcaac tgggcggctt ccgcggctg  ggccttcacg cgccttaaga    20820
ctaaggaaac cccatcactg ggctcgggct acgacccta  ttacacctac tctggctcta    20880
taccctacct agatggaacc ttttacctca accacacctt taagaaggtg gccattacct    20940
ttgactcttc tgtcagctgg cctggcaatg accgcctgct taccccaac  gagtttgaaa    21000 ttaagcgctc agttgacggg gagggttaca acgttgccca gtgtaacatg accaaagact    21060
ggttcctggt acaaatgcta gctaactata acattggcta ccagggcttc tatatcccag    21120
agagctacaa ggaccgcatg tactccttct ttagaaactt ccagcccatg agccgtcagg    21180
tggtggatga tactaaatac aaggactacc aacaggtggg catcctacac caacacaaca    21240
actctggatt tgttggctac cttgccccca ccatgcgcga aggacaggcc taccctgcta    21300
acttccccta tccgcttata ggcaagaccg cagttgacag cattacccag aaaaagtttc    21360
tttgcgatcg caccctttgg cgcatcccat ctccagtaa  ctttatgtcc atgggcgcac    21420
tcacagacct gggccaaaac cttctctacg ccaactccgc ccacgcgcta gacatgactt    21480
ttgaggtgga tcccatggac gagcccaccc ttctttatgt tttgtttgaa gtctttgacg    21540
tggtccgtgt gcaccagccg caccgcggcg tcatcgaaac cgtgtacctg cgcacgccct    21600
tctcggccgg caacgccaca acataaagaa gcaagcaaca tcaacaacag ctgccgccat    21660
gggctccagt gagcaggaac tgaaagccat tgtcaaagat cttggttgtg gccatatttt    21720
tttgggcacc tatgacaagc gctttccagg cttttgtttct ccacacaagc tcgcctgcgc    21780
catagtcaat acggccggtc gcgagactgg gggcgtacac tggatggcct ttgcctggaa    21840
cccgcactca aaaacatgct acctctttga gccctttggc ttttctgacc agcgactcaa    21900
gcaggtttac cagtttgagt acgagtcact cctgcgccgt agcgccattg cttcttcccc    21960
cgaccgctgt ataacgctgg aaaagtccac ccaaagcgta caggggccca actcggccgc    22020
ctgtggacta ttctgctgca tgtttctcca cgcctttgcc aactggcccc aaactcccat    22080
ggatcacaac cccaccatga accttattac cggggtaccc aactccatgc tcaacagtcc    22140
ccaggtacag cccaccctgc gtcgcaacca ggaacagctc tacagcttcc tggagcgcca    22200
ctcgccctac ttccgcagcc acagtgcgca gattaggagc gccacttctt tttgtcactt    22260
gaaaaacatg taaaaataat gtactagaga cactttcaat aaaggcaaat gcttttattt    22320
gtacactctc gggtgattat ttaccccac  ccttgccgtc tgcgccgttt aaaaatcaaa    22380
ggggttctgc cgcgcatcgc tatgcgccac tggcagggac acgttgcgat actggtgttt    22440
agtgctccac ttaaactcag gcacaaccat ccgcggcagc tcggtgaagt tttcactcca    22500
caggctgcgc accatcacca acgcgtttag caggtcgggc gccgatatct tgaagtcgca    22560
gttggggcct ccgccctgcg cgcgcgagtt gcgatacaca gggttgcagc actggaacac    22620
tatcagcgcc gggtggtgca cgctggccag cacgctcttg tcggagatca gatccgcgtc    22680
caggtcctcc gcgttgctca gggcgaacgg agtcaacttt ggtagctgcc ttcccaaaaa    22740
```

```
gggcgcgtgc ccaggctttg agttgcactc gcaccgtagt ggcatcaaaa ggtgaccgtg    22800
cccggtctgg gcgttaggat acagcgcctg cataaaagcc ttgatctgct taaaagccac    22860
ctgagccttt gcgccttcag agaagaacat gccgcaagac ttgccggaaa actgattggc    22920
cggacaggcc gcgtcgtgca cgcagcacct tgcgtcggtg tttggagatct gcaccacatt    22980 tcggccccac cggttcttca cgatcttggc cttgctagac tgctccttca gcgcgcgctg    23040
cccgttttcg ctcgtcacat ccatttcaat cacgtgctcc ttatttatca taatgcttcc    23100
gtgtagacac ttaagctcgc cttcgatctc agcgcagcgg tgcagccaca acgcgcagcc    23160
cgtgggctcg tgatgcttgt aggtcacctc tgcaaacgac tgcaggtacg cctgcaggaa    23220
tcgccccatc atcgtcacaa aggtcttgtt gctggtgaag gtcagctgca acccgcggtg    23280
ctcctcgttc agccaggtct tgcatacggc cgccagagct tccacttggt caggcagtag    23340
tttgaagttc gcctttagat cgttatccac gtggtacttg tccatcagcg cgcgcgcagc    23400
ctccatgccc ttctcccacg cagacacgat cggcacactc agcgggttca tcaccgtaat    23460
ttcactttcc gcttcgctgg gctcttcctc ttcctcttgc gtccgcatac cacgcgccac    23520
tgggtcgtct tcattcagcc gccgcactgt gcgcttacct cctttgccat gcttgattag    23580
caccggtggg ttgctgaaac ccaccatttg tagcgccaca tcttctcttt cttcctcgct    23640
gtccacgatt acctctggtg atggcgggcg ctcgggcttg ggagaagggc gcttcttttt    23700
cttcttgggc gcaatggcca aatccgccgc cgaggtcgat ggccgcgggc tgggtgtgcg    23760
cggcaccagc gcgtcttgtg atgagtcttc ctcgtcctcg gactcgatac gccgcctcat    23820 ccgcttttt ggggcgccc ggggaggcgg cggcgacggg gacggggacg acacgtcctc    23880
catggttggg ggacgtcgcg ccgcaccgcg tccgcgctcg ggggtggttt cgcgctgctc    23940
ctcttcccga ctggccattt ccttctccta taggcagaaa aagatcatgg agtcagtcga    24000
gaagaaggac agcctaaccg cccctctga gttcgccacc accgcctcca ccgatgccgc    24060
caacgcgcct accaccttcc ccgtcgaggc accccgctt gaggaggagg aagtgattat    24120
cgagcaggac ccaggttttg taagcgaaga cgacgaggac cgctcagtac caacagagga    24180
taaaaagcaa gaccaggaca acgcagaggc aaacgaggaa caagtcgggc gggggacga    24240 aaggcatggc gactacctag atgtgggaga cgacgtgctg ttgaagcatc tgcagcgcca    24300
gtgcgccatt atctgcgacg cgttgcaaga gcgcagcgat gtgcccctcg ccatagcgga    24360
tgtcagcctt gcctacgaac gccacctatt ctcaccgcgc gtaccccca acgccaaga    24420 aaacggcaca tgcgagccca acccgcgcct caacttctac cccgtatttg ccgtgccaga    24480
ggtgcttgcc acctatcaca tctttttcca aaactgcaag ataccctat cctgccgtgc    24540 caaccgcagc cgagcggaca agcagctggc cttgcggcag ggcgctgtca tacctgatat    24600
cgcctcgctc aacgaagtgc caaaaatctt tgagggtctt ggacgcgacg agaagcgcgc    24660
ggcaaacgct ctgcaacagg aaaacagcga aaatgaaagt cactctggag tgttggtgga    24720
actcgagggt gacaacgcgc gcctagccgt actaaaacgc agcatcgagg tcacccactt    24780
tgcctacccg gcacttaacc tacccccaa ggtcatgagc acagtcatga gtgagctgat    24840
cgtgcgccgt gcgcagcccc tggagaggga tgcaaatttg caagaacaaa cagaggaggg    24900
cctacccgca gttggcgacg agcagctagc gcgctggctt caaacgcgcg agcctgccga    24960
cttggaggag cgacgcaaac taatgatggc cgcagtgctc gttaccgtgg agcttgagtg    25020
catgcagcgg ttctttgctg acccggagat gcagcgcaag ctagaggaaa cattgcacta    25080 caccttcga cagggctacg tacgccaggc ctgcaagatc tccaacgtgg agctctgcaa    25140
```

```
cctggtctcc taccttggaa ttttgcacga aaaccgcctt gggcaaaacg tgcttcattc   25200
cacgctcaag ggcgaggcgc gccgcgacta cgtccgcgac tgcgtttact tatttctatg   25260
ctacacctgg cagacggcca tgggcgtttg gcagcagtgc ttggaggagt gcaacctcaa   25320
ggagctgcag aaactgctaa agcaaaactt gaaggaccta tggacggcct tcaacgagcg   25380
ctccgtggcc gcgcacctgg cggacatcat tttccccgaa cgcctgctta aaccctgca    25440 acagggtctg ccagacttca ccagtcaaag catgttgcag aactttagga actttatcct   25500
agagcgctca ggaatcttgc ccgccacctg ctgtgcactt cctagcgact ttgtgcccat   25560
taagtaccgc gaatgccctc cgccgctttg gggccactgc taccttctgc agctagccaa   25620
ctaccttgcc taccactctg acataatgga agacgtgagc ggtgacggtc tactggagtg   25680
tcactgtcgc tgcaacctat gcaccccgca ccgctccctg gtttgcaatt cgcagctgct   25740
taacgaaagt caaattatcg gtacctttga gctgcagggt ccctcgcctg acgaaaagtc   25800
cgcggctccg gggttgaaac tcactccggg gctgtgacg  tcggcttacc ttcgcaaatt   25860
tgtacctgag gactaccacg cccacgagat taggttctac gaagaccaat cccgcccgcc   25920
taatgcggag cttaccgcct gcgtcattac ccagggccac attcttggcc aattgcaagc   25980
catcaacaaa gcccgccaag agtttctgct acgaaaggga cgggggggttt acttggaccc   26040 ccagtccggc gaggagctca acccaatccc ccgccgccg  cagccctatc agcagcagcc   26100 gcgggcccttgcttcccagg atggcaccca aaaagaagct gcagctgccg ccgccaccca    26160
cggacgagga ggaatactgg gacagtcagg cagaggaggt tttggacgag gaggaggagg   26220
acatgatgga agactgggag agcctagacg aggaagcttc cgaggtcgaa gaggtgtcag   26280
acgaaacacc gtcaccctcg gtcgcattcc cctcgccggc gccccagaaa tcggcaaccg   26340
gttccagcat ggctacaacc tccgctcctc aggcgccgcc ggcactgccc gttcgccgac   26400
ccaaccgtag atgggacacc actggaacca gggccggtaa gtccaagcag ccgccgccgt   26460
tagcccaaga gcaacaacag cgccaaggct accgctcatg gcgcgggcac aagaacgcca   26520
tagttgcttg cttgcaagac tgtgggggca acatctcctt cgcccgccgc tttcttctct   26580
accatcacgg cgtggccttc ccccgtaaca tcctgcatta ctaccgtcat ctctacagcc   26640
catactgcac cggcggcagc ggcagcaaca gcagcggcca cacagaagca aaggcgaccg   26700
gatagcaaga ctctgacaaa gcccaagaaa tccacagcgg cggcagcagc aggaggagga   26760
gcgctgcgtc tggcgcccaa cgaacccgta tcgaccgcg  agcttagaaa caggattttt   26820
cccactctgt atgctatatt tcaacagagc aggggccaag aacaagagct gaaaataaaa   26880
aacaggtctc tgcgatccct cacccgcagc tgcctgtatc acaaaagcga agatcagctt   26940
cggcgcacgc tggaagacgc ggaggctctc ttcagtaaat actgcgcgct gactcttaag   27000
gactagtttc gcgcccttc tcaaatttaa gcgcgaaaac tacgtcatct ccagcggcca   27060
cacccggcgc cagcacctgt tgtcagcgcc attatgagca aggaaattcc cacgccctac   27120
atgtggagtt accagccaca aatgggactt gcggctggag ctgcccaaga ctactcaacc   27180
cgaataaact acatgagcgc gggacccac  atgatatccc gggtcaacgg aatacgcgcc   27240
caccgaaacc gaattctcct ggaacaggcg gctattacca ccacacctcg taataacctt   27300
aatccccgta gttggcccgc tgccctggtg taccaggaaa gtcccgctcc caccactgtg   27360
gtacttccca gagacgccca ggccgaagtt cagatgacta actcagggc  gcagcttgcg   27420 ggcggctttc gtcacagggt gcggtcgccc gggcagggta taactcacct gacaatcaga   27480
```

```
gggcgaggta ttcagctcaa cgacgagtcg gtgagctcct cgcttggtct ccgtccggac   27540
gggacatttc agatcggcgg cgccggccgc tcttcattca cgcctcgtca ggcaatccta   27600
actctgcaga cctcgtcctc tgagccgcgc tctggaggca ttggaactct gcaatttatt   27660
gaggagtttg tgccatcggt ctactttaac cccttctcgg gacctccggg ccactatccg   27720
gatcaattta ttcctaactt tgacgcggta aaggactcgg cggacggcta cgactgaatg   27780
ttaagtggag aggcagagca actgcgcctg aaacacctgg tccactgtcg ccgccacaag   27840
tgctttgccc gcgactccgg tgagttttgc tactttgaat tgcccgagga tcatatcgag   27900
ggcccggcgc acggcgtccg gcttaccgcc caggagagc ttgcccgtag cctgattcgg    27960
gagtttaccc agcgcccct gctagttgag cgggacaggg gaccctgtgt tctcactgtg    28020
atttgcaact gtcctaaccc tggattacat caagatcctc tagttaatgt caggtcgcct   28080
aagtcgatta actagagtac ccggggatct tattccctt aactaataaa aaaaaataat    28140
aaagcatcac ttacttaaaa tcagttagca aatttctgtc cagtttattc agcagcacct   28200
ccttgccctc ctcccagctc tggtattgca gcttcctcct ggctgcaaac tttctccaca   28260
atctaaatgg aatgtcagtt tcctcctgtt cctgtccatc cgcacccact atcttcatgt   28320
tgttgcagat gaagcgcgca agaccgtctg aagataccct caaccccgtg tatccatatg   28380
acacggaaac cggtcctcca actgtgcctt ttcttactcc tccctttgta tcccccaatg   28440
ggtttcaaga gagtccccct gggtactct ctttgcgcct atccgaacct ctagttacct    28500
ccaatggcat gcttgcgctc aaaatgggca acggcctctc tctggacgag gccggcaacc   28560
ttacctccca aaatgtaacc actgtgagcc cacctctcaa aaaaccaag tcaaacataa    28620 acctggaaat atctgcaccc ctcacagtta cctcagaagc cctaactgtg ctgccgccg    28680 cacctctaat ggtcgcgggc aacacactca ccatgcaatc acaggccccg ctaaccgtgc   28740
acgactccaa acttagcatt gccacccaag gaccctcac agtgtcagaa ggaaagctag    28800
ccctgcaaac atcaggcccc ctcaccacca ccgatagcag tacccttact atcactgcct   28860
caccccctct aactactgcc actggtagct tgggcattga cttgaaagag cccatttata   28920
cacaaaatgg aaaactagga ctaaagtacg gggctccttt gcatgtaaca gacgacctaa   28980
acactttgac cgtagcaact ggtccaggtg tgactattaa taatacttcc ttgcaaacta   29040
aagttactgg agccttgggt tttgattcac aaggcaatat gcaacttaat gtagcaggag   29100
gactaaggat tgattctcaa aacagacgcc ttatacttga tgttagttat ccgtttgatg   29160
ctcaaaacca actaaatcta agactaggac agggccctct tttttataaac tcagcccaca   29220 acttggatat taactacaac aaaggccttt acttgtttac agcttcaaac aattccaaaa   29280
agcttgaggt taacctaagc actgccaagg ggttgatgtt tgacgctaca gccatagcca   29340
ttaatgcagg agatgggctt gaatttggtt cacctaatgc accaaacaca aatccctca    29400 aaacaaaaat tggccatggc ctagaatttg attcaaacaa ggctatggtt cctaaactag   29460
gaactggcct tagttttgac agcacaggtg ccattacagt aggaaacaaa ataatgata    29520 agctaacttt gtggaccaca ccagctccat ctcctaactg tagactaaat gcagagaaag   29580
atgctaaact cactttggtc ttaacaaaat gtggcagtca atacttgct acagtttcag    29640 ttttggctgt taaaggcagt ttggctccaa tatctggaac agttcaaagt gctcatctta   29700
ttataagatt tgacgaaaat ggagtgctac taaacaattc cttcctggac ccagaatatt   29760
ggaactttag aaatggagat cttactgaag gcacagccta tacaaacgct gttgattta    29820 tgcctaacct atcagcttat ccaaaatctc acggtaaaac tgccaaaagt aacattgtca   29880
```

```
gtcaagttta cttaaacgga gacaaaacta aacctgtaac actaaccatt acactaaacg   29940
gtacacagga aacaggagac acaactccaa gtgcatactc tatgtcattt tcatgggact   30000
ggtctggcca caactacatt aatgaaatat ttgccacatc ctcttacact ttttcataca   30060
ttgcccaaga ataaagaatc gtttgtgtta tgtttcaacg tgtttatttt tcaattgcag   30120
aaaatttcaa gtcattttc attcagtagt atagccccac caccacatag cttatacaga   30180
tcaccgtacc ttaatcaaac tcacagaacc ctagtattca acctgccacc tccctcccaa   30240
cacacagagt acacagtcct ttctccccgg ctggccttaa aaagcatcat atcatgggta   30300
acagacatat tcttaggtgt tatattccac acggtttcct gtcgagccaa acgctcatca   30360
gtgatattaa taaactcccc gggcagctca cttaagttca tgtcgctgtc cagctgctga   30420
gccacaggct gctgtccaac ttgcggttgc ttaacgggcg gcgaaggaga agtccacgcc   30480
tacatggggg tagagtcata atcgtgcatc aggatagggc ggtggtgctg cagcagcgcg   30540
cgaataaact gctgccgccg ccgctccgtc ctgcaggaat acaacatggc agtggtctcc   30600
tcagcgatga ttcgcaccgc ccgcagcata aggcgccttg tcctccgggc acagcagcgc   30660
accctgatct cacttaaatc agcacagtaa ctgcagcaca gcaccacaat attgttcaaa   30720
atcccacagt gcaaggcgct gtatccaaag ctcatggcgg ggaccacaga acccacgtgg   30780
ccatcatacc acaagcgcag gtagattaag tggcgacccc tcataaacac gctggacata   30840
aacattacct cttttggcat gttgtaattc accacctccc ggtaccatat aaacctctga   30900
ttaaacatgg cgccatccac caccatccta aaccagctgg ccaaaacctg cccgccggct   30960
atacactgca gggaaccggg actggaacaa tgacagtgga gagcccagga ctcgtaacca   31020
tggatcatca tgctcgtcat gatatcaatg ttggcacaac acaggcacac gtgcatacac   31080
ttcctcagga ttacaagctc ctcccgcgtt agaaccatat cccagggaac aacccattcc   31140
tgaatcagcg taaatcccac actgcaggga agacctcgca cgtaactcac gttgtgcatt   31200
gtcaaagtgt tacattcggg cagcagcgga tgatcctcca gtatggtagc gcgggtttct   31260
gtctcaaaag gaggtagacg atccctactg tacggagtgc gccgagacaa ccgagatcgt   31320
gttggtcgta gtgtcatgcc aaatggaacg ccggacgtag tcatatttcc tgaagcaaaa   31380
ccaggtgcgg gcgtgacaaa cagatctgcg tctccggtct cgccgcttag atcgctctgt   31440
gtagtagttg tagtatatcc actctctcaa agcatccagg cgcccctgg cttcgggttc   31500 tatgtaaact ccttcatgcg ccgctgccct gataacatcc accaccgcag aataagccac   31560
acccagccaa cctacacatt cgttctgcga gtcacacacg ggaggagcgg gaagagctgg   31620
aagaaccatg tttttttttt tattccaaaa gattatccaa aacctcaaaa tgaagatcta   31680
ttaagtgaac gcgctcccct ccggtggcgt ggtcaaactc tacagccaaa gaacagataa   31740
tggcatttgt aagatgttgc acaatggctt ccaaaaggca aacggccctc acgtccaagt   31800
ggacgtaaag gctaaccct tcagggtgaa tctcctctat aaacattcca gcaccttcaa   31860
ccatgcccaa ataattctca tctcgccacc ttctcaatat atctctaagc aaatcccgaa   31920
tattaagtcc ggccattgta aaatctgct ccagagcgcc ctccaccttc agcctcaagc   31980
agcgaatcat gattgcaaaa attcaggttc ctcacagacc tgtataagat tcaaaagcgg   32040
aacattaaca aaaataccgc gatcccgtag gtcccttcgc agggccagct gaacataatc   32100
gtgcaggtct gcacggacca gcgcggccac ttccccgcca ggaaccatga caaaagaacc   32160
cacactgatt atgacacgca tactcggagc tatgctaacc agcgtagccc cgatgtaagc   32220
```

```
ttgttgcatg ggcggcgata taaaatgcaa ggtgctgctc aaaaaatcag gcaaagcctc    32280
gcgcaaaaaa gaaagcacat cgtagtcatg ctcatgcaga taaaggcagg taagctccgg    32340
aaccaccaca gaaaaagaca ccattttttct ctcaaacatg tctgcgggtt tctgcataaa   32400
cacaaaataa aataacaaaa aaacatttaa acattagaag cctgtcttac aacaggaaaa    32460
acaaccctta taagcataag acggactacg gccatgccgg cgtgaccgta aaaaaactgg    32520
tcaccgtgat taaaaagcac caccgacagc tcctcggtca tgtccggagt cataatgtaa    32580
gactcggtaa acacatcagg ttgattcaca tcggtcagtg ctaaaaagcg accgaaatag    32640
cccgggggaa tacatacccg caggcgtaga gacaacatta cagcccccat aggaggtata    32700
acaaaattaa taggagagaa aaacacataa acacctgaaa aaccctcctg cctaggcaaa    32760
atagcaccct cccgctccag aacaacatac agcgcttcca cagcggcagc cataacagtc    32820
agccttacca gtaaaaaaga aaacctatta aaaaaacacc actcgacacg gcaccagctc    32880
aatcagtcac agtgtaaaaa agggccaagt gcagagcgag tatatatagg actaaaaaat    32940
gacgtaacgg ttaaagtcca caaaaaacac ccagaaaacc gcacgcgaac ctacgcccag    33000
aaacgaaagc caaaaaaccc acaacttcct caaatcgtca cttccgtttt cccacgttac    33060
gtcacttccc atttttaagaa aactacaatt cccaacacat acaagttact ccgccctaaa    33120
acctacgtca cccgccccgt tcccacgccc cgcgccacgt cacaaactcc acccccctcat   33180 tatcatattg gcttcaatcc aaaataaggt atattattga tgatg                    33225
```

<210> SEQ ID NO 95
<211> LENGTH: 34665
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 95

```
ttttggattg aagccaatat gataatgagg gggtggagtt tgtgacgtgg cgcggggcgt      60
gggaacgggg cgggtgacgt agtagtgtgg cggaagtgtg atgttgcaag tgtggcggaa     120
cacatgtaag cgacggatgt ggcaaaagtg acgttttttgg tgtgcgccgg tgttttgggc    180
gtaaccgagt aagatttggc cattttcgcg ggaaaactga ataagaggaa gtgaaatctg     240
aataattttg tgttactcat agcgcgtaat atttgtctag gccgcgggg actttgaccg      300 tttacgtgga gactcgccca ggtgtttttc tcaggtgttt tccgcgttcc gggtcaaagt     360
tggcgtttta ttattatagt cagctgacgt gtagtgtatt tatacccggt gagttcctca     420
agaggccact cttgagtgcc agcgagtaga gttttctcct ccgagccgct ccgacaccgg     480
gactgaaaat gagacatatt atctgccacg gaggtgttat taccgaagaa atggccgcca     540
gtcttttgga ccagctgatc gaagaggtac tggctgataa tcttccacct cctagccatt     600
ttgaaccacc tacccttcac gaactgtatg atttagacgt gacggccccc gaagatccca     660
acgaggaggc ggtttcgcag attttttccg actctgtaat gttggcggtg caggaaggga    720
ttgacttact cacttttccg ccggcgcccg gttctccgga gccgcctcac ctttcccggc     780
agcccgagca gccggagcag agagccttgg gtccggtttc tatgccaaac cttgtaccgg     840
aggtgatcga tcttacctgc cacgaggctg gctttccacc cagtgacgac gaggatgaag     900
agggtgagga gtttgtgtta gattatgtgg agcaccccgg gcacggttgc aggtcttgtc     960
attatcaccg gaggaatacg ggggacccag atattatgtg ttcgctttgc tatatgagga    1020
```

```
cctgtggcat gtttgtctac agtaagtgaa aattatgggc agtgggtgat agagtggtgg    1080
gtttggtgtg gtaattttt ttttaatttt tacagttttg tggtttaaag aattttgtat    1140
tgtgattttt ttaaaaggtc ctgtgtctga acctgagcct gagcccgagc cagaaccgga    1200
gcctgcaaga cctacccgcc gtcctaaaat ggcgcctgct atcctgagac gcccgacatc    1260
acctgtgtct agagaatgca atagtagtac ggatagctgt gactccggtc cttctaacac    1320
acctcctgag atacacccgg tggtcccgct gtgccccatt aaaccagttg ccgtgagagt    1380
tggtgggcgt cgccaggctg tggaatgtat cgaggacttg cttaacgagc ctgggcaacc    1440
tttggacttg agctgtaaac gccccaggcc ataaggtgta aacctgtgat tgcgtgtgtg    1500
gttaacgcct ttgtttgctg aatgagttga tgtaagttta ataaagggtg agataatgtt    1560
taacttgcat ggcgtgttaa atggggcggg gcttaaaggg tatataatgc gccgtgggct    1620
aatcttggtt acatctgacc tcgtcgacgc caccatgtgt caccagcagc tcgtgattag    1680
ctggttcagc ctggtgtttc tggctagccc tctggtggcc atctgggagc tgaagaagga    1740
cgtgtacgtg gtggagctcg actggtaccc tgacgctccc ggcgagatgg tcgtgctgac    1800
ctgcgacacc cctgaggaag atggcatcac ctggaccctg atcaaagct ccgaagtgct    1860
cggcagcggc aagacactca ccatccaggt gaaagagttc ggagacgccg gccagtacac    1920
ctgccacaaa ggcggcgagg tgctgtccca ttccctgctg ctgctgcaca agaaagagga    1980
tggcatctgg tccaccgaca tcctgaagga ccagaaggaa cccaagaaca gaccttttct    2040
gagatgtgag gccaagaact acagcggcag gttcacctgc tggtggctga caacaatctc    2100
caccgacctg accttcagcg tcaagagcag caggggcagc agcgaccctc aaggcgtgac    2160
atgtggagcc gctaccctga gcgctgagag agtcaggggc gacaataagg agtacgagta    2220
ctccgtggaa tgccaggagg actccgcctg ccctgccgcc gaagagtccc tcccctatcga    2280
agtgatggtt gatgccgtgc acaagctcaa gtatgagaat tacaccagca gcttttttcat    2340
cagggacatc atcaagcccg acccccccaa aaaacctccag ctgaaacccc tcaagaatag    2400
caggcaggtg gaggtctcct gggagtatcc tgacacctgg agcacccccc acagctactt    2460
ctccctgacc ttctgtgtgc aggtgcaggg caagagcaaa agggagaaga aggatagggt    2520
ctttaccgac aagaccagcg ccacagtgat ctgcaggaag aacgccagca tttccgtcag    2580
ggcccaggac aggtactaca gcagcagctg gtccgagtgg gctagcgtgc cttgttccgg    2640
cggcggagga tctggcggag gcggaagtgg cggaggggc tctagaaacc tccccgtggc    2700
cacacccgac cctggcatgt tcccctgcct ccaccacagc cagaacctgc tgagagccgt    2760
gagcaatatg ctgcagaagg ccaggcaaac cctggagttc taccccctgta cctccgagga    2820
gattgaccat gaggacatca caaaggacaa aaccagcacc gtggaggcct gtctcccct    2880
cgaactgacc aagaacgagt cctgcctgaa ctccaggagg acatccttca tcaccaacgg    2940
ctcctgcctg gcctccagaa agaccagctt catgatggcc ctctgcctga gcagcatcta    3000
cgaggacctc aagatgtacc aggtggagtt taaaacaatg aacgccaagc tcctcatgga    3060
ccctaagagg cagatttcc tcgaccagaa tatgctggct gtcattgacg agctgatgca    3120
ggcccctcaat ttcaactccg agaccgtccc ccagaagtcc tccctggaag agcccgactt    3180
ttacaagacc aagatcaagc tctgcatcct gctgcacgcc ttcagaatta gagccgtgac    3240
cattgacagg gtgatgagct acctcaacgc ctcctgatga ctcgagtcac caggcgcttt    3300
tccaagagaa ggtcatcaag actttggatt ttttccacacc ggggcgcgct gcggctgctg    3360
ttgctttttt gagtttatat aaggataaat ggagcgaaga aacccatctg agcgggggt    3420
```

```
acctgctgga ttttctggcc atgcatctgt ggagagcggt tgtgagacac aagaatcgcc   3480
tgctactgtt gtcttccgtc cgcccggcga taataccgac ggaggagcag cagcagcagc   3540
aggaggaagc caggcggcgg cggcaggagc agagcccatg gaacccgaga gccggcctgg   3600
accctcggga atgaatgttg tacaggtggc tgaactgtat ccagaactga dacgcatttt   3660
gacaattaca gaggatgggc aggggctaaa ggggtaaag agggagcggg gggcttgtga    3720
ggctacagag gaggctagga atctagcttt tagcttaatg accagacacc gtcctgagtg   3780
tattactttt caacagatca aggataattg cgctaatgag cttgatctgc tggcgcagaa   3840
gtattccata gagcagctga ccacttactg gctgcagcca ggggatgatt ttgaggaggc   3900
tattagggta tatgcaaagg tggcacttag gccagattgc aagtacaaga tcagcaaact   3960
tgtaaatatc aggaattgtt gctacatttc tgggaacggg gccgaggtgg agatagatac   4020
ggaggatagg gtggccttta gatgtagcat gataaatatg tggccggggg tgcttggcat   4080
ggacggggtg gttattatga atgtaaggtt tactggcccc aattttagcg gtacggtttt   4140
cctggccaat accaacctta tcctacacgg tgtaagcttc tatgggttta caatacctg    4200
tgtgaagcc tggaccgatg taagggttcg ggctgtgcc ttttactgct gctgaaggg      4260
ggtggtgtgt cgccccaaaa gcagggcttc aattaagaaa tgcctctttg aaaggtgtac   4320
cttgggtatc ctgtctgagg gtaactccag ggtgcgccac aatgtggcct ccgactgtgg   4380
ttgcttcatg ctagtgaaaa gcgtggctgt gattaagcat aacatggtat gtggcaactg   4440
cgaggacagg gcctctcaga tgctgacctg ctcggacggc aactgtcacc tgctgaagac   4500
cattcacgta gccagccact ctcgcaaggc ctggccagtg tttgagcata acatactgac   4560
ccgctgttcc ttgcatttgg gtaacaggag ggggtgttc ctaccttacc aatgcaattt    4620
gagtcacact aagatattgc ttgagcccga gagcatgtcc aaggtgaacc tgaacggggt   4680
gtttgacatg accatgaaga tctggaaggt gctgaggtac gatgagaccc gcaccaggtg   4740
cagaccctgc gagtgtggcg gtaaacatat taggaaccag cctgtgatgc tggatgtgac   4800
cgaggagctg aggcccgatc acttggtgct ggcctgcacc cgcgctgagt ttggctctag   4860
cgatgaagat acagattgag gtactgaaat gtgtgggcgt ggcttaaggg tgggaaagaa   4920
tatataaggt gggggtctta tgtagttttg tatctgtttt gcagcagccg ccgccgccat   4980
gagcaccaac tcgtttgatg gaagcattgt gagctctatat ttgacaacgc gcatgccccc   5040
atgggccggg gtgcgtcaga atgtgatggg ctccagcatt gatggtcgcc ccgtcctgcc   5100
cgcaaactct actaccttga cctacgagac cgtgtctgga acgccgttgg agactgcagc   5160
ctccgccgcc gcttcagccg ctgcagccac cgcccgcggg attgtgactg actttgcttt   5220
cctgagcccg cttgcaagca gtgcagcttc ccgttcatcc gcccgcgatg acaagttgac   5280
ggctcttttg gcacaattgg attctttgac ccgggaactt aatgtcgttt ctcagcagct   5340
gttggatctg cgccagcagg tttctgccct gaaggcttcc tcccctccca atgcggttta   5400
aaacataaat aaaaaaccag actctgtttg gatttggatc aagcaagtgt cttgctgtct   5460
ttatttaggg gttttgcgcg cgcggtaggc ccgggaccag cggtctcggt cgttgagggt   5520
cctgtgtatt ttttccagga cgtggtaaag gtgactctgg atgttcagat acatgggcat   5580
aagcccgtct ctggggtgga ggtagcacca ctgcagagct tcatgctgcg gggtggtgtt   5640
gtagatgatc cagtcgtagc aggagcgctg gcgtggtgc ctaaaaatgt ctttcagtag   5700
caagctgatt gccaggggca ggcccttggt gtaagtgttt acaaagcggt taagctggga   5760
```

```
tgggtgcata cgtggggata tgagatgcat cttggactgt attttaggt tggctatgtt      5820
cccagccata tccctccggg gattcatgtt gtgcagaacc accagcacag tgtatccggt      5880
gcacttggga aatttgtcat gtagcttaga aggaaatgcg tggaagaact tggagacgcc      5940
cttgtgacct ccaagatttt ccatgcattc gtccataatg atggcaatgg gcccacgggc      6000
ggcggcctgg gcgaagatat ttctgggatc actaacgtca tagttgtgtt ccaggatgag      6060
atcgtcatag gccattttta caaagcgcgg cggagggtg ccagactgcg gtataatggt       6120
tccatccggc ccaggggcgt agttaccctc acagatttgc atttcccacg ctttgagttc      6180
agatgggggg atcatgtcta cctgcggggc gatgaagaaa acggtttccg ggtaggga        6240
gatcagctgg gaagaaagca ggttcctgag cagctgcgac ttaccgcagc cggtgggccc      6300
gtaaatcaca cctattaccg gctgcaactg gtagttaaga gagctgcagc tgccgtcatc      6360
cctgagcagg ggggccactt cgttaagcat gtccctgact cgcatgtttt ccctgaccaa      6420
atccgccaga aggcgctcgc cgcccagcga tagcagttct tgcaaggaag caaagttttt      6480
caacggtttg agaccgtccg ccgtaggcat gcttttgagc gtttgaccaa gcagttccag      6540
gcggtcccac agctcggtca cctgctctac ggcatctcga tccagcatat ctcctcgttt      6600
cgcgggttgg ggcggctttc gctgtacggc agtagtcggt gctcgtccag acgggccagg     6660
gtcatgtctt ccacgggcg cagggtcctc gtcagcgtag tctgggtcac ggtgaagggg      6720
tgcgctccgg gctgcgcgct ggccagggtg cgcttgaggc tggtcctgct ggtgctgaag      6780
cgctgccggt cttcgccctg cgcgtcggcc aggtagcatt tgaccatggt gtcatagtcc     6840
agcccctccg cggcgtggcc cttggcgcgc agcttgccct tggaggaggc gccgcacgag     6900
gggcagtgca gacttttgag ggcgtagagc ttgggcgcga gaataccga ttccggggag      6960
taggcatccg cgccgcaggc cccgcagacg gtctcgcatt ccacgagcca ggtgagctct     7020
ggccgttcgg ggtcaaaaac caggtttccc ccatgctttt tgatgcgttt cttacctctg     7080
gtttccatga gccggtgtcc acgctcggtg acgaaaaggc tgtccgtgtc cccgtataca     7140
gacttgagag gcctgtcctc gagcggtgtt ccgcggtcct cctcgtatag aaactcggac     7200
cactctgaga caaaggctcg cgtccaggcc agcacgaagg aggctaagtg ggaggggtag     7260
cggtcgttgt ccactagggg gtccactcgc tccaggtgt gaagacacat gtcgccctct      7320
tcggcatcaa ggaaggtgat tggttttgtag gtgtaggcca cgtgaccggg tgttcctgaa    7380
gggggggctat aaaaggggt ggggggcgcgt tcgtcctcac tctcttccgc atcgctgtct    7440
gcgagggcca gctgttgggg tgagtactcc ctctgaaaag cgggcatgac ttctgcgcta     7500
agattgtcag tttccaaaaa cgaggaggat ttgatattca cctggcccgc ggtgatgcct    7560
ttgagggtgg ccgcatccat ctggtcagaa aagacaatct ttttgttgtc aagcttggtg    7620
gcaaacgacc cgtagagggc gttggacagc aacttggcga tggagcgcag ggtttggttt    7680
ttgtcgcgat cggcgcgctc cttggccgcg atgtttagct gcacgtattc gcgcgcaacg    7740
caccgccatt cgggaaagac ggtggtgcgc tcgtcgggca ccaggtgcac gcgccaaccg    7800
cggttgtgca gggtgacaag gtcaacgctg gtggctacct ctccgcgtag gcgctcgttg    7860
gtccagcaga ggcggccgcc cttcgcgag cagaatggcg gtaggggtc tagctgcgtc      7920
tcgtccgggg ggtctgcgtc cacggtaaag accccgggca gcaggcgcgc gtcgaagtag    7980
tctatcttgc atccttgcaa gtctagcgcc tgctgccatg cgcgggcggc aagcgcgcgc    8040
tcgtatgggt tgagtggggg accccatggc atggggtggg tgagcgcgga ggcgtacatg    8100
ccgcaaatgt cgtaaacgta gagggctct ctgagtattc caagatatgt agggtagcat     8160
```

-continued

```
cttccaccgc ggatgctggc gcgcacgtaa tcgtatagtt cgtgcgaggg agcgaggagg      8220
tcggaccga ggttgctacg ggcgggctgc tctgctcgga agactatctg cctgaagatg      8280
gcatgtgagt tggatgatat ggttggacgc tggaagacgt tgaagctggc gtctgtgaga      8340
cctaccgcgt cacgcacgaa ggaggcgtag gagtcgcgca gcttgttgac cagctcggcg      8400
gtgacctgca cgtctagggc gcagtagtcc agggtttcct tgatgatgtc atacttatcc      8460
tgtccctttt ttttccacag ctcgcggttg aggacaaact cttcgcgtc tttccagtac       8520
tcttggatcg gaaacccgtc ggcctccgaa cggtaagagc ctagcatgta gaactggttg      8580
acggcctggt aggcgcagca tccctttcct acgggtagcg cgtatgcctg cgcggccttc     8640
cggagcgagg tgtgggtgag cgcaaaggtg tccctgacca tgactttgag gtactggtat     8700
ttgaagtcag tgtcgtcgca tccgccctgc tcccagagca aaaagtccgt gcgcttttg      8760
gaacgcggat ttggcagggc gaaggtgaca tcgttgaaga gtatctttcc cgcgcgaggc     8820
ataaagttgc gtgtgatgcg gaagggtccc ggcacctcgg aacggttgtt aattacctgg     8880
gcggcgagca cgatctcgtc aaagccgttg atgttgtggc ccacaatgta aagttccaag     8940
aagcgcggga tgcccttgat ggaaggcaat tttttaagtt cctcgtaggt gagctcttca     9000
ggggagctga gcccgtgctc tgaaagggcc cagtctgcaa gatgagggtt ggaagcgacg     9060
aatgagctcc acaggtcacg ggccattagc atttgcaggt ggtcgcgaaa ggtcctaaac     9120
tggcgaccta tggccatttt ttctggggtg atgcagtaga aggtaagcgg tcttgttcc     9180
cagcggtccc atccaaggtt cgcggctagg tctcgcgcgg cagtcactag aggctcatct     9240
ccgccgaact tcatgaccag catgaagggc acgagctgct tcccaaaggc ccccatccaa     9300
gtataggtct ctacatcgta ggtgacaaag agacgctcgg tgcgaggatg cgagccgatc     9360
gggaagaact ggatctcccg ccaccaattg gaggagtggc tattgatgtg gtgaaagtag     9420
aagtccctgc gacgggccga acactcgtgc tggcttttgt aaaaacgtgc gcagtactgg     9480
cagcggtgca cgggctgtac atcctgcacg aggttgacct gacgaccgcg cacaaggaag     9540
cagagtggga atttgagccc ctcgcctggc gggtttggct ggtggtcttc tacttcggct     9600
gcttgtcctt gaccgtctgg ctgctcgagg ggagttacgg tggatcggac caccacgccg     9660
cgcgagccca aagtccagat gtccgcgcgc ggcggtcgga gcttgatgac aacatcgcgc     9720
agatgggagc tgtccatggt ctggagctcc cgcggcgtca ggtcaggcgg gagctcctgc     9780
aggtttacct cgcatagacg ggtcagggcg cgggctagat ccaggtgata cctaatttcc     9840
aggggctggt tggtggcggc gtcgatggct tgcaagaggc cgcatccccg cggcgcgact     9900
acggtaccgc gcggcgggcg gtgggccgcg ggggtgtcct tggatgatgc atctaaaagc     9960
ggtgacgcgg gcgagccccc ggaggtaggg ggggctccgg acccgccggg agaggggca     10020
ggggcacgtc ggcgccgcgc gcgggcagga gctggtgctg cgcgcgtagg ttgctggcga     10080
acgcgacgac gcgcgcggttg atctcctgaa tctggcgcct ctgcgtgaag acgacggcc     10140
cggtgagctt gaacctgaaa gagagttcga cagaatcaat ttcggtgtcg ttgacggcgg     10200
cctggcgcaa aatctcctgc acgtctcctg agttgtcttg ataggcgatc tcggccatga     10260
actgctcgat ctcttcctcc tggagatctc cgcgtccggc tcgctccacg gtggcggcga     10320
ggtcgttgga aatgcgggcc atgagctgcg agaaggcgtt gaggcctccc tcgttccaga     10380
cgcggctgta gaccacgccc ccttcggcat cgcgggcgcg catgaccacc tgcgcgagat     10440
tgagctccac gtgccgggcg aagacggcgt agtttcgcag gcgctgaaag aggtagttga     10500
```

```
gggtggtggc ggtgtgttct gccacgaaga agtacataac ccagcgtcgc aacgtggatt   10560
cgttgatatc ccccaaggcc tcaaggcgct ccatggcctc gtagaagtcc acggcgaagt   10620
tgaaaaactg ggagttgcgc gccgacacgg ttaactcctc ctccagaaga cggatgagct   10680
cggcgacagt gtcgcgcacc tcgcgctcaa aggctacagg ggcctcttct tcttcttcaa   10740
tctcctcttc cataagggcc tccccttctt cttcttctgg cggcggtggg ggaggggga   10800 cacggcggcg acgacggcgc accgggaggc ggtcgacaaa gcgctcgatc atctcccgc   10860 ggcgacggcg catggtctcg gtgacggcgc ggccgttctc gcggggcgc agttggaaga   10920 cgccgcccgt catgtcccgg ttatggggttg gcgggggggct gccatgcggc agggatacgg   10980
cgctaacgat gcatctcaac aattgttgtg taggtactcc gccgccgagg acctgagcg   11040 agtccgcatc gaccggatcg gaaaacctct cgagaaaggc gtctaaccag tcacagtcgc   11100
aaggtaggct gagcaccgtg gcgggcggca gcggcgggcg gtcggggttg tttctggcgg   11160
aggtgctgct gatgatgtaa ttaaagtagg cggtcttgag acggcggatg gtcgacagaa   11220
gcaccatgtc cttgggtccg gcctgctgaa tgcgcaggcg gtcggccatg ccccaggctt   11280
cgttttgaca tcggcgcagg tctttgtagt agtcttgcat gagcctttct accggcactt   11340
cttcttctcc ttcctcttgt cctgcatctc ttgcatctat cgctgcggcg gcggcggagt   11400
ttggccgtag gtggcgccct cttcctccca tgcgtgtgac cccgaagccc ctcatcggct   11460
gaagcagggc taggtcggcg acaacgcgct cggctaatat ggcctgctgc acctgcgtga   11520
gggtagactg gaagtcatcc atgtccacaa agcggtggta tgcgcccgtg ttgatggtgt   11580
aagtgcagtt ggccataacg gaccagttaa cggtctggtg acccggctgc gagagctcgg   11640
tgtacctgag acgcgagtaa gccctcgagt caaatacgta gtcgttgcaa gtccgcacca   11700
ggtactggta tcccaccaaa aagtgcggcg gcggctggcg gtagagggc cagcgtaggg   11760 tggccggggc tccggggggcg agatcttcca acataaggcg atgatatccg tagatgtacc   11820
tggacatcca ggtgatgccg gcggcggtgg tggaggcgcg cggaaagtcg cggacgcggt   11880
tccagatgtt gcgcagcggc aaaaagtgct ccatggtcgg gacgctctgg ccggtcaggc   11940
gcgcgcaatc gttgacgctc tagcgtgcaa aaggagagcc tgtaagcggg cactcttccg   12000
tggtctggtg gataaattcg caagggtatc atggcggacg accggggttc gagccccgta   12060 tccgccgtc cgccgtgatc catgcggtta ccgcccgcgt gtcgaaccca ggtgtgcgac   12120
gtcagacaac gggggagtgc tccttttggc ttccttccag gcgcggcggc tgctgcgcta   12180
gcttttttgg ccactggccg cgcgcagcgt aagcggttag gctggaaagc gaaagcatta   12240
agtggctcgc tccctgtagc cggagggtta ttttccaagg gttgagtcgc gggaccccg   12300 gttcgagtct cggaccggcc ggactgcggc gaacgggggt ttgcctcccc gtcatgcaag   12360 acccccgcttg caaattcctc cggaaacagg gacgagcccc ttttttgctt ttcccagatg   12420
catccggtgc tgcggcagat gcgcccccct cctcagcagc ggcaagagca agagcagcgg   12480
cagacatgca gggcaccctc ccctcctcct accgcgtcag gaggggcgac atccgcggtt   12540
gacgcggcag cagatggtga ttacgaaccc ccgcggcgcc gggcccggca ctacctggac   12600
ttggaggagg gcgagggcct ggcgcggcta ggagcgccct ctcctgagcg gcacccaagg   12660
gtgcagctga agcgtgatac gcgtgaggcg tacgtgccgc ggcagaacct gtttcgcgac   12720
cgcgagggag aggagcccga ggagatgcgc gatcgaaagt tccacgcagg gcgcgagctg   12780
cggcatggcc tgaatcgcga gcggttgctg cgcgaggagg actttgagcc cgacgcgcga   12840
accgggatta gtcccgcgcg cgcacacgtg gcggccgccg acctggtaac cgcatacgag   12900
```

```
cagacggtga accaggagat taactttcaa aaaagcttta acaaccacgt gcgtacgctt    12960
gtggcgcgcg aggaggtggc tataggactg atgcatctgt gggactttgt aagcgcgctg    13020
gagcaaaacc caaatagcaa gccgctcatg gcgcagctgt tccttatagt gcagcacagc    13080
agggacaacg aggcattcag ggatgcgctg ctaaacatag tagagcccga gggccgctgg    13140
ctgctcgatt tgataaacat cctgcagagc atagtggtgc aggagcgcag cttgagcctg    13200
gctgacaagg tggccgccat caactattcc atgcttagcc tgggcaagtt ttacgcccgc    13260
aagatatacc ataccccttg cgttcccata gacaaggagg taaagatcga ggggttctac    13320
atgcgcatgg cgctgaaggt gcttaccttg agcgacgacc tgggcgttta tcgcaacgag    13380
cgcatccaca aggccgtgag cgtgagccgg cggcgcgagc tcagcgaccg cgagctgatg    13440
cacagcctgc aaagggccct ggctggcacg ggcagcggcg atagagaggc cgagtcctac    13500
tttgacgcgg gcgctgacct gcgctgggcc ccaagccgac gcgccctgga ggcagctggg    13560
gccggacctg ggctggcggt ggcacccgcg cgcgctggca acgtcggcgg cgtggaggaa    13620
tatgacgagg acgatgagta cgagccagag gacggcgagt actaagcggt gatgtttctg    13680
atcagatgat gcaagacgca acggaccccgg cggtgcgggc ggcgctgcag agccagccgt    13740
ccggccttaa ctccacggac gactggcgcc aggtcatgga ccgcatcatg tcgctgactg    13800
cgcgcaatcc tgacgcgttc cggcagcagc cgcaggccaa ccggctctcc gcaattctgg    13860
aagcggtggt cccggcgcgc gcaaaccca cgcacgagaa ggtgctggcg atcgtaaacg    13920
cgctggccga aaacagggcc atccggcccg acgaggccgg cctggtctac gacgcgctgc    13980
ttcagcgcgt ggctcgttac aacagcggca acgtgcagac caacctggac cggctggtgg    14040
gggatgtgcg cgaggccgtg gcgcagcgtg agcgcgcgca gcagcagggc aacctgggct    14100
ccatggttgc actaaacgcc ttcctgagta cacagcccgc caacgtgccg cggggacagg    14160
aggactacac caactttgtg agcgcactgc ggctaatggt gactgagaca ccgcaaagtg    14220
aggtgtacca gtctgggcca gactattttt tccagaccag tagacaaggc ctgcagaccg    14280
taaacctgag ccaggctttc aaaaacttgc aggggctgtg gggggtgcgg gctcccacag    14340
gcgaccgcgc gaccgtgtct agcttgctga cgcccaactc gcgcctgttg ctgctgctaa    14400
tagcgcccct cacggacagt ggcagcgtgt cccgggacac ataccctaggt cacttgctga    14460 cactgtaccg cgaggccata ggtcaggcgc atgtggacga gcatactttc caggagatta    14520
caagtgtcag ccgcgcgctg ggcaggagg acacgggcag cctggaggca accctaaact    14580
acctgctgac caaccggcgg cagaagatcc cctcgttgca cagtttaaac agcgaggagg    14640
agcgcatttt gcgctacgtg cagcagagcg tgagccttaa cctgatgcgc gacggggtaa    14700
cgcccagcgt ggcgctggac atgaccgcgc gcaacatgga accgggcatg tatgcctcaa    14760
accggccgtt tatcaaccgc ctaatggact acttgcatcg cgcggccgcc gtgaaccccg    14820
agtatttcac caatgccatc ttgaacccgc actggctacc gcccctggt ttctacaccg    14880 ggggattcga ggtgcccgag ggtaacgatg gattcctctg gacgacata gacgacagcg    14940 tgttttcccc gcaaccgcag accctgctag agttgcaaca gcgcgagcag gcagaggcgg    15000
cgctgcgaaa ggaaagcttc cgcaggccaa gcagcttgtc cgatctaggc gctgcggccc    15060 gcggtcaga tgctagtagc ccatttccaa gcttgatagg gtctcttacc agcactcgca    15120
ccacccgccc gcgcctgctg ggcgaggagg agtacctaaa caactcgctg ctgcagccgc    15180
agcgcgaaaa aaacctgcct ccggcatttc ccaacaacgg gatagagagc ctagtggaca    15240
```

```
agatgagtag atggaagacg tacgcgcagg agcacaggga cgtgccaggc ccgcgcccgc    15300
ccacccgtcg tcaaaggcac gaccgtcagc ggggtctggt gtgggaggac gatgactcgg    15360
cagacgacag cagcgtcctg gatttgggag ggagtggcaa cccgtttgcg caccttcgcc    15420
ccaggctggg gagaatgttt taaaaaaaaa aaagcatgat gcaaataaaa aactcacca     15480
aggccatggc accgagcgtt ggttttcttg tattccccctt agtatgcggc gcgcggcgat   15540
gtatgaggaa ggtcctcctc cctcctacga gagtgtggtg agcgcggcgc cagtggcggc    15600
ggcgctgggt tctcccttcg atgctcccct ggacccgccg tttgtgcctc cgcggtacct    15660
gcggcctacc gggggagaa acagcatccg ttactctgag ttggcacccc tattcgacac     15720
cacccgtgtg tacctggtgg acaacaagtc aacggatgtg gcatccctga actaccagaa    15780
cgaccacagc aactttctga ccacggtcat tcaaaacaat gactacagcc gggggaggc     15840
aagcacacag accatcaatc ttgacgaccg gtcgcactgg ggcggcgacc tgaaaaccat    15900
cctgcatacc aacatgccaa atgtgaacga gttcatgttt accaataagt ttaaggcgcg    15960
ggtgatggtg tcgcgcttgc ctactaagga caatcaggtg gagctgaaat acgagtgggt    16020
ggagttcacg ctgcccgagg gcaactactc cgagaccatg accatagacc ttatgaacaa    16080
cgcgatcgtg gagcactact tgaaagtggg cagacagaac ggggttctgg aaagcgacat    16140
cggggtaaag tttgacaccc gcaacttcag actgggggttt gaccccgtca ctggtcttgt    16200
catgcctggg gtatatacaa acgaagcctt ccatccagac atcattttgc tgccaggatg    16260
cggggtggac ttcacccaca gccgcctgag caacttgttg ggcatccgca agcggcaacc    16320
cttccaggag ggctttagga tcacctacga tgatctggag ggtggtaaca ttccccgcact    16380
gttggatgtg gacgcctacc aggcgagctt gaaagatgac accgaacagg gcggggggtgg   16440
cgcaggcgga agcaacagca gtggcagcgg cgcggaagag aactccaacg cggcagccgc    16500
ggcaatgcag ccggtggagg acatgaacga tcatgccatt cgcggcgaca cctttgccac    16560
acgggctgag gagaagcgcg ctgaggccga agcagcggcc gaagctgccg cccccgctgc    16620
gcaacccgag gtcgagaagc ctcagaagaa accggtgatc aaaccccctga cagaggacag    16680
caagaaacgc agttacaacc taataagcaa tgacagcacc ttcacccagt accgcagctg    16740
gtaccttgca tacaactacg cgaccctca gaccggaatc cgctcatgga ccctgctttg     16800
cactcctgac gtaacctgcg gctcggagca ggtctactgg tcgttgccag acatgatgca    16860
agaccccgtg accttccgct ccacgcgcca gatcagcaac tttccggtgg tgggcgccga    16920
gctgttgccc gtgcactcca agagcttcta caacgaccag gccgtctact cccaactcat    16980
ccgccagtttt acctctctga cccacgtgtt caatcgcttt cccgagaacc agattttggc    17040
gcgcccgcca gccccacca tcaccaccgt cagtgaaaac gttcctgctc tcacagatca    17100
cgggacgcta ccgctgcgca acagcatcgg aggagtccag cgagtgacca ttactgacgc    17160
cagacgccgc acctgcccct acgtttacaa ggccctgggc atagtctcgc cgcgcgtcct    17220
atcgagccgc actttttgag caagcatgtc catccttata tcgcccagca ataacacagg    17280
ctggggcctg cgcttcccaa gcaagatgtt tggcgggggcc aagaagcgct ccgaccaaca    17340
cccagtgcgc gtgcgcgggc actaccgcgc gccctgggc gcgcacaaac gcggccgcac     17400
tgggcgcacc accgtcgatg acgccatcga cgcggtggtg gaggaggcgc gcaactacac    17460
gcccacgccg ccaccagtgt ccacagtgga cgcggccatt cagaccgtgg tgcgcggagc    17520
ccggcgctat gctaaaatga agagacgcg gaggcgcgta gcacgtcgcc accgccgccg    17580
acccggcact gccgcccaac gcgcggcggc ggccctgctt aaccgcgcac gtcgcaccgg    17640
```

```
ccgacgggcg gccatgcggg ccgctcgaag gctggccgcg ggtattgtca ctgtgccccc   17700
caggtccagg cgacgagcgg ccgccgcagc agccgcggcc attagtgcta tgactcaggg   17760
tcgcaggggc aacgtgtatt gggtgcgcga ctcggttagc ggcctgcgcg tgcccgtgcg   17820
cacccgcccc ccgcgcaact agattgcaag aaaaaactac ttagactcgt actgttgtat   17880
gtatccagcg gcggcggcgc gcaacgaagc tatgtccaag cgcaaaatca agaagagat    17940
gctccaggtc atcgcgccgg agatctatgg ccccccgaag aaggaagagc aggattacaa   18000
gccccgaaag ctaaagcggg tcaaaaagaa aaagaaagat gatgatgatg aacttgacga   18060
cgaggtggaa ctgctgcacg ctaccgcgcc caggcgacgg gtacagtgga aaggtcgacg   18120
cgtaaaacgt gttttgcgac ccggcaccac cgtagtcttt acgcccggtg agcgctccac   18180
ccgcacctac aagcgcgtgt atgatgaggt gtacggcgac gaggacctgc ttgagcaggc   18240
caacgagcgc ctcggggagt ttgcctacgg aaagcggcat aaggacatgc tggcgttgcc   18300
gctggacgag ggcaacccaa cacctagcct aaagcccgta acactgcagc aggtgctgcc   18360
cgcgcttgca ccgtccgaag aaaagcgcgg cctaaagcgc gagtctggtg acttggcacc   18420
caccgtgcag ctgatggtac ccaagcgcca gcgactggaa gatgtcttgg aaaaaatgac   18480
cgtggaacct gggctggagc ccgaggtccg cgtgcggcca atcaagcagg tggcgccggg   18540
actgggcgtg cagaccgtgg acgttcagat acccactacc agtagcacca gtattgccac   18600
cgccacagag ggcatggaga cacaaacgtc cccggttgcc tcagcggtgg cggatgccgc   18660
ggtgcaggcg gtcgctgcgg ccgcgtccaa gacctctacg gaggtgcaaa cggacccgtg   18720
gatgtttcgc gtttcagccc cccggcgccc gcgccgttcg aggaagtacg gcgccgccag   18780
cgcgctactg cccgaatatg ccctacatcc ttccattgcg cctacccccg gctatcgtgg   18840
ctacacctac cgccccagaa gacgagcaac tacccgacgc cgaaccacca ctggaacccg   18900
ccgccgccgt cgccgtcgcc agccgtgct ggccccgatt tccgtgcgca gggtggctcg    18960
cgaaggaggc aggaccctgg tgctgccaac agcgcgctac cacccccagca tcgtttaaaa   19020
gccggtctt gtggttcttg cagatatggc cctcacctgc cgcctccgtt tcccggtgcc    19080
gggattccga ggaagaatgc accgtaggag gggcatggcc ggccacggcc tgacgggcgg   19140
catgcgtcgt gcgcaccacc ggcggcggcg cgcgtcgcac cgtcgcatgc gcggcggtat   19200
cctgcccctc cttattccac tgatcgccgc ggcgattggc gccgtgcccg gaattgcatc   19260
cgtggccttg caggcgcaga gacactgatt aaaaacaagt tgcatgtgga aaaatcaaaa   19320
taaaaagtct ggactctcac gctcgcttgg tcctgtaact attttgtaga atggaagaca   19380
tcaactttgc gtctctggcc ccgcgacacg gctcgcgccc gttcatggga aactggcaag   19440
atatcggcac cagcaatatg agcggtggcg ccttcagctg gggctcgctg tggagcggca   19500
ttaaaatttt cggttccacc gttaagaact atggcagcaa ggcctggaac agcagcacag   19560
gccagatgct gagggataag ttgaaagagc aaaatttcca acaaaaggtg gtagatggcc   19620
tggcctctgg cattagcggg gtggtggacc tggccaacca ggcagtgcaa aataagatta   19680
acagtaagct tgatccccgc cctcccgtag aggagcctcc accggccgtg gagacagtgt   19740
ctccagaggg gcgtggcgaa aagcgtccgc gccccgacag ggaagaaact ctggtgacgc   19800
aaatagacga gcctccctcg tacgaggagg cactaaagca aggcctgccc accacccgtc   19860
ccatcgcgcc catggctacc ggagtgctgg gccagcacac acccgtaacg ctggaccgtc   19920
ctccccccgc cgacacccag cagaaacctg tgctgccagg cccgaccgcc gttgttgtaa   19980
```

```
cccgtcctag ccgcgcgtcc ctgcgccgcg ccgccagcgg tccgcgatcg ttgcggcccg   20040
tagccagtgg caactggcaa agcacactga acagcatcgt gggtctgggg gtgcaatccc   20100
tgaagcgccg acgatgcttc tgatagctaa cgtgtcgtat gtgtgtcatg tatgcgtcca   20160
tgtcgccgcc agaggagctg ctgagccgcc gcgcgcccgc tttccaagat ggctacccct   20220
tcgatgatgc cgcagtggtc ttacatgcac atctcgggcc aggacgcctc ggagtacctg   20280
agccccgggc tggtgcagtt tgcccgcgcc accgagacgt acttcagcct gaataacaag   20340
tttagaaacc ccacggtggc gcctacgcac gacgtgacca cagaccggtc ccagcgtttg   20400
acgctgcggt tcatccctgt ggaccgtgag gatactgcgt actcgtacaa ggcgcggttc   20460
accctagctg tgggtgataa ccgtgtgctg gacatggctt ccacgtactt tgacatccgc   20520
ggcgtgctgg acaggggccc tacttttaag ccctactctg gcactgccta caacgccctg   20580
gctcccaagg gtgccccaaa tccttgcgaa tgggatgaag ctgctactgc tcttgaaata   20640
aacctagaag aagaggacga tgacaacgaa gacgaagtag acgagcaagc tgagcagcaa   20700
aaaactcacg tatttgggca ggcgccttat tctggtataa atattacaaa ggagggtatt   20760
caaataggtg tcgaaggtca aacacctaaa tatgccgata aaacatttca acctgaacct   20820
caaataggag aatctcagtg gtacgaaaca gaaattaatc atgcagctgg gagagtccta   20880
aaaaagacta ccccaatgaa accatgttac ggttcatatg caaaacccac aaatgaaaat   20940
ggagggcaag gcattcttgt aaagcaacaa atggaaagc tagaaagtca agtggaaatg   21000 caattttct caactactga ggcagccgca ggcaatggtg ataacttgac tcctaaagtg   21060
gtattgtaca gtgaagatgt agatatagaa accccagaca ctcatatttc ttacatgccc   21120
actattaagg aagtaactc acgagaacta atgggccaac aatctatgcc caacaggcct   21180
aattacattg cttttaggga caattttatt ggtctaatgt attacaacag cacgggtaat   21240
atgggtgttc tggcgggcca agcatcgcag ttgaatgctg ttgtagattt gcaagacaga   21300
aacacagagc tttcatacca gcttttgctt gattccattg gtgatagaac caggtacttt   21360
tctatgtgga atcaggctgt tgacagctat gatccagatg ttagaattat tgaaaatcat   21420
ggaactgaag atgaacttcc aaattactgc tttccactgg gaggtgtgat taatacagag   21480
actcttacca aggtaaaacc taaaacaggt caggaaaatg gatgggaaaa agatgctaca   21540
gaattttcag ataaaaatga aataagagtt ggaaataatt ttgccatgga aatcaatcta   21600
aatgccaacc tgtggagaaa tttcctgtac tccaacatag cgctgtattt gcccgacaag   21660
ctaaagtaca gtccttccaa cgtaaaaatt tctgataacc caaacaccta cgactacatg   21720
aacaagcgag tggtggctcc cgggctagtg gactgctaca ttaaccttgg agcacgctgg   21780
tcccttgact atatggacaa cgtcaaccca tttaaccacc accgcaatgc tggcctgcgc   21840
taccgctcaa tgttgctggg caatggtcgc tatgtgccct tccacatcca ggtgcctcag   21900
aagttctttg ccattaaaaa cctccttctc ctgccgggct catacaccta cgagtggaac   21960
ttcaggaagg atgttaacat ggttctgcag agctccctag gaaatgacct aagggttgac   22020
ggagccagca ttaagtttga tagcatttgc ctttacgcca ccttcttccc catggcccac   22080
aacaccgcct ccacgcttga ggccatgctt agaaacgaca ccaacgacca gtcctttaac   22140
gactatctct ccgccgccaa catgctctac cctataccg ccaacgctac caacgtgccc   22200
atatccatcc cctcccgcaa ctgggcggct ttcgcggct gggccttcac gcgccttaag   22260
actaaggaaa ccccatcact gggctcgggc tacgaccctt attacccta ctctggctct   22320 ataccctacc tagatggaac cttttacctc aaccacacct ttaagaaggt ggccattacc   22380
```

```
tttgactctt ctgtcagctg gcctggcaat gaccgcctgc ttaccccaa cgagtttgaa   22440 attaagcgct cagttgacgg ggagggttac aacgttgccc agtgtaacat gaccaaagac   22500
tggttcctgg tacaaatgct agctaactat aacattggct accagggctt ctatatccca   22560
gagagctaca aggaccgcat gtactccttc tttagaaact tccagcccat gagccgtcag   22620
gtggtggatg atactaaata caaggactac caacaggtgg gcatcctaca ccaacacaac   22680
aactctggat ttgttggcta ccttgccccc accatgcgcg aaggacaggc ctaccctgct   22740
aacttcccct atccgcttat aggcaagacc gcagttgaca gcattaccca gaaaaagttt   22800 cttttgcgatc gcacccttg gcgcatccca ttctccagta actttatgtc catgggcgca   22860
ctcacagacc tgggccaaaa ccttctctac gccaactccg cccacgcgct agacatgact   22920
tttgaggtgg atcccatgga cgagcccacc cttctttatg ttttgtttga agtctttgac   22980
gtggtccgtg tgcaccagcc gcaccgcggc gtcatcgaaa ccgtgtacct gcgcacgccc   23040
ttctcggccg gcaacgccac aacataaaga agcaagcaac atcaacaaca gctgccgcca   23100
tgggctccag tgagcaggaa ctgaaagcca ttgtcaaaga tcttggttgt gggccatatt   23160
ttttgggcac ctatgacaag cgcttccag gctttgtttc tccacacaag ctcgcctgcg   23220
ccatagtcaa tacggccggt cgcgagactg ggggcgtaca ctggatggcc tttgcctgga   23280
acccgcactc aaaaacatgc tacctctttg agccctttgg cttttctgac cagcgactca   23340
agcaggttta ccagtttgag tacgagtcac tcctgcgccg tagcgccatt gcttcttccc   23400
ccgaccgctg tataacgctg gaaaagtcca cccaaagcgt acaggggccc aactcggccg   23460
cctgtggact attctgctgc atgtttctcc acgcctttgc caactggccc caaactccca   23520
tggatcacaa ccccaccatg aaccttatta ccggggtacc caactccatg ctcaacagtc   23580
cccaggtaca gcccaccctg cgtcgcaacc aggaacagct ctacagcttc ctggagcgcc   23640
actcgcccta cttccgcagc cacagtgcgc agattaggag cgccacttct ttttgtcact   23700
tgaaaaacat gtaaaaataa tgtactagag acactttcaa taaaggcaaa tgcttttatt   23760
tgtacactct cgggtgatta tttacccca cccttgccgt ctgcgccgtt taaaaatcaa   23820
aggggttctg ccgcgcatcg ctatgcgcca ctggcaggga cacgttgcga tactggtgtt   23880
tagtgctcca cttaaactca ggcacaacca tccgcggcag ctcggtgaag ttttcactcc   23940
acaggctgcg caccatcacc aacgcgttta gcaggtcggg cgccgatatc ttgaagtcgc   24000
agttggggcc tccgccctgc gcgcgcgagt tgcgatacac agggttgcag cactggaaca   24060
ctatcagcgc cgggtggtgc acgctggcca gcacgctctt gtcggagatc agatccgcgt   24120
ccaggtcctc cgcgttgctc agggcgaacg gagtcaactt tggtagctgc cttcccaaaa   24180
agggcgcgtg cccaggcttt gagttgcact cgcaccgtag tggcatcaaa aggtgaccgt   24240
gcccggtctg ggcgttagga tacagcgcct gcataaaagc cttgatctgc ttaaaagcca   24300
cctgagcctt tgcgccttca gagaagaaca tgccgcaaga cttgccggaa aactgattgg   24360
ccggacaggc cgcgtcgtgc acgcagcacc ttgcgtcggt gttggagatc tgcaccacat   24420
ttcggcccca ccggttcttc acgatcttgg ccttgctaga ctgctccttc agcgcgcgct   24480
gcccgttttc gctcgtcaca tccatttcaa tcacgtgctc cttatttatc ataatgcttc   24540
cgtgtagaca cttaagctcg ccttcgatct cagcgcagcg gtgcagccac aacgcgcagc   24600
ccgtgggctc gtgatgcttg taggtcacct ctgcaaacga ctgcaggtac gcctgcagga   24660
atcgccccat catcgtcaca aaggtcttgt tgctggtgaa ggtcagctgc aacccgcggt   24720
```

| | |
|---|---|
| gctcctcgtt cagccaggtc ttgcatacgg ccgccagagc ttccacttgg tcaggcagta | 24780 |
| gtttgaagtt cgcctttaga tcgttatcca cgtggtactt gtccatcagc gcgcgcgcag | 24840 |
| cctccatgcc cttctcccac gcagacacga tcggcacact cagcgggttc atcaccgtaa | 24900 |
| tttcactttc cgcttcgctg ggctcttcct cttcctcttg cgtccgcata ccacgcgcca | 24960 |
| ctgggtcgtc ttcattcagc cgccgcactg tgcgcttacc tcctttgcca tgcttgatta | 25020 |
| gcaccggtgg gttgctgaaa cccaccattt gtagcgccac atcttctctt tcttcctcgc | 25080 |
| tgtccacgat tacctctggt gatggcgggc gctcgggctt gggagaaggg cgcttctttt | 25140 |
| tcttcttggg cgcaatggcc aaatccgccg ccgaggtcga tggccgcggg ctgggtgtgc | 25200 |
| gcggcaccag cgcgtcttgt gatgagtctt cctcgtcctc ggactcgata cgccgcctca | 25260 |
| tccgcttttt tgggggcgcc cggggaggcg gcggcgacgg ggacggggac gacacgtcct | 25320 |
| ccatggttgg gggacgtcgc gccgcaccgc gtccgcgctc ggggtggtt tcgcgctgct | 25380 |
| cctcttcccg actggccatt tccttctcct ataggcagaa aaagatcatg gagtcagtcg | 25440 |
| agaagaagga cagcctaacc gccccctctg agttcgccac caccgcctcc accgatgccg | 25500 |
| ccaacgcgcc taccaccttc cccgtcgagg caccccgct tgaggaggag gaagtgatta | 25560 |
| tcgagcagga cccaggtttt gtaagcgaag acgacgagga ccgctcagta ccaacagagg | 25620 |
| ataaaaagca agaccaggac aacgcagagg caaacgagga acaagtcggg cgggggacg | 25680 |
| aaaggcatgg cgactaccta gatgtgggag acgacgtgct gttgaagcat ctgcagcgcc | 25740 |
| agtgcgccat tatctgcgac gcgttgcaag agcgcagcga tgtgcccctc gccatagcgg | 25800 |
| atgtcagcct tgcctacgaa cgccacctat tctcaccgcg cgtacccccc aaacgccaag | 25860 |
| aaaacggcac atgcgagccc aacccgcgcc tcaacttcta ccccgtattt gccgtgccag | 25920 |
| aggtgcttgc cacctatcac atcttttttcc aaaactgcaa gataccccta tcctgccgtg | 25980 |
| ccaaccgcag ccgagcggac aagcagctgg ccttgcggca gggcgctgtc atacctgata | 26040 |
| tcgcctcgct caacgaagtg ccaaaaatct ttgagggtct tggacgcgac gagaagcgcg | 26100 |
| cggcaaacgc tctgcaacag gaaaacagcg aaaatgaaag tcactctgga gtgttggtgg | 26160 |
| aactcgaggg tgacaacgcg cgcctagccg tactaaaacg cagcatcgag gtcacccact | 26220 |
| ttgcctaccc ggcacttaac ctaccccca aggtcatgag cacagtcatg agtgagctga | 26280 |
| tcgtgcgccg tgcgcagccc ctggagaggg atgcaaattt gcaagaacaa acagaggagg | 26340 |
| gcctacccgc agttggcgac gagcagctag cgcgctggct tcaaacgcgc gagcctgccg | 26400 |
| acttggagga gcgacgcaaa ctaatgatgg ccgcagtgct cgttaccgtg gagcttgagt | 26460 |
| gcatgcagcg gttctttgct gacccggaga tgcagcgcaa gctagaggaa acattgcact | 26520 |
| acacctttcg acagggctac gtacgccagg cctgcaagat ctccaacgtg gagctctgca | 26580 |
| acctggtctc ctaccttgga atttgcacg aaaaccgcct tgggcaaaac gtgcttcatt | 26640 |
| ccacgctcaa gggcgaggcg cgccgcgact acgtccgcga ctgcgtttac ttatttctat | 26700 |
| gctacacctg gcagacggcc atgggcgttt ggcagcagtg cttggaggag tgcaacctca | 26760 |
| aggagctgca gaaactgcta aagcaaaact tgaaggacct atggacggcc ttcaacgagc | 26820 |
| gctccgtggc cgcgcacctg gcggacatca ttttccccga acgcctgctt aaaacctgc | 26880 |
| aacagggtct gccagacttc accagtcaaa gcatgttgca gaactttagg aactttatcc | 26940 |
| tagagcgctc aggaatcttg cccgccacct gctgtgcact tcctagcgac tttgtgccca | 27000 |
| ttaagtaccg cgaatgccct ccgccgcttt ggggccactg ctaccttctg cagctagcca | 27060 |
| actaccttgc ctaccactct gacataatgg aagacgtgag cggtgacggt ctactggagt | 27120 |

```
gtcactgtcg ctgcaaccta tgcaccccgc accgctccct ggtttgcaat tcgcagctgc   27180
ttaacgaaag tcaaattatc ggtacctttg agctgcaggg tccctcgcct gacgaaaagt   27240
ccgcggctcc ggggttgaaa ctcactccgg ggctgtggac gtcggcttac cttcgcaaat   27300
ttgtacctga ggactaccac gcccacgaga ttaggttcta cgaagaccaa tcccgcccgc   27360
ctaatgcgga gcttaccgcc tgcgtcatta cccagggcca cattcttggc caattgcaag   27420
ccatcaacaa agcccgccaa gagtttctgc tacgaaaggg acgggggggtt tacttggacc   27480 cccagtccgg cgaggagctc aacccaatcc ccccgccgcc gcagccctat cagcagcagc   27540
cgcgggccct tgcttcccag gatggcaccc aaaaagaagc tgcagctgcc gccgccaccc   27600
acggacgagg aggaatactg ggacagtcag gcagaggagg ttttggacga ggaggaggag   27660
gacatgatgg aagactggga gagcctagac gaggaagctt ccgaggtcga agaggtgtca   27720
gacgaaacac cgtcaccctc ggtcgcattc ccctcgccgg cgccccagaa atcggcaacc   27780
ggttccagca tggctacaac ctccgctcct caggcgccgc cggcactgcc cgttcgccga   27840
cccaaccgta gatgggacac cactggaacc agggccggta agtccaagca gccgccgccg   27900
ttagcccaag agcaacaaca gcgccaaggc taccgctcat ggcgcgggca caagaacgcc   27960
atagttgctt gcttgcaaga ctgtgggggc aacatctcct tcgcccgccg ctttcttctc   28020
taccatcacg gcgtggcctt cccccgtaac atcctgcatt actaccgtca tctctacagc   28080
ccatactgca ccggcggcag cggcagcaac agcagcggcc acacagaagc aaaggcgacc   28140
ggatagcaag actctgacaa agcccaagaa atccacagcg gcggcagcag caggaggagg   28200
agcgctgcgt ctggcgccca acgaacccgt atcgacccgc gagcttagaa acaggatttt   28260
tcccactctg tatgctatat ttcaacagag caggggccaa gaacaagagc tgaaaataaa   28320
aaacaggtct ctgcgatccc tcacccgcag ctgcctgtat cacaaaagcg aagatcagct   28380
tcggcgcacg ctggaagacg cggaggctct cttcagtaaa tactgcgcgc tgactcttaa   28440
ggactagttt cgcgcccttt ctcaaattta agcgcgaaaa ctacgtcatc tccagcggcc   28500
acacccggcg ccagcacctg ttgtcagcgc cattatgagc aaggaaattc ccacgcccta   28560
catgtggagt taccagccac aaatgggact tgcggctgga gctgcccaag actactcaac   28620
ccgaataaac tacatgagcg cgggacccca catgatatcc cgggtcaacg gaatacgcgc   28680
ccaccgaaac cgaattctcc tggaacaggc ggctattacc accacacctc gtaataacct   28740
taatccccgt agttggcccg ctgccctggt gtaccaggaa agtcccgctc ccaccactgt   28800
ggtacttccc agagacgccc aggccgaagt tcagatgact aactcagggg cgcagcttgc   28860
gggcggcttt cgtcacaggg tgcggtcgcc cgggcagggt ataactcacc tgacaatcag   28920
agggcgaggt attcagctca acgacgagtc ggtgagctcc tcgcttggtc tccgtccgga   28980
cgggacattt cagatcggcg gcgccggccg ctcttcattc acgcctcgtc aggcaatcct   29040
aactctgcag acctcgtcct ctgagccgcg ctctggaggc attggaactc tgcaatttat   29100
tgaggagttt gtgccatcgg tctactttaa ccccttctcg ggacctcccg gccactatcc   29160
ggatcaattt attcctaact ttgacgcggt aaaggactcg gcggacggct acgactgaat   29220
gttaagtgga gaggcagagc aactgcgcct gaaacacctg gtccactgtc gccgccacaa   29280
gtgctttgcc cgcgactccg gtgagttttg ctactttgaa ttgcccgagg atcatatcga   29340
gggcccggcg cacggcgtcc ggcttaccgc ccagggagag cttgcccgta gcctgattcg   29400
ggagtttacc cagcgccccc tgctagttga gcgggacagg ggaccctgtg ttctcactgt   29460
```

```
gatttgcaac tgtcctaacc ctggattaca tcaagatcct ctagttaatg tcaggtcgcc    29520
taagtcgatt aactagagta cccggggatc ttattccctt taactaataa aaaaaaataa    29580
taaagcatca cttacttaaa atcagttagc aaatttctgt ccagtttatt cagcagcacc    29640
tccttgccct cctcccagct ctggtattgc agcttcctcc tggctgcaaa ctttctccac    29700
aatctaaatg gaatgtcagt ttcctcctgt tcctgtccat ccgcacccac tatcttcatg    29760
ttgttgcaga tgaagcgcgc aagaccgtct gaagatacct tcaacccgt gtatccatat     29820
gacacggaaa ccggtcctcc aactgtgcct tttcttactc ctcccttgt atcccccaat     29880
gggtttcaag agagtccccc tggggtactc tctttgcgcc tatccgaacc tctagttacc    29940
tccaatggca tgcttgcgct caaaatgggc aacggcctct ctctggacga ggccggcaac    30000
cttacctccc aaaatgtaac cactgtgagc ccacctctca aaaaaccaa gtcaaacata     30060
aacctggaaa tatctgcacc cctcacagtt acctcagaag ccctaactgt ggctgccgcc    30120
gcacctctaa tggtcgcggg caacacactc accatgcaat cacaggcccc gctaaccgtg    30180
cacgactcca aacttagcat tgccacccaa ggacccctca cagtgtcaga aggaaagcta    30240
gccctgcaaa catcaggccc cctcaccacc accgatagca gtaccttac tatcactgcc     30300
tcacccctc taactactgc cactggtagc ttgggcattg acttgaaaga gcccatttat     30360
acacaaaatg gaaaactagg actaaagtac gggctcctt tgcatgtaac agacgaccta     30420
aacactttga ccgtagcaac tggtccaggt gtgactatta ataatacttc cttgcaaact    30480
aaagttactg gagccttggg ttttgattca caaggcaata tgcaacttaa tgtagcagga    30540
ggactaagga ttgattctca aaacagacgc cttatacttg atgttagtta ccgtttgat     30600
gctcaaaacc aactaaatct aagactagga cagggccctc tttttataaa ctcagcccac    30660
aacttggata ttaactacaa caaggccctt tacttgttta cagcttcaaa caattccaaa    30720
aagcttgagg ttaacctaag cactgccaag gggttgatgt ttgacgctac agccatagcc    30780
attaatgcag gagatgggct tgaatttggt tcacctaatg caccaaacac aaatcccctc    30840
aaaacaaaaa ttggccatgg cctagaattt gattcaaaca aggctatggt tcctaaacta    30900
ggaactggcc ttagttttga cagcacaggt gccattacag taggaaacaa aaataatgat    30960
aagctaactt tgtggaccac accagctcca tctcctaact gtagactaaa tgcagagaaa    31020
gatgctaaac tcactttggt cttaacaaaa tgtggcagtc aaatacttgc tacagtttca    31080
gttttggctg ttaaaggcag tttggctcca atatctggaa cagttcaaag tgctcatctt    31140
attataagat ttgacgaaaa tggagtgcta ctaaacaatt ccttcctgga cccagaatat    31200
tggaacttta gaaatggaga tcttactgaa ggcacagcct atacaaacgc tgttggattt    31260
atgcctaacc tatcagctta tccaaaatct cacggtaaaa ctgccaaaag taacattgtc    31320
agtcaagttt acttaaacgg agacaaaact aaacctgtaa cactaaccat tacactaaac    31380
ggtacacagg aaacaggaga cacaactcca agtgcatact ctatgtcatt tcatgggac    31440
tggtctggcc acaactacat taatgaaata tttgccacat cctcttacac tttttcatac    31500
attgcccaag aataaagaat cgtttgtgtt atgtttcaac gtgtttattt ttcaattgca    31560
gaaaatttca agtcattttt cattcagtag tatagcccca ccaccacata gcttatacag    31620
atcaccgtac cttaatcaaa ctcacagaac cctagtattc aacctgccac ctccctccca    31680
acacacagag tacacagtcc tttctccccg gctggcctta aaaagcatca tatcatgggt    31740
aacagacata ttcttaggtg ttatattcca cacggtttcc tgtcgagcca acgctcatc    31800
agtgatatta ataaactccc cgggcagctc acttaagttc atgtcgctgt ccagctgctg    31860
```

```
agccacaggc tgctgtccaa cttgcggttg cttaacgggc ggcgaaggag aagtccacgc  31920
ctacatgggg gtagagtcat aatcgtgcat caggataggg cggtggtgct gcagcagcgc  31980
gcgaataaac tgctgccgcc gccgctccgt cctgcaggaa tacaacatgg cagtggtctc  32040
ctcagcgatg attcgcaccg cccgcagcat aaggcgcctt gtcctccggg cacagcagcg  32100
caccctgatc tcacttaaat cagcacagta actgcagcac agcaccacaa tattgttcaa  32160
aatcccacag tgcaaggcgc tgtatccaaa gctcatggcg gggaccacag aacccacgtg  32220
gccatcatac cacaagcgca ggtagattaa gtggcgaccc ctcataaaca cgctggacat  32280
aaacattacc tcttttggca tgttgtaatt caccacctcc cggtaccata taaacctctg  32340
attaaacatg gcgccatcca ccaccatcct aaaccagctg gccaaaacct gcccgccggc  32400
tatacactgc agggaaccgg gactggaaca atgacagtgg agagcccagg actcgtaacc  32460
atggatcatc atgctcgtca tgatatcaat gttggcacaa cacaggcaca cgtgcataca  32520
cttcctcagg attacaagct cctcccgcgt tagaaccata tcccagggaa caacccattc  32580
ctgaatcagc gtaaatccca cactgcaggg aagacctcgc acgtaactca cgttgtgcat  32640
tgtcaaagtg ttacattcgg gcagcagcgg atgatcctcc agtatggtag cgcgggtttc  32700
tgtctcaaaa ggaggtagac gatccctact gtacggagtg cgccgagaca accgagatcg  32760
tgttggtcgt agtgtcatgc caaatggaac gccggacgta gtcatatttc ctgaagcaaa  32820
accaggtgcg ggcgtgacaa acagatctgc gtctccggtc tcgccgctta gatcgctctg  32880
tgtagtagtt gtagtatatc cactctctca aagcatccag gcgcccctg gcttcgggtt   32940
ctatgtaaac tccttcatgc gccgctgccc tgataacatc caccaccgca gaataagcca  33000
cacccagcca acctacacat tcgttctgcg agtcacacac gggaggagcg ggaagagctg  33060
gaagaaccat gttttttttt ttattccaaa agattatcca aaacctcaaa atgaagatct  33120
attaagtgaa cgcgctcccc tccggtggcg tggtcaaact ctacagccaa agaacagata  33180
atggcatttg taagatgttg cacaatggct tccaaaaggc aaacggccct cacgtccaag  33240
tggacgtaaa ggctaaaccc ttcagggtga atctcctcta taaacattcc agcaccttca  33300
accatgccca ataattctc atctcgccac cttctcaata tatctctaag caaatcccga  33360
atattaagtc cggccattgt aaaaatctgc tccagagcgc cctccacctt cagcctcaag  33420
cagcgaatca tgattgcaaa aattcaggtt cctcacagac ctgtataaga ttcaaaagcg  33480
gaacattaac aaaaataccg cgatcccgta ggtcccttcg cagggccagc tgaacataat  33540
cgtgcaggtc tgcacggacc agcgcggcca cttccccgcc aggaaccatg acaaaagaac  33600
ccacactgat tatgacacgc atactcggag ctatgctaac cagcgtagcc ccgatgtaag  33660
cttgttgcat gggcggcgat ataaaatgca aggtgctgct caaaaaatca ggcaaagcct  33720
cgcgcaaaaa agaaagcaca tcgtagtcat gctcatgcag ataaaggcag gtaagctccg  33780
gaaccaccac agaaaagac accattttc tctcaaacat gtctgcgggt ttctgcataa  33840
acacaaaata aaataacaaa aaaacattta aacattagaa gcctgtctta caacaggaaa  33900
aacaacccctt ataagcataa gacggactac ggccatgccg gcgtgaccgt aaaaaaactg  33960
gtcaccgtga ttaaaaagca ccaccgacag ctcctcggtc atgtccggag tcataatgta  34020
agactcggta aacacatcag gttgattcac atcggtcagt gctaaaaagc gaccgaaata  34080
gcccggggga atacatatcccc gcaggcgtag agacaacatt acagccccca taggaggtat  34140
aacaaaatta ataggagaga aaaacacata aacacctgaa aaaccctcct gcctaggcaa  34200
```

| | |
|---|---|
| aatagcaccc tcccgctcca gaacaacata cagcgcttcc acagcggcag ccataacagt | 34260 |
| cagccttacc agtaaaaaag aaaacctatt aaaaaaacac cactcgacac ggcaccagct | 34320 |
| caatcagtca cagtgtaaaa aagggccaag tgcagagcga gtatatatag gactaaaaaa | 34380 |
| tgacgtaacg gttaaagtcc acaaaaaaca cccagaaaac cgcacgcgaa cctacgccca | 34440 |
| gaaacgaaag ccaaaaaacc cacaacttcc tcaaatcgtc acttccgttt tcccacgtta | 34500 |
| cgtcacttcc cattttaaga aaactacaat tcccaacaca tacaagttac tccgccctaa | 34560 |
| aacctacgtc acccgccccg ttcccacgcc ccgcgccacg tcacaaactc cacccccctca | 34620 |
| ttatcatatt ggcttcaatc caaataagg tatattattg atgat | 34665 |

<210> SEQ ID NO 96
<211> LENGTH: 1644
<212> TYPE: DNA
<213> ORGANISM: Homo sapiens

<400> SEQUENCE: 96

| | |
|---|---|
| gtcgacgcca ccatgtgtca ccagcagctc gtgattagct ggttcagcct ggtgtttctg | 60 |
| gctagccctc tggtggccat ctgggagctg aagaaggacg tgtacgtggt ggagctcgac | 120 |
| tggtaccctg acgctcccgg cgagatggtc gtgctgacct cgacaccccc tgaggaagat | 180 |
| ggcatcacct ggaccctgga tcaaagctcc gaagtgctcg gcagcggcaa gacactcacc | 240 |
| atccaggtga aagagttcgg agacgccggc cagtacacct gccacaaagg cggcgaggtg | 300 |
| ctgtcccatt ccctgctgct gctgcacaag aaagaggatg gcatctggtc caccgacatc | 360 |
| ctgaaggacc agaaggaacc caagaacaag acctttctga gatgtgaggc caagaactac | 420 |
| agcggcaggt tcacctgctg gtggctgaca acaatctcca ccgacctgac cttcagcgtc | 480 |
| aagagcagca ggggcagcag cgaccctcaa ggcgtgacat gtggagccgc taccctgagc | 540 |
| gctgagagag tcagggcga caataaggag tacgagtact ccgtggaatg ccaggaggac | 600 |
| tccgcctgcc ctgccgccga agagtccctc cctatcgaag tgatggttga tgccgtgcac | 660 |
| aagctcaagt atgagaatta caccagcagc ttttcatca gggacatcat caagcccgac | 720 |
| cccccaaaa acctccagct gaaacccctc aagaatagca ggcaggtgga ggtctcctgg | 780 |
| gagtatcctg acacctggag caccccccac agctacttct ccctgacctt ctgtgtgcag | 840 |
| gtgcagggca agagcaaaag ggagaagaag gatagggtct ttaccgacaa gaccagcgcc | 900 |
| acagtgatct gcaggaagaa cgccagcatt tccgtcaggg cccaggacag gtactacagc | 960 |
| agcagctggt ccgagtgggc tagcgtgcct tgttccggcg gcggaggatc tggcggaggc | 1020 |
| ggaagtggcg gagggggctc tagaaacctc cccgtggcca cacccgaccc tggcatgttc | 1080 |
| ccctgcctcc accacagcca gaacctgctg agagccgtga gcaatatgct gcagaaggcc | 1140 |
| aggcaaaccc tggagttcta cccctgtacc tccgaggaga ttgaccatga ggacatcaca | 1200 |
| aaggacaaaa ccagcaccgt ggaggcctgt ctcccctcg aactgaccaa gaacgagtcc | 1260 |
| tgcctgaact ccagggagac atccttcatc accaacggct cctgcctggc ctccagaaag | 1320 |
| accagcttca tgatggccct ctgcctgagc agcatctacg aggacctcaa gatgtaccag | 1380 |
| gtggagttta aaacaatgaa cgccaagctc ctcatggacc taagaggca gattttcctc | 1440 |
| gaccagaata tgctggctgt cattgacgag ctgatgcagg ccctcaattt caactccgag | 1500 |
| accgtcccc agaagtcctc cctggaagag cccgactttt acaagaccaa gatcaagctc | 1560 |
| tgcatcctgc tgcacgcctt cagaattaga gccgtgacca ttgacagggt gatgagctac | 1620 |
| ctcaacgcct cctgatgact cgag | 1644 |

<210> SEQ ID NO 97
<211> LENGTH: 2101
<212> TYPE: DNA
<213> ORGANISM: Homo sapiens

<400> SEQUENCE: 97

| | | | | | |
|---|---|---|---|---|---|
| gtcgacgcca | ccacatccgc | ggcaacgcct | ccttggtgtc | gtccgcttcc | aataacccag | 60 |
| cttgcgtcct | gcacacttgt | ggcttccgtg | cacacattaa | caactcatgg | ttctagctcc | 120 |
| cagtcgccaa | gcgttgccaa | ggcgttgaga | gatcatctgg | gaagtctttt | acccagaatt | 180 |
| gctttgattc | aggccagctg | gttttcctg | cggtgattcg | gaaattcgcg | aattcctctg | 240 |
| gtcctcatcc | aggtgcgcgg | gaagcaggtg | cccaggagag | aggggataat | gaagattcca | 300 |
| tgctgatgat | cccaaagatt | gaacctgcag | accaagcgca | agtagaaac | tgaaagtaca | 360 |
| ctgctggcgg | atcctacgga | agttatgaa | aaggcaaagc | gcagagccac | gccgtagtgt | 420 |
| gtgccgcccc | ccttgggatg | gatgaaactg | cagtcgcggc | gtgggtaaga | ggaaccagct | 480 |
| gcagagatca | ccctgcccaa | cacagactcg | gcaactccgc | ggaagaccag | ggtcctggga | 540 |
| gtgactatgg | gcggtgagag | cttgctcctg | ctccagttgc | ggtcatcatg | actacgcccg | 600 |
| cctcccgcag | accatgttcc | atgtttcttt | taggtatatc | tttggacttc | ctcccctgat | 660 |
| ccttgttctg | ttgccagtag | catcatctga | ttgtgatatt | gaaggtaaag | atggcaaaca | 720 |
| atatgagagt | gttctaatgg | tcagcatcga | tcaattattg | acagcatga | aagaaattgg | 780 |
| tagcaattgc | ctgaataatg | aatttaactt | ttttaaaaga | catatctgtg | atgctaataa | 840 |
| ggaaggtatg | ttttattcc | gtgctgctcg | caagttgagg | caatttctta | aaatgaatag | 900 |
| cactggtgat | tttgatctcc | acttattaaa | agtttcagaa | ggcacaacaa | tactgttgaa | 960 |
| ctgcactggc | caggttaaag | gaagaaaacc | agctgccctg | ggtgaagccc | aaccaacaaa | 1020 |
| gagtttggaa | gaaaataaat | ctttaaagga | acagaaaaaa | ctgaatgact | tgtgtttcct | 1080 |
| aaagagacta | ttacaagaga | taaaaacttg | ttggaataaa | attttgatgg | gcactaaaga | 1140 |
| acactgaaaa | atatggagtg | gcaatataga | aacacgaact | ttagctgcat | cctccaagaa | 1200 |
| tctatctgct | tatgcagttt | ttcagagtgg | aatgcttcct | agaagttact | gaatgcacca | 1260 |
| tggtcaaaac | ggattagggc | atttgagaaa | tgcatattgt | attactagaa | gatgaataca | 1320 |
| aacaatggaa | actgaatgct | ccagtcaaca | aactatttct | tatatatgtg | aacatttatc | 1380 |
| aatcagtata | attctgtact | gattttttgta | agacaatcca | tgtaaggtat | cagttgcaat | 1440 |
| aatacttctc | aaacctgttt | aaatatttca | agacattaaa | tctatgaagt | atataatggt | 1500 |
| ttcaaagatt | caaaattgac | attgctttac | tgtcaaaata | attttatggc | tcactatgaa | 1560 |
| tctattatac | tgtattaaga | gtgaaaattg | tcttcttctg | tgctggagat | gttttagagt | 1620 |
| taacaatgat | atatggataa | tgccggtgag | aataagagag | tcataaacct | taagtaagca | 1680 |
| acagcataac | aaggtccaag | atacctaaaa | gagatttcaa | gagatttaat | taatcatgaa | 1740 |
| tgtgtaacac | agtgccttca | ataaatggta | tagcaaatgt | tttgacatga | aaaaggaca | 1800 |
| atttcaaaaa | aataaaataa | aataaaaata | aattcaccta | gtctaaggat | gctaaacctt | 1860 |
| agtactgagt | tacattgtca | tttatataga | ttataacttg | tctaaataag | tttgcaattt | 1920 |
| gggagatata | tttttaagat | aataatatat | gtttacctt | taattaatga | aatatctgta | 1980 |
| tttaattttg | acactatatc | tgtatataaa | atattttcat | acagcattac | aaattgctta | 2040 |
| ctttggaata | catttctcct | ttgataaaat | aaatgagcta | tgtattaaaa | aaaaaaaaa | 2100 |
| a | | | | | | 2101 |

-continued

<210> SEQ ID NO 98
<211> LENGTH: 925
<212> TYPE: DNA
<213> ORGANISM: Homo sapiens

<400> SEQUENCE: 98
gtcgacgcca ccccagagag gggcaggctg gtcccctgac aggttgaagc aagtagacgc    60
ccaggagccc cgggaggggg ctgcagtttc cttccttcct tctcggcagc gctccgcgcc   120
cccatcgccc ctcctgcgct agcggagtg atcgccgcgg cgatgccgga ggagggttcg    180
ggctgctcgg tgcggcgcag gccctatggg tgcgtcctgc gggctgcttt ggtcccattg    240
gtcgcgggct tggtgatctg cctcgtggtg tgcatccagc gcttcgcaca ggctcagcag    300
cagctgccgc tcgagtcact tgggtgggac gtagctgagc tgcagctgaa tcacacagga    360
cctcagcagg accccaggct atactggcag ggggcccag cactgggccg ctccttcctg    420
catggaccag agctggacaa ggggcagcta cgtatccatc gtgatggcat ctacatggta    480
cacatccagg tgacgctggc catctgctcc tccacgacgg cctccaggca ccacccccacc   540 accctggccg tgggaatctg ctctcccgcc tcccgtagca tcagcctgct gcgtctcagc    600
ttccaccaag gttgtaccat tgcctcccag cgcctgacgc ccctggcccg aggggacaca    660
ctctgcacca acctcactgg gacactttg ccttcccgaa acactgatga gaccttcttt     720
ggagtgcagt gggtgcgccc ctgaccactg ctgctgatta gggtttttta aattttattt    780
tattttattt aagttcaaga gaaaaagtgt acacacaggg gccacccggg gttggggtgg    840
gagtgtggtg gggggtagtg gtggcaggac aagagaaggc attgagcttt ttcttcatt    900 ttcctattaa aaatacaaa aatca                                           925

<210> SEQ ID NO 99
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99
ggcggaagtg tgatgttgca agtgtggcgg aacacatgta agcgacggat gtggcgcaag    60
tctatgttgt agtaaatttg ggcgtaaccg agtaagattt ggccattttc gcgggaaaac   120
tgaataagag gaagtgaaat c                                              141

<210> SEQ ID NO 100
<211> LENGTH: 142
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
acaggaagtg acatgttgca agtgtggcgg aacacatgta agcgacggat gtggcgcaag    60
tctatgttgt agtaaatttg ggcgtaaccg agtaagattt ggccattttc gcgggaaaac   120
tgaataagag gaagtgaaat ct                                             142

<210> SEQ ID NO 101
<211> LENGTH: 129
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 101
acaggaagtg acaattttcg cgcggtttta ggcggatgtg gcgcaagtct atgttgtagt    60
aaatttgggc gtaaccgagt aagatttggc cattttcgcg ggaaaactga ataagaggaa   120
gtgaaatct                                                           129

<210> SEQ ID NO 102
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
ggcggaagtg tgatgttgca agtgtggcgg aacacatgta agcgacggat gtggcaaaag    60
tgacgttttt ggtgtgcgcc ggtgtacggc ggaagtgtga attttcgcgc ggttttagac   120
ggatgtggca gtaaatttgg gcgtaaccga gtaagatttg gccattttcg cgggaaaact   180
gaataagagg aagtgaaatc t                                             201

<210> SEQ ID NO 103
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
ggcggaagtg tgatgttgca agtgtggcgg aacacatgta agcgacggat gtggcaaaag    60
tgacgttttt ggtgtgcgcc ggtgtacggc ggaagtgtga attttcgcgc ggttttagac   120
ggatgtggca gtaaatttgg gcgtaaccga gtaagatttg gccattttcg cgggaaaact   180
gaataagagg atgtgaaatc t                                             201

<210> SEQ ID NO 104
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104
ggcggaagtg tgatgttgca agtgtggcgg aacacatgta agcgacggat gtggcaaaag    60
tgacgttttt ggtgtgcgcc ggtgtacggc ggaagtgtga attttcgcgc ggttttagac   120
ggatgtggca gtaaatttgg gcgtaaccga gtaagatttg gccattttcg cgggaaaact   180
gaataggcgg aagtgtgatc t                                             201

<210> SEQ ID NO 105
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide
```

-continued

```
<400> SEQUENCE: 105
ggcggaagtg tgatgttgca agtgtggcgg aacacatgta agcgacggat gtggcaaaag     60
tgacgttttt ggtgtgcgcc ggtgtacaca ggaagtgaca attttcgcgc ggttttagac    120
ggatgtggca gtaaatttgg gcgtaaccga gtaagatttg gccattttcg cgggaaaact    180
gaataggcgg aagtgtgatc t                                              201

<210> SEQ ID NO 106
<211> LENGTH: 177
<212> TYPE: PRT
<213> ORGANISM: Homo sapiens

<400> SEQUENCE: 106
```

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His

```
<210> SEQ ID NO 107
<211> LENGTH: 193
<212> TYPE: PRT
<213> ORGANISM: Artificial Sequence
<220> FEATURE:
<223> OTHER INFORMATION: Description of Artificial Sequence: Synthetic
      polynucleotide

<400> SEQUENCE: 107
```

Met Asp Met Arg Val Pro Ala Gln Leu Leu Gly Leu Leu Leu Leu Trp
1               5                   10                  15

Leu Arg Gly Ala Arg Cys Arg Met Lys Gln Ile Glu Asp Lys Ile Glu
            20                  25                  30

Glu Ile Leu Ser Lys Ile Tyr His Ile Glu Asn Glu Ile Ala Arg Ile
        35                  40                  45

Lys Lys Leu Ile Gly Glu Arg Gly Gly Ser Gly Gly Gly Ser Gly
    50                  55                  60

Gly Gly Ser Glu Thr Ala Lys Glu Pro Cys Met Ala Lys Phe Gly Pro
65                  70                  75                  80

-continued

```
Leu Pro Ser Lys Trp Gln Met Ala Ser Ser Glu Pro Pro Cys Val Asn
            85                      90                  95

Lys Val Ser Asp Trp Lys Leu Glu Ile Leu Gln Asn Gly Leu Tyr Leu
            100             105             110

Ile Tyr Gly Gln Val Ala Pro Asn Ala Asn Tyr Asn Asp Val Ala Pro
        115                 120                 125

Phe Glu Val Arg Leu Tyr Lys Asn Lys Asp Met Ile Gln Thr Leu Thr
    130                 135             140

Asn Lys Ser Lys Ile Gln Asn Val Gly Gly Thr Tyr Glu Leu His Val
145                 150                 155                 160

Gly Asp Thr Ile Asp Leu Ile Phe Asn Ser Glu His Gln Val Leu Lys
                165                 170                 175

Asn Asn Thr Tyr Trp Gly Ile Ile Leu Leu Ala Asn Pro Gln Phe Ile
                180                 185                 190

Ser
```

IMMUNOMODULATORY ONCOLYTIC ADENOVIRAL VECTORS, AND METHODS OF PRODUCTION AND USE THEREOF FOR TREATMENT OF CANCER

SEQUENCE LISTING

The instant application contains a Sequence Listing which has been submitted electronically in ASCII format and is hereby incorporated by reference in its entirety. Said ASCII copy, created on Dec. 21, 2017, is named 39354US_CRF_sequencelisting.txt and is 266,186 bytes in size.

FIELD

The invention described herein relates generally to the fields of immunology, virology, molecular biology, and more specifically to oncolytic adenoviruses having therapeutic applications.

BACKGROUND

Cancer is a leading cause of death in the United States and elsewhere. Depending on the type of cancer, it is typically treated with surgery, chemotherapy, and/or radiation. These treatments often fail, and it is clear that new therapies are necessary, to be used alone or in combination with current standards of care.

Originally conceived as solely tumor-lysing therapeutics, viruses that can preferentially target tumor cells for destruction are being used experimentally as vectors for the delivery of immune-stimulating cargo. The propagation of a lasting anti-tumor host immune response in combination with the destruction of tumor cells is described in, e.g., Lichty et al., 2014, Nature Reviews Cancer, 14: 559-567.

Clinical trials employing adenovirus, reovirus, measles, herpes simplex, Newcastle disease virus and vaccinia as oncolytic viruses have suggested that these platforms may all be safe treatment approaches.

Adenoviruses are medium-sized (90-100 nm), non-enveloped icosahedral viruses, which have double stranded linear DNA of about 36 kilobase pairs in a protein capsid. The viral capsid has fiber structures that participate in attachment of the virus to the target cell. First, the knob domain of the fiber protein binds to the receptor of the target cell (e.g., CD46 or Coxsackie and adenovirus receptor (CAR)), secondly, the virus interacts with an integrin molecule and thirdly, the virus is endocytosed into the target cell. Next, the viral genome is transported from endosomes into the nucleus and the replication machinery of the target cell is utilized also for viral purposes.

The adenoviral genome has early (E1-E4), intermediate (IX and IVa2) and late genes (L1-L5), which are transcribed in sequential order. Early gene products affect defense mechanisms, cell cycle and cellular metabolism of the host cell. Intermediate and late genes encode structural viral proteins for production of new virions.

More than 60 different serotypes of adenoviruses have been found in humans. Serotypes are classified into six subgroups A-F and different serotypes are known to be associated with different conditions i.e. respiratory diseases, conjunctivitis and gastroenteritis. Adenovirus serotype 5 (Ad-5) is known to cause respiratory diseases and it is the most common serotype studied in the field of gene therapy. In the first Ad5 vectors E1 and/or E3 regions were deleted enabling insertion of foreign DNA to the vectors.

Furthermore, deletions of other regions as well as further mutations have provided extra properties to viral vectors. Indeed, various modifications of adenoviruses have been suggested for achieving efficient anti-tumor effects.

Adenoviral vectors mediate gene transfer at a high efficacy compared to other vector systems, and they are currently the most frequently used vectors for cancer gene therapy. A non-replicating p53 expressing adenoviral vector and a replication selective virus (H101) have received regulatory approval in China. Several attempts to achieve tumor-selective control through the insertion of tumor selective promoter elements upstream of the E1 or other adenovirus critical promoters have had variable levels of success, but ultimately were limited by "leaky" gene expression of viral proteins in non-tumor cells and by reduced ability to propagate and lyse tumor cells compared to wild-type virus infections.

SUMMARY

In a first aspect, a pharmaceutical composition is provided comprising an effective amount of a recombinant adenoviral vector comprising: a transgene insertion site located between the start site of adenoviral E1b-19K and the start site of adenoviral E1b-55K, wherein a first DNA sequence and a second DNA sequence are each inserted into the transgene insertion site; wherein the first DNA sequence encodes a polypeptide selected from the group consisting of: a chimeric human IL-12, a human IL-7, an anti-CTLA-4 antibody, an IL-10Rtrap, a human CD70, a human IL-2 polypeptide, a human CD40 ligand, and a human OX40 ligand, and wherein the second DNA sequence encodes a polypeptide selected from the group consisting of: a chimeric human IL-12, a human IL-7, an anti-CTLA-4 antibody, an IL-10Rtrap, a human CD70, a human IL-2 polypeptide, a human CD40 ligand, and a human OX40 ligand; and wherein the adenoviral vector comprises a modified adenoviral E1a regulatory sequence wherein at least one Pea3 binding site, or a functional portion thereof, of the recombinant adenoviral vector is modified or deleted.

In one embodiment, the adenoviral vector comprises an IRES element or encodes a self-cleaving 2A peptide sequence between the first DNA sequence and the second DNA sequence. In another embodiment, the vector comprises a modified E3 region. In another embodiment, the vector comprises an intact E3 region. In another embodiment, the vector comprises a third DNA sequence inserted into the E3 region, wherein the third DNA sequence encodes a polypeptide selected from the group consisting of: a chimeric human IL-12, a human IL-7, an anti-CTLA-4 antibody, an IL-10Rtrap, a human CD70, a human IL-2 polypeptide, a human CD40 ligand, or a human OX40 ligand. In one embodiment, the chimeric human IL-12 polypeptide comprises a p40 polypeptide, a p35 polypeptide, and a linker polypeptide. In another embodiment, the chimeric human IL-12 polypeptide comprises a sequence as set forth in SEQ ID NO:46.

In one embodiment, the adenoviral vector comprises a nucleic acid sequence at least 95% identical in an E3 region to vector d1327. In another embodiment, the adenoviral vector comprises a nucleic acid sequence at least 85% identical in an E3 region to vector d1327. In another embodiment, the adenoviral vector comprises a nucleic acid sequence at least 75% identical in an E3 region to vector d1327.

In one embodiment, the pharmaceutical composition is formulated for systemic administration.

In another embodiment, the pharmaceutical composition is formulated for systemic administration.

In a second aspect is provided a pharmaceutical composition comprising an effective amount of a recombinant adenoviral vector comprising: a first transgene insertion site located between the start site of adenoviral E1b-19K and the start site of adenoviral E1b-55K; a second transgene insertion site located in adenoviral E3 region; a first DNA sequence, present in the first transgene insertion site, encoding one or a plurality of polypeptides selected from the group consisting of: a chimeric human IL-12, a human IL-7, an anti-CTLA-4 antibody, an IL-10Rtrap, a human CD70, a human IL-2 polypeptide, a human CD40 ligand, and a human OX40 ligand; and a second DNA sequence, present in the second transgene insertion site, encoding one or a plurality of polypeptides selected from the group consisting of: a chimeric human IL-12, a human IL-7, an anti-CTLA-4 antibody, an IL-10Rtrap, a human CD70, a human IL-2 polypeptide, a human CD40 ligand, and a human OX40 ligand, wherein the adenoviral vector comprises a modified adenoviral E1a regulatory sequence. In one embodiment, the pharmaceutical composition further comprises a third DNA sequence inserted into a third transgene insertion site, encoding one or a plurality of polypeptides selected from the group consisting of: a chimeric human IL-7, an anti-CTLA-4 antibody, an IL-10Rtrap, a human CD70, a human IL-2 polypeptide, a human CD40 ligand, and a human OX40 ligand.

In another embodiment, at least one of the first DNA sequence, the second DNA sequence, and the third DNA sequence independently comprises an IRES element and/or a self-cleaving 2A peptide. In one embodiment, at least one E1a regulatory sequence Pea3 binding site, or a functional portion thereof of the adenoviral vector, is modified or deleted. In another embodiment, a sequence between two Pea3 sites of the adenoviral vector is deleted. In one embodiment, the adenoviral vector comprises a modified E3 region. In another embodiment the adenoviral vector comprises a nucleic acid sequence at least 95% identical in an E3 region to vector dl327. In another embodiment, the adenoviral vector comprises a nucleic acid sequence at least 85% identical in an E3 region to vector dl327. In another embodiment, the adenoviral vector comprises a nucleic acid sequence at least 75% identical in an E3 region to vector dl327.

In one embodiment, the chimeric human IL-12 polypeptide comprises a p40 polypeptide, a p35 polypeptide, and a linker polypeptide.

In another aspect is provided a method for treating a tumor in a human subject in need thereof, comprising administering to the human with the tumor a therapeutic amount of the pharmaceutical composition of the first aspect by systemic or intratumoral administration.

In another aspect is provided method for treating a tumor in a human subject in need thereof, comprising administering to the human with the tumor a therapeutic amount of the pharmaceutical composition of the second aspect by systemic or intratumoral administration.

BRIEF DESCRIPTION OF THE DRAWINGS

FIG. 6A shows the activity of various oncolytic viruses compared to the empty virus ("d19k"), 38 days after cell implantation (primary tumor). Black bars represent virus alone and hatched bars represent virus+anti-PD-L1 antibody.

FIG. 6B is a graph comparing the average tumor size (primary tumor) over time of tumors injected with virus buffer (black circles), empty vector (blue solid squares), anti-PD-L1 alone (antibody given on days 16, 20, 24, and 28, right-hand arrow in each pair of arrows), each of five viruses alone (CTLA-4, IL-12, IL-7, CD70, and IL-10) or combined with anti-PD-L1 antibody.

FIG. 6C is a graph comparing the average tumor size (primary tumor) over time of tumors injected with virus buffer (black circles), empty vector (blue solid squares), anti-PD-L1 alone (antibody given on days 16, 20, 24, and 28, right-hand arrow in each pair of arrows), showing three viruses—OX40L, CD40L, and GM-CSF alone or combined with anti-PD-L1 antibody.

FIG. 6D shows virus buffer and control IgG only (left) and virus buffer and anti-PD-L1 antibody (right); the thick line in each graph shows the average tumor volume in mm$^3$. The pairs of arrows on the x-axis represent day of treatment with virus (intratumoral, left arrows) and the anti-PD-L1 antibody, if used (intraperitoneal, right arrows).

FIG. 6E shows d19k (empty virus) and control IgG only (left) and d19k and anti-PD-L1 antibody (right); the thick line in each graph shows the average tumor volume in mm$^3$. The pairs of arrows on the x-axis represent day of treatment with virus (intratumoral, left arrows) and the anti-PD-L1 antibody, if used (intraperitoneal, right arrows).

FIG. 6F is graph(s) showing results of treatment of tumor bearing mice (n=8 in each group) with oncolytic viruses comprising transgene(s), with or without anti-PD-L1. FIG. 6F shows CTLA-4 virus with control IgG (left) or anti-PD-L1 (right); the thick line in each graph shows the average tumor volume in mm$^3$. The pairs of arrows on the x-axis represent day of treatment with virus (intratumoral, left arrows) and the anti-PD-L1 antibody, if used (intraperitoneal, right arrows).

FIG. 6G shows IL-12 virus with control IgG (left) or anti-PD-L1 antibody (right); the thick line in each graph shows the average tumor volume in mm$^3$. The pairs of arrows on the x-axis represent day of treatment with virus (intratumoral, left arrows) and the anti-PD-L1 antibody, if used (intraperitoneal, right arrows).

FIG. 6H shows GM-CSF virus with control IgG (left) or anti-PD-L1 antibody (right); The thick line in each graph shows the average tumor volume in mm$^3$. The pairs of arrows on the x-axis represent day of treatment with virus (intratumoral, left arrows) and the anti-PD-L1 antibody, if used (intraperitoneal, right arrows).

FIG. 6I shows IL-7 virus with control IgG (left) or anti-PD-L1 antibody (right); The thick line in each graph shows the average tumor volume in mm$^3$. The pairs of arrows on the x-axis represent day of treatment with virus (intratumoral, left arrows) and the anti-PD-L1 antibody, if used (intraperitoneal, right arrows).

FIG. 6J shows CD40L virus with control IgG (left) or anti-PD-L1 antibody (right); The thick line in each graph shows the average tumor volume in mm$^3$. The pairs of arrows on the x-axis represent day of treatment with virus (intratumoral, left arrows) and the anti-PD-L1 antibody, if used (intraperitoneal, right arrows).

FIG. 6K shows L10 trap virus with control IgG (left) or anti-PD-L1 antibody (right); The thick line in each graph shows the average tumor volume in mm$^3$. The pairs of arrows on the x-axis represent day of treatment with virus (intratumoral, left arrows) and the anti-PD-L1 antibody, if used (intraperitoneal, right arrows).

FIG. 6L shows OX40L virus with control IgG (left) or anti-PD-L1 antibody. The thick line in each graph shows the average tumor volume in mm$^3$. The pairs of arrows on the x-axis represent day of treatment with virus (intratumoral, left arrows) and the anti-PD-L1 antibody, if used (intraperitoneal, right arrows).

FIG. 7A shows virus buffer only.

FIG. 7B shows empty virus only (TRZ000).

FIG. 7C shows TRZ010 (IL-10trap)+empty virus.

FIG. 7D shows TRZ011 (OX40 ligand)+empty virus.

FIG. 7E shows TRZ009 (CD70)+empty virus.

FIG. 7F shows TRZ007 (IL-7)+empty virus.

FIG. 7G shows TRZ002 (IL-12)+empty virus.

FIG. 7H shows TRZ004 (GM-CSF)+empty virus.

FIG. 7I shows TRZ003 (flagellin)+empty virus.

FIG. 7J shows TRZ002+TRZ010.

FIG. 7K shows TRZ002+TRZ007.

FIG. 7L shows TRZ007+TRZ010.

FIG. 7M shows TRZ011+TRZ004.

FIG. 7N shows TRZ009+TRZ003.

FIG. 7O is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in mm$^3$. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements). FIG. 7O shows TRZ002+TRZ009.

FIG. 7P shows TRZ007+TRZ009.

FIG. 7Q shows TRZ007+TRZ004.

FIG. 7R shows TRZ002+TRZ011.

FIG. 7S shows TRZ010+TRZ004.

FIG. 7T shows TRZ002+TRZ004.

FIG. 7U shows virus buffer and anti-PD-L1.

FIG. 7V shows TRZ002+empty virus+anti-PD-L1.

FIG. 7W shows TRZ009+anti-PD-L1.

FIG. 7X shows TRZ007+empty virus+anti-PD-L1.

FIG. 7Y shows TRZ002+TRZ007+anti-PD-L1.

FIG. 7Z shows TRZ007+TRZ009+anti-PD-L1.

FIG. 8A is an illustration of a wild-type adenoviral genome (top) and the TAV-255 adenoviral construct in which residues −305 to −255 are deleted (bottom).

FIG. 8B is an illustration of the potential method of action of the TAV-255 construct, in which the deletion removes Pea3 sites II and III, which moves Pea3 sites IV and V closer to the promoter as distal control elements.

FIG. 9A is a cartoon of the contrast between the single transgene constructs (top) used in the virus mixing examples, and the dual transgene vectors used to make the E1/E3 transgene adenoviruses.

FIG. 9B shows the results of mice injected i.t. with Empty virus+/−anti-PD-L1 or with TRZ-409 (IL-12/IL-7 dual transgene)+/−anti-PD-L1. The tumor volume of the injected tumor is shown in the left panel, and the tumor volume of the contralateral tumor is shown in the right panel. For each pair of arrows, the left arrow indicates virus injection and the right arrow indicates anti-PD-L1 injection. As can be seen for both the primary and contralateral tumors, TRZ-409 injection reduced tumor volume significantly compared to empty virus. The combination with anti-PD-L1 was slightly more efficacious in this study.

FIG. 9C shows the results of a second experiment using the inverse of TRZ-409, TRZ-403, in which the IL-7 transgene occupies the E1 region and the IL-12 gene occupies the E3 region (which has a stronger promoter than the E1). As can be seen in the Figure, TRZ-403 strongly inhibits primary and distant tumor growth, with or without anti-PD-L1.

FIG. 9F compares a mixture of two single transgene viruses with a dual transgene virus having the same transgenes. As can be seen in the primary tumor (left panel) TRZ-403 showed the most efficacy in reducing tumor volume, followed by the mixture of IL-7 and IL-12 single transgene viruses. The single transgene IL-12 virus showed a small amount of efficacy by comparison. In the contralateral tumor, however (right panel) only the dual transgene virus, TRZ-403, reduced the tumor volume, showing significant superiority over the mixture of viruses.

FIG. 7AA shows TRZ002+TRZ009+anti-PD-L1.

DEFINITIONS

Figure 1:
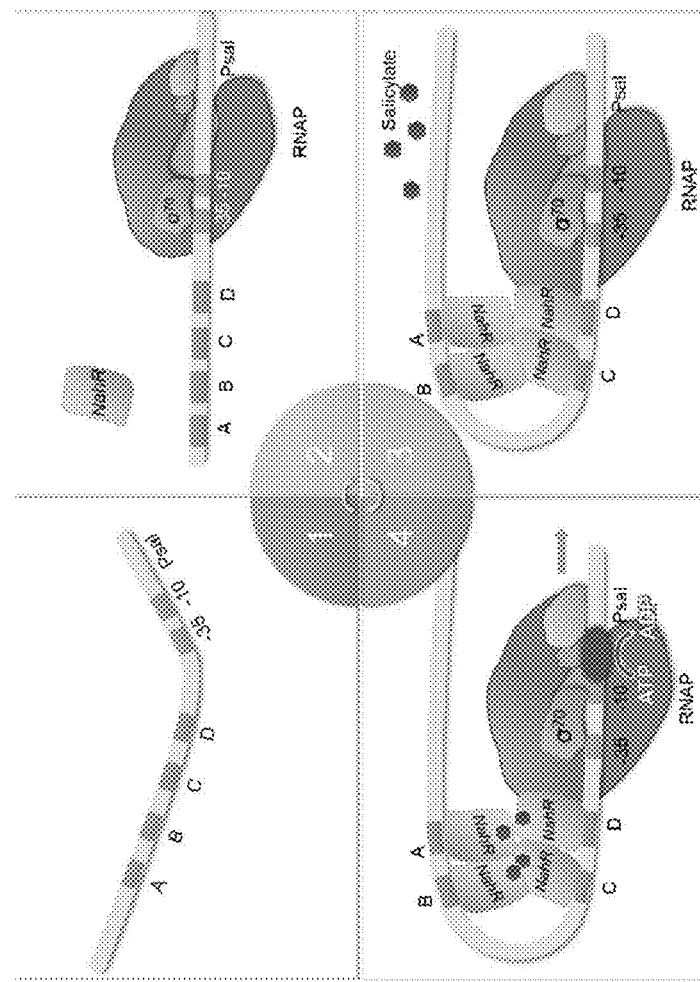
FIG. 1 is a cartoon illustrating transcription factor binding regulation of conformational structure/activity of E1a enhancer region.

The term "replicating virus" is meant to include a virus that undergoes the process of intracellular viral multiplication, consisting of the synthesis of proteins, nucleic acids, and sometimes lipids, and their assembly into a new infectious particle.

As used herein, the term "adenovirus" refers to any of a group of DNA-containing viruses (small infectious agents) that cause conjunctivitis and upper respiratory tract infections in humans. Adenoviral vectors are described in Peng, Z., "Current Status of Gendicine in China: Recombinant Human Ad-p53 Agent for Treatment of Cancers," *Hum Gene Ther* 16:1016-1027 (2005); No authors listed, "The End of the Beginning: Oncolytic Virotherapy Achieves Clinical Proof-of-concept," *Mol Ther* 13:237-238 (2006); Vile et al., "The Oncolytic Virotherapy Treatment Platform for Cancer: Unique Biological and Biosafety Points to Consider," *Cancer Gene Ther* 9:1062-1067 (2002); Harrison et al., "Wild-type Adenovirus Decreases Tumor Xenograft Growth, but Despite Viral Persistence Complete Tumor Responses are Rarely Achieved—Deletion of the Viral E1b-19-kD Gene Increases the Viral Oncolytic Effect," *Hum Gene Ther* 12:1323-1332 (2001); Kim et al., "Clinical Research Results with dl1520 (Onyx-015), a Replication-selective Adenovirus for the Treatment of Cancer: What Have We Learned?," *Gene Ther* 8:89-98 (2001); and Thorne et al., "Oncolytic Virotherapy: Approaches to Tumor Targeting and Enhancing Antitumor Effects," *Semin Oncol* 32:537-548 (2005), each of which is hereby incorporated by reference in their entirety. Adenoviral positions referenced herein are to positions in Adenovirus type 5 (GenBank 10 accession #M73260; the virus is available from the American Type Culture Collection, Rockville, Md., U.S.A., under accession number VR-5). It will be understood that corresponding positions can be identified in other adenovirus vectors by alignment using BLAST 2.0 under default settings (Altschul et al., *J. Mol. Biol.* 215:403-410 (1990)). Software for performing BLAST analyses is publicly available on the Web through the National Center for Biotechnology Information (www.ncbi.nlm.nih.gov/).

Current research in the field of viral vectors is producing improved viral vectors with high-titer and high-efficiency of transduction in mammalian cells (see, e.g., U.S. Pat. No. 6,218,187 to Finer et al., which is hereby incorporated by reference in its entirety). Such vectors are suitable in the present invention, as is any viral vector that comprises a combination of desirable elements derived from one or more of the viral vectors described herein. It is not intended that the expression vector be limited to a particular viral vector.

Certain "control elements" or "regulatory sequences" can also be incorporated into the vector-construct. The term "control elements" refers collectively to promoter regions, polyadenylation signals, transcription termination sequences, upstream regulatory domains, origins of replication, internal ribosome entry sites ("IRES"), enhancers, and the like, which collectively provide for the replication, transcription, and translation of a coding sequence(s) in a recipient cell. Not all of these control elements need always be present so long as the selected coding sequence is capable of being replicated, transcribed, and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcriptional control signals in eukaryotes comprise "promoter" and "enhancer" elements. Promoter and enhancer elements have been isolated from a variety of eukaryotic sources, including genes in yeast, insect, and mammalian cells, and viruses. Analogous control elements, i.e., promoters, are also found in prokaryotes. Such elements may vary in their strength and specificity. For example, promoters may be "constitutive" or "inducible."

A constitutive promoter is a promoter that directs expression of a gene throughout the development and life of an organism. Examples of some constitutive promoters that are widely used for inducing expression of transgenes include the cytomegalovirus (CMV) early promoter, those derived from any of the several actin genes, which are known to be expressed in most cells types (U.S. Pat. No. 6,002,068 to Privalle et al., which is hereby incorporated by reference in its entirety), and the ubiquitin promoter, which is a gene product known to accumulate in many cell types.

To ensure efficient expression, 3' polyadenylation regions can be present to provide for proper maturation of the mRNA transcripts. The 3' polyadenylation region will preferably be from the adenovirus sequence downstream of the inserted transgene, but the native 3'-untranslated region of the immunomodulatory gene may be used, or an alternative polyadenylation signal from, for example, SV40, particularly including a splice site, which provides for more efficient expression, could also be used. Alternatively, the 3'-untranslated region derived from a gene highly expressed in a particular cell type could be fused with the immunomodulatory gene.

"Inhibitors," "activators," and "modulators" of expression or of activity are used to refer to inhibitory, activating, or modulating molecules, respectively, identified using in vitro and in vivo assays for expression or activity of a described target protein, e.g., ligands, agonists, antagonists, and their homologs and mimetics. The term "modulator" includes inhibitors and activators. Inhibitors are agents that, e.g., inhibit expression or bind to, partially or totally block stimulation or protease inhibitor activity, decrease, prevent, delay activation, inactivate, desensitize, or down regulate the activity of the described target protein, e.g., antagonists. Activators are agents that, e.g., induce or activate the expression of a described target protein or bind to, stimulate, increase, open, activate, facilitate, enhance activation or protease inhibitor activity, sensitize or up regulate the activity of described target protein (or encoding polynucleotide), e.g., agonists. Modulators include naturally occurring and synthetic ligands, antagonists and agonists (e.g., small chemical molecules, antibodies and the like that function as either agonists or antagonists). Such assays for inhibitors and activators include, e.g., applying putative modulator compounds to cells expressing the described target protein and then determining the functional effects on the described target protein activity, as described above. Samples or assays comprising described target protein that are treated with a potential activator, inhibitor, or modulator are compared to control samples without the inhibitor, activator, or modulator to examine the extent of effect. Control samples (untreated with modulators) are assigned a relative activity value of 100%. Inhibition of a described target protein is achieved when the activity value relative to the control is about 80%, optionally 50% or 25, 10%, 5% or 1%. Activation of the described target protein is achieved when the activity value relative to the control is 110%, optionally 150%, optionally 200, 300%, 400%, 500%, or 1000-3000% or higher.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

Naturally occurring immunoglobulins have a common core structure in which two identical light chains (about 24 kD) and two identical heavy chains (about 55 or 70 kD) form a tetramer. The amino-terminal portion of each chain is known as the variable (V) region and can be distinguished from the more conserved constant (C) regions of the remainder of each chain. Within the variable region of the light chain is a C-terminal portion known as the J region. Within the variable region of the heavy chain, there is a D region in addition to the J region. Most of the amino acid sequence variation in immunoglobulins is confined to three separate locations in the V regions known as hypervariable regions or complementarity determining regions (CDRs) which are directly involved in antigen binding. Proceeding from the amino-terminus, these regions are designated CDR1, CDR2 and CDR3, respectively. The CDRs are held in place by more conserved framework regions (FRs). Proceeding from the amino-terminus, these regions are designated FR1, FR2, FR3, and FR4, respectively. The locations of CDR and FR regions and a numbering system have been defined by, e.g., Kabat et al. (Kabat et al., Sequences of Proteins of Immunological Interest, Fifth Edition, U.S. Department of Health and Human Services, U.S. Government Printing Office (1991)).

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_{H1}$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see FUNDAMENTAL IMMUNOLOGY (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

For preparation of monoclonal or polyclonal antibodies, any technique known in the art can be used (see, e.g., Kohler & Milstein, Nature 256:495-497 (1975); Kozbor et al., Immunology Today 4:72 (1983); Cole et al., pp. 77-96 in Monoclonal Antibodies and Cancer Therapy (1985)). "Monoclonal" antibodies refer to antibodies derived from a single clone. Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., Nature 348: 552-554 (1990); Marks et al., Biotechnology 10:779-783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts. See, e.g., Morrison et al., Proc. Natl. Acad. Sci. USA, 81:6851-6855 (1984); Morrison and Oi, Adv. Immunol., 44:65-92 (1988); Verhoeyen et al., Science, 239:1534-1536 (1988); Padlan, Molec. Immun., 28:489-498 (1991); Padlan, Molec. Immun., 31(3):169-217 (1994).

As used herein, the terms "treat" and "treating" in the context of the administration of a therapy refers to a treatment/therapy from which a subject receives a beneficial effect, such as the reduction, decrease, attenuation, diminishment, stabilization, remission, suppression, inhibition or arrest of the development or progression of cancer, or a symptom thereof. In certain embodiments, the treatment/therapy that a subject receives results in at least one or more of the following effects: (i) the reduction or amelioration of the severity of cancer and/or a symptom associated therewith; (ii) the reduction in the duration of a symptom associated with cancer; (iii) the prevention in the recurrence of a symptom associated with cancer; (iv) the regression of cancer and/or a symptom associated therewith; (v) the reduction in hospitalization of a subject; (vi) the reduction in hospitalization length; (vii) the increase in the survival of a subject; (viii) the inhibition of the progression of cancer and/or a symptom associated therewith; (ix) the enhancement or improvement the therapeutic effect of another therapy; (x) a reduction or elimination in the cancer cell population; (xi) a reduction in the growth of a tumor or neoplasm; (xii) a decrease in tumor size; (xiii) a reduction in the formation of a tumor; (xiv) eradication, removal, or control of primary, regional and/or metastatic cancer; (xv) a decrease in the number or size of metastases; (xvi) a reduction in mortality; (xvii) an increase in cancer-free survival rate of patients; (xviii) an increase in relapse-free survival; (xix) an increase in the number of patients in remission; (xx) a decrease in hospitalization rate; (xxi) the size of the tumor is maintained and does not increase in size or increases the size of the tumor by less 5% or 10% after administration of a therapy as measured by conventional methods available to one of skill in the art, such as MRI, X-ray, and CAT Scan; (xxii) the prevention of the development or onset of cancer and/or a symptom associated therewith; (xxiii) an increase in the length of remission in patients; (xxiv) the reduction in the number of symptoms associated with cancer; (xxv) an increase in symptom-free survival of cancer patients; and/or (xxvi) limitation of or reduction in metastasis. In some embodiments, the treatment/therapy that a subject receives does not cure cancer, but prevents the progression or worsening of the disease. In certain embodiments, the treatment/therapy that a subject receives does not prevent the onset/development of cancer, but may prevent the onset of cancer symptoms.

As used herein, the term "in combination" in the context of the administration of (a) therapy(ies) to a subject, refers to the use of more than one therapy. The use of the term "in combination" does not restrict the order in which therapies are administered to a subject. A first therapy can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, or 95% identity over a specified region, e.g., of the entire polypeptide sequences or specific region, if indicated), when compared and aligned for maximum correspondence over a comparison window, or designated region as measured using one of the following sequence comparison algorithms or by manual alignment and visual inspection. Such sequences are then said to be "substantially identical."

For sequence comparison, one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full-length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison are conducted by a BLAST 2.0 algorithm, which is described in Altschul et al. (1990) *J. Mol. Biol.* 215:403-410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=-4 and a comparison of both strands. For amino acid sequences, the BLASTP program uses as defaults a word length of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=-4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

DETAILED DESCRIPTION

Disclosed herein are compositions and methods of treating cancer in a subject. Provided are replicating viral vectors, specifically oncolytic adenoviral vectors, that contain one or more recombinant nucleic acid sequences encoding therapeutic polypeptides.

Oncolytic adenovirus (AV) expressing a transgene display highly oncolytic and immunogenic properties. Therefore, the recombinant adenoviral vectors provided herein have the potential to have broad activity against a primary tumor infected with adenovirus but also against tumors in the metastatic disease setting. In some embodiments, the metastatic tumors need not be directly injected with virus nor does the virus injected into the primary site travel to the metastatic setting (e.g. through the blood stream). However, due to expression of an immune stimulatory transgene from the adenovirus (for example, including but not limited to an E1b 19K deleted region in an exemplary vector such as TAV-255 (e.g., TAV-255 Δ19)), the immune system will be primed to fight cancer systemically in the entire body of the cancer patient as long as the metastatic tumor cells express the same tumor antigens as the primary tumor cells. Since metastases are derived from the primary tumors and genetically very similar to the primary tumor cells, metastatic tumor growth will be inhibited, in some embodiments, to the same extent as the primary tumor.

Provided are adenoviruses as described herein. In another aspect, a cell transformed with any one of the recombinant adenoviruses described herein is provided.

In another aspect, a method is provided of selectively expressing a peptide in a target cell comprises contacting the target cell with any one of the recombinant adenoviruses described herein. In one aspect, the recombinant adenovirus comprises a E1a regulatory sequence deletion mutant operably linked to a nucleotide sequence encoding a peptide, e.g., a peptide associated with viral replication or with cancer.

Also provided herein are methods of adenoviral therapy that utilize the oncolytic adenoviruses of the instant invention as adenoviral vectors that express one, two, or more recombinant immunomodulatory genes. The oncolytic adenovirus contains a heterologous gene that encodes a therapeutic protein, incorporated within the viral genome, such that the heterologous gene is expressed within an infected cell. A therapeutic protein, as used herein, refers to a protein that provides one or more therapeutic benefit when expressed in a given cell. In particular, the therapeutic benefit includes recruitment of the host immune system to the tumor.

Modified Regulatory Regions

E1a is the first protein produced by an adenovirus upon infection of a cell, activating other adenoviral promoters and facilitating infected cells to enter cell division. Rendering expression of this protein under tumor-selective control is an effective means of limiting expression of viral proteins and oncolysis to tumor cells.

Normal cells require mitogenic growth signals (GS) before they can move from a quiescent state into an active proliferative state. Tumor cells are able to generate many of their own growth signals or mimic normal growth signals, and transcription factors such as E2F1 and Pea3 are commonly overexpressed in tumor cells at levels that can cooperate in forming conformational structures optimal for driving E1a transcription during adenovirus infection and replication. (Hanahan D, Weinberg R A. The Hallmarks of Cancer. *Cell* 2000; 100: 57-70; de Launoit Y, Chotteau-Lelievre A, Beaudoin C, Coutte L, Netzer S, Brenner C et al., The PEA3 Group of ETS-Related Transcription Factors: Role in Breast Cancer Metastasis, *Adv Exp Med Biol* 2000; 480: 107-116; Bruder J T, Hearing P: Cooperative Binding of EF-1A to the E1A Enhancer Region Mediates Synergistic Effects on E1A Transcription During Adenovirus *Infection. J Virol* 1991; 65:5084-5087).

Small deletions selectively targeting the binding sites for E2F1 and Pea3 sites in the E1a enhancer region are an alternative and less disruptive method than complete replacement of the E1a enhancer region with a transcriptionally restricted promoter element. Cooperative binding and transcriptionally optimized conformation of the E1a enhancer region could still take place due to the overabundance of transcription factors found in tumor cells, while in normal, non-dividing cells, the disruption of binding sites would further inhibit the ability to form optimized conformations in the limiting level of mitogenic growth signals.

Thus, disclosed herein are methods of engineering adenoviral vectors via the Pea3 binding sites. The five Pea3 transcription factor binding sites, also known as E1AF (or originally as EF-1A-enhancer binding factor to the E1a core motif) have differential effects on the production of E1a mRNA levels as demonstrated by specific deletions of individual and paired sites. The murine Pea3 sites are described herein as Pea3 sites I, II, III, IV, and V. The main binding sites for Pea3 are sites I and III, while sites II, IV, and V are slightly degenerate versions. Pea3 binds cooperatively between sites II and III, IV and V, and II and I, and this cooperative binding activates E1a transcription. (see, e.g., Hearing (J. Virol 65, 1991, Mol Cell Biol 9, 1989, and Nuc Acids Res 20, 1992). Pea3 itself is a dimer of both $\alpha$ and $\beta$ subunits, where the a subunit makes the primary DNA contact and the $\beta$ subunit forms a heteromultimeric complex with the $\beta$ subunit both in solution or on a dimeric binding site. During normal infection conditions, binding at sites I and III, followed by the cooperative binding at site II would cause conformational changes that serve to bring this protein/DNA complex closer to the activation transcription factor (ATF) binding site and TATA box for full activation of E1a mRNA expression. The two lower affinity sites, Pea3 IV and Pea3 5, do not appear to contribute much to activation under these normal circumstances, as they may be too far away or unoccupied. Deletion of site II causes the greatest reduction in transcriptional activity, pointing to the importance of the cooperative binding effect it has for sites III and I in activating transcription, presumably through a conformational change. Deletion of either site III or I had much less of a reduction, since presumably you could still have cooperative binding between site II and the remaining site III or I. Deletion of both sites I and III (but not II) reduces transcription to the levels seen with Pea3 site II deletion alone, and the combination of deleting both sites III and II, or sites II and I also results in similar (but not greater) levels of reduction.

Deletion of the region encompassing sites III and II removes this cooperative binding capacity derived from site II, but it also moves sites IV and V closer to site I. Although lower affinity, sites IV and V do show cooperative binding, and by moving them closer to site I, binding at these three sites may be able to mimic the conformation change normally occurring with binding of sites I-III, leading to transcriptional activation. Because sites IV and V are lower affinity sites, there may not be enough of this transcription factor around in normal cells to get full binding on the deleted construct for activation, but there are several publications reporting increased levels of E1AF/Pea3 with tumor progression and invasiveness (i.e., Horiuchi S. et. al., *J Pathol* 2003 August; 200(5): 568-76), indicating that tumor cells may have enough E1AF to bind the lower affinity binding sites IV and V, along with site I, and potentially lead to a conformational change needed to activate transcription of E1a in tumor but not normal cells with this deleted virus.

The present invention provides replicating adenoviruses. In some embodiments, the replicating vectors of the instant invention contain recombinant (e.g., exogenous) transgene(s) expressing immunomodulatory polypeptides that are controlled by endogenous adenovirus early promoters, thereby driving meaningfully higher expression levels than can be generally achieved in replication deficient viruses. In addition to the enhanced anti-tumor efficacy resulting from tumor-specific oncolysis from the replicating adenovirus, the higher expression levels from the recombinant transgenes in a replicating virus results in enhanced immunomodulatory effect(s) over the lower expression levels in replication deficient viruses.

In one aspect, a recombinant virus comprises a modified E1a regulatory sequence, wherein at least one Pea3 binding site, or a functional portion thereof, is deleted. In one aspect, a sufficient number of nucleotides in the range of −305 to −141 are retained to maintain functional activity of the Ad packaging signal function and (near) optimal transcription of the E1a protein in tumor but not growth arrested normal cells.

Additional deletions or modifications of individual or combinations of Pea3V, Pea3IV, Pea3III, Pea3II and/or E2F1 binding sites between base pairs −394 and −218 designed to inhibit binding of Pea3 and/or E2F1 to these sites and take part in cooperative binding induced conformational changes in the E1a enhancer region are also encompassed by this description.

In one aspect, at least one of Pea3 II, Pea3 III, Pea3 IV, and Pea3 V, or a functional portion thereof, is deleted or modified (e.g., at least one nucleotide of the sequence is changed or an additional nucleotide is inserted into the sequence). In another aspect, at least one of Pea3 II and Pea3 III, or a functional portion thereof, is deleted or modified. In one aspect, Pea3 II or a functional portion thereof, and Pea3 III or a functional portion thereof, is deleted or modified. In another aspect, at least one of Pea3 IV and Pea3 V, or a functional portion thereof, is deleted or modified. In another aspect, Pea3 I, or a functional portion thereof, is retained. By "retained" is meant that the element is present in the recombinant adenoviral vector, preferably at the same location as a reference adenoviral vector. In one aspect, at least one E2F1 binding site, or a functional portion thereof, is retained.

In one aspect, the vector is dl309-6, TAV-255, d155, d1200, d1230, or d1200+230. In another aspect, the vector is TAV-255. In another aspect, the E1a deletions in dl309-6, TAV-255, d155, d1200, d1230, d1200+230, or other E1a modifications affecting Pea3 and/or E2F1 binding sites between −394 to −218, are paired with a non-dl309 based E3 deletion such as the E3 deletion found in pBHG10 (Microbix, Ad5 base pairs (bp) 28133-30818), d1327 (Ad5 bp 28593-30470) or a similar size E3 deletion such that >3 kb of exogenous DNA can be successfully packaged and expressed from a recombinant adenovirus with the E1a deletions listed above, in combination with a deletion between the start site of the E1b 19K protein and the start site of the E1b 55K protein of approximately 202 base pairs. In one aspect, the vector is a dl309 vector having one or more mutations in reference to the wild type sequence of Ad5 (see, e.g., Chroboczek et al., Virology (1992) January; 186(1):280-5, herein incorporated by reference), including a disruption in the coding sequences for one or more of the 10.4K, 14.5K, and 14.7K proteins in the E3 region.

In one aspect, a recombinant virus selectively expresses at least one E1a isoform, e.g., E1a-12S or E1a-13S. In one aspect, the sequence encoding the E1a isoform is operably linked to a modified E1a regulatory sequence, wherein at least one Pea3 binding site, or a functional portion thereof, is deleted or modified.

In one aspect, a recombinant virus comprises a DNA sequence, e.g., a transgene, inserted into an E1b-19K insertion site. In one aspect, the insertion site is located between the start site of E1b-19K and the start site of E1b 55K. In another aspect, the insertion site comprises a deletion of 202 base pairs following the start site of E1b-19K. A transgene (also, "insert") may be a full natural sequence of the gene of interest or a fragment thereof. It may be modified too include a Kozak sequence, stop codon, or other regulatory elements. A transgene may include one or more endonuclease restriction sites.

In another aspect, expression the transgene is operably linked to a modified E1a regulatory sequence, wherein at least one Pea3 binding site, or a functional portion thereof, is modified or deleted. The transgene may be located in the E1, E2, E3 and/or E4 regions of the adenovirus but its expression is controlled by E1a mediated activation of the endogenous upstream adenovirus promoter, generating high levels of transgene expression only during E1a mediated viral replication.

In specific embodiments, the transgene is located in the E3 region. Exogenous transgenes can be inserted into one or more deleted regions of the adenovirus E3 region, generally such transgenes are inserted into the adenoviral vector as to have their expression controlled by the endogenous E3 promoter (Luo J et al, Clin Cancer Res 2008: 14 2450-2457). This results in high levels of transgene expression that are specifically expressed during periods of viral replication, as the E3 promoter only becomes transcriptionally active during these times. Using a modified adenovirus backbone, such as the E1a enhancer modification described herein, to limit viral replication to infected tumor cells, expression from the introduced transgene is also limited to infected tumor cells and, generally, not normal cells. In certain embodiments, the entire E3 region, or a substantial portion of the E3 region, is deleted.

In specific embodiments, the transgene is located in the E4 region. In a similar fashion to inserting exogenous transgenes into deleted regions in the E3 or E1 regions of adenovirus, there are regions in the E4 region of adenovirus that can be deleted without significant effect on viral growth characteristics (Gao, G P et al, J. Virol 1996: 70; 8934-8943). Generally, at least ORF3 and/or ORF6 are retained in the adenoviral vector in which the remainder of the E4 region. It should be possible to insert a foreign transgene into one of these deletions in the E4 region and drive expression of this gene with the endogenous E4 promoter of adenovirus, restricting high level expression of this gene to conditions where viral replication is expected to occur.

Tumor-Directed Recombinant Immunomodulatory Polypeptide Production.

The adenoviruses described herein can be engineered to express an immunomodulatory agent or immunomodulatory polypeptide, e.g., a polypeptide agonist of a co-stimulatory signal of an immune cell. In some embodiments, the polypeptide agonist is an agonist of a T effector cell and/or the polypeptide agonist functions as a polypeptide antagonist of an inhibitory signal of an immune cell such as a regulatory T cell. As provided herein, an "immunomodulatory protein" or an "immunomodulatory polypeptide" includes any polypeptide or set of polypeptides capable of modulating (e.g., stimulating) the anti-tumor immune response induced by the adenovirus. Generally, an "immunomodulatory polypeptide" includes a desired immunostimulatory activity. An immunomodulatory polypeptide can include a set of polypeptides, linked or unlinked, that can form a multimer (e.g., a dimer) capable of modulating the anti-tumor immune response induced by adenovirus, e.g., IL-12 dimer formed from p40 and p35, with or without a linker. Immunomodulatory polypeptides can be full length proteins as occur in nature or can be fusions, variants, or fragments thereof that retain at least about 90%, 80%, 70%, 60%, 50%, 40%, 30%, 20%, or 10% of the immunomodulatory activity of the full-length protein.

As used herein, the term "agonist(s)" refers to a molecule(s) that binds to another molecule and induces an increased biological reaction. In a specific embodiment, an agonist is a molecule that binds to a receptor on a cell and triggers or stimulates one or more signal transduction pathways. For example, an agonist can include an antibody or ligand that binds to a receptor on a cell and induces one or more signal transduction pathways. In other embodiments, the agonist facilitates the interaction of the native ligand with the native receptor. As used herein, the term "antagonist(s)" refers to a molecule(s) that inhibits the action of another molecule, optionally without provoking an independent biological response itself. In a specific embodiment, an antagonist is a molecule that binds to a receptor on a cell and blocks or dampens the biological activity of an agonist. For example, an antagonist can include an antibody or ligand that binds to a receptor on a cell and blocks or dampens binding of the native ligand to the cell, optionally without inducing one or more signal transduction pathways. Another example of an antagonist includes an antibody or soluble receptor that competes with the native receptor on cells for binding to the native ligand, and thus, blocks or dampens one or more signal transduction pathways induced when the native receptor binds to the native ligand. A further example of an antagonist includes an antibody or soluble receptor that competes with the native receptor on cells for binding to the native ligand or blocks receptor internalization, and thus, blocks or dampens one or more signal transduction pathways induced when the native receptor binds to the native ligand.

In specific embodiments, the immunomodulatory polypeptide expressed by the adenovirus is a costimulatory ligand, e.g., GITR ligand (GITRL), OX40 ligand (OX40L), or CD40 ligand (CD40L). Expression of one or more costimulatory ligands in the tumor microenvironment and the specific binding to the cognate receptor results in an increase in activity of a tumor-infiltrating lymphocyte (TIL), such activity including TIL proliferation and cytokine release, thereby increasing the anti-tumor activity of the pharmaceutical composition.

In specific embodiments, the immunomodulatory polypeptide expressed by the adenovirus is a pro-inflammatory cytokine, e.g., GMCSF, IL-7, IL-12, or an IL-15 hybrid (e.g., a hybrid of IL-15 and IL-15 receptor alpha). Expression of one or more pro-inflammatory cytokine in the tumor microenvironment results in a tumor-localized increase in the inflammatory milieu, thereby increasing the anti-tumor activity of the pharmaceutical composition, and also increasing safety of the composition by decreasing or eliminating undesired effects of systemic administration of a pro-inflammatory cytokine.

In specific embodiments, the immunomodulatory polypeptide expressed by the adenovirus is an inhibitor (e.g., a "receptor trap" or a "trap") of an inhibitory cytokine, e.g., IL-10 or IL-27. In other embodiments, the immunomodulatory agent/inhibitor of an inhibitory cytokine is an antibody against, e.g., TGFB or IL-10R. Such inhibitory cytokines decrease T effector cell function. Expression of one or more inhibitory cytokine receptor traps in the tumor microenvironment results in a tumor-localized binding to and neutralization of the inhibitory cytokine, thereby reducing or preventing its inhibitory activity and increasing the anti-tumor activity of the pharmaceutical composition, and also increasing safety of the composition by decreasing or eliminating undesired effects of systemic administration of a blockage of an inhibitory cytokine.

In specific embodiments, the immunomodulatory polypeptide expressed by the adenovirus is an initiator of a localized immune response, e.g., a protein (e.g., secreted flagellin) that activates a toll-like receptor ligand such as TLR-5. Expression of one or more immune response initiators in the tumor microenvironment results in a tumor-localized immune response (e.g., infiltration of TILs and antigen presenting cells (APCs) and increasing the anti-tumor activity of the pharmaceutical composition.

In specific embodiments, the immunomodulatory polypeptide expressed by the adenovirus is an inhibitor (e.g., an antibody antagonist) of a co-inhibitory checkpoint molecule, e.g., CTLA4. Such inhibitory checkpoint molecules decrease T effector cell function. Expression of one or more inhibitory checkpoint molecules at the surface of an activated T cell (e.g., an activated T effector cell) attenuates the functional activity of the T cell. Thus, expression of an antagonist of the co-inhibitory checkpoint molecule in the tumor microenvironment results in blocking the co-inhibitory activity and increasing the anti-tumor activity of the pharmaceutical composition, and also increasing safety of the composition by decreasing or eliminating undesired effects of systemic administration of a blockage of a co-inhibitory checkpoint molecule.

In specific embodiments, the immunomodulatory polypeptide expressed by the adenovirus is a cluster of differentiation (CD) molecule or a ligand of a cluster of differentiation (CD) molecule such as CD27, e.g., CD70. Expression of a CD27 ligand in the tumor microenvironment results in a tumor-localized NK-mediated tumor clearance and promotes the adaptive immune response against the tumor, thereby increasing the anti-tumor activity of the pharmaceutical composition. Other suitable CD molecules include CD1d, CD2, CD3, CD4, CD5, CD6, CD7, CD8a, CD8b, CD9, CD21, CD25, CD37, CD40, CD49b, CD53, CD57, CD69, CD80, CD81, CD82, CD86, CD99, CD103, CD134, CD152, CD154, CD165, CD244, CD267, CD272, CD273, CD274, CD278, CD305, CD314, CD357, and CD360, or the ligands thereof, or any modulator (e.g., a stimulator or an inhibitor) thereof.

In specific embodiments, the immunomodulatory polypeptide expressed by the adenovirus is selected from a polypeptide provided in Table 1.

TABLE 1

Exemplary Immunomodulatory polypeptides

| SEQ ID NO: | Immunomodulatory Polypeptide | Accession Number(s) |
|---|---|---|
| 1 | GITR-Ligand (GITR-L; TNFSF18) | NP_005083 |
| 2 | GITR-Ligand (GITR-L; TNFSF18) | NM_183391 |
| 3 | CD28 ligand or agonist (CD80) | EAW79565 |
| 4 | TNFα | CAA78745 |
| 5 | Non-cleavable TNFα | NM_013693 |
| 6 | GM-CSF | NM_009969 |
| 7 | ICOS ligand or agonist | NP_056074 |
| 8 | 4-1BB ligand or agonist | AAA53134 (human) |
| 9 | OX40 ligand or agonist | CAE11757 |
| 10 | OX40 ligand | NM_009452 |
| 11 | CD40 ligand or agonist | NP_000065 |
| 12 | CD40 ligand | NM_011616 |
| 13 | CD27 ligand or agonist | AAA36175 |
| 14 | CD70 ligand or agonist | NM_011617 |
| 15 | Interleukin-2 (IL-2) | AAB46883 |
| 16 | Interleukin-7 (IL-7) | AAH47698 |

TABLE 1-continued

Exemplary Immunomodulatory polypeptides

| SEQ ID NO: | Immunomodulatory Polypeptide | Accession Number(s) |
|---|---|---|
| 17 | Interleukin-7 (IL-7) | NM_00837 |
| 18 | Interleukin-12 (IL-12) alpha subunit | AAD16432 |
| 19 | Interleukin-12 (IL-12) beta subunit | NP_005526 |
| 20 | Interleukin-12 fusion polypeptide | N/A |
| 21 | IL-15 | CAA62616 |
| 22 | IL-15 hybrid | N/A |
| 23 | IL-10R TRAP (IL-10 antagonist) [alpha] | NP_001549 |
| 24 | IL-10R Trap | N/A |
| 25 | IL-27R TRAP (IL-27 antagonist) | NP_004834 |
| 26 | IL-13 | AAH96140 |
| 27 | IL-17 | AAC50341 |
| 28 | IL-33 Isoform a | NP_001300974 |
| 29 | IL-33 Isoform a | NP_001300973 |
| 30 | IL-33 Isoform b | NP_001186569 |
| 31 | IL-33 Isoform c | NP_001186570 |
| 32 | IL-33 Isoform d | NP_001300975; NP_001300976 |
| 33 | IL-33 Isoform e | NP_001300977 |
| 34 | IFN-gamma | AAB59534 |
| 35 | secreted flagellin | N/A |
| 36 | anti-CTLA4 (CTLA-4 antagonist antibody) | N/A |
| 38 | Interleukin-2 (IL-2) (murine) | NM_008366.3 |
| 39 | Xcl1 (murine) | GenBank: BC062249.1 |
| 42 | 4-1BBL (TNFSF9) (murine) | GenBank: BC138767.1 |
| 55 | IL-15Rα | N/A |
| 58 | hαCTLA4 Anti-PD-1 (PD-1 antagonist antibody) Anti-PD-L1 (PD-L1 antagonist antibody) Anti-TIGIT (TIGIT antagonist antibody) Anti-TGFβ (TGFβ antagonist antibody) Anti-IL6R (IL-6 receptor antibody) | N/a com1-19 |

Additional detail about the above-discussed agonists that can be expressed from an adenovirus vector as described herein is provided below:

GITR Ligand.

In one embodiment, the heterologous gene is a GITR ligand family gene, such as TNFSF18 (also known as GITRL) (See, e.g., Tone, M., Tone, Y., Adams, E., Yates, S. F., Frewin, M. R., Cobbold, S. P., & Waldmann, H. (2003). Mouse glucocorticoid-induced tumor necrosis factor receptor ligand is costimulatory for T cells. *Proceedings of the National Academy of Sciences of the United States of America*, 100(25), 15059-15064. doi:10.1073/pnas.2334901100). The GITR/GITRL signaling pathway is associated with activation of immune cells Nocentini, G., Ronchetti, S., Petrillo, M. G., & Riccardi, C. (2012). Pharmacological modulation of GITRL/GITR system: therapeutic perspectives. *British Journal of Pharmacology*, 165(7), 2089-99. doi:10.1111/j.1476-5381.2011.01753.x). Specifically, the GITRL protein has an immunomodulatory activity including inhibiting the suppressive activity of T regulatory cells and activation of T effector cells. The intratumoral localization of effective amounts of GITRL protein results in stimulation of the immune system and inhibition of the tumor, resulting in more effective viral-based therapeutic treatment of human subjects suffering from cancer. Moreover, the costimulatory activity of GITRL protein has a synergistic effect with the tumor-directed cell-lytic activity of the adenovirus, resulting from activation and/or recruitment of the immune system to the tumor and enhanced antigen presentation IL-10 Trap.

In one embodiment, the heterologous gene is an engineered IL-10 trap, such as IL-10 receptor fused to a human immunoglobulin Fc domain. Examples include IL10RA-Fc fusion protein or IL10RA-IL10RB-Fc fusion protein. (See, e.g., Economides, A. N., Carpenter, L. R., Rudge, J. S., Wong, V., Koehler-Stec, E. M., Hartnett, C., . . . Stahl, N. (2003). Cytokine traps: multi-component, high-affinity blockers of cytokine action. *Nature Medicine*, 9(1), 47-52. doi:10.1038/nm811). The IL-10 family is associated with inhibition of inflammatory response in immune cells through inhibition of the expression of proinflammatory cytokines and co-stimulatory molecules. Expression of IL-10 by T regulatory cells suppresses the activity of T effector cells (Mosser D M, Zhang X. Immunol Rev. 2008 December; 226:205-18. Interleukin-10: new perspectives on an old cytokine). Specifically, the IL-10 trap protein has an immunomodulatory activity by inhibiting the anti-inflammatory activity of IL-10. The intratumoral localization of effective amounts of IL-10 trap protein results in stimulation of the immune system and inhibition of the tumor, resulting in more effective viral-based therapeutic treatment of human subjects suffering from cancer. Moreover, IL-10 trap protein inhibition of IL-10's anti-inflammatory activity has a synergistic effect with the tumor-directed cell-lytic activity of the adenovirus, resulting from activation and/or recruitment of the immune system to the tumor and enhanced antigen presentation. In one embodiment, the IL-10 Receptor Trap includes all or a portion of the extracellular domains of IL-10Rα and IL-10Rα.

ANTI-CTLA4.

In one embodiment, the heterologous gene is an antibody (or domain or fragment thereof) that inhibits the function of CTLA4 (See, e.g., Leach D R, Krummel M F, Allison J P. Enhancement of antitumor immunity by CTLA-4 blockade. Science. 1996 Mar. 22; 271(5256):1734-6.) The CTLA4 family is associated with inhibition of T cells through the interaction with ligands CD80 and CD86 (Krummel M F, Allison J P (1995). "CD28 and CTLA-4 have opposing effects on the response of T cells to stimulation". J. Exp. Med. 182 (2): 459-65.) Specifically, the anti-CTLA4 antibody has an immunomodulatory activity including blocking the inhibitory function of CTLA4 resulting in more efficient activation of T effector cells. The intratumoral localization of effective amounts of anti-CTLA4 antibody results in stimulation of the immune system and inhibition of the tumor, resulting in more effective viral-based therapeutic treatment of human subjects suffering from cancer. Moreover, anti-CTLA4 inhibition of CTLA4's T cell inhibitory activity has a synergistic effect with the tumor-directed cell-lytic activity of the adenovirus, resulting from activation and/or recruitment of the immune system to the tumor and enhanced antigen presentation.

IL-12:

In one embodiment, the heterologous gene is a member of the Interleukin cytokine family such as IL-12. The IL-12 cytokine family is associated with induction of IFNγ and mediating T-cell dependent immunity. Specifically, IL-12 is an immunostimulatory cytokine with strong antiangiogenic effects. IL-12 has immunomodulatory activity including cell proliferation, lymphocyte differentiation and NK cell activation. The intratumoral localization of effective amounts of IL-12 results in the differentiation, proliferation, and maintenance of T helper 1 (Th1) responses that lead to IFNγ and IL-2 production that in turn, promote T cell responses and macrophage activation. The local expression of effective amounts of IL-12 from intratumoral injections may provide a safety benefit over systemic administration and side effects associated with high IL-12 serum levels. Moreover, the immunostimulatory activity and induction of cytotoxicity mediated by natural killer cells and T cells by IL-12 may have a synergistic effect with the tumor-directed cell-lytic and immune stimulating activity of our adenovirus providing a more effective viral-based therapeutic treatment of human subjects suffering from cancer. In one embodiment, the IL-12 polypeptide is a fusion of IL-12 subunits p35 and p40, linked by a 45 bp linker, including IL-12 β:p40 (NM_001303244) and IL-12 Alpha:p35 (NM_008351.1).

GM-CSF:

In one embodiment, the heterologous gene is a cytokine such as Granulocyte-macrophage colony-stimulating factor (GM-CSF), also known as colony stimulating factor 2 (CSF2). Cytokines are secreted proteins or peptides that mediate and regulate immunity and inflammation. Specifically, GM-CSF has an immunomodulatory activity of functioning as an immune adjuvant and facilitates development of the immune system, acting as a growth factor for DCs and APCs. The localized secretion of effective amounts of GM-CSF results in an increase in dendritic cell (DC) maturation and function as well as macrophage activity, recruiting immune cells to the inflammatory site of tumor treatment, resulting in more effective therapeutic treatment of human subjects suffering from cancer. Moreover, GM-CSF has been demonstrated to be capable of induced long-lasting, specific anti-tumor immunity when combined with cancer vaccines, potentially providing a synergistic effect with the tumor-directed cell-lytic activity of our adenovirus. In a recent phase III clinical trial, an oncolytic herpes simplex virus armed with GM-CSF (T-VEC) showed durable response rates in advanced melanoma patients compared with GM-CSF protein alone.

Secreted Flagellin:

In one embodiment, the heterologous gene comes from a gram-negative bacterium in the Salmonellae family, such as the gene encoding flagellin. Bacterial proteins, including flagellin, are associated with the activation of the innate immune response, leading to production of proinflammatory cytokines and the up-regulation of costimulatory molecules. Specifically, flagellin is a TLR5 agonist, and binding of secreted flagellin to TLR5 stimulates production of TNFα, and induces infiltration of APC's and TIL's to the local tumor environment. By acting as a strong adjuvant, flagellin is able to prime the immune system to elicit strong adaptive immune responses, resulting in enhanced and broadened immune response a more effective viral-based therapeutic treatment of human subjects suffering from cancer. In some embodiments, secreted Flagellin contains a murine IL-2 signal sequence (See NM_008366) and *Salmonella* Flagellin, GenBank: D13689.

TNFA and Non-Cleavable TNFA.

In one embodiment, the heterologous gene is an engineered TNFα ligand family gene, such as a non-cleavable (membrane-bound, transmembrane) form of TNFα (See, e.g., Li Q, Li L, Shi W, Jiang X, Xu Y, Gong F, Zhou M, Edwards C K 3rd, Li Z., Mechanism of action differences in the antitumor effects of transmembrane and secretory tumor necrosis factor-alpha in vitro and in vivo. Cancer Immunol Immunother. 2006: 55, 1470-9.). TNFα belongs to a family of pro-inflammatory cytokines (Calcinotto A, Grioni M, Jachetti E, Curnis F, Mondino A, Parmiani G, Corti A, Bellone M. Targeting TNF-α to neoangiogenic vessels enhances lymphocyte infiltration in tumors and increases the therapeutic potential of immunotherapy. J Immunol. 2012; 188: 2687-94.). Specifically, expression of TNFα in the tumor microenvironment is expected to increase the inflammatory milieu resulting in increased anti-tumor immune responses. Use of a non-cleavable TNFα results in a tethered form of TNFα which remains membrane-bound. The intratumoral localization of effective amounts of TNFα protein results in stimulation of the immune system and inhibition of growth of the tumor, resulting in more effective viral-based therapeutic treatment of human subjects suffering from cancer. In addition, local expression may provide a safety benefit over systemic administration of TNFα. Moreover, the immunomodulatory activity of the membrane-bound TNFα protein has a synergistic effect with the tumor-directed cell-lytic activity of the adenovirus, resulting from activation and/or recruitment of the immune system to the tumor and enhanced antigen presentation.

OX40L.

In one embodiment, the heterologous gene is an OX40L family gene, such as TNFSF4 (also called OX40L, CD252) (See, e.g., Dannull J, Nair S, Su Z, Boczkowski D, DeBeck C, Yang B, Gilboa E, Vieweg J. Enhancing the immunostimulatory function of dendritic cells by transfection with mRNA encoding OX40 ligand. *Blood*. 2005, 105: 3206-13.). The TNFSF is associated with activation of immune cells (Croft M, So T, Duan W, Soroosh P. The significance of OX40 and OX40L to T-cell biology and immune disease. *Immunol Rev*. 2009; 229:173-91.). Specifically, OX40L is a co-stimulatory ligand for TNFRSF4 (OX40, CD134) resulting in activation of T cells. Expression of OX40L in the tumor microenvironment and binding to its cognate receptor (OX40) is expected to increase the activity (proliferation, cytokine release) of tumor infiltrating lymphocytes (TILs) resulting in antitumor activity. The intratumoral localization of effective amounts of OX40L protein results in stimulation of the immune system and inhibition of growth of the tumor, resulting in more effective viral-based therapeutic treatment of human subjects suffering from cancer. Local expression may provide a safety benefit over systemic administration of OX40L. Moreover, the immunomodulatory activity of the OX40L protein has a synergistic effect with the tumor-directed cell-lytic activity of the adenovirus, resulting from activation and/or recruitment of the immune system to the tumor and enhanced antigen presentation

IL-7.

In one embodiment, the heterologous gene is an IL-7 cytokine family gene, such as IL-7 (See, e.g., Gao J, Zhao L, Wan Y Y, Zhu B., Mechanism of Action of IL-7 and Its Potential Applications and Limitations in Cancer Immunotherapy. *Int J Mol Sci*. 2015, 16: 10267-80.). IL-7 belongs to a family of pro-inflammatory cytokines (Geiselhart L A, Humphries C A, Gregorio T A, Mou S, Subleski J, Komschlies K L. IL-7 administration alters the CD4:CD8 ratio, increases T cell numbers, and increases T cell function in the absence of activation. *J Immunol*. 2001; 166: 3019-27.). Specifically, expression of IL-7 in the tumor microenvironment is expected to increase the inflammatory milieu resulting in increased anti-tumor immune responses. The intratumoral localization of effective amounts of IL-7 protein results in stimulation of the immune system and inhibition of growth of the tumor, resulting in more effective viral-based therapeutic treatment of human subjects suffering from cancer. Moreover, the immunomodulatory activity of the IL-7 protein has a synergistic effect with the tumor-directed cell-lytic activity of the adenovirus, resulting from activation and/or recruitment of the immune system to the tumor and enhanced antigen presentation.

CD40L

In one embodiment, the heterologous gene is a member of the TNF superfamily, such as CD40L (also known as CD40LG or CD154) (See, e.g., Hassan G S, et al., 2015. "Role of CD154 in cancer pathogenesis and immunotherapy." Cancer Treat Rev 4 1(5):431-40). The CD40L is the ligand for CD40 expressed on antigen presenting cells. Specifically, the CD40L protein has a costimulatory activity important for activation of T cell dependent immune responses (Sotomayor E M, et al., 1999. "Conversion of tumor-directed CD4+ T-cell tolerance to T-cell priming through in vivo ligation of CD40." Nat Med. 5:780-787; French R R, et al., 1999. "CD40 antibody evokes a cytotoxic T-cell response that eradicates lymphoma and bypasses T-cell help. Nat Med. 5:548-553). The intratumoral localization of effective amounts of CD40 protein results in activation of the immune system and lysis of the tumor, resulting in more effective viral-based therapeutic treatment of human subjects suffering from cancer. Moreover, the costimulatory immunomodulatory activity of CD40 protein has a synergistic effect with the tumor-directed cell-lytic activity of the adenovirus, resulting in a local and systemic immune response against the tumor.

IL-15 and IL-15 Hybrid

In one embodiment, the heterologous gene is a cytokine family gene, such as Interleukin 15 (IL-15) (See, e.g., Di Sabatino A, et. al., 2011 "Role of IL-15 in immune-mediated and infectious diseases". *Cytokine Growth Factor Rev.* 22 (1): 19-33.; Steel J C, et al., 2012, "Interleukin-15 biology and its therapeutic implications in cancer". *Trends Pharmacol. Sci.* 33 (1): 35-41). IL-15 is a cytokine that regulates T cell and NK cell activation and proliferation. (Waldmann T A, et al., (1999). "The multifaceted regulation of interleukin-15 expression and the role of this cytokine in NK cell differentiation and host response to intracellular pathogens". *Annu. Rev. Immunol.* 17: 19-49). Specifically, the IL-15 protein has an immunomodulatory activity by providing survival signals to maintain memory T cells in the absence of antigen. IL-15 has also been shown to enhance the anti-tumor immunity of CD8+ T cells (See, Klebanoff C A, et al., "IL-15 enhances the in vivo antitumor activity of tumor-reactive CD8+ T Cells" *Proc. Natl. Acad. Sci. U.S.A.* 101 (7): 1969-74; and Teague R M, et al., "Interleukin-15 rescues tolerant CD8+ T cells for use in adoptive immunotherapy of established tumors" *Nat. Med.* 12 (3): 335-41). Expression of an IL-15 hybrid molecule (IL-15 linked to the IL-15 Receptor alpha, see Tosic et al., *PLos ONE* 9(10): e109801 (2014)) leads to stabilization and increased bioactivity (Bergamaschi et al., 2008. "Intracellular Interaction of Interleukin-15 with Its Receptor a during Production Leads to Mutual Stabilization and Increased Bioactivity", *JBC*, 283(7):4189-99; Bergamaschi et al., 2013. "Circulating IL-15 exists as heterodimeric complex with soluble IL-15Rα in human and mouse serum", *Blood* 120(1):e1). The intratumoral localization of effective amounts of IL-15 protein results in activation of the immune system and lysis of the tumor, resulting in more effective viral-based therapeutic treatment of human subjects suffering from cancer. Moreover, the survival signals provided by IL-15 protein has a synergistic effect with the tumor-directed cell-lytic activity of the adenovirus, resulting in a local and systemic immune response against the tumor. In some embodiments, an IL-15 hybrid includes IL-15, P2A, and IL-15Rα, IL-15 (NM_008357), 68 bp P2A, and IL-15Rα (GenBank: BC132233.1).

CD70

In one embodiment, the heterologous gene is a member of the TNF superfamily, such as CD70 (also known asTNFSF7 or CD27L). (See, e.g., Denoeud J and Moser M., 2011. "Role of CD27/CD70 pathway of activation in immunity and tolerance." *J Leukoc Biol.* 89(2):195-203). CD70 is expressed on activated T and B cells, as well as mature dendritic cells, and acts as a ligand for CD27. CD70 plays a costimulatory role in promoting T cell expansion and differentiation (Keller A M, et al., 2008. "Expression of costimulatory ligand CD70 on steady-state dendritic cells breaks CD8+ T cell tolerance and permits effective immunity," *Immunity* 29(6):934-46; Bonehill A, et al., 2008. "Enhancing the T-cell stimulatory capacity of human dendritic cells by co-electroporation with CD40L, CD70 and constitutively active TLR4 encoding mRNA," *Mol Ther.* 16(6):1170-80). In addition, CD70 expression in the tumor microenvironment will increase NK-mediated tumor clearance and promote an adaptive immune response against the tumor (Kelly J M, et al., 2002. "Induction of tumor-directed T cell memory by NK cell-mediated tumor rejection," *Nat Immunol.* 3(1):83-90). The intratumoral localization of effective amounts of CD70 protein results in activation of the immune system and lysis of the tumor, resulting in more effective viral-based therapeutic treatment of human subjects suffering from cancer. Moreover, the immunomodulatory activity of CD70 protein has a synergistic effect with the tumor-directed cell-lytic activity of the adenovirus, resulting in a local and systemic immune response against the tumor.

In a specific embodiment, the agonist of a co-stimulatory signal of an immune cell expressed by the adenovirus is an agonist of a co-stimulatory receptor expressed by an immune cell. Specific examples of co-stimulatory receptors that can be expressed by the adenovirus include glucocorticoid-induced tumor necrosis factor receptor (GITR), Inducible T-cell co-stimulator (ICOS or CD278), OX40 (CD134), CD27, CD28, 4-IBB (CD137), CD40, CD226, cytotoxic and regulatory T cell molecule (CRT AM), death receptor 3 (DR3), lymphotoxin-beta receptor (LTBR), transmembrane activator and CAML interactor (TACI), B cell-activating factor receptor (BAFFR), and B cell maturation protein (BCMA). In a specific embodiment, the agonist of a co-stimulatory receptor expressed by an immune cell is an antibody (or an antigen-binding fragment thereof) or ligand that specifically binds to the co-stimulatory receptor. In one embodiment, the antibody is a monoclonal antibody. In another embodiment, the antibody is an sc-Fv. In a specific embodiment, the antibody is a bispecific antibody that binds to two receptors on an immune cell. In one embodiment, the bispecific antibody binds to a receptor on an immune cell and to another receptor on a cancer cell. In specific embodiments, the antibody is a human or humanized antibody. In certain embodiments, the ligand or antibody is a chimeric protein.

In a specific embodiment, the antagonist of an inhibitory signal of an immune cell is an antagonist of an inhibitory receptor expressed by an immune cell. Specific examples of inhibitory receptors include cytotoxic T-lymphocyte-associated antigen 4 (CTLA-4 or CD52), programmed cell death protein 1 (PD1 or CD279), B and T-lymphocyte attenuator (BTLA), killer cell immunoglobulin-like receptor (KIR), lymphocyte activation gene 3 (LAG3), T-cell membrane protein 3 (TIM3), adenosine A2a receptor (A2aR), T cell immunoreceptor with immunoglobulin and ITIM domains (TIGIT), leukocyte-associated immunoglobulin-like receptor 1 (LAIR1), and CD160. In a specific embodiment, the antagonist of an inhibitory receptor expressed by an immune cell is an antibody (or an antigen-binding fragment thereof) that specifically binds to the co-stimulatory receptor.

Antibodies include, but are not limited to, monoclonal antibodies, bispecific antibodies, multispecific antibodies, human antibodies, humanized antibodies, synthetic antibodies, chimeric antibodies, polyclonal antibodies, single domain antibodies, camelid or camelized antibodies, single-chain Fvs (scFv), single chain antibodies, Fab fragments, F(ab') fragments, disulfide-linked bispecific Fvs (sdFv), intrabodies, and anti-idiotypic (anti-Id) antibodies (including, e.g., anti-Id and anti-anti-Id antibodies to antibodies), and epitope-binding fragments of any of the above. In particular, antibodies include immunoglobulin molecules and immunologically active fragments of immunoglobulin molecules. Immunoglobulin molecules can be of any type (e.g., IgG, IgE, IgM, IgD, IgA and IgY), class (e.g., IgG1, IgG2, IgG3, IgG4, IgA1 and IgA2) or subclass. In a specific embodiment, an antibody is a human or humanized antibody. In another specific embodiment, an antibody is a monoclonal antibody or scFv. In certain embodiments, an antibody is a human or humanized monoclonal antibody or scFv. In other specific embodiments, the antibody is a bispecific antibody. In certain embodiments, the bispecific antibody specifically binds to a co-stimulatory receptor of an immune cell or an inhibitory receptor of an immune, and a receptor on a cancer cell. In some embodiments, the bispecific antibody specifically binds to two receptors immune cells, e.g., two co-stimulatory receptors on immune cells, two inhibitory receptors on immune cells, or one co-stimulatory receptor on immune cells and one inhibitory receptor on immune cells.

The recombinant AVs described herein may be engineered to express any agonist of a co-stimulatory signal and/or any antagonist of an inhibitory signal of an immune cell, such as, e.g., a T-lymphocyte, NK cell or antigen-presenting cell (e.g., a dendritic cell or macrophage). In specific embodiments, the agonist and/or antagonist is an agonist of a human co-stimulatory signal of an immune cell and/or antagonist of a human inhibitory signal of an immune cell. In certain embodiments, the agonist of a co-stimulatory signal is an agonist of a co-stimulatory molecule (e.g., co-stimulatory receptor) found on immune cells, such as, e.g., T-lymphocytes (e.g., CD4+ or CD8+ T-lymphocytes), NK cells and/or antigen-presenting cells (e.g., dendritic cells or macrophages). Specific examples of co-stimulatory molecules include glucocorticoid-induced tumor necrosis factor receptor (GITR), Inducible T-cell co-stimulator (ICOS or CD278), OX40 (CD134), CD27, CD28, 4-IBB (CD137), CD40, lymphotoxin alpha (LT alpha), LIGHT (lymphotoxin-like, exhibits inducible expression, and competes with herpes simplex virus glycoprotein D for HVEM, a receptor expressed by T lymphocytes), CD226, cytotoxic and regulatory T cell molecule (CRT AM), death receptor 3 (DR3), lymphotoxin-beta receptor (LTBR), transmembrane activator and CAML interactor (TACI), B cell-activating factor receptor (BAFFR), and B cell maturation protein (BCMA). In specific embodiments, the agonist is an agonist of a human co-stimulatory receptor of an immune cell. In certain embodiments, the agonist of a co-stimulatory receptor is not an agonist of ICOS. In some embodiments, the antagonist is an antagonist of an inhibitory molecule (e.g., inhibitory receptor) found on immune cells, such as, e.g., T-lymphocytes (e.g., CD4+ or CD8+ T-lymphocytes), NK cells and/or antigen-presenting cells (e.g., dendritic cells or macrophages). Specific examples of inhibitory molecules include cytotoxic T-lymphocyte-associated antigen 4 (CTLA-4 or CD52), programmed cell death protein 1 (PD1 or CD279), B and T-lymphocyte attenuator (BTLA), killer cell immunoglobulin-like receptor (KIR), lymphocyte activation gene 3 (LAG3), T-cell membrane protein 3 (TIM3), CD 160, adenosine A2a receptor (A2aR), T cell immunoreceptor with immunoglobulin and ITIM domains (TIGIT), leukocyte-associated immunoglobulin-like receptor 1 (LAIR1), and CD 160. In specific embodiments, the antagonist is an antagonist of a human inhibitory receptor of an immune cell.

In a specific embodiment, the agonist of a co-stimulatory receptor is an antibody or antigen-binding fragment thereof that specifically binds to the co-stimulatory receptor. Specific examples of co-stimulatory receptors include GITR, ICOS, OX40, CD27, CD28, 4-1BB, CD40, LT alpha, LIGHT, CD226, CRT AM, DR3, LTBR, TACI, BAFFR, and BCMA. In certain specific embodiments, the antibody is a monoclonal antibody. In other specific embodiments, the antibody is an sc-Fv. In a specific embodiment, the antibody is a bispecific antibody that binds to two receptors on an immune cell. In other embodiments, the bispecific antibody binds to a receptor on an immune cell and to another receptor on a cancer cell. In specific embodiments, the antibody is a human or humanized antibody.

In another embodiment, the agonist of a co-stimulatory receptor expressed by the adenovirus is a ligand of the co-stimulatory receptor. In certain embodiments, the ligand is fragment of a native ligand. Specific examples of native ligands include ICOSL, B7RP1, CD137L, OX40L, CD70, herpes virus entry mediator (HVEM), CD80, and CD86. The nucleotide sequences encoding native ligands as well as the amino acid sequences of native ligands are known in the art. For example, the nucleotide and amino acid sequences of B7RP1 (otherwise known as ICOSL; GenBank human: NM_015259.4, NP_056074.1 murine: NM_015790.3, NP_056605.1), CD137L (GenBank human: NM 003811.3, NP 003802.1, murine: NM 009404.3, NP 033430.1), OX40L (GenBank human: NM_003326.3, NP_003317.1, murine: NM_009452.2, NP_033478.1), CD70 (GenBank human: NM_001252.3, NP_001243.1, murine: NM_011617.2, AAD00274.1), CD80 (GenBank human: NM_005191.3, NP_005182.1, murine: NM_009855.2, NP_033985.3), and CD86 (GenBank human: NM_005191.3, CAG46642.1, murine: NM_019388.3, NP_062261.3) can be found in GenBank. In other embodiments, the ligand is a derivative (e.g., a fragment, domain, fusion, or other modification of a full-length polypeptide) a native ligand. In some embodiments, the ligand is a fusion protein comprising at least a portion of the native ligand or a derivative of the native ligand that specifically binds to the co-stimulatory receptor, and a heterologous amino acid sequence. In specific embodiments, the fusion protein comprises at least a portion of the native ligand or a derivative of the native ligand that specifically binds to the co-stimulatory receptor, and the Fc portion of an immunoglobulin or a fragment thereof. An example of a ligand fusion protein is a 4-IBB ligand fused to Fc portion of immunoglobulin (described by Meseck M et al., J Immunother. 2011 34: 175-82).

In another embodiment, the antagonist of an inhibitory receptor expressed by the adenovirus is an antibody (or an antigen-binding fragment) or a soluble receptor that specifically binds to the native ligand for the inhibitory receptor and blocks the native ligand from binding to the inhibitory receptor and transducing an inhibitory signal(s). Specific examples of native ligands for inhibitory receptors include PDL-1, PDL-2, B7-H3, B7-H4, HVEM, Gal9 and adenosine. Specific examples of inhibitory receptors that bind to a native ligand include CTLA-4, PD-1, BTLA, KIR, LAG3, TIM3, and A2aR.

In specific embodiments, the antagonist of an inhibitory receptor expressed by the adenovirus is a soluble receptor that specifically binds to the native ligand for the inhibitory receptor and blocks the native ligand from binding to the inhibitory receptor and transducing an inhibitory signal(s). In certain embodiments, the soluble receptor is a fragment of a native inhibitory receptor or a fragment of a derivative of a native inhibitory receptor that specifically binds to native ligand {e.g., the extracellular domain of a native inhibitory receptor or a derivative of an inhibitory receptor). In some embodiments, the soluble receptor is a fusion protein comprising at least a portion of the native inhibitory receptor or a derivative of the native inhibitory receptor (e.g., the extracellular domain of the native inhibitory receptor or a derivative of the native inhibitory receptor), and a heterologous amino acid sequence. In specific embodiments, the fusion protein comprises at least a portion of the native inhibitory receptor or a derivative of the native inhibitory receptor, and the Fc portion of an immunoglobulin or a fragment thereof. An example of a soluble receptor fusion protein is a LAG3-Ig fusion protein (described by Huard B et al, *Eur J Immunol* (1995) 25:2718-21).

In specific embodiments, the antagonist of an inhibitory receptor expressed by the adenovirus is an antibody (or an antigen-binding fragment) that specifically binds to the native ligand for the inhibitory receptor and blocks the native ligand from binding to the inhibitory receptor and transducing an inhibitory signal(s). In certain specific embodiments, the antibody is a monoclonal antibody. In other specific embodiments, the antibody is an scFv. In particular embodiments, the antibody is a human or humanized antibody. A specific example of an antibody to inhibitory ligand is anti-PD-L1 antibody (Iwai Y, et al. *PNAS* 2002; 99: 12293-12297).

In another embodiment, the antagonist of an inhibitory receptor expressed by the adenovirus is an antibody (or an antigen-binding fragment) or ligand that binds to the inhibitory receptor, but does not transduce an inhibitory signal(s). Specific examples of inhibitory receptors include CTLA-4, PD1, BTLA, TIGIT, KIR, LAG3, TIM3, and A2aR. In certain specific embodiments, the antibody is a monoclonal antibody. In other specific embodiments, the antibody is an scFv. In particular embodiments, the antibody is a human or humanized antibody. A specific example of an antibody to inhibitory receptor is anti-CTLA-4 antibody (Leach D R, et al. *Science* 1996; 271: 1734-1736). Another example of an antibody to inhibitory receptor is anti-PD-1 antibody (Topalian S L, *NEJM* 2012; 28:3167-75).

In certain embodiments, a chimeric adenovirus described herein is engineered to produce an antagonist of CTLA-4, such as, e.g., ipilimumab or tremelimumab. In certain embodiments, a chimeric adenovirus described herein is engineered to an antagonist of PD1, such as, e.g., MDX-1106 (BMS-936558), MK3475, CT-011, AMP-224, or MDX-1105. In certain embodiments, a chimeric adenovirus described herein is engineered to express an antagonist of LAG3, such as, e.g., IMP321. In certain embodiments, a chimeric adenovirus described herein is engineered to express an antibody (e.g., a monoclonal antibody or an antigen-binding fragment thereof, or scFv) that binds to B7-H3, such as, e.g., MGA271. In specific embodiments, a chimeric adenovirus described herein is engineered to express an agonist of a co-stimulatory signal of an immune cell and/or an antagonist of an inhibitory signal of an immune cell. In specific embodiments, adenovirus described herein is engineered to express anti-CD28 scFv, ICOSL, CD40L, OX40L, CD137L, GITRL, and/or CD70.

In certain embodiments, an agonist of a co-stimulatory signal of an immune cell expressed by the adenovirus induces (e.g., selectively) induces one or more of the signal transduction pathways induced by the binding of a co-stimulatory receptor to its ligand. In specific embodiments, an agonist of a co-stimulatory receptor induces one or more of the signal transduction pathways induced by the binding of the co-stimulatory receptor to one or more of its ligands by at least 25%, 30%, 40%>, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of the co-stimulatory receptor to one or more of its ligands in the absence of the agonist. In specific embodiments, an agonist of a co-stimulatory receptor: (i) induces one or more of the signal transduction pathways induced by the binding of the co-stimulatory receptor to one particular ligand by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of the co-stimulatory receptor to the particular ligand in the absence of the agonist; and (ii) does not induce, or induces one or more of the signal transduction pathways induced by the binding of the co-stimulatory receptor to one or more other ligands by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of the co-stimulatory receptor to such one or more other ligands in the absence of the agonist.

In certain embodiments, an agonist of a co-stimulatory signal of an immune cell activates or enhances (e.g., selectively activates or enhances) one or more of the signal transduction pathways induced by the binding of a co-stimulatory receptor to its ligand. In specific embodiments, an agonist of a co-stimulatory receptor activates or enhances one or more of the signal transduction pathways induced by the binding of the co-stimulatory receptor to one or more of its ligands by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%), or 75%) to 100% relative to the one or more signal transduction pathways induced by the binding of co-stimulatory receptor to one or more of its ligands in the absence of the agonist. In specific embodiments, an agonist of a co-stimulatory receptor: (i) an agonist of a co-stimulatory signal activates or enhances one or more of the signal transduction pathways induced by the binding of the co-stimulatory receptor to one particular ligand by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of the co-stimulatory receptor to the particular ligand in the absence of the agonist; and (ii) does not activate or enhance, or activates or enhances one or more of the signal transduction pathways induced by the binding of the co-stimulatory receptor to one or more other ligands by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of the co-stimulatory receptor to such one or more other ligands in the absence of the agonist.

In some embodiments, an antagonist of an inhibitory signal of an immune cell (e.g., selectively) inhibits or reduces one or more of the signal transduction pathways induced by the binding of an inhibitory receptor to its ligand. In specific embodiments, an antagonist of an inhibitory receptor inhibits or reduces one or more of the signal transduction pathways induced by the binding of the inhibitory receptor to one or more of its ligands by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of the inhibitory receptor to one or more of its ligands in the absence of the antagonist. In specific embodiments, an antagonist of an inhibitory receptor: (i) inhibits or reduces one or more of the signal transduction pathways induced by the binding of the inhibitory receptor to one particular ligand by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of the inhibitory receptor to the one particular ligand in the absence of the antagonist; and (ii) does not inhibit or reduce, or inhibits or reduces one or more of the signal transduction pathways induced by the binding of the inhibitory receptor to one or more other ligands by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of inhibitory receptor to such one or more other ligands in the absence of the antagonist.

In specific embodiments, an agonist of a co-stimulatory signal of an immune cell and/or an antagonist of an inhibitory signal of an immune cell induces, activates and/or enhances one or more immune activities, functions or responses. The one or more immune activities, functions or responses can be in the form of, e.g., an antibody response (humoral response) or a cellular immune response, e.g., cytokine secretion (e.g., interferon-gamma), helper activity or cellular cytotoxicity. In one embodiment, expression of an activation marker on immune cells (e.g., CD44, Granzyme, or Ki-67), expression of a co-stimulatory receptor on immune cells (e.g., ICOS, CD28, OX40, or CD27), expression of a ligand for a co-stimulatory receptor (e.g., B7HRP1, CD80, CD86, OX40L, or CD70), cytokine secretion, infiltration of immune cells (e.g., T-lymphocytes, B lymphocytes and/or NK cells) to a tumor, antibody production, effector function, T cell activation, T cell differentiation, T cell proliferation, B cell differentiation, B cell proliferation, and/or NK cell proliferation is induced, activated and/or enhanced following contact with an agonist of a co-stimulatory signal of an immune cell and/or an antagonist of an inhibitory signal of an immune cell. In another embodiment, myeloid-derived suppressor cell (MDSC) tumor infiltration and proliferation, Treg tumor infiltration, activation and proliferation, peripheral blood MDSC and Treg counts are inhibited following contact with an agonist of a co-stimulatory signal of an immune cell and/or an antagonist of an inhibitory signal of an immune cell.

In certain embodiments, a chimeric adenovirus described herein is engineered to produce two or more immunomodulatory polypeptides. In some embodiments, the chimeric adenovirus produces a first immunomodulatory polypeptide and a second immunomodulatory polypeptide.

For example, a first immunomodulatory polypeptide is a costimulatory ligand, a proinflammatory cytokine, an inhibitor of an inhibitory cytokine, an initiator of a localized immune response, an inhibitor of a co-inhibitory checkpoint molecule, or a ligand of a cluster of differentiation (CD) molecule, and the second immunomodulatory polypeptide is a costimulatory ligand, a proinflammatory cytokine, an inhibitor of an inhibitory cytokine, an initiator of a localized immune response, an inhibitor of a co-inhibitory checkpoint molecule, or a ligand of a cluster of differentiation (CD) molecule.

For example, a first immunomodulatory polypeptide is a costimulatory ligand, and the second immunomodulatory polypeptide is a costimulatory ligand.

For another example, a first immunomodulatory polypeptide is a costimulatory ligand and the second immunomodulatory polypeptide is a pro-inflammatory cytokine.

In some embodiments, two or more immunomodulatory polypeptides are expressed from a single transcript. To express two or more proteins from a single transcript determined by a viral or non-viral vector, an internal ribosome entry site (IRES) sequence is commonly used to drive expression of the second, third, fourth coding sequence, etc. When two coding sequences are linked via an IRES, the translational expression level of the second coding sequence is often significantly reduced (Furler et al. 2001. Gene Therapy 8:864-873). In fact, the use of an IRES to control transcription of two or more coding sequences operably linked to the same promoter can result in lower level expression of the second, third, etc. coding sequence relative to the coding sequence adjacent the promoter. In addition, an IRES sequence may be sufficiently long to impact complete packaging of the vector, e.g., the eCMV IRES has a length of 507 base pairs.

Internal ribosome entry site (IRES) elements were first discovered in picornavirus mRNAs (Jackson et al. 1990. *Trends Biochem. Sci.* 15:477-83) and Jackson and Kaminski, *RNA* (1995) 1:985-1000). Examples of IRES generally employed by those of skill in the art include those referenced in Table I and Appendix A, as well as those described in U.S. Pat. No. 6,692,736. Examples of "IRES" known in the art include, but are not limited to IRES obtainable from picornavirus (Jackson et al., 1990) and IRES obtainable from viral or cellular mRNA sources, such as for example, immunoglobulin heavy-chain binding protein (BiP), the vascular endothelial growth factor (VEGF) (Huez et al. 1998, *Mol. Cell. Biol.* 18:6178-6190), the fibroblast growth factor 2 (FGF-2), and insulin-like growth factor (IGFII), the translational initiation factor eIF4G and yeast transcription factors TFIID and HAP4, the encephelomyocarditis virus (EMCV) which is commercially available from Novagen (Duke et al. 1992. *J. Virol* 66:1602-9) and the VEGF IRES (Huez et al. 1998. *Mol. Cell. Biol.* 18:6178-90). IRES have also been reported in different viruses such as cardiovirus, rhinovirus, aphthovirus, HCV, Friend murine leukemia virus (FrMLV) and Moloney murine leukemia virus (MoMLV). As used herein, "IRES" encompasses functional variations of IRES sequences as long as the variation is able to promote direct internal ribosome entry to the initiation codon of a cistron. An IRES may be mammalian, viral or protozoan. The IRES promotes direct internal ribosome entry to the initiation codon of a downstream cistron, leading to cap-independent translation. Thus, the product of a downstream cistron can be expressed from a bicistronic (or multicistronic) mRNA, without requiring either cleavage of a polyprotein or generation of a monocistronic mRNA. Internal ribosome entry sites are approximately 450 nucleotides in length and are characterized by moderate conservation of primary sequence and strong conservation of secondary structure. The most significant primary sequence feature of the IRES is a pyrimidine-rich site whose start is located approximately 25 nucleotides upstream of the 3' end of the IRES. See Jackson et al. (1990). Three major classes of picornavirus IRES have been identified and characterized: the cardio- and aphthovirus class (for example, the encephalomyocarditis virus, Jang et al. 1990. *Gene Dev* 4:1560-1572); the entero- and rhinovirus class (for example, polioviruses, Borman et al. 1994. *EMBO J.* 13:3149-3157); and the hepatitis A virus (HAV) class, Glass et al. 1993. *Virol* 193:842-852). For the first two classes, two general principles apply. First, most of the 450-nucleotide sequence of the IRES functions to maintain particular secondary and tertiary structures conducive to ribosome binding and translational initiation. Second, the ribosome entry site is an AUG triplet located at the 3' end of the IRES, approximately 25 nucleotides downstream of a conserved oligopyrimidine tract. Translation initiation can occur either at the ribosome entry site (cardioviruses) or at the next downstream AUG (entero/rhinovirus class). Initiation occurs at both sites in aphthoviruses. HCV and pestiviruses such as bovine viral diarrhea virus (BVDV) or classical swine fever virus (CSFV) have 341 nt and 370 nt long 5'-UTR respectively. These 5'-UTR fragments form similar RNA secondary structures and can have moderately efficient IRES function (Tsukiyama-Kohara et al. 1992. *J. Virol.* 66:1476-1483; Frolov et al. 1998. *RNA* 4:1418-1435). Recent studies showed that both Friend-murine leukemia virus (MLV) 5'-UTR and rat retrotransposon virus-like 30S (VL30) sequences contain IRES structure of retroviral origin (Torrent et al. 1996. *Hum. Gene Ther* 7:603-612). In eukaryotic cells, translation is normally initiated by the ribosome scanning from the capped mRNA 5' end, under the control of initiation factors. However, several cellular mRNAs have been found to have IRES structure to mediate the cap-independent translation (van der Velde, et al. 1999. *Int J Biochem Cell Biol.* 31:87-106). Examples of IRES elements include, without limitation, immunoglobulin heavy-chain binding protein (BiP) (Macejak et al. 1991. *Nature* 353:90-94), antennapedia mRNA of *Drosophila* (Oh et al. 1992. Gene and Dev 6:1643-1653), fibroblast growth factor-2 (FGF-2) (Vagner et al. 1995. *Mol. Cell. Biol.* 15:35-44), platelet-derived growth factor B (PDGF-B) (Bernstein et al. 1997. J. Biol. Chem. 272:9356-9362), insulin-like growth factor II (Teerink et al. (1995) *Biochim. Biophys. Acta* 1264:403-408), and the translation initiation factor eIF4G (Gan et al. 1996. J. Biol. Chem. 271:623-626). Recently, vascular endothelial growth factor (VEGF) was also found to have IRES element (Stein et al. 1998. Mol. Cell. Biol. 18:3112-3119; Huez et al. 1998. Mol. Cell. Biol. 18:6178-6190). Further examples of IRES sequences include Picornavirus HAV (Glass et al. 1993. Virology 193:842-852); EMCV (Jang and Wimmer. 1990. *Gene Dev.* 4:1560-1572); Poliovirus (Borman et al. 1994. EMBO J. 13:3149-3157); HCV (Tsukiyama-Kohara et al. 1992. J. Virol. 66:1476-1483); pestivirus BVDV (Frolov et al. 1998. RNA. 4:1418-1435); *Leishmania* LRV-1 (Maga et al. 1995. Mol. Cell. Biol. 15:4884-4889); Retroviruses: MoMLV (Torrent et al. 1996. *Hum. Gene Ther.* 7:603-612). VL30, Harvey murine sarcoma virus, REV (Lopez-Lastra et al. 1997. *Hum. Gene Ther.* 8:1855-1865). IRES may be prepared using standard recombinant and synthetic methods known in the art. For cloning convenience, restriction sites may be engineered into the ends of the IRES fragments to be used.

In some embodiments, two immunomodulatory polypeptides are expressed from separate transcripts, i.e., a first transcript and a second transcript. In some embodiments, the two transcripts are encoded by a DNA insertion at the same location in the adenovirus, e.g., both inserted in E1b, E3, or E4. In some embodiments, the two transcripts are encoded by a DNA insertion at the different locations in the adenovirus, e.g., a first transcript DNA inserted in E1b and a second transcript DNA inserted in E3 or E4, or alternatively, a first transcript DNA inserted in E3 and a second transcript DNA inserted in E4.

Another aspect of the invention provides a virus for causing expression in a target cell of a plurality of recombinant immunomodulatory polypeptides or other protein(s) or polypeptides of interest, wherein the vector also includes a promoter operably linked to a first coding sequence for a first recombinant immunomodulatory polypeptide, a self-processing or other cleavage coding sequence, such as a 2A or 2A-like sequence or a protease recognition site, and a second coding sequence for a second recombinant immunomodulatory polypeptide, wherein the self-processing cleavage sequence or protease recognition site coding sequence is inserted between the first and the second coding sequences. In a related embodiment, the viral vector comprises an expression vector as described above wherein the expression vector further comprises an additional proteolytic cleavage site between the first and second recombinant immunomodulatory polypeptides. A preferred additional proteolytic cleavage site is a furin cleavage site with the consensus sequence RXR/K-R.

Interaction of Oncolytic Activity and Immunomodulatory Activity.

Oncolytic viruses (OVs) were originally conceived as simply a means of targeted destruction of cancer cells. However, it is now thought that the most effective OV therapies will be those that combine tumor cell death with the stimulation of a host anti-tumor immune response. OVs engineered to express particular immunomodulatory cytokines in tumor cells will be able to specifically guide the immune system toward combating cancer cells. Combining the expression of these cytokines with the release of tumor-associated antigens (TAAs, i.e. tumor cell debris) upon viral lysis of cancer cells will allow for the development of cellular or antibody-mediated anti-tumor immune responses (Lichty et al., 2014, Nature Reviews Cancer, 14: 559-567).

Pharmaceutical Compositions.

A pharmaceutical composition of the invention comprises at least one of the vectors of the invention as described herein. Furthermore, the composition may comprise at least two, three or four different (i.e., expressing different transgenes) vectors of the invention. In addition to the vector, a pharmaceutical composition may also comprise any other vectors, such as other adenoviral vectors, other therapeutically effective agents, any other agents such as pharmaceutically acceptable carriers, buffers, excipients, adjuvants, antiseptics, filling, stabilizing or thickening agents, and/or any components, e.g., such as components found in corresponding viral or pharmaceutical products.

The vector(s) described herein can be administered (e.g., in a pharmaceutical composition) to any human or animal, including but not limited to a human or non-human animal having or diagnosed with cancer. According to one embodiment, the cancer is nasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, brain cancer, oligodendroglioma, neuroblastoma, meningioma, spinal cord tumor, bone cancer, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, colorectal cancer, rectal cancer, esophagus cancer, gall bladder cancer, head cancer, eye cancer, neck cancer, kidney cancer, Wilms' tumor, liver cancer, Kaposi's sarcoma, prostate cancer, lung cancer, testicular cancer, Hodgkin's disease, non-Hodgkin's lymphoma, oral cancer, skin cancer, mesothelioma, multiple myeloma, ovarian cancer, endocrine pancreatic cancer, glucagonoma, pancreatic cancer, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer, tonsil cancer. The vector or pharmaceutical composition of the invention may be administered to any eukaryotic subject selected from a group consisting of animals and human beings, in a preferred embodiment of the invention, the subject is a human or a non-human animal. An animal may be selected from a group consisting of pets, domestic animals and production animals.

The adenoviral vector(s) of the present invention may be administered to a subject, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The therapeutic of the present invention may also be administered directly to the tumor in the form of a liquid, gel or suspension introduced by intratumoral injection. A study examining the treatment of mice bearing subcutaneous human pancreatic adenocarcinoma xenografts with recombinant Newcastle disease virus (rNDV) showed that intratumoral injection yielded better tumor regression than intravenous injection. In this study, animals were injected intratumorally every other day for a total of 4 injections, each containing $5 \times 10^7$ 50% Tissue Culture Infective Dose (TCID50) rNDV in 50 µl (Buijs et al., 2015, Viruses, 6: 2980-2998). Similarly, another study examining the treatment of mice bearing subcutaneous bladder cancer xenografts with modified oncolytic adenovirus found that intratumoral injection significantly suppressed tumor growth. In this study, animals were injected intratumorally twice at a 1-day interval with $5 \times 10^8$ infectious unit (IFU) viruses in 100 µl (Yang et al., 2015, Cell Death and Disease, e1760). Shown to be well-tolerated in Phase 1 trials, Pexa-Vec (JX-594), an oncolytic and immunotherapeutic vaccinia virus has been examined as an intratumorally-administered treatment for patients with advanced hepatocellular carcinoma (HCC). In this study design, patients were to be injected intratumorally 3 times every 2 weeks at one of 2 dose levels: $1 \times 10^8$ plaque forming units (pfu), or $1 \times 10^9$ pfu (Walther and Stein, 2015, Methods in Molecular Biology, 1317: 343-357).

A single administration of oncolytic adenoviral vectors of the invention may have therapeutic effects. However, in some embodiments of the invention, oncolytic adenoviral vectors or pharmaceutical compositions are administered several times during the treatment period. Oncolytic adenoviral vectors or pharmaceutical compositions may be administered for example from 1 to 10 times in the first 2 weeks, 4 weeks, monthly or during the treatment period. In one embodiment of the invention, administration is done three to seven times in the first 2 weeks, then at 4 weeks and then monthly, in a specific embodiment of the invention, administration is done four times in the first 2 weeks, then at 4 weeks and then monthly. The length of the treatment period may vary, and for example may last from two to 12 months or more.

To improve the efficacy of the present invention, in some embodiments, the therapeutic of the present invention is administered with an adjuvant. Suitable adjuvants include aluminum salts (alum) such as aluminum hydroxide, aluminum phosphate, and aluminum sulfate, Incomplete Freund's Adjuvant (IFA), and monophosphoryl lipid A (MPL). These adjuvants are suitable for human administration, either alone or optionally all combinations thereof (Chang et al., "Adjuvant Activity of Incomplete Freund's Adjuvant," Adv Drug Deliv Rev 32:173-186 (1998), which is hereby incorporated by reference in its entirety). Other adjuvants include cytokines, such as interleukins (IL-1, IL-2, and IL-12), macrophage colony stimulating factor (M-CSF), tumor necrosis factor (TNF), di- and tri-palmitoyl-S-glyceryl cysteine ($Pam_2Cys$ and $Pam_3Cys$, respectively), a TLR2 agonist, an anti-granulocyte macrophage colony-stimulating factor (GM-CSF) antibody, RR-XS15, Montanide®, and MALP-2.

The adenoviral vector of the present invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid (e.g., aqueous) form such as, tablets, capsules, powders, solutions, suspensions, or emulsions.

The therapeutic of the present invention may be orally administered, for example, with an inert diluent, or with a suitable edible carrier, or they may be enclosed in hard or soft-shell capsules, or they may be compressed into tablets, or they may be incorporated directly with the food of the diet. For oral therapeutic administration, the therapeutic may be incorporated with excipients and used in the form of tablets, capsules, elixirs, suspensions, syrups, and the like. Various other materials may be present as coatings or to modify the physical form of the dosage unit.

The therapeutic may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The therapeutic of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The therapeutic of this invention may be administered in sufficient amounts to transfect the desired cells and provide sufficient levels of integration and expression of the replicating virus to provide a therapeutic benefit without undue adverse effects or with medically acceptable physiological effects which can be determined by those skilled in the medical arts.

Dosages of the therapeutic will depend primarily on factors, such as the condition being treated, the age, weight, and health of the patient, and may thus vary among patients. The dosage will be adjusted to balance the therapeutic benefit against any viral toxicity or side effects.

The present invention also relates to a method of enhancing the delivery to and distribution within a tumor mass of therapeutic proteins expressed from viruses. For example, an adenovirus as described herein, optionally in a pharmaceutical composition as described herein, can be injected into a tumor mass such that the virus infects and lyses one or more tumor cell. Combination Therapy.

The viral immunotherapy of the invention is effective alone, but combination of multiple adenoviral immunotherapies, or one or more adenoviral immunotherapies with any other therapies, such as traditional therapy, may be more effective than either one alone. For example, each agent of the combination therapy may work independently in the tumor tissue, the adenoviral vectors may sensitize cells to chemotherapy or radiotherapy and/or chemotherapeutic agents may enhance the level of virus replication or effect the receptor status of the target cells. The agents of combination therapy may be administered simultaneously or sequentially.

In a preferred embodiment of the invention, the method or use further comprises administration of concurrent radiotherapy to a subject. In another preferred embodiment of the invention, the method or use further comprises administration of concurrent chemotherapy to a subject. As used herein "concurrent" refers to a therapy, which has been administered before, after or simultaneously with the gene therapy of the invention. The period for a concurrent therapy may vary from minutes to several weeks. In some embodiments, the concurrent therapy lasts for some hours.

Agents suitable for combination therapy include but are not limited to afatinib, all-trans retinoid acid, azacitidine, azathioprine, bleomycin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, 5-fluorouracil, gemcitabine, hydroxyurea, idarubicin, imatinib, mechlorethamine, mercaptopurine, methotrexate, mitoxantrone, oxaliplatin, paclitaxel, pemetrexed, temozolomide, teniposide, tioguanine, valrubicin, vinblastine, vincristine, vindesine and vinorelbine.

In some embodiments, the method or use further comprises administration of verapamil or another calcium channel blocker to a subject. "Calcium channel blocker" refers to a class of drugs and natural substances which disrupt the conduction of calcium channels, and if may be selected from a group consisting of verapamil, dihydropyridines, gallopamil, diltiazem, mibefradil, bepridil, fluspirilene and fendiline.

In some embodiments, the method or use further comprises administration of autophagy inducing agents to a subject. Autophagy refers to a catabolic process involving the degradation of a cell's own components through the lysosomal machinery. "Autophagy inducing agents" refer to agents capable of inducing autophagy and may be selected from a group consisting of, but not limited to, mTOR inhibitors (e.g., temsirolimus, sirolimus, everolimus, and ridaforolimus), P13K inhibitors (e.g., wortmannin, lithium, tamoxifen, chloroquine, bafilomycin, and temozolomide. In a specific embodiment of the invention, the method further comprises administration of temozolomide to a subject. Temozolomide may be either oral or intravenous temozolomide.

In some embodiments, the method or use further comprises administration of chemotherapy or anti-CD20 therapy or other approaches for blocking of neutralizing antibodies. "Anti-CD20 therapy" refers to agents capable of killing CD20 positive cells, and may be selected from a group consisting of rituximab and other anti-CD20 monoclonal antibodies. "Approaches for blocking of neutralizing antibodies" refers to agents capable of inhibiting the generation of anti-viral antibodies that normally result from infection and may be selected from a group consisting of different chemotherapeutics, immunomodulatory substances, corticoids and other drugs. These substances may be selected from a group consisting of, but not limited to, cyclophosphamide, ciclosporin, azathioprine, methylprednisolone, etoposide, CD40L, CTLA4, FK506 (tacrolimus), IL-12, IFN-γ, interleukin 10, anti-CD8, anti-CD4 antibodies, hematopoietic stem cell transplantation (HSCT) and oral adenoviral proteins.

In some embodiments, the oncolytic adenoviral vector of the invention induces virion-mediated oncolysis of tumor cells and activates human immune response against tumor cells. In some embodiments, the method or use further comprises administration of substances capable to downregulating regulatory T-cells in a subject in an amount to downregulate (e.g., by at least 10%, 20%, 50%, 70%, 90% or more) regulatory T-cells in the subject. "Substances capable to downregulating regulatory T-cells" refers to agents that reduce the numbers of cells identified as T-suppressor or Regulatory T-cells. These cells have been identified as consisting one or many of the following immunophenotypic markers: CD4+, CD25+, FoxP3+, CD127− and GITR+. Such agents reducing T-suppressor or Regulatory T-cells may be selected from a group consisting of anti-CD25 antibodies or chemotherapeutics.

In some embodiments, the method or use further comprises administration of cyclophosphamide to a subject. Cyclophosphamide is a common chemotherapeutic agent, which has also been used in some autoimmune disorders. In the present invention, cyclophosphamide can be used to enhance viral replication and the effects of GM-CSF induced stimulation of NK and cytotoxic T-cells for enhanced immune response against the tumor. It can be used as intravenous bolus doses or low-dose oral metronomic administration.

Kits

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

EXAMPLES

The present invention is further described by the following examples, which are illustrative of specific embodiments of the invention, and various uses thereof. These exemplifications, which illustrating certain specific aspects of the invention, do not portray the limitations or circumscribe the scope of the disclosed invention.

Unless otherwise indicated, the practice of the present invention employs conventional techniques of cell culture, molecular biology, microbiology, recombinant DNA manipulation, immunology science, which are within the skill of the art. Such techniques are explained fully in the literature. See, e.g. Cell Biology: a Laboratory Handbook: J. Cells (Ed). Academic Press. N.Y. (1996); Graham, F. L. and Prevec, L. Adenovirus-based expression vectors and recombinant vaccines. In: Vaccines: New Approaches to Immunological Problems. R. W. Ellis (ed) Butterworth. Pp 363-390; Grahan and Prevec Manipulation of adenovirus vectors. In: Methods in Molecular Biology, Vol. 7: Gene Transfer and Expression Techniques. E. J. Murray and J. M. Walker (eds) Humana Press Inc., Clifton, N.J. pp 109-128, 1991; Sambrook et al. (1989), Molecular Cloning, A Laboratory Manual, 2nd ed., Cold Spring Harbor Laboratory Press; Sambrook et al. (1989), and Ausubel et al. (1995), Short Protocols in Molecular Biology, John Wiley and Sons.

Example 1. Virology and Recombinant Nucleic Acids

Standard techniques are used for recombinant nucleic acid methods, polynucleotide synthesis, and microbial culture and transformation (e.g., electroporation, lipofection). Generally, enzymatic reactions and purification steps are performed according to the manufacturer's specifications. The techniques and procedures are generally performed according to conventional methods in the art and various general references (see generally, Sambrook et al., Molecular Cloning: A Laboratory Manual, 2nd. edition (1989) Cold Spring Harbor Laboratory Press, Cold Spring Harbor, N.Y.), which are provided throughout this document. The nomenclature used herein and the laboratory procedures in analytical chemistry, organic synthetic chemistry, and pharmaceutical formulation and delivery, and treatment of patients. Methods for the construction of adenoviral mutants are generally known in the art. See Bett, A. J. et al, PNAS 1994 vol: 91, pages 8802-8806, Mittal, S. K., Virus Res., 1993, vol: 28, pages 67-90; and Hermiston, T. et al., Methods in Molecular Medicine: Adenovirus Methods and Protocols, W. S. M. Wold, ed, Humana Press, 1999. Further, the adenovirus 5 genome is registered as GenBank 10 accession #M73260, and the virus is available from the American Type Culture Collection, Rockville, Md., U.S.A., under accession number VR-5.

Viruses and Cell Lines.

Adenoviruses and cell lines were generally obtained from American Type Culture Collection (ATCC), Manassas, Va.) unless otherwise noted. Cell lines used in the Examples below may include one or more of the cell lines listed in Table 2.

TABLE 2

Viruses and Cell Lines

| Cell Line | Cell/Tissue Type | Catalog # |
| --- | --- | --- |
| HEK-293 | Normal human embryonic kidney | ATCC ® CRL-1573 ™ |
| MRC-5 | Normal human lung | ATCC ® CCL-171 ™ |
| HMEC-1 | Normal human endothelium | ATCC ® CRL3243 ™ |
| MCF 10A | Normal human mammary epithelial | ATCC ® CRL-10317 ™ |
| NHLF | Normal human lung fibroblasts | Lonza CC-2512 |
| HUVEC | Normal human umbilical endothelium | ATCC ® CRL-1730 ™ |
| HCC827 | lung adenocarcinoma | ATCC ® CRL-2868 ™ |
| A549 | human lung carcinoma | ATCC ® CCL-185 ™ |
| ADS-12 | | a derivative from a murine KRAS mutant lung adenocarcinoma cell line (LKR-13) |
| NCI-H1734 | NSCLC adenocarcinoma | ATCC ® CRL-5891 ™ |
| NCI-H2110 | NSCLC metastatic carcinoma | ATCC ® CRL-5924 ™ |
| HT-1080 | Connective tissue fibrosarcoma | ATCC ® CCL121 ™ |
| PC-3 | Prostate adenocarcinoma | ATCC ® CRL1435 ™, |
| SNU-449 | Hepatocellular carcinoma | ATCC ® CRL-2234 ™ |
| HepG2 | Hepatocellular carcinoma | ATCC ® HB-8065 ™ |
| MDA-MB-231 | Breast adenocarcinoma | ATCC ® HTB-26 ™ |
| PANC-1 | Pancreatic carcinoma | ATCC ® CRL-1469 ™ |
| SW780 | Bladder carcinoma | ATCC ® CRL-2169 ™ |
| FaDu | Head and neck squamous cell carcinoma | ATCC ® HTB43 ™ |
| DLD-1 | Colorectal adenocarcinoma | ATCC ® CCL-221 ™ |
| CT26 | Murine colon carcinoma | ATCC ® CRL-2638 ™ |
| U-87 | brain glioblastoma | ATCC ® HTB14 ™ |

TABLE 2-continued

Viruses and Cell Lines

| Cell Line | Cell/Tissue Type | Catalog # |
|---|---|---|
| MBT-2 | Murine bladder cancer | described, e.g., in Takahashi et al., J Urol, 166(6), 2506-2511 |
| B16F10 | Murine skin melanoma | ATCC ® CRL-6475 ™ |
| TAV-255 D19 | Adeno virus | described in, e.g., Zhang et al., Cancer Gene Ther. (2015) 22(1): 17-22. |
| Ad5 | Adenoid 75 strain | ATCC ® VR-5 ™ |

Viral Purification and Quantitation

Viral stocks were propagated on HEK-293 cells and purified by standard methods such as column purification kits (Virapure, Millipore) or CsCl gradient centrifugation (as described in Tollefson, A., Hermiston, T. W., and Wold, W. S. M.; "Preparation and Titration of CsCl-banded Adenovirus Stock" in Adenovirus Methods and Protocols, Humana Press, 1999, pp 1-10, W. S. M. Wold, Ed.). The method used to quantitate viral particles is based on simple OD 260/280 readings, e.g., using the method of Lehmberg et al. (1999) J. Chrom. B, 732:411-423. In the viral concentration range used, the A260 nm peak area of each sample is directly proportional to the number of viral particles in the sample. The number of viral particles per ml in each test sample was calculated by multiplying the known number of viral particles per ml in the standard by the ratio of the A260 nm viral peak area of the sample to the A260 nm viral peak area of the standard. One A260 unit contains approximately $1 \times 10^{12}$ viral particles. Virus Infectious Units/ml (IU/ml) were determined by hexon staining of infected cells (e.g., using Adeno-X™ Rapid titer kit from Takara Bio USA, Inc. (TBUSA, formerly known as Clontech Laboratories, Inc.).

Example 2. Bioselection

Initial screening of recombinant virus was based on isolated viral DNA rescued from transfected 293 cells where viral propagation based cytopathic effects (CPE) were observed. Viral DNA was used as a template for PCR based detection of sequences flanking the site of the TAV-255 E1a enhancer deletion region. Wild-type sequence would produce a band of 350 bp, while DNA which had the E1a enhancer deletion would only generate a clearly distinguishable 300 bp band. In addition, primers specific for internal sequences of the IL-12 transgene and for Ad hexon sequences were used to verify 400 bp and 3 kb PCR amplified bands respectively that would only be present in viral DNA generated by recombination between the two parental plasmids containing either the E1 region and transgene insert or the late Ad structural proteins derived solely from the pAdEasy™ plasmid. Individual constructs were isolated by two rounds of plaque purification on A549 or 293 cells using standard methods (Tollefson, A., Hermiston, T. W., and Wold, W. S. M.; "Preparation and Titration of CsCl-banded Adenovirus Stock" in Adenovirus Methods and Protocols, Humana Press, 1999, pp 1-10, W. S. M. Wold, Ed). Dilutions of adenoviral lysates were used to infect A549 or 293 cells in a standard plaque assay. Well-individuated plaques were harvested, and the same plaque assay method was used to generate a second round of individual plaques from these harvests. Well isolated plaques from the second round of plaque purification were deemed pure, infected cultures are prepared using these purified plaques, and the oncolytic potency and selectivity of these culture supernatants was determined.

Example 3. Cytolytic Assay

Tumor specific viral lysis was evaluated in both tumor and non-tumor cell lines of murine and human origin by infection of the cells in vitro with the viruses, followed by standard crystal violet for cell viability over time as instructed in the kit manuals.

Example 4. DNA Sequencing

DNA sequencing of the human Ad5-based recombinant adenovirus genomic DNAs was performed as follows. Viral DNA was purified from recombinant adenoviruses such as TAV-255 or other modifications of these constructs by standard column purification methods such as the QiaAmp® blood DNA purification kit from Qiagen®. PCR primers were used to amplify and isolate regions covering the E1a modified regions and the regions containing the transgene insert and sent out for sequencing at a CRO. Isolated DNA was also analyzed by standard restriction digestion and SDS PAGE analysis for verification of appropriate sized bands of digested DNA. Sequence information was analyzed using the Vector NTI program (Informatix).

Example 5. Construction of Recombinant Viruses

The base shuttle transfer vector includes pXC1 TAV 255 d19k (Zhang et al., Cancer Gene Ther. (2015) 22(1):17-22). This plasmid has a deletion between bp −305 to −255 of the E1a enhancer region, removing two Pea3 and one E2F binding sites which restrict replication and oncolysis of an adenovirus with this deletion to infected tumor cells (Hedrun, F. H., Shantanu K., and Reid, T. (2011) Cancer Gene Therapy 18; 717-723.) It also contains sites allowing deletion of the E1b 19k region and exogenous transgene insert by a Sal I/Xho I digest. Without the digest, the majority of the E1b 19k region is intact, but non-functional. cDNAs for each transgene of interest were synthesized (GeneArt™) or isolated from commercial plasmid sources (GE Lifesciences or GeneCopoeia™) by PCR using primers which added on 5' SalI and 3' XhoI restriction sequences for insertion into the SalI/XhoI digested pXC1 TAV 255 plasmids. The modified pXC1 TAV 255 gene insert plasmids were amplified in E. coli and purified using Qiagen® Maxi-prep plasmid kits.

To obtain recombinant adenoviruses, the pXC1 TAV 255 gene insert-containing plasmids were co-transfected into HEK-293 cells (ATCC) with pBHG10 (Microbix) as described (Bett, A. J., Haddara, W., Prevec, L., and Graham, F. (1994) PNAS 91; 8802-8806), using the calcium phosphate transfection protocol from Molecular Cloning: A laboratory manual (Maniatis Vol. 3; 16.30-16.36) for 2-5 µg plasmid DNA (for both plasmids so the pXC1 will be in molar excess) per 60 mm dish of cells. Recombination between homologous adenovirus sequences from each plasmid generates a full length, replication competent adenovirus containing the E1 modifications described earlier and a specific transgene inserted into the E1b 19k deletion site and the E3 deletion supplied by the pBHG10 plasmid. Optionally, the pBHG10 is provided as the adenoviral genome source, having substantial additional utility over vectors such as pJM17 (See, e.g., Hedrun et al, (2011)). Preferentially, an E3 deletion and/or other modifications allow increased packaging capacity for exogenous genes in excess of pJM17 capacity.

In another embodiment, the human IL-12 virus, TRZ627, was constructed using a modification of the pAdEasy™ Adenoviral Vector System (Agilent Technologies). First, sequences from pXC1-TAV d19K plasmid (Hedjran F et al., *Cancer Gene Therapy* (2011) 18, 717-723) which included the 50-nucleotide deletion in the enhancer of E1A which restricts viral propagation to tumor vs. non-tumor cells, were subcloned into the pShuttle™ vector supplied in the pAdEasy™ kit to create the TAV-255 Shuttle E1 cloning plasmid. Sequences between the first Pac I site (6) and the single Mfe I site (807) in pShuttle were replaced by pXC1 TAV d19K sequences from the beginning of the 5' ITR sequence (21) to the Mfe I site (3874), corresponding to the same Mfe I site in pShuttle. A Pac I cloning site was added by PCR onto the 5' end of this fragment, which brought in Ad E1a and E1b sequence not found in the original pShuttle plasmid. The TAV-255 deletion of 50 bp in the E1a enhancer region removes the Pea3 III, Pea3 II, and an E2F transcription factor binding sites and corresponds to human wild-type Ad5 sequence of bases 194-244. The added sequences also included a modification introducing Sal I/Xho I cloning sites into the E1b 19k coding region which can be used to replace the E1b 19k ORF with an exogenous transgene insert whose expression would be driven by the Ad E1b promoter during viral replication. Recombination between Pme I linearized pTAV-255 Shuttle E1 containing hIL-12 cloned in at the E1b 19k site and the pAdEasy vector took place in the recA proficient BJ5183 bacterial strain, which had been modified to already contain the pAdEasy plasmid. DNA isolated from Kanamycin resistant plated colonies was screened for full-length viral DNA recombinants by restriction digest. Positive clones (TRZ-627, hIL-12) were subsequently digested with Pac I to free up the Ad ITRs and then transfected into 293 cells to amplify the virus.

Infected HEK-293 cells were collected when visible sign of cytopathic effects due to viral replication were observed up to 2 weeks post-infection and resuspended in their media and lysed by 3 rounds of freeze/thaw. Virus can be purified from the lysate by several methods, including Anion-exchange HPLC (Shabram, P. W., et al (1997) Human Gene Therapy 8; 453-465) or several commercially available kits based on affinity chromatography or size exclusion membranes or columns (e.g., Adeno-X™ Maxi Purification Kit, Clontech® (Takara), Adenovirus Purification Virakit®, Virapur®). Purified virus can also undergo clonal isolation by standard plaque purification methods, followed by re-amplification and purification of the plaque purified viral clone.

Example 6. In Vivo Demonstration of Reduction in Tumor Volume with Oncolytic Adenoviral Vectors Encoding Immunomodulatory Polypeptides: Single Viruses with and without Antibody Treatment Materials and Methods An anti-mPD-L1 antibody is, e.g., from BioXCell®, Catalog# BE0101 (Rat IgG2b). This antibody was used in the below experiments.

Virus samples were stored in 25 mM NaCl, 10 mM Tris Tris(hydroxymethyl)aminomethane), and 5% glycerol with a pH value of 8.0. Vials were stored protected from light at −80° C. On each day of dosing, one vial was thawed at room temperature for approximately 20 minutes. A single dose is $1 \times 10^9$ pfu.

The mouse tumor model in this Example uses syngeneic immunocompetent mice. Female Jackson 129S1 (129S1/Sv1mJ) mice were used in this study. They were 6-7 weeks old on Day 1 of the experiment. The animals were fed irradiated Harlan 2918.15 Rodent Diet and water ad libitum.

Animals were housed in static cages with Bed-O'Cobs™ bedding inside bioBubble® Clean Rooms that provide H.E.P.A filtered air into the bubble environment at 100 complete air changes per hour.

All treatments, body weight determinations, and tumor measurements were carried out in the bubble environment. The environment was controlled to a temperature range of 70°±2° F. and a humidity range of 30-70%.

Cell Preparation

ADS-12 cells were grown in RPMI 1640 medium which was modified with 1% 100 mM Na pyruvate, 1% 200 mM L-glutamine, 1% 1M HEPES buffer, 1% of a 45% glucose solution and supplemented with 10% non-heat-inactivated Fetal Bovine Serum (FBS) and 1% 100× Penicillin/Streptomycin/L-Glutamine (PSG). The growth environment was maintained in an incubator with a 5% $CO_2$ atmosphere at 37° C. When expansion was complete, the cells (passage 7) were trypsinized using 0.25% trypsin/2.21 mM EDTA in HBSS solution. Following cell detachment, the trypsin was inactivated by dilution with complete growth medium and any clumps of cells were separated by pipetting. The cells were centrifuged at 200 rcf for 8 minutes at 4° C., the supernatant was aspirated, and the pellet was re-suspended in cold Dulbecco's Phosphate Buffered Saline (DPBS) by pipetting. An aliquot of the homogeneous cell suspension was diluted in a trypan blue solution and counted using a Luna automated cell counter. The cell suspension was centrifuged at 200 rcf for 8 minutes at 4° C. The supernatant was aspirated and the cell pellet was re-suspended in cold Dulbecco's Phosphate Buffered Saline (DPBS) to generate a final concentration of $1 \times 10^7$ trypan-excluding cells/ml. The cell suspension was maintained on wet ice during implantation. Following implantation, an aliquot of the remaining cells was diluted with a trypan blue solution and counted to determine the post-implantation cell viability. The cell viabilities of the suspensions used for implantation (two preps) are listed in Table 3.

TABLE 3

| Implantation Cell Viability | | |
|---|---|---|
| | Pre-Implant Viability (%) | Post-Implant Viability (%) |
| Cell Prep 1 | 95 | 89 |
| Cell Prep 2 | 95 | 89 |

Test animals were implanted subcutaneously on both flanks (on the back between the spine and the hip), the right flank on Day 0 and the left flank on Day 8, with $1 \times 10^6$ cells in 0.1 ml of serum-free medium using a 28-gauge insulin syringe with a fixed needle.

All mice were sorted into study groups based on caliper measurement estimation of tumor burden on Day 15 when the mean tumor burden for all animals on the right flank was approximately 82 mm$^3$ (range of group means, 75-90 mm$^3$). The mice were distributed to ensure that the mean tumor burden on the right flank for all groups was within 10% of the overall mean tumor burden for the study population.

Results

The mean estimated right side tumor burden for all groups in the experiment on the first day of treatment was 82 mm3 and all of the groups in the experiment were well-matched (range of group means, 75-90 mm3). All animals weighed at least 13.3 g at the initiation of therapy. Mean group body weights at first treatment were also well-matched (range, 15.4-18.3 g). A tumor burden of 500 mm3 was chosen for evaluation of efficacy by tumor growth delay for the right and left tumors. The median Control Group (FIG. 6A) tumor burdens reached 500 mm3 on Day 47 for right tumors and Day 43 for left tumors. The median tumor volume doubling times for the Control Group were 12.1 and 10.1 days for the right and left tumors, respectively. Control animals experienced a 7.3% mean weight gain during the treatment regimen. There were no spontaneous regressions in the Control Group for either right or left side tumors, however, 50% of the tumors on the left side never reached the palpation limit. In some embodiments, mice with palpable left side tumors were put on study. Since in this experiment the implant was delayed 8 days, the left side tumors were not palpable at staging. These mice that had a left side tumor that remained a 0 throughout the study could have been triaged out of the study if implanted on the same day as the right side.

Results of mouse inoculation and tumor growth are shown in FIG. 6. The series of graphs shows treatment of tumor bearing mice (n=8 in each group) with oncolytic viruses comprising various transgenes, with or without anti-PD-L1.

Figure 6A:
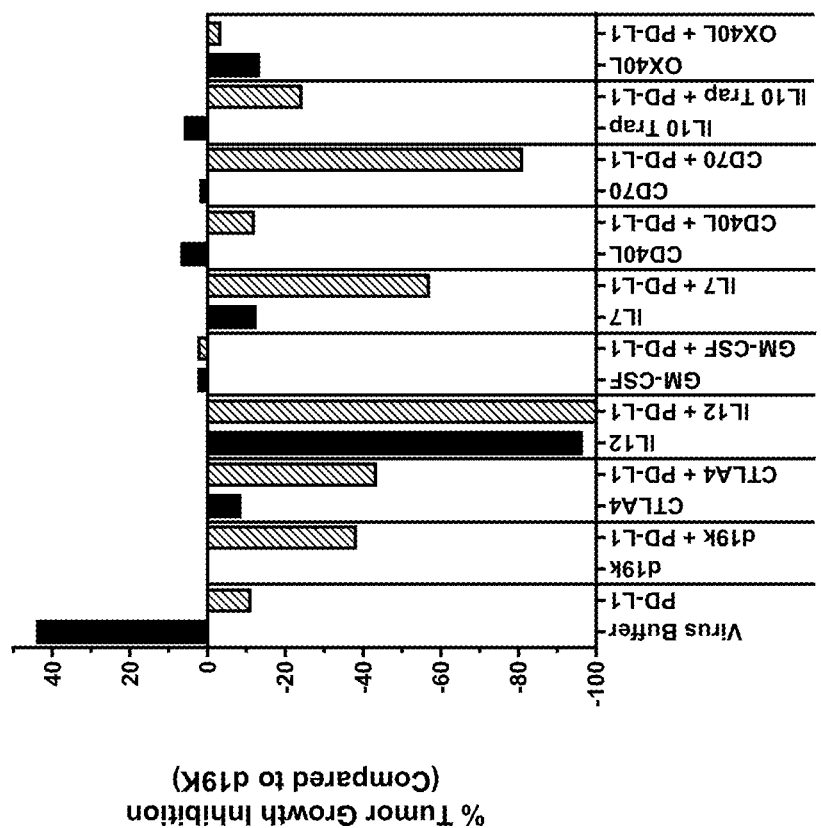
FIG. 6A is graph(s) showing results of treatment of tumor bearing mice (n=8 in each group) with oncolytic viruses comprising transgene(s), with or without anti-PD-L1.
Figure 6B:
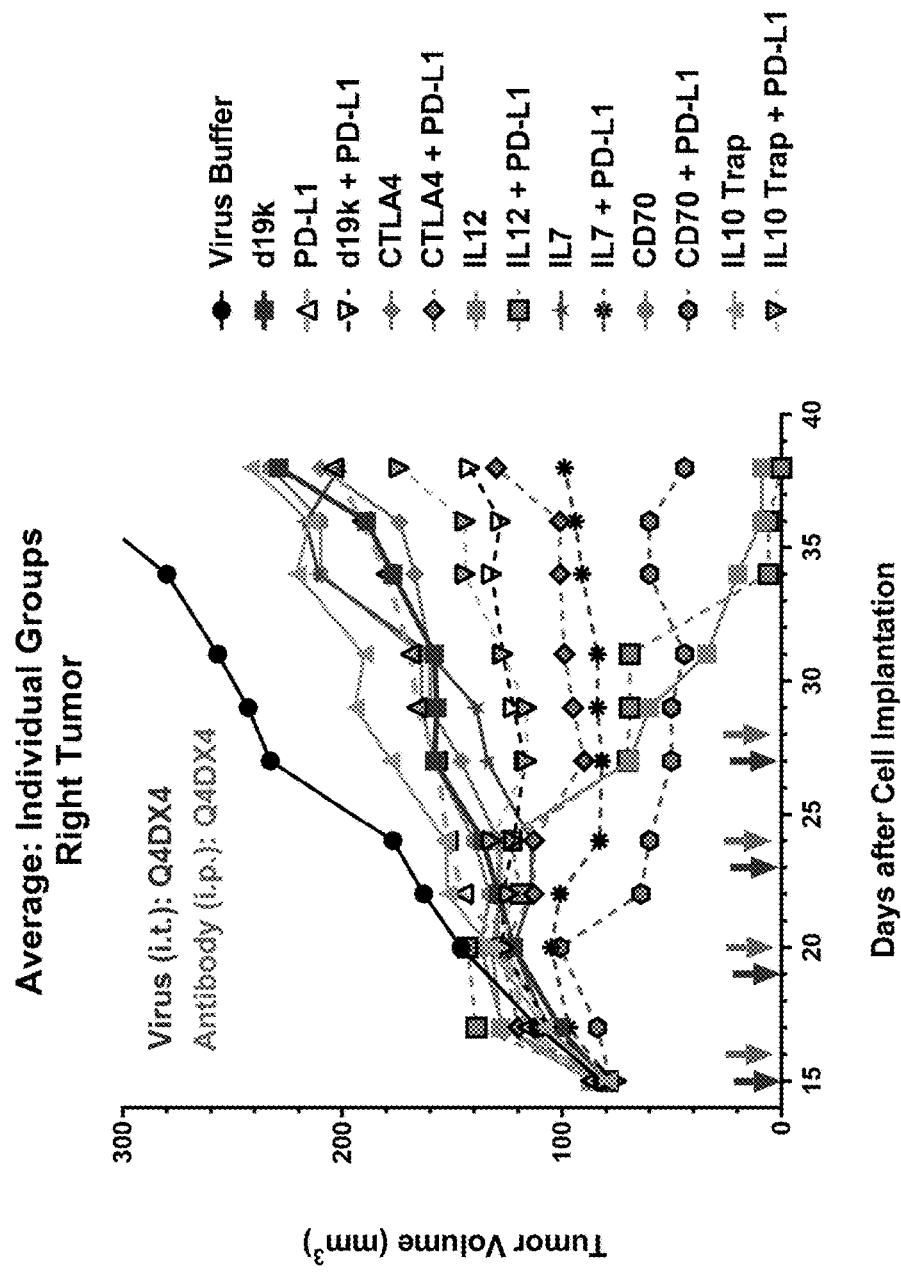
FIG. 6B is graph(s) showing results of treatment of tumor bearing mice (n=8 in each group) with oncolytic viruses comprising transgene(s), with or without anti-PD-L1.
Figure 6C:
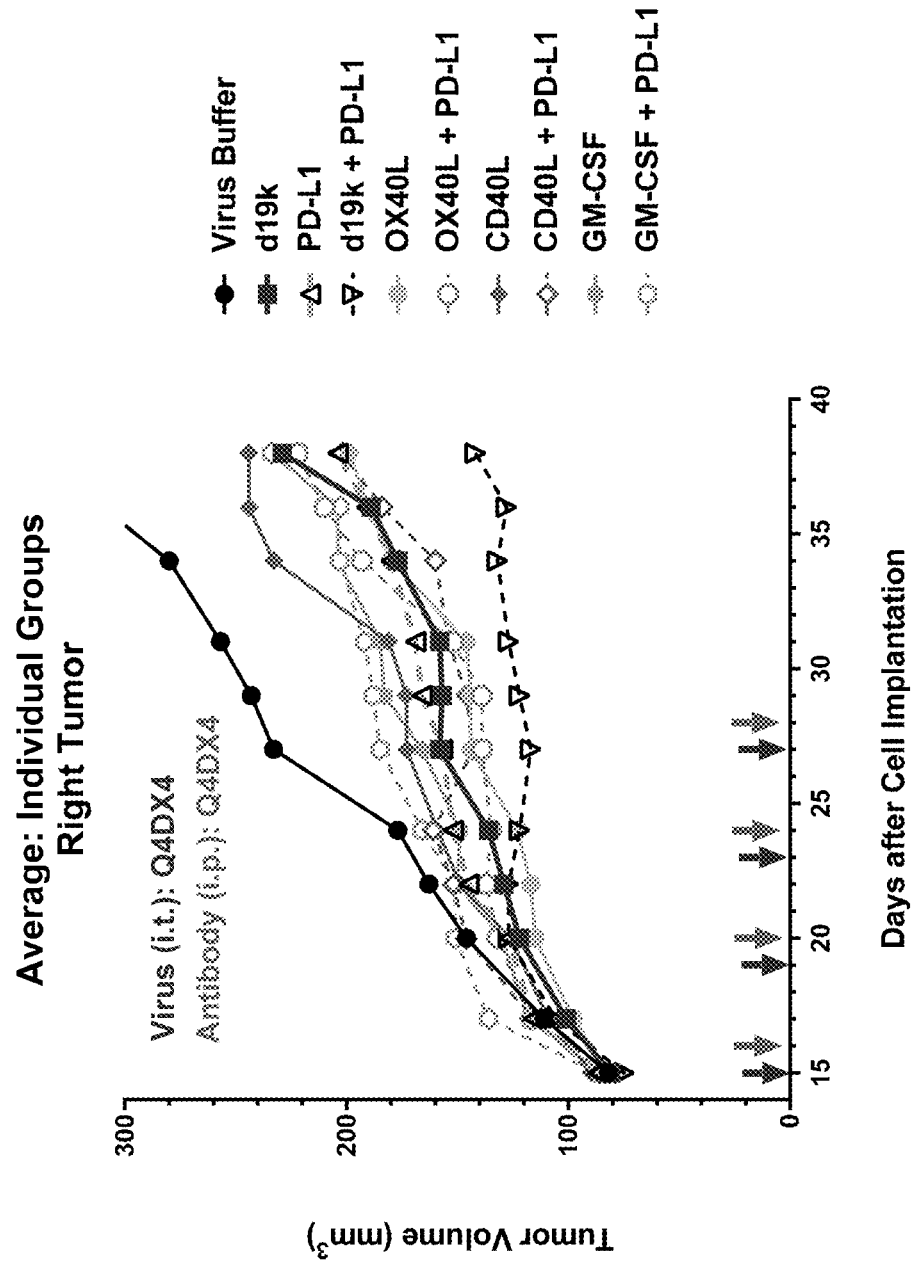
FIG. 6C is graph(s) showing results of treatment of tumor bearing mice (n=8 in each group) with oncolytic viruses comprising transgene(s), with or without anti-PD-L1.
Figure 6D:
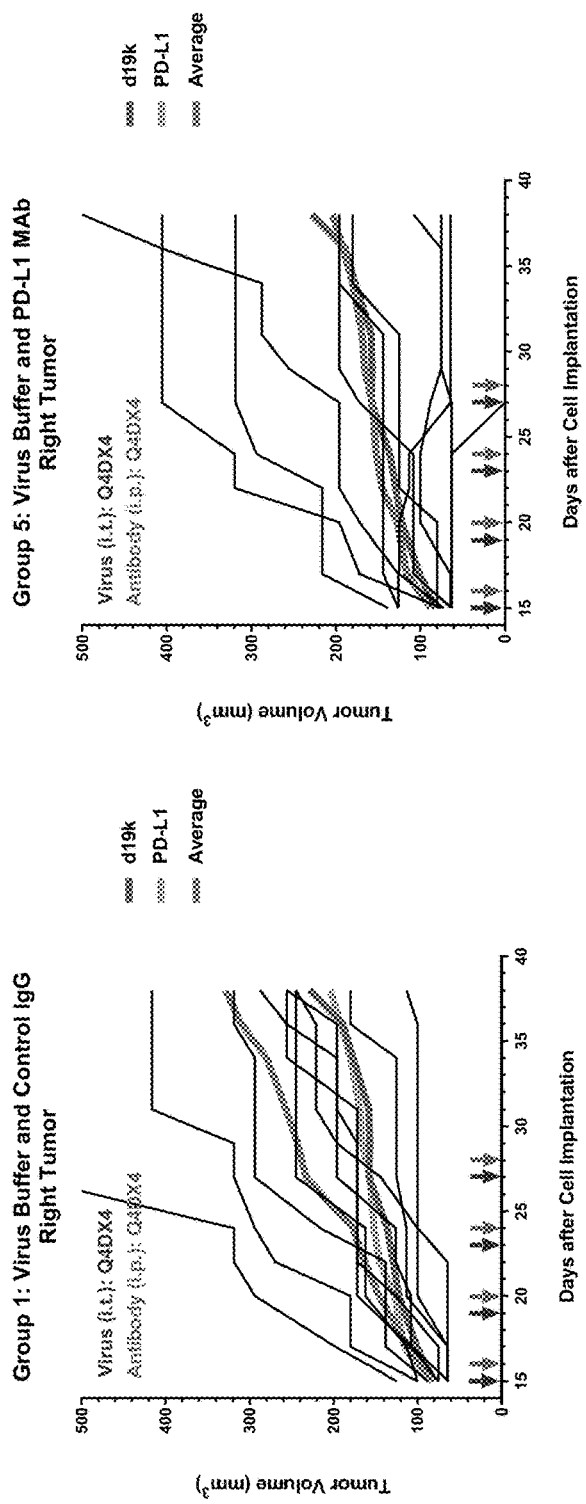
FIG. 6D is graph(s) showing results of treatment of tumor bearing mice (n=8 in each group) with oncolytic viruses comprising transgene(s), with or without anti-PD-L1.
Figure 6E:
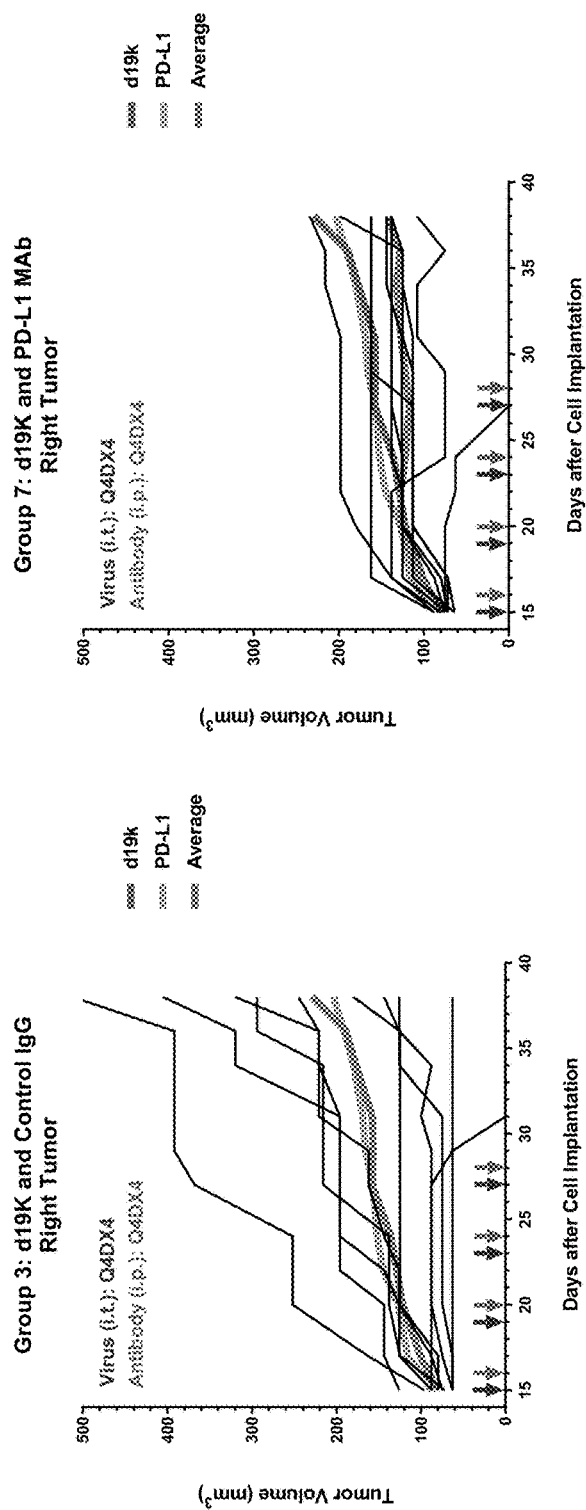
FIG. 6E is graph(s) showing results of treatment of tumor bearing mice (n=8 in each group) with oncolytic viruses comprising transgene(s), with or without anti-PD-L1.
Figure 6G:
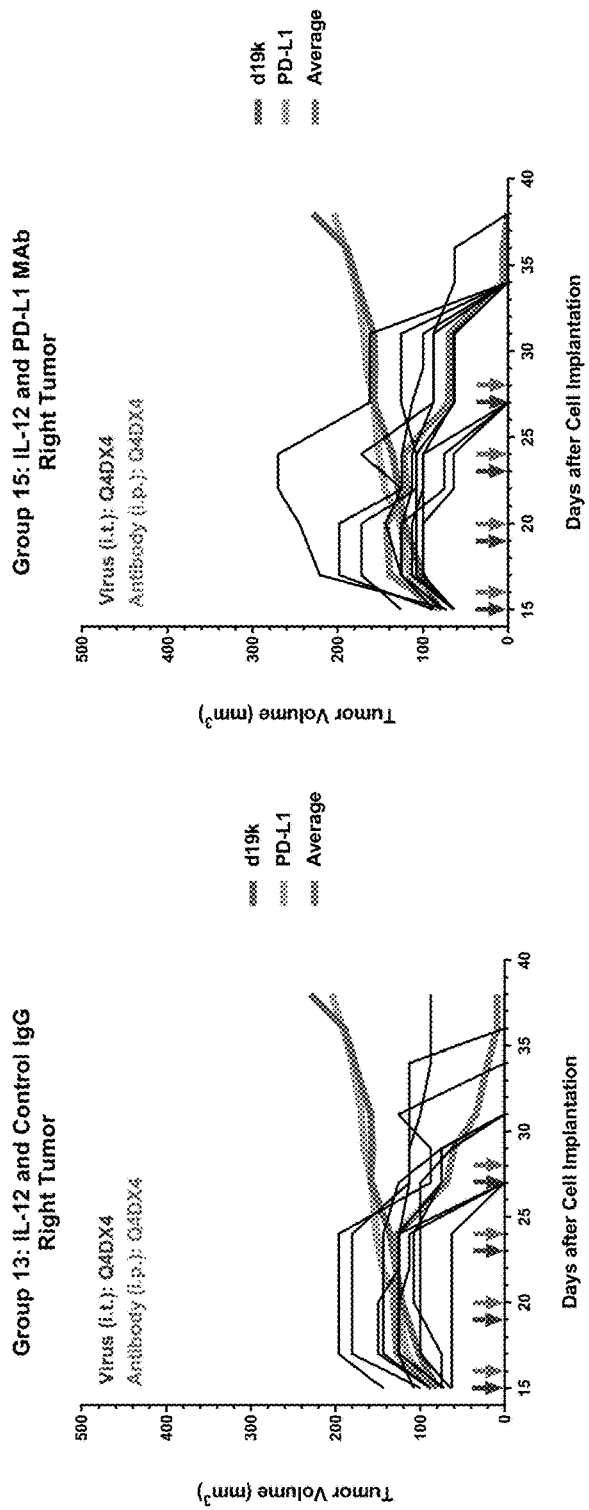
FIG. 6G is graph(s) showing results of treatment of tumor bearing mice (n=8 in each group) with oncolytic viruses comprising transgene(s), with or without anti-PD-L1.
Figure 6H:
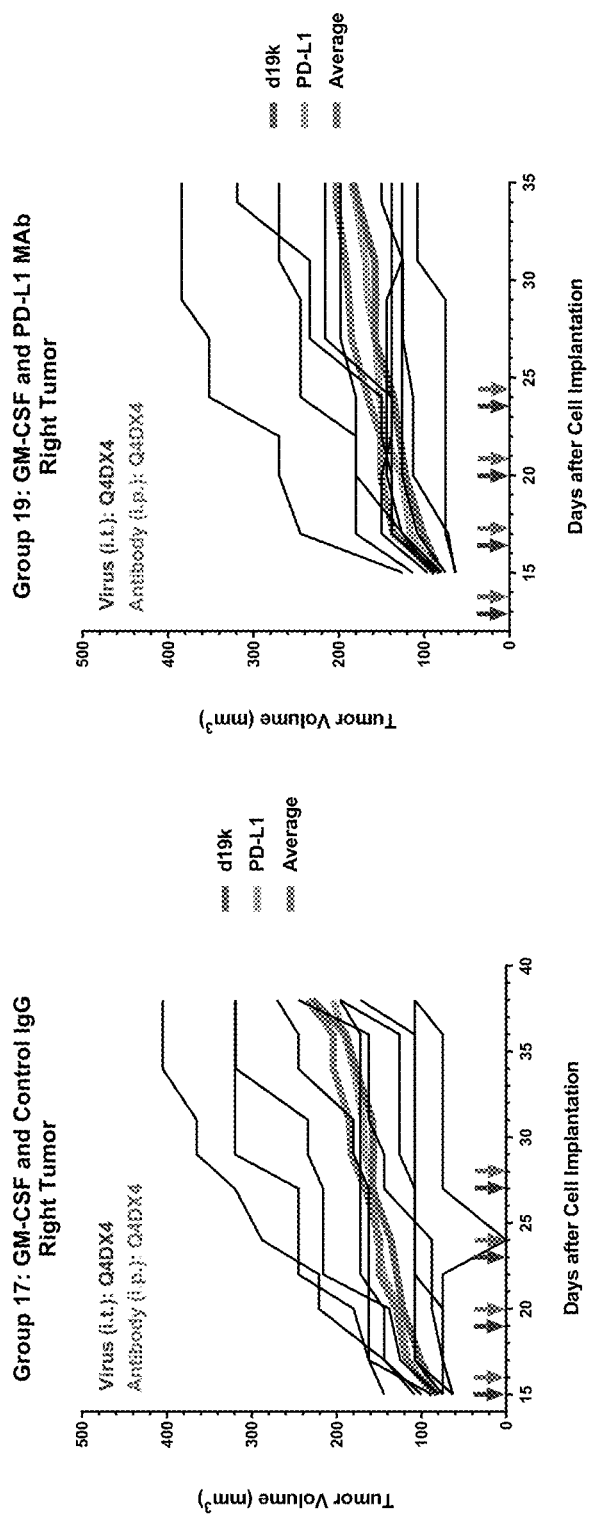
FIG. 6H is graph(s) showing results of treatment of tumor bearing mice (n=8 in each group) with oncolytic viruses comprising transgene(s), with or without anti-PD-L1.
Figure 6I:
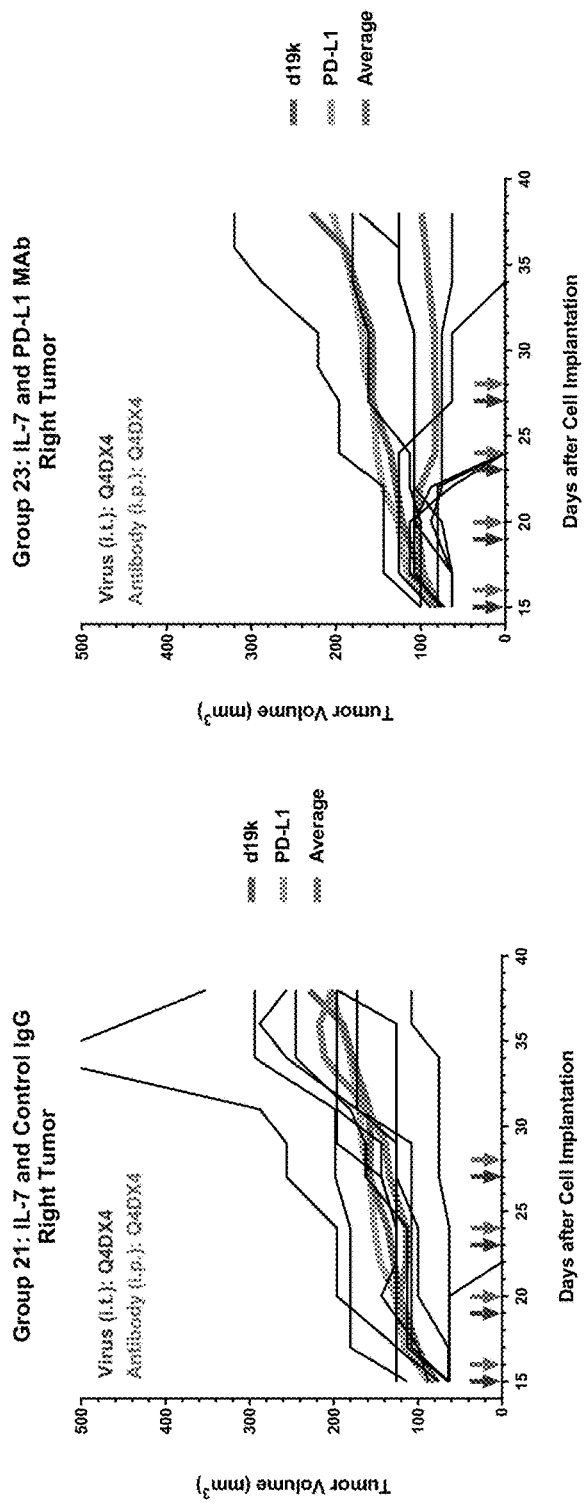
FIG. 6I is graph(s) showing results of treatment of tumor bearing mice (n=8 in each group) with oncolytic viruses comprising transgene(s), with or without anti-PD-L1.

FIG. 6A is a graph showing the activity of various oncolytic viruses compared to the empty virus ("d19k"), 38 days after cell implantation (primary tumor) as a function of tumor growth inhibition. Black bars represent virus alone and hatched bars represent virus+anti-PD-L1 antibody. FIG. 6B is a graph comparing the average tumor size (primary tumor) over time of tumors injected with virus buffer (black circles), empty vector (blue solid squares), anti-PD-L1 alone (antibody given on days 16, 20, 24, and 28, right-hand arrow in each pair of arrows), each of five viruses alone (viruses carrying CTLA-4, IL-12, IL-7, CD70, and IL-10 transgenes) or combined with anti-PD-L1 antibody. FIG. 6C shows similar data for three more viruses (viruses carrying OX40L, CD40L, and GM-CSF transgenes). As shown in the Figures, the IL-12 oncolytic virus treatment, alone or in combination with an anti-PD-L1 antibody, were the most effective at reducing tumor growth. CD70, IL-7, and CTLA-4 viruses were also able to reduce tumor volume significantly when combined with the anti-PD-L1 antibody.

The following Figures demonstrate efficacy (or lack thereof) of various viruses with transgenes with or without PD-L1 on the primary tumor only; the thick line in each graph shows the average tumor volume in mm$^3$. The pairs of arrows on the x-axis represent day of treatment with virus (intratumoral, left arrows) and the anti-PD-L1 antibody, if used (intraperitoneal, right arrows). Treatments are shown for the primary tumor (receiving the oncolytic virus injection) and are as follows: 6D, virus buffer and control IgG only (left) and virus buffer and anti-PD-L1 antibody (right); 6E, d19k (empty virus) and control IgG only (left) and d19k and anti-PD-L1 antibody (right); 6F, CTLA-4 virus with control IgG (left) or anti-PD-L1 (right); 6G, IL-12 virus with control IgG (left) or anti-PD-L1 antibody (right); 6H, GM-CSF virus with control IgG (left) or anti-PD-L1 antibody (right); 6I, IL-7 virus with control IgG (left) or anti-PD-L1 antibody (right); 6J, CD40L virus with control IgG (left) or anti-PD-L1 antibody (right); 6K, L10 trap virus with control IgG (left) or anti-PD-L1 antibody (right); and 6L, OX40L virus with control IgG (left) or anti-PD-L1 antibody.

Figure 6J:
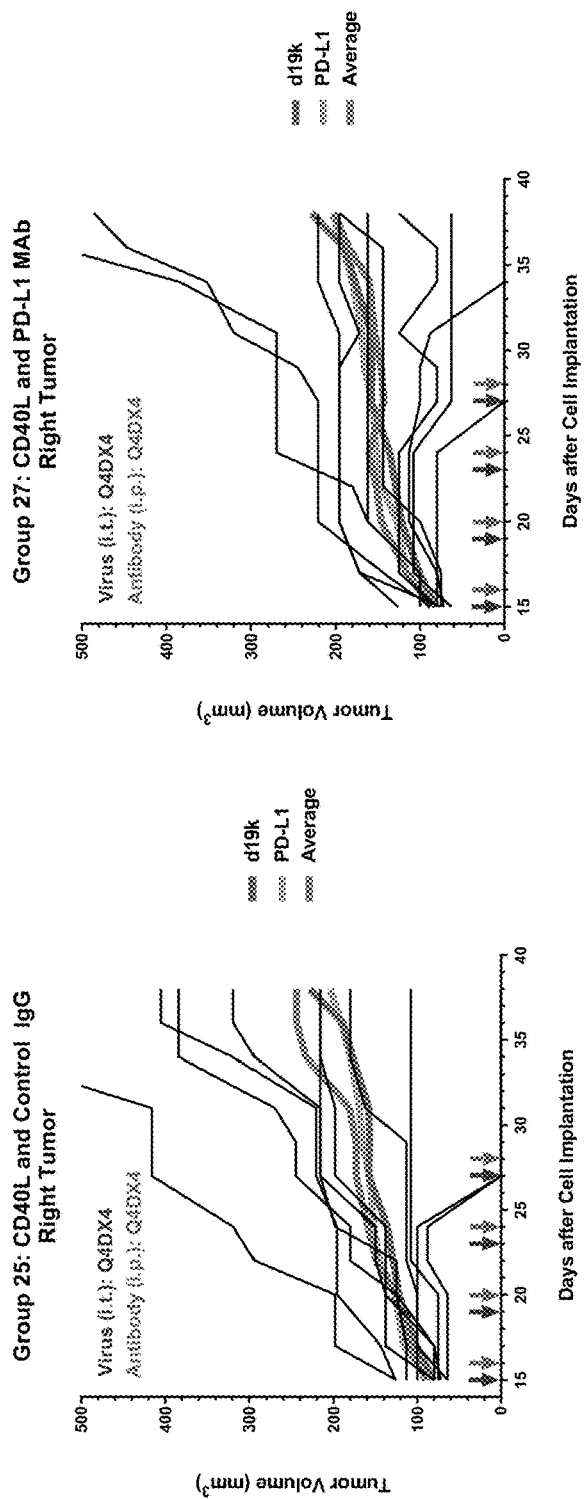
FIG. 6J is graph(s) showing results of treatment of tumor bearing mice (n=8 in each group) with oncolytic viruses comprising transgene(s), with or without anti-PD-L1.
Figure 6K:
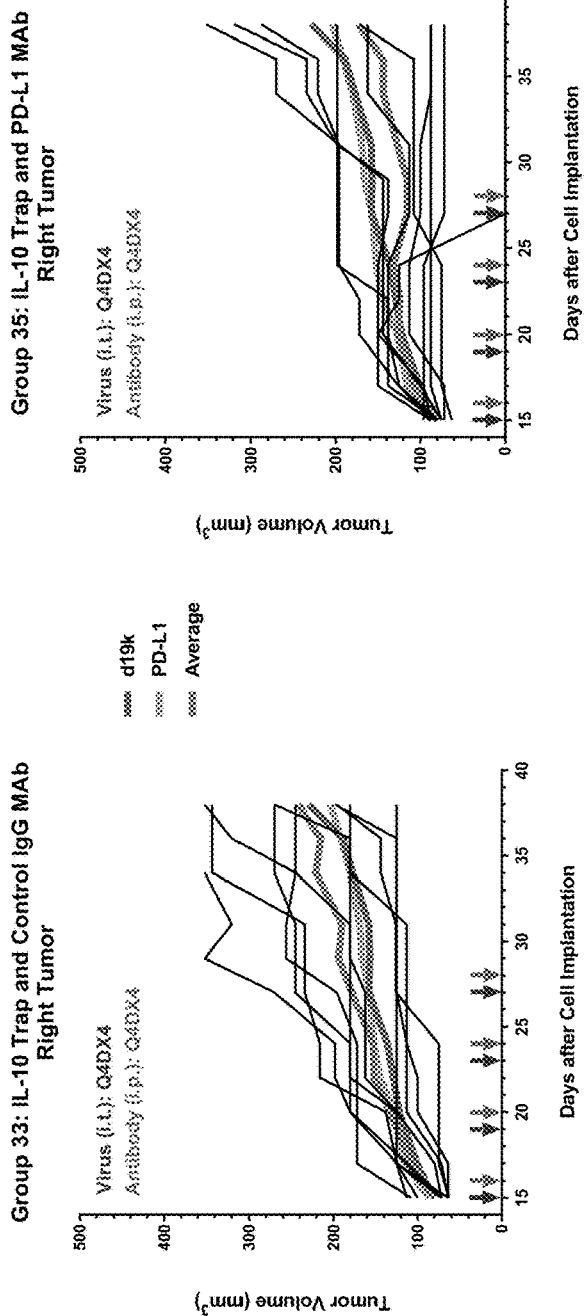
FIG. 6K is graph(s) showing results of treatment of tumor bearing mice (n=8 in each group) with oncolytic viruses comprising transgene(s), with or without anti-PD-L1.
Figure 6L:
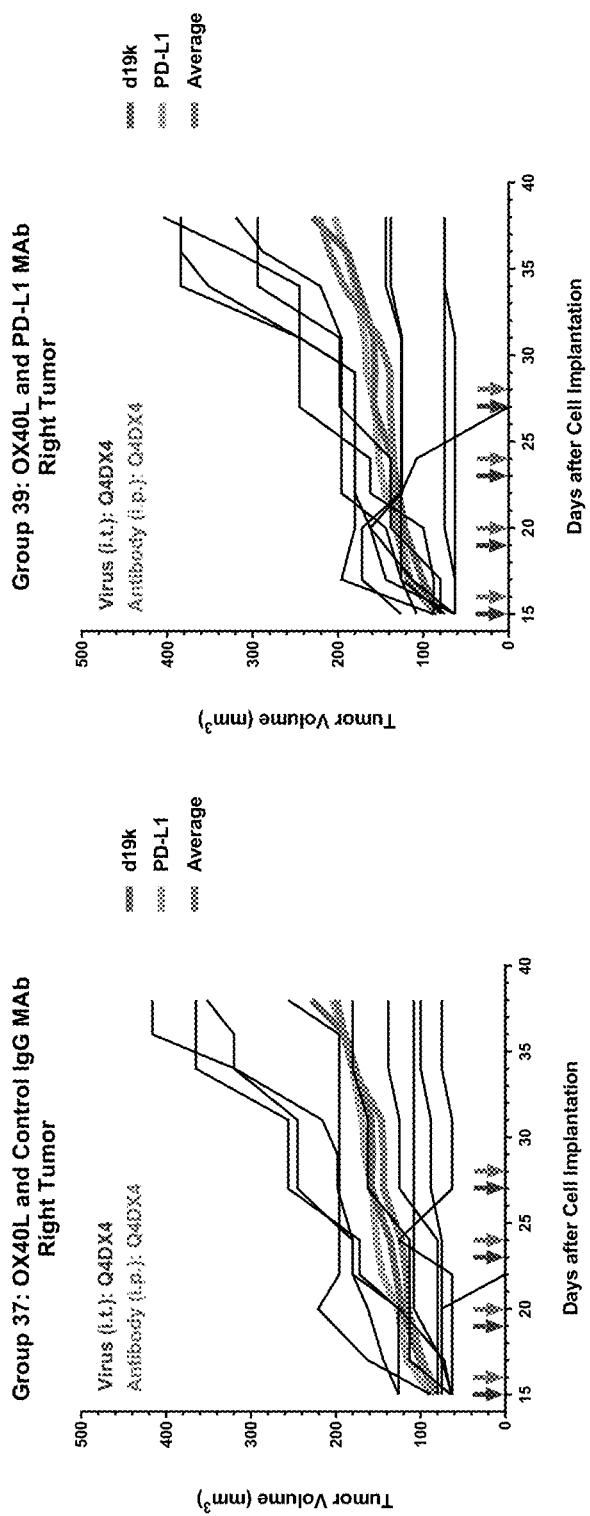
FIG. 6L is graph(s) showing results of treatment of tumor bearing mice (n=8 in each group) with oncolytic viruses comprising transgene(s), with or without anti-PD-L1.

As shown in the Figures, combinations with the IL-12 adenovirus (FIG. 6G), showed the greatest ability to reduce tumor volume. As in FIG. 6A, the IL-7 (FIG. 6I) and CTLA-4 (FIG. 6F) oncolytic viruses also showed activity when combined with anti-PD-L1 antibody. Treatment with the oncolytic virus encoding the CD40 ligand also showed some activity when combined with the anti-PD-L1 antibody (FIG. 6J).

Example 7. In Vivo Demonstration of Reduction in Tumor Volume with Oncolytic Adenoviral Vectors Encoding Immunomodulatory Polypeptides: Virus Mixing Study The mouse tumor model in this Example uses syngeneic immunocompetent mice. Animals were injected with approximately 1,000,000 cells subcutaneously (s.c.) into the right hind flank of the mouse. At the same time, the mice were also injected with 1,000,000 cells s.c. into the left hind flank of the mouse to create a bilateral tumor model. When the right (primary) tumors reached 63-80 mm$^3$ in size and the left tumor was palpable, they were injected with 25 µl of virus buffer or 25 µl of virus at 4×10$^9$ pfu/ml (plaque forming units per ml) directly into the center of the primary tumor every fourth day for a total of three doses. The mice were also treated intraperitoneally with 250 µl of an anti-PD-L1 antibody at 2 mg/ml every fourth day for a total of three doses. The antibody was administered 24 hours after administration of the virus. A reduction in the size of the primary and distal (contralateral) tumor would be noted relative to the virus buffer control and additional controls such as the wild-type virus (not expressing a transgene) with or without administration of the anti-PD-L1 antibody. A specific example of the treatment with oncolytic adenoviral vectors is described in more detail below for a panel of such vectors.

Evaluation of the primary tumor (right flank) was used to determine the direct effect of the oncolytic viruses whereas evaluation of the contralateral tumor (left flank) was used to see the systemic effects of the oncolytic viruses. ADS-12 (a murine KRAS-mutant lung adenocarcinoma cell line) grown in its syngeneic mouse strain is a tumor model known to support adenoviral infection and replication and is useful in the evaluation of host immune responses to oncolytic human adenoviruses.

Materials and Methods

An anti-mPD-L1 antibody is, e.g., from BioXCell®, Catalog# BE0101 (Rat IgG2b). This antibody was used in the below experiments.

Virus samples were stored in 25 mM NaCl, 10 mM Tris Tris(hydroxymethyl)aminomethane), and 5% glycerol with a pH value of 8.0. Vials were stored protected from light at −80° C. On each day of dosing, one vial was thawed at room temperature for approximately 20 minutes.

Animal Studies

Female 129S1 (129S1/SvImJ) mice from The Jackson Laboratory were used in this study. They were approximately 7-8 weeks old on Day 14 of the experiment. The animals were fed irradiated Harlan 2918.15 Rodent Diet and water ad libitum. Animals were housed in static cages with Bed-O'Cobs™ bedding inside Biobubble® Clean Rooms that provide H.E.P.A filtered air into the bubble environment at 100 complete air changes per hour. All treatments, body weight determinations, and tumor measurements were carried out in the bubble environment. The environment was controlled to a temperature range of 70°±2° F. and a humidity range of 30-70%. All procedures carried out in this experiment were conducted in compliance with all the laws, regulations and guidelines of the National Institutes of Health (NIH) and with the approval of Molecular Imaging, Inc.'s Animal Care and Use Committee. Molecular Imaging, Inc. is an AAALAC accredited facility.

Cell Preparation

ADS-12 cells (murine KRAS-mutant lung adenocarcinoma) were grown in RPMI 1640 medium which is modified with 1% 100 mM Na pyruvate, 1% 200 mM L-glutamine, 1% 1M HEPES buffer, 1% of a 45% glucose solution and supplemented with 10% non-heat-inactivated Fetal Bovine Serum (FBS) and 1% 100× Penicillin/Streptomycin/L-Glutamine (PSG). The growth environment was maintained in an incubator with a 5% $CO_2$ atmosphere at 37° C. When expansion as complete, the cells are trypsinized using 0.25% trypsin/2.21 mM EDTA in HBSS solution. Following the cell viabilities of the suspensions used for implantation (two preps) are listed in the table below.

TABLE 4

Implantation Cell Viability

| | Pre-Implant Viability (%) | Post-Implant Viability (%) |
|---|---|---|
| Cell Prep 1 | 94 | 92 |
| Cell Prep 2 | 97 | 92 |

Test animals were implanted subcutaneously, on both flanks (on the back between the spine and the hip) on Day 0 with $1.00 \times 10^6$ cells in 0.1 ml of serum-free medium using a 28-gauge insulin syringe with a fixed needle.

Treatment

All mice were sorted into study groups based on caliper measurement estimation of tumor burden on Day 14 when the mean tumor burden for all animals on the right flank is approximately 68 mm³ (range of group means, 65-71 mm³). The mice were distributed to ensure that the mean tumor burden for all groups was within 10% of the overall mean tumor burden for the study population.

Measurement and Endpoints

Tumor burden (mm³) was estimated from caliper measurements by the formula for the volume of a prolate ellipsoid assuming unit density as: Tumor burden (mm³)= $(L \times W^2)/2$, where L and W are the respective orthogonal tumor length and width measurements (mm). All groups were compared to the virus buffer control group.

The primary endpoints used to evaluate efficacy were: tumor growth delay, complete and partial tumor response, and the number of tumor-free survivors at the end of the study for both left and right tumors. A complete response (CR) is defined as a decrease in tumor mass to an undetectable size (<63 mm³), and a partial response (PR) is defined as a smaller tumor mass at the last measurement compared to at the first treatment. PRs are exclusive of CRs.

All animals were observed for clinical signs at least once daily. Animals were weighed on each day of treatment. Individual body weights were recorded three times weekly. Animals with combined tumor burdens in excess of 2000 mm³ were euthanized, as were those found in obvious distress or in a moribund condition. Treatment-related weight loss in excess of 20% is generally considered unacceptably toxic. In this Example, a dosage level was determined to be tolerated if treatment-related weight loss (during and two weeks after treatment) was <20% and mortality during this period in the absence of potentially lethal tumor burdens was <10%.

Results

Results of mouse inoculation and tumor growth are shown in FIG. 7. The series of graphs shows treatment of tumor bearing mice (n=8 in each group) with single and combinations of oncolytic viruses comprising various transgenes, with or without anti-PD-L1. The left-hand panel of each Figure represents the primary tumor into which the virus was injected; the right-hand panel represents the contralateral tumor. The thick line in each graph shows the average tumor volume in mm³. The pairs of arrows on the x-axis represent day of treatment with virus (intratumoral, left arrows) and the anti-PD-L1 antibody, if used (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements). Treatments shown are as follows: 7A, virus buffer only; 7B, empty virus only (TRZ000); 7C, TRZ010 (IL-10trap)+empty virus; 7D, TRZ011 (OX40 ligand)+empty virus; 7E, TRZ009 (CD70)+empty virus; 7F, TRZ007 (IL-7)+empty virus, 7G, TRZ002 (IL-12)+empty virus; 7H, TRZ004 (GM-CSF)+empty virus; 7I, TRZ003 (flagellin)+empty virus; 7J, TRZ002+TRZ010; 7K, TRZ002+TRZ007; 7L, TRZ007+TRZ010; 7M, TRZ011+TRZ004; 7N, TRZ009+TRZ003; 7O, TRZ002+TRZ009; 7P, TRZ007+TRZ009; 7Q, TRZ007+TRZ004; 7R, TRZ002+TRZ011; 7S, TRZ010+TRZ004; 7T, TRZ002+TRZ004; 7U, virus buffer and anti-PD-L1; 7V, TRZ002+empty virus+anti-PD-L1; 7W, TRZ009+anti-PD-L1; 7X, TRZ007+empty virus+anti-PD-L1; 7Y, TRZ002+TRZ007+anti-PD-L1; 7Z, TRZ007+TRZ009+anti-PD-L1; 7AA, TRZ002+TRZ009+anti-PD-L1. All viruses were administered at $1 \times 10^8$ pfu/dose for each virus, resulting in $2 \times 10^8$ pfu total in virus combinations.

Figure 7A:
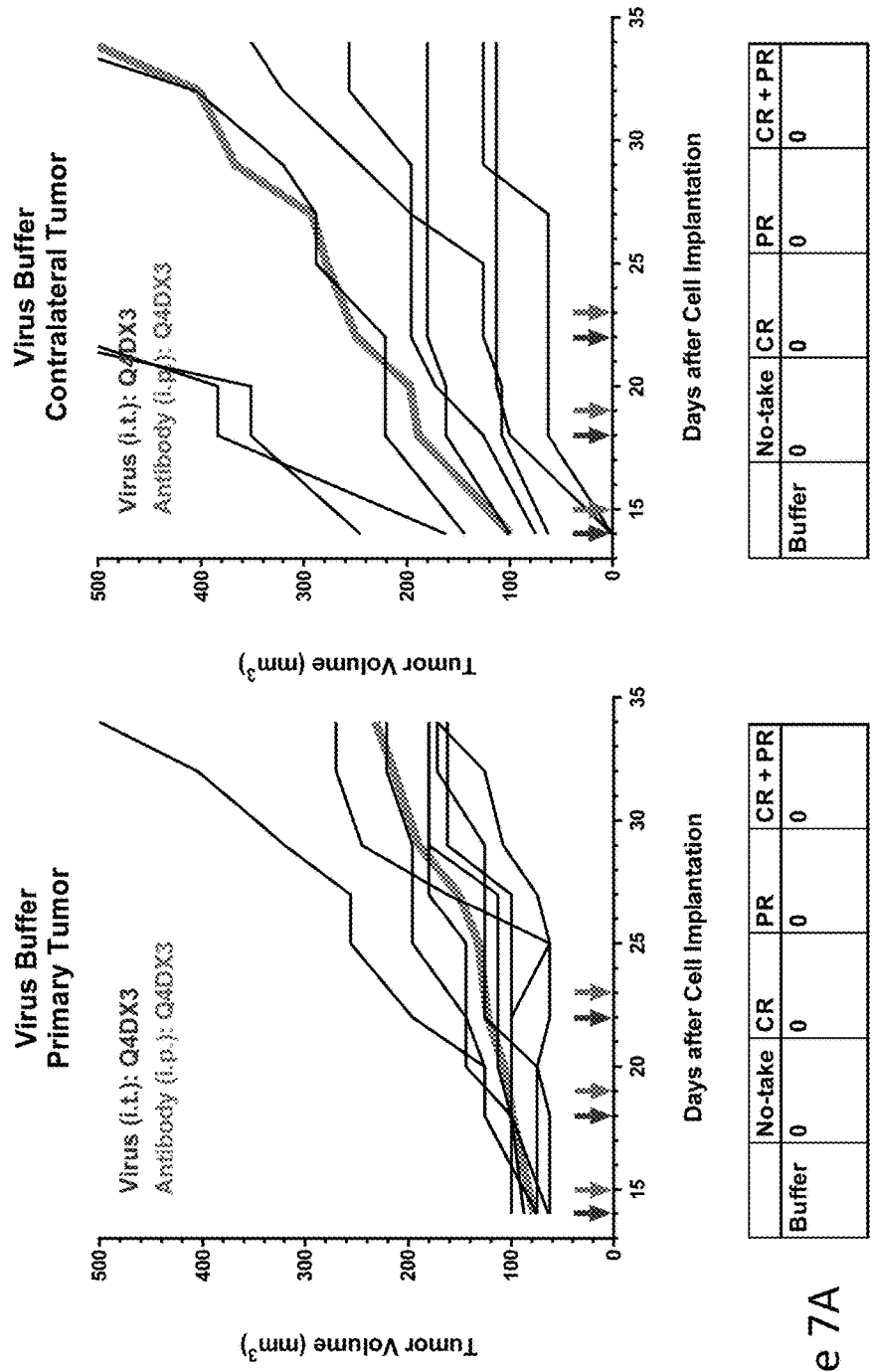
FIG. 7A is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in mm$^3$. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements).
Figure 7B:
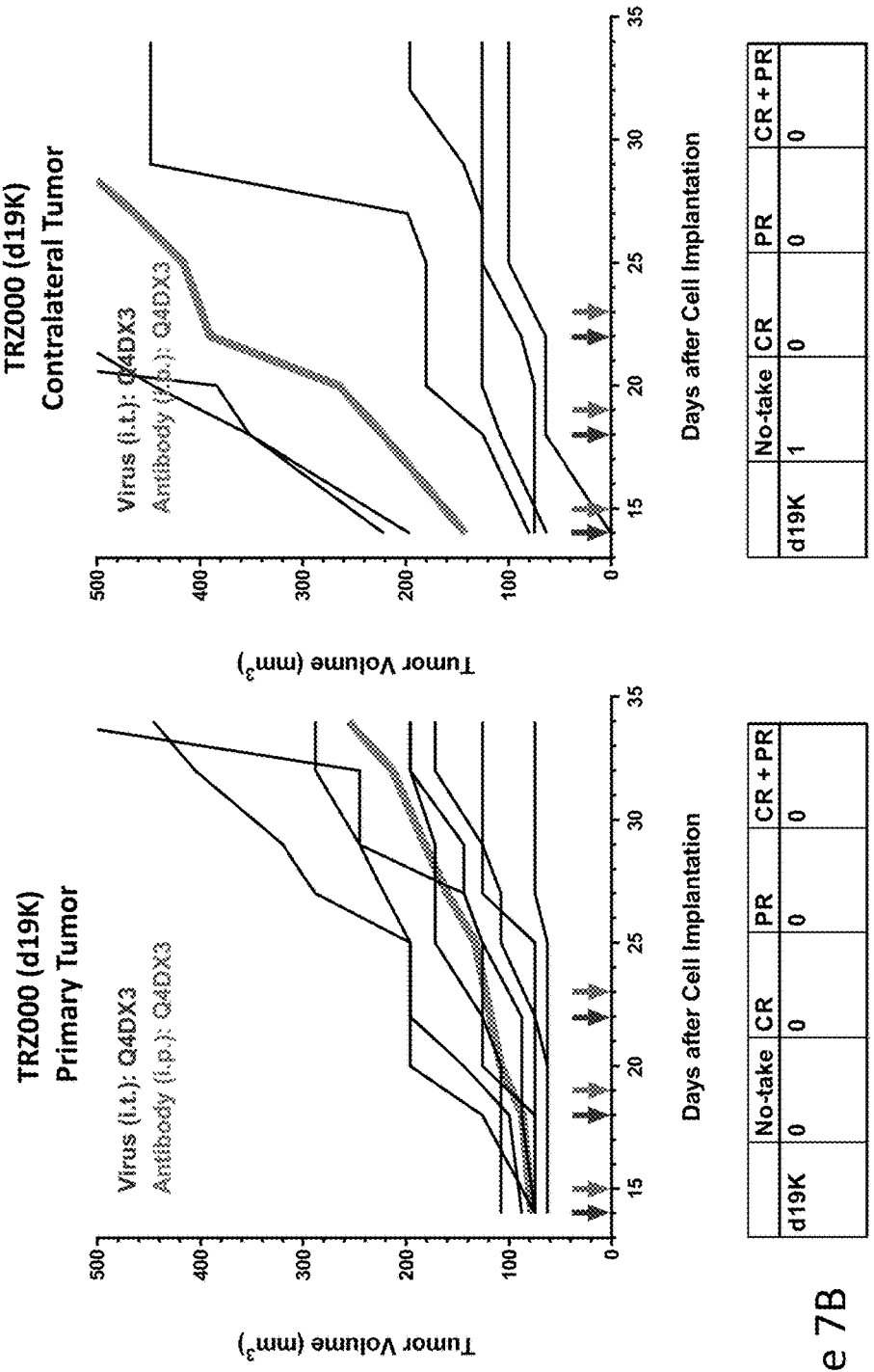
FIG. 7B is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in mm$^3$. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements).
Figure 7C:
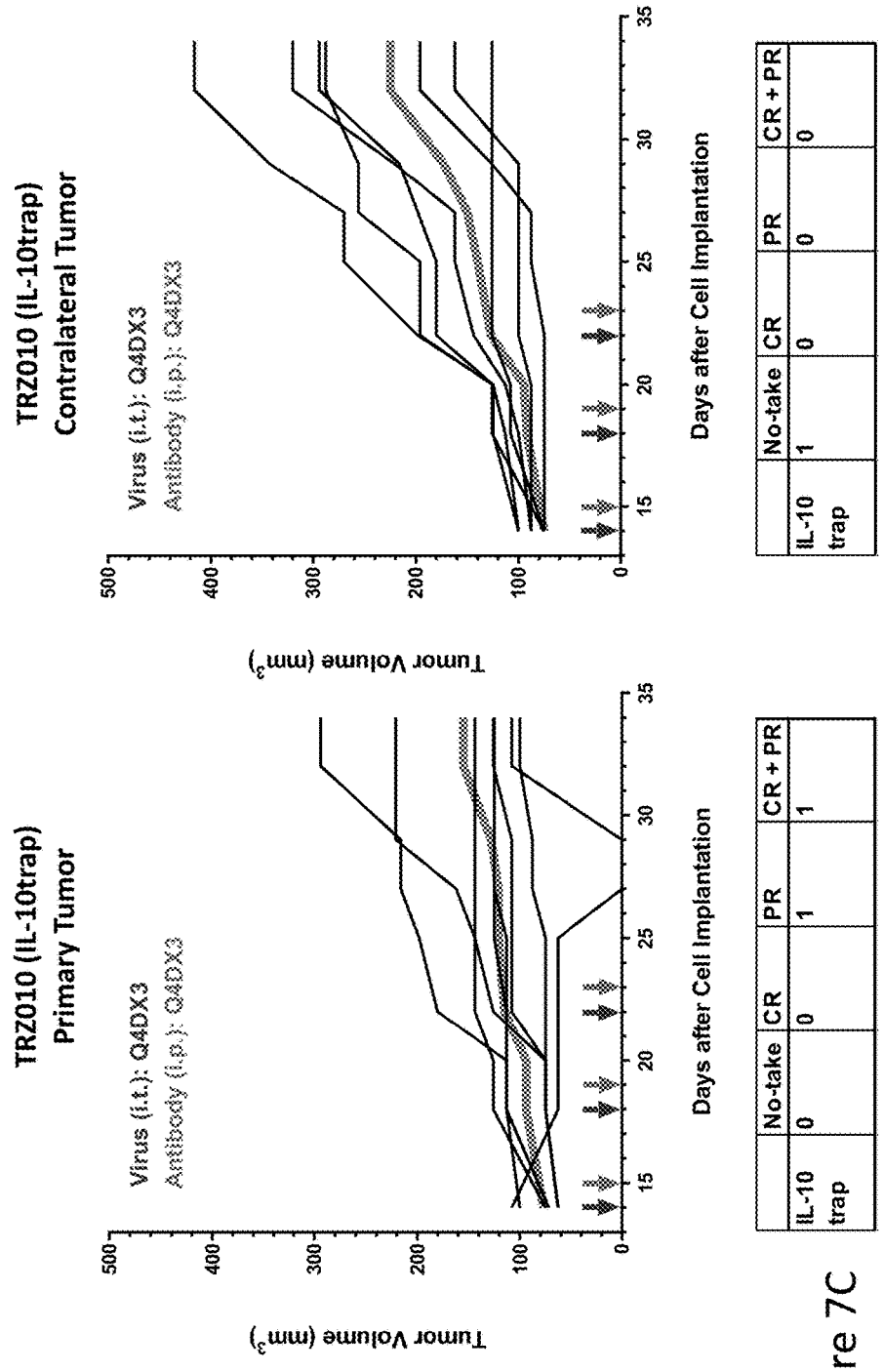
FIG. 7C is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in mm$^3$. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements).
Figure 7D:
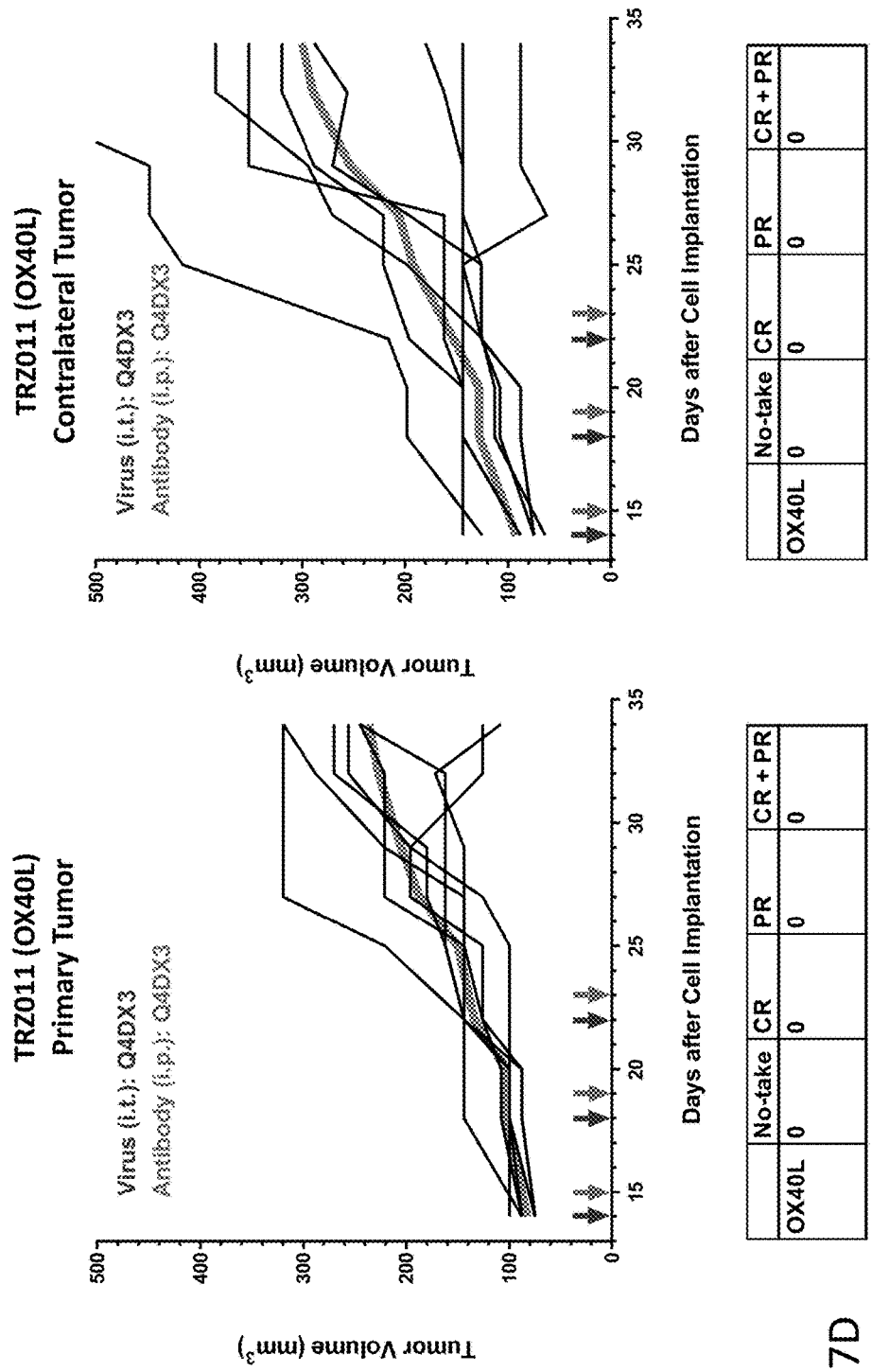
FIG. 7D is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in mm$^3$. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements).
Figure 7E:
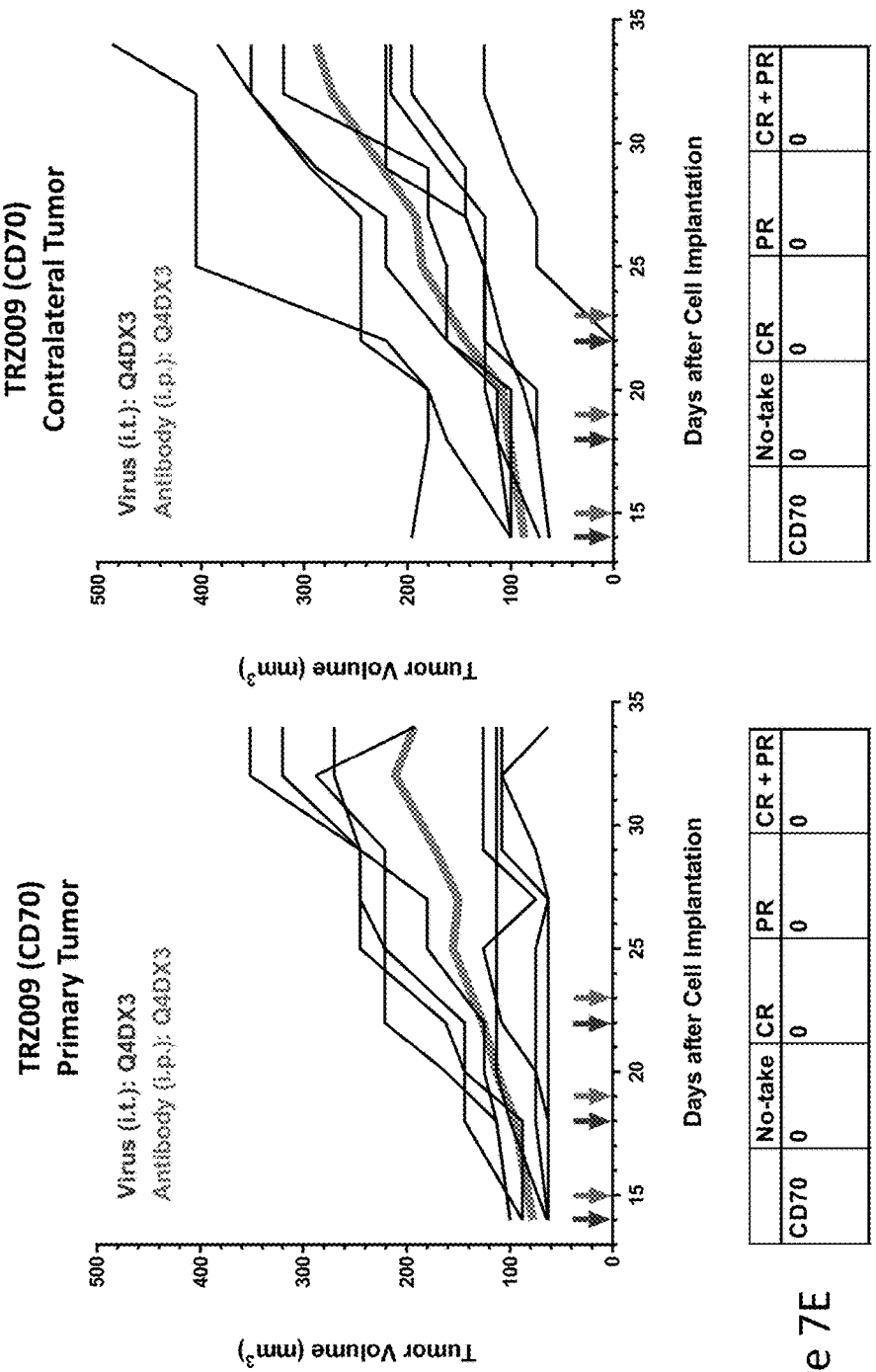
FIG. 7E is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in mm$^3$. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements).
Figure 7F:
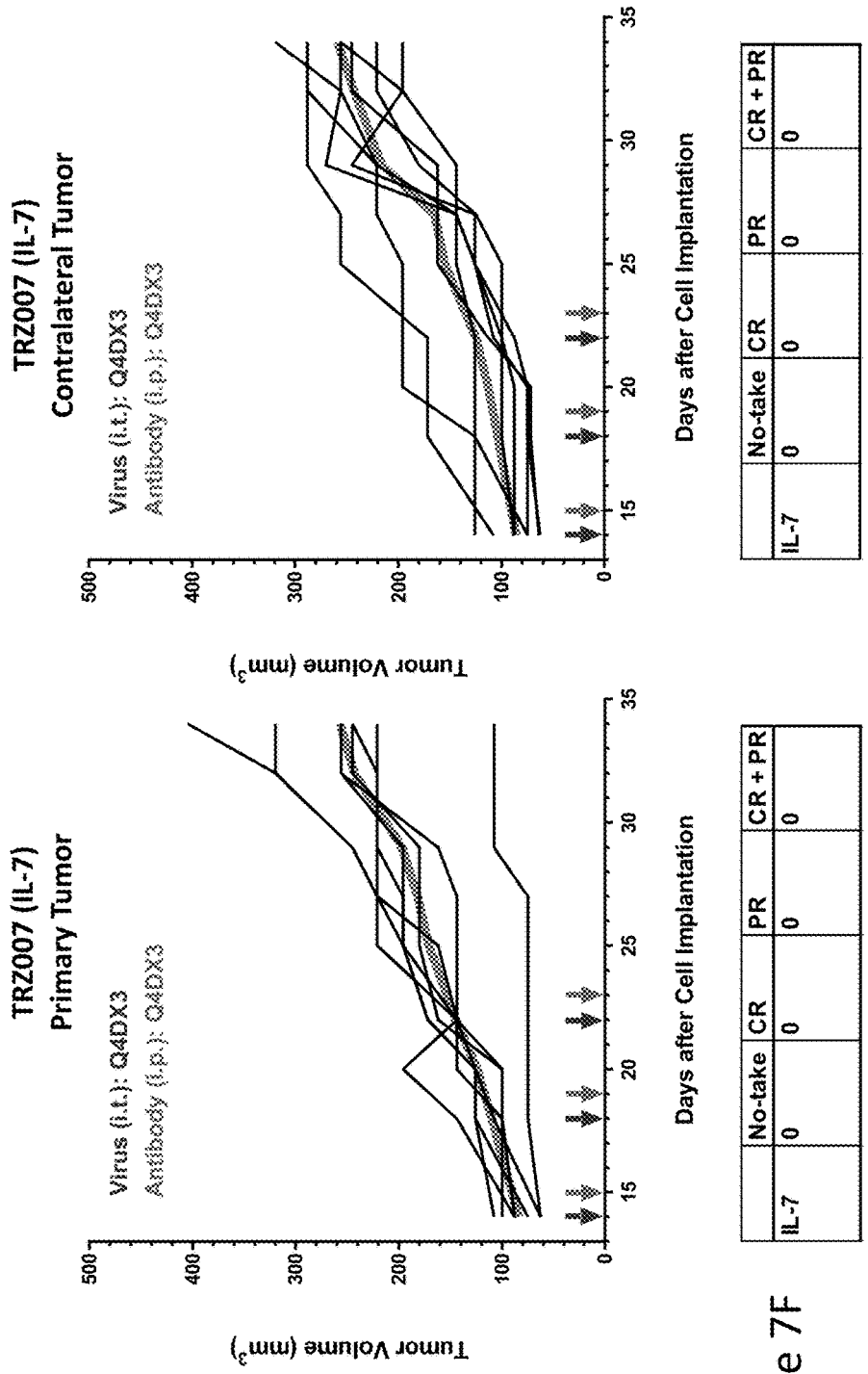
FIG. 7F is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in mm$^3$. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements).
Figure 7G:
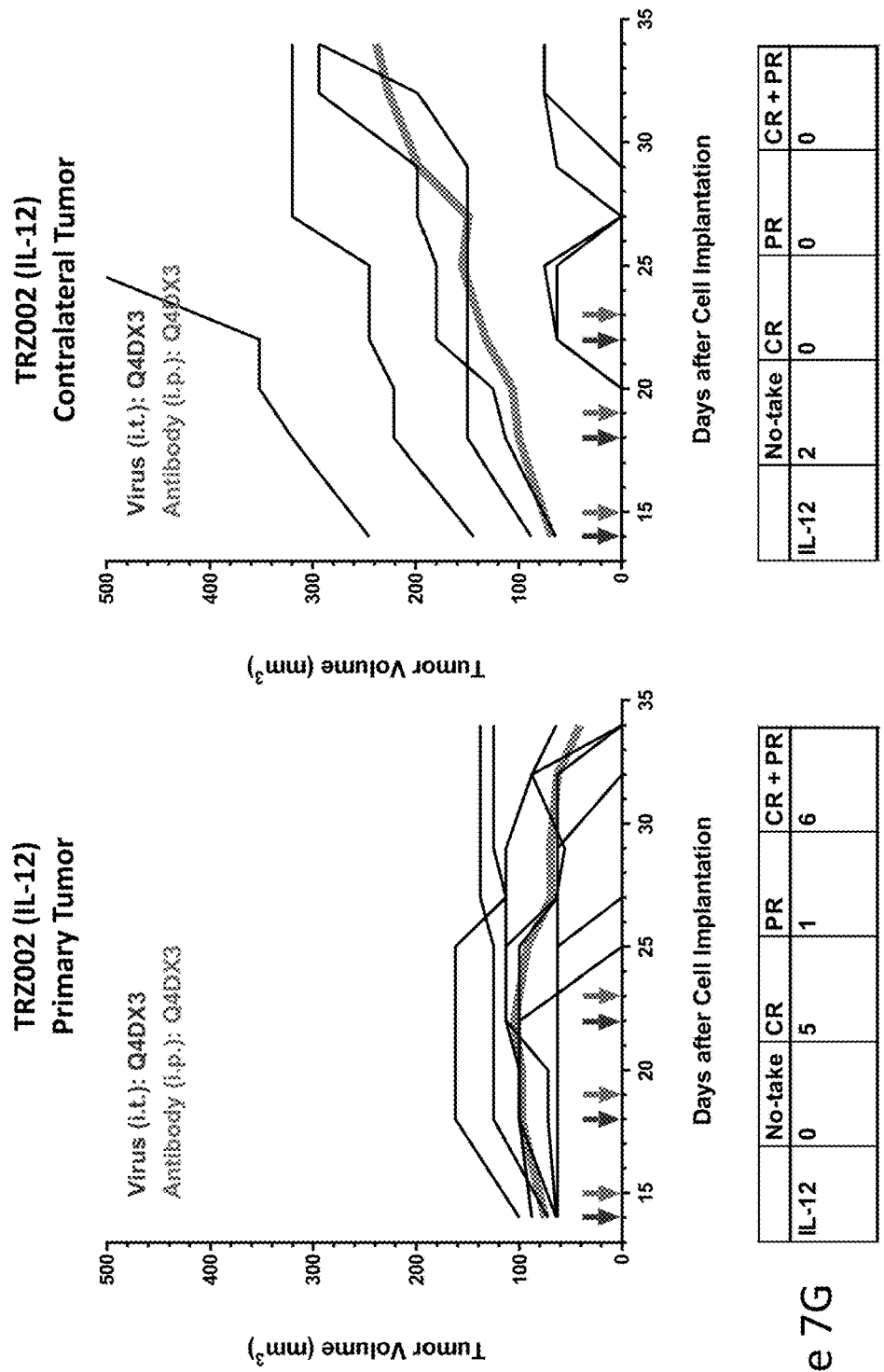
FIG. 7G is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in mm$^3$. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements).
Figure 7H:
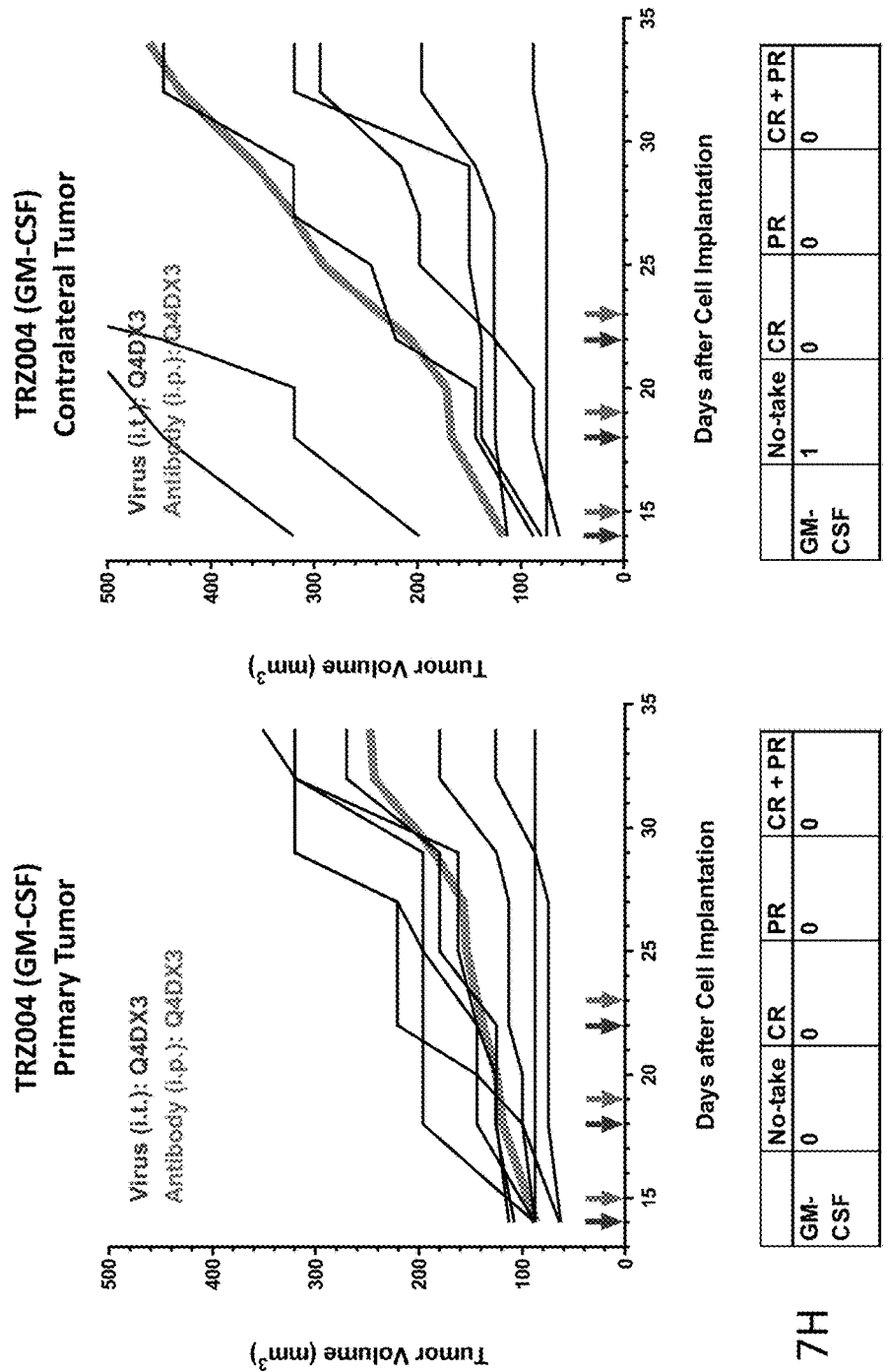
FIG. 7H is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in mm$^3$. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements).
Figure 7I:
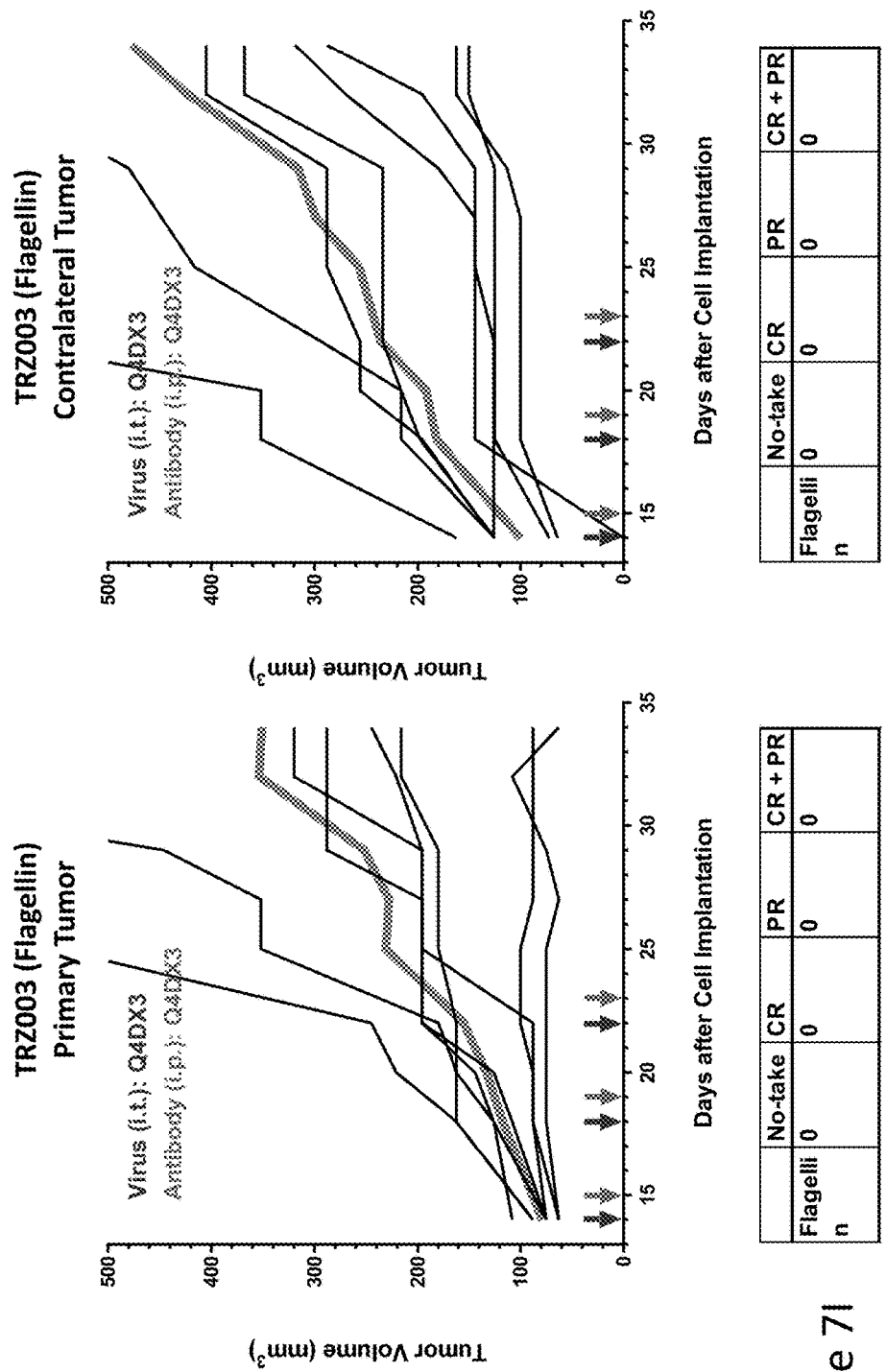
FIG. 7I is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in mm$^3$. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements).
Figure 7J:
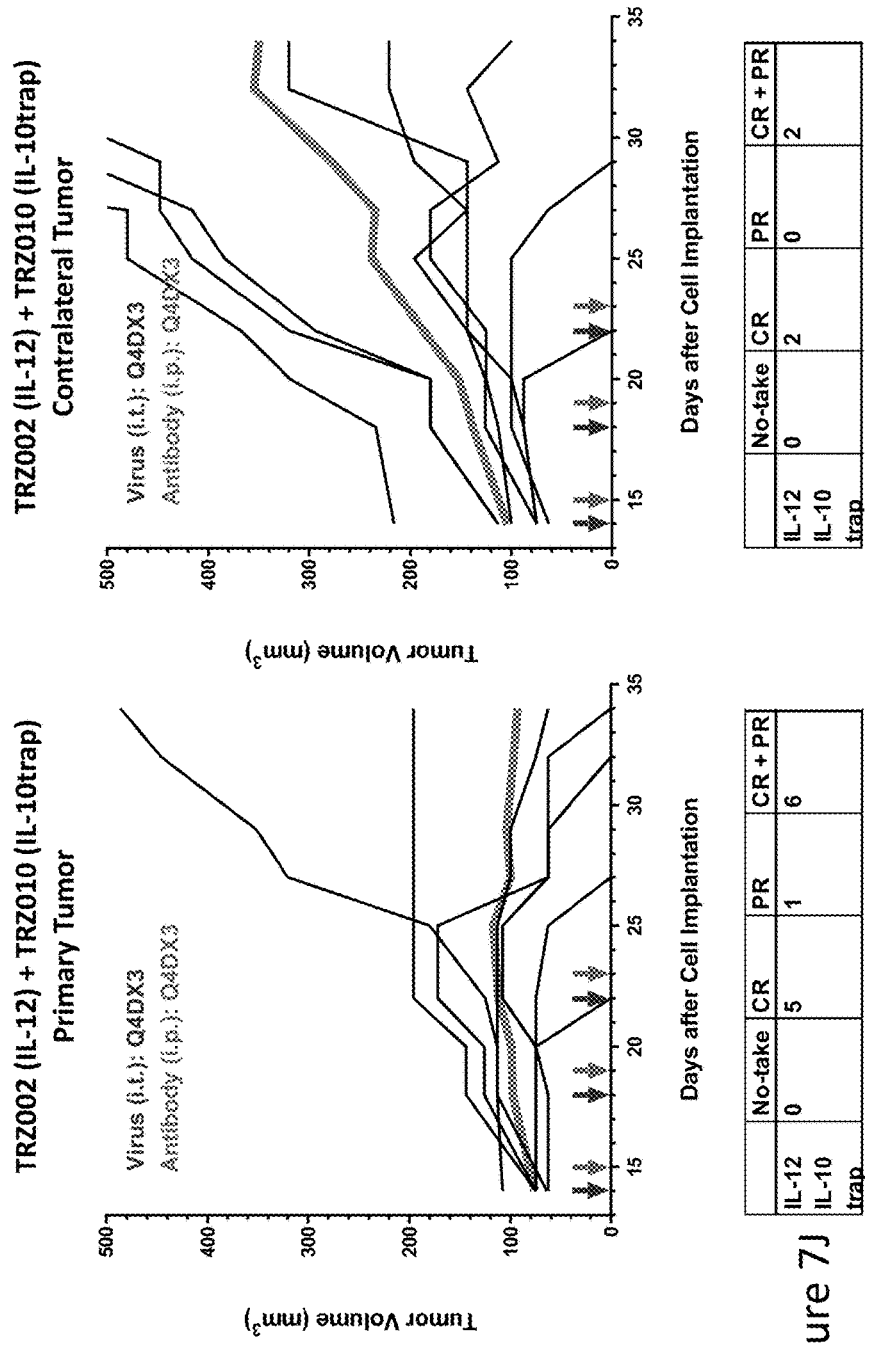
FIG. 7J is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in mm$^3$. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements).
Figure 7K:
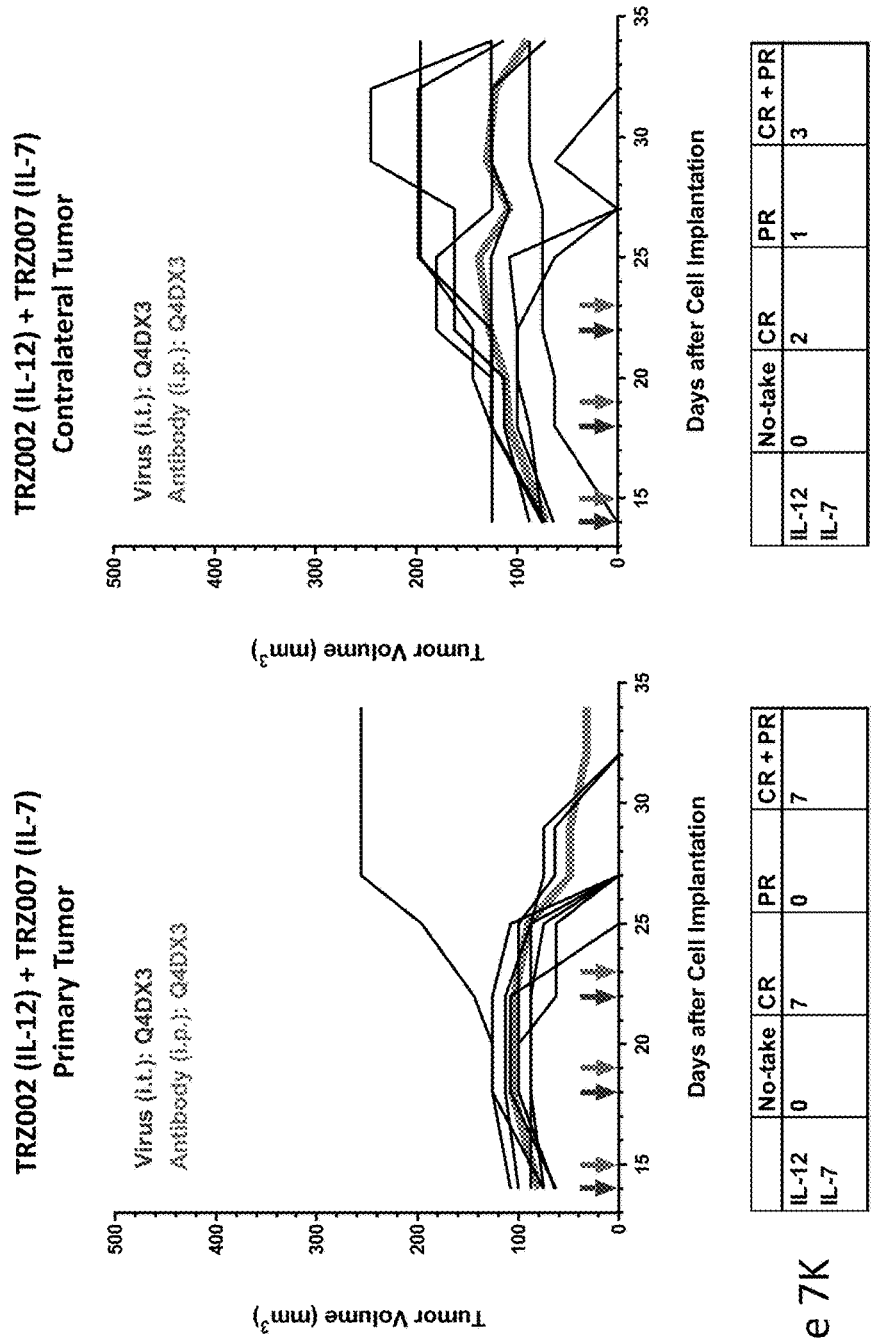
FIG. 7K is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in mm$^3$. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements).
Figure 7L:
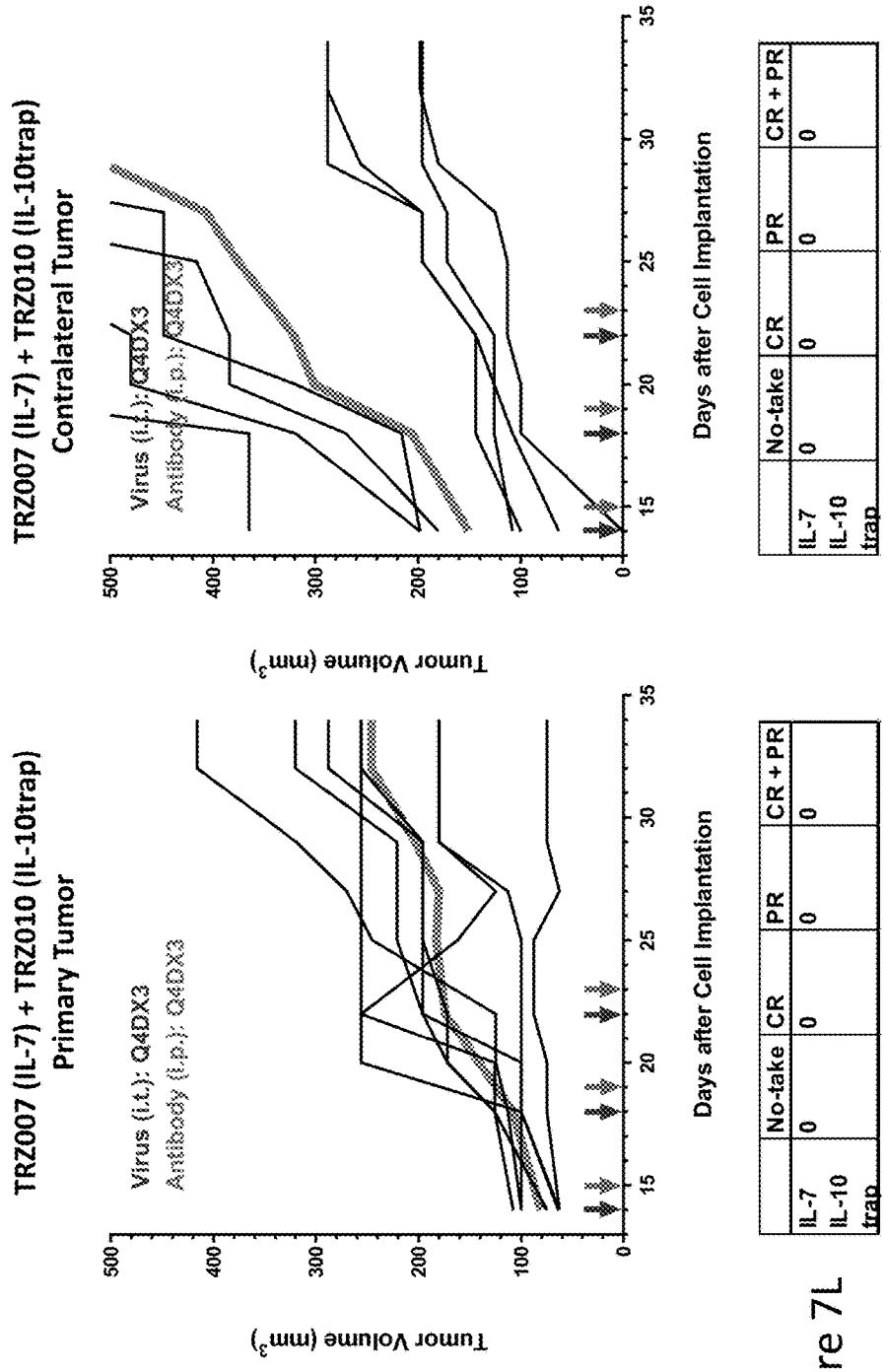
FIG. 7L is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in mm$^3$. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements).
Figure 7M:
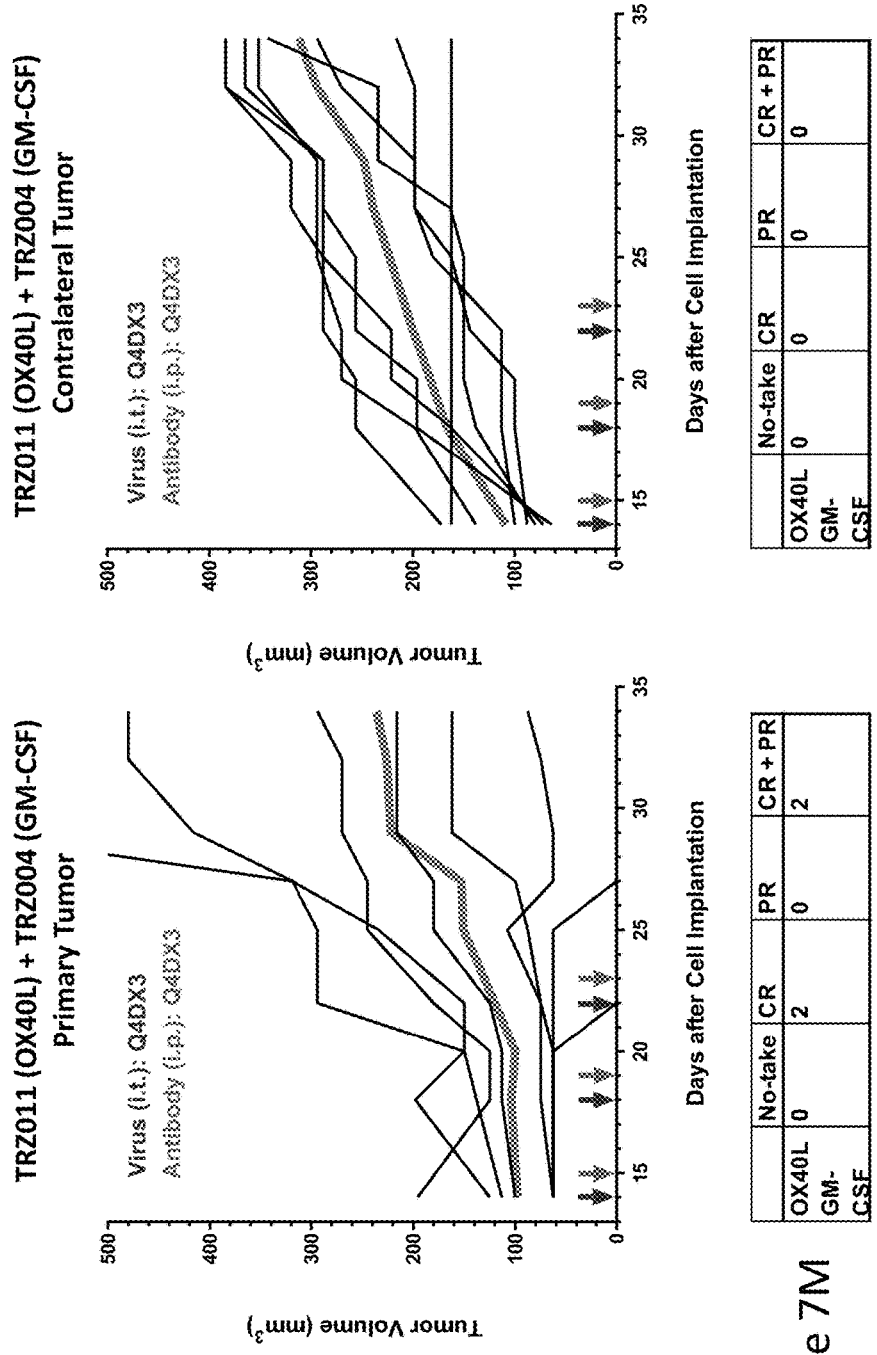
FIG. 7M is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in mm$^3$. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements).
Figure 7N:
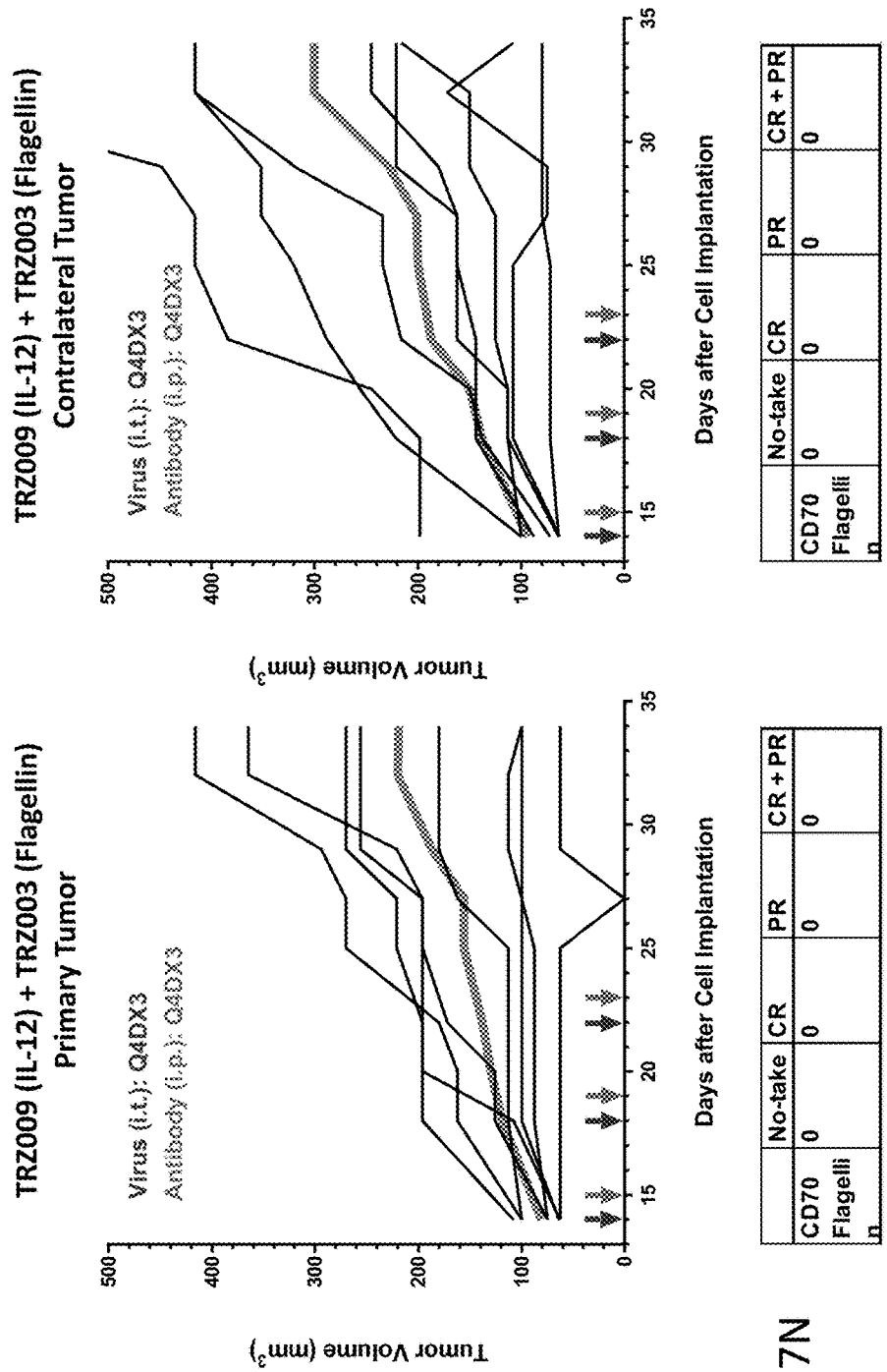
FIG. 7N is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in mm$^3$. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements).
Figure 70:
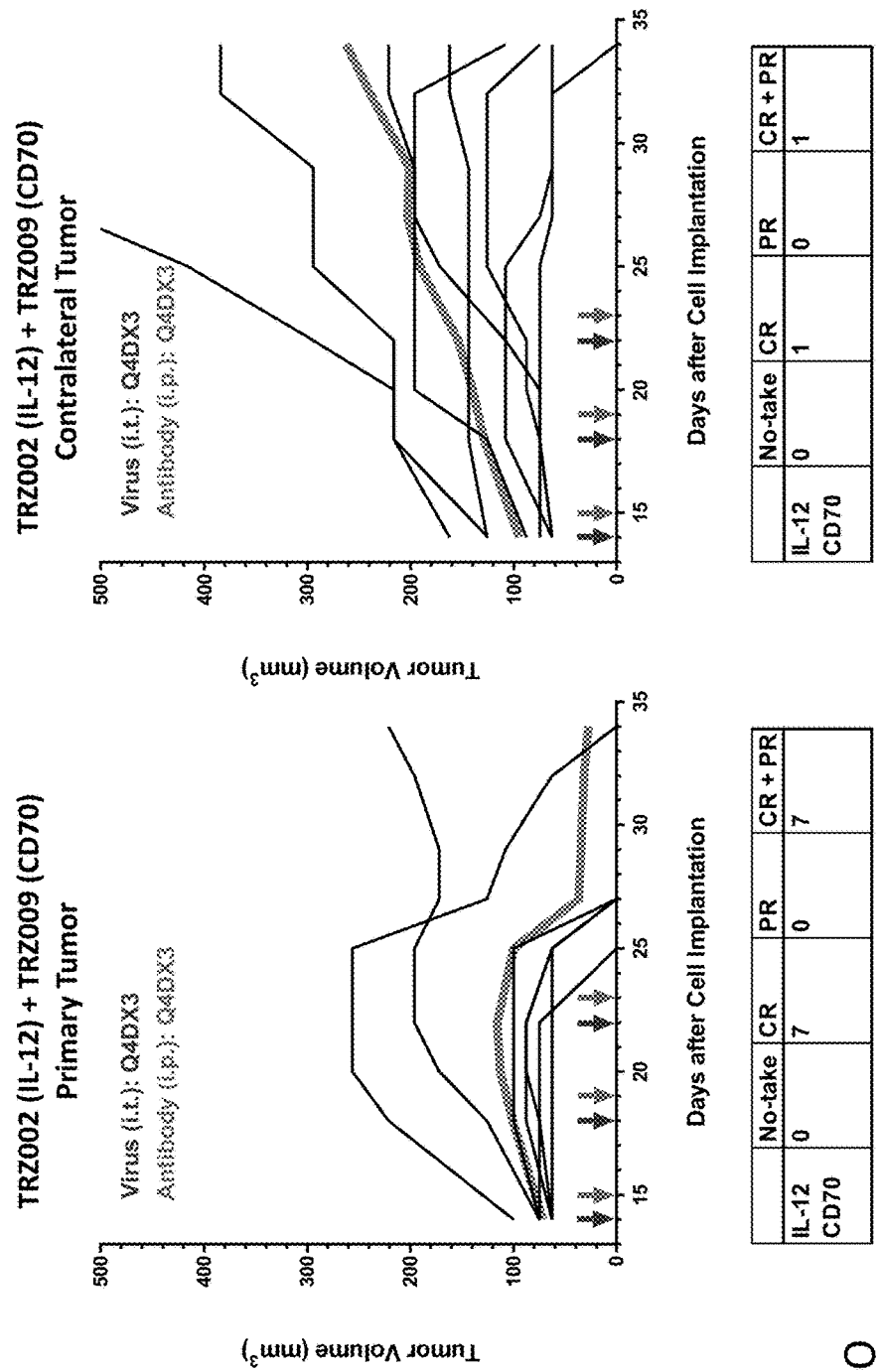
Figure 7P:
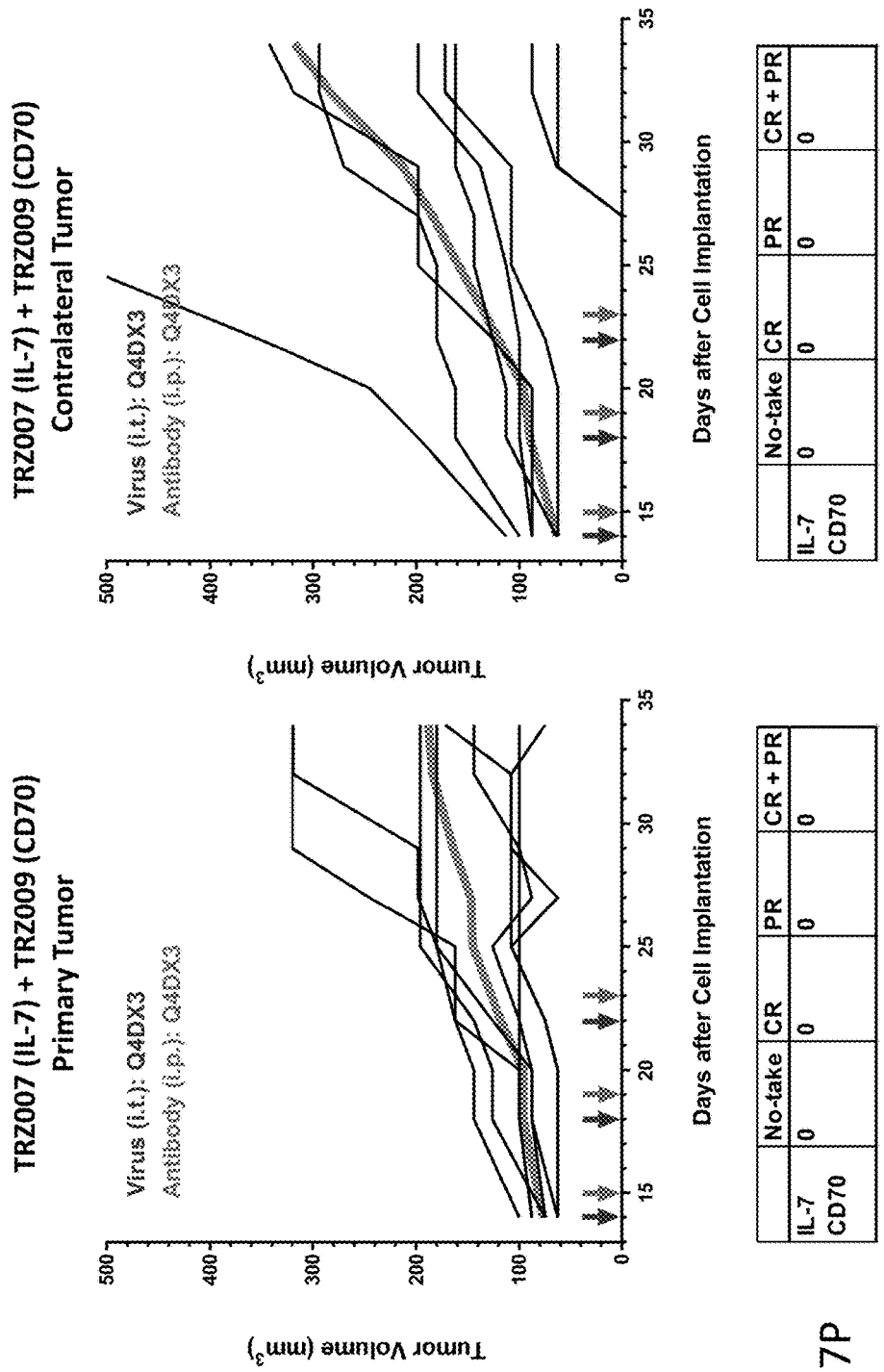
FIG. 7P is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in mm$^3$. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements).
Figure 7Q:
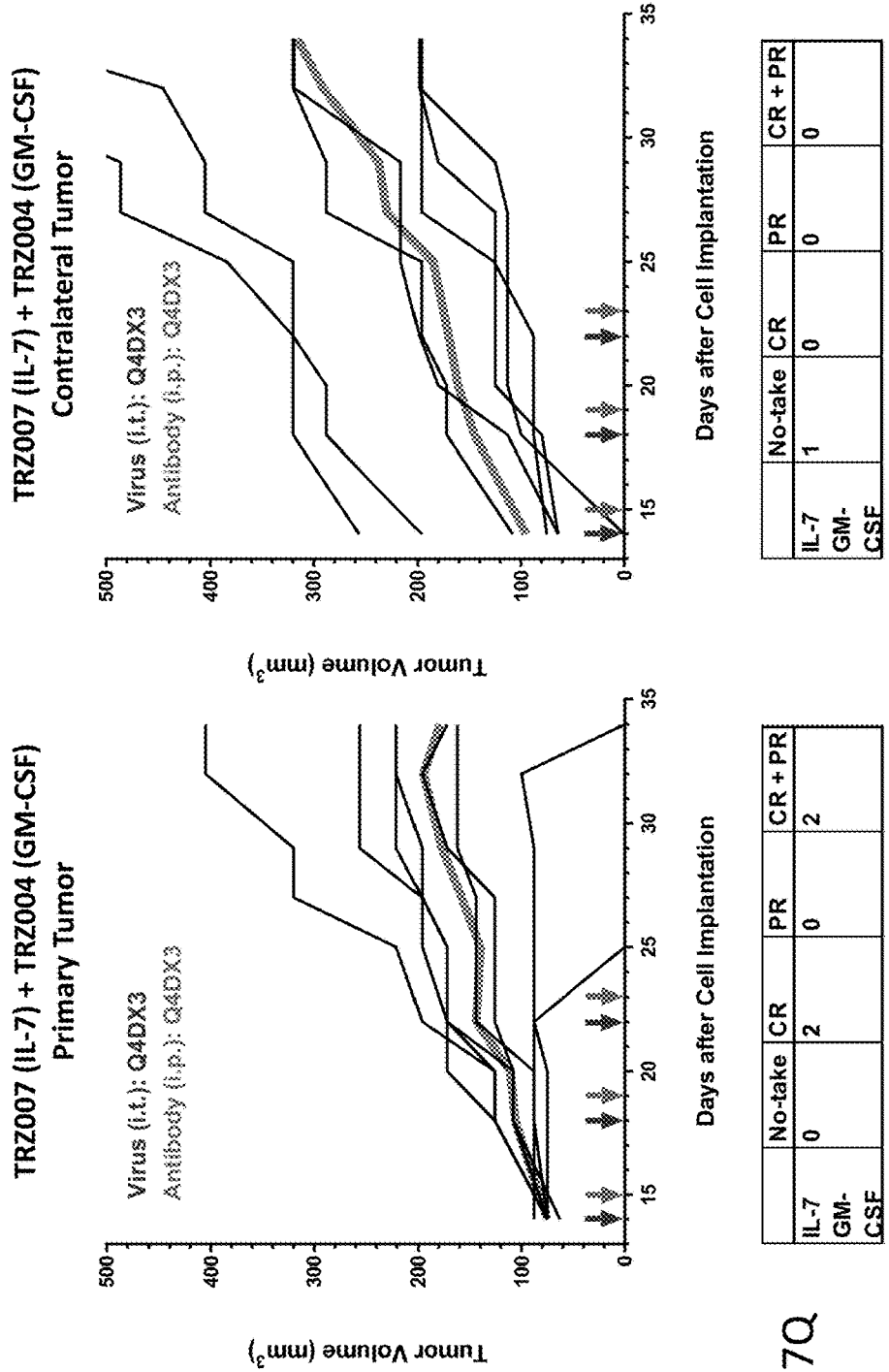
FIG. 7Q is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in mm$^3$. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements).
Figure 7R:
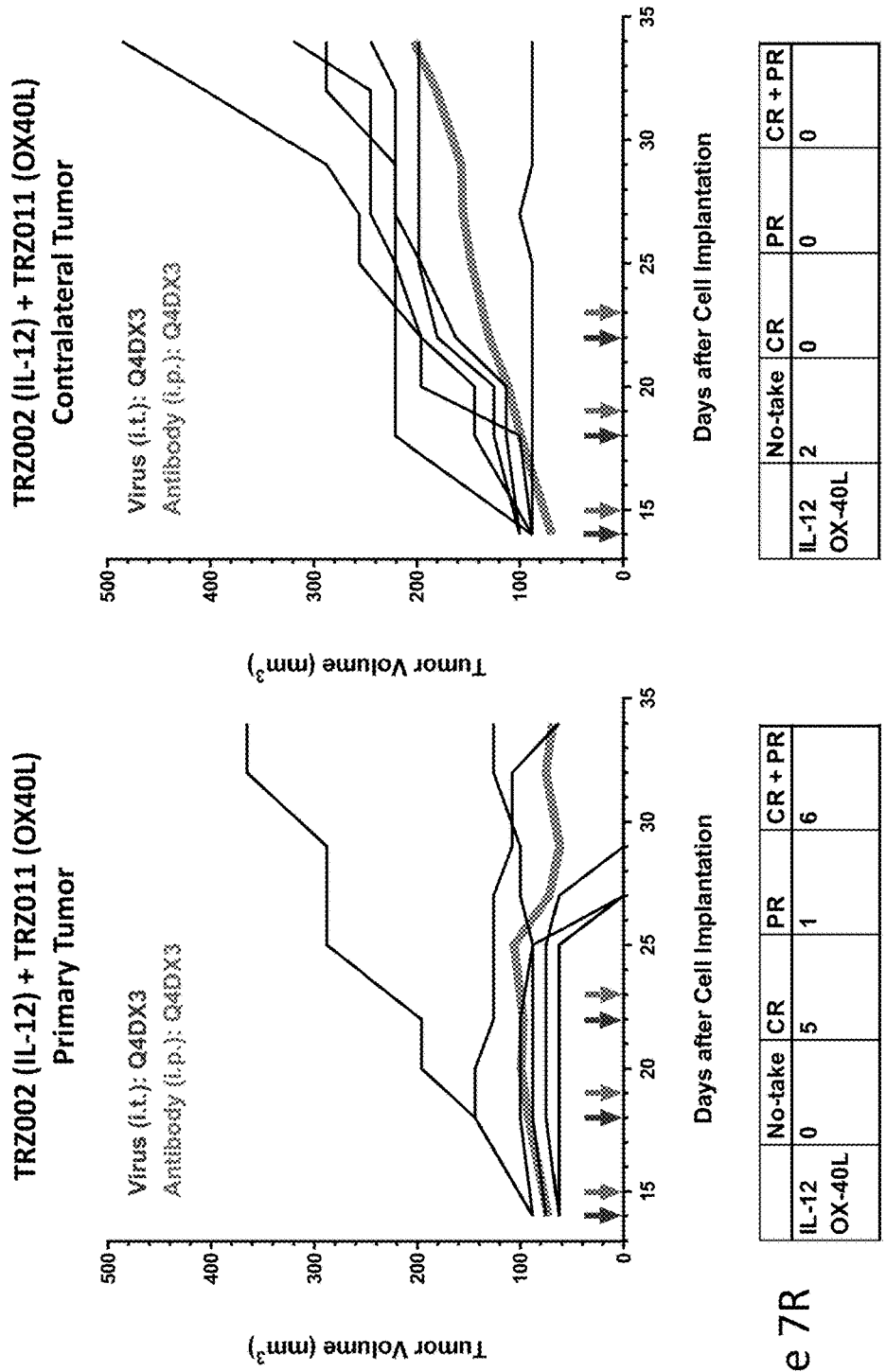
FIG. 7R is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in mm$^3$. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements).
Figure 7S:
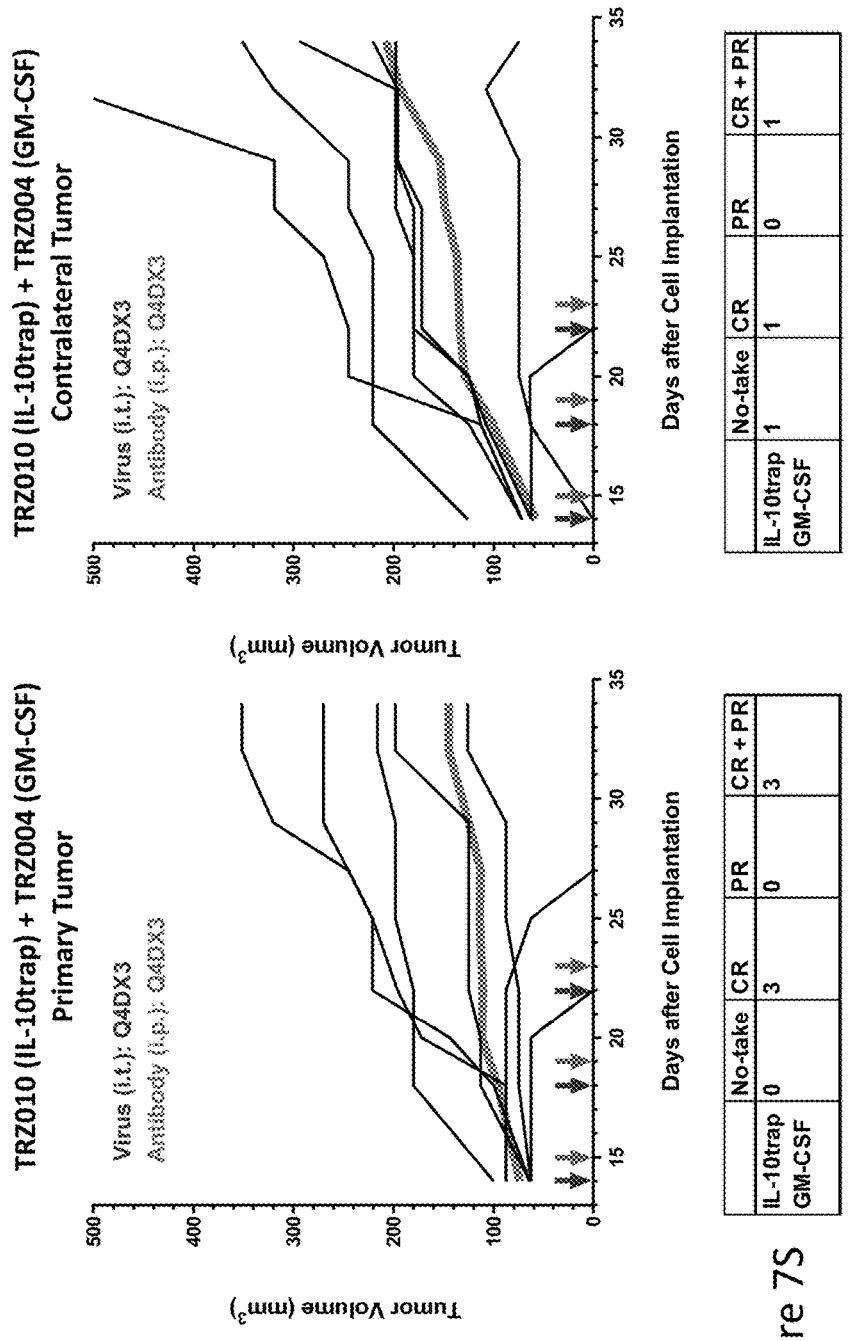
FIG. 7S is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in mm$^3$. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements).
Figure 7T:
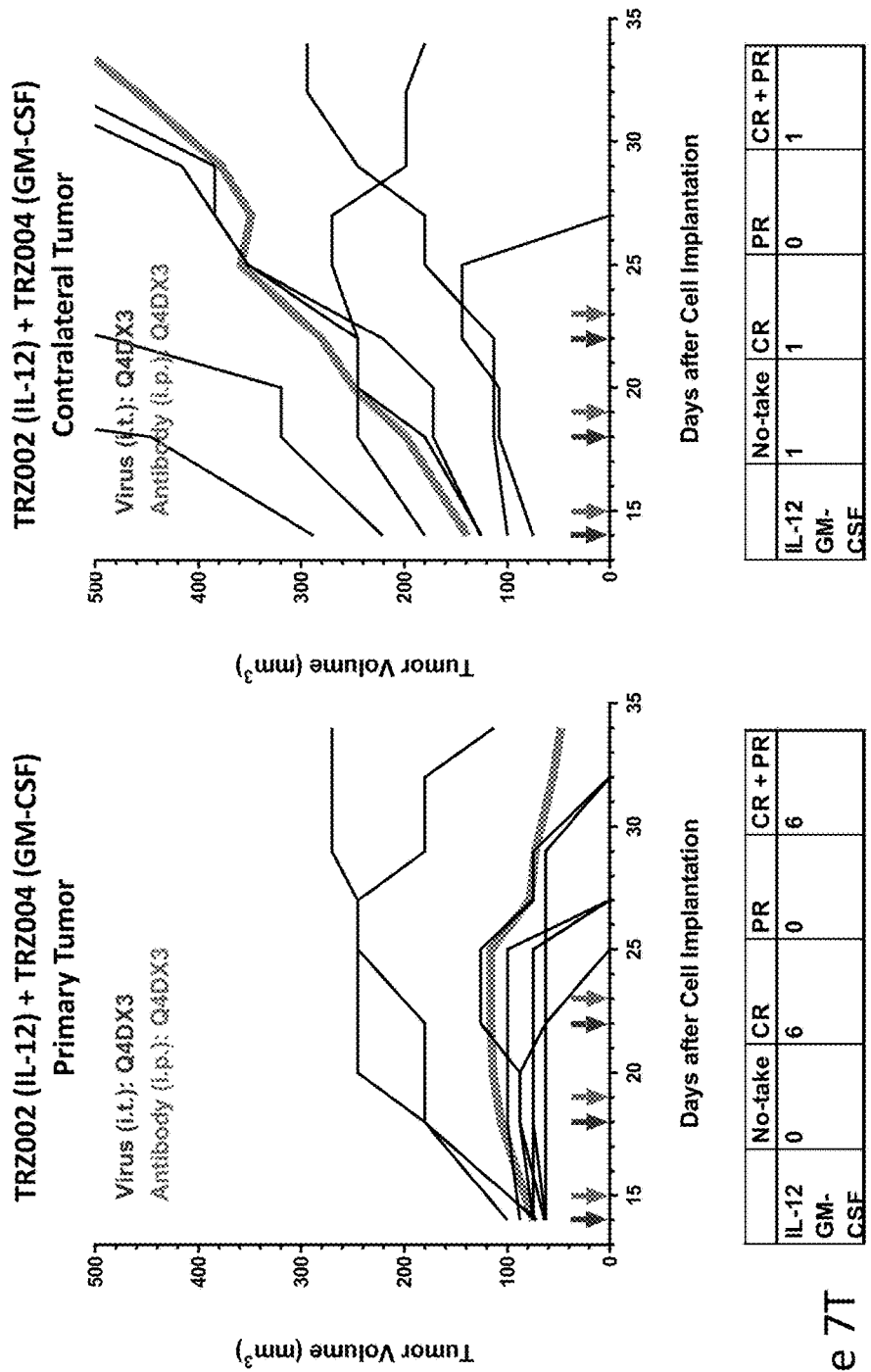
FIG. 7T is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in mm$^3$. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements).
Figure 7U:
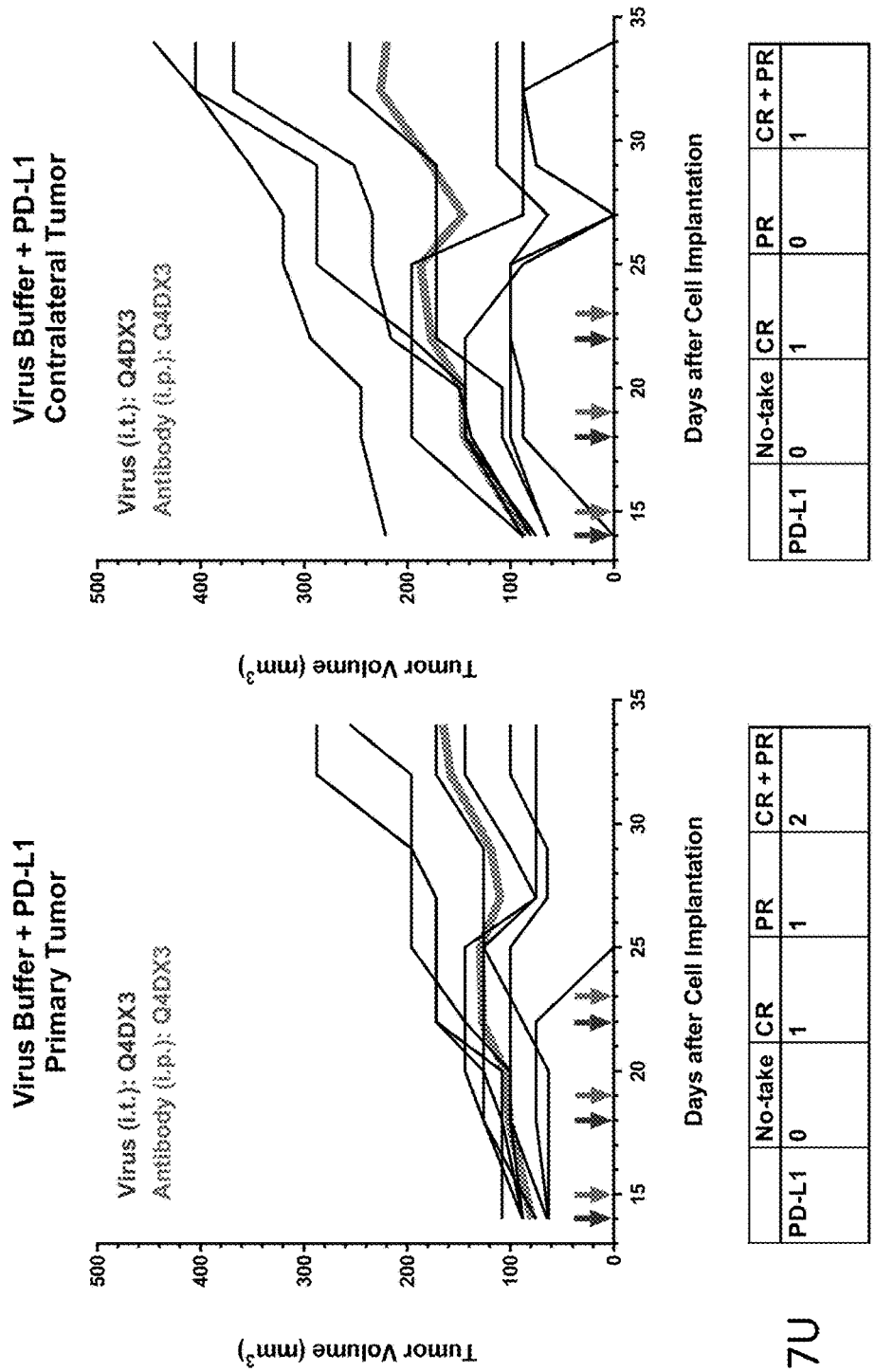
FIG. 7U is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in mm$^3$. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements).
Figure 7V:
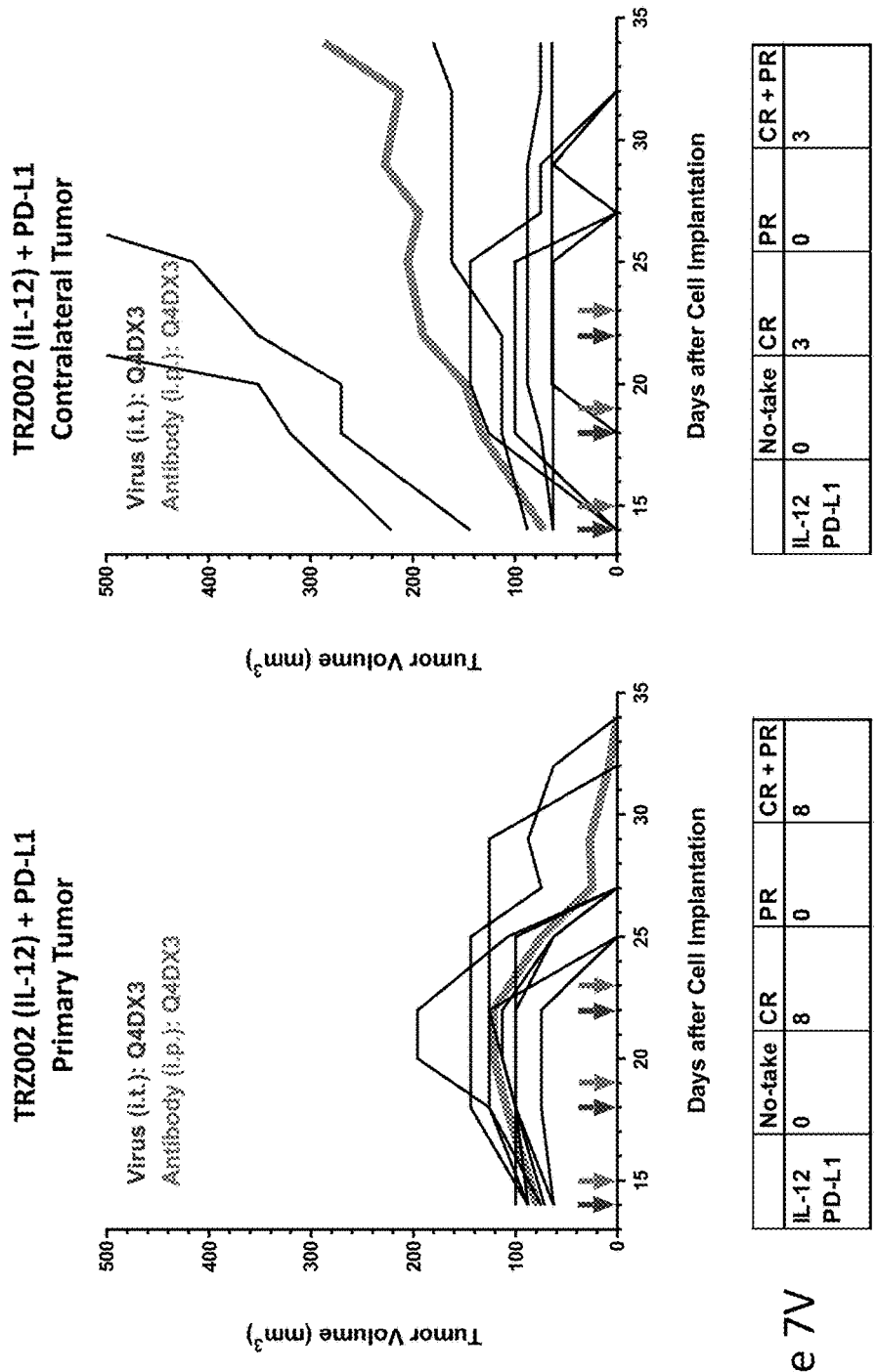
FIG. 7V is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in mm$^3$. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements).
Figure 7W:
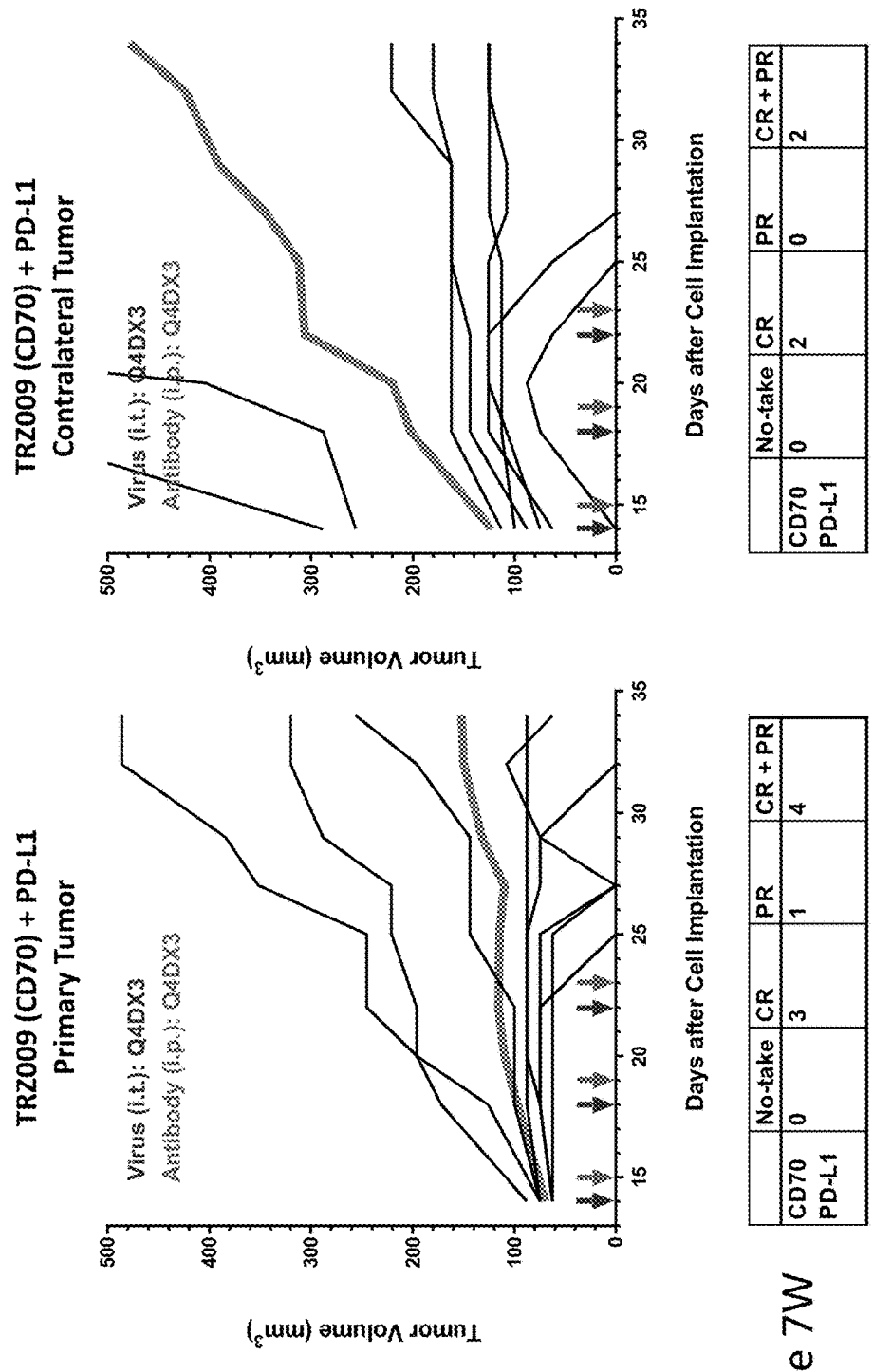
FIG. 7W is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in mm$^3$. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements).
Figure 7X:
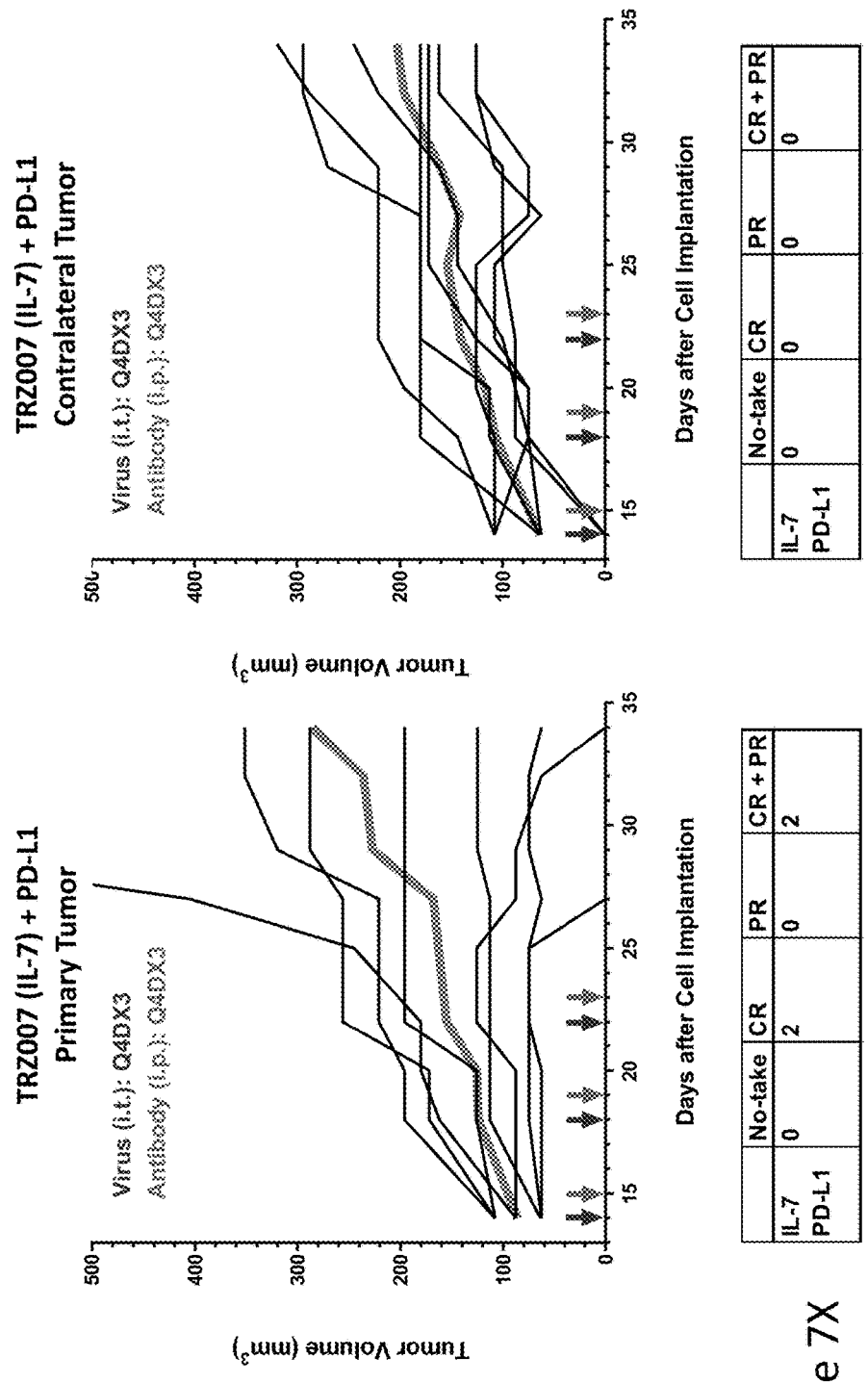
FIG. 7X is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in mm$^3$. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements).
Figure 7Y:
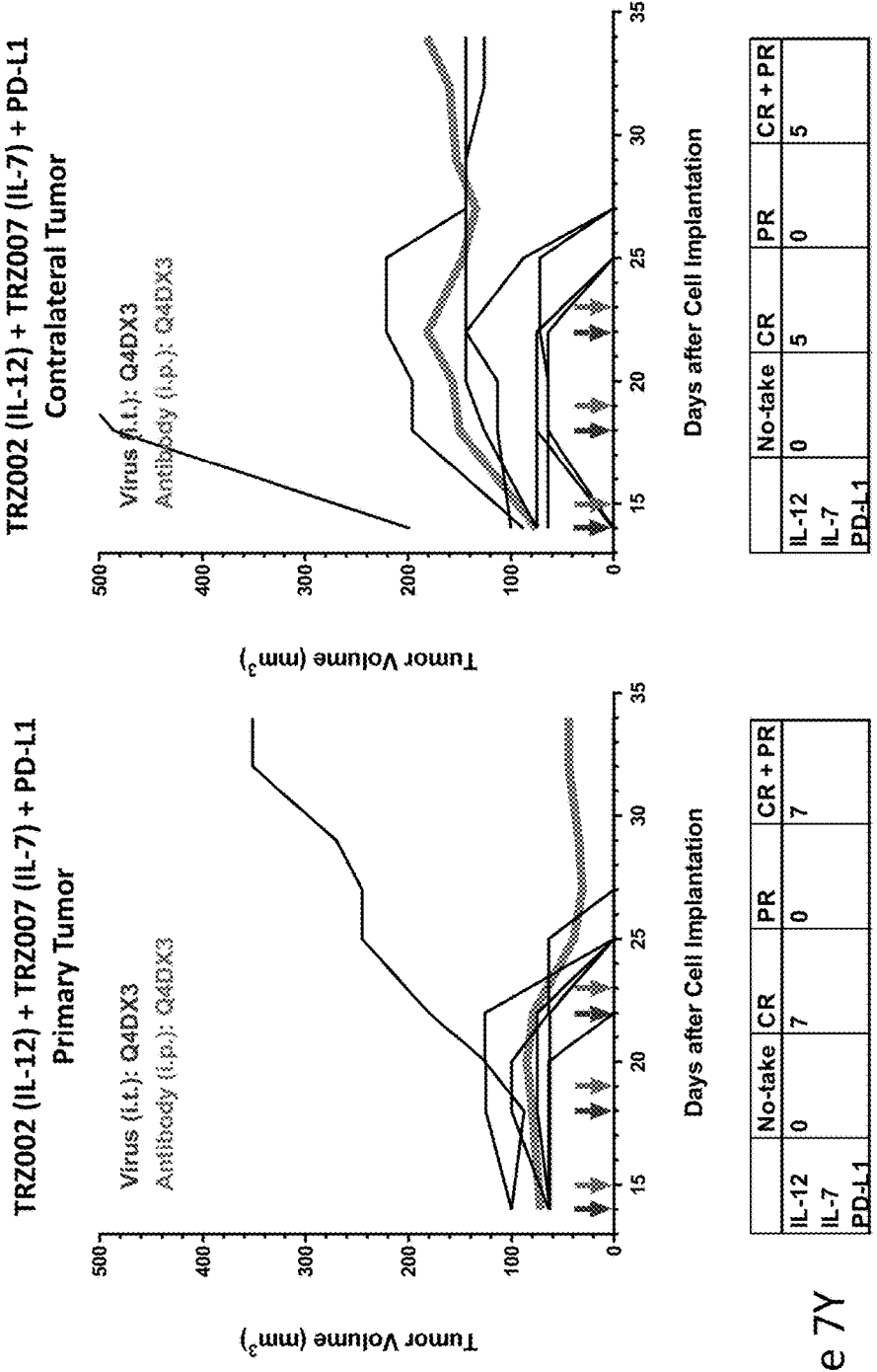
FIG. 7Y is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in $mm^3$. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements).
Figure 7Z:
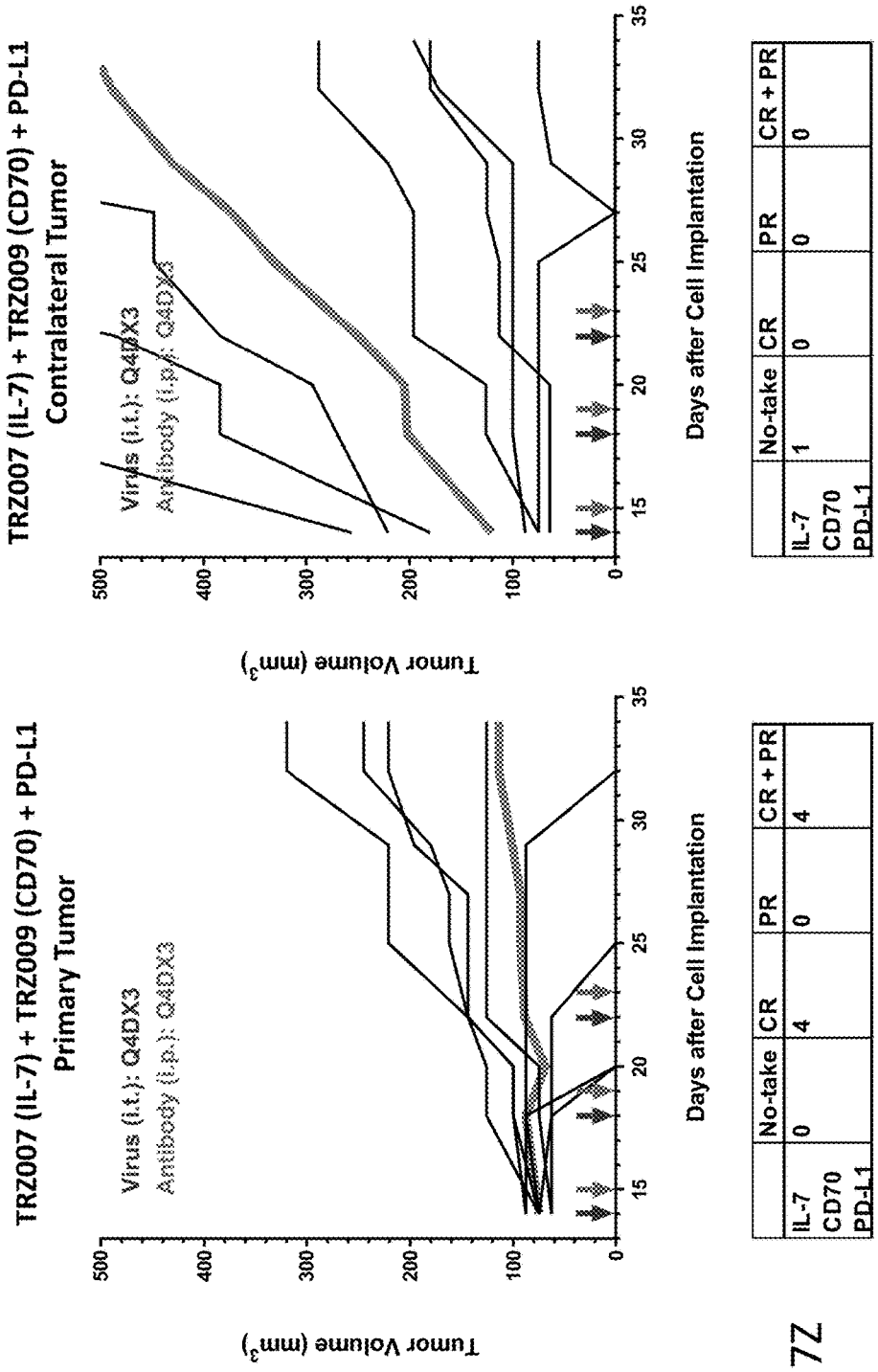
FIG. 7Z is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in $mm^3$. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements).
Figure 7A:
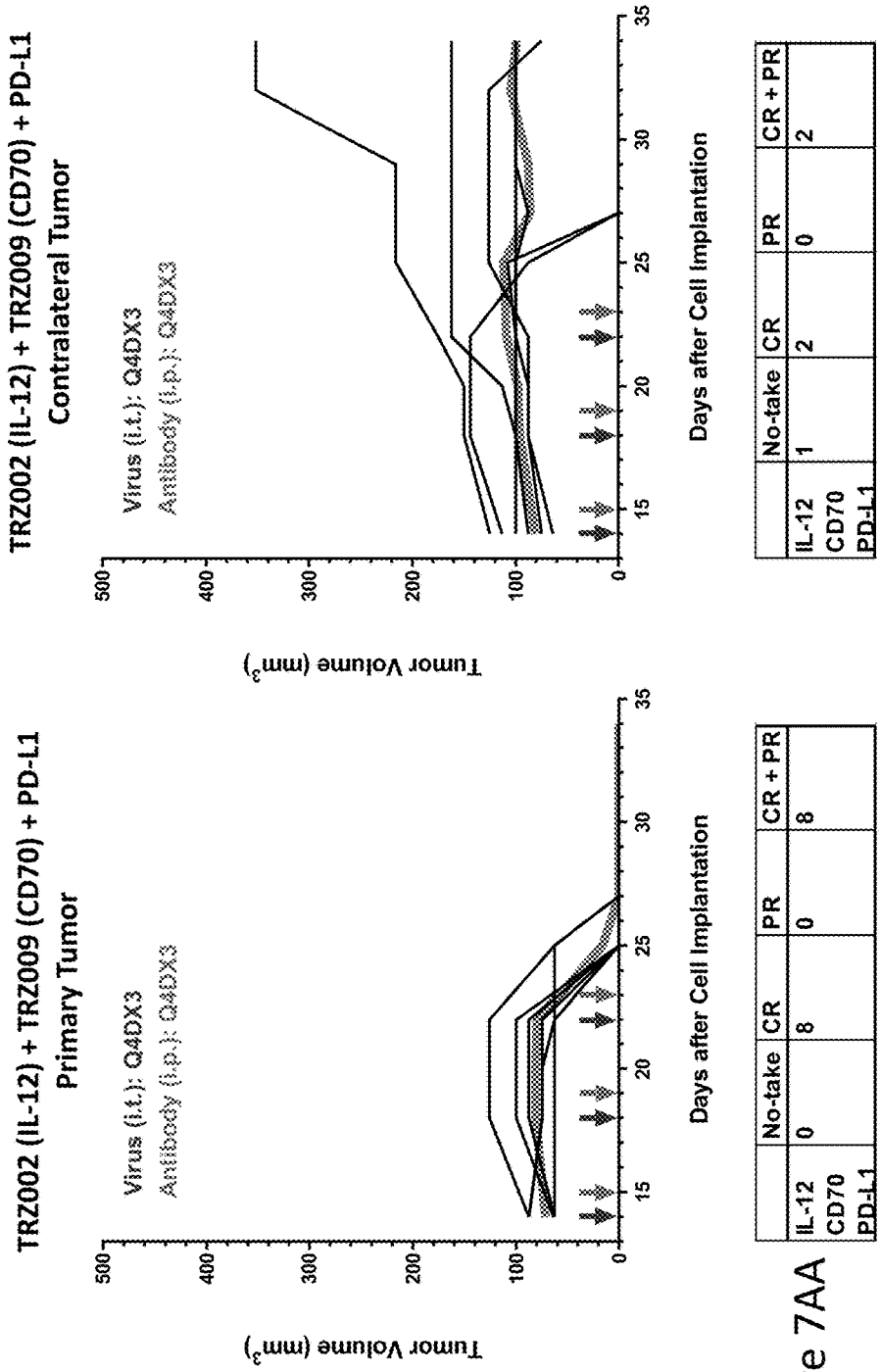
Figure 8A:
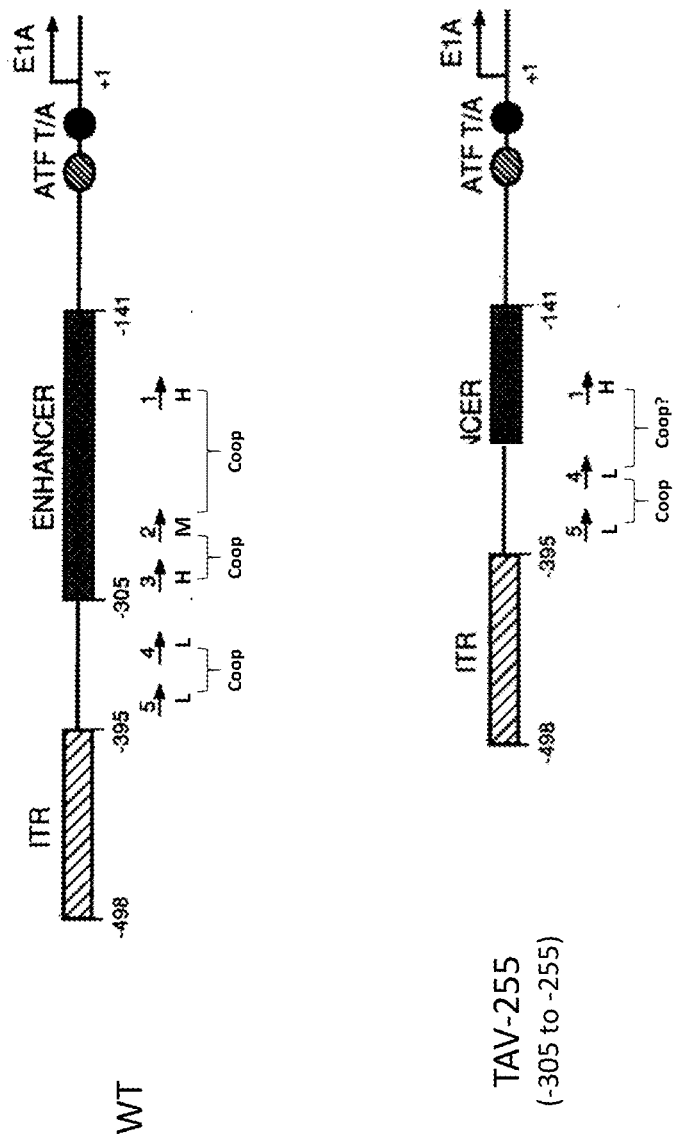
FIG. 8A is schematic representations of the rationale for modifications of the E1a Enhancer region of adenoviral vectors, in which Pea3 sites are altered, moved, or deleted in order to produce vectors with a variety of expression characteristics.
Figure 8B:
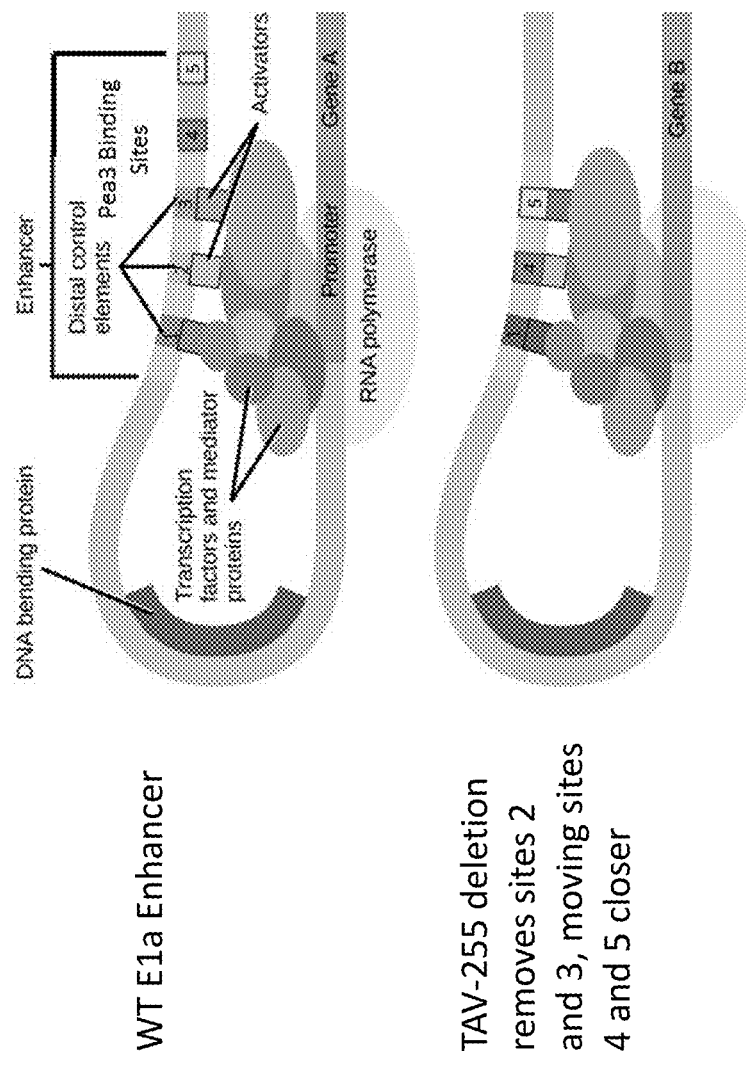
FIG. 8B is schematic representations of the rationale for modifications of the E1a Enhancer region of adenoviral vectors, in which Pea3 sites are altered, moved, or deleted in order to produce vectors with a variety of expression characteristics.

As can be seen in the Figure, certain combinations of virus transgenes were extremely successful in lysing tumor cells, including a number of examples of complete response. For example, FIG. 7G shows tumor volume in mice treated with an IL-12 adenovirus. 5 out of 8 mice in this Figure had a complete response, and one mouse had a partial response. In the contralateral tumor, however, no complete or partial responses were seen, indicating that there were no systemic immune effects from treatment with the IL-12 virus alone. A better result is seen in FIG. 7K, which shows mice treated with the same IL-12 adenovirus in combination with an IL-7 adenovirus. In this group of mice, 7 out of 8 had a complete response in the primary tumor (into which the virus was injected) and in the contralateral tumor two mice showed a complete response and one a partial response. In FIG. 7V (IL-12 adenovirus+anti-PD-L1 antibody) and 7AA (IL-12 adenovirus+CD70 adenovirus+anti-PD-L1 antibody), each group of 8 mice had 8 complete responses in the primary tumor and several in the contralateral tumor. These data demonstrate that certain combination therapies comprising oncolytic adenoviruses can be useful in treating primary and metastatic tumors.

Example 8. Adenoviral Vectors Expressing Multiple Immunomodulatory Polypeptides

If deletions in the adenovirus backbone are sufficiently large enough to allow packaging of viral DNA containing two exogenously added transgenes into the viral capsids, the two genes can be co-expressed by several methods from a single deletion site in adenovirus. Both added genes can be linked to each other by methods described below and have their expression controlled by an endogenous adenovirus promoter, not an exogenously added promoter, so that high expression will only occur during conditions of viral replication. Control of restricting viral replication to certain conditions such as after infection of tumor cells, is described elsewhere in this document. Co-expression of two proteins from a single transcript can be achieved through the use of virus components such as internal ribosome entry site (IRES) elements (Renaud-Gabardos E et al, *World J Exp Med* 2015, 5: 11-20), insertion of self-cleaving 2A peptide sequences derived from viruses such as Foot and Mouth Disease virus (FMDV) (Garry A. Luke (2012), Translating 2A Research into Practice, *Innovations in Biotechnology*, Dr. Eddy C. Agbo (Ed.), ISBN: 978-953-51-0096-6, InTech), or by combining the sequences of the two transgenes into a single fusion protein. An exemplary method would use one of the 2A sequences to direct more equal level of expression from both transgenes as opposed to lower expression levels typically seen from the second transgene when using IRES elements.

Descriptions of exemplary dual transgene constructs shown in Table 5 in this Example and Table 6 in Example 13. As can be seen in the table, any of the transgenes may be inserted into the E1 or E3 region. For example, in one embodiment a dual transgene construct may have IL-12 inserted into the E1 region and IL-2 in the E3 region. In another embodiment, a dual transgene construct may have IL-2 inserted into the E1 region and IL-12 in the E3 region. Use of the dual transgene constructs in therapeutic oncolytic adenoviruses is described in Examples 9 and 13.

TABLE 5

Exemplary dual transgene constructs.

| TRZ Number | Brief Description |
|---|---|
| TRZ402* | TAV-255-d19kE1-mIL-10T-E3-mIL-12 |
| TRZ403* | TAV-255-d19kE1-mIL-7-E3-mIL-12 |
| TRZ404* | TAV-255-d19kE1-mCD70-E3-IL-12 |
| TRZ405 | TAV-255-d19kE1-mOX40L-E3-mGM-CSF |
| TRZ406 | TAV-255-d19kE1-mIL-10T-E3-mIL-7 |
| TRZ407 | TAV-255-d19kE1-mIL-12-E3-mIL-10T |
| TRZ408 | TAV-255-d19k-E3-mIL-12 |
| TRZ409 | E1-mIL-12/E3-mIL-7 |
| TRZ413 | E1-mIL-7/E3-mIL-12-P2A-ADP |
| TRZ418* | E1-trimeric mCD70/E3-mIL-12 |
| TRZ421* | E1-mIL-2/E3-mIL-12 |
| TRZ501 | TAV-255-d19K Dual mIL-10T-P2A-mIL-12, E3 deleted |
| TRZ510 | E1-mIL-7-P2A-mIL-12 |
| TRZ512 | E1-mIL-12-P2A-mIL-7 | m = murine;
P2A = cleavage site
*See also Table 6

Example 9. Adenoviral Vectors Expressing Multiple Immunomodulatory Polypeptides

To maintain co-expression from two single gene inserts at different sites, the cDNA for each transgene can be inserted into separate deleted regions of adenovirus so that expression of each would be controlled separately by the endogenous upstream adenovirus promoter. No exogenous promoter would be added with the exogenous transgene sequence. Expression of the E1a proteins leads to the activation of the other adenovirus promoters and viral replication, so expression from each endogenous adenovirus promoter is linked to viral replication. Exogenous transgenes inserted behind different adenovirus promoters, such as the E1b promoter, the E3 promoter, and the E4 promoter, in place of deletions in these regions, leads to a construct where co-expression from each inserted transgene is limited to conditions of where viral replication occurs. Combined with modifications in the E1a enhancer region as described previously in this document to restrict viral replication to tumor cells, co-expression of both exogenous transgenes is restricted to tumor cells.

Figure 2:
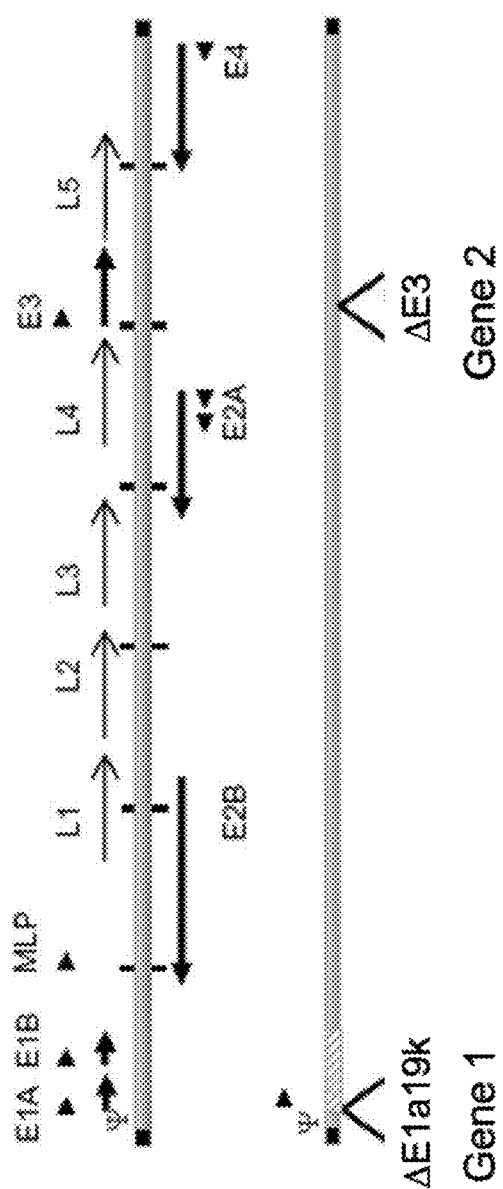
FIG. 2 is an illustration of a vector map demonstrating an adenoviral vector expressing two immunomodulatory polypeptides.

As shown schematically in FIG. 2, provided is an ΔE1b19K site that includes a deletion of bp 1714-1916 (numbered according to hAd5 vector sequence), which increases packaging capacity by approximately 200 bp. Also provided is a deletion at the E3 site (ΔE3 site as shown in FIG. 2); this deletion can be any deletion in the E3 region, generally at or about bp 27,900-30,800 bp (numbered according to hAd5 vector sequence), which increases packaging capacity up to an additional approximately 2400 bp, as compared to most wild type adenoviruses, which are typically limited to containing (i.e., packaging) approximately 1800 bp of exogenous sequences.

Provided herein are deletions in E3 open reading frames that are suitable for modification (e.g., truncation or deletion) without substantially decreasing viral propagation. By way of non-limiting example, provided are adenoviral vectors wherein the E3 12.5K coding region (27,852-28,175 bp) is truncated (e.g., at least 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 250, 300, 320 or greater than 320 bases are deleted from one or more truncation sites within the region) or entirely deleted. Also provided are adenoviral vectors wherein the E3 7.1K coding region (28,541-28,732) is truncated (e.g., at least 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, or greater than 190 bases are deleted from one or more truncation sites within the region) or entirely deleted. The 7.1K sequence is associated with inhibition of TRAIL apoptosis and associated with one or more RID proteins. Also provided are adenoviral vectors wherein the E3 gp19K (28,729-29211) is truncated (e.g., at least 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 250, 300, 350, 400, 450 or greater than 450 bases are deleted from one or more truncation sites within the region) or entirely deleted. The gp19K sequence is associated with inhibition of CTL killing. Also provided are adenoviral vectors wherein the E3 10.5 (also called E3 11.6 (ADP)) (29, 485-29,766) is truncated (e.g., at least 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 250, or greater than 250 bases are deleted from one or more truncation sites within the region) or entirely deleted. The 10.5 sequence is associated with promotion of virus release. Also provided are adenoviral vectors wherein the E3 (RIDα) (29,778-29,969) and/or the E3 (RIDβ) (30,057-30,455) is truncated (e.g., with respect to E3 (RIDα) at least 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, or greater than 190 bases are deleted from one or more truncation sites within the region) or entirely deleted, or truncated (e.g., with respect to E3 (RIDβ) at least 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 250, 300, 350, 390, or greater than 390 bases are deleted from one or more truncation sites within the region) or entirely deleted. These RID sequences are associated with inhibition of TNF, FasL, and TRAIL apoptosis and degrade EGFR. Any combination of the above-referenced deletions is also provided.

Also provided are adenoviral vectors wherein the E3 14.7K (30,488-30,834) is truncated (e.g., at least 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 250, 300, 340, or greater than 340 bases are deleted from one or more truncation sites within the region) or entirely deleted. The 14.7K sequence is associated with inhibition of TNF, FasL, and TRAIL apoptosis.

Figure 3:
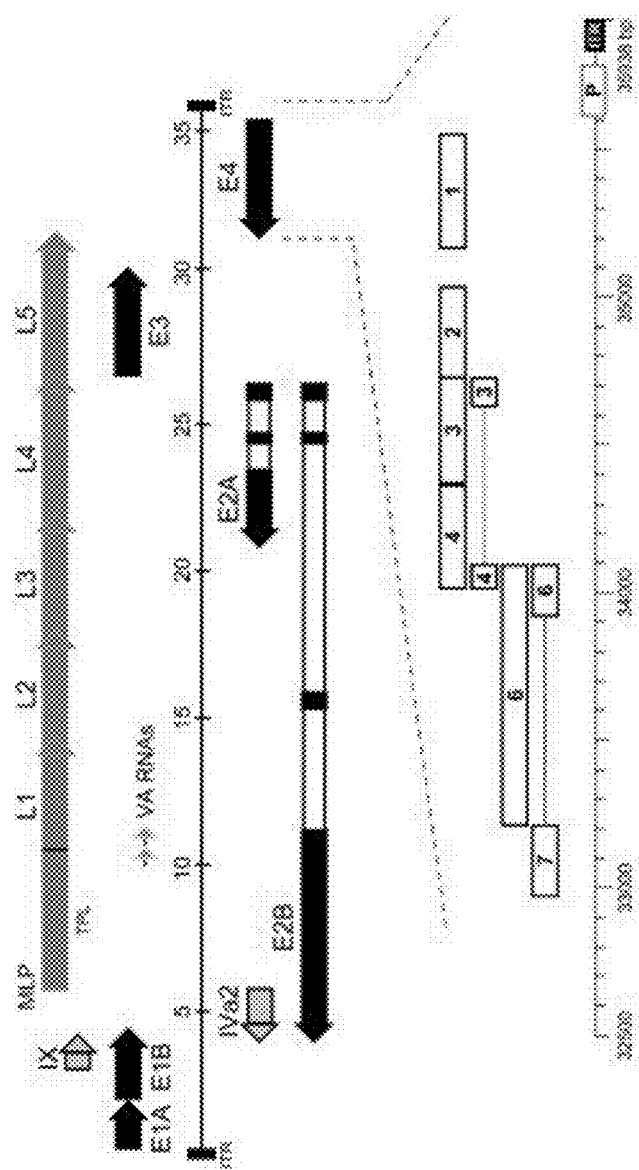
FIG. 3 is an illustration of a vector map demonstrating an adenoviral vector expressing at least one immunomodulatory polypeptide at an E4 site.
Figure 4:
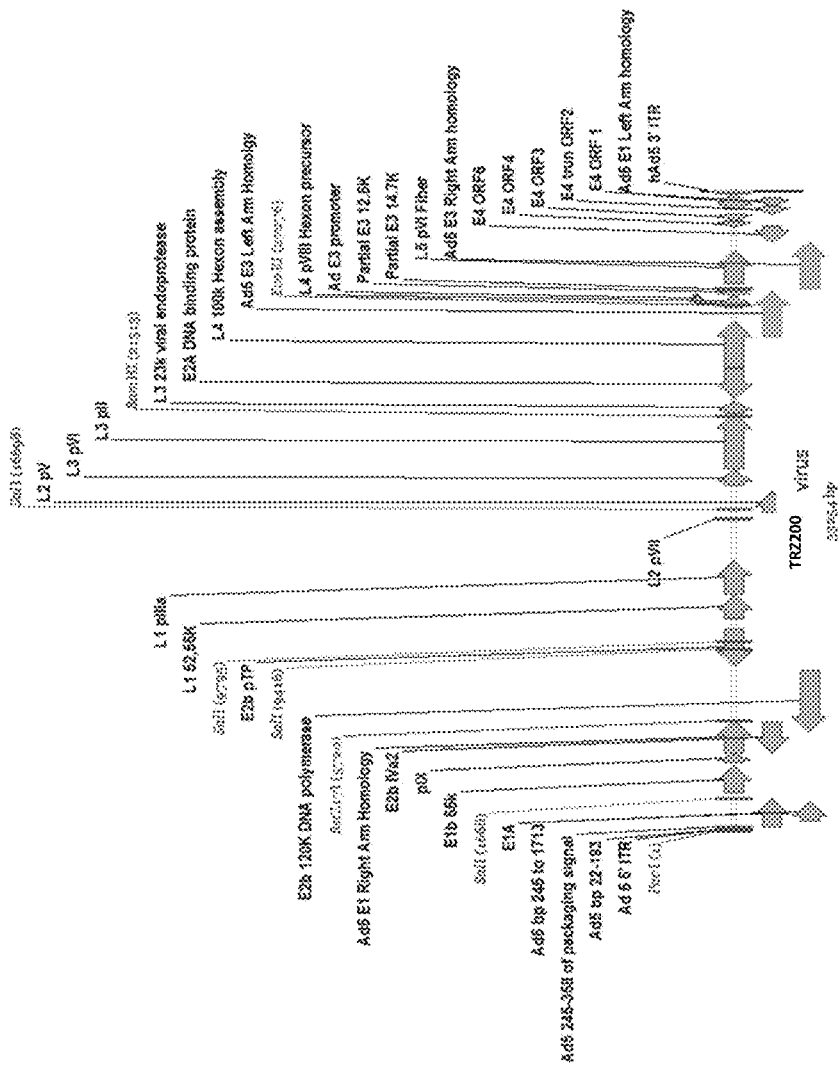
FIG. 4 is an illustration of the TRZ200 virus genome: an E1b 19k empty, E3-deleted virus.
Figure 5:
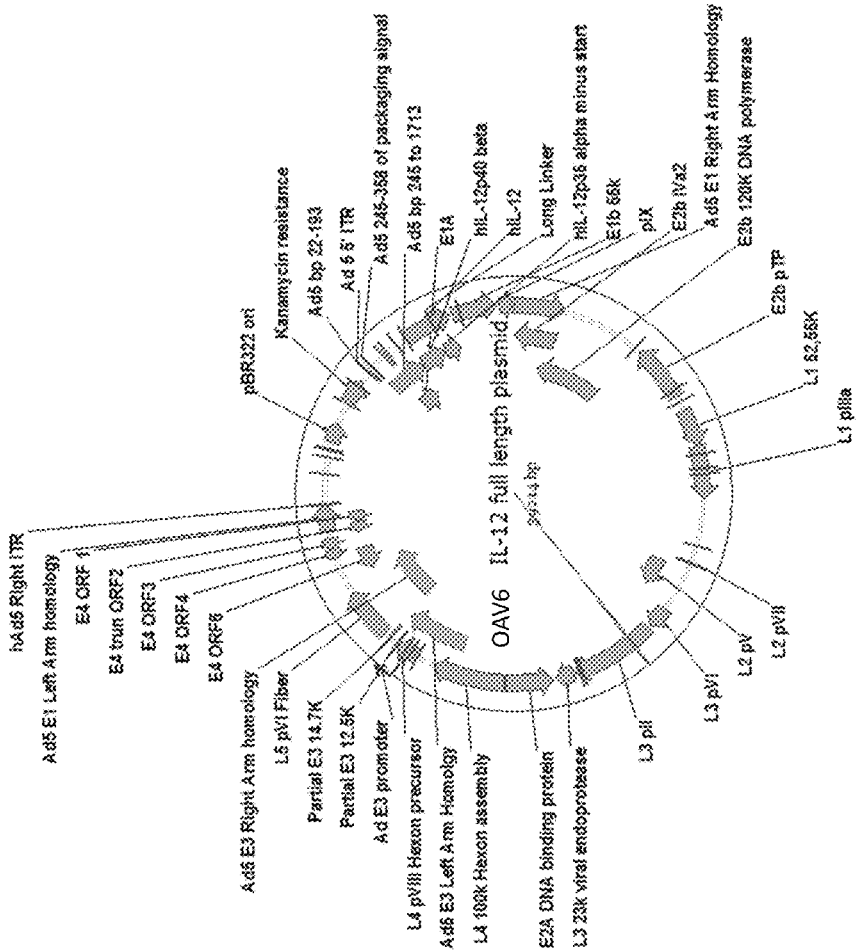
FIG. 5 is an illustration of a vector map showing the plasmid comprising the TRZ6 hIL-12 plasmid.

Example 10. Adenoviral Vectors Expressing an Immunomodulatory Polypeptide from the E4 Region A nucleic acid sequence encoding one or more immunomodulatory polypeptides is inserted into the adenoviral genome by truncation or deletion of a portion of the E4 region of the viral genome. An E4 deletion and exogenous insertion can be utilized in combination with any other viral modification provided herein or otherwise known in the art, or alternatively, without any other viral modification. Exemplary E4 regions useful as insertion sites include truncation or deletion of E4 ORF1 (35,136-35,522 bp) and/or E4 ORF2 (34,696-35,106 bp) (each numbered according to hAd5 vector sequence). The expression of the one or more immunomodulatory polypeptides is controlled by the endogenous E4 promoter. A schematic illustration of this embodiment is provided in FIG. 3.

Figure 9A:
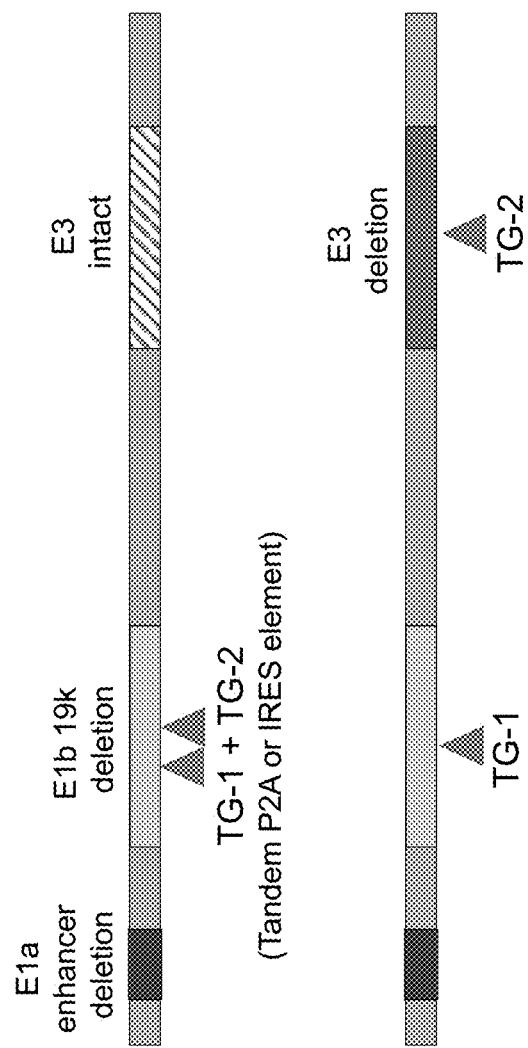
FIG. 9A is graph(s) showing treatment of tumor bearing mice (n=8 in each group) with dual transgene (expressed from E1 and E3) oncolytic viruses comprising transgene(s), with either anti-PD-L1 antibody or anti-PD-1 antibody treatment.
Figure 9B:
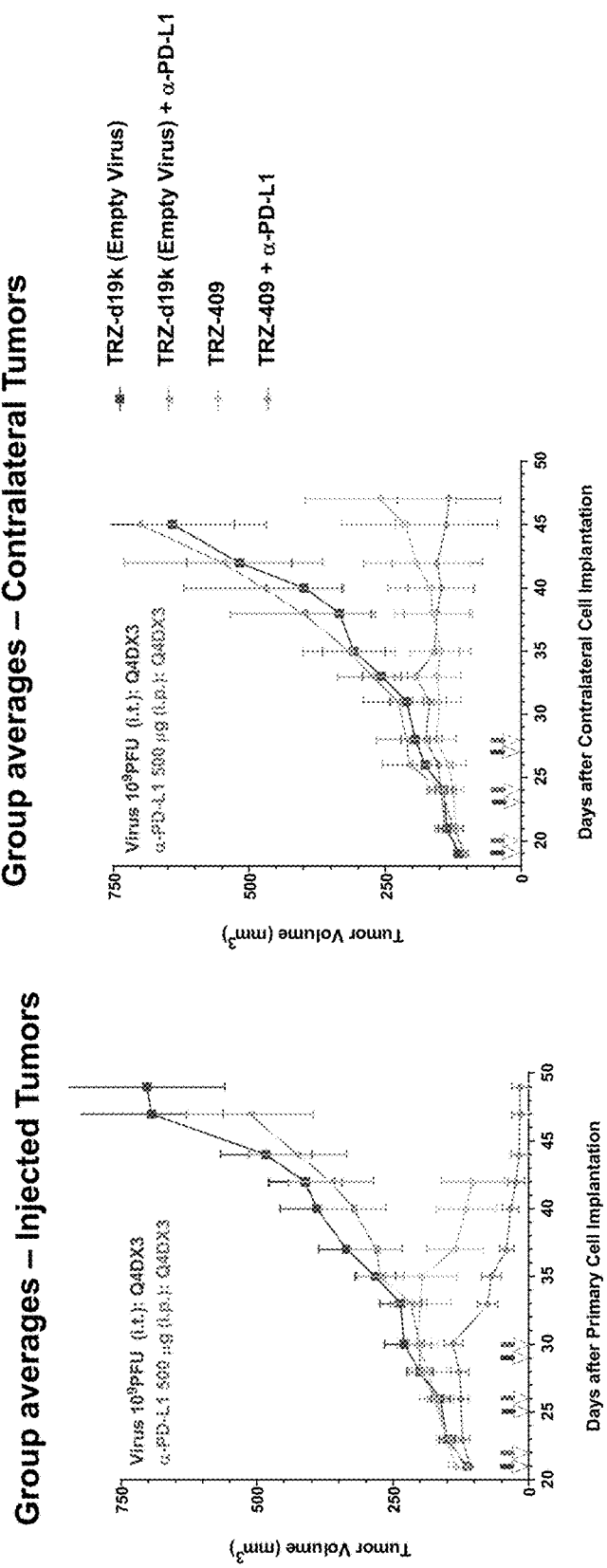
FIG. 9B is graph(s) showing treatment of tumor bearing mice (n=8 in each group) with dual transgene (expressed from E1 and E3) oncolytic viruses comprising transgene(s), with either anti-PD-L1 antibody or anti-PD-1 antibody treatment.

Example 11. Adenoviral Vectors Comprising Altered Configuration of Pea3 Sites Adenoviral vectors are designed in which sequences in and around Pea3 sites I-V near the E1a Enhancer region of adenoviral vectors, in which sequences in and around Pea3 sites are altered, moved, or deleted in order to produce vectors with a variety of expression characteristics. In one embodiment, adenovirus vectors are engineered which have lower affinity Pea3 sites compared to wild-type adenoviral vectors. Such vectors are designed to be efficient in cells in the tumor microenvironment where the concentration of transcription factors is high, but to be relatively inactive in normal (e.g., non-neoplastic) cells, thus reducing the possibility of side effects caused by damage to normal tissue cells. An illustration of the E1a area of wild-type and TAV-255 constructs is shown in FIG. 9A. A cartoon illustration of the proposed method of action of the E1a enhancer region mutants is shown in FIG. 9B. Constructs NV1 to NV7 are based in part on the TAV-255 construct.

In one embodiment, a vector is provided wherein, (in relation to the wild-type sequence) the sequence is removed between Pea3 IV and Pea3 III sites, a single mutation is made in Pea3 III, the sequence between Pea3 III and Pea3 II, and the Pea3 II site is mutated. The sequence of the E1a enhancer region of the exemplary construct NV1 is set forth in SEQ ID NO:99.

In another embodiment, a vector is provided wherein, (in relation to the wild-type sequence) the sequence is removed between Pea3 IV and Pea3 III sites, both Pea3 III and Pea3 II are mutated, and Pea3 V flanking sites are mutated such that the resultant Pea3 V site has an affinity more similar to Pea3 III and enhancer 1. The sequence of the E1a enhancer region of the exemplary construct NV2 is set forth in SEQ ID NO:100.

In another embodiment, a vector is provided wherein, (in relation to the wild-type sequence) the sequence between Pea3 V and Pea3 IV sites is replaced with the sequence between the Pea3 III and Pea3 II sites; the sequence between the Pea3 IV and Pea3 III is deleted; the sequence between the Pea3 III and Pea3 II is deleted; and the Pea3 III and Pea3 II sites are both mutated, as well as the residues 3 bp that are immediately 5' of the Pea3 V site. The sequence of the E1a enhancer region of the exemplary construct NV3 is set forth in SEQ ID NO:101.

In another embodiment, a vector is provided wherein, (in relation to the wild-type sequence) the flanking sequences around the Pea3 III and Pea3 II sites are altered to mimic the lower affinity Pea3 V and Pea3 IV sites (thus engineering a vector in which all Pea3 sites except Pea3 I are lower affinity). The sequence of the E1a enhancer region of the exemplary construct NV4 is set forth in SEQ ID NO:102.

In another embodiment, a vector is provided wherein, (in relation to the wild-type sequence) the flanking sequences around the Pea3 III and Pea3 II sites are altered to mimic the lower affinity Pea3 V and Pea3 IV sites, and a single point mutation is introduced in the Pea3 I site, rendering it a lower affinity Pea3 I site (thus engineering a vector in which all Pea3 sites are lower affinity). The sequence of the E1a enhancer region of the exemplary construct NV5 is set forth in SEQ ID NO:103.

In another embodiment, a vector is provided wherein, (in relation to the wild-type sequence), the flanking sequences around the Pea3 III and Pea3 II sites are altered to mimic the lower affinity Pea3 V and Pea3 IV sites, and the flanking regions of the Pea3 I site are altered, rendering it a lower affinity Pea3 I site (thus engineering a vector in which all Pea3 sites are lower affinity). The sequence of the E1a enhancer region of the exemplary construct NV6 is set forth in SEQ ID NO:104.

In another embodiment, a vector is provided wherein, (in relation to the wild-type sequence) the flanking sequences around the Pea3 I site are altered to produce a lower-affinity Pea3 I site, and the flanking sequences around the Pea3 II site is altered to mimic the lower affinity Pea3 IV site (thus engineering a vector in which all Pea3 sites except Pea3 III are lower affinity). The sequence of the E1a enhancer region of the exemplary construct NV7 is set forth in SEQ ID NO:105.

Example 12. In Vivo Demonstration of Reduction in Tumor Volume with Oncolytic Adenoviral Vectors Comprising E1a Enhancer Region Alterations and Encoding Immunomodulatory Polypeptides: Single Viruses with and without Antibody Treatment Materials and Methods An anti-mPD-L1 antibody is, e.g., from BioXCell®, Catalog# BE0101 (Rat IgG2b). This antibody was used in the below experiments.

Virus samples are stored in 25 mM NaCl, 10 mM Tris Tris(hydroxymethyl)aminomethane), and 5% glycerol with a pH value of 8.0. Vials are stored protected from light at −80° C. On each day of dosing, one vial is thawed at room temperature for approximately 20 minutes. A single dose is $1 \times 10^9$ pfu. Viruses to be combined with anti-PD-L1 in this Example include NV1-NV7 (having E1a enhancer region sequences set forth in SEQ ID Nos:99-105).

The mouse tumor model in this Example uses syngeneic immunocompetent mice. Female Jackson 129S1 (129S1/Sv1mJ) mice are used in this study. Mice are 6-7 weeks old on Day 1 of the experiment. The animals are fed irradiated Harlan 2918.15 Rodent Diet and water ad libitum. Animals are housed in static cages with Bed-O'Cobs™ bedding inside bioBubble® Clean Rooms that provide H.E.P.A filtered air into the bubble environment at 100 complete air changes per hour. All treatments, body weight determinations, and tumor measurements are carried out in the bubble environment. The environment is controlled to a temperature range of 70°±2° F. and a humidity range of 30-70%.

Cell Preparation

ADS-12 cells are grown in RPMI 1640 medium which is modified with 1% 100 mM Na pyruvate, 1% 200 mM L-glutamine, 1% 1M HEPES buffer, 1% of a 45% glucose solution and supplemented with 10% non-heat-inactivated Fetal Bovine Serum (FBS) and 1% 100× Penicillin/Streptomycin/L-Glutamine (PSG). The growth environment is maintained in an incubator with a 5% $CO_2$ atmosphere at 37° C. When expansion is complete, the cells (passage 7) are trypsinized using 0.25% trypsin/2.21 mM EDTA in HBSS solution. Following cell detachment, the trypsin is inactivated by dilution with complete growth medium and any clumps of cells are separated by pipetting. The cells are centrifuged at 200 rcf for 8 minutes at 4° C., the supernatant is aspirated, and the pellet is re-suspended in cold Dulbecco's Phosphate Buffered Saline (DPBS) by pipetting. An aliquot of the homogeneous cell suspension is diluted in a trypan blue solution and counted using a Luna automated cell counter. The cell suspension is centrifuged at 200 rcf for 8 minutes at 4° C. The supernatant is aspirated and the cell pellet is re-suspended in cold Dulbecco's Phosphate Buffered Saline (DPBS) to generate a final concentration of $1 \times 10^7$ trypan-excluding cells/ml. The cell suspension is maintained on wet ice during implantation. Following implantation, an aliquot of the remaining cells is diluted with a trypan blue solution and counted to determine the post-implantation cell viability.

Test animals are implanted subcutaneously on both flanks (on the back between the spine and the hip), the right flank on Day 0 and the left flank on Day 8, with $1 \times 10^6$ cells in 0.1 ml of serum-free medium using a 28-gauge insulin syringe with a fixed needle.

All mice are sorted into study groups based on caliper measurement estimation of tumor burden on Day 15 when the mean tumor burden for all animals on the right flank is approximately 82 mm³ (range of group means, 75-90 mm³). The mice are distributed to ensure that the mean tumor burden on the right flank for all groups is within 10% of the overall mean tumor burden for the study population.

Results

The mean estimated right side tumor burden for all groups in the experiment on the first day of treatment is approximately 82 mm³ and all of the groups in the experiment are well-matched (range of group means, 75-90 mm³). All animals weigh at least 13.3 g at the initiation of therapy. Mean group body weights at first treatment are also well-matched (range, approximately 15.4-18.3 g). A tumor burden of 500 mm³ is chosen for evaluation of efficacy by tumor growth delay for the right and left tumors. The median Control Group tumor burdens will reach 500 mm³ on or about Day 47 for right tumors and on or about Day 43 for left tumors. The median tumor volume doubling times for the Control Group will be approximately 12 and 10 days for the right and left tumors, respectively.

Results of mouse inoculation and tumor growth will show that treatment of tumor bearing mice with oncolytic viruses comprising altered E1a regions and encoding various transgenes, with or without anti-PD-L1, show efficacy in reducing tumor volume.

Example 13. In Vivo Efficacy of Dual-Specificity Oncolytic Adenoviral Vectors in a Bilateral Tumor Model Cancer immunotherapy is moving toward use of combinations to increase efficacy. Combining cancer immunotherapies can expand clinical benefits of existing approved monotherapies; however, systemically-administered combinations can produce excessive toxicity. Therefore, novel dual specificity oncolytic adenoviral vectors were developed having a transgene at both the E1 and the E3 regions in order to evaluate combinations of adenoviral-delivered immunomodulators to enhance systemic antitumor immunity. A summary of exemplary constructs contemplated for use by the methods disclosed herein (with additions to those disclosed in Table 5) is listed in Table 6.

TABLE 6

Exemplary E1/E3 Dual Transgene Constructs and Single Transgene Comparators*

| Name | E1 | E3 |
|---|---|---|
| TRZ-001* | CTLA-4 | Del |
| TRZ-009* | CD70 | intact |
| TRZ-018* | CD70 trimer | Del |
| TRZ-021* | Empty | IL-2 |
| TRZ-032* | IL-2 | Empty (has 12.5K protein) |
| TRZ-401 | CTLA4 | IL-12 |
| TRZ-402 | IL-10 Trap | IL-12 |
| TRZ-403 | IL-7 | IL-12 (has 12.5K protein) |
| TRZ-404 | CD70 | IL-12 |
| TRZ-408* | Empty | IL-12 |
| TRZ-409 | IL-12 | IL-7 |
| TRZ-411 | OX40L | IL-12 |
| TRZ-412 | IL-2 | IL-12 |
| TRZ-414 | CD40L | IL-12 |
| TRZ-415 | IL-12 | CTLA4 |
| TRZ-416 | OX40L (trimer) | IL-12 |
| TRZ-417 | CD40L (trimer) | IL-12 |
| TRZ-418 | CD70 (trimer) | IL-12 |
| TRZ-421 | IL-12 | IL-2 |
| TRZ-510 | IL-7-P2A-IL-12 | TRZ-202-like (no 12.5) |
| TRZ-TBD | IL-7-P2A-IL-12 | IL-2 |

A bilateral tumor model was prepared using ADS-12 tumor cells as described in the Examples above (e.g., Example 7). $1 \times 10^6$ ADS-12 tumor cells injected into primary (−2 days) and contralateral (0 days) flanks. At staging, mice are randomized based on contralateral tumors (88-150 mm³) and primary tumors (88-250 mm³). There are 8 mice/group, with tumors and body weight measured 3 times per week. An anti-PD-L1 (500 μg/dose) or an anti-PD-1 antibody (250 μg/dose) is administered i.p. to induce systemic T cell activation.

In this model, the virus is injected intratumorally (i.t.) into primary tumors only; such injection leads to oncolysis, immune infiltration, and tumor shrinkage. The contralateral tumor is not injected, and no oncolysis occurs. Rather, tumor shrinkage is solely due to antigen-specific activated tumor infiltrating lymphocytes.

Results are shown in FIG. 9. FIG. 9A is a cartoon of the contrast between the single transgene constructs (top) used in the virus mixing examples, and the dual transgene vectors used to make the E1/E3 transgene adenoviruses. FIG. 9B shows the results of mice injected i.t. with Empty virus+/− anti-PD-L1 or with TRZ-409 (IL-12/IL-7 dual transgene)+/− anti-PD-L1. The tumor volume of the injected tumor is shown in the left panel, and the tumor volume of the contralateral tumor is shown in the right panel. For each pair of arrows, the left arrow indicates virus injection and the right arrow indicates anti-PD-L1 injection. As can be seen for both the primary and contralateral tumors, TRZ-409 injection reduced tumor volume significantly compared to empty virus. The combination with anti-PD-L1 was slightly more efficacious in this study.

Figure 9C:
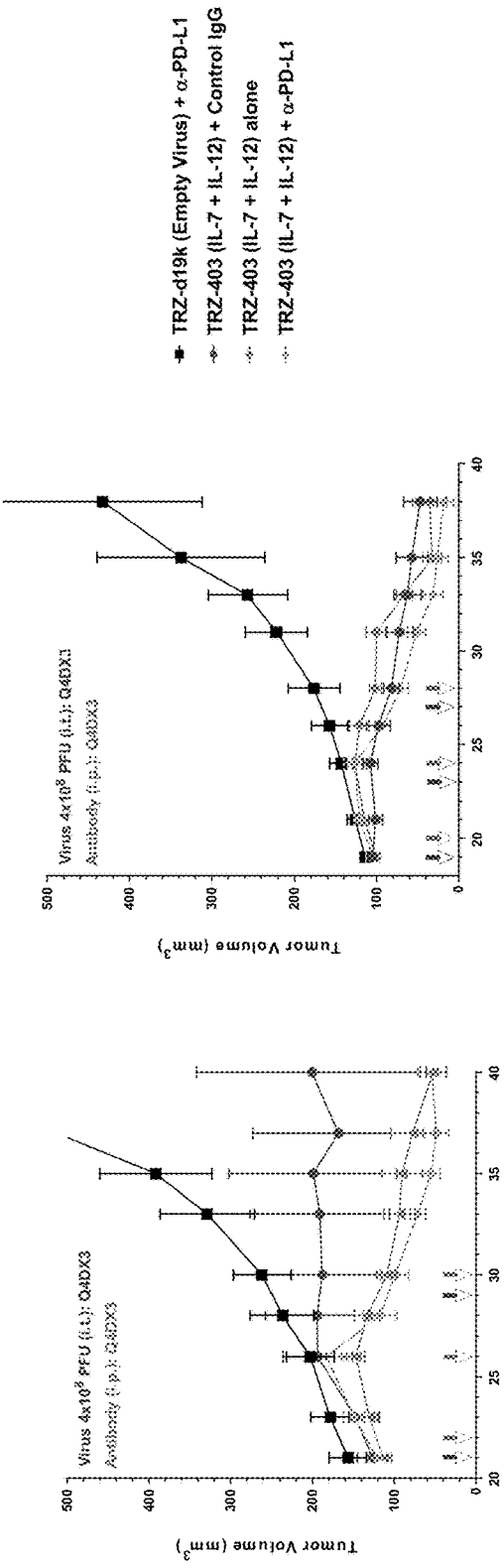
FIG. 9C is graph(s) showing treatment of tumor bearing mice (n=8 in each group) with dual transgene (expressed from E1 and E3) oncolytic viruses comprising transgene(s), with either anti-PD-L1 antibody or anti-PD-1 antibody treatment.
Figure 9D:
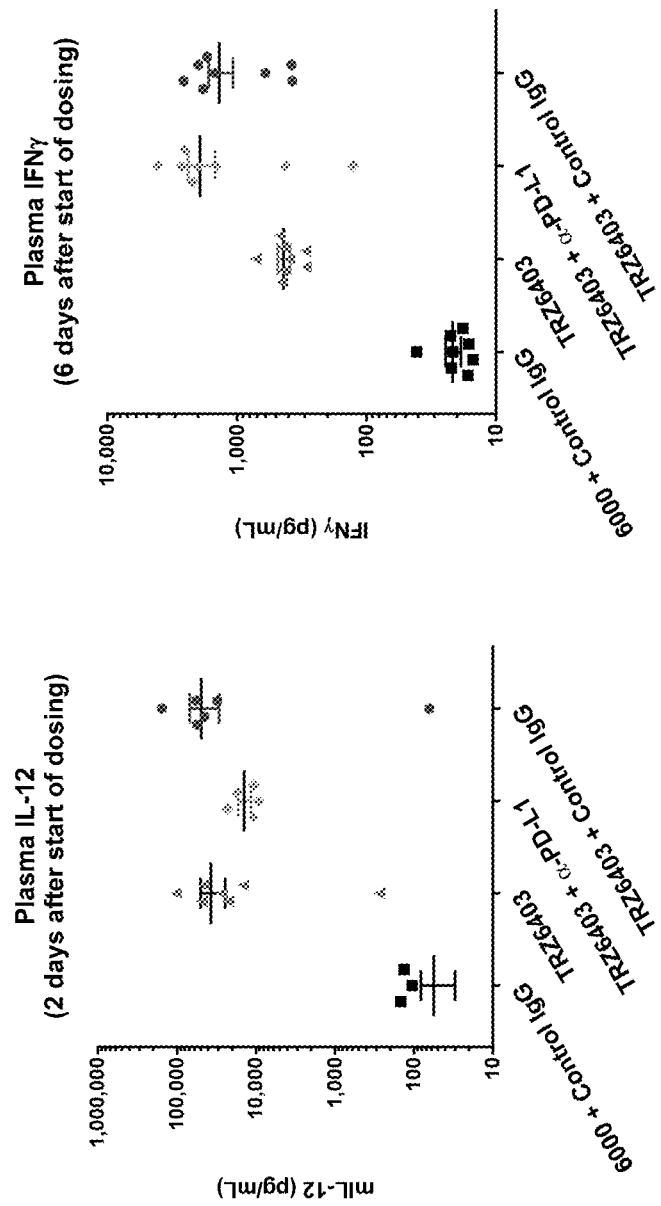
FIG. 9D is graph(s) showing treatment of tumor bearing mice (n=8 in each group) with dual transgene (expressed from E1 and E3) oncolytic viruses comprising transgene(s), with either anti-PD-L1 antibody or anti-PD-1 antibody treatment. As can be seen in the Figure, TRZ-403 strongly inhibits primary and distant tumor growth, with or without anti-PD-L1. Plasma levels of IL-12 and IFN-γ (FIG. 9D) for all mice injected with TRZ-403 show that expression of the transgenes is well tolerated. The study was extended for all mice having tumors over 500 $mm^3$.

FIG. 9C shows the results of a second experiment using the inverse of TRZ-409, TRZ-403, in which the IL-7 transgene occupies the E1 region and the IL-12 gene occupies the E3 region (which has a stronger promoter than the E1). As can be seen in the Figure, TRZ-403 strongly inhibits primary and distant tumor growth, with or without anti-PD-L1. Plasma levels of IL-12 and IFN-γ (FIG. 9D) for all mice injected with TRZ-403 show that expression of the transgenes is well tolerated.

Figure 9E:
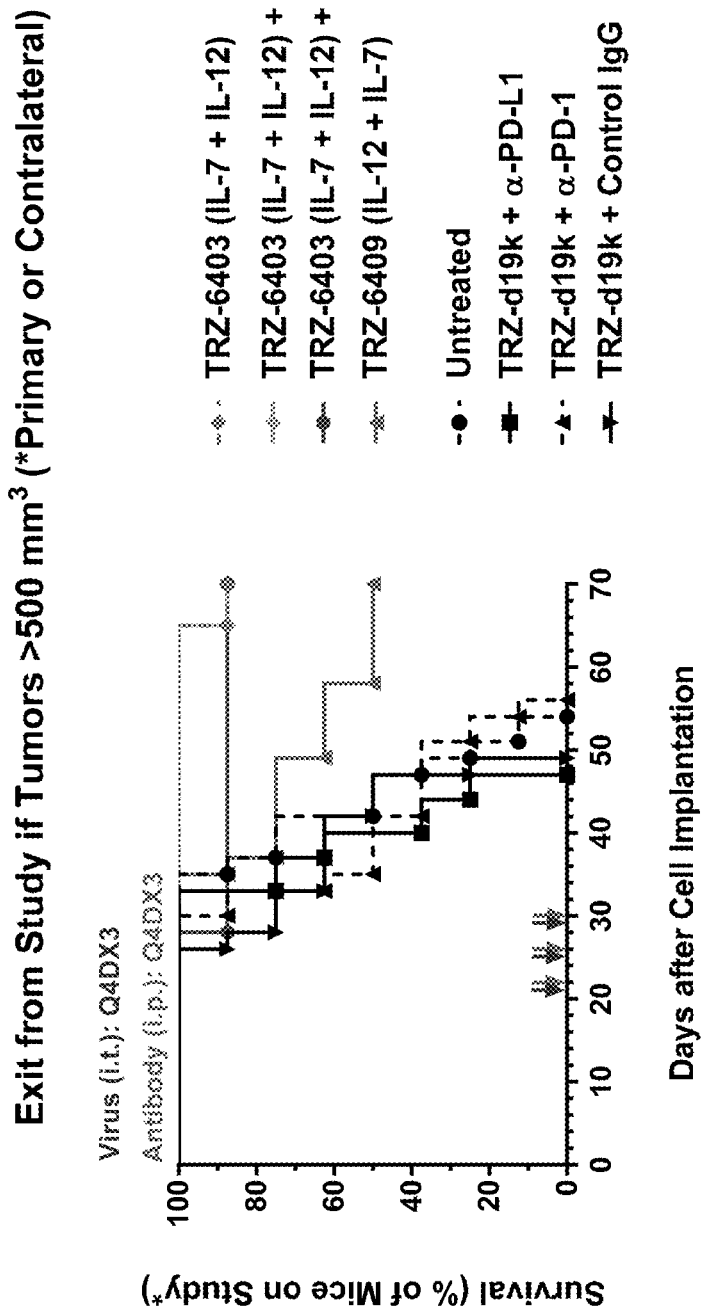
FIG. 9E is graph(s) showing treatment of tumor bearing mice (n=8 in each group) with dual transgene (expressed from E1 and E3) oncolytic viruses comprising transgene(s), with either anti-PD-L1 antibody or anti-PD-1 antibody treatment. As can be seen in the FIG. 9E, mice injected with TRZ-403 had a much higher percentage of survival over TRZ-409 at the time end of the study (70 days). Mice having primary tumors injected with TRZ-403 (IL-7+IL-12), TRZ-403+anti-PD-L1, TRZ-403+control IgG, or TRZ-409 (IL-12+1L-7), and controls including untreated mice and mice injected with empty vector TRZ-d19K with anti-PD-L1, anti-PD-1, or a control IgG. As can be seen in the Figure, mice injected with TRZ-403 had a much higher percentage of survival over TRZ-409 at the time end of the study (70 days). Both TRZ-403 and TRZ-409 showed efficacy over the controls; all mice receiving control injections were deceased by day 56 of the study.

The study was extended for all mice having tumors over 500 mm³. Mice having primary tumors injected with TRZ-403 (IL-7+IL-12), TRZ-403+anti-PD-L1, TRZ-403+control IgG, or TRZ-409 (IL-12+1L-7), and controls including untreated mice and mice injected with empty vector TRZ-d19K with anti-PD-L1, anti-PD-1, or a control IgG are shown in FIG. 9E, which illustrates the survival as a percentage of mice still on study. As can be seen in the Figure, mice injected with TRZ-403 had a much higher percentage of survival over TRZ-409 at the time end of the study (70 days). Both TRZ-403 and TRZ-409 showed efficacy over the controls; all mice receiving control injections were deceased by day 56 of the study.

Figure 9F:
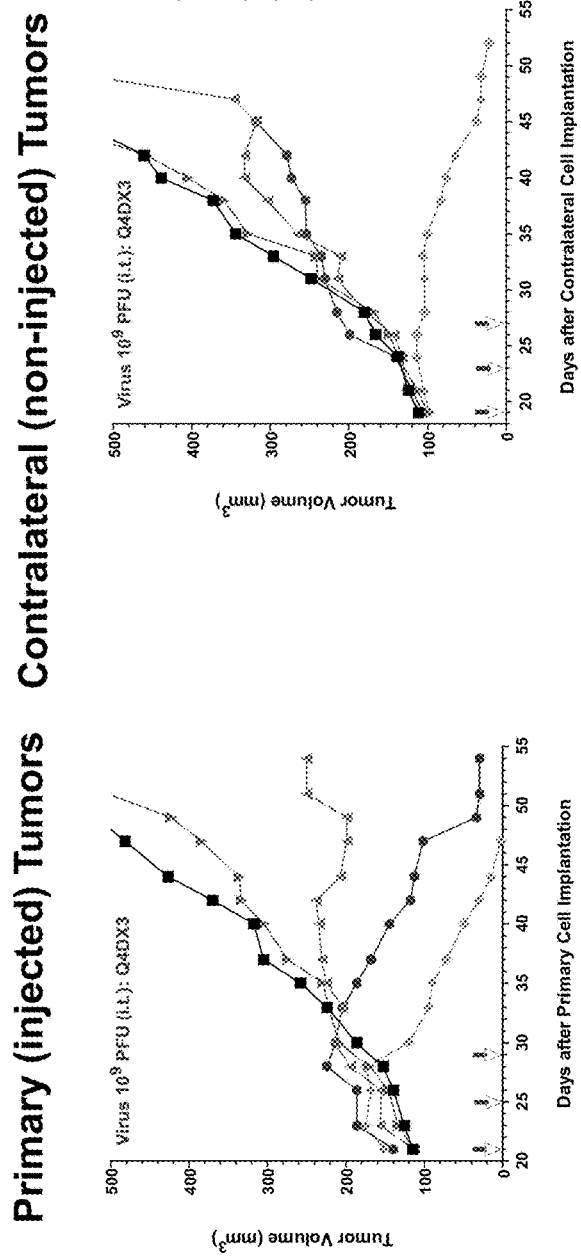
FIG. 9F is graph(s) showing treatment of tumor bearing mice (n=8 in each group) with dual transgene (expressed from E1 and E3) oncolytic viruses comprising transgene(s), with either anti-PD-L1 antibody or anti-PD-1 antibody treatment.
Figure 10:
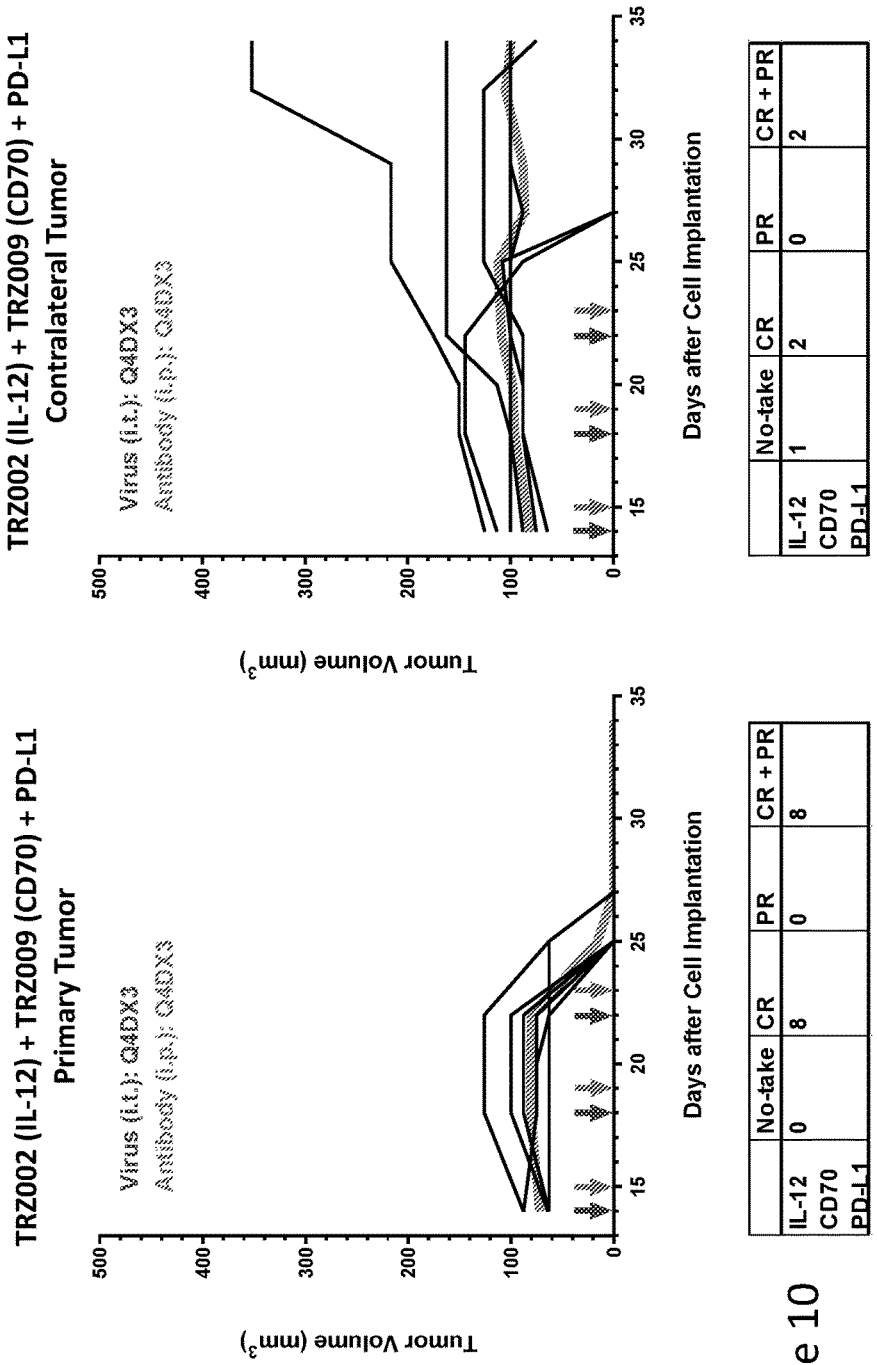
FIG. 10 is graph(s) showing treatment of tumor bearing mice (n=8 in each group) with single and combinations of oncolytic viruses comprising transgene(s), with or without anti-PD-L1 treatment. The left-hand panel of represents the primary tumor into which the virus was injected; the right-hand panel represents the contralateral tumor. The thick line in each graph shows the average tumor volume in mm³. The pairs of arrows on the x-axis represent day of treatment with virus (intratumoral, left arrows) and antibody (intraperitoneal, right arrows). A summary of the responses of the 8 mice is shown in a table at the bottom of each graph, wherein CR=Complete Response (tumor volume=0) and PR=Partial Response (tumor volume on last day of measurements is smaller than tumor volume on the first day of measurements).

Next, a direct comparison was made between the dual transgene virus TRZ-403 (11-7+IL-12) and a mixture of IL-7 and IL-12 single transgene viruses. As can be seen in FIG. 9F, in the primary tumor (left panel) TRZ-403 showed the most efficacy in reducing tumor volume, followed by the mixture of viruses. The single transgene IL-12 virus showed a small amount of efficacy by comparison. In the contralateral tumor, however (right panel) only the dual transgene virus, TRZ-403, reduced the tumor volume, showing significant superiority over the mixture of viruses.

Endnotes

Although the invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, databases, GenBank sequences, patents, and patent applications cited in this specification are herein incorporated by reference as if each specifically and individually indicated to be incorporated by reference.

APPENDIX A

SEQUENCE REFERENCE

| SEQ ID NO: | Molecule | Accession Number(s) or description | Sequence |
|---|---|---|---|
| 1 | hGITR-Ligand (GITR-L; TNFSF18) | NP_005083 | MTLHPSPITCEFLFSTALISPKMCLSHLENMPL SHSRTQGAQRSSWKLWLFCSIVMLLFLCSFS WLIFIFLQLETAKEPCMAKFGPLPSKWQMASS EPPCVNKVSDWKLEILQNGLYLIY GQVAPNANYNDVAPFEVRLYKNKDMIQTLT NKSKIQNVGGTYELHVGDTIDLIFNSEHQVLK NNTYWGIILLANPQFIS |
| 2 | mGITR-Ligand (GITR-L; TNFSF18) | NM_183391 | MEEMPLRESSPQRAERCKKSWLLCIVALLLM LLCSLGTLIYTSLKPTAIESCMVKFELSSSKWH MTSPKPHCVNTTSDGKLKILQSGTYLIYGQVI PVDKKYIKDNAPFVVQIYKKNDVLQTLMNDF QILPIGGVYELHAGDNIYLKFNSKDHIQKTNT YWGIILMPDLPFIS |
| 3 | hCD28 ligand or agonist (CD80) | EAW79565 | MGHTRRQGTSPSKCPYLNFFQLLVLAGLSHF CSGVIHVTKEVKEVATLSCGHNVSVEELAQT RIYWQKEKKMVLTMMSGDMNIWPEYKNRTI FDITNNLSIVILALRPSDEGTYECVVLK YEKDAFKREHLAEVTLSVKADFPTPSISDFEIP TSNIRRIICSTSGGFPEPHLSWLENGEELNAINT TVSQDPETELYAVSSKLDFNMTTNHSFMCLIK YGHLRVNQTFNWNTTKQEHFP DNLLPSWAITLISVNGIFVICCLTYCFAPRCRE RRRNERLRRESVRPV |
| 4 | hTNFα | CAA78745 | MSTESMIRDVELAEEALPKKTGGPQGSRRCLF LSLFSFLIVAGATTLFCLLHFGVIGPQREEFPR DLSLISPLAQAVRSSSRTPSDKPVAHVVANPQ AEGQLQWLNRRANALLANGVELR DNQLVVPSEGLYLIYSQVLFKGQGCPSTHVLL THTISRIAVSYQTKVNLLSAIKSPCQRETPEGA EAKPWYEPIYLGGVFQLEKGDRLSAEINRPDY LDFAESGQVYFGIIAL |
| 5 | Non-cleavable mTNFα | NM_013693 | MIETYSQPSPRSVATGLPASMKIFMYLLTVFLI TQMIGSVLFAVYLHRRLDKVEEEVNLHEDFV FIKKLKRCNKGEGSLSLLNCEEMRRQFEDLV KDITLNKEEKKEDEDPVAHVVANHQVEEQLE WLSQRANALLANGMDLKDNQLVVPADGLY LVYSQVLFKGQGCPDYVLLTHTVSRFAISYQE KVNLLSAVKSPCPKDTPEGAELKPWYEPIYLG GVFQLEKGDQLSAEVNLPKYLDFAESGQVYF GIIAL |

APPENDIX A-continued

SEQUENCE REFERENCE

| SEQ ID NO: | Molecule | Accession Number(s) or description | Sequence |
|---|---|---|---|
| 6 | mGM-CSF | NM_009969 | MWLQNLLFLGIVVYSLSAPTRSPITVTRPWKH VEAIKEALNLLDDMPVTLNEEVEVVSNEFSFK KLTCVQTRLKIFEQGLRGNFTKLKGALNMTA SYYQTYCPPTPETDCETQVTTYADFIDSLKTF LTDIPFECKKPGQK |
| 7 | hICOS ligand or agonist | NP_056074 | MRLGSPGLLFLLFSSLRADTQEKEVRAMVGS DVELSCACPEGSRFDLNDVYVYWQTSESKTV VTYHIPQNSSLENVDSRYRNRALMSPAGMLR GDFSLRLFNVTPQDEQKFHCLVLSQSL GFQEVLSVEVTLHVAANFSVPVVSAPHSPSQ DELTFTCTSINGYPRPNVYWINKTDNSLLDQA LQNDTVFLNMRGLYDVVSVLRIARTPSVNIG CCIENVLLQQNLTVGSQTGNDIGERD KITENPVSTGEKNAATWSILAVLCLLVVVAV AIGWVCRDRCLQHSYAGAWAVSPETELTGHV |
| 8 | h4-1BB ligand or agonist | AAA53134 | MEYASDASLDPEAPWPPAPRARACRVLPWA LVAGLLLLLLLAAACAVFLACPWAVSGARAS PGSAASPRLREGPELSPDDPAGLLDLRQGMFA QLVAQNVLLIDGPLSWYSDPGLAGVSL TGGLSYKEDTKELVVAKAGVYYVFFQLELRR VVAGEGSGSVSLALHLQPLRSAAGAAALT VDLPPASSEARNSAFGFQGRLLHLSAGQRLG VHLHTEARARHAWQLTQGATVLGLFRV TPEIPAGLPSPRSE |
| 9 | hOX40 ligand or agonist | CAE11757 | MCVGARRLGRGPCAALLLLGLGLSTVTGLHC VGDTYPSNDRCCHECRPGNGMVSRCSRSQNT VCRPCGPGFYNDVVSSKPCKPCTWCNLRSGS ERKQLCTATQDTVCRCRAGTQPLDSYK PGVDCAPCPPGHFSPGDNQACKPWTNCTLAG KHTLQPASNSSDAICEDRDPPATQPQETQGPP ARPITVQPTEAWPRTSQGPSTRPVEVPGGRAV AAILGLGLVLGLLGPLAILLALYLL RRDQRLPPDAHKPPGGGSFRTPIQEEQADAHS TLAKI |
| 10 | mOX40 ligand | NM_009452 | MEGEGVQPLDENLENGSRPRFKWKKTLRLV VSGIKGAGMLLCFIYVCLQLSSSPAKDPPIQRL RGAVTRCEDGQLFISSYKNEYQTMEVQNNSV VIKCDGLYIIYLKGSFFQEVKIDLHFREDHNPI SIPMLNDGRRIVFTVVASLAFKDKVYLTVNAP DTLCEHLQINDGELIVVQLTPGYCAPEGSYHS TVNQVPL |
| 11 | hCD40 ligand or agonist | NP_000065 | MIETYNQTSPRSAATGLPISMKIFMYLLTVFLI TQMIGSALFAVYLHRRLDKIEDERNLHEDFVF MKTIQRCNTGERSLSLLNCEEIKSQFEGFVKDI MLNKEETKKENSFEMQKGDQNP QIAAHVISEASSKTTSVLQWAEKGYYTMSNN LVTLENGKQLTVKRQGLYYIYAQVTFCSNRE ASSQAPFIASLCLKSPGRFERILLRAANTHSSA KPCGQQSIHLGGVFELQPGASVFVN VTDPSQVSHGTGFTSFGLLKL |
| 12 | mCD40 ligand | NM_011616 | MIETYSQPSPRSVATGLPASMKIFMYLLTVFLI TQMIGSVLFAVYLHRRLDKVEEEVNLHEDFV FIKKLKRCNKGEGSLSLLNCEEMRRQFEDLV KDITLNKEEKKENSFEMQRGDEDPQIAAHVV SEANSNAASVLQWAKKGYYTMKSNLVMLE NGKQLTVKREGLYYVYTQVTFCSNREPSSQR PFIVGLWLKSSGSERILLKAANTHSSSQLCEQ QSVHLGGVFELQAGASVFVNVTEASQVIHRV GFSSFGLLKL |
| 13 | hCD27 ligand or agonist | AAA36175 | MPEEGSGCSVRRRPYGCVLRAALVPLVAGLV ICLVVCIQRFAQAQQQLPLESLGWDVAELQL NHTGPQQDPRLYWQGGPALGRSFLHGPELDK GQLRIHRDGIYMVHIQVTLAICSSTTA SRHHPTTLAVGICSPASRSISLLRLSFHQGCTIV SQRLTPLARGDTLCTNLGTLLPSRNTDETFF GVQWVRP |

APPENDIX A-continued

SEQUENCE REFERENCE

| SEQ ID NO: | Molecule | Accession Number(s) or description | Sequence |
|---|---|---|---|
| 14 | mCD70 ligand or agonist | NM_011617 | MPEEGRPCPWVRWSGTAFQRQWPWLLLVVF ITVFCCWFHCSGLLSKQQQRLLEHPEPHTAEL QLNLTVPRKDPTLRWGAGPALGRSFTHGPEL EEGHLRIHQDGLYRLHIQVTLANCSSPGSTLQ HRATLAVGICSPAAHGISLLRGRFGQDCTVAL QRLTYLVHGDVLCTNLTLPLLPSRNADETFFG VQWICP |
| 15 | hInterleukin-2 (IL-2) | AAB46883 | MYRMQLLSCIALSLALVTNSAPTSSSTKKTQL QLEHLLLDLQMILNGINNYKNPKLTRMLTFK FYMPKKATELKHLQCLEEELKPLEEVLNLAQ SKNFHLRPRDLISNINVIVLELKGSE TTFMCEYADETATIVEFLNRWITFCQSIISTLT |
| 16 | hInterleukin-7 (IL-7) | AAH47698 | MFHVSFRYIFGLPPLILVLLPVASSDCDIEGKD GKQYESVLMVSIDQLLDSMKEIGSNCLNNEF NFFKRHICDANKEGMFLFRAARKLRQFLKMN STGDFDLHLLKVSEGTTILLNCTGQ VKGRKPAALGEAQPTKSLEENKSLKEQKKLN DLCFLKRLLQEIKTCWNKILMGTKEH |
| 17 | murine Interleukin-7 (IL-7) | MM_008371.5 | MFHVSFRYIFGIPPLILVLLPVTSSECHIKDKEG KAYESVLMISIDELDKMTGTDSNCPNNEPNFF RKHVCDDTKEAAFLNRAARKLKQFLKMNISE EFNVHLLTVSQGTQTLVNCTSKEEKNVKEQK KNDACFLKRLLREIKTCWNKILKGSI |
| 18 | Interleukin-12 (IL-12) alpha subunit | AAD16432 | MWPPGSASQPPPSPAAATGLHPAARPVSLQC RLSMCPARSLLLVATLVLLDHLSLARNLPVA TPDPGMFPCLHHSQNLLRAVSNMLQKARQTL EFYPCTSEEIDHEDITKDKTSTVEACL PLELTKNESCLNSRETSFITNGSCLASRKTSFM MALCLSSIYEDLKMYQVEFKTMNAKLLMDP KRQIFLDQNMLAVIDELMQALNFNSETVPQK SSLEEPDFYKTKIKLCILLHAFRIRAVTIDRVM SYLNAS |
| 19 | hInterleukin-12 (IL-12) receptor subunit beta-1 isoform precursor | NP_005526 | MEPLVTWVVPLLFLFLLSRQGAACRTSECCF QDPPYPDADSGSASGPRDLRCYRISSDRYECS WQYEGPTAGVSHFLRCCLSSGRCCYFAAGSA TRLQFSDQAGVSVLYTVTLWVESWAR NQTEKSPEVTLQLYNSVKYEPPLGDIKVSKLA GQLRMEWETPDNQVGAEVQFRHRTPSSPWK LGDCGPQDDDTESCLCPLEMNVAQEFQLRRR QLGSQGSSWSKWSSPVCVPPENPPQPQ VRFSVEQLGQDGRRRLTLKEQPTQLELPEGC QGLAPGTEVTYRLQLHMLSCPCKAKATRTLH LGKMPYLSGAAYNVAVISSNQFGPGLNQTW HIPADTHTEPVALNISVGTNGTTMYWPA RAQSMTYCIEWQPVGQDGGLATCSLTAPQDP DPAGMATYSWSRESGAMGQEKCYYITIFASA HPEKLTLWSTVLSTYHFGGNASAAGTPHHVS VKNHSLDSVSVDWAPSLLSTCPGVLKE YVVRCRDEDSKQVSEHPVQPTETQVTLSGLR AGVAYTVQVRADTAWLRGVWSQPQRFSIEV QVSDWLIFFASLGSFLSILLVGVLGYLGLNRA ARHLCPPLPTPCASSAIEFPGGKETWQ WINTPVDFQEEASLQEALVVEMSWDKGERTEP LEKTELPEGAPELALDTELSLEDGDRCKAKM |
| 20 | murine Interleukin-12 fusion polypeptide | N/A | MCPQKLTISWFAIVLLVSPLMAMWELEKDVY VVEVDWTPDAPGETVNLTCDTPEEDDITWTS DQRHGVIGSGKTLTITVKEFLDAGQYTCHKG GETLSHSHLLLHKKENGIWSTEILKNFKNKTF LKCEAPNYSGRFTCSWLVQRNMDLKFNIKSS SSSPDSRAVTCGMASLSAEKVTLDQRDYEKY SVSCQEDVTCPTAEETLPIELALEARQQNKYE NYSTSFFIRDIIKPDPPKNLQMKPLKNSQVEVS WEYPDSWSTPHSYFSLKFFVRIQRKKEKMKE TEEGCNQKGAFLVEKTSTEVQCKGGNVCVQ AQDRYYNSSCSKWACVPCRVRSGGGGSGGG GSGGGGSRVIPVSGPARCLSQSRNLLKTTDD MVKTAREKLKHYSCTAEDIDHEDITRDQTST LKTCLPLELHKNESCLATRETSSTTRGSCLPPQ |

APPENDIX A-continued

SEQUENCE REFERENCE

| SEQ ID NO: | Molecule | Accession Number(s) or description | Sequence |
|---|---|---|---|
| | | | KTSLMMTLCLGSIYEDLKMYQTEFQAINAAL QNHNHQQIILDKGMLVAIDELMQSLNHNGET LRQKPPVGEADPYRVKMKLCILLHAFSTRVV TINRVMGYLSSA |
| 21 | hIL-15 | CAA62616 | MRISKPHLRSISIQCYLCLLLNSHFLTEAGIHV FILGCFSAGLPKTEANWVNVISDLKKIEDLIQS MHIDATLYTESDVHPSCKVTAMKCFLLELQV ISLESGDASIHDTVENLIILANNSLSSNGNVTES GCKECEELEEKNIKEFLQSFVHIVQMFINTS |
| 22 | mIL-15 hybrid | N/A | MKILKPYMRNTSISCYLCFLLNSHFLTEAGIH VFILGCVSVGLPKTEANWIDVRYDLEKIESLIQ SIHIDTTLYTDSDFHPSCKVTAMNCFLLELQVI LHEYSNMTLNETVRNVLYLANSTLSSNKNVA ESGCKECEELEEKTFTEFLQSFIRIVQMFINTS GSGATNFSLLKQAGDVEENPGPGTTCPPPVSI EHADIRVKNYSVNSRERYVCNSGFKRKAGTS TLIECVINKNTNVAHWTTPSLKCIRDPSLAHY SPVPTVVTPKVTSQPESPSPSAKEPEAFSPKSD TAMTTETAIMPGSRLTPSQTTSAGTTGTGSHK SSRAPSLAATMTLEPTASTSLRITEISPHSSKM TK |
| 23 | hIL-10 receptor subunit alpha precursor | NP_001549 | MLPCLVVLLAALLSLRLGSDAHGTELPSPPSV WFEAEFFHHILHWTPIPNQSESTCYEVALLRY GIESWNSISNCSQTLSYDLTAVTLDLYHSNGY RARVRAVDGSRHSNWTVTNTRFSV DEVTLTVGSVNLEIHNGFILGKIQLPRPKMAP ANDTYESIFSHFREYEIAIRKVPGNFTFTHKKV KHENFSLLTSGEVGEFCVQVKPSVASRSNKG MWSKEECISLTRQYFTVTNVIIFF AFVLLLSGALAYCLALQLYVRRRKKLPSVLL FKKPSPFIFISQRPSPETQDTIHPLDEEAFLKVS PELKNLDLHGSTDSGFGSTKPSLQTEEPQFLLP DPHPQADRTLGNREPPVLGDSC SSGSSNSTDSGICLQEPSLSPSTGPTWEQQVGS NSRGQDDSGIDLVQNSEGRAGDTQGGSALGH HSPPEPEVPGEEDPAAVAFQGYLRQTRCAEE KATKTGCLEEESPLTDGLGPKFGRC LVDEAGLHPPALAKGYLKQDPLEMTLASSGA PTGQWNQPTEEWSLLALSSCSDLGISDWSFA HDLAPLGCVAAPGGLLGSFNSDLVTLPLISSL QSSE |
| 24 | mIL-10R Trap | N/A | MLSRLLPFLVTISSLSLEFIAYGTELPSPSYVW FEARFFQHILHWKPIPNQSESTYYEVALKQYG NSTWNDIHICRKAQALSCDLTTFTLDLYHRSY GYRARVRAVDNSQYSNWTTTETRFTVDEVIL TVDSVTLKAMDGIIYGTIHPPRPTITPAGDEYE QVFKDLRVYKISIRKFSELKNATKRVKQETFT LTVPIGVRKFCVKVLPRLESRINKAEWSEEQC LLITTEQYFTVTNLSHPASSTKVDKKIVPRDC GCKPCICTVPEVSSVFIFPPKPKDVLTITLTPKV TCVVVDISKDDPEVQFSWFVDDVEVHTAQTQ PREEQFNSTFRSVSELPIMHQDWLNGKEFKCR VNSAAFPAPIEKTISKTKGRPKAPQVYTIPPPK EQMAKDKVSLTCMITDFFPEDITVEWQWNG QPAENYKNTQPIMDTDGSYFVYSKLNVQKSN WEAGNTFTCSVLHEGLHNHHTEKSLSHSPGK |
| 25 | hIL-27 Receptor subunit alpha precursor | NP_004834 | MRGGRGAPFWLWPLPKLALLPLLWVLFQRT RPQGSAGPLQCYGVGPLGDLNCSWEPLGDLG APSELHLQSQKYRSNKTQTVAVAAGRSWVAI PREQLTMSDKLLVWGTKAGQPLWPPVFV NLETQMKPNAPRLGPDVDFSEDDPLEATVHW APPTWPSHKVLICQFHYRRCQEAAWTLLEPE LKTIPLTPVEIQDLELATGYKVYGRCRMEKEE DLWGEWSPILSFQTPPSAPKDVWVSG NLCGTPGGEEPLLLWKAPGPCVQVSYKVWF WVGGRELSPEGITCCCSLIPSGAEWARVSAVN ATSWEPLTNLSLVCLDSASAPRSVAVSSIAGS TELLVTWQPGPGEPLEHVVDWARDGD PLEKLNWVRLPPGNLSALLPGNFTVGVPYRIT |

APPENDIX A-continued

SEQUENCE REFERENCE

| SEQ ID NO: | Molecule | Accession Number(s) or description | Sequence |
|---|---|---|---|
| | | | VTAVSASGLASASSVWGFREELAPLVGPTLW RLQDAPPGTPAIAWGEVPRHQLRGHLTHYTL CAQSGTSPSVCMNVSGNTQSVTLPDL PWGPCELWVTASTIAGQGPPGPILRLHLPDNT LRWKVLPGILFLWGLFLLGCGLSLATSGRCY HLRHKVLPRWVWEKVPDPANSSSGQPHMEQ VPEAQPLGDLPILEVEEMEPPPVMESS QPAQATAPLDSGYEKHFLPTPEELGLLGPPRP QVLA |
| 26 | hIL-13 | AAH96140 | MVWSINLTAGMYCAALESLINVSGCSAIEKT QRMLSGFCPHKVSAGQFSSLHVRDTKIEVAQ FVKDLLLHLKKLFREGRFN |
| 27 | hIL-17 | AAC50341 | MTPGKTSLVSLLLLLSLEAIVKAGITIPRNPGC PNSEDKNFPRTVMVNLNIHNRNTNTNPKRSS DYYNRSTSPWNLHRNEDPERYPSVIWEAKCR HLGCINADGNVDYHMNSVPIQQEIL VLRREPPHCPNSFRLEKILVSVGCTCVTPIVHH VA |
| 28 | hIL-33 Isoform a | NP_001300 974 | MKPKMKYSTNKISTAKWKNTASKALCFKLG KSQQKAKEVCPMYFMKLRSGLMIKKEACYF RRETTKRPSLKTGRKHKRHLVLAACQQQSTV ECFAFGIS GVQKYTRALHDSSITGISPIT EYLASLSTYNDQSITFALEDESYEIYVEDLKK DEKKDKVLLSYYESQHPSNESGDGVDGKML MVTLSPTKDFWLHANNKEHSVELHKCEKPLP DQAFFVLHNMHSNCVSFECKTDPGVFI GVKDNHLALIKVDSSENLCTENILFKLSET |
| 29 | hIL-33 Isoform a | NP_001300 973 | MKPKMKYSTNKISTAKWKNTASKALCFKLG KSQQKAKEVCPMYFMKLRSGLMIKKEACYF RRETTKRPSLKTGRKHKRHLVLAACQQQSTV ECFAFGISGVQKYTRALHDSSITGISPIT EYLASLSTYNDQSITFALEDESYEIYVEDLKK DEKKDKVLLSYYESQHPSNESGDGVDGKML MVTLSPTKDFWLHANNKEHSVELHKCEKPLP DQAFFVLHNMHSNCVSFECKTDPGVFI GVKDNHLALIKVDSSENLCTENILFKLSET |
| 30 | hIL-33 Isoform b | NP_001186 569 | MKPKMKYSTNKISTAKWKNTASKALCFKLG KSQQKAKEVCPMYFMKLRSGLMIKKEACYF RRETTKRPSLKTGRKHKRHLVLAACQQQSTV ECFAFGISGVQKYTRALHDSSITDKVLLS YYESQHPSNESGDGVDGKMLMVTLSPTKDF WLHANNKEHSVELHKCEKPLPDQAFFVLHN MHSNCVSFECKTDPGVFIGVKDNHLALIKVD SSENLCTENILFKLSET |
| 31 | hIL-33 Isoform c | NP_001186 570 | MKPKMKYSTNKISTAKWKNTASKALCFKLG NKVLLSYYESQHPSNESGDGVDGKMLMVTL SPTKDFWLHANNKEHSVELHKCEKPLPDQAF FVLHNMHSNCVSFECKTDPGVFIGVKDNH LALIKVDSSENLCTENILFKLSET |
| 32 | hIL-33 Isoform d | NP_001300 975; NP_001300 976 | MKPKMKYSTNKISTAKWKNTASKALCFKLG KSQQKAKEVCPMYFMKLRSGLMIKKEACYF RRETTKRPSLKTGRKHKRHLVLAACQQQSTV ECFAFGISGVQKYTRALHDSSITEYLASL STYNDQSITFALEDESYEIYVEDLKKDEKDK VLLSYYESQHPSNESGDGVDGKMLMVTLSPT KDFWLHANNKEHSVELHKCEKPLPDQAFFVL HNMHSNCVSFECKTDPGVFIGVKDNH LALIKVDSSENLCTENILFKLSET |
| 33 | hIL-33 Isoform e | NP—001300 977 | MKPKMKYSTNKISTAKWKNTASKALCFKLG KSQQKAKEVCPMYFMKLRSGLMIKKEACYF RRETTKRPSLKTGISPITEYLASLSTYNDQSITF ALEDESYEIYVEDLKKDEKKDKVLLS YYESQHPSNESGDGVDGKMLMVTLSPTKDF WLHANNKEHSVELHKCEKPLPDQAFFVLHN MHSNCVSFECKTDPGVFIGVKDNHLALIKVD SSENLCTENILFKLSET |

APPENDIX A-continued

SEQUENCE REFERENCE

| SEQ ID NO: | Molecule | Accession Number(s) or description | Sequence |
|---|---|---|---|
| 34 | hIFN-γ | AAB59534 | MKYTSYILAFQLCIVLGSLGCYCQDPYVKEA ENLKKYFNAGHSDVADNGTLFLGILKNWKEE SDRKIMQSQIVSFYFKLFKNFKDDQSIQKSVE TIKEDMNVKFFNSNKKKRDDFEKLTN YSVTDLNVQRKAIHELIQVMAELSPAAKTGK RKRSQMLFRGRRASQ |
| 35 | Flagellin | p06179 | MAQVINTNSLSLLTQNNLNKSQSALGTAIERL SSGLRINSAKDDAAGQAIANRFTANIKGLTQA SRNANDGISIAQTTEGALNEINNNLQRVRELA VQSANSTNSQSDLDSIQAEITQRLNEIDRVSG QTQFNGVKVLAQDNTLTIQVGANDGETIDID LKQINSQTLGLDTLNVQQKYKVSDTAATVTG YADTTIALDNSTFKASATGLGGTDQKIDGDL KFDDTTGKYYAKVTVTGGTGKDGYYEVSVD KTNGEVTLAGGATSPLTGGLPATATEDVKNV QVANADLTEAKAALTAAGVTGTASVVKMSY TDNNGKTIDGGLAVKVGDDYYSATQNKDGSI SINITTKYTADDGTSKTALNKLGGADGKTEVV SIGGKTYAASKAEGHNFKAQPDLAEAAATTT ENPLQKIDAALAQVDTLRSDLGAVQNRFNSA ITNLGNTVNNLTSARSRIEDSDYATEVSNMSR AQILQQAGTSVLAQANQVPQNVLSLLR |
| 36 | anti-CTLA4 (CTLA-4 antagonist antibody) | N/A | MDMRVPAQLLGLLLLWLRGARCDIVMTQTT LSLPVSLGDQASISCRSSQSIVHSNGNTYLEW YLQKPGQSPKLLIYKVSNRFSGVPDRFSGSGS GTDFTLKISRVEAEDLGVYYCFQGSHVPYTFG GGTKLEIKRADAAPTVSGSGGGSGGGSGGGS EAKLQESGPVLVKPGASVKMSCKASGYTFTD YYMNWVKQSHGKSLEWIGVINPYNGDTSYN QKFKGKATLTVDKSSTAYMELNSLTSEDSA VYYCARYYGSWFAYWGQGTLITVSTEPRGPT IKPCPPCKCPAPNLLGGPSVFIFPPKIKDVLMIS LSPIVTCVVVDVSEDDPDVQISWFVNNVEVH TAQTQTHREDYNSTLRVVSALPIQHQDWMSG KEFKCKVNNKDLPAPIERTISKPKGSVRAPQV YVLPPPEEEMTKKQVTLTCMVTDFMPEDIYV EWTNNGKTELNYKNTEPVLDSDGSYFMYSK LRVEKKNWVERNSYSCSVVHEGLHNHHTTK SFSRTPGK |
| 37 | murine IL-2 | DNA (NM_008366.3) | TATCACCCTTGCTAATCACTCCTCACAGTGA CCTCAAGTCCTGCAGGCATGTACAGCATGC AGCTCGCATCCTGTGTCACATTGACACTTGT GCTCCTTGTCAACAGCGCACCCACTTCAAG CTCCACTTCAAGCTCTACAGCGGAAGCACA GCAGCAGCAGCAGCAGCAGCAGCAGCAGC AGCAGCACCTGGAGCAGCTGTTGATGGACC TACAGGAGCTCCTGAGCAGGATGGAGAATT ACAGGAACCTGAAACTCCCCAGGATGCTCA CCTTCAAATTTTACTTGCCCAAGCAGGCCA CAGAATTGAAAGATCTTCAGTGCCTAGAAG ATGAACTTGGACCTCTGCGGCATGTTCTGG ATTTGACTCAAAGCAAAAGCTTTCAATTGG AAGATGCTGAGAATTTCATCAGCAATATCA GAGTAACTGTTGTAAAACTAAAGGGCTCTG ACAACACATTTGAGTGCCAATTCGATGATG AGTCAGCAACTGTGGTGGACTTTCTGAGGA GATGGATAGCCTTCTGTCAAAGCATCATCT CAACAAGCCCTCAATAACTATGTACCTCCT GCTTACAACACATAAGGCTCTCTATTTATTT AAATATTTAACTTTAATTTATTTTTGGATGT ATTGTTTACTATCTTTTGTAACTACTAGTCT TCAGATGATAAATATGGATCTTTAAAGATT CTTTTTGTAAGCCCCAAGGGCTCAAAAATG TTTTAAACTATTTATCTGAAATTATTTATTA TATTGAATTGTTAAATATCATGTGTAGGTA GACTCATTAATAAAAGTATTTAGATGATTC AAATATAAATAAGCTCAGATGTCTGTCATT TTAGGACAGCACAAAGTAAGCGCTAAAAT AACTTCTCAGTTATTCCTGTGAACTCTATGT TAATCAGTGTTTTCAAGAAATAAAGCTCTC CTCTAAAAAAAAAAAAAAA |

APPENDIX A-continued

SEQUENCE REFERENCE

| SEQ ID NO: | Molecule | Accession Number(s) or description | Sequence |
|---|---|---|---|
| 38 | murine IL-2 | amino acid CAA25909 | MYSMQLASCVTLTLVLLVNSAPTSSSTSSSTA EAQQQQQQQQQQQQHLEQLLMDLQELLSRM ENYRNLKLPRMLTFKFYLPKQATELKDLQCL EDELGPLRHVLDLTQSKSFQLEDAENFISNIRV TVVKLKGSDNTFECQFDDESATVVDFLRRWI AFCQSIISTSPQ |
| 39 | murine Xcl1 | DNA (GenBank: BC062249.1) | AGCCCAGCAAGACCTCAGCCATGAGACTTC TCCTCCTGACTTTCCTGGGAGTCTGCTGCCT CACCCCATGGGTTGTGGAAGGTGTGGGGAC TGAAGTCCTAGAAGAGAGTAGCTGTGTGAA CTTACAAACCCAGCGGCTGCCAGTTCAAAA AATCAAGACCTATATCATCTGGGAGGGGGC CATGAGAGCTGTAATTTTTGTCACCAAACG AGGACTAAAAATTTGTGCTGATCCAGAAGC CAAATGGGTGAAAGCAGCGATCAAGACTGT GGATGGCAGGGCCAGTACCAGAAAGAACA TGGCTGAAACTGTTCCCACAGGAGCCCAGA GGTCCACCAGCACAGCGATAACCCTGACTG GGTAACAGCCTCCAGGACAATGTTTCCTCA CTCGTTAAGCAGCTCATCTCAGTTCCCAAA CCCATTGCACAAATACTTATTTTTATTTTTA ACGACATTCACATTCATTTCAAATGTTATAA GTAATAAATATTTATTATTGATGAAAAAAA AAAAAAAAAAAA |
| 40 | murine Xcl1 | amino acid (GenBank: BC062249.1) | MRLLLLTFLGVCCLTPWVVEGVGTEVLEESS CVNLQTQRLPVQKIKTYIIWEGAMRAVIFVTK RGLKICADPEAKWVKAAIKTVDGRASTRKN MAETVPTGAQRSTSTAITLTG |
| 41 | Murine 4-1BBL (TNFSF9) | (DNA) GenBank: BC138767.1 | GAGACGTGCACTGACCGACCGTGGTAATGG ACCAGCACACACTTGATGTGGAGGATACCG CGGATGCCAGACATCCAGCAGGTACTTCGT GCCCCTCGGATGCGGCGCTCCTCAGAGATA CCGGGCTCCTCGCGGACGCTGCGCTCCTCT CAGATACTGTGCGCCCCACAAATGCCGCGC TCCCCACGGATGCTGCCTACCCTGCGGTTA ATGTTCGGGATCGCGAGGCCGCGTGGCCGC CTGCACTGAACTTCTGTTCCCGCCACCCAA AGCTCTATGGCCTAGTCGCTTTGGTTTTGCT GCTTCTGATCGCCGCCTGTGTTCCTATCTTC ACCCGCACCGAGCCTCGGCCAGCGCTCACA ATCACCACCTCGCCCAACCTGGGTACCCGA GAGAATAATGCAGACCAGGTCACCCCTGTT TCCCACATTGGCTGCCCCAACACTACACAA CAGGGCTCTCCTGTGTTCGCCAAGCTACTG GCTAAAAACCAAGCATCGTTGTGCAATACA ACTCTGAACTGGCACAGCCAAGATGGAGCT GGGAGCTCATACCTATCTCAAGGTCTGAGG TACGAAGAAGACAAAAAGGAGTTGGTGGT AGACAGTCCCGGGCTCTACTACGTATTTTTG GAACTGAAGCTCAGTCCAACATTCACAAAC ACAGGCCACAAGGTGCAGGGCTGGGTCTCT CTTGTTTTGCAAGCAAAGCCTCAGGTAGAT GACTTTGACAACTTGGCCCTGACAGTGGAA CTGTTCCCTTGCTCCATGGAGAACAAGTTA GTGGACCGTTCCTGGAGTCAACTGTTGCTC CTGAAGGCTGGCCACCGCCTCAGTGTGGGT CTGAGGGCTTATCTGCATGGAGCCCAGGAT GCATACAGAGACTGGGAGCTGTCTTATCCC AACACCACCAGCTTTGGACTCTTTCTTGTGA AACCCGACAACCCATGGGAATGAGAACTAT CCTTCTTGTGACTCCTAGTTGCTAAGTCCTC AAGCTGCTATGTTTTATGGGGTCTGAGCAG GGGT |
| 42 | Murine 4-1BBL (TNFSF9) | (protein) GenBank: BC138767.1 | MDQHTLDVEDTADARHPAGTSCPSDAALLR DTGLLADAALLSDTVRPTNAALPTDAAYPAV NVRDREAAWPPALNFCSRHPKLYGLVALVLL LLIAACVPIFTRTEPRPALTITTSPNLGTRENNA DQVTPVSHIGCPNTTQQGSPVFAKLLAKNQA SLCNTTLNWHS QDGAGSSYLS QGLRYEEDKK ELVVDSPGLYYVFLELKLSPTFTNTGHKVQG |

APPENDIX A-continued

SEQUENCE REFERENCE

| SEQ ID NO: | Molecule | Accession Number(s) or description | Sequence |
|---|---|---|---|
| | | | WVSLVLQAKPQVDDFDNLALTVELFPCSMEN KLVDRSWSQLLLLKAGHRLSVGLRAYLHGA QDAYRDWELSYPNTTSFGLFLVKPDNPWE |
| 43 | Mouse 4-1BBL trimeric version | with human IGKV1-39 kappa LC signal sequence, trimerization domain from yeast, and Linker 1, followed by 4-1BBL (TNFSF9, Acc# P41274) residues 104-309 (minus ECD and transmembrane domain) | MDMRVPAQLLGLLLLWLRGARCRMKQIEDK IEEILSKIYHIENEIARIKKLIGERGGGSGGGSG GGSRTEPRPALTITTSPNLGTRENNADQVTPV SHIGCPNTTQQGSPVFAKLLAKNQASLCNTTL NWHSQDGAGSSYLSQGLRYEEDKKELVVDS PGLYYVFLELKLSPTFTNTGHKVQGWVSLVL QAKPQVDDFDNLALTVELFPCSMENKLVDRS WSQLLLLKAGHRLSVGLRAYLHGAQDAYRD WELSYPNTTSFGLFLVKPDNPWE** |
| 44 | murine 4-1BBL (TNFSF9, p41274) | residues 104-209 (minus ECD and transmembrane domain) | RTEPRPALTITTSPNLGTRENNADQVTPVSHIG CPNTTQQGSPVFAKLLAKNQASLCNTTLNWH SQDGAGSSYLSQGLRYEEDKKELVVDSPGLY YVFLELKLSPTFTNTGHKVQGWVSLVLQAKP QVDDFDNLALTVELFPCSMENKLVDRSWSQL LLLKAGHRLSVGLRAYLHGAQDAYRDWELS YPNTTSFGLFLVKPDNPWE** |
| 45 | Linker 1 | 15-mer | GGGGSGGGGSGGGGS |
| 46 | TRZ202 (hIL-12 Insert) | AA Sequence | MCHQQLVISWFSLVFLASPLVAIWELKKDVY VVELDWYPDAPGEMVVLTCDTPEEDGITWTL DQSSEVLGSGKTLTIQVKEFGDAGQYTCHKG GEVLSHSLLLLHKKEDGIWSTDILKDQKEPKN KTFLRCEAKNYSGRFTCWWLTTISTDLTFSVK SSRGSSDPQGVTCGAATLSAERVRGDNKEYE YSVECQEDSACPAAEESLPIEVMVDAVHKLK YENYTSSFFIRDIIKPDPPKNLQLKPLKNSRQV EVSWEYPDTWSTPHSYFSLTFCVQVQGKSKR EKKDRVFTDKTSATVICRKNASISVRAQDRY YSSSWSEWASVPCSGGGGSGGGGSGGGGSR NLPVATPDPGMFPCLHHSQNLLRAVSNMLQK ARQTLEFYPCTSEEIDHEDITKDKTSTVEACLP LELTKNESCLNSRETSFITNGSCLASRKTSFM MALCLSSIYEDLKMYQVEFKTMNAKLLMDP KRQIFLDQNMLAVIDELMQALNFNSETVPQK SSLEEPDFYKTKIKLCILLHAFRIRAVTIDRVM SYLNAS** |
| 47 | hIL-12 p40β | AF180563 | MCHQQLVISWFSLVFLASPLVAIWELKKDVY VVELDWYPDAPGEMVVLTCDTPEEDGITWTL DQSSEVLGSGKTLTIQVKEFGDAGQYTCHKG GEVLSHSLLLLHKKEDGIWSTDILKDQKEPKN KTFLRCEAKNYSGRFTCWWLTTISTDLTFSVK SSRGSSDPQGVTCGAATLSAERVRGDNKEYE YSVECQEDSACPAAEESLPIEVMVDAVHKLK YENYTSSFFIRDIIKPDPPKNLQLKPLKNSRQV EVSWEYPDTWSTPHSYFSLTFCVQVQGKSKR EKKDRVFTDKTSATVICRKNASISVRAQDRY YSSSWSEWASVPCS |
| 48 | hIL-12 p35α | AA Sequence of Accession #AF101062.1 (native start codon and signal sequence removed) | RNLPVATPDPGMFPCLHHSQNLLRAVSNMLQ KARQTLEFYPCTSEEIDHEDITKDKTSTVEAC LPLELTKNESCLNSRETSFITNGSCLASRKTSF MMALCLSSIYEDLKMYQVEFKTMNAKLLMD PKRQIFLDQNMLAVIDELMQALNFNSETVPQ KSSLEEPDFYKTKIKLCILLHAFRIRAVTIDRV MSYLNAS** |

APPENDIX A-continued

SEQUENCE REFERENCE

| SEQ ID NO: | Molecule | Accession Number(s) or description | Sequence |
|---|---|---|---|
| SEQ ID NOS 49 and 107 | (TRZ015) hGITRL insert, Trimeric version | AA Sequence, including Kozak sequences, RE sites, and stop codons | GTCGACGCCACCMDMRVPAQLLGLLLLWL RGARCRMKQIEDKIEEILSKIYHIENEIARIKKL IGERGGGSGGGSGGGSETAKEPCMAKFGPLP SKWQMASSEPPCVNKVSDWKLEILQNGLYLI YGQVAPNANYNDVAPFEVRLYKNKDMIQTL TNKSKIQNVGGTYELHVGDTIDLIFNSEHQVL KNNTYWGIILLANPQFIS CTCGAG** |
| 50 | hIGKV1-39 kappa LC signal sequence | AA Sequence | MDMRVPAQLLGLLLLWLRGARC |
| 51 | Trimerization domain (yeast) | AA Sequence | RMKQIEDKIEEILSKIYHIENEIARIKKLIGER |
| 52 | GITRL minus ECD and transmembrane domains | AA Sequence | ETAKEPCMAKFGPLPSKWQMASSEPPCVNKV SDWKLEILQNGLYLIYGQVAPNANYNDVAPF EVRLYKNKDMIQTLTNKSKIQNVGGTYELHV GDTIDLIFNSEHQVLKNNTYWGIILLANPQFIS ** |
| 53 | Linker 2 | 12-mer | GGGSGGGSGGGS |
| 54 | TRZ006: hIL-15 hybrid | hIL-15Rα-Linker-hIL-15 | MAPRRARGCRTLGLPALLLLLLRPPATRGIT CPPPMSVEHADIWVKSYSLYSRERYICNSGFK RKAGTSSLTECVLNKATNVAHWTTPSLKCIR DPALVHQRPAPPSTVTTASGGSGGGSGGGS GGGGSNWVNVISDLKKIEDLIQSMHIDATLYT ESDVHPSCKVTAMKCFLLELQVISLESGDASI HDTVENLIILANNSLSSNGNVTESGCKECEEL EEKNIKEFLQSFVHIVQMFINTS** |
| 55 | hIL-15Rα endogenous signal peptide | AA Sequence | MAPRRARGCRTLGLPALLLLLLRPPATRG |
| 56 | Sushi domain from IL-15Rα | AA Sequence | MSVEHADIWVKSYSLYSRERYICNSGFKRKA GTSSLTECVLNKATNVAHWTTPSLKCIRDPAL VHQRPAPPSTVTTA |
| 57 | mature hIL-15 | AA Sequence | NWVNVISDLKKIEDLIQSMHIDATLYTESDVH PSCKVTAMKCFLLELQVISLESGDASIHDTVE NLIILANNSLSSNGNVTESGCKECEELEEKNIK EFLQSFVHIVQMFINTS |
| 58 | TRZ201: hαCTLA4 | Orientation 2 ANT2054 scFv-IgG1 Fc | MDMRVPAQLLGLLLLWLRGARCEIVLTQSPA TLSLSPGERATLSCSASSSISYMHWFQQRPGQ SPRRWIYDTSKLASGVPARFSGSGSGTDYTLT ISSLEPEDFATYYCHQRTSYPLTFGQGTKLEIK GGGGSGGGGSGGGGSQVQLVQSGAELKKPG ASVKVSCKASGYTFTSYWINWIRQAPGQGLE WIGRIAPGSGTTYYNEVFKGRVTITVDKSTST AYMELSSLRSEDTAVYFCARGDYGSYWGQG TLVTVSSDKTHTCPPCPAPELLGGPSVFLFPPK PKDTLMISRTPEVTCVVVDVSHEDPEVKFNW YVDGVEVHNAKTKPREEQYNSTYRVVSVLT VLHQDWLNGKEYKCKVSNKALPAPIEKTISK AKGQPREPQVYTLPPSREEMTKNQVSLTCLV KGFYPSDIAVEWESNGQPENNYKTTPPVLDS DGSFFLYSKLTVDKSRWQQGNVFSCSVMHE ALHNHYTQKSLSLSPGK** |
| 59 | Kappa variable | AA Sequence | EIVLTQSPATLSLSPGERATLSCSASSSISYMH WFQQRPGQSPRRWIYDTSKLASGVPARFSGS GSGTDYTLTISSLEPEDFATYYCHQRTSYPLTF GQGTKLEIK |
| 60 | Heavy variable | AA Sequence | QVQLVQSGAELKKPGASVKVSCKASGYTFTS YWINWIRQAPGQGLEWIGRIAPGSGTTYYNE VFKGRVTITVDKSTSTAYMELSSLRSEDTAVY FCARGDYGSYWGQGTLVTVSS |

APPENDIX A-continued

SEQUENCE REFERENCE

| SEQ ID NO: | Molecule | Accession Number(s) or description | Sequence |
|---|---|---|---|
| 61 | human Fc IgG1 | AA Sequence | DKTHTCPPCPAPELLGGPSVFLFPPKPKDTLMI SRTPEVTCVVVDVSHEDPEVKFNWYVDGVE VHNAKTKPREEQYNSTYRVVSVLTVLHQDW LNGKEYKCKVSNKALPAPIEKTISKAKGQPRE PQVYTLPPSREEMTKNQVSLTCLVKGFYPSDI AVEWESNGQPENNYKTTPPVLDSDGSFFLYS KLTVDKSRWQQGNVFSCSVMHEALHNHYTQ KSLSLSPGK** |
| 62 | TRZ106 | hIL-15 hybrid (hIL-15Rα-Linker 2-hIL-15) (hIL-15Rα endogenous signal peptide, Sushi domain from IL-15Rα, linker, mature hIL-15) | MAPRRARGCRTLGLPALLLLLLRPPATRGIT CPPPMSVEHADIWVKSYSLYSRERYICNSGFK RKAGTSSLTECVLNKATNVAHWTTPSLKCIR DPALVHQRPAPPSTVTTASGGSGGGGSGGGS GGGGSNWVNVISDLKKIEDLIQSMHIDATLYT ESDVHPSCKVTAMKCFLLELQVISLESGDASI HDTVENLIILANNSLSSNGNVTESGCKECEEL EEKNIKEFLQSFVHIVQMFINTS** |
| 63 | hIL-15Rα endogenous signal peptide | | MAPRRARGCRTLGLPALLLLLLRPPATRG |
| 64 | mature hIL-15 | | NWVNVISDLKKIEDLIQSMHIDATLYTESDVH PSCKVTAMKCFLLELQVISLESGDASIHDTVE NLIILANNSLSSNGNVTESGCKECEELEEKNIK EFLQSFVHIVQMFINTS |
| 65 | TRZ108: hCD40 | full length monomeric version, membrane bound | MIETYNQTSPRSAATGLPISMKIFMYLLTVFLI TQMIGSALFAVYLHRRLDKIEDERNLHEDFVF MKTIQRCNTGERSLSLLNCEEIKSQFEGFVKDI MLNKEETKKENSFEMQKGDQNPQIAAHVISE ASSKTTSVLQWAEKGYYTMSNNLVTLENGK QLTVKRQGLYYIYAQVTFCSNREASSQAPFIA SLCLKSPGRFERILLRAANTHSSAKPCGQQSIH LGGVFELQPGASVFVNVTDPSQVSHGTGFTSF GLLKL** |
| 66 | TRZ111: hOX40L variant 1 | full length monomeric version, membrane bound | MERVQPLEENVGNAARPRFERNKLLLVASVI QGLGLLLCFTYICLHFSALQVSHRYPRIQSIKV QFTEYKKEKGFILTSQKEDEIMKVQNNSVIIN CDGFYLISLKGYFSQEVNISLHYQKDEEPLFQ LKKVRSVNSLMVASLTYKDKVYLNVTTDNT SLDDFHVNGGELILIHQNPGEFCVL** |
| 67 | TRZ114: hIL-10RTrap Version2 | Extracellular domain of hIL-10Rα with endogenous signal sequence, without stop and human Fc IgG1 | MLPCLVVLLAALLSLRLGSDAHGTELPSPPSV WFEAEFFHHILHWTPIPNQSESTCYEVALLRY GIESWNSISNCSQTLSYDLTAVTLDLYHSNGY RARVRAVDGSRHSNWTVTNTRFSVDEVTLT VGSVNLEIHNGFILGKIQLPRPKMAPANDTYE SIFSHFREYEIAIRKVPGNFTFTHKKVKHENFS LLTSGEVGEFCVQVKPSVASRSNKGMWSKEE CISLTRQYFTVTNDKTHTCPPCPAPELLGGPS VFLFPPKPKDTLMISRTPEVTCVVVDVSHEDP EVKFNWYVDGVEVHNAKTKPREEQYNSTYR VVSVLTVLHQDWLNGKEYKCKVSNKALPAPI EKTISKAKGQPREPQVYTLPPSREEMTKNQVS LTCLVKGFYPSDIAVEWESNGQPENNYKTTPP VLDSDGSFFLYSKLTVDKSRWQQGNVFSCSV MHEALHNHYTQKSLSLSPGK** |
| 68 | Extracellular domain of hIL-10Rα | | HGTELPSPPSVWFEAEFFHHILHWTPlPNQSES TCYEVALLRYGIESWNSISNCSQTLSYDLTAV TLDLYHSNGYRARVRAVDGSRHSNWTVTNT RFSVDEVTLTVGSVNLEIHNGFILGKIQLPRPK MAPANDTYESIFSHFREYEIAIRKVPGNFTFTH KKVKHENFSLLTSGEVGEFCVQVKPSVASRS NKGMWSKEECISLTRQYFTVTN |

APPENDIX A-continued

SEQUENCE REFERENCE

| SEQ ID NO: | Molecule | Accession Number(s) or description | Sequence |
|---|---|---|---|
| 69 | endogenous signal sequence in TRZ114 | | MLPCLVVLLAALLSLRLGSDA |
| 70 | human Fc IgG1 | | DKTHTCPPCPAPELLGGPSVFLFPPKPKDTLMI SRTPEVTCVVVDVSHEDPEVKFNWYVDGVE VHNAKTKPREEQYNSTYRVVSVLTVLHQDW LNGKEYKCKVSNKALPAPIEKTISKAKGQPRE PQVYTLPPSREEMTKNQVSLTCLVKGFYPSDI AVEWESNGQPENNYKTTPPVLDSDGSFFLYS KLTVDKSRWQQGNVFSCSVMHEALHNHYTQ KSLSLSPGK** |
| 71 | TRZ116: hOX40L | Trimeric version w/human IGKV1-39 kappa LC signal sequence, trimerization domain from yeast, and Linker 1, followed by OX40L minus ECD and transmembrane domains | MDMRVPAQLLGLLLLWLRGARCRMKQIEDK IEEILSKIYHIENEIARIKKLIGERGGGSGGGSG GGSETAKEPCMAKFGPLPSKWQMASSEPPCV NKVSDWKLEILQNGLYLIYGQVAPNANYND VAPFEVRLYKNKDMIQTLTNKSKIQNVGGTY ELHVGDTIDLIFNSEHQVLKNNTYWGIILLAN PQFIS** |
| 72 | hOX40L minus ECD and transmembrane domains | | QVSHRYPRIQSIKVQFTEYKKEKGFILTSQKE DEIMKVQNNSVIINCDGFYLISLKGYFSQEVNI SLHYQKDEEPLFQLKKVRSVNSLMVASLTYK DKVYLNVTTDNTSLDDFHVNGGELILIHQNP GEFCVL** |
| 73 | TRZ117: hCD40L | Trimeric version w/human IGKV1-39 kappa LC signal sequence, trimerization domain from yeast, and Linker 1, followed by CD40L minus ECD and transmembrane domains | MDMRVPAQLLGLLLLWLRGARCRMKQIEDK IEEILSKIYHIENEIARIKKLIGERGGGSGGGSG GGSMQKGDQNPQIAAHVISEASSKTTSVLQW AEKGYYTMSNNLVTLENGKQLTVKRQGLYY IYAQVTFCSNREASSQAPFIASLCLKSPGRFER ILLRAANTHSSAKPCGQQSIHLGGVFELQPGA SVFVNVTDPSQVSHGTGFTSFGLLKL** |
| 76 | hCD40L minus ECD and transmembrane domains | | MQKGDQNPQIAAHVISEASSKTTSVLQWAEK GYYTMSNNLVTLENGKQLTVKRQGLYYIYA QVTFCSNREASSQAPFIASLCLKSPGRFERILL RAANTHSSAKPCGQQSIHLGGVFELQPGASVF VNVTDPSQVSHGTGFTSFGLLKL** |
| 77 | TRZ307: hIL-7 variant 1 | | MFHVSFRYIFGLPPLILVLLPVASSDCDIEGKD GKQYESVLMVSIDQLLDSMKEIGSNCLNNEF NFFKRHICDANKEGMFLFRAARKLRQFLKMN STGDFDLHLLKVSEGTTILLNCTGQVKGRKPA ALGEAQPTKSLEENKSLKEQKKLNDLCFLKR LLQEIKTCWNKILMGTKEH** |

APPENDIX A-continued

SEQUENCE REFERENCE

| SEQ ID NO: | Molecule | Accession Number(s) or description | Sequence |
|---|---|---|---|
| 106 | hIL-7 | | MFHVSFRYIFGLPPLILVLLPVASSDCDIEGKD GKQYESVLMVSIDQLLDSMKEIGSNCLNNEF NFFKRHICDANKEGMFLFRAARKLRQFLKMN STGDFDLHLLKVSEGTTILLNCTGQVKGRKPA ALGEAQPTKSLEENKSLKEQKKLNDLCFLKR LLQEIKTCWNKILMGTKEH** |
| 78 | TRZ304: hGM-CSF | | MWLQSLLLLGTVACSISAPARSPSPSTQPWEH VNAIQEARRLLNLSRDTAAEMNETVEVISEM FDLQEPTCLQTRLELYKQGLRGSLTKLKGPLT MMASHYKQHCPPTPETSCATQIITFESFKENL KDFLLVIPFDCWEPVQE** |
| 79 | hGM-CSF | | MWLQSLLLLGTVACSISAPARSPSPSTQPWEH VNAIQEARRLLNLSRDTAAEMNETVEVISEM FDLQEPTCLQTRLELYKQGLRGSLTKLKGPLT MMASHYKQHCPPTPETSCATQIITFESFKENL KDFLLVIPFDCWEPVQE** |
| 80 | TRZ309: hCD70 | (residue in bold to be removed) | MPEEGSGCSVRRRPYGCVLRAALVPLVAGLV ICLVVCIQRFAQAQQQLPLESLGWDVAELQL NHTGPQQDPRLYWQGGPALGRSFLHGPELDK GQLRIHRDGIYMVHIQVTLAICSSTTASRHHP TTLAVGICSPASRSISLLRLSFHQGCTIASQRLT PLARGDTLCTNLTGTLLPSRNTDETFFGVQW VRP** |
| 81 | hCD70 | (residue in bold to be modified to avoid introducing new Xho I site) | MPEEGSGCSVRRRPYGCVLRAALVPLVAGLV ICLVVCIQRFAQAQQQLPLESLGWDVAELQL NHTGPQQDPRLYWQGGPALGRSFLHGPELDK GQLRIHRDGIYMVHIQVTLAICSSTTASRHHP TTLAVGICSPASRSISLLRLSFHQGCTIASQRLT PLARGDTLCTNLTGTLLPSRNTDETFFGVQW VRP** |
| 82 | E3 14.7k | Region overlapping with E3 14.5k ORF in bold | ATGACTGACACCCTAGATCTAGAAATGGA CGGAATTATTACAGAGCAGCGCCTGCTAGA AAGACGCAGGGCAGCGGCCGAGCAACAGC GCATGAATCAAGAGCTCCAAGACATGGTTA ACTTGCACCAGTGCAAAAGGGGTATCTTTT GTCTGGTAAAGCAGGCCAAAGTCACCTACG ACAGTAATACCACCGGACACCGCCTTAGCT ACAAGTTGCCAACCAAGCGTCAGAAATTGG TGGTCATGGTGGGAGAAAAGCCCATTACCA TAACTCAGCACTCGGTAGAAACCGAAGGCT GCATTCACTCACCTTGTCAAGGACCTGAGG ATCTCTGCACCCTTATTAAGACCCTGTGCGG TCTCAAAGATCTTATTCCCTTTAACTAA |
| 83 | E3 14.5k | Region overlapping with E3 14.7k in bold | ATGAAATTTACTGTGACTTTTCTGCTGATTA TTTGCACCCTATCTGCGTTTTGTTCCCCGAC CTCCAAGCCTCAAAGACATATATCATGCAG ATTCACTCGTATATGGAATATTCCAAGTTGC TACAATGAAAAAAGCGATCTTTCCGAAGCC TGGTTATATGCAATCATCTCTGTTATGGTGT TCTGCAGTACCATCTTAGCCCTAGCTATATA TCCCTACCTTGACATTGGCTGGAACGCAAT AGATGCCATGAACCACCCAACTTTCCCCGC GCCCGCTATGCTTCCACTGCAACAAGTTGTT GCCGGCGGCTTTGTCCCAGCCAATCAGCCT CGCCCACCTTCTCCCACCCCCACTGAAATC AGCTACTTTAATCTAACAGGAGGAGATGAC TGA |
| 84 | E3 10.4K | | ATGATTCCTCGAGTTTTTATATTACTGACCC TTGTTGCGCTTTTTTTGTGCGTGCTCCACAT TGGCTGCGGTTTCTCACATCGAAGTAGACT GCATTCCAGCCTTCACAGTCTATTTGCTTTA CGGATTTGTCACCCTCACGCTCATCTGCAGC CTCATCACTGTGGTCATCGCCTTTATCCAGT GCATTGA |

APPENDIX A-continued

SEQUENCE REFERENCE

| SEQ ID NO: | Molecule | Accession Number(s) or description | Sequence |
|---|---|---|---|
| 85 | E3 10.5k (ADP) | | ATGACCAACACAACCAACGCGGCCGCCGCT ACCGGACTTACATCTACCACAAATACACCC CAAGTTTCTGCCTTTGTCAATAACTGGGATA ACTTGGGCATGTGGTGGTTCTCCATAGCGC TTATGTTTGTATGCCTTATTATTATGTGGCT CATCTGCTGCCTAAAGCGCAAACGCGCCCG ACCACCCATCTATAGTCCCATCATTGTGCTA CACCCAAACAATGATGGAATCCATAGATTG GACGGACTGAAACACATGTTCTTTTCTCTTA CAGTATGA |
| 86 | TRZ000 intact E3 gp19k ORF | Region overlapping with E3 gp19k ORF in bold | ATGATTAGGTACATAATCCTAGGTTTACTC ACCCTTGCGTCAGCCCACGGTACCACCCAA AAGGTGGATTTTAAGGAGCCAGCCTGTAAT GTTACATTCGCAGCTGAAGCTAATGAGTGC ACCACTCTTATAAAATGCACCACAGAACAT GAAAAGCTGCTTATTCGCCACAAAAACAAA ATTGGCAAGTATGCTGTTTATGCTATTTGGC AGCCAGGTGACACTACAGAGTATAATGTTA CAGTTTTCCAGGGTAAAAGTCATAAAACTT TTATGTATACTTTTCCATTTTATGAAATGTG CGACATTACCATGTACATGAGCAAACAGTA TAAGTTGTGGCCCCCACAAAATTGTGTGGA AAACACTGGCACTTTCTGCTGCACTGCTAT GCTAATTACAGTGCTCGCTTTGGTCTGTACC CTACTCTATATTAAATACAAAAGCAGACGC AGCTTTATTGAGGAAAGAAAATGCCTTAA |
| 87 | TRZ000 intact E3 7.1K | Region overlapping with E3 gP19k ORF in bold | ATGAACAATTCAAGCAACTCTACGGGCTAT TCTAATTCAGGTTTCTCTAGAATCGGGGTTG GGGTTATTCTCTGTCTTGTGATTCTCTTTATT CTTATACTAACGCTTCTCTGCCTAAGGCTCG CCGCCTGCTGTGTGCACATTTGCATTTATTG TCAGCTTTTTAAACGCTGGGGTCGCCACCC AAGATGA |
| 88 | TRZ200 intact E3 12.5k | | ATGTTAAGTGGAGAGGCAGAGCAACTGCGC CTGAAACACCTGGTCCACTGTCGCCGCCAC AAGTGCTTTGCCCGCGACTCCGGTGAGTTTT GCTACTTTGAATTGCCCGAGGATCATATCG AGGGCCCGGCGCACGGCGTCCGGCTTACCG CCCAGGGAGAGCTTGCCCGTAGCCTGATTC GGGAGTTTACCCAGCGCCCCCTGCTAGTTG AGCGGGACAGGGGACCCTGTGTTCTCACTG TGATTTGCAACTGTCCTAACCCTGGATTACA TCAAGATCTTTGTTGCCATCTCTGTGCTGAG TATAATAAATACAGAAATTAA |
| 89 | TRZ000 intact E3 14.7k ORF | | CACCCTAGATCTAGAAATGGACGGAATTAT TACAGAGCAGCGCCTGCTAGAAAGACGCA GGGCAGCGGCCGAGCAACAGCGCATGAAT CAAGAGCTCCAAGACATGGTTAACTTGCAC CAGTGCAAAAGGGGTATCTTTTGTCTGGTA AAGCAGGCCAAAGTCACCTACGACAGTAAT ACCACCGGACACCGCCTTAGCTACAAGTTG CCAACCAAGCGTCAGAAATTGGTGGTCATG GTGGGAGAAAAGCCCATTACCATAACTCAG CACTCGGTAGAAACCGAAGGCTGCATTCAC TCACCTTGTCAAGGACCTGAGGATCTCTGC ACCCTTATTAAGACCCTGTGCGGTCTCAAA GATCTTATTCCCTTTAACTAA |
| 90 | TRZ200 E3 region (not full E3-this is deleted version) | | AGACGCCCAGGCCGAAGTTCAGATGACTAA CTCAGGGGCGCAGCTTGCGGGCGGCTTTCG TCACAGGGTGCGGTCGCCCGGGCAGGGTAT AACTCACCTGACAATCAGAGGGCGAGGTAT TCAGCTCAACGACGAGTCGGTGAGCTCCTC GCTTGGTCTCCGTCCGGACGGGACATTTCA GATCGGCGGCGCCGGCCGCTCTTCATTCAC GCCTCGTCAGGCAATCCTAACTCTGCAGAC CTCGTCCTCTGAGCCGCGCTCTGGAGGCAT TGGAACTCTGCAATTTATTGAGGAGTTTGT GCCATCGGTCTACTTTAACCCCTTCTCGGGA CCTCCCGGCCACTATCCGGATCAATTTATTC |

APPENDIX A-continued

SEQUENCE REFERENCE

| SEQ ID NO: | Molecule | Accession Number(s) or description | Sequence |
|---|---|---|---|
| | | | CTAACTTTGACGCGGTAAAGGACTCGGCGG ACGGCTACGACTGAATGTTAAGTGGAGAGG CAGAGCAACTGCGCCTGAAACACCTGGTCC ACTGTCGCCGCCACAAGTGCTTTGCCCGCG ACTCCGGTGAGTTTTGCTACTTTGAATTGCC CGAGGATCATATCGAGGGCCCGGCGCACGG CGTCCGGCTTACCGCCCAGGGAGAGCTTGC CCGTAGCCTGATTCGGGAGTTTACCCAGCG CCCCCTGCTAGTTGAGCGGGACAGGGGACC CTGTGTTCTCACTGTGATTTGCAACTGTCCT AACCCTGGATTACATCAAGATCCTCTAGTT AATGTCAGGTCGCCTAAGTCGATTAACTAG AGTACCCGGGGATCTTATTCCCTTTAACTAA |
| 91 | TRZ200 deleted E3 14.7k partial ORF | | GATCTTATTCCCTTTAACTAA |
| 92 | TRZ200 deleted E3 12.5K partial ORF | | ATGTTAAGTGGAGAGGCAGAGCAACTGCGC CTGAAACACCTGGTCCACTGTCGCCGCCAC AAGTGCTTTGCCCGCGACTCCGGTGAGTTTT GCTACTTTGAATTGCCCGAGGATCATATCG AGGGCCCGGCGCACGGCGTCCGGCTTACCG CCCAGGGAGAGCTTGCCCGTAGCCTGATTC GGGAGTTTACCCAGCGCCCCCTGCTAGTTG AGCGGGACAGGGGACCCTGTGTTCTCACTG TGATTTGCAACTGTCCTAACCCTGGATTACA TCAAGAT |
| 93 | E3 Promoter (E3 deleted or E3 intact) | | AGACGCCCAGGCCGAAGTTCAGATGACTA |
| 94 | Full TRZ200 virus sequence beginning at 5' ITR through 3' ITR | | TTTTGGATTGAAGCCAATATGATAATGAGG GGGTGGAGTTTGTGACGTGGCGCGGGGCGT GGGAACGGGGCGGGTGACGTAGTAGTGTG GCGGAAGTGTGATGTTGCAAGTGTGGCGGA ACACATGTAAGCGACGGATGTGGCAAAAGT GACGTTTTTGGTGTGCGCCGGTGTTTTGGGC GTAACCGAGTAAGATTTGGCCATTTTCGCG GGAAAACTGAATAAGAGGAAGTGAAATCT GAATAATTTTGTGTTACTCATAGCGCGTAAT ATTTGTCTAGGGCCGCGGGGACTTTGACCG TTTACGTGGAGACTCGCCCAGGTGTTTTTCT CAGGTGTTTTCCGCGTTCCGGGTCAAAGTT GGCGTTTTATTATTATAGTCAGCTGACGTGT AGTGTATTTATACCCGGTGAGTTCCTCAAG AGGCCACTCTTGAGTGCCAGCGAGTAGAGT TTTCTCCTCCGAGCCGCTCCGACACCGGGA CTGAAAATGAGACATATTATCTGCCACGGA GGTGTTATTACCGAAGAAATGGCCGCCAGT CTTTTGGACCAGCTGATCGAAGAGGTACTG GCTGATAATCTTCCACCTCCTAGCCATTTTG AACCACCTACCCTTCACGAACTGTATGATTT AGACGTGACGGCCCCGAAGATCCCAACGA GGAGGCGGTTTCGCAGATTTTTCCCGACTCT GTAATGTTGGCGGTGCAGGAAGGGATTGAC TTACTCACTTTTCCGCCGGCGCCCGGTTCTC CGGAGCCGCCTCACCTTTCCCGGCAGCCCG AGCAGCCGGAGCAGAGAGCCTTGGGTCCG GTTTCTATGCCAAACCTTGTACCGGAGGTG ATCGATCTTACCTGCCACGAGGCTGGCTTTC CACCCAGTGACGACGAGGATGAAGAGGGT GAGGAGTTTGTGTTAGATTATGTGGAGCAC CCCGGGCACGGTTGCAGGTCTTGTCATTAT CACCGGAGGAATACGGGGACCCAGATATT ATGTGTTCGCTTTGCTATATGAGGACCTGTG GCATGTTTGTCTACAGTAAGTGAAAATTAT GGGCAGTGGGTGATAGAGTGGTGGGTTTGG TGTGGTAATTTTTTTTTAATTTTTACAGTTT TGTGGTTTAAAGAATTTTGTATTGTGATTTT TTAAAAGGTCCTGTGTCTGAACCTGAGCC TGAGCCCGAGCCAGAACCGGAGCCTGCAA |

APPENDIX A-continued

SEQUENCE REFERENCE

| SEQ ID NO: | Molecule | Accession Number(s) or description | Sequence |
|---|---|---|---|
| | | | GACCTACCCGCCGTCCTAAAATGGCGCCTG CTATCCTGAGACGCCCGACATCACCTGTGT CTAGAGAATGCAATAGTAGTACGGATAGCT GTGACTCCGGTCCTTCTAACACACCTCCTGA GATACACCCGGTGGTCCCGCTGTGCCCCAT TAAACCAGTTGCCGTGAGAGTTGGTGGGCG TCGCCAGGCTGTGGAATGTATCGAGGACTT GCTTAACGAGCCTGGGCAACCTTTGGACTT GAGCTGTAAACGCCCCAGGCCATAAGGTGT AAACCTGTGATTGCGTGTGTGGTTAACGCC TTTGTTTGCTGAATGAGTTGATGTAAGTTTA ATAAAGGGTGAGATAATGTTTAACTTGCAT GGCGTGTTAAATGGGGCGGGGCTTAAAGGG TATATAATGCGCCGTGGGCTAATCTTGGTT ACATCTGACCTCGTCGACGCTTGGGAGTGT TTGGAAGATTTTTCTGCTGTGCGTAACTTGC TGGAACAGAGCTCTAACAGTACCTCTTGGT TTTGGAGGTTTCTGTGGGCTCATCCCAGG CAAAGTTAGTCTGCAGAATTAAGGAGGATT ACAAGTGGGAATTTGAAGAGCTTTTGAAAT CCTGTGGTGAGCTGTTTGATTCTTTGAACTC GAGTCACCAGGCGCTTTTCCAAGAGAAGGT CATCAAGACTTTGGATTTTTCCACACCGGG GCGCGCTGCGGCTGCTGTTGCTTTTTTGAGT TTTATAAAGGATAAATGGAGCGAAGAAACC CATCTGAGCGGGGGTACCTGCTGGATTTT CTGGCCATGCATCTGTGGAGAGCGGTTGTG AGACACAAGAATCGCCTGCTACTGTTGTCT TCCGTCCGCCCGGCGATAATACCGACGGAG GAGCAGCAGCAGCAGCAGGAGGAAGCCAG GCGGCGGCGGCAGGAGCAGAGCCCATGGA ACCCGAGAGCCGGCCTGGACCCTCGGGAAT GAATGTTGTACAGGTGGCTGAACTGTATCC AGAACTGAGACGCATTTTGACAATTACAGA GGATGGGCAGGGGCTAAAGGGGGTAAAGA GGGAGCGGGGGCTTGTGAGGCTACAGAG GAGGCTAGGAATCTAGCTTTTAGCTTAATG ACCAGACACCGTCCTGAGTGTATTACTTTTC AACAGATCAAGGATAATTGCGCTAATGAGC TTGATCTGCTGGCGCAGAAGTATTCCATAG AGCAGCTGACCACTTACTGGCTGCAGCCAG GGGATGATTTTGAGGAGGCTATTAGGGTAT ATGCAAAGGTGGCACTTAGGCCAGATTGCA AGTACAAGATCAGCAAACTTGTAAATATCA GGAATTGTTGCTACATTTCTGGGAACGGGG CCGAGGTGGAGATAGATACGGAGGATAGG GTGGCCTTTAGATGTAGCATGATAAATATG TGGCCGGGGGTGCTTGGCATGGACGGGGTG GTTATTATGAATGTAAGGTTTACTGGCCCC AATTTTAGCGGTACGGTTTTCCTGGCCAATA CCAACCTTATCCTACACGGTGTAAGCTTCTA TGGGTTTAACAATACCTGTGTGGAAGCCTG GACCGATGTAAGGGTTCGGGGCTGTGCCTT TTACTGCTGCTGGAAGGGGGTGGTGTGTCG CCCCAAAAGCAGGGCTTCAATTAAGAAATG CCTCTTTGAAAGGTGTACCTTGGGTATCCTG TCTGAGGGTAACTCCAGGGTGCGCCACAAT GTGGCCTCCGACTGTGGTTGCTTCATGCTAG TGAAAAGCGTGGCTGTGATTAAGCATAACA TGGTATGTGGCAACTGCGAGGACAGGGCCT CTCAGATGCTGACCTGCTCGGACGGCAACT GTCACCTGCTGAAGACCATTCACGTAGCCA GCCACTCTCGCAAGGCCTGGCCAGTGTTTG AGCATAACATACTGACCCGCTGTTCCTTGC ATTTGGGTAACAGGAGGGGGTGTTCCTAC CTTACCAATGCAATTTGAGTCACACTAAGA TATTGCTTGAGCCCGAGAGCATGTCCAAGG TGAACCTGAACGGGGTGTTTGACATGACCA TGAAGATCTGGAAGGTGCTGAGGTACGATG AGACCCGCACCAGGTGCAGACCCTGCGAGT GTGGCGGTAAACATATTAGGAACCAGCCTG TGATGCTGGATGTGACCGAGGAGCTGAGGC CCGATCACTTGGTGCTGGCCTGCACCCGCG CTGAGTTTGGCTCTAGCGATGAAGATACAG |

APPENDIX A-continued

SEQUENCE REFERENCE

| SEQ ID NO: | Molecule | Accession Number(s) or description | Sequence |
|---|---|---|---|
| | | | ATTGAGGTACTGAAATGTGTGGGCGTGGCT
TAAGGGTGGGAAAGAATATATAAGGTGGG
GGTCTTATGTAGTTTTGTATCTGTTTTGCAG
CAGCCGCCGCCGCCATGAGCACCAACTCGT
TTGATGGAAGCATTGTGAGCTCATATTTGA
CAACGCGCATGCCCCCATGGGCCGGGGTGC
GTCAGAATGTGATGGGCTCCAGCATTGATG
GTCGCCCCGTCCTGCCCGCAAACTCTACTA
CCTTGACCTACGAGACCGTGTCTGGAACGC
CGTTGGAGACTGCAGCCTCCGCCGCCGCTT
CAGCCGCTGCAGCCACCGCCCGCGGGATTG
TGACTGACTTTGCTTTCCTGAGCCCGCTTGC
AAGCAGTGCAGCTTCCCGTTCATCCGCCCG
CGATGACAAGTTGACGGCTCTTTTGGCACA
ATTGGATTCTTTGACCCGGGAACTTAATGTC
GTTTCTCAGCAGCTGTTGGATCTGCGCCAG
CAGGTTTCTGCCCTGAAGGCTTCCTCCCCTC
CCAATGCGGTTTAAAACATAAATAAAAAAC
CAGACTCTGTTTGGATTTGGATCAAGCAAG
TGTCTTGCTGTCTTTATTTAGGGGTTTTGCG
CGCGCGGTAGGCCCGGGACCAGCGGTCTCG
GTCGTTGAGGGTCCTGTGTATTTTTTCCAGG
ACGTGGTAAAGGTGACTCTGGATGTTCAGA
TACATGGGCATAAGCCCGTCTCTGGGGTGG
AGGTAGCACCACTGCAGAGCTTCATGCTGC
GGGGTGGTGTTGTAGATGATCCAGTCGTAG
CAGGAGCGCTGGGCGTGGTGCCTAAAAATG
TCTTTCAGTAGCAAGCTGATTGCCAGGGGC
AGGCCCTTGGTGTAAGTGTTTACAAAGCGG
TTAAGCTGGGATGGGTGCATACGTGGGGAT
ATGAGATGCATCTTGGACTGTATTTTTAGGT
TGGCTATGTTCCCAGCCATATCCCTCCGGG
GATTCATGTTGTGCAGAACCACCAGCACAG
TGTATCCGGTGCACTTGGGAAATTTGTCAT
GTAGCTTAGAAGGAAATGCGTGGAAGAACT
TGGAGACGCCCTTGTGACCTCCAAGATTTT
CCATGCATTCGTCCATAATGATGGCAATGG
GCCCACGGGCGGCGGCCTGGGCGAAGATAT
TTCTGGGATCACTAACGTCATAGTTGTGTTC
CAGGATGAGATCGTCATAGGCCATTTTTAC
AAAGCGCGGGCGGAGGGTGCCAGACTGCG
GTATAATGGTTCCATCCGGCCCAGGGGCGT
AGTTACCCTCACAGATTTGCATTTCCCACGC
TTTGAGTTCAGATGGGGGATCATGTCTAC
CTGCGGGGCGATGAAGAAAACGGTTTCCGG
GGTAGGGGAGATCAGCTGGGAAGAAAGCA
GGTTCCTGAGCAGCTGCGACTTACCGCAGC
CGGTGGGCCCGTAAATCACACCTATTACCG
GCTGCAACTGGTAGTTAAGAGAGCTGCAGC
TGCCGTCATCCCTGAGCAGGGGGGCCACTT
CGTTAAGCATGTCCCTGACTCGCATGTTTTC
CCTGACCAAATCCGCCAGAAGGCGCTCGCC
GCCCAGCGATAGCAGTTCTTGCAAGGAAGC
AAAGTTTTTCAACGGTTTGAGACCGTCCGC
CGTAGGCATGCTTTTGAGCGTTTGACCAAG
CAGTTCCAGGCGGTCCCACAGCTCGGTCAC
CTGCTCTACGGCATCTCGATCCAGCATATCT
CCTCGTTTCGCGGGTTGGGGCGGCTTTCGCT
GTACGGCAGTAGTCGGTGCTCGTCCAGACG
GGCCAGGGTCATGTCTTTCCACGGGCGCAG
GGTCCTCGTCAGCGTAGTCTGGGTCACGGT
GAAGGGGTGCGCTCCGGGCTGCGCGCTGGC
CAGGGTGCGCTTGAGGCTGGTCCTGCTGGT
GCTGAAGCGCTGCCGGTCTTCGCCCTGCGC
GTCGGCCAGGTAGCATTTGACCATGGTGTC
ATAGTCCAGCCCCTCCGCGGCGTGGCCCTT
GGCGCGCAGCTTGCCCTTGGAGGAGGCGCC
GCACGAGGGGCAGTGCAGACTTTTGAGGGC
GTAGAGCTTGGGCGCGAGAAATACCGATTC
CGGGGAGTAGGCATCCGCGCCGCAGGCCCC
GCAGACGGTCTCGCATTCCACGAGCCAGGT
GAGCTCTGGCCGTTCGGGGTCAAAAACCAG
GTTTCCCCCATGCTTTTTGATGCGTTTCTTA
CCTCTGGTTTCCATGAGCCGGTGTCCACGCT |

APPENDIX A-continued

SEQUENCE REFERENCE

| SEQ ID NO: | Molecule | Accession Number(s) or description | Sequence |
|---|---|---|---|
| | | | CGGTGACGAAAAGGCTGTCCGTGTCCCCGT ATACAGACTTGAGAGGCCTGTCCTCGAGCG GTGTTCCGCGGTCCTCCTCGTATAGAAACTC GGACCACTCTGAGACAAAGGCTCGCGTCCA GGCCAGCACGAAGGAGGCTAAGTGGGAGG GGTAGCGGTCGTTGTCCACTAGGGGGTCCA CTCGCTCCAGGGTGTGAAGACACATGTCGC CCTCTTCGGCATCAAGGAAGGTGATTGGTT TGTAGGTGTAGGCCACGTGACCGGGTGTTC CTGAAGGGGGCTATAAAAGGGGGTGGGG GCGCGTTCGTCCTCACTCTCTTCCGCATCGC TGTCTGCGAGGGCCAGCTGTTGGGGTGAGT ACTCCCTCTGAAAAGCGGGCATGACTTCTG CGCTAAGATTGTCAGTTTCCAAAAACGAGG AGGATTTGATATTCACCTGGCCCGCGGTGA TGCCTTTGAGGGTGGCCGCATCCATCTGGT CAGAAAAGACAATCTTTTTGTTGTCAAGCT TGGTGGCAAACGACCCGTAGAGGGCGTTGG ACAGCAACTTGGCGATGGAGCGCAGGGTTT GGTTTTTGTCGCGATCGGCGCGCTCCTTGGC CGCGATGTTTAGCTGCACGTATTCGCGCGC AACGCACCGCCATTCGGGAAAGACGGTGGT GCGCTCGTCGGGCACCAGGTGCACGCGCCA ACCGCGGTTGTGCAGGGTGACAAGGTCAAC GCTGGTGGCTACCTCTCCGCGTAGGCGCTC GTTGGTCCAGCAGAGGCGGCCGCCCTTGCG CGAGCAGAATGGCGGTAGGGGGTCTAGCTG CGTCTCGTCCGGGGGGTCTGCGTCCACGGT AAAGACCCCGGGCAGCAGGCGCGCGTCGA AGTAGTCTATCTTGCATCCTTGCAAGTCTAG CGCCTGCTGCCATGCGCGGGCGGCAAGCGC GCGCTCGTATGGGTTGAGTGGGGGACCCCA TGGCATGGGGTGGGTGAGCGCGGAGGCGT ACATGCCGCAAATGTCGTAAACGTAGAGGG GCTCTCTGAGTATTCCAAGATATGTAGGGT AGCATCTTCCACCGCGGATGCTGGCGCGCA CGTAATCGTATAGTTCGTGCGAGGGAGCGA GGAGGTCGGGACCGAGGTTGCTACGGGCG GGCTGCTCTGCTCGGAAGACTATCTGCCTG AAGATGGCATGTGAGTTGGATGATATGTT GGACGCTGGAAGACGTTGAAGCTGGCGTCT GTGAGACCTACCGCGTCACGCACGAAGGAG GCGTAGGAGTCGCGCAGCTTGTTGACCAGC TCGGCGGTGACCTGCACGTCTAGGGCGCAG TAGTCCAGGGTTTCCTTGATGATGTCATACT TATCCTGTCCCTTTTTTTTCCACAGCTCGCG GTTGAGGACAAACTCTTCGCGGTCTTTCCA GTACTCTTGGATCGGAAACCCGTCGGCCTC CGAACGGTAAGAGCCTAGCATGTAGAACTG GTTGACGGCCTGGTAGGCGCAGCATCCCTT TTCTACGGGTAGCGCGTATGCCTGCGCGGC CTTCCGGAGCGAGGTGTGGGTGAGCGCAAA GGTGTCCCTGACCATGACTTTGAGGTACTG GTATTTGAAGTCAGTGTCGTCGCATCCGCC CTGCTCCCAGAGCAAAAAGTCCGTGCGCTT TTTGGAACGCGGATTTGGCAGGGCGAAGGT GACATCGTTGAAGAGTATCTTTCCCGCGCG AGGCATAAAGTTGCGTGTGATGCGGAAGGG TCCCGGCACCTCGGAACGGTTGTTAATTAC CTGGGCGGCGAGCACGATCTCGTCAAAGCC GTTGATGTTGTGGCCCACAATGTAAAGTTC CAAGAAGCGCGGGATGCCCTTGATGGAAG GCAATTTTTTAAGTTCCTCGTAGGTGAGCTC TTCAGGGGAGCTGAGCCCGTGCTCTGAAAG GGCCCAGTCTGCAAGATGAGGGTTGGAAGC GACGAATGAGCTCCACAGGTCACGGGCCAT TAGCATTTGCAGGTGGTCGCGAAAGGTCCT AAACTGGCGACCTATGGCCATTTTTTCTGG GGTGATGCAGTAGAAGGTAAGCGGGTCTTG TTCCCAGCGGTCCCATCCAAGGTTCGCGGC TAGGTCTCGCGCGGCAGTCACTAGAGGCTC ATCTCCGCCGAACTTCATGACCAGCATGAA GGGCACGAGCTGCTTCCCAAAGGCCCCCAT CCAAGTATAGGTCTCTACATCGTAGGTGAC |

APPENDIX A-continued

SEQUENCE REFERENCE

| SEQ ID NO: | Molecule | Accession Number(s) or description | Sequence |
|---|---|---|---|
| | | | AAAGAGACGCTCGGTGCGAGGATGCGAGC CGATCGGGAAGAACTGGATCTCCCGCCACC AATTGGAGGAGTGGCTATTGATGTGGTGAA AGTAGAAGTCCCTGCGACGGGCCGAACACT CGTGCTGGCTTTTGTAAAAACGTGCGCAGT ACTGGCAGCGGTGCACGGGCTGTACATCCT GCACGAGGTTGACCTGACGACCGCGCACAA GGAAGCAGAGTGGGAATTTGAGCCCCTCGC CTGGCGGGTTTGGCTGGTGGTCTTCTACTTC GGCTGCTTGTCCTTGACCGTCTGGCTGCTCG AGGGGAGTTACGGTGGATCGGACCACCACG CCGCGCGAGCCCAAAGTCCAGATGTCCGCG CGCGGCGGTCGGAGCTTGATGACAACATCG CGCAGATGGGAGCTGTCCATGGTCTGGAGC TCCCGCGGCGTCAGGTCAGGCGGGAGCTCC TGCAGGTTTACCTCGCATAGACGGGTCAGG GCGCGGGCTAGATCCAGGTGATACCTAATT TCCAGGGGCTGGTTGGTGGCGGCGTCGATG GCTTGCAAGAGGCCGCATCCCCGCGGCGCG ACTACGGTACCGCGCGGCGGGCGGTGGGCC GCGGGGGTGTCCTTGGATGATGCATCTAAA AGCGGTGACGCGGGCGAGCCCCCGGAGGT AGGGGGGGCTCCGGACCCGCCGGGAGAGG GGGCAGGGGCACGTCGGCGCCGCGCGCGG GCAGGAGCTGGTGCTGCGCGCGTAGGTTGC TGGCGAACGCGACGACGCGGCGGTTGATCT CCTGAATCTGGCGCCTCTGCGTGAAGACGA CGGGCCCGGTGAGCTTGAACCTGAAAGAGA GTTCGACAGAATCAATTTCGGTGTCGTTGA CGGCGGCCTGGCGCAAAATCTCCTGCACGT CTCCTGAGTTGTCTTGATAGGCGATCTCGGC CATGAACTGCTCGATCTCTTCCTCCTGGAGA TCTCCGCGTCCGGCTCGCTCCACGGTGGCG GCGAGGTCGTTGGAAATGCGGGCCATGAGC TGCGAGAAGGCGTTGAGGCCTCCCTCGTTC CAGACGCGGCTGTAGACCACGCCCCCTTCG GCATCGCGGGCGCGCATGACCACCTGCGCG AGATTGAGCTCCACGTGCCGGGCGAAGACG GCGTAGTTTCGCAGGCGCTGAAAGAGGTAG TTGAGGGTGGTGGCGGTGTGTTCTGCCACG AAGAAGTACATAACCCAGCGTCGCAACGTG GATTCGTTGATATCCCCCAAGGCCTCAAGG CGCTCCATGGCCTCGTAGAAGTCCACGGCG AAGTTGAAAAACTGGGAGTTGCGCGCCGAC ACGGTTAACTCCTCCTCCAGAAGACGGATG AGCTCGGCGACAGTGTCGCGCACCTCGCGC TCAAAGGCTACAGGGGCCTCTTCTTCTTCTT CAATCTCCTCTTCCATAAGGGCCTCCCCTTC TTCTTCTTCTGGCGGCGGTGGGGGAGGGGG GACACGGCGGCGACGACGGCGCACCGGGA GGCGGTCGACAAAGCGCTCGATCATCTCCC CGCGGCGACGGCGCATGGTCTCGGTGACGG CGCGGCCGTTCTCGCGGGGGCGCAGTTGGA AGACGCCGCCCGTCATGTCCCGGTTATGGG TTGGCGGGGGCTGCCATGCGGCAGGGATA CGGCGCTAACGATGCATCTCAACAATTGTT GTGTAGGTACTCCGCCGCCGAGGGACCTGA GCGAGTCCGCATCGACCGGATCGGAAAACC TCTCGAGAAAGGCGTCTAACCAGTCACAGT CGCAAGGTAGGCTGAGCACCGTGGCGGGC GGCAGCGGGCGGCGGTCGGGGTTGTTTCTG GCGGAGGTGCTGCTGATGATGTAATTAAAG TAGGCGGTCTTGAGACGGCGGATGGTCGAC AGAAGCACCATGTCCTTGGGTCCGGCCTGC TGAATGCGCAGGCGGTCGGCCATGCCCCAG GCTTCGTTTTGACATCGGCGCAGGTCTTTGT AGTAGTCTTGCATGAGCCTTTCTACCGGCA CTTCTTCTTCTCCTTCCTCTTGTCCTGCATCT CTTGCATCTATCGCTGCGGCGGCGGCGGAG TTTGGCCGTAGGTGGCGCCCTCTTCCTCCCA TGCGTGTGACCCCGAAGCCCCTCATCGGCT GAAGCAGGGCTAGGTCGGCGACAACGCGC TCGGCTAATATGGCCTGCTGCACCTGCGTG AGGGTAGACTGGAAGTCATCCATGTCCACA |

APPENDIX A-continued

SEQUENCE REFERENCE

| SEQ ID NO: | Molecule | Accession Number(s) or description | Sequence |
|---|---|---|---|
| | | | AAGCGGTGGTATGCGCCCGTGTTGATGGTG TAAGTGCAGTTGGCCATAACGGACCAGTTA ACGGTCTGGTGACCCGGCTGCGAGAGCTCG GTGTACCTGAGACGCGAGTAAGCCCTCGAG TCAAATACGTAGTCGTTGCAAGTCCGCACC AGGTACTGGTATCCCACCAAAAAGTGCGGC GGCGGCTGGCGGTAGAGGGGCCAGCGTAG GGTGGCCGGGGCTCCGGGGGCGAGATCTTC CAACATAAGGCGATGATATCCGTAGATGTA CCTGGACATCCAGGTGATGCCGGCGGCGGT GGTGGAGGCGCGCGGAAAGTCGCGGACGC GGTTCCAGATGTTGCGCAGCGGCAAAAAGT GCTCCATGGTCGGGACGCTCTGGCCGGTCA GGCGCGCGCAATCGTTGACGCTCTAGCGTG CAAAAGGAGAGCCTGTAAGCGGGCACTCTT CCGTGGTCTGGTGGATAAATTCGCAAGGGT ATCATGGCGGACGACCGGGGTTCGAGCCCC GTATCCGGCCGTCCGCCGTGATCCATGCGG TTACCGCCCGCGTGTCGAACCCAGGTGTGC GACGTCAGACAACGGGGGAGTGCTCCTTTT GGCTTCCTTCCAGGCGCGGCGGCTGCTGCG CTAGCTTTTTTGGCCACTGGCCGCGCGCAG CGTAAGCGGTTAGGCTGGAAAGCGAAAGC ATTAAGTGGCTCGCTCCCTGTAGCCGGAGG GTTATTTTCCAAGGGTTGAGTCGCGGGACC CCCGGTTCGAGTCTCGGACCGGCCGGACTG CGGCGAACGGGGGTTTGCCTCCCCGTCATG CAAGACCCCGCTTGCAAATTCCTCCGGAAA CAGGGACGAGCCCCTTTTTTGCTTTTCCCAG ATGCATCCGGTGCTGCGGCAGATGCGCCCC CCTCCTCAGCAGCGGCAAGAGCAAGAGCA GCGGCAGACATGCAGGGCACCCTCCCCTCC TCCTACCGCGTCAGGAGGGGCGACATCCGC GGTTGACGCGGCAGCAGATGGTGATTACGA ACCCCCGCGGCGCCGGGCCCGGCACTACCT GGACTTGGAGGAGGGCGAGGGCCTGGCGC GGCTAGGAGCGCCCTCTCCTGAGCGGCACC CAAGGGTGCAGCTGAAGCGTGATACGCGTG AGGCGTACGTGCCGCGGCAGAACCTGTTTC GCGACCGCGAGGGAGAGGAGCCCGAGGAG ATGCGGGATCGAAAGTTCCACGCAGGGCGC GAGCTGCGGCATGGCCTGAATCGCGAGCGG TTGCTGCGCGAGGAGGACTTTGAGCCCGAC GCGCGAACCGGGATTAGTCCCGCGCGCGCA CACGTGGCGGCCGCCGACCTGGTAACCGCA TACGAGCAGACGGTGAACCAGGAGATTAA CTTTCAAAAAAGCTTTAACAACCACGTGCG TACGCTTGTGGCGCGCGAGGAGGTGGCTAT AGGACTGATGCATCTGTGGGACTTTGTAAG CGCGCTGGAGCAAAACCCAAATAGCAAGC CGCTCATGGCGCAGCTGTTCCTTATAGTGC AGCACAGCAGGGACAACGAGGCATTCAGG GATGCGCTGCTAAACATAGTAGAGCCCGAG GGCCGCTGGCTGCTCGATTTGATAAACATC CTGCAGAGCATAGTGGTGCAGGAGCGCAGC TTGAGCCTGGCTGACAAGGTGGCCGCCATC AACTATTCCATGCTTAGCCTGGGCAAGTTTT ACGCCCGCAAGATATACCATACCCCTTACG TTCCCATAGACAAGGAGGTAAAGATCGAGG GGTTCTACATGCGCATGGCGCTGAAGGTGC TTACCTTGAGCGACGACCTGGGCGTTTATC GCAACGAGCGCATCCACAAGGCCGTGAGC GTGAGCCGGCGGCGCGAGCTCAGCGACCGC GAGCTGATGCACAGCCTGCAAAGGGCCCTG GCTGGCACGGGCAGCGGCGATAGAGAGGC CGAGTCCTACTTTGACGCGGGCGCTGACCT GCGCTGGGCCCCAAGCCGACGCGCCCTGGA GGCAGCTGGGGCCGGACCTGGGCTGGCGGT GGCACCCGCGCGCTGGCAACGTCGGCGG CGTGGAGGAATATGACGAGGACGATGAGT ACGAGCCAGAGGACGGCGAGTACTAAGCG GTGATGTTTCTGATCAGATGATGCAAGACG CAACGGACCCGGCGGTGCGGGCGGCGCTGC AGAGCCAGCCGTCCGGCCTTAACTCCACGG |

APPENDIX A-continued

SEQUENCE REFERENCE

| SEQ ID NO: | Molecule | Accession Number(s) or description | Sequence |
|---|---|---|---|
| | | | ACGACTGGCGCCAGGTCATGGACCGCATCA TGTCGCTGACTGCGCGCAATCCTGACGCGT TCCGGCAGCAGCCGCAGGCCAACCGGCTCT CCGCAATTCTGGAAGCGGTGGTCCCGGCGC GCGCAAACCCCACGCACGAGAAGGTGCTG GCGATCGTAAACGCGCTGGCCGAAAACAG GGCCATCCGGCCCGACGAGGCCGGCCTGGT CTACGACGCGCTGCTTCAGCGCGTGGCTCG TTACAACAGCGGCAACGTGCAGACCAACCT GGACCGGCTGGTGGGGGATGTGCGCGAGG CCGTGGCGCAGCGTGAGCGCGCGCAGCAGC AGGGCAACCTGGGCTCCATGGTTGCACTAA ACGCCTTCCTGAGTACACAGCCCGCCAACG TGCCGCGGGGACAGGAGGACTACACCAACT TTGTGAGCGCACTGCGGCTAATGGTGACTG AGACACCGCAAAGTGAGGTGTACCAGTCTG GGCCAGACTATTTTTTCCAGACCAGTAGAC AAGGCCTGCAGACCGTAAACCTGAGCCAGG CTTTCAAAAACTTGCAGGGGCTGTGGGGGG TGCGGGCTCCCACAGGCGACCGCGCGACCG TGTCTAGCTTGCTGACGCCCAACTCGCGCCT GTTGCTGCTGCTAATAGCGCCCTTCACGGA CAGTGGCAGCGTGTCCCGGGACACATACCT AGGTCACTTGCTGACACTGTACCGCGAGGC CATAGGTCAGGCGCATGTGGACGAGCATAC TTTCCAGGAGATTACAAGTGTCAGCCGCGC GCTGGGGCAGGAGGACACGGGCAGCCTGG AGGCAACCCTAAACTACCTGCTGACCAACC GGCGGCAGAAGATCCCCTCGTTGCACAGTT TAAACAGCGAGGAGGAGCGCATTTTGCGCT ACGTGCAGCAGAGCGTGAGCCTTAACCTGA TGCGCGACGGGGTAACGCCCAGCGTGGCGC TGGACATGACCGCGCGCAACATGGAACCGG GCATGTATGCCTCAAACCGGCCGTTTATCA ACCGCCTAATGGACTACTTGCATCGCGCGG CCGCCGTGAACCCCGAGTATTTCACCAATG CCATCTTGAACCCGCACTGGCTACCGCCCC CTGGTTTCTACACCGGGGGATTCGAGGTGC CCGAGGGTAACGATGGATTCCTCTGGGACG ACATAGACGACAGCGTGTTTTCCCCGCAAC CGCAGACCCTGCTAGAGTTGCAACAGCGCG AGCAGGCAGAGGCGGCGCTGCGAAAGGAA AGCTTCCGCAGGCCAAGCAGCTTGTCCGAT CTAGGCGCTGCGGCCCCGCGGTCAGATGCT AGTAGCCCATTTCCAAGCTTGATAGGGTCT CTTACCAGCACTCGCACCACCCGCCCGCGC CTGCTGGGCGAGGAGGAGTACCTAAACAAC TCGCTGCTGCAGCCGCAGCGCGAAAAAAAC CTGCCTCCGGCATTTCCCAACAACGGGATA GAGAGCCTAGTGGACAAGATGAGTAGATG GAAGACGTACGCGCAGGAGCACAGGGACG TGCCAGGCCCGCGCCCGCCCACCCGTCGTC AAAGGCACGACCGTCAGCGGGGTCTGGTGT GGGAGGACGATGACTCGGCAGACGACAGC AGCGTCCTGGATTTGGGAGGGAGTGGCAAC CCGTTTGCGCACCTTCGCCCCAGGCTGGGG AGAATGTTTTAAAAAAAAAAAAGCATGATG CAAAATAAAAAACTCACCAAGGCCATGGC ACCGAGCGTTGGTTTTCTTGTATTCCCCTTA GTATGCGGCGCGGCGATGTATGAGGAAG GTCCTCCTCCCTCCTACGAGAGTGTGGTGA GCGCGGCGCCAGTGGCGGCGGCGCTGGGTT CTCCCTTCGATGCTCCCCTGGACCCGCCGTT TGTGCCTCCGCGGTACCTGCGGCCTACCGG GGGGAGAAACAGCATCCGTTACTCTGAGTT GGCACCCCTATTCGACACCACCCGTGTGTA CCTGGTGGACAACAAGTCAACGGATGTGGC ATCCCTGAACTACCAGAACGACCACAGCAA CTTTCTGACCACGGTCATTCAAAACAATGA CTACAGCCCGGGGGAGGCAAGCACACAGA CCATCAATCTTGACGACCGGTCGCACTGGG GCGGCGACCTGAAAACCATCCTGCATACCA ACATGCCAAATGTGAACGAGTTCATGTTTA CCAATAAGTTTAAGGCGCGGGTGATGGTGT |

APPENDIX A-continued

SEQUENCE REFERENCE

| SEQ ID NO: | Molecule | Accession Number(s) or description | Sequence |
|---|---|---|---|
| | | | CGCGCTTGCCTACTAAGGACAATCAGGTGG AGCTGAAATACGAGTGGGTGGAGTTCACGC TGCCCGAGGGCAACTACTCCGAGACCATGA CCATAGACCTTATGAACAACGCGATCGTGG AGCACTACTTGAAAGTGGGCAGACAGAAC GGGGTTCTGGAAAGCGACATCGGGGTAAA GTTTGACACCCGCAACTTCAGACTGGGGTT TGACCCCGTCACTGGTCTTGTCATGCCTGGG GTATATACAAACGAAGCCTTCCATCCAGAC ATCATTTTGCTGCCAGGATGCGGGGTGGAC TTCACCCACAGCCGCCTGAGCAACTTGTTG GGCATCCGCAAGCGGCAACCCTTCCAGGAG GGCTTTAGGATCACCTACGATGATCTGGAG GGTGGTAACATTCCCGCACTGTTGGATGTG GACGCCTACCAGGCGAGCTTGAAAGATGAC ACCGAACAGGGCGGGGGTGGCGCAGGCGG CAGCAACAGCAGTGGCAGCGGCGCGGAAG AGAACTCCAACGCGGCAGCCGCGGCAATGC AGCCGGTGGAGGACATGAACGATCATGCCA TTCGCGGCGACACCTTTGCCACACGGGCTG AGGAGAAGCGCGCTGAGGCCGAAGCAGCG GCCGAAGCTGCCGCCCCCGCTGCGCAACCC GAGGTCGAGAAGCTCAGAAGAAACCGGT GATCAAACCCCTGACAGAGGACAGCAAGA AACGCAGTTACAACCTAATAAGCAATGACA GCACCTTCACCCAGTACCGCAGCTGGTACC TTGCATACAACTACGGCGACCCTCAGACCG GAATCCGCTCATGGACCCTGCTTTGCACTCC TGACGTAACCTGCGGCTCGGAGCAGGTCTA CTGGTCGTTGCCAGACATGATGCAAGACCC CGTGACCTTCCGCTCCACGCGCCAGATCAG CAACTTTCCGGTGGTGGGCGCCGAGCTGTT GCCCGTGCACTCCAAGAGCTTCTACAACGA CCAGGCCGTCTACTCCCAACTCATCCGCCA GTTTACCTCTCTGACCCACGTGTTCAATCGC TTTCCCGAGAACCAGATTTTGGCGCGCCCG CCAGCCCCCACCATCACCACCGTCAGTGAA AACGTTCCTGCTCTCACAGATCACGGGACG CTACCGCTGCGCAACAGCATCGGAGGAGTC CAGCGAGTGACCATTACTGACGCCAGACGC CGCACCTGCCCCTACGTTTACAAGGCCCTG GGCATAGTCTCGCCGCGCGTCCTATCGAGC CGCACTTTTTGAGCAAGCATGTCCATCCTTA TATCGCCCAGCAATAACACAGGCTGGGGCC TGCGCTTCCCAAGCAAGATGTTTGGCGGGG CCAAGAAGCGCTCCGACCAACACCCAGTGC GCGTGCGCGGGCACTACCGCGCGCCCTGGG GCGCGCACAAACGCGGCCGCACTGGGCGC ACCACCGTCGATGACGCCATCGACGCGGTG GTGGAGGAGGCGCGCAACTACACGCCCAC GCCGCCACCAGTGTCCACAGTGGACGCGGC CATTCAGACCGTGGTGCGCGGAGCCCGGCG CTATGCTAAAATGAAGAGACGGCGGAGGC GCGTAGCACGTCGCCACCGCCGCCGACCCG GCACTGCCGCCCAACGCGCGGCGGCGGCCC TGCTTAACCGCGCACGTCGCACCGGCCGAC GGGCGGCCATGCGGGCCGCTCGAAGGCTGG CCGCGGGTATTGTCACTGTGCCCCCCAGGT CCAGGCGACGAGCGGCCGCCGCAGCAGCC GCGGCCATTAGTGCTATGACTCAGGGTCGC AGGGGCAACGTGTATTGGGTGCGCGACTCG GTTAGCGGCCTGCGCGTGCCCGTGCGCACC CGCCCCCGCGCAACTAGATTGCAAGAAAA AACTACTTAGACTCGTACTGTTGTATGTATC CAGCGGCGGCGGCGCGCAACGAAGCTATGT CCAAGCGCAAAATCAAAGAAGAGATGCTC CAGGTCATCGCGCCGGAGATCTATGGCCCC CCGAAGAAGGAAGAGCAGGATTACAAGCC CCGAAAGCTAAAGCGGGTCAAAAAGAAAA AGAAAGATGATGATGATGAACTTGACGACG AGGTGGAACTGCTGCACGCTACCGCGCCCA GGCGACGGGTACAGTGGAAAGGTCGACGC GTAAAACGTGTTTTGCGACCCGGCACCACC GTAGTCTTTACGCCCGGTGAGCGCTCCACC |

APPENDIX A-continued

SEQUENCE REFERENCE

| SEQ ID NO: | Molecule | Accession Number(s) or description | Sequence |
|---|---|---|---|
| | | | CGCACCTACAAGCGCGTGTATGATGAGGTG |
| | | | TACGGCGACGAGGACCTGCTTGAGCAGGCC |
| | | | AACGAGCGCCTCGGGGAGTTTGCCTACGGA |
| | | | AAGCGGCATAAGGACATGCTGGCGTTGCCG |
| | | | CTGGACGAGGGCAACCCAACACCTAGCCTA |
| | | | AAGCCCGTAACACTGCAGCAGGTGCTGCCC |
| | | | GCGCTTGCACCGTCCGAAGAAAAGCGCGGC |
| | | | CTAAAGCGCGAGTCTGGTGACTTGGCACCC |
| | | | ACCGTGCAGCTGATGGTACCCAAGCGCCAG |
| | | | CGACTGGAAGATGTCTTGGAAAAAATGACC |
| | | | GTGGAACCTGGGCTGGAGCCCGAGGTCCGC |
| | | | GTGCGGCCAATCAAGCAGGTGGCGCCGGG |
| | | | ACTGGGCGTGCAGACCGTGGACGTTCAGAT |
| | | | ACCCACTACCAGTAGCACCAGTATTGCCAC |
| | | | CGCCACAGAGGGCATGGAGACACAAACGT |
| | | | CCCCGGTTGCCTCAGCGGTGGCGGATGCCG |
| | | | CGGTGCAGGCGGTCGCTGCGGCCGCGTCCA |
| | | | AGACCTCTACGGAGGTGCAAACGGACCCGT |
| | | | GGATGTTTCGCGTTTCAGCCCCCCGGCGCC |
| | | | CGCGCCGTTCGAGGAAGTACGGCGCCGCCA |
| | | | GCGCGCTACTGCCCGAATATGCCCTACATC |
| | | | CTTCCATTGCGCCTACCCCCGGCTATCGTGG |
| | | | CTACACCTACCGCCCCAGAAGACGAGCAAC |
| | | | TACCCGACGCCGAACCACCACTGGAACCCG |
| | | | CCGCCGCCGTCGCCGTCGCCAGCCCGTGCT |
| | | | GGCCCCGATTTCCGTGCGCAGGGTGGCTCG |
| | | | CGAAGGAGGCAGGACCCTGGTGCTGCCAAC |
| | | | AGCGCGCTACCACCCCAGCATCGTTTAAAA |
| | | | GCCGGTCTTTGTGGTTCTTGCAGATATGGCC |
| | | | CTCACCTGCCGCCTCCGTTTCCCGGTGCCGG |
| | | | GATTCCGAGGAAGAATGCACCGTAGGAGG |
| | | | GGCATGGCCGGCCACGGCCTGACGGGCGGC |
| | | | ATGCGTCGTGCGCACCACCGGCGGCGGCGC |
| | | | GCGTCGCACCGTCGCATGCGCGGCGGTATC |
| | | | CTGCCCCTCCTTATTCCACTGATCGCCGCGG |
| | | | CGATTGGCGCCGTGCCCGGAATTGCATCCG |
| | | | TGGCCTTGCAGGCGCAGAGACACTGATTAA |
| | | | AAACAAGTTGCATGTGGAAAAATCAAAATA |
| | | | AAAAGTCTGGACTCTCACGCTCGCTTGGTC |
| | | | CTGTAACTATTTTGTAGAATGGAAGACATC |
| | | | AACTTTGCGTCTCTGGCCCCGCGACACGGC |
| | | | TCGCGCCCGTTCATGGGAAACTGGCAAGAT |
| | | | ATCGGCACCAGCAATATGAGCGGTGGCGCC |
| | | | TTCAGCTGGGGCTCGCTGTGGAGCGGCATT |
| | | | AAAAATTTCGGTTCCACCGTTAAGAACTAT |
| | | | GGCAGCAAGGCCTGGAACAGCAGCACAGG |
| | | | CCAGATGCTGAGGGATAAGTTGAAAGAGC |
| | | | AAAATTTCCAACAAAGGTGGTAGATGGCC |
| | | | TGGCCTCTGGCATTAGCGGGGTGGTGGACC |
| | | | TGGCCAACCAGGCAGTGCAAAATAAGATTA |
| | | | ACAGTAAGCTTGATCCCCGCCCTCCCGTAG |
| | | | AGGAGCCTCCACCGGCCGTGGAGACAGTGT |
| | | | CTCCAGAGGGCGTGGCGAAAAGCGTCCGC |
| | | | GCCCCGACAGGGAAGAAACTCTGGTGACGC |
| | | | AAATAGACGAGCCTCCCTCGTACGAGGAGG |
| | | | CACTAAAGCAAGGCCTGCCCACCACCCGTC |
| | | | CCATCGCGCCCATGGCTACCGGAGTGCTGG |
| | | | GCCAGCACACACCCGTAACGCTGGACCTGC |
| | | | CTCCCCCCGCCGACACCCAGCAGAAACCTG |
| | | | TGCTGCCAGGCCCGACCGCCGTTGTTGTAA |
| | | | CCCGTCCTAGCCGCGCGTCCCTGCGCCGCG |
| | | | CCGCCAGCGGTCCGCGATCGTTGCGGCCCG |
| | | | TAGCCAGTGGCAACTGGCAAAGCACACTGA |
| | | | ACAGCATCGTGGGTCTGGGGGTGCAATCCC |
| | | | TGAAGCGCCGACGATGCTTCTGATAGCTAA |
| | | | CGTGTCGTATGTGTGTCATGTATGCGTCCAT |
| | | | GTCGCCGCCAGAGGAGCTGCTGAGCCGCCG |
| | | | CGCGCCCGCTTTCCAAGATGGCTACCCCTTC |
| | | | GATGATGCCGCAGTGGTCTTACATGCACAT |
| | | | CTCGGGCCAGGACGCCTCGGAGTACCTGAG |
| | | | CCCCGGGCTGGTGCAGTTTGCCCGCGCCAC |
| | | | CGAGACGTACTTCAGCCTGAATAACAAGTT |
| | | | TAGAAACCCCACGGTGGCGCCTACGCACGA |
| | | | CGTGACCACAGACCGGTCCCAGCGTTTGAC |

APPENDIX A-continued

SEQUENCE REFERENCE

| SEQ ID NO: | Molecule | Accession Number(s) or description | Sequence |
|---|---|---|---|
| | | | GCTGCGGTTCATCCCTGTGGACCGTGAGGA TACTGCGTACTCGTACAAGGCGCGGTTCAC CCTAGCTGTGGGTGATAACCGTGTGCTGGA CATGGCTTCCACGTACTTTGACATCCGCGG CGTGCTGGACAGGGGCCCTACTTTTAAGCC CTACTCTGGCACTGCCTACAACGCCCTGGC TCCCAAGGGTGCCCCAAATCCTTGCGAATG GGATGAAGCTGCTACTGCTCTTGAAATAAA CCTAGAAGAAGAGGACGATGACAACGAAG ACGAAGTAGACGAGCAAGCTGAGCAGCAA AAAACTCACGTATTTGGGCAGGCGCCTTAT TCTGGTATAAATATTACAAAGGAGGGTATT CAAATAGGTGTCGAAGGTCAAACACCTAAA TATGCCGATAAAACATTTCAACCTGAACCT CAAATAGGAGAATCTCAGTGGTACGAAACA GAAATTAATCATGCAGCTGGGAGAGTCCTA AAAAAGACTACCCCAATGAAACCATGTTAC GGTTCATATGCAAAACCCACAAATGAAAAT GGAGGGCAAGGCATTCTTGTAAAGCAACAA AATGGAAAGCTAGAAAGTCAAGTGGAAAT GCAATTTTTCTCAACTACTGAGGCAGCCGC AGGCAATGGTGATAACTTGACTCCTAAAGT GGTATTGTACAGTGAAGATGTAGATATAGA AACCCCAGACACTCATATTTCTTACATGCCC ACTATTAAGGAAGGTAACTCACGAGAACTA ATGGGCCAACAATCTATGCCCAACAGGCCT AATTACATTGCTTTTAGGGACAATTTTATTG GTCTAATGTATTACAACAGCACGGGTAATA TGGGTGTTCTGGCGGGCCAAGCATCGCAGT TGAATGCTGTTGTAGATTTGCAAGACAGAA ACACAGAGCTTTCATACCAGCTTTTGCTTGA TTCCATTGGTGATAGAACCAGGTACTTTTCT ATGTGGAATCAGGCTGTTGACAGCTATGAT CCAGATGTTAGAATTATTGAAAATCATGGA ACTGAAGATGAACTTCCAAATTACTGCTTT CCACTGGGAGGTGTGATTAATACAGAGACT CTTACCAAGGTAAAACCTAAAACAGGTCAG GAAAATGGATGGGAAAAAGATGCTACAGA ATTTTCAGATAAAAATGAAATAAGAGTTGG AAATAATTTTGCCATGGAAATCAATCTAAA TGCCAACCTGTGGAGAAATTTCCTGTACTC CAACATAGCGCTGTATTTGCCCGACAAGCT AAAGTACAGTCCTTCCAACGTAAAAATTTC TGATAACCCAAACACCTACGACTACATGAA CAAGCGAGTGGTGGCTCCCGGGCTAGTGGA CTGCTACATTAACCTTGGAGCACGCTGGTC CCTTGACTATATGGACAACGTCAACCCATT TAACCACCACCGCAATGCTGGCCTGCGCTA CCGCTCAATGTTGCTGGGCAATGGTCGCTA TGTGCCCTTCCACATCCAGGTGCCTCAGAA GTTCTTTGCCATTAAAAACCTCCTTCTCCTG CCGGGCTCATACACCTACGAGTGGAACTTC AGGAAGGATGTTAACATGGTTCTGCAGAGC TCCCTAGGAAATGACCTAAGGGTTGACGGA GCCAGCATTAAGTTTGATAGCATTTGCCTTT ACGCCACCTTCTTCCCCATGGCCCACAACA CCGCCTCCACGCTTGAGGCCATGCTTAGAA ACGACACCAACGACCAGTCCTTTAACGACT ATCTCTCCGCCGCCAACATGCTCTACCCTAT ACCCGCCAACGCTACCAACGTGCCCATATC CATCCCCTCCCGCAACTGGGCGGCTTTCCG CGGCTGGGCCTTCACGCGCCTTAAGACTAA GGAAACCCCATCACTGGGCTCGGGCTACGA CCCTTATTACACCTACTCTGGCTCTATACCC TACCTAGATGGAACCTTTTACCTCAACCAC ACCTTTAAGAAGGTGGCCATTACCTTTGAC TCTTCTGTCAGCTGGCCTGGCAATGACCGC CTGCTTACCCCCAACGAGTTTGAAATTAAG CGCTCAGTTGACGGGGAGGGTTACAACGTT GCCCAGTGTAACATGACCAAAGACTGGTTC CTGGTACAAATGCTAGCTAACTATAACATT GGCTACCAGGGCTTCTATATCCCAGAGAGC TACAAGGACCGCATGTACTCCTTCTTTAGA AACTTCCAGCCCATGAGCCGTCAGGTGGTG |

APPENDIX A-continued

SEQUENCE REFERENCE

| SEQ ID NO: | Molecule | Accession Number(s) or description | Sequence |
|---|---|---|---|
| | | | GATGATACTAAATACAAGGACTACCAACAG |
| | | | GTGGGCATCCTACACCAACACAACAACTCT |
| | | | GGATTTGTTGGCTACCTTGCCCCCACCATGC |
| | | | GCGAAGGACAGGCCTACCCTGCTAACTTCC |
| | | | CCTATCCGCTTATAGGCAAGACCGCAGTTG |
| | | | ACAGCATTACCCAGAAAAAGTTTCTTTGCG |
| | | | ATCGCACCCTTTGGCGCATCCCATTCTCCAG |
| | | | TAACTTTATGTCCATGGGCGCACTCACAGA |
| | | | CCTGGGCCAAAACCTTCTCTACGCCAACTC |
| | | | CGCCCACGCGCTAGACATGACTTTTGAGGT |
| | | | GGATCCCATGGACGAGCCCACCCTTCTTTA |
| | | | TGTTTTGTTTGAAGTCTTTGACGTGGTCCGT |
| | | | GTGCACCAGCCGCACCGCGGCGTCATCGAA |
| | | | ACCGTGTACCTGCGCACGCCCTTCTCGGCC |
| | | | GGCAACGCCACAACATAAAGAAGCAAGCA |
| | | | ACATCAACAACAGCTGCCGCCATGGGCTCC |
| | | | AGTGAGCAGGAACTGAAAGCCATTGTCAAA |
| | | | GATCTTGGTTGTGGGCCATATTTTTTGGGCA |
| | | | CCTATGACAAGCGCTTTCCAGGCTTTGTTTC |
| | | | TCCACACAAGCTCGCCTGCGCCATAGTCAA |
| | | | TACGGCCGGTCGCGAGACTGGGGGCGTACA |
| | | | CTGGATGGCCTTTGCCTGGAACCCGCACTC |
| | | | AAAAACATGCTACCTCTTTGAGCCCTTTGG |
| | | | CTTTTCTGACCAGCGACTCAAGCAGGTTTA |
| | | | CCAGTTTGAGTACGAGTCACTCCTGCGCCG |
| | | | TAGCGCCATTGCTTCTTCCCCCGACCGCTGT |
| | | | ATAACGCTGGAAAAGTCCACCCAAAGCGTA |
| | | | CAGGGGCCCAACTCGGCCGCCTGTGGACTA |
| | | | TTCTGCTGCATGTTTCTCCACGCCTTTGCCA |
| | | | ACTGGCCCCAAACTCCCATGGATCACAACC |
| | | | CCACCATGAACCTTATTACCGGGGTACCCA |
| | | | ACTCCATGCTCAACAGTCCCCAGGTACAGC |
| | | | CCACCCTGCGTCGCAACCAGGAACAGCTCT |
| | | | ACAGCTTCCTGGAGCGCCACTCGCCCTACT |
| | | | TCCGCAGCCACAGTGCGCAGATTAGGAGCG |
| | | | CCACTTCTTTTTGTCACTTGAAAAACATGTA |
| | | | AAAATAATGTACTAGAGACACTTTCAATAA |
| | | | AGGCAAATGCTTTTATTTGTACACTCTCGGG |
| | | | TGATTATTTACCCCCACCCTTGCCGTCTGCG |
| | | | CCGTTTAAAAATCAAAGGGGTTCTGCCGCG |
| | | | CATCGCTATGCGCCACTGGCAGGGACACGT |
| | | | TGCGATACTGGTGTTTAGTGCTCCACTTAAA |
| | | | CTCAGGCACAACCATCCGCGGCAGCTCGGT |
| | | | GAAGTTTTCACTCCACAGGCTGCGCACCAT |
| | | | CACCAACGCGTTTAGCAGGTCGGGCGCCGA |
| | | | TATCTTGAAGTCGCAGTTGGGGCCTCCGCC |
| | | | CTGCGCGCGCGAGTTGCGATACACAGGGTT |
| | | | GCAGCACTGGAACACTATCAGCGCCGGGTG |
| | | | GTGCACGCTGGCCAGCACGCTCTTGTCGGA |
| | | | GATCAGATCCGCGTCCAGGTCCTCCGCGTT |
| | | | GCTCAGGGCGAACGGAGTCAACTTTGGTAG |
| | | | CTGCCTTCCCAAAAAGGGCGCGTGCCCAGG |
| | | | CTTTGAGTTGCACTCGCACCGTAGTGGCAT |
| | | | CAAAAGGTGACCGTGCCCGGTCTGGGCGTT |
| | | | AGGATACAGCGCCTGCATAAAAGCCTTGAT |
| | | | CTGCTTAAAAGCCACCTGAGCCTTTGCGCC |
| | | | TTCAGAGAAGAACATGCCGCAAGACTTGCC |
| | | | GGAAAACTGATTGGCCGGACAGGCCGCGTC |
| | | | GTGCACGCAGCACCTTGCGTCGGTGTTGGA |
| | | | GATCTGCACCACATTTCGGCCCCACCGGTT |
| | | | CTTCACGATCTTGGCCTTGCTAGACTGCTCC |
| | | | TTCAGCGCGCGCTGCCCGTTTTCGCTCGTCA |
| | | | CATCCATTTCAATCACGTGCTCCTTATTTAT |
| | | | CATAATGCTTCCGTGTAGACACTTAAGCTC |
| | | | GCCTTCGATCTCAGCGCAGCGGTGCAGCCA |
| | | | CAACGCGCAGCCCGTGGGCTCGTGATGCTT |
| | | | GTAGGTCACCTCTGCAAACGACTGCAGGTA |
| | | | CGCCTGCAGGAATCGCCCCATCATCGTCAC |
| | | | AAAGGTCTTGTTGCTGGTGAAGGTCAGCTG |
| | | | CAACCCGCGGTGCTCCTCGTTCAGCCAGGT |
| | | | CTTGCATACGGCCGCCAGAGCTTCCACTTG |
| | | | GTCAGGCAGTAGTTTGAAGTTCGCCTTTAG |
| | | | ATCGTTATCCACGTGGTACTTGTCCATCAGC |
| | | | GCGCGCGCAGCCTCCATGCCCTTCTCCCAC |

APPENDIX A-continued

SEQUENCE REFERENCE

| SEQ ID NO: | Molecule | Accession Number(s) or description | Sequence |
|---|---|---|---|
| | | | GCAGACACGATCGGCACACTCAGCGGGTTC<br>ATCACCGTAATTTCACTTTCCGCTTCGCTGG<br>GCTCTTCCTCTTCCTCTTGCGTCCGCATACC<br>ACGCGCCACTGGGTCGTCTTCATTCAGCCG<br>CCGCACTGTGCGCTTACCTCCTTTGCCATGC<br>TTGATTAGCACCGGTGGGTTGCTGAAACCC<br>ACCATTTGTAGCGCCACATCTTCTCTTTCTT<br>CCTCGCTGTCCACGATTACCTCTGGTGATGG<br>CGGGCGCTCGGGCTTGGGAGAAGGGCGCTT<br>CTTTTTCTTCTTGGGCGCAATGGCCAAATCC<br>GCCGCCGAGGTCGATGGCCGCGGGCTGGGT<br>GTGCGCGGCACCAGCGCGTCTTGTGATGAG<br>TCTTCCTCGTCCTCGGACTCGATACGCCGCC<br>TCATCCGCTTTTTTGGGGGCGCCCGGGGAG<br>GCGGCGGCGACGGGGACGGGGACGACACG<br>TCCTCCATGGTTGGGGGACGTCGCGCCGCA<br>CCGCGTCCGCGCTCGGGGGTGGTTTCGCGC<br>TGCTCCTCTTCCCGACTGGCCATTTCCTTCT<br>CCTATAGGCAGAAAAAGATCATGGAGTCAG<br>TCGAGAAGAAGGACAGCCTAACCGCCCCCT<br>CTGAGTTCGCCACCACCGCCTCCACCGATG<br>CCGCCAACGCGCCTACCACCTTCCCCGTCG<br>AGGCACCCCCGCTTGAGGAGGAGGAAGTG<br>ATTATCGAGCAGGACCCAGGTTTTGTAAGC<br>GAAGACGACGAGGACCGCTCAGTACCAAC<br>AGAGGATAAAAAGCAAGACCAGGACAACG<br>CAGAGGCAAACGAGGAACAAGTCGGGCGG<br>GGGGACGAAAGGCATGGCGACTACCTAGA<br>TGTGGGAGACGACGTGCTGTTGAAGCATCT<br>GCAGCGCCAGTGCGCCATTATCTGCGACGC<br>GTTGCAAGAGCGCAGCGATGTGCCCCTCGC<br>CATAGCGGATGTCAGCCTTGCCTACGAACG<br>CCACCTATTCTCACCGCGCGTACCCCCCAA<br>ACGCCAAGAAAACGGCACATGCGAGCCCA<br>ACCCGCGCCTCAACTTCTACCCCGTATTTGC<br>CGTGCCAGAGGTGCTTGCCACCTATCACAT<br>CTTTTTCCAAAACTGCAAGATACCCCTATCC<br>TGCCGTGCCAACCGCAGCCGAGCGGACAAG<br>CAGCTGGCCTTGCGGCAGGGCGCTGTCATA<br>CCTGATATCGCCTCGCTCAACGAAGTGCCA<br>AAAATCTTTGAGGGTCTTGGACGCGACGAG<br>AAGCGCGCGGCAAACGCTCTGCAACAGGA<br>AAACAGCGAAAATGAAAGTCACTCTGGAGT<br>GTTGGTGGAACTCGAGGGTGACAACGCGCG<br>CCTAGCCGTACTAAAACGCAGCATCGAGGT<br>CACCCACTTTGCCTACCCGGCACTTAACCTA<br>CCCCCCAAGGTCATGAGCACAGTCATGAGT<br>GAGCTGATCGTGCGCCGTGCGCAGCCCCTG<br>GAGAGGGATGCAAATTTGCAAGAACAAAC<br>AGAGGAGGGCCTACCCGCAGTTGGCGACG<br>AGCAGCTAGCGCGCTGGCTTCAAACGCGCG<br>AGCCTGCCGACTTGGAGGAGCGACGCAAAC<br>TAATGATGGCCGCAGTGCTCGTTACCGTGG<br>AGCTTGAGTGCATGCAGCGGTTCTTTGCTG<br>ACCCGGAGATGCAGCGCAAGCTAGAGGAA<br>ACATTGCACTACACCTTTCGACAGGGCTAC<br>GTACGCCAGGCCTGCAAGATCTCCAACGTG<br>GAGCTCTGCAACCTGGTCTCCTACCTTGGA<br>ATTTTGCACGAAAACCGCCTTGGGCAAAAC<br>GTGCTTCATTCCACGCTCAAGGGCGAGGCG<br>CGCCGCGACTACGTCCGCGACTGCGTTTAC<br>TTATTTCTATGCTACACCTGGCAGACGGCC<br>ATGGGCGTTTGGCAGCAGTGCTTGGAGGAG<br>TGCAACCTCAAGGAGCTGCAGAAACTGCTA<br>AAGCAAAACTTGAAGGACCTATGGACGACC<br>TTCAACGAGCGCTCCGTGGCCGCGCACCTG<br>GCGGACATCATTTTCCCCGAACGCCTGCTT<br>AAAACCCTGCAACAGGGTCTGCCAGACTTC<br>ACCAGTCAAAGCATGTTGCAGAACTTTAGG<br>AACTTTATCCTAGAGCGCTCAGGAATCTTG<br>CCCGCCACCTGCTGTGCACTTCCTAGCGACT<br>TTGTGCCCATTAAGTACCGCGAATGCCCTC<br>CGCCGCTTTGGGGCCACTGCTACCTTCTGCA<br>GCTAGCCAACTACCTTGCCTACCACTCTGA |

APPENDIX A-continued

SEQUENCE REFERENCE

| SEQ ID NO: | Molecule | Accession Number(s) or description | Sequence |
|---|---|---|---|
| | | | CATAATGGAAGACGTGAGCGGTGACGGTCT ACTGGAGTGTCACTGTCGCTGCAACCTATG CACCCCGCACCGCTCCCTGGTTTGCAATTCG CAGCTGCTTAACGAAAGTCAAATTATCGGT ACCTTTGAGCTGCAGGGTCCCTCGCCTGAC GAAAAGTCCGCGGCTCCGGGGTTGAAACTC ACTCCGGGGCTGTGGACGTCGGCTTACCTT CGCAAATTTGTACCTGAGGACTACCACGCC CACGAGATTAGGTTCTACGAAGACCAATCC CGCCCGCCTAATGCGGAGCTTACCGCCTGC GTCATTACCCAGGGCCACATTCTTGGCCAA TTGCAAGCCATCAACAAAGCCCGCCAAGAG TTTCTGCTACGAAAGGGACGGGGGGTTTAC TTGGACCCCCAGTCCGGCGAGGAGCTCAAC CCAATCCCCCGCCGCCGCAGCCCTATCAG CAGCAGCCGCGGGCCCTTGCTTCCCAGGAT GGCACCCAAAAAGAAGCTGCAGCTGCCGCC GCCACCCACGGACGAGGAGGAATACTGGG ACAGTCAGGCAGAGGAGGTTTTGGACGAG GAGGAGGAGGACATGATGGAAGACTGGGA GAGCCTAGACGAGGAAGCTTCCGAGGTCGA AGAGGTGTCAGACGAAACACCGTCACCCTC GGTCGCATTCCCTCGCCGGCGCCCCAGAA ATCGGCAACCGGTTCCAGCATGGCTACAAC CTCCGCTCCTCAGGCGCCGCCGGCACTGCC CGTTCGCCGACCCAACCGTAGATGGGACAC CACTGGAACCAGGGCCGGTAAGTCCAAGCA GCCGCCGCCGTTAGCCCAAGAGCAACAACA GCGCCAAGGCTACCGCTCATGGCGCGGGCA CAAGAACGCCATAGTTGCTTGCTTGCAAGA CTGTGGGGGCAACATCTCCTTCGCCCGCCG CTTTCTTCTCTACCATCACGGCGTGGCCTTC CCCCGTAACATCCTGCATTACTACCGTCATC TCTACAGCCCATACTGCACCGGCGGCAGCG GCAGCAACAGCAGCGGCCACACAGAAGCA AAGGCGACCGGATAGCAAGACTCTGACAA AGCCCAAGAAATCCACAGCGGCGGCAGCA GCAGGAGGAGGAGCGCTGCGTCTGGCGCCC AACGAACCCGTATCGACCCGCGAGCTTAGA AACAGGATTTTTCCCACTCTGTATGCTATAT TTCAACAGAGCAGGGGCCAAGAACAAGAG CTGAAAATAAAAAACAGGTCTCTGCGATCC CTCACCCGCAGCTGCCTGTATCACAAAAGC GAAGATCAGCTTCGGCGCACGCTGGAAGAC GCGGAGGCTCTCTTCAGTAAATACTGCGCG CTGACTCTTAAGGACTAGTTTCGCGCCCTTT CTCAAATTTAAGCGCGAAAACTACGTCATC TCCAGCGGCCACACCCGGCGCCAGCACCTG TTGTCAGCGCCATTATGAGCAAGGAAATTC CCACGCCCTACATGTGGAGTTACCAGCCAC AAATGGGACTTGCGGCTGGAGCTGCCCAAG ACTACTCAACCCGAATAAACTACATGAGCG CGGGACCCCACATGATATCCCGGGTCAACG GAATACGCGCCCACCGAAACCGAATTCTCC TGGAACAGGCGGCTATTACCACCACACCTC GTAATAACCTTAATCCCCGTAGTTGGCCCG CTGCCCTGGTGTACCAGGAAAGTCCCGCTC CCACCACTGTGGTACTTCCCAGAGACGCCC AGGCCGAAGTTCAGATGACTAACTCAGGGG CGCAGCTTGCGGGCGGCTTTCGTCACAGGG TGCGGTCGCCCGGGCAGGGTATAACTCACC TGACAATCAGAGGGCGAGGTATTCAGCTCA ACGACGAGTCGGTGAGCTCCTCGCTTGGTC TCCGTCCGGACGGGACATTTCAGATCGGCG GCGCCGGCCGCTCTTCATTCACGCCTCGTCA GGCAATCCTAACTCTGCAGACCTCGTCCTCT GAGCCGCGCTCTGGAGGCATTGGAACTCTG CAATTTATTGAGGAGTTTGTGCCATCGGTCT ACTTTAACCCCTTCTCGGGACCTCCCGGCCA CTATCCGGATCAATTTATTCCTAACTTTGAC GCGGTAAAGGACTCGGCGGACGGCTACGA CTGAATGTTAAGTGGAGAGGCAGAGCAACT GCGCCTGAAACACCTGGTCCACTGTCGCCG CCACAAGTGCTTTGCCCGCGACTCCGGTGA |

APPENDIX A-continued

SEQUENCE REFERENCE

| SEQ ID NO: | Molecule | Accession Number(s) or description | Sequence |
|---|---|---|---|
| | | | GTTTTGCTACTTTGAATTGCCCGAGGATCAT ATCGAGGGCCCGGCGCACGGCGTCCGGCTT ACCGCCCAGGGAGAGCTTGCCCGTAGCCTG ATTCGGGAGTTTACCCAGCGCCCCCTGCTA GTTGAGCGGGACAGGGGACCCTGTGTTCTC ACTGTGATTTGCAACTGTCCTAACCCTGGAT TACATCAAGATCCTCTAGTTAATGTCAGGT CGCCTAAGTCGATTAACTAGAGTACCCGGG GATCTTATTCCCTTTAACTAATAAAAAAAA ATAATAAAGCATCACTTACTTAAAATCAGT TAGCAAATTTCTGTCCAGTTTATTCAGCAGC ACCTCCTTGCCCTCCTCCCAGCTCTGGTATT GCAGCTTCCTCCTGGCTGCAAACTTTCTCCA CAATCTAAATGGAATGTCAGTTTCCTCCTGT TCCTGTCCATCCGCACCCACTATCTTCATGT TGTTGCAGATGAAGCGCGCAAGACCGTCTG AAGATACCTTCAACCCCGTGTATCCATATG ACACGGAAACCGGTCCTCCAACTGTGCCTT TTCTTACTCCTCCCTTTGTATCCCCCAATGG GTTTCAAGAGAGTCCCCCTGGGGTACTCTC TTTGCGCCTATCCGAACCTCTAGTTACCTCC AATGGCATGCTTGCGCTCAAAATGGGCAAC GGCCTCTCTCTGGACGAGGCCGGCAACCTT ACCTCCCAAAATGTAACCACTGTGAGCCCA CCTCTCAAAAAAACCAAGTCAAACATAAAC CTGGAAATATCTGCACCCCTCACAGTTACC TCAGAAGCCCTAACTGTGGCTGCCGCCGCA CCTCTAATGGTCGCGGGCAACACACTCACC ATGCAATCACAGGCCCCGCTAACCGTGCAC GACTCCAAACTTAGCATTGCCACCCAAGGA CCCCTCACAGTGTCAGAAGGAAAGCTAGCC CTGCAAACATCAGGCCCCCTCACCACCACC GATAGCAGTACCCTTACTATCACTGCCTCA CCCCCTCTAACTACTGCCACTGGTAGCTTGG GCATTGACTTGAAAGAGCCCATTTATACAC AAAATGGAAAACTAGGACTAAAGTACGGG GCTCCTTTGCATGTAACAGACGACCTAAAC ACTTTGACCGTAGCAACTGGTCCAGGTGTG ACTATTAATAATACTTCCTTGCAAACTAAA GTTACTGGAGCCTTGGGTTTTGATTCACAA GGCAATATGCAACTTAATGTAGCAGGAGGA CTAAGGATTGATTCTCAAAACAGACGCCTT ATACTTGATGTTAGTTATCCGTTTGATGCTC AAAACCAACTAAATCTAAGACTAGGACAG GGCCCTCTTTTTATAAACTCAGCCCACAACT TGGATATTAACTACAACAAAGGCCTTTACT TGTTTACAGCTTCAAACAATTCCAAAAAGC TTGAGGTTAACCTAAGCACTGCCAAGGGGT TGATGTTTGACGCTACAGCCATAGCCATTA ATGCAGGAGATGGGCTTGAATTTGGTTCAC CTAATGCACCAAACACAAATCCCCTCAAAA CAAAAATTGGCCATGGCCTAGAATTTGATT CAAACAAGGCTATGGTTCCTAAACTAGGAA CTGGCCTTAGTTTTGACAGCACAGGTGCCA TTACAGTAGGAAACAAAAATAATGATAAGC TAACTTTGTGGACCACACCAGCTCCATCTCC TAACTGTAGACTAAATGCAGAGAAAGATGC TAAACTCACTTTGGTCTTAACAAAATGTGG CAGTCAAATACTTGCTACAGTTTCAGTTTTG GCTGTTAAAGGCAGTTTGGCTCCAATATCT GGAACAGTTCAAAGTGCTCATCTTATTATA AGATTTGACGAAAATGGAGTGCTACTAAAC AATTCCTTCCTGGACCCAGAATATTGGAAC TTTAGAAATGGAGATCTTACTGAAGGCACA GCCTATACAAACGCTGTTGGATTTATGCCT AACCTATCAGCTTATCCAAAATCTCACGGT AAAACTGCCAAAAGTAACATTGTCAGTCAA GTTTACTTAAACGGAGACAAAACTAAACCT GTAACACTAACCATTACACTAAACGGTACA CAGGAAACAGGAGACACAACTCCAAGTGC ATACTCTATGTCATTTTCATGGGACTGGTCT GGCCACAACTACATTAATGAAATATTTGCC ACATCCTCTTACACTTTTTCATACATTGCCC AAGAATAAAGAATCGTTTGTGTTATGTTTC |

APPENDIX A-continued

SEQUENCE REFERENCE

| SEQ ID NO: | Molecule | Accession Number(s) or description | Sequence |
|---|---|---|---|
| | | | AACGTGTTTATTTTTCAATTGCAGAAAATTT
CAAGTCATTTTTCATTCAGTAGTATAGCCCC
ACCACCACATAGCTTATACAGATCACCGTA
CCTTAATCAAACTCACAGAACCCTAGTATT
CAACCTGCCACCTCCCTCCCAACACACAGA
GTACACAGTCCTTTCTCCCCGGCTGGCCTTA
AAAAGCATCATATCATGGGTAACAGACATA
TTCTTAGGTGTTATATTCCACACGGTTTCCT
GTCGAGCCAAACGCTCATCAGTGATATTAA
TAAACTCCCCGGGCAGCTCACTTAAGTTCA
TGTCGCTGTCCAGCTGCTGAGCCACAGGCT
GCTGTCCAACTTGCGGTTGCTTAACGGGCG
GCGAAGGAGAAGTCCACGCCTACATGGGG
GTAGAGTCATAATCGTGCATCAGGATAGGG
CGGTGGTGCTGCAGCAGCGCGCGAATAAAC
TGCTGCCGCCGCCGCTCCGTCCTGCAGGAA
TACAACATGGCAGTGGTCTCCTCAGCGATG
ATTCGCACCGCCCGCAGCATAAGGCGCCTT
GTCCTCCGGGCACAGCAGCGCACCCTGATC
TCACTTAAATCAGCACAGTAACTGCAGCAC
AGCACCACAATATTGTTCAAAATCCCACAG
TGCAAGGCGCTGTATCCAAAGCTCATGGCG
GGGACCACAGAACCCACGTGGCCATCATAC
CACAAGCGCAGGTAGATTAAGTGGCGACCC
CTCATAAACACGCTGGACATAAACATTACC
TCTTTTGGCATGTTGTAATTCACCACCTCCC
GGTACCATATAAACCTCTGATTAAACATGG
CGCCATCCACCACCATCCTAAACCAGCTGG
CCAAAACCTGCCCGCCGGCTATACACTGCA
GGGAACCGGGACTGGAACAATGACAGTGG
AGAGCCCAGGACTCGTAACCATGGATCATC
ATGCTCGTCATGATATCAATGTTGGCACAA
CACAGGCACACGTGCATACACTTCCTCAGG
ATTACAAGCTCCTCCCGCGTTAGAACCATA
TCCCAGGGAACAACCCATTCCTGAATCAGC
GTAAATCCCACACTGCAGGGAAGACCTCGC
ACGTAACTCACGTTGTGCATTGTCAAAGTG
TTACATTCGGGCAGCAGCGGATGATCCTCC
AGTATGGTAGCGCGGGTTTCTGTCTCAAAA
GGAGGTAGACGATCCCTACTGTACGGAGTG
CGCCGAGACAACCGAGATCGTGTTGGTCGT
AGTGTCATGCCAAATGGAACGCCGGACGTA
GTCATATTTCCTGAAGCAAAACCAGGTGCG
GGCGTGACAAACAGATCTGCGTCTCCGGTC
TCGCCGCTTAGATCGCTCTGTGTAGTAGTTG
TAGTATATCCACTCTCTCAAAGCATCCAGG
CGCCCCCTGGCTTCGGGTTCTATGTAAACTC
CTTCATGCGCCGCTGCCCTGATAACATCCA
CCACCGCAGAATAAGCCACACCCAGCCAAC
CTACACATTCGTTCTGCGAGTCACACACGG
GAGGAGCGGGAAGAGCTGGAAGAACCATG
TTTTTTTTTTTATTCCAAAAGATTATCCAAA
ACCTCAAAATGAAGATCTATTAAGTGAACG
CGCTCCCCTCCGGTGGCGTGGTCAAACTCT
ACAGCCAAAGAACAGATAATGGCATTTGTA
AGATGTTGCACAATGGCTTCCAAAAGGCAA
ACGGCCCTCACGTCCAAGTGGACGTAAAGG
CTAAACCCTTCAGGGTGAATCTCCTCTATA
AACATTCCAGCACCTTCAACCATGCCCAAA
TAATTCTCATCTCGCCACCTTCTCAATATAT
CTCTAAGCAAATCCCGAATATTAAGTCCGG
CCATTGTAAAAATCTGCTCCAGAGCGCCCT
CCACCTTCAGCCTCAAGCAGCGAATCATGA
TTGCAAAAATTCAGGTTCCTCACAGACCTG
TATAAGATTCAAAAGCGGAACATTAACAAA
AATACCGCGATCCCGTAGGTCCCTTCGCAG
GGCCAGCTGAACATAATCGTGCAGGTCTGC
ACGGACCAGCGCGGCCACTTCCCCGCCAGG
AACCATGACAAAAGAACCCACACTGATTAT
GACACGCATACTCGGAGCTATGCTAACCAG
CGTAGCCCCGATGTAAGCTTGTTGCATGGG
CGGCGATATAAAATGCAAGGTGCTGCTCAA
AAAATCAGGCAAAGCCTCGCGCAAAAAAG
AAAGCACATCGTAGTCATGCTCATGCAGAT |

APPENDIX A-continued

SEQUENCE REFERENCE

| SEQ ID NO: | Molecule | Accession Number(s) or description | Sequence |
|---|---|---|---|
| | | | AAAGGCAGGTAAGCTCCGGAACCACCACA GAAAAAGACACCATTTTTCTCTCAAACATG TCTGCGGGTTTCTGCATAAACACAAAATAA AATAACAAAAAAACATTTAAACATTAGAAG CCTGTCTTACAACAGGAAAAACAACCCTTA TAAGCATAAGACGGACTACGGCCATGCCGG CGTGACCGTAAAAAAACTGGTCACCGTGAT TAAAAAGCACCACCGACAGCTCCTCGGTCA TGTCCGGAGTCATAATGTAAGACTCGGTAA ACACATCAGGTTGATTCACATCGGTCAGTG CTAAAAAGCGACCGAAATAGCCCGGGGGA ATACATACCCGCAGGCGTAGAGACAACATT ACAGCCCCCATAGGAGGTATAACAAATTA ATAGGAGAGAAAAACACATAAACACCTGA AAAACCCTCCTGCCTAGGCAAAATAGCACC CTCCCGCTCCAGAACAACATACAGCGCTTC CACAGCGGCAGCCATAACAGTCAGCCTTAC CAGTAAAAAAGAAAACCTATTAAAAAAAC ACCACTCGACACGGCACCAGCTCAATCAGT CACAGTGTAAAAAAGGGCCAAGTGCAGAG CGAGTATATATAGGACTAAAAAATGACGTA ACGGTTAAAGTCCACAAAAAACACCCAGA AAACCGCACGCGAACCTACGCCCAGAAAC GAAAGCCAAAAAACCCACAACTTCCTCAAA TCGTCACTTCCGTTTTCCCACGTTACGTCAC TTCCCATTTTAAGAAAACTACAATTCCCAA CACATACAAGTTACTCCGCCCTAAAACCTA CGTCACCCGCCCCGTTCCCACGCCCCGCGC CACGTCACAAACTCCACCCCCTCATTATCAT ATTGGCTTCAATCCAAAATAAGGTATATTA TTGATGATG |
| 95 | Full nucleotide sequence of TRZ627 hIL-12 virus (beginning at Ad5 5' end ITR) | (human IL-12 insert sequence in grey highlight-codon optimized) | TTTTGGATTGAAGCCAATATGATAATGAGG GGGTGGAGTTTGTGACGTGGCGCGGGGCGT GGGAACGGGGCGGGTGACGTAGTAGTGTG GCGGAAGTGTGATGTTGCAAGTGTGGCGGA ACACATGTAAGCGACGGATGTGGCAAAAGT GACGTTTTTGGTGTGCGCCGGTGTTTTGGGC GTAACCGAGTAAGATTTGGCCATTTTCGCG GGAAAACTGAATAAGAGGAAGTGAAATCT GAATAATTTTGTGTTACTCATAGCGCGTAAT ATTTGTCTAGGGCCGCGGGGACTTTGACCG TTTACGTGGAGACTCGCCCAGGTGTTTTTCT CAGGTGTTTTCCGCGTTCCGGGTCAAAGTT GGCGTTTTATTATTATAGTCAGCTGACGTGT AGTGTATTTATACCCGGTGAGTTCCTCAAG AGGCCACTCTTGAGTGCCAGCGAGTAGAGT TTTCTCCTCCGAGCCGCTCCGACACCGGGA CTGAAAATGAGACATATTATCTGCCACGGA GGTGTTATTACCGAAGAAATGGCCGCCAGT CTTTTGGACCAGCTGATCGAAGAGGTACTG GCTGATAATCTTCCACCTCCTAGCCATTTTG AACCACCTACCCTTCACGAACTGTATGATTT AGACGTGACGGCCCCCGAAGATCCCAACGA GGAGGCGGTTTCGCAGATTTTTCCCGACTCT GTAATGTTGGCGGTGCAGGAAGGGATTGAC TTACTCACTTTTCCGCCGGCGCCCGGTTCTC CGGAGCCGCCTCACCTTTCCCGGCAGCCCG AGCAGCCGGAGCAGAGAGCCTTGGGTCCG GTTTCTATGCCAAACCTTGTACCGGAGGTG ATCGATCTTACCTGCCACGAGGCTGGCTTTC CACCCAGTGACGACGAGGATGAAGAGGGT GAGGAGTTTGTGTTAGATTATGTGGAGCAC CCCGGGCACGGTTGCAGGTCTTGTCATTAT CACCGGAGGAATACGGGGACCCAGATATT ATGTGTTCGCTTTGCTATATGAGGACCTGTG GCATGTTTGTCTACAGTAAGTGAAAATTAT GGGCAGTGGGTGATAGAGTGGTGGGTTTGG TGTGGTAATTTTTTTTTAATTTTTACAGTTT TGTGGTTTAAAGAATTTTGTATTGTGATTTT TTTAAAAGGTCCTGTGTCTGAACCTGAGCC TGAGCCCGAGCCAGAACCGGAGCCTGCAA GACCTACCCGCCGTCCTAAAATGGCGCCTG CTATCCTGAGACGCCCGACATCACCTGTGT |

APPENDIX A-continued

SEQUENCE REFERENCE

| SEQ ID NO: | Molecule | Accession Number(s) or description | Sequence |
|---|---|---|---|
| | | | CTAGAGAATGCAATAGTAGTACGGATAGCT GTGACTCCGGTCCTTCTAACACACCTCCTGA GATACACCCGGTGGTCCCGCTGTGCCCCAT TAAACCAGTTGCCGTGAGAGTTGGTGGGCG TCGCCAGGCTGTGGAATGTATCGAGGACTT GCTTAACGAGCCTGGGCAACCTTTGGACTT GAGCTGTAAACGCCCCAGGCCATAAGGTGT AAACCTGTGATTGCGTGTGTGGTTAACGCC TTTGTTTGCTGAATGAGTTGATGTAAGTTTA ATAAAGGGTGAGATAATGTTTAACTTGCAT GGCGTGTTAAATGGGGCGGGGCTTAAAGGG TATATAATGCGCCGTGGGCTAATCTTGGTT ACATCTGACCTCGTCGACGCCACCATGTGT |
| | | | CACCAGCAGCTCGTGATTAGCTGGTTCAGC |
| | | | CTGGTGTTTCTGGCTAGCCCTCTGGTGGCCA |
| | | | TCTGGGAGCTGAAGAAGGACGTGTACGTGG |
| | | | TGGAGCTCGACTGGTACCCTGACGCTCCCG |
| | | | GCGAGATGGTCGTGCTGACCTGCGACACCC |
| | | | CTGAGGAAGATGGCATCACCTGGACCCTGG |
| | | | ATCAAAGCTCCGAAGTGCTCGGCAGCGGCA |
| | | | AGACACTCACCATCCAGGTGAAAGAGTTCG |
| | | | GAGACGCCGGCCAGTACACCTGCCACAAAG |
| | | | GCGGCGAGGTGCTGTCCCATTCCCTGCTGC |
| | | | TGCTGCACAAGAAAGAGGATGGCATCTGGT |
| | | | CCACCGACATCCTGAAGGACCAGAAGGAA |
| | | | CCCAAGAACAAGACCTTTCTGAGATGTGAG |
| | | | GCCAAGAACTACAGCGGCAGGTTCACCTGC |
| | | | TGGTGGCTGACAACAATCTCCACCGACCTG |
| | | | ACCTTCAGCGTCAAGAGCAGCAGGGGCAGC |
| | | | AGCGACCCCTCAAGGCGTGACATGTGGAGCC |
| | | | GCTACCCTGAGCGCTGAGAGAGTCAGGGGC |
| | | | GACAATAAGGAGTACGAGTACTCCGTGGAA |
| | | | TGCCAGGAGGACTCCGCCTGCCCTGCCGCC |
| | | | GAAGAGTCCCTCCCTATCGAAGTGATGGTT |
| | | | GATGCCGTGCACAAGCTCAAGTATGAGAAT |
| | | | TACACCAGCAGCTTTTTCATCAGGGACATC |
| | | | ATCAAGCCCGACCCCCCCAAAAACCTCCAG |
| | | | CTGAAACCCCTCAAGAATAGCAGGCAGGTG |
| | | | GAGGTCTCCTGGGAGTATCCTGACACCTGG |
| | | | AGCACCCCCCACAGCTACTTCTCCCTGACCT |
| | | | TCTGTGTGCAGGTGCAGGGCAAGAGCAAAA |
| | | | GGGAGAAGAAGGATAGGGTCTTTACCGAC |
| | | | AAGACCAGCGCCACAGTGATCTGCAGGAA |
| | | | GAACGCCAGCATTTCCGTCAGGGCCCAGGA |
| | | | CAGGTACTACAGCAGCAGCTGGTCCGAGTG |

APPENDIX A-continued

SEQUENCE REFERENCE

| SEQ ID NO: | Molecule | Accession Number(s) or description | Sequence |
|---|---|---|---|
| | | | GGCTAGCGTGCCTTGTTCCGGCGGCGGAGG |
| | | | ATCTGGCGGAGGCGGAAGTGGCGGAGGGG |
| | | | GCTCTAGAAACCTCCCCGTGGCCACACCCG |
| | | | ACCCTGGCATGTTCCCCTGCCTCCACCACA |
| | | | GCCAGAACCTGCTGAGAGCCGTGAGCAATA |
| | | | TGCTGCAGAAGGCCAGGCAAACCCTGGAGT |
| | | | TCTACCCCTGTACCTCCGAGGAGATTGACC |
| | | | ATGAGGACATCACAAAGGACAAAACCAGC |
| | | | ACCGTGGAGGCCTGTCTCCCCCTCGAACTG |
| | | | ACCAAGAACGAGTCCTGCCTGAACTCCAGG |
| | | | GAGACATCCTTCATCACCAACGGCTCCTGC |
| | | | CTGGCCTCCAGAAAGACCAGCTTCATGATG |
| | | | GCCCTCTGCCTGAGCAGCATCTACGAGGAC |
| | | | CTCAAGATGTACCAGGTGGAGTTTAAAACA |
| | | | ATGAACGCCAAGCTCCTCATGGACCCTAAG |
| | | | AGGCAGATTTTCCTCGACCAGAATATGCTG |
| | | | GCTGTCATTGACGAGCTGATGCAGGCCCTC |
| | | | AATTTCAACTCCGAGACCGTCCCCCAGAAG |
| | | | TCCTCCCTGGAAGAGCCCGACTTTTACAAG |
| | | | ACCAAGATCAAGCTCTGCATCCTGCTGCAC |
| | | | GCCTTCAGAATTAGAGCCGTGACCATTGAC |
| | | | AGGGTGATGAGCTACCTCAACGCCTCCTGA |
| | | | TGACTCGAGTCACCAGGCGCTTTTCCAAGA |
| | | | GAAGGTCATCAAGACTTTGGATTTTTCCAC |
| | | | ACCGGGGCGCGCTGCGGCTGCTGTTGCTTT |
| | | | TTTGAGTTTTATAAAGGATAAATGGAGCGA |
| | | | AGAAACCCATCTGAGCGGGGGGTACCTGCT |
| | | | GGATTTTCTGGCCATGCATCTGTGGAGAGC |
| | | | GGTTGTGAGACACAAGAATCGCCTGCTACT |
| | | | GTTGTCTTCCGTCCGCCCGGCGATAATACC |
| | | | GACGGAGGAGCAGCAGCAGCAGCAGGAGG |
| | | | AAGCCAGGCGGCGGCGGCAGGAGCAGAGC |
| | | | CCATGGAACCCGAGAGCCGGCCTGGACCCT |
| | | | CGGGAATGAATGTTGTACAGGTGGCTGAAC |
| | | | TGTATCCAGAACTGAGACGCATTTTGACAA |
| | | | TTACAGAGGATGGGCAGGGGCTAAAGGGG |
| | | | GTAAAGAGGGAGCGGGGGGCTTGTGAGGC |
| | | | TACAGAGGAGGCTAGGAATCTAGCTTTTAG |
| | | | CTTAATGACCAGACACCGTCCTGAGTGTAT |
| | | | TACTTTTCAACAGATCAAGGATAATTGCGC |
| | | | TAATGAGCTTGATCTGCTGGCGCAGAAGTA |
| | | | TTCCATAGAGCAGCTGACCACTTACTGGCT |
| | | | GCAGCCAGGGGATGATTTTGAGGAGGCTAT |
| | | | TAGGGTATATGCAAAGGTGGCACTTAGGCC |
| | | | AGATTGCAAGTACAAGATCAGCAAACTTGT |
| | | | AAATATCAGGAATTGTTGCTACATTTCTGG |
| | | | GAACGGGGCCGAGGTGGAGATAGATACGG |
| | | | AGGATAGGGTGGCCTTTAGATGTAGCATGA |
| | | | TAAATATGTGGCCGGGGTGCTTGGCATGG |
| | | | ACGGGGTGGTTATTATGAATGTAAGGTTTA |
| | | | CTGGCCCCAATTTTAGCGGTACGGTTTTCCT |
| | | | GGCCAATACCAACCTTATCCTACACGGTGT |
| | | | AAGCTTCTATGGGTTTAACAATACCTGTGT |
| | | | GGAAGCCTGGACCGATGTAAGGGTTCGGGG |

APPENDIX A-continued

SEQUENCE REFERENCE

| SEQ ID NO: | Molecule | Accession Number(s) or description | Sequence |
|---|---|---|---|
| | | | CTGTGCCTTTTACTGCTGCTGGAAGGGGGT
GGTGTGTCGCCCCAAAAGCAGGGCTTCAAT
TAAGAAATGCCTCTTTGAAAGGTGTACCTT
GGGTATCCTGTCTGAGGGTAACTCCAGGGT
GCGCCACAATGTGGCCTCCGACTGTGGTTG
CTTCATGCTAGTGAAAAGCGTGGCTGTGAT
TAAGCATAACATGGTATGTGGCAACTGCGA
GGACAGGGCCTCTCAGATGCTGACCTGCTC
GGACGGCAACTGTCACCTGCTGAAGACCAT
TCACGTAGCCAGCCACTCTCGCAAGGCCTG
GCCAGTGTTTGAGCATAACATACTGACCCG
CTGTTCCTTGCATTTGGGTAACAGGAGGGG
GGTGTTCCTACCTTACCAATGCAATTTGAGT
CACACTAAGATATTGCTTGAGCCCGAGAGC
ATGTCCAAGGTGAACCTGAACGGGGTGTTT
GACATGACCATGAAGATCTGGAAGGTGCTG
AGGTACGATGAGACCCGCACCAGGTGCAG
ACCCTGCGAGTGTGGCGGTAAACATATTAG
GAACCAGCCTGTGATGCTGGATGTGACCGA
GGAGCTGAGGCCCGATCACTTGGTGCTGGC
CTGCACCCGCGCTGAGTTTGGCTCTAGCGA
TGAAGATACAGATTGAGGTACTGAAATGTG
TGGGCGTGGCTTAAGGGTGGGAAAGAATAT
ATAAGGTGGGGTCTTATGTAGTTTTGTATC
TGTTTTGCAGCAGCCGCCGCCGCCATGAGC
ACCAACTCGTTTGATGGAAGCATTGTGAGC
TCATATTTGACAACGCGCATGCCCCCATGG
GCCGGGGTGCGTCAGAATGTGATGGGCTCC
AGCATTGATGGTCGCCCCGTCCTGCCCGCA
AACTCTACTACCTTGACCTACGAGACCGTG
TCTGGAACGCCGTTGGAGACTGCAGCCTCC
GCCGCCGCTTCAGCCGCTGCAGCCACCGCC
CGCGGGATTGTGACTGACTTTGCTTTCCTGA
GCCCGCTTGCAAGCAGTGCAGCTTCCCGTT
CATCCGCCCGCGATGACAAGTTGACGGCTC
TTTTGGCACAATTGGATTCTTTGACCCGGGA
ACTTAATGTCGTTTCTCAGCAGCTGTTGGAT
CTGCGCCAGCAGGTTTCTGCCCTGAAGGCT
TCCTCCCCTCCCAATGCGGTTTAAAACATA
AATAAAAAACCAGACTCTGTTTGGATTTGG
ATCAAGCAAGTGTCTTGCTGTCTTTATTTAG
GGGTTTTGCGCGCGCGGTAGGCCCGGGACC
AGCGGTCTCGGTCGTTGAGGGTCCTGTGTA
TTTTTTCCAGGACGTGGTAAAGGTGACTCT
GGATGTTCAGATACATGGGCATAAGCCCGT
CTCTGGGGTGGAGGTAGCACCACTGCAGAG
CTTCATGCTGCGGGGTGGTGTTGTAGATGA
TCCAGTCGTAGCAGGAGCGCTGGGCGTGGT
GCCTAAAAATGTCTTTCAGTAGCAAGCTGA
TTGCCAGGGCAGGCCCTTGGTGTAAGTGT
TTACAAAGCGGTTAAGCTGGGATGGGTGCA
TACGTGGGGATATGAGATGCATCTTGGACT
GTATTTTTAGGTTGGCTATGTTCCCAGCCAT
ATCCCTCCGGGGATTCATGTTGTGCAGAAC
CACCAGCACAGTGTATCCGGTGCACTTGGG
AAATTTGTCATGTAGCTTAGAAGGAAATGC
GTGGAAGAACTTGGAGACGCCCTTGTGACC
TCCAAGATTTTCCATGCATTCGTCCATAATG
ATGGCAATGGGCCCACGGGCGCGGCCTGG
GCGAAGATATTTCTGGGATCACTAACGTCA
TAGTTGTGTTCCAGGATGAGATCGTCATAG
GCCATTTTTACAAAGCGCGGGCGGAGGGTG
CCAGACTGCGGTATAATGGTTCCATCCGGC
CCAGGGGCGTAGTTACCCTCACAGATTTGC
ATTTCCCACGCTTTGAGTTCAGATGGGGGG
ATCATGTCTACCTGCGGGGCGATGAAGAAA
ACGGTTTCCGGGGTAGGGGAGATCAGCTGG
GAAGAAAGCAGGTTCCTGAGCAGCTGCGAC
TTACCGCAGCCGGTGGGCCCGTAAATCACA
CCTATTACCGGCTGCAACTGGTAGTTAAGA
GAGCTGCAGCTGCCGTCATCCCTGAGCAGG
GGGGCCACTTCGTTAAGCATGTCCCTGACT
CGCATGTTTTCCCTGACCAAATCCGCCAGA
AGGCGCTCGCCGCCCAGCGATAGCAGTTCT |

APPENDIX A-continued

SEQUENCE REFERENCE

| SEQ ID NO: | Molecule | Accession Number(s) or description | Sequence |
|---|---|---|---|
| | | | TGCAAGGAAGCAAAGTTTTTCAACGGTTTG
AGACCGTCCGCCGTAGGCATGCTTTTGAGC
GTTTGACCAAGCAGTTCCAGGCGGTCCCAC
AGCTCGGTCACCTGCTCTACGGCATCTCGA
TCCAGCATATCTCCTCGTTTCGCGGGTTGGG
GCGGCTTTCGCTGTACGGCAGTAGTCGGTG
CTCGTCCAGACGGGCCAGGGTCATGTCTTT
CCACGGGCGCAGGGTCCTCGTCAGCGTAGT
CTGGGTCACGGTGAAGGGGTGCGCTCCGGG
CTGCGCGCTGGCCAGGGTGCGCTTGAGGCT
GGTCCTGCTGGTGCTGAAGCGCTGCCGGTC
TTCGCCCTGCGCGTCGGCCAGGTAGCATTT
GACCATGGTGTCATAGTCCAGCCCCTCCGC
GGCGTGGCCCTTGGCGCGCAGCTTGCCCTT
GGAGGAGGCGCCGCACGAGGGGCAGTGCA
GACTTTTGAGGGCGTAGAGCTTGGGCGCGA
GAAATACCGATTCCGGGGAGTAGGCATCCG
CGCCGCAGGCCCCGCAGACGGTCTCGCATT
CCACGAGCCAGGTGAGCTCTGGCCGTTCGG
GGTCAAAAACCAGGTTTCCCCCATGCTTTTT
GATGCGTTTCTTACCTCTGGTTTCCATGAGC
CGGTGTCCACGCTCGGTGACGAAAAGGCTG
TCCGTGTCCCCGTATACAGACTTGAGAGGC
CTGTCCTCGAGCGGTGTTCCGCGGTCCTCCT
CGTATAGAAACTCGGACCACTCTGAGACAA
AGGCTCGCGTCCAGGCCAGCACGAAGGAG
GCTAAGTGGGAGGGGTAGCGGTCGTTGTCC
ACTAGGGGGTCCACTCGCTCCAGGGTGTGA
AGACACATGTCGCCCTCTTCGGCATCAAGG
AAGGTGATTGGTTTGTAGGTGTAGGCCACG
TGACCGGGTGTTCCTGAAGGGGGGCTATAA
AAGGGGGTGGGGGCGCGTTCGTCCTCACTC
TCTTCCGCATCGCTGTCTGCGAGGGCCAGC
TGTTGGGGTGAGTACTCCCTCTGAAAAGCG
GGCATGACTTCTGCGCTAAGATTGTCAGTTT
CCAAAAACGAGGAGGATTTGATATTCACCT
GGCCCGCGGTGATGCCTTTGAGGGTGGCCG
CATCCATCTGGTCAGAAAAGACAATCTTTT
TGTTGTCAAGCTTGGTGGCAAACGACCCGT
AGAGGGCGTTGGACAGCAACTTGGCGATGG
AGCGCAGGGTTTGGTTTTTGTCGCGATCGG
CGCGCTCCTTGGCCGCGATGTTTAGCTGCA
CGTATTCGCGCGCAACGCACCGCCATTCGG
GAAAGACGGTGGTGCGCTCGTCGGGCACCA
GGTGCACGCGCCAACCGCGGTTGTGCAGGG
TGACAAGGTCAACGCTGGTGGCTACCTCTC
CGCGTAGGCGCTCGTTGGTCCAGCAGAGGC
GGCCGCCCTTGCGCGAGCAGAATGGCGGTA
GGGGGTCTAGCTGCGTCTCGTCCGGGGGGT
CTGCGTCCACGGTAAAGACCCCGGGCAGCA
GGCGCGCGTCGAAGTAGTCTATCTTGCATC
CTTGCAAGTCTAGCGCCTGCTGCCATGCGC
GGGCGGCAAGCGCGCGCTCGTATGGGTTGA
GTGGGGGACCCCATGGCATGGGTGGGTGA
GCGCGGAGGCGTACATGCCGCAAATGTCGT
AAACGTAGAGGGGCTCTCTGAGTATTCCAA
GATATGTAGGGTAGCATCTTCCACCGCGGA
TGCTGGCGCGCACGTAATCGTATAGTTCGT
GCGAGGGAGCGAGGAGGTCGGGACCGAGG
TTGCTACGGGCGGCTGCTCTGCTCGGAAG
ACTATCTGCCTGAAGATGGCATGTGAGTTG
GATGATATGGTTGGACGCTGGAAGACGTTG
AAGCTGGCGTCTGTGAGACCTACCGCGTCA
CGCACGAAGGAGGCGTAGGAGTCGCGCAG
CTTGTTGACCAGCTCGGCGGTGACCTGCAC
GTCTAGGGCGCAGTAGTCCAGGGTTTCCTT
GATGATGTCATACTTATCCTGTCCCTTTTTT
TTCCACAGCTCGCGGTTGAGGACAAACTCT
TCGCGGTCTTTCCAGTACTCTTGGATCGGAA
ACCCGTCGGCCTCCGAACGGTAAGAGCCTA
GCATGTAGAACTGGTTGACGGCCTGGTAGG
CGCAGCATCCCTTTTCTACGGGTAGCGCGT
ATGCCTGCGCGGCCTTCCGGAGCGAGGTGT
GGGTGAGCGCAAAGGTGTCCCTGACCATGA |

APPENDIX A-continued

SEQUENCE REFERENCE

| SEQ ID NO: | Molecule | Accession Number(s) or description | Sequence |
|---|---|---|---|
| | | | CTTTGAGGTACTGGTATTTGAAGTCAGTGTC
GTCGCATCCGCCCTGCTCCCAGAGCAAAAA
GTCCGTGCGCTTTTTGGAACGCGGATTTGG
CAGGGCGAAGGTGACATCGTTGAAGAGTAT
CTTTCCCGCGCGAGGCATAAAGTTGCGTGT
GATGCGGAAGGGTCCCGGCACCTCGGAACG
GTTGTTAATTACCTGGGCGGCGAGCACGAT
CTCGTCAAAGCCGTTGATGTTGTGGCCCAC
AATGTAAAGTTCCAAGAAGCGCGGGATGCC
CTTGATGGAAGGCAATTTTTTAAGTTCCTCG
TAGGTGAGCTCTTCAGGGGAGCTGAGCCCG
TGCTCTGAAAGGGCCCAGTCTGCAAGATGA
GGGTTGGAAGCGACGAATGAGCTCCACAG
GTCACGGGCCATTAGCATTTGCAGGTGGTC
GCGAAAGGTCCTAAACTGGCGACCTATGGC
CATTTTTTCTGGGGTGATGCAGTAGAAGGT
AAGCGGGTCTTGTTCCCAGCGGTCCCATCC
AAGGTTCGCGGCTAGGTCTCGCGCGGCAGT
CACTAGAGGCTCATCTCCGCCGAACTTCAT
GACCAGCATGAAGGGCACGAGCTGCTTCCC
AAAGGCCCCCATCCAAGTATAGGTCTCTAC
ATCGTAGGTGACAAAGAGACGCTCGGTGCG
AGGATGCGAGCCGATCGGGAAGAACTGGA
TCTCCCGCCACCAATTGGAGGAGTGGCTAT
TGATGTGGTGAAAGTAGAAGTCCCTGCGAC
GGGCCGAACACTCGTGCTGGCTTTTGTAAA
AACGTGCGCAGTACTGGCAGCGGTGCACGG
GCTGTACATCCTGCACGAGGTTGACCTGAC
GACCGCGCACAAGGAAGCAGAGTGGGAAT
TTGAGCCCCTCGCCTGGCGGGTTTGGCTGG
TGGTCTTCTACTTCGGCTGCTTGTCCTTGAC
CGTCTGGCTGCTCGAGGGGAGTTACGGTGG
ATCGGACCACCACGCCGCGCGAGCCCAAAG
TCCAGATGTCCGCGCGCGGCGGTCGGAGCT
TGATGACAACATCGCGCAGATGGGAGCTGT
CCATGGTCTGGAGCTCCCGCGGCGTCAGGT
CAGGCGGGAGCTCCTGCAGGTTTACCTCGC
ATAGACGGGTCAGGGCGCGGGCTAGATCCA
GGTGATACCTAATTTCCAGGGGCTGGTTGG
TGGCGGCGTCGATGGCTTGCAAGAGGCCGC
ATCCCCGCGGCGCGACTACGGTACCGCGCG
GCGGGCGGTGGGCCGCGGGGGTGTCCTTGG
ATGATGCATCTAAAAGCGGTGACGCGGGCG
AGCCCCCGGAGGTAGGGGGGGCTCCGGAC
CCGCCGGGAGAGGGGGCAGGGGCACGTCG
GCGCCGCGCGGGCAGGAGCTGGTGCTGC
GCGCGTAGGTTGCTGGCGAACGCGACGACG
CGGCGGTTGATCTCCTGAATCTGGCGCCTCT
GCGTGAAGACGACGGGCCCGGTGAGCTTGA
ACCTGAAAGAGAGTTCGACAGAATCAATTT
CGGTGTCGTTGACGGCGGCCTGGCGCAAAA
TCTCCTGCACGTCTCCTGAGTTGTCTTGATA
GGCGATCTCGGCCATGAACTGCTCGATCTC
TTCCTCCTGGAGATCTCCGCGTCCGGCTCGC
TCCACGGTGGCGGCGAGGTCGTTGGAAATG
CGGGCCATGAGCTGCGAGAAGGCGTTGAG
GCCTCCCTCGTTCCAGACGCGGCTGTAGAC
CACGCCCCTTCGGCATCGCGGGCGCGCAT
GACCACCTGCGCGAGATTGAGCTCCACGTG
CCGGGCGAAGACGGCGTAGTTTCGCAGGCG
CTGAAAGAGGTAGTTGAGGGTGGTGGCGGT
GTGTTCTGCCACGAAGAAGTACATAACCCA
GCGTCGCAACGTGGATTCGTTGATATCCCC
CAAGGCCTCAAGGCGCTCCATGGCCTCGTA
GAAGTCCACGGCGAAGTTGAAAAACTGGG
AGTTGCGCGCCGACACGGTTAACTCCTCCT
CCAGAAGACGGATGAGCTCGGCGACAGTGT
CGCGCACCTCGCGCTCAAAGGCTACAGGGG
CCTCTTCTTCTTCAATCTCCTCTTCCATA
AGGGCCTCCCCTTCTTCTTCTTCTGGCGGCG
GTGGGGGAGGGGGACACGGCGGCGACGA
CGGCGCACCGGGAGGCGGTCGACAAAGCG
CTCGATCATCTCCCCGCGGCGACGGCGCAT
GGTCTCGGTGACGGCGCGGCCGTTCTCGCG |

APPENDIX A-continued

SEQUENCE REFERENCE

| SEQ ID NO: | Molecule | Accession Number(s) or description | Sequence |
|---|---|---|---|
| | | | GGGGCGCAGTTGGAAGACGCCGCCCGTCAT |
| | | | GTCCCGGTTATGGGTTGGCGGGGGGCTGCC |
| | | | ATGCGGCAGGGATACGGCGCTAACGATGCA |
| | | | TCTCAACAATTGTTGTGTAGGTACTCCGCCG |
| | | | CCGAGGGACCTGAGCGAGTCCGCATCGACC |
| | | | GGATCGGAAAACCTCTCGAGAAAGGCGTCT |
| | | | AACCAGTCACAGTCGCAAGGTAGGCTGAGC |
| | | | ACCGTGGCGGGCGGCAGCGGGCGGCGGTC |
| | | | GGGGTTGTTTCTGGCGGAGGTGCTGCTGAT |
| | | | GATGTAATTAAAGTAGGCGGTCTTGAGACG |
| | | | GCGGATGGTCGACAGAAGCACCATGTCCTT |
| | | | GGGTCCGGCCTGCTGAATGCGCAGGCGGTC |
| | | | GGCCATGCCCCAGGCTTCGTTTTGACATCG |
| | | | GCGCAGGTCTTTGTAGTAGTCTTGCATGAG |
| | | | CCTTTCTACCGGCACTTCTTCTTCTCCTTCCT |
| | | | CTTGTCCTGCATCTCTTGCATCTATCGCTGC |
| | | | GGCGGCGGCGGAGTTTGGCCGTAGGTGGCG |
| | | | CCCTCTTCCTCCCATGCGTGTGACCCCGAAG |
| | | | CCCCTCATCGGCTGAAGCAGGGCTAGGTCG |
| | | | GCGACAACGCGCTCGGCTAATATGGCCTGC |
| | | | TGCACCTGCGTGAGGGTAGACTGGAAGTCA |
| | | | TCCATGTCCACAAAGCGGTGGTATGCGCCC |
| | | | GTGTTGATGGTGTAAGTGCAGTTGGCCATA |
| | | | ACGGACCAGTTAACGGTCTGGTGACCCGGC |
| | | | TGCGAGAGCTCGGTGTACCTGAGACGCGAG |
| | | | TAAGCCCTCGAGTCAAATACGTAGTCGTTG |
| | | | CAAGTCCGCACCAGGTACTGGTATCCCACC |
| | | | AAAAAGTGCGGCGGCGGCTGGCGGTAGAG |
| | | | GGGCCAGCGTAGGGTGGCCGGGGCTCCGG |
| | | | GGGCGAGATCTTCCAACATAAGGCGATGAT |
| | | | ATCCGTAGATGTACCTGGACATCCAGGTGA |
| | | | TGCCGGCGGCGGTGGTGGAGGCGCGCGGA |
| | | | AAGTCGCGGACGCGGTTCCAGATGTTGCGC |
| | | | AGCGGCAAAAAGTGCTCCATGGTCGGGACG |
| | | | CTCTGGCCGGTCAGGCGCGCGCAATCGTTG |
| | | | ACGCTCTAGCGTGCAAAAGGAGAGCCTGTA |
| | | | AGCGGGCACTCTTCCGTGGTCTGGTGGATA |
| | | | AATTCGCAAGGGTATCATGGCGGACGACCG |
| | | | GGGTTCGAGCCCCGTATCCGGCCGTCCGCC |
| | | | GTGATCCATGCGGTTACCGCCCGCGTGTCG |
| | | | AACCCAGGTGTGCGACGTCAGACAACGGG |
| | | | GGAGTGCTCCTTTTGGCTTCCTTCCAGGCGC |
| | | | GGCGGCTGCTGCGCTAGCTTTTTTGGCCACT |
| | | | GGCCGCGCGCAGCGTAAGCGGTTAGGCTGG |
| | | | AAAGCGAAAGCATTAAGTGGCTCGCTCCCT |
| | | | GTAGCCGGAGGGTTATTTTCCAAGGGTTGA |
| | | | GTCGCGGGACCCCCGGTTCGAGTCTCGGAC |
| | | | CGGCCGGACTGCGGCGAACGGGGGTTTGCC |
| | | | TCCCCGTCATGCAAGACCCCGCTTGCAAAT |
| | | | TCCTCCGGAAACAGGGACGAGCCCCTTTTT |
| | | | TGCTTTTCCCAGATGCATCCGGTGCTGCGGC |
| | | | AGATGCGCCCCCCTCCTCAGCAGCGGCAAG |
| | | | AGCAAGAGCAGCGGCAGACATGCAGGGCA |
| | | | CCCTCCCCTCCTCCTACCGCGTCAGGAGGG |
| | | | GCGACATCCGCGGTTGACGCGGCAGCAGAT |
| | | | GGTGATTACGAACCCCCGCGGCGCCGGGCC |
| | | | CGGCACTACCTGGACTTGGAGGAGGGCGAG |
| | | | GGCCTGGCGCGGCTAGGAGCGCCCTCTCCT |
| | | | GAGCGGCACCCAAGGGTGCAGCTGAAGCG |
| | | | TGATACGCGTGAGGCGTACGTGCCGCGGCA |
| | | | GAACCTGTTTCGCGACCGCGAGGGAGAGGA |
| | | | GCCCGAGGAGATGCGGGATCGAAAGTTCCA |
| | | | CGCAGGGCGCGAGCTGCGGCATGGCCTGAA |
| | | | TCGCGAGCGGTTGCTGCGCGAGGAGGACTT |
| | | | TGAGCCCGACGCGCGAACCGGGATTAGTCC |
| | | | CGCGCGCGCACACGTGGCGGCCGCCGACCT |
| | | | GGTAACCGCATACGAGCAGACGGTGAACC |
| | | | AGGAGATTAACTTTCAAAAAAGCTTTAACA |
| | | | ACCACGTGCGTACGCTTGTGGCGCGCGAGG |
| | | | AGGTGGCTATAGGACTGATGCATCTGTGGG |
| | | | ACTTTGTAAGCGCGCTGGAGCAAAACCCAA |
| | | | ATAGCAAGCCGCTCATGGCGCAGCTGTTCC |
| | | | TTATAGTGCAGCACAGCAGGGACAACGAG |
| | | | GCATTCAGGGATGCGCTGCTAAACATAGTA |

APPENDIX A-continued

SEQUENCE REFERENCE

| SEQ ID NO: | Molecule | Accession Number(s) or description | Sequence |
|---|---|---|---|
| | | | GAGCCCGAGGGCCGCTGGCTGCTCGATTTG ATAAACATCCTGCAGAGCATAGTGGTGCAG GAGCGCAGCTTGAGCCTGGCTGACAAGGTG GCCGCCATCAACTATTCCATGCTTAGCCTG GGCAAGTTTTACGCCCGCAAGATATACCAT ACCCCTTACGTTCCCATAGACAAGGAGGTA AAGATCGAGGGGTTCTACATGCGCATGGCG CTGAAGGTGCTTACCTTGAGCGACGACCTG GGCGTTTATCGCAACGAGCGCATCCACAAG GCCGTGAGCGTGAGCCGGCGGCGCGAGCTC AGCGACCGCGAGCTGATGCACAGCCTGCAA AGGGCCCTGGCTGGCACGGGCAGCGGCGAT AGAGAGGCCGAGTCCTACTTTGACGCGGGC GCTGACCTGCGCTGGGCCCCAAGCCGACGC GCCCTGGAGGCAGCTGGGGCCGGACCTGGG CTGGCGGTGGCACCCGCGCGCTGGCAAC GTCGGCGGCGTGGAGGAATATGACGAGGA CGATGAGTACGAGCCAGAGGACGGCGAGT ACTAAGCGGTGATGTTTCTGATCAGATGAT GCAAGACGCAACGGACCCGGCGGTGCGGG CGGCGCTGCAGAGCCAGCCGTCCGGCCTTA ACTCCACGGACGACTGGCGCCAGGTCATGG ACCGCATCATGTCGCTGACTGCGCGCAATC CTGACGCGTTCCGGCAGCAGCCGCAGGCCA ACCGGCTCTCCGCAATTCTGGAAGCGGTGG TCCCGGCGCGCGCAAACCCCACGCACGAGA AGGTGCTGGCGATCGTAAACGCGCTGGCCG AAAACAGGGCCATCCGGCCCGACGAGGCC GGCCTGGTCTACGACGCGCTGCTTCAGCGC GTGGCTCGTTACAACAGCGGCAACGTGCAG ACCAACCTGGACCGGCTGGTGGGGGATGTG CGCGAGGCCGTGGCGCAGCGTGAGCGCGC GCAGCAGCAGGGCAACCTGGGCTCCATGGT TGCACTAAACGCCTTCCTGAGTACACAGCC CGCCAACGTGCCGCGGGGACAGGAGGACT ACACCAACTTTGTGAGCGCACTGCGGCTAA TGGTGACTGAGACACCGCAAAGTGAGGTGT ACCAGTCTGGGCCAGACTATTTTTTCCAGA CCAGTAGACAAGGCCTGCAGACCGTAAACC TGAGCCAGGCTTTCAAAAACTTGCAGGGGC TGTGGGGGGTGCGGGCTCCCACAGGCGACC GCGCGACCGTGTCTAGCTTGCTGACGCCCA ACTCGCGCCTGTTGCTGCTGCTAATAGCGC CCTTCACGGACAGTGGCAGCGTGTCCCGGG ACACATACCTAGGTCACTTGCTGACACTGT ACCGCGAGGCCATAGGTCAGGCGCATGTGG ACGAGCATACTTTCCAGGAGATTACAAGTG TCAGCCGCGCGCTGGGGCAGGAGGACACG GGCAGCCTGGAGGCAACCCTAAACTACCTG CTGACCAACCGGCGGCAGAAGATCCCCTCG TTGCACAGTTTAAACAGCGAGGAGGAGCGC ATTTTGCGCTACGTGCAGCAGAGCGTGAGC CTTAACCTGATGCGCGACGGGGTAACGCCC AGCGTGGCGCTGGACATGACCGCGCGCAAC ATGGAACCGGGCATGTATGCCTCAAACCGG CCGTTTATCAACCGCCTAATGGACTACTTGC ATCGCGCGCCGCCGTGAACCCCGAGTATT TCACCAATGCCATCTTGAACCCGCACTGGC TACCGCCCCCTGGTTTCTACACCGGGGGAT TCGAGGTGCCCGAGGGTAACGATGGATTCC TCTGGGACGACATAGACGACAGCGTGTTTT CCCCGCAACCGCAGACCCTGCTAGAGTTGC AACAGCGCGAGCAGGCAGAGGCGGCGCTG CGAAAGGAAAGCTTCCGCAGGCCAAGCAG CTTGTCCGATCTAGGCGCTGCGGCCCCGCG GTCAGATGCTAGTAGCCCATTTCCAAGCTT GATAGGGTCTCTTACCAGCACTCGCACCAC CCGCCCGCGCCTGCTGGGCGAGGAGGAGTA CCTAAACAACTCGCTGCTGCAGCCGCAGCG CGAAAAAAACCTGCCTCCGGCATTTCCCAA CAACGGGATAGAGAGCCAGTGGACAAGA TGAGTAGATGGAAGACGTACGCGCAGGAG CACAGGGACGTGCCAGGCCCGCGCCCGCCC ACCCGTCGTCAAAGGCACGACCGTCAGCGG |

APPENDIX A-continued

SEQUENCE REFERENCE

| SEQ ID NO: | Molecule | Accession Number(s) or description | Sequence |
|---|---|---|---|
| | | | GGTCTGGTGTGGGAGGACGATGACTCGGCA |
| | | | GACGACAGCAGCGTCCTGGATTTGGGAGGG |
| | | | AGTGGCAACCCGTTTGCGCACCTTCGCCCC |
| | | | AGGCTGGGGAGAATGTTTTAAAAAAAAAA |
| | | | AAGCATGATGCAAATAAAAACTCACCA |
| | | | AGGCCATGGCACCGAGCGTTGGTTTTCTTG |
| | | | TATTCCCCTTAGTATGCGGCGCGCGGCGAT |
| | | | GTATGAGGAAGGTCCTCCTCCCTCCTACGA |
| | | | GAGTGTGGTGAGCGCGGCGCCAGTGGCGGC |
| | | | GGCGCTGGGTTCTCCCTTCGATGCTCCCCTG |
| | | | GACCCGCCGTTTGTGCCTCCGCGGTACCTG |
| | | | CGGCCTACCGGGGGGAGAAACAGCATCCGT |
| | | | TACTCTGAGTTGGCACCCCTATTCGACACC |
| | | | ACCCGTGTGTACCTGGTGGACAACAAGTCA |
| | | | ACGGATGTGGCATCCCTGAACTACCAGAAC |
| | | | GACCACAGCAACTTTCTGACCACGGTCATT |
| | | | CAAAACAATGACTACAGCCCGGGGGAGGC |
| | | | AAGCACACAGACCATCAATCTTGACGACCG |
| | | | GTCGCACTGGGGCGGCGACCTGAAAACCAT |
| | | | CCTGCATACCAACATGCCAAATGTGAACGA |
| | | | GTTCATGTTTACCAATAAGTTTAAGGCGCG |
| | | | GGTGATGGTGTCGCGCTTGCCTACTAAGGA |
| | | | CAATCAGGTGGAGCTGAAATACGAGTGGGT |
| | | | GGAGTTCACGCTGCCCGAGGGCAACTACTC |
| | | | CGAGACCATGACCATAGACCTTATGAACAA |
| | | | CGCGATCGTGGAGCACTACTTGAAAGTGGG |
| | | | CAGACAGAACGGGGTTCTGGAAAGCGACA |
| | | | TCGGGGTAAAGTTTGACACCCGCAACTTCA |
| | | | GACTGGGGTTTGACCCCGTCACTGGTCTTGT |
| | | | CATGCCTGGGGTATATACAAACGAAGCCTT |
| | | | CCATCCAGACATCATTTTGCTGCCAGGATG |
| | | | CGGGGTGGACTTCACCCACAGCCGCCTGAG |
| | | | CAACTTGTTGGGCATCCGCAAGCGGCAACC |
| | | | CTTCCAGGAGGGCTTTAGGATCACCTACGA |
| | | | TGATCTGGAGGGTGGTAACATTCCCGCACT |
| | | | GTTGGATGTGGACGCCTACCAGGCGAGCTT |
| | | | GAAAGATGACACCGAACAGGGCGGGGGTG |
| | | | GCGCAGGCGGCAGCAACAGCAGTGGCAGC |
| | | | GGCGCGGAAGAGAACTCCAACGCGGCAGC |
| | | | CGCGGCAATGCAGCCGGTGGAGGACATGA |
| | | | ACGATCATGCCATTCGCGGCGACACCTTTG |
| | | | CCACACGGGCTGAGGAGAAGCGCGCTGAG |
| | | | GCCGAAGCAGCGGCCGAAGCTGCCGCCCCC |
| | | | GCTGCGCAACCCGAGGTCGAGAAGCCTCAG |
| | | | AAGAAACCGGTGATCAAACCCCTGACAGA |
| | | | GGACAGCAAGAAACGCAGTTACAACCTAAT |
| | | | AAGCAATGACAGCACCTTCACCCAGTACCG |
| | | | CAGCTGGTACCTTGCATACAACTACGGCGA |
| | | | CCCTCAGACCGGAATCCGCTCATGGACCCT |
| | | | GCTTTGCACTCCTGACGTAACCTGCGGCTC |
| | | | GGAGCAGGTCTACTGGTCGTTGCCAGACAT |
| | | | GATGCAAGACCCCGTGACCTTCCGCTCCAC |
| | | | GCGCCAGATCAGCAACTTTCCGGTGGTGGG |
| | | | CGCCGAGCTGTTGCCCGTGCACTCCAAGAG |
| | | | CTTCTACAACGACCAGGCCGTCTACTCCCA |
| | | | ACTCATCCGCCAGTTTACCTCTCTGACCCAC |
| | | | GTGTTCAATCGCTTTCCCGAGAACCAGATTT |
| | | | TGGCGCGCCCGCCAGCCCCCACCATCACCA |
| | | | CCGTCAGTGAAAACGTTCCTGCTCTCACAG |
| | | | ATCACGGGACGCTACCGCTGCGCAACAGCA |
| | | | TCGGAGGAGTCCAGCGAGTGACCATTACTG |
| | | | ACGCCAGACGCCGCACCTGCCCCTACGTTT |
| | | | ACAAGGCCCTGGGCATAGTCTCGCCGCGCG |
| | | | TCCTATCGAGCCGCACTTTTTGAGCAAGCA |
| | | | TGTCCATCCTTATATCGCCCAGCAATAACA |
| | | | CAGGCTGGGGCCTGCGCTTCCCAAGCAAGA |
| | | | TGTTTGCGGGGCCAAGAAGCGCTCCGACC |
| | | | AACACCCAGTGCGCGTGCGCGGGCACTACC |
| | | | GCGCGCCCTGGGGCGCGCACAAACGCGGCC |
| | | | GCACTGGGCGCACCACCGTCGATGACGCCA |
| | | | TCGACGCGGTGGTGGAGGAGGCGCGCAACT |
| | | | ACACGCCCACGCCGCCACCAGTGTCCACAG |
| | | | TGGACGCGGCCATTCAGACCGTGGTGCGCG |
| | | | GAGCCCGGCGCTATGCTAAAATGAAGAGAC |

APPENDIX A-continued

SEQUENCE REFERENCE

| SEQ ID NO: | Molecule | Accession Number(s) or description | Sequence |
|---|---|---|---|
| | | | GGCGGAGGCGCGTAGCACGTCGCCACCGCC |
| | | | GCCGACCCGGCACTGCCGCCCAACGCGCGG |
| | | | CGGCGGCCCTGCTTAACCGCGCACGTCGCA |
| | | | CCGGCCGACGGGCGGCCATGCGGGCCGCTC |
| | | | GAAGGCTGGCCGCGGGTATTGTCACTGTGC |
| | | | CCCCCAGGTCCAGGCGACGAGCGGCCGCCG |
| | | | CAGCAGCCGCGGCCATTAGTGCTATGACTC |
| | | | AGGGTCGCAGGGGCAACGTGTATTGGGTGC |
| | | | GCGACTCGGTTAGCGGCCTGCGCGTGCCCG |
| | | | TGCGCACCCGCCCCCCGCGCAACTAGATTG |
| | | | CAAGAAAAAACTACTTAGACTCGTACTGTT |
| | | | GTATGTATCCAGCGGCGGCGGCGCGCAACG |
| | | | AAGCTATGTCCAAGCGCAAAATCAAAGAA |
| | | | GAGATGCTCCAGGTCATCGCGCCGGAGATC |
| | | | TATGGCCCCCCGAAGAAGGAAGAGCAGGA |
| | | | TTACAAGCCCCGAAAGCTAAAGCGGGTCAA |
| | | | AAAGAAAAAGAAAGATGATGATGATGAAC |
| | | | TTGACGACGAGGTGGAACTGCTGCACGCTA |
| | | | CCGCGCCCAGGCGACGGGTACAGTGGAAA |
| | | | GGTCGACGCGTAAAACGTGTTTTGCGACCC |
| | | | GGCACCACCGTAGTCTTTACGCCCGGTGAG |
| | | | CGCTCCACCCGCACCTACAAGCGCGTGTAT |
| | | | GATGAGGTGTACGGCGACGAGGACCTGCTT |
| | | | GAGCAGGCCAACGAGCGCCTCGGGGAGTTT |
| | | | GCCTACGGAAAGCGGCATAAGGACATGCTG |
| | | | GCGTTGCCGCTGGACGAGGGCAACCCAACA |
| | | | CCTAGCCTAAAGCCCGTAACACTGCAGCAG |
| | | | GTGCTGCCCGCGCTTGCACCGTCCGAAGAA |
| | | | AAGCGCGGCCTAAAGCGCGAGTCTGGTGAC |
| | | | TTGGCACCCACCGTGCAGCTGATGGTACCC |
| | | | AAGCGCCAGCGACTGGAAGATGTCTTGGAA |
| | | | AAAATGACCGTGGAACCTGGGCTGGAGCCC |
| | | | GAGGTCCGCGTGCGGCCAATCAAGCAGGTG |
| | | | GCGCCGGGACTGGGCGTGCAGACCGTGGAC |
| | | | GTTCAGATACCCACTACCAGTAGCACCAGT |
| | | | ATTGCCACCGCCACAGAGGGCATGGAGACA |
| | | | CAAACGTCCCCGGTTGCCTCAGCGGTGGCG |
| | | | GATGCCGCGGTGCAGGCGGTCGCTGCGGCC |
| | | | GCGTCCAAGACCTCTACGGAGGTGCAAACG |
| | | | GACCCGTGGATGTTTCGCGTTTCAGCCCCCC |
| | | | GGCGCCCGCGCCGTTCGAGGAAGTACGGCG |
| | | | CCGCCAGCGCGCTACTGCCCGAATATGCCC |
| | | | TACATCCTTCCATTGCGCCTACCCCCGGCTA |
| | | | TCGTGGCTACACCTACCGCCCCAGAAGACG |
| | | | AGCAACTACCCGACGCCGAACCACCACTGG |
| | | | AACCCGCCGCCGCCGTCGCCGTCGCCAGCC |
| | | | CGTGCTGGCCCCGATTTCCGTGCGCAGGGT |
| | | | GGCTCGCGAAGGAGGCAGGACCCTGGTGCT |
| | | | GCCAACAGCGCGCTACCACCCCAGCATCGT |
| | | | TTAAAAGCCGGTCTTTGTGGTTCTTGCAGAT |
| | | | ATGGCCCTCACCTGCCGCCTCCGTTTCCCGG |
| | | | TGCCGGGATTCCGAGGAAGAATGCACCGTA |
| | | | GGAGGGGCATGGCCGGCCACGGCCTGACG |
| | | | GGCGGCATGCGTCGTGCGCACCACCGGCGG |
| | | | CGGCGCGCGTCGCACCGTCGCATGCGCGGC |
| | | | GGTATCCTGCCCCTCCTTATTCCACTGATCG |
| | | | CCGCGGCGATTGGCGCCGTGCCCGGAATTG |
| | | | CATCCGTGGCCTTGCAGGCGCAGAGACACT |
| | | | GATTAAAAACAAGTTGCATGTGGAAAAATC |
| | | | AAAATAAAAAGTCTGGACTCTCACGCTCGC |
| | | | TTGGTCCTGTAACTATTTTGTAGAATGGAA |
| | | | GACATCAACTTTGCGTCTCTGGCCCCGCGA |
| | | | CACGGCTCGCGCCCGTTCATGGGAAACTGG |
| | | | CAAGATATCGGCACCAGCAATATGAGCGGT |
| | | | GGCGCCTTCAGCTGGGGCTCGCTGTGGAGC |
| | | | GGCATTAAAAATTTCGGTTCCACCGTTAAG |
| | | | AACTATGGCAGCAAGGCCTGGAACAGCAG |
| | | | CACAGGCCAGATGCTGAGGGATAAGTTGAA |
| | | | AGAGCAAAATTTCCAACAAAAGGTGGTAG |
| | | | ATGGCCTGGCCTCTGGCATTAGCGGGGTGG |
| | | | TGGACCTGGCCAACCAGGCAGTGCAAAATA |
| | | | AGATTAACAGTAAGCTTGATCCCCGCCCTC |
| | | | CCGTAGAGGAGCCTCCACCGGCCGTGGAGA |
| | | | CAGTGTCTCCAGAGGGGCGTGGCGAAAAGC |

APPENDIX A-continued

SEQUENCE REFERENCE

| SEQ ID NO: | Molecule | Accession Number(s) or description | Sequence |
|---|---|---|---|
| | | | GTCCGCGCCCCGACAGGGAAGAAACTCTGG
TGACGCAAATAGACGAGCCTCCCTCGTACG
AGGAGGCACTAAAGCAAGGCCTGCCCACC
ACCCGTCCCATCGCGCCCATGGCTACCGGA
GTGCTGGGCCAGCACACACCCGTAACGCTG
GACCTGCCTCCCCCCGCCGACACCCAGCAG
AAACCTGTGCTGCCAGGCCCGACCGCCGTT
GTTGTAACCCGTCCTAGCCGCGCGTCCCTG
CGCCGCGCCGCCAGCGGTCCGCGATCGTTG
CGGCCCGTAGCCAGTGGCAACTGGCAAAGC
ACACTGAACAGCATCGTGGGTCTGGGGGTG
CAATCCCTGAAGCGCCGACGATGCTTCTGA
TAGCTAACGTGTCGTATGTGTGTCATGTATG
CGTCCATGTCGCCGCCAGAGGAGCTGCTGA
GCCGCCGCGCGCCCGCTTTCCAAGATGGCT
ACCCCTTCGATGATGCCGCAGTGGTCTTAC
ATGCACATCTCGGGCCAGGACGCCTCGGAG
TACCTGAGCCCCGGGCTGGTGCAGTTTGCC
CGCGCCACCGAGACGTACTTCAGCCTGAAT
AACAAGTTTAGAAACCCCACGGTGGCGCCT
ACGCACGACGTGACCACAGACCGGTCCCAG
CGTTTGACGCTGCGGTTCATCCCTGTGGACC
GTGAGGATACTGCGTACTCGTACAAGGCGC
GGTTCACCCTAGCTGTGGGTGATAACCGTG
TGCTGGACATGGCTTCCACGTACTTTGACAT
CCGCGGCGTGCTGGACAGGGGCCCTACTTT
TAAGCCCTACTCTGGCACTGCCTACAACGC
CCTGGCTCCCAAGGGTGCCCCAAATCCTTG
CGAATGGGATGAAGCTGCTACTGCTCTTGA
AATAAACCTAGAAGAAGAGGACGATGACA
ACGAAGACGAAGTAGACGAGCAAGCTGAG
CAGCAAAAAACTCACGTATTTGGGCAGGCG
CCTTATTCTGGTATAAATATTACAAAGGAG
GGTATTCAAATAGGTGTCGAAGGTCAAACA
CCTAAATATGCCGATAAAACATTTCAACCT
GAACCTCAAATAGGAGAATCTCAGTGGTAC
GAAACAGAAATTAATCATGCAGCTGGGAG
AGTCCTAAAAAGACTACCCCAATGAAACC
ATGTTACGGTTCATATGCAAAACCCACAAA
TGAAAATGGAGGGCAAGGCATTCTTGTAAA
GCAACAAAATGGAAAGCTAGAAAGTCAAG
TGGAAATGCAATTTTTCTCAACTACTGAGG
CAGCCGCAGGCAATGGTGATAACTTGACTC
CTAAAGTGGTATTGTACAGTGAAGATGTAG
ATATAGAAACCCCAGACACTCATATTTCTT
ACATGCCCACTATTAAGGAAGGTAACTCAC
GAGAACTAATGGGCCAACAATCTATGCCCA
ACAGGCCTAATTACATTGCTTTTAGGGACA
ATTTTATTGGTCTAATGTATTACAACAGCAC
GGGTAATATGGGTGTTCTGGCGGGCCAAGC
ATCGCAGTTGAATGCTGTTGTAGATTTGCA
AGACAGAAACACAGAGCTTTCATACCAGCT
TTTGCTTGATTCCATTGGTGATAGAACCAG
GTACTTTCTATGTGGAATCAGGCTGTTGAC
AGCTATGATCCAGATGTTAGAATTATTGAA
AATCATGGAACTGAAGATGAACTTCCAAAT
TACTGCTTTCCACTGGGAGGTGTGATTAAT
ACAGAGACTCTTACCAAGGTAAAACCTAAA
ACAGGTCAGGAAAATGGATGGGAAAAAGA
TGCTACAGAATTTTCAGATAAAAATGAAAT
AAGAGTTGGAAATAATTTTGCCATGGAAAT
CAATCTAAATGCCAACCTGTGGAGAAATTT
CCTGTACTCCAACATAGCGCTGTATTTGCCC
GACAAGCTAAAGTACAGTCCTTCCAACGTA
AAAATTTCTGATAACCCAAACACCTACGAC
TACATGAACAAGCGAGTGGTGGCTCCCGGG
CTAGTGGACTGCTACATTAACCTTGGAGCA
CGCTGGTCCCTTGACTATATGGACAACGTC
AACCCATTTAACCACCACCGCAATGCTGGC
CTGCGCTACCGCTCAATGTTGCTGGGCAAT
GGTCGCTATGTGCCCTTCCACATCCAGGTG
CCTCAGAAGTTCTTTGCCATTAAAAACCTCC
TTCTCCTGCCGGGCTCATACACCTACGAGT
GGAACTTCAGGAAGGATGTTAACATGGTTC |

APPENDIX A-continued

SEQUENCE REFERENCE

| SEQ ID NO: | Molecule | Accession Number(s) or description | Sequence |
|---|---|---|---|
| | | | TGCAGAGCTCCCTAGGAAATGACCTAAGGG<br>TTGACGGAGCCAGCATTAAGTTTGATAGCA<br>TTTGCCTTTACGCCACCTTCTTCCCCATGGC<br>CCACAACACCGCCTCCACGCTTGAGGCCAT<br>GCTTAGAAACGACACCAACGACCAGTCCTT<br>TAACGACTATCTCTCCGCCGCCAACATGCT<br>CTACCCTATACCCGCCAACGCTACCAACGT<br>GCCCATATCCATCCCCTCCCGCAACTGGGC<br>GGCTTTCCGCGGCTGGGCCTTCACGCGCCTT<br>AAGACTAAGGAAACCCCATCACTGGGCTCG<br>GGCTACGACCCTTATTACACCTACTCTGGCT<br>CTATACCCTACCTAGATGGAACCTTTTACCT<br>CAACCACACCTTTAAGAAGGTGGCCATTAC<br>CTTTGACTCTTCTGTCAGCTGGCCTGGCAAT<br>GACCGCCTGCTTACCCCCAACGAGTTTGAA<br>ATTAAGCGCTCAGTTGACGGGGAGGGTTAC<br>AACGTTGCCCAGTGTAACATGACCAAAGAC<br>TGGTTCCTGGTACAAATGCTAGCTAACTAT<br>AACATTGGCTACCAGGGCTTCTATATCCCA<br>GAGAGCTACAAGGACCGCATGTACTCCTTC<br>TTTAGAAACTTCCAGCCCATGAGCCGTCAG<br>GTGGTGGATGATACTAAATACAAGGACTAC<br>CAACAGGTGGGCATCCTACACCAACACAAC<br>AACTCTGGATTTGTTGGCTACCTTGCCCCCA<br>CCATGCGCGAAGGACAGGCCTACCCTGCTA<br>ACTTCCCCTATCCGCTTATAGGCAAGACCG<br>CAGTTGACAGCATTACCCAGAAAAAGTTTC<br>TTTGCGATCGCACCCTTTGGCGCATCCCATT<br>CTCCAGTAACTTTATGTCCATGGGCGCACTC<br>ACAGACCTGGGCCAAAACCTTCTCTACGCC<br>AACTCCGCCCACGCGCTAGACATGACTTTT<br>GAGGTGGATCCCATGGACGAGCCCACCCTT<br>CTTTATGTTTTGTTTGAAGTCTTTGACGTGG<br>TCCGTGTGCACCAGCCGCACCGCGGCGTCA<br>TCGAAACCGTGTACCTGCGCACGCCCTTCT<br>CGGCCGGCAACGCCACAACATAAAGAAGC<br>AAGCAACATCAACAACAGCTGCCGCCATGG<br>GCTCCAGTGAGCAGGAACTGAAAGCCATTG<br>TCAAAGATCTTGGTTGTGGGCCATATTTTTT<br>GGGCACCTATGACAAGCGCTTTCCAGGCTT<br>TGTTTCTCCACACAAGCTCGCCTGCGCCATA<br>GTCAATACGGCCGGTCGCGAGACTGGGGGC<br>GTACACTGGATGGCCTTTGCCTGGAACCCG<br>CACTCAAAAACATGCTACCTCTTTGAGCCC<br>TTTGGCTTTTCTGACCAGCGACTCAAGCAG<br>GTTTACCAGTTTGAGTACAGTCACTCCTGC<br>GCCGTAGCGCCATTGCTTCTTCCCCCGACCG<br>CTGTATAACGCTGGAAAAGTCCACCCAAAG<br>CGTACAGGGGCCCAACTCGGCCGCCTGTGG<br>ACTATTCTGCTGCATGTTTCTCCACGCCTTT<br>GCCAACTGGCCCCAAACTCCCATGGATCAC<br>AACCCCACCATGAACCTTATTACCGGGGTA<br>CCCAACTCCATGCTCAACAGTCCCCAGGTA<br>CAGCCCACCCTGCGTCGCAACCAGGAACAG<br>CTCTACAGCTTCCTGGAGCGCCACTCGCCCT<br>ACTTCCGCAGCCACAGTGCGCAGATTAGGA<br>GCGCCACTTCTTTTTGTCACTTGAAAAACAT<br>GTAAAAATAATGTACTAGAGACACTTTCAA<br>TAAAGGCAAATGCTTTTATTTGTACACTCTC<br>GGGTGATTATTTACCCCCACCCTTGCCGTCT<br>GCGCCGTTTAAAAATCAAAGGGGTTCTGCC<br>GCGCATCGCTATGCGCCACTGGCAGGGACA<br>CGTTGCGATACTGGTGTTTAGTGCTCCACTT<br>AAACTCAGGCACAACCATCCGCGGCAGCTC<br>GGTGAAGTTTTCACTCCACAGGCTGCGCAC<br>CATCACCAACGCGTTTAGCAGGTCGGGCGC<br>CGATATCTTGAAGTCGCAGTTGGGGCCTCC<br>GCCCTGCGCGCGCGAGTTGCGATACACAGG<br>GTTGCAGCACTGGAACACTATCAGCGCCGG<br>GTGGTGCACGCTGGCCAGCACGCTCTTGTC<br>GGAGATCAGATCCGCGTCCAGGTCCTCCGC<br>GTTGCTCAGGGCGAACGGAGTCAACTTTGG<br>TAGCTGCCTTCCCAAAAAGGGCGCGTGCCC<br>AGGCTTTGAGTTGCACTCGCACCGTAGTGG |

APPENDIX A-continued

SEQUENCE REFERENCE

| SEQ ID NO: | Molecule | Accession Number(s) or description | Sequence |
|---|---|---|---|
| | | | CATCAAAAGGTGACCGTGCCCGGTCTGGGC GTTAGGATACAGCGCCTGCATAAAAGCCTT GATCTGCTTAAAAGCCACCTGAGCCTTTGC GCCTTCAGAGAAGAACATGCCGCAAGACTT GCCGGAAAACTGATTGGCCGGACAGGCCGC GTCGTGCACGCAGCACCTTGCGTCGGTGTT GGAGATCTGCACCACATTTCGGCCCCACCG GTTCTTCACGATCTTGGCCTTGCTAGACTGC TCCTTCAGCGCGCGCTGCCCGTTTTCGCTCG TCACATCCATTTCAATCACGTGCTCCTTATT TATCATAATGCTTCCGTGTAGACACTTAAG CTCGCCTTCGATCTCAGCGCAGCGGTGCAG CCACAACGCGCAGCCCGTGGGCTCGTGATG CTTGTAGGTCACCTCTGCAAACGACTGCAG GTACGCCTGCAGGAATCGCCCCATCATCGT CACAAAGGTCTTGTTGCTGGTGAAGGTCAG CTGCAACCCGCGGTGCTCCTCGTTCAGCCA GGTCTTGCATACGGCCGCCAGAGCTTCCAC TTGGTCAGGCAGTAGTTTGAAGTTCGCCTTT AGATCGTTATCCACGTGGTACTTGTCCATCA GCGCGCGCGCAGCCTCCATGCCCTTCTCCC ACGCAGACACGATCGGCACACTCAGCGGGT TCATCACCGTAATTTCACTTTCCGCTTCGCT GGGCTCTTCCTCTTCCTCTTGCGTCCGCATA CCACGCGCCACTGGGTCGTCTTCATTCAGC CGCCGCACTGTGCGCTTACCTCCTTTGCCAT GCTTGATTAGCACCGGTGGGTTGCTGAAAC CCACCATTTGTAGCGCCACATCTTCTCTTTC TTCCTCGCTGTCCACGATTACCTCTGGTGAT GGCGGGCGCTCGGGCTTGGGAGAAGGGCG CTTCTTTTTCTTCTTGGGCGCAATGGCCAAA TCCGCCGCCGAGGTCGATGGCCGCGGGCTG GGTGTGCGCGGCACCAGCGCGTCTTGTGAT GAGTCTTCCTCGTCCTCGGACTCGATACGCC GCCTCATCCGCTTTTTTGGGGGCGCCCGGG GAGGCGGCGGCGACGGGGACGGGGACGAC ACGTCCTCCATGGTTGGGGGACGTCGCGCC GCACCGCGTCCGCGCTCGGGGGTGGTTTCG CGCTGCTCCTCTTCCCGACTGGCCATTTCCT TCTCCTATAGGCAGAAAAAGATCATGGAGT CAGTCGAGAAGAAGGACAGCCTAACCGCC CCCTCTGAGTTCGCCACCACCGCCTCCACC GATGCCGCCAACGCGCCTACCACCTTCCCC GTCGAGGCACCCCCGCTTGAGGAGGAGGA AGTGATTATCGAGCAGGACCCAGGTTTTGT AAGCGAAGACGACGAGGACCGCTCAGTAC CAACAGAGGATAAAAAGCAAGACCAGGAC AACGCAGAGGCAAACGAGGAACAAGTCGG GCGGGGGGACGAAAGGCATGGCGACTACC TAGATGTGGGAGACGACGTGCTGTTGAAGC ATCTGCAGCGCCAGTGCGCCATTATCTGCG ACGCGTTGCAAGAGCGCAGCGATGTGCCCC TCGCCATAGCGGATGTCAGCCTTGCCTACG AACGCCACCTATTCTCACCGCGCGTACCCC CCAAACGCCAAGAAAACGGCACATGCGAG CCCAACCCGCGCCTCAACTTCTACCCCGTAT TTGCCGTGCCAGAGGTGCTTGCCACCTATC ACATCTTTTTCCAAAACTGCAAGATACCCCT ATCCTGCCGTGCCAACCGCAGCCGAGCGGA CAAGCAGCTGGCCTTGCGGCAGGGCGCTGT CATACCTGATATCGCCTCGCTCAACGAAGT GCCAAAAATCTTTGAGGGTCTTGGACGCGA CGAGAAGCGCGCGGCAAACGCTCTGCAAC AGGAAAACAGCGAAAATGAAAGTCACTCT GGAGTGTTGGTGGAACTCGAGGGTGACAAC GCGCGCCTAGCCGTACTAAAACGCAGCATC GAGGTCACCCACTTTGCCTACCCGGCACTT AACCTACCCCCAAGGTCATGAGCACAGTC ATGAGTGAGCTGATCGTGCGCCGTGCGCAG CCCCTGGAGAGGGATGCAAATTTGCAAGAA CAAACAGAGGAGGGCCTACCCGCAGTTGGC GACGAGCAGCTAGCGCGCTGGCTTCAAACG CGCGAGCCTGCCGACTTGGAGGAGCGACGC AAACTAATGATGGCCGCAGTGCTCGTTACC |

APPENDIX A-continued

SEQUENCE REFERENCE

| SEQ ID NO: | Molecule | Accession Number(s) or description | Sequence |
|---|---|---|---|
| | | | GTGGAGCTTGAGTGCATGCAGCGGTTCTTT |
| | | | GCTGACCCGGAGATGCAGCGCAAGCTAGA |
| | | | GGAAACATTGCACTACACCTTTCGACAGGG |
| | | | CTACGTACGCCAGGCCTGCAAGATCTCCAA |
| | | | CGTGGAGCTCTGCAACCTGGTCTCCTACCTT |
| | | | GGAATTTTGCACGAAAACCGCCTTGGGCAA |
| | | | AACGTGCTTCATTCCACGCTCAAGGGCGAG |
| | | | GCGCGCCGCGACTACGTCCGCGACTGCGTT |
| | | | TACTTATTTCTATGCTACACCTGGCAGACGG |
| | | | CCATGGGCGTTTGGCAGCAGTGCTTGGAGG |
| | | | AGTGCAACCTCAAGGAGCTGCAGAAACTGC |
| | | | TAAAGCAAAACTTGAAGGACCTATGGACGG |
| | | | CCTTCAACGAGCGCTCCGTGGCCGCGCACC |
| | | | TGGCGGACATCATTTTCCCCGAACGCCTGC |
| | | | TTAAAACCCTGCAACAGGGTCTGCCAGACT |
| | | | TCACCAGTCAAAGCATGTTGCAGAACTTTA |
| | | | GGAACTTTATCCTAGAGCGCTCAGGAATCT |
| | | | TGCCCGCCACCTGCTGTGCACTTCCTAGCG |
| | | | ACTTTGTGCCCATTAAGTACCGCGAATGCC |
| | | | CTCCGCCGCTTTGGGGCCACTGCTACCTTCT |
| | | | GCAGCTAGCCAACTACCTTGCCTACCACTC |
| | | | TGACATAATGGAAGACGTGAGCGGTGACG |
| | | | GTCTACTGGAGTGTCACTGTCGCTGCAACC |
| | | | TATGCACCCCGCACCGCTCCCTGGTTTGCA |
| | | | ATTCGCAGCTGCTTAACGAAAGTCAAATTA |
| | | | TCGGTACCTTTGAGCTGCAGGGTCCCTCGC |
| | | | CTGACGAAAAGTCCGCGGCTCCGGGGTTGA |
| | | | AACTCACTCCGGGGCTGTGGACGTCGGCTT |
| | | | ACCTTCGCAAATTTGTACCTGAGGACTACC |
| | | | ACGCCCACGAGATTAGGTTCTACGAAGACC |
| | | | AATCCCGCCCGCCTAATGCGGAGCTTACCG |
| | | | CCTGCGTCATTACCCAGGGCCACATTCTTG |
| | | | GCCAATTGCAAGCCATCAACAAAGCCCGCC |
| | | | AAGAGTTTCTGCTACGAAAGGGACGGGGG |
| | | | GTTTACTTGGACCCCCAGTCCGGCGAGGAG |
| | | | CTCAACCCAATCCCCCGCCGCCGCAGCCC |
| | | | TATCAGCAGCAGCCGCGGGCCCTTGCTTCC |
| | | | CAGGATGGCACCCAAAAAGAAGCTGCAGC |
| | | | TGCCGCCGCCACCCACGGACGAGGAGGAAT |
| | | | ACTGGGACAGTCAGGCAGAGGAGGTTTTGG |
| | | | ACGAGGAGGAGGAGGACATGATGGAAGAC |
| | | | TGGGAGAGCCTAGACGAGGAAGCTTCCGA |
| | | | GGTCGAAGAGGTGTCAGACGAAACACCGTC |
| | | | ACCCTCGGTCGCATTCCCCTCGCCGGCGCC |
| | | | CCAGAAATCGGCAACCGGTTCCAGCATGGC |
| | | | TACAACCTCCGCTCCTCAGGCGCCGCCGGC |
| | | | ACTGCCCGTTCGCCGACCCAACCGTAGATG |
| | | | GGACACCACTGGAACCAGGGCCGGTAAGTC |
| | | | CAAGCAGCCGCCGCCGTTAGCCCAAGAGCA |
| | | | ACAACAGCGCCAAGGCTACCGCTCATGGCG |
| | | | CGGGCACAAGAACGCCATAGTTGCTTGCTT |
| | | | GCAAGACTGTGGGGGCAACATCTCCTTCGC |
| | | | CCGCCGCTTTCTTCTCTACCATCACGGCGTG |
| | | | GCCTTCCCCCGTAACATCCTGCATTACTACC |
| | | | GTCATCTCTACAGCCCATACTGCACCGGCG |
| | | | GCAGCGGCAGCAACAGCAGCGGCCACACA |
| | | | GAAGCAAAGGCGACCGGATAGCAAGACTC |
| | | | TGACAAAGCCCAAGAAATCCACAGCGGCG |
| | | | GCAGCAGCAGGAGGAGGAGCGCTGCGTCT |
| | | | GGCGCCCAACGAACCCGTATCGACCCGCGA |
| | | | GCTTAGAAACAGGATTTTTCCCACTCTGTAT |
| | | | GCTATATTTCAACAGAGCAGGGGCCAAGAA |
| | | | CAAGAGCTGAAAATAAAAAACAGGTCTCTG |
| | | | CGATCCCTCACCCGCAGCTGCCTGTATCAC |
| | | | AAAAGCGAAGATCAGCTTCGGCGCACGCTG |
| | | | GAAGACGCGGAGGCTCTCTTCAGTAAATAC |
| | | | TGCGCGCTGACTCTTAAGGACTAGTTTCGC |
| | | | GCCCTTTCTCAAATTTAAGCGCGAAAACTA |
| | | | CGTCATCTCCAGCGGCCACACCCGGCGCCA |
| | | | GCACCTGTTGTCAGCGCCATTATGAGCAAG |
| | | | GAAATTCCCACGCCCTACATGTGGAGTTAC |
| | | | CAGCCACAAATGGGACTTGCGGCTGGAGCT |
| | | | GCCCAAGACTACTCAACCCGAATAAACTAC |
| | | | ATGAGCGCGGGACCCCACATGATATCCCGG |

APPENDIX A-continued

SEQUENCE REFERENCE

| SEQ ID NO: | Molecule | Accession Number(s) or description | Sequence |
|---|---|---|---|
| | | | GTCAACGGAATACGCGCCCACCGAAACCGA<br>ATTCTCCTGGAACAGGCGGCTATTACCACC<br>ACACCTCGTAATAACCTTAATCCCCGTAGTT<br>GGCCCGCTGCCCTGGTGTACCAGGAAAGTC<br>CCGCTCCCACCACTGTGGTACTTCCCAGAG<br>ACGCCCAGGCCGAAGTTCAGATGACTAACT<br>CAGGGGCGCAGCTTGCGGGCGGCTTTCGTC<br>ACAGGGTGCGGTCGCCCGGGCAGGGTATAA<br>CTCACCTGACAATCAGAGGGCGAGGTATTC<br>AGCTCAACGACGAGTCGGTGAGCTCCTCGC<br>TTGGTCTCCGTCCGGACGGGACATTTCAGA<br>TCGGCGGCGCCGGCCGCTCTTCATTCACGC<br>CTCGTCAGGCAATCCTAACTCTGCAGACCT<br>CGTCCTCTGAGCCGCGCTCTGGAGGCATTG<br>GAACTCTGCAATTTATTGAGGAGTTTGTGC<br>CATCGGTCTACTTTAACCCCTTCTCGGGACC<br>TCCCGGCCACTATCCGGATCAATTTATTCCT<br>AACTTTGACGCGGTAAAGGACTCGGCGGAC<br>GGCTACGACTGAATGTTAAGTGGAGAGGCA<br>GAGCAACTGCGCCTGAAACACCTGGTCCAC<br>TGTCGCCGCCACAAGTGCTTTGCCCGCGAC<br>TCCGGTGAGTTTTGCTACTTTGAATTGCCCG<br>AGGATCATATCGAGGGCCCGGCGCACGGCG<br>TCCGGCTTACCGCCCAGGGAGAGCTTGCCC<br>GTAGCCTGATTCGGGAGTTTACCCAGCGCC<br>CCCTGCTAGTTGAGCGGGACAGGGGACCCT<br>GTGTTCTCACTGTGATTTGCAACTGTCCTAA<br>CCCTGGATTACATCAAGATCCTCTAGTTAAT<br>GTCAGGTCGCCTAAGTCGATTAACTAGAGT<br>ACCCGGGGATCTTATTCCCTTTAACTAATAA<br>AAAAAAATAATAAAGCATCACTTACTTAAA<br>ATCAGTTAGCAAATTTCTGTCCAGTTTATTC<br>AGCAGCACCTCCTTGCCCTCCTCCCAGCTCT<br>GGTATTGCAGCTTCCTCCTGGCTGCAAACTT<br>TCTCCACAATCTAAATGGAATGTCAGTTTCC<br>TCCTGTTCCTGTCCATCCGCACCCACTATCT<br>TCATGTTGTTGCAGATGAAGCGCGCAAGAC<br>CGTCTGAAGATACCTTCAACCCCGTGTATC<br>CATATGACACGGAAACCGGTCCTCCAACTG<br>TGCCTTTTCTTACTCCTCCCTTTGTATCCCCC<br>AATGGGTTTCAAGAGAGTCCCCCTGGGGTA<br>CTCTCTTTGCGCCTATCCGAACCTCTAGTTA<br>CCTCCAATGGCATGCTTGCGCTCAAATGG<br>GCAACGGCCTCTCTCTGGACGAGGCCGGCA<br>ACCTTACCTCCCAAAATGTAACCACTGTGA<br>GCCCACCTCTCAAAAAAACCAAGTCAAACA<br>TAAACCTGGAAATATCTGCACCCCTCACAG<br>TTACCTCAGAAGCCCTAACTGTGGCTGCCG<br>CCGCACCTCTAATGGTCGCGGGCAACACAC<br>TCACCATGCAATCACAGGCCCCGCTAACCG<br>TGCACGACTCCAAACTTAGCATTGCCACCC<br>AAGGACCCCTCACAGTGTCAGAAGGAAAG<br>CTAGCCCTGCAAACATCAGGCCCCCTCACC<br>ACCACCGATAGCAGTACCCTTACTATCACT<br>GCCTCACCCCCTCTAACTACTGCCACTGGTA<br>GCTTGGGCATTGACTTGAAAGAGCCCATTT<br>ATACACAAAATGGAAAACTAGGACTAAAG<br>TACGGGGCTCCTTTGCATGTAACAGACGAC<br>CTAAACACTTTGACCGTAGCAACTGGTCCA<br>GGTGTGACTATTAATAATACTTCCTTGCAA<br>ACTAAAGTTACTGGAGCCTTGGGTTTTGATT<br>CACAAGGCAATATGCAACTTAATGTAGCAG<br>GAGGACTAAGGATTGATTCTCAAAACAGAC<br>GCCTTATACTTGATGTTAGTTATCCGTTTGA<br>TGCTCAAAACCAACTAAATCTAAGACTAGG<br>ACAGGGCCCTCTTTTTATAAACTCAGCCCA<br>CAACTTGGATATTAACTACAACAAAGGCCT<br>TTACTTGTTTACAGCTTCAAACAATTCCAAA<br>AAGCTTGAGGTTAACCTAAGCACTGCCAAG<br>GGGTTGATGTTTGACGCTACAGCCATAGCC<br>ATTAATGCAGGAGATGGGCTTGAATTTGGT<br>TCACCTAATGCACCAAACACAAATCCCCTC<br>AAAACAAAAATTGGCCATGGCCTAGAATTT<br>GATTCAAACAAGGCTATGGTTCCTAAACTA |

APPENDIX A-continued

SEQUENCE REFERENCE

| SEQ ID NO: | Molecule | Accession Number(s) or description | Sequence |
|---|---|---|---|
| | | | GGAACTGGCCTTAGTTTTGACAGCACAGGT GCCATTACAGTAGGAAACAAAAATAATGAT AAGCTAACTTTGTGGACCACACCAGCTCCA TCTCCTAACTGTAGACTAAATGCAGAGAAA GATGCTAAACTCACTTTGGTCTTAACAAAA TGTGGCAGTCAAATACTTGCTACAGTTTCA GTTTTGGCTGTTAAAGGCAGTTTGGCTCCA ATATCTGGAACAGTTCAAAGTGCTCATCTT ATTATAAGATTTGACGAAATGGAGTGCTA CTAAACAATTCCTTCCTGGACCCAGAATAT TGGAACTTTAGAAATGGAGATCTTACTGAA GGCACAGCCTATACAAACGCTGTTGGATTT ATGCCTAACCTATCAGCTTATCCAAATCTC ACGGTAAAACTGCCAAAAGTAACATTGTCA GTCAAGTTTACTTAAACGGAGACAAAACTA AACCTGTAACACTAACCATTACACTAAACG GTACACAGGAAACAGGAGACACAACTCCA AGTGCATACTCTATGTCATTTTCATGGGACT GGTCTGGCCACAACTACATTAATGAAATAT TTGCCACATCCTCTTACACTTTTTCATACAT TGCCCAAGAATAAAGAATCGTTTGTGTTAT GTTTCAACGTGTTTATTTTTCAATTGCAGAA AATTTCAAGTCATTTTTCATTCAGTAGTATA GCCCCACCACCACATAGCTTATACAGATCA CCGTACCTTAATCAAACTCACAGAACCCTA GTATTCAACCTGCCACCTCCCTCCCAACAC ACAGAGTACACAGTCCTTTCTCCCCGGCTG GCCTTAAAAAGCATCATATCATGGGTAACA GACATATTCTTAGGTGTTATATTCCACACGG TTTCCTGTCGAGCCAAACGCTCATCAGTGA TATTAATAAACTCCCCGGGCAGCTCACTTA AGTTCATGTCGCTGTCCAGCTGCTGAGCCA CAGGCTGCTGTCCAACTTGCGGTTGCTTAA CGGGCGGCGAAGGAGAAGTCCACGCCTAC ATGGGGGTAGAGTCATAATCGTGCATCAGG ATAGGGCGGTGGTGCTGCAGCAGCGCGCGA ATAAACTGCTGCCGCCGCCGCTCCGTCCTG CAGGAATACAACATGGCAGTGGTCTCCTCA GCGATGATTCGCACCGCCCGCAGCATAAGG CGCCTTGTCCTCCGGGCACAGCAGCGCACC CTGATCTCACTTAAATCAGCACAGTAACTG CAGCACAGCACCACAATATTGTTCAAAATC CCACAGTGCAAGGCGCTGTATCCAAAGCTC ATGGCGGGGACCACAGAACCCACGTGGCC ATCATACCACAAGCGCAGGTAGATTAAGTG GCGACCCCTCATAAACACGCTGGACATAAA CATTACCTCTTTTGGCATGTTGTAATTCACC ACCTCCCGGTACCATATAAACCTCTGATTA AACATGGCGCCATCCACCACCATCCTAAAC CAGCTGGCCAAAACCTGCCCGCCGGCTATA CACTGCAGGGAACCGGGACTGGAACAATG ACAGTGGAGAGCCCAGGACTCGTAACCATG GATCATCATGCTCGTCATGATATCAATGTTG GCACAACACAGGCACACGTGCATACACTTC CTCAGGATTACAAGCTCCTCCCGCGTTAGA ACCATATCCCAGGGAACAACCCATTCCTGA ATCAGCGTAAATCCCACACTGCAGGGAAGA CCTCGCACGTAACTCACGTTGTGCATTGTCA AAGTGTTACATTCGGGCAGCAGCGGATGAT CCTCCAGTATGGTAGCGCGGGTTTCTGTCTC AAAAGGAGGTAGACGATCCCTACTGTACGG AGTGCGCCGAGACAACCGAGATCGTGTTGG TCGTAGTGTCATGCCAAATGGAACGCCGGA CGTAGTCATATTTCCTGAAGCAAAACCAGG TGCGGGCGTGACAAACAGATCTGCGTCTCC GGTCTCGCCGCTTAGATCGCTCTGTGTAGTA GTTGTAGTATATCCACTCTCTCAAAGCATCC AGGCGCCCCCTGGCTTCGGGTTCTATGTAA ACTCCTTCATGCGCCGCTGCCCTGATAACAT CCACCACCGCAGAATAAGCCACACCCAGCC AACCTACACATTCGTTCTGCGAGTCACACA CGGGAGGAGCGGGAAGAGCTGGAAGAACC ATGTTTTTTTTTTATTCCAAAAGATTATCC AAAACCTCAAAATGAAGATCTATTAAGTGA |

APPENDIX A-continued

SEQUENCE REFERENCE

| SEQ ID NO: | Molecule | Accession Number(s) or description | Sequence |
|---|---|---|---|
| | | | ACGCGCTCCCCTCCGGTGGCGTGGTCAAAC TCTACAGCCAAAGAACAGATAATGGCATTT GTAAGATGTTGCACAATGGCTTCCAAAAGG CAAACGGCCCTCACGTCCAAGTGGACGTAA AGGCTAAACCCTTCAGGGTGAATCTCCTCT ATAAACATTCCAGCACCTTCAACCATGCCC AAATAATTCTCATCTCGCCACCTTCTCAATA TATCTCTAAGCAAATCCCGAATATTAAGTC CGGCCATTGTAAAAATCTGCTCCAGAGCGC CCTCCACCTTCAGCCTCAAGCAGCGAATCA TGATTGCAAAAATTCAGGTTCCTCACAGAC CTGTATAAGATTCAAAAGCGGAACATTAAC AAAAATACCGCGATCCCGTAGGTCCCTTCG CAGGGCCAGCTGAACATAATCGTGCAGGTC TGCACGGACCAGCGCGGCCACTTCCCCGCC AGGAACCATGACAAAAGAACCCACACTGA TTATGACACGCATACTCGGAGCTATGCTAA CCAGCGTAGCCCCGATGTAAGCTTGTTGCA TGGGCGGCGATATAAAATGCAAGGTGCTGC TCAAAAAATCAGGCAAAGCCTCGCGCAAA AAAGAAAGCACATCGTAGTCATGCTCATGC AGATAAAGGCAGGTAAGCTCCGGAACCAC CACAGAAAAAGACACCATTTTTCTCTCAAA CATGTCTGCGGGTTTCTGCATAAACACAAA ATAAAATAACAAAAAAACATTTAAACATTA GAAGCCTGTCTTACAACAGGAAAAACAACC CTTATAAGCATAAGACGGACTACGGCCATG CCGGCGTGACCGTAAAAAAACTGGTCACCG TGATTAAAAAGCACCACCGACAGCTCCTCG GTCATGTCCGGAGTCATAATGTAAGACTCG GTAAACACATCAGGTTGATTCACATCGGTC AGTGCTAAAAAGCGACCGAAATAGCCCGG GGGAATACATACCCGCAGGCGTAGAGACA ACATTACAGCCCCCATAGGAGGTATAACAA AATTAATAGGAGAGAAAAACACATAAACA CCTGAAAAACCCTCCTGCCTAGGCAAAATA GCACCCTCCCGCTCCAGAACAACATACAGC GCTTCCACAGCGGCAGCCATAACAGTCAGC CTTACCAGTAAAAAAGAAAACCTATTAAAA AAACACCACTCGACACGGCACCAGCTCAAT CAGTCACAGTGTAAAAAAGGGCCAAGTGC AGAGCGAGTATATATAGGACTAAAAAATG ACGTAACGGTTAAAGTCCACAAAAAACACC CAGAAAACCGCACGCGAACCTACGCCCAG AAACGAAAGCCAAAAAACCCACAACTTCCT CAAATCGTCACTTCCGTTTTCCCACGTTACG TCACTTCCCATTTTAAGAAAACTACAATTCC CAACACATACAAGTTACTCCGCCCTAAAAC CTACGTCACCCGCCCCGTTCCCACGCCCCG CGCCACGTCACAAACTCCACCCCCTCATTA TCATATTGGCTTCAATCCAAAATAAGGTAT ATTATTGATGAT |
| 96 | human IL-12 insert (including restriction sites and Kozak sequence) | DNA Sequence | GTCGACGCCACCATGTGTCACCAGCAGCT CGTGATTAGCTGGTTCAGCCTGGTGTTTCTG GCTAGCCCTCTGGTGGCCATCTGGGAGCTG AAGAAGGACGTGTACGTGGTGGAGCTCGAC TGGTACCCTGACGCTCCCGGCGAGATGGTC GTGCTGACCTGCGACACCCCTGAGGAAGAT GGCATCACCTGGACCCTGGATCAAAGCTCC GAAGTGCTCGGCAGCGGCAAGACACTCACC ATCCAGGTGAAAGAGTTCGGAGACGCCGGC CAGTACACCTGCCACAAAGGCGGCGAGGTG CTGTCCCATTCCCTGCTGCTGCTGCACAAGA AAGAGGATGGCATCTGGTCCACCGACATCC TGAAGGACCAGAAGGAACCCAAGAACAAG ACCTTTCTGAGATGTGAGGCCAAGAACTAC AGCGGCAGGTTCACCTGCTGGTGGCTGACA ACAATCTCCACCGACCTGACCTTCAGCGTC AAGAGCAGCAGGGGCAGCAGCGACCCTCA AGGCGTGACATGTGGAGCCGCTACCCTGAG CGCTGAGAGAGTCAGGGGCGACAATAAGG AGTACGAGTACTCCGTGGAATGCCAGGAGG ACTCCGCCTGCCCTGCCGCCGAAGAGTCCC |

APPENDIX A-continued

SEQUENCE REFERENCE

| SEQ ID NO: | Molecule | Accession Number(s) or description | Sequence |
|---|---|---|---|
| | | | TCCCTATCGAAGTGATGGTTGATGCCGTGC<br>ACAAGCTCAAGTATGAGAATTACACCAGCA<br>GCTTTTTCATCAGGGACATCATCAAGCCCG<br>ACCCCCCCAAAAACCTCCAGCTGAAACCCC<br>TCAAGAATAGCAGGCAGGTGGAGGTCTCCT<br>GGGAGTATCCTGACACCTGGAGCACCCCCC<br>ACAGCTACTTCTCCCTGACCTTCTGTGTGCA<br>GGTGCAGGGCAAGAGCAAAAGGGAGAAGA<br>AGGATAGGGTCTTTACCGACAAGACCAGCG<br>CCACAGTGATCTGCAGGAAGAACGCCAGCA<br>TTTCCGTCAGGGCCCAGGACAGGTACTACA<br>GCAGCAGCTGGTCCGAGTGGGCTAGCGTGC<br>CTTGTTCCGGCGGCGGAGGATCTGGCGGAG<br>GCGGAAGTGGCGGAGGGGGCTCTAGAAAC<br>CTCCCCGTGGCCACACCCGACCCTGGCATG<br>TTCCCCTGCCTCCACCACAGCCAGAACCTG<br>CTGAGAGCCGTGAGCAATATGCTGCAGAAG<br>GCCAGGCAAACCCTGGAGTTCTACCCCTGT<br>ACCTCCGAGGAGATTGACCATGAGGACATC<br>ACAAAGGACAAAACCAGCACCGTGGAGGC<br>CTGTCTCCCCCTCGAACTGACCAAGAACGA<br>GTCCTGCCTGAACTCCAGGGAGACATCCTT<br>CATCACCAACGGCTCCTGCCTGGCCTCCAG<br>AAAGACCAGCTTCATGATGGCCCTCTGCCT<br>GAGCAGCATCTACGAGGACCTCAAGATGTA<br>CCAGGTGGAGTTTAAAACAATGAACGCCAA<br>GCTCCTCATGGACCCTAAGAGGCAGATTTT<br>CCTCGACCAGAATATGCTGGCTGTCATTGA<br>CGAGCTGATGCAGGCCCTCAATTTCAACTC<br>CGAGACCGTCCCCCAGAAGTCCTCCCTGGA<br>AGAGCCCGACTTTTACAAGACCAAGATCAA<br>GCTCTGCATCCTGCTGCACGCCTTCAGAATT<br>AGAGCCGTGACCATTGACAGGGTGATGAGC<br>TACCTCAACGCCTCCTGATGACTCGAG |
| 97 | human IL-7 insert | | GTCGACGCCACCACATCCGCGGCAACGCC<br>TCCTTGGTGTCGTCCGCTTCCAATAACCCAG<br>CTTGCGTCCTGC<br>ACACTTGTGGCTTCCGTGCACACATTAACA<br>ACTCATGGTTCTAGCTCCCAGTCGCCAAGC<br>GTTGCCAAGGCGTTGAGAGATCATCTGGGA<br>AGTCTTTTACCCAGAATTGCTTTGATTCAG<br>GCCAGCTGGTTTTTCCTGCGGTGATTCGGA<br>AATTCGCGAATTCCTCTGGTCCTCATCCAG<br>GTGCGCGGGAAGCAGGTGCCCAGGAGAGA<br>GGGGATAATGAAGATTCCATGCTGATGATCC<br>CAAAGATTGAACCTGCAGACCAAGCGCAA<br>AGTAGAAACTGAAAGTACACTGCTGGCGGAT<br>CCTACGGAAGTTATGGAAAAGGCAAAGCG<br>CAGAGCCACGCCGTAGTGTGTGCCGCCCCCC<br>TTGGGATGGATGAAACTGCAGTCGCGGCGT<br>GGGTAAGAGGAACCAGCTGCAGAGATCACC<br>CTGCCCAACACAGACTCGGCAACTCCGCGG<br>AAGACCAGGGTCCTGGGAGTGACTATGGGC<br>GGTGAGAGCTTGCTCCTGCTCCAGTTGCGG<br>TCATCATGACTACGCCCGCCTCCCGCAGAC<br>CATGTTCCATGTTTCTTTTAGGTATATCTTT<br>GGACTTCCTCCCCTGATCCTTGTTCTGTT<br>GCCAGTAGCATCATCTGATTGTGATATTGA<br>AGGTAAAGATGGCAAACAATATGAGAGTGT<br>TCTAATGGTCAGCATCGATCAATTATTGGA<br>CAGCATGAAAGAAATTGGTAGCAATTGCCT<br>GAATAATGAATTTAACTTTTTTAAAAGACA<br>TATCTGTGATGCTAATAAGGAAGGTATGTT<br>TTTATTCCGTGCTGCTCGCAAGTTGAGGCA<br>ATTTCTTAAAATGAATAGCACTGGTGATTT<br>TGATCTCCACTTATTAAAAGTTTCAGAAGG<br>CACAACAATACTGTTGAACTGCACTGGCCA<br>GGTTAAAGGAAGAAAACCAGCTGCCCTGG<br>GTGAAGCCCAACCAACAAAGAGTTTGGAAGA<br>AAATAAATCTTTAAAGGAACAGAAAAAACT<br>GAATGACTTGTGTTTCCTAAAGAGACTATT<br>ACAAGAGATAAAAACTTGTTGGAATAAAAT<br>TTTGATGGGCACTAAAGAACACTGAAAAAT |

APPENDIX A-continued

SEQUENCE REFERENCE

| SEQ ID NO: | Molecule | Accession Number(s) or description | Sequence |
|---|---|---|---|
| | | | ATGGAGTGGCAATATAGAAACACGAACTTT AGCTGCATCCTCCAAGAATCTATCTGCTTA TGCAGTTTTTCAGAGTGGAATGCTTCCTAG AAGTTACTGAATGCACCATGGTCAAAACGG ATTAGGGCATTTGAGAAATGCATATTGTAT TACTAGAAGATGAATACAAACAATGGAAAC TGAATGCTCCAGTCAACAAACTATTTCTTAT ATATGTGAACATTTATCAATCAGTATAAT TCTGTACTGATTTTTGTAAGACAATCCATGT AAGGTATCAGTTGCAATAATACTTCTCAA ACCTGTTTAAATATTTCAAGACATTAAATCT ATGAAGTATATAATGGTTTCAAAGATTCA AAATTGACATTGCTTTACTGTCAAAATAATT TTATGGCTCACTATGAATCTATTATACTG TATTAAGAGTGAAAATTGTCTTCTTCTGTGC TGGAGATGTTTTAGAGTTAACAATGATAT ATGGATAATGCCGGTGAGAATAAGAGAGTC ATAAACCTTAAGTAAGCAACAGCATAACAA GGTCCAAGATACCTAAAAGAGATTTCAAGA GATTTAATTAATCATGAATGTGTAACACAG TGCCTTCAATAAATGGTATAGCAAATGTTTT GACATGAAAAAAGGACAATTTCAAAAAAA TAAAATAAAATAAAAATAAATTCACCTAGT CTAAGGATGCTAAACCTTAGTACTGAGTTA CATTGTCATTTATATAGATTATAACTTGTCT AAATAAGTTTGCAATTTGGGAGATATATT TTTAAGATAATAATATATGTTTACCTTTTAA TTAATGAAATATCTGTATTTAATTTTGAC ACTATATCTGTATATAAAATATTTTCATACA GCATTACAAATTGCTTACTTTGGAATACA TTTCTCCTTTGATAAAATAAATGAGCTATGT ATTAAAAAAAAAAAAAA |
| 98 | human CD70 insert | NCBI Reference Sequence: NM_001252.4 | GTCGACGCCACCCCAGAGAGGGGCAGGCT GGTCCCCTGACAGGTTGAAGCAAGTAGACG CCCAGGGAGCCCCG GGAGGGGGCTGCAGTTTCCTTCCTTCCTTCT CGGCAGCGCTCCGCGCCCCCATCGCCCCT CCTGCGCTAGCGGAGGTGATCGCCGCGGCG ATGCCGGAGGAGGGTTCGGGCTGCTCGGTG CGGCGCAGGCCCTATGGGTGCGTCCTGCGG GCTGCTTTGGTCCCATTGGTCGCGGGCTTG GTGATCTGCCTCGTGGTGTGCATCCAGCGC TTCGCACAGGCTCAGCAGCAGCTGCCGCTC GAGTCACTTGGGTGGGACGTAGCTGAGCTG CAGCTGAATCACACAGGACCTCAGCAGGAC CCCAGGCTATACTGGCAGGGGGGCCCAGCA CTGGGCCGCTCCTTCCTGCATGGACCAGAG CTGGACAAGGGGCAGCTACGTATCCATCGT GATGGCATCTACATGGTACACATCCAGGTG ACGCTGGCCATCTGCTCCTCCACGACGGCC TCCAGGCACCACCCCACCACCCTGGCCGTG GGAATCTGCTCTCCCGCCTCCCGTAGCATC AGCCTGCTGCGTCTCAGCTTCCACCAAGGT TGTACCATTGCCTCCCAGCGCCTGACGCCC CTGGCCCGAGGGGACACACTCTGCACCAAC CTCACTGGGACACTTTTGCCTTCCCGAAAC ACTGATGAGACCTTCTTTGGAGTGCAGTGG GTGCGCCCCTGACCACTGCTGCTGATTAGG GTTTTTTAAATTTTATTTTATTTTATTTAA GTTCAAGAGAAAAAGTGTACACACAGGGG CCACCCGGGGTTGGGGTGGGAGTGTGGTGGG GGGTAGTGGTGGCAGGACAAGAGAAGGCA TTGAGCTTTTCTTTCATTTTCCTATTAAAA AATACAAAATCA |
| 99 | NV1 | Adenovirus E1a Enhancer Region Mutant 1 | GGCGGAAGTGTGATGTTGCAAGTGTGGCGG AACACATGTAAGCGACGGATGTGGCGCAA GTCTATGTTGTAGTAAATTTGGGCGTAACC GAGTAAGATTTGGCCATTTTCGCGGGAAAA CTGAATAAGAGGAAGTGAAATC |

APPENDIX A-continued

SEQUENCE REFERENCE

| SEQ ID NO: | Molecule | Accession Number(s) or description | Sequence |
|---|---|---|---|
| 100 | NV2 | Adenovirus E1a Enhancer Region Mutant 2 | ACAGGAAGTGACATGTTGCAAGTGTGGCGG AACACATGTAAGCGACGGATGTGGCGCAA GTCTATGTTGTAGTAAATTTGGGCGTAACC GAGTAAGATTTGGCCATTTTCGCGGGAAAA CTGAATAAGAGGAAGTGAAATCT |
| 101 | NV3 | Adenovirus E1a Enhancer Region Mutant 3 | ACAGGAAGTGACAATTTTCGCGCGGTTTTA GGCGGATGTGGCGCAAGTCTATGTTGTAGT AAATTTGGGCGTAACCGAGTAAGATTTGGC CATTTTCGCGGGAAAACTGAATAAGAGGAA GTGAAATCT |
| 102 | NV4 | Adenovirus E1a Enhancer Region Mutant 4 | GGCGGAAGTGTGATGTTGCAAGTGTGGCGG AACACATGTAAGCGACGGATGTGGCAAAA GTGACGTTTTTGGTGTGCGCCGGTGTACGG CGGAAGTGTGAATTTTCGCGCGGTTTTAGA CGGATGTGGCAGTAAATTTGGGCGTAACCG AGTAAGATTTGGCCATTTTCGCGGGAAAAC TGAATAAGAGGAAGTGAAATCT |
| 103 | NV5 | Adenovirus E1a Enhancer Region Mutant 5 | GGCGGAAGTGTGATGTTGCAAGTGTGGCGG AACACATGTAAGCGACGGATGTGGCAAAA GTGACGTTTTTGGTGTGCGCCGGTGTACGG CGGAAGTGTGAATTTTCGCGCGGTTTTAGA CGGATGTGGCAGTAAATTTGGGCGTAACCG AGTAAGATTTGGCCATTTTCGCGGGAAAAC TGAATAAGAGGATGTGAAATCT |
| 104 | NV6 | Adenovirus E1a Enhancer Region Mutant 6 | GGCGGAAGTGTGATGTTGCAAGTGTGGCGG AACACATGTAAGCGACGGATGTGGCAAAA GTGACGTTTTTGGTGTGCGCCGGTGTACGG CGGAAGTGTGAATTTTCGCGCGGTTTTAGA CGGATGTGGCAGTAAATTTGGGCGTAACCG AGTAAGATTTGGCCATTTTCGCGGGAAAAC TGAATAGGCGGAAGTGTGATCT |
| 105 | NV7 | Adenovirus E1a Enhancer Region Mutant 7 | GGCGGAAGTGTGATGTTGCAAGTGTGGCGG AACACATGTAAGCGACGGATGTGGCAAAA GTGACGTTTTTGGTGTGCGCCGGTGTACAC AGGAAGTGACAATTTTCGCGCGGTTTTAGA CGGATGTGGCAGTAAATTTGGGCGTAACCG AGTAAGATTTGGCCATTTTCGCGGGAAAAC TGAATAGGCGGAAGTGTGATCT |

What is claimed is:

1. A pharmaceutical composition comprising an effective amount of a recombinant adenoviral vector comprising:
   (a) a first transgene insertion site located between the start site of adenoviral E1b-19K and the start site of adenoviral E1b-55K;
   (b) a second transgene insertion site located in adenoviral E3 region;
   (c) a first DNA sequence encoding a first polypeptide selected from the group consisting of: a chimeric human IL-12, a human IL-7, an anti-CTLA-4 antibody, an IL-10Rtrap, a human CD70, a human IL-2 polypeptide, a human CD40 ligand, and a human OX40 ligand, wherein the first DNA sequence is present in the first transgene insertion site and is operably linked to a first endogenous promoter;
   (d) a second DNA sequence encoding a second polypeptide selected from the group consisting of: a chimeric human IL-12, a human IL-7, an anti-CTLA-4 antibody, an IL-10Rtrap, a human CD70, a human IL-2 polypeptide, a human CD40 ligand, and a human OX40 ligand, wherein the second DNA sequence is present in the second transgene insertion site and is operably linked to a second endogenous promoter; and
   (e) a modified adenoviral E1a regulatory sequence, wherein at least one Pea3 binding site of the adenoviral E1a regulatory sequence is modified or deleted.

2. The pharmaceutical composition of claim 1, wherein the recombinant adenoviral vector further comprises:
   a third DNA sequence encoding a third polypeptide selected from the group consisting of: a chimeric human IL-12, a human IL-7, an anti-CTLA-4 antibody, an IL-10Rtrap, a human CD70, a human IL-2 polypeptide, a human CD40 ligand, and a human OX40 ligand,
   wherein the third DNA sequence further comprises an IRES element or a self-cleaving 2A peptide, and expression of the third polypeptide is controlled by the first endogenous promoter.

3. The pharmaceutical composition of claim 1, wherein a sequence between two Pea3 sites of the adenoviral E1a regulatory sequence is deleted.

4. The pharmaceutical composition of claim 1, wherein the first DNA sequence or the second DNA sequence encodes the chimeric human IL-12, wherein the chimeric human IL-12 comprises a p40 polypeptide, a p35 polypeptide, and a linker polypeptide.

5. A method for treating a tumor in a human subject in need thereof, comprising administering to the human with the tumor a therapeutic amount of the pharmaceutical composition of claim 1 by systemic or intratumoral administration.

* * * * *